United States Patent [19]

Blackburn et al.

[11] Patent Number: 5,403,836
[45] Date of Patent: Apr. 4, 1995

[54] BENZAZEPINE PLATELET AGGREGATION INHIBITORS HAVING SPECIFICITY FOR THE GPII$_b$III$_a$ RECEPTOR

[75] Inventors: Brent Blackburn; Robert McDowell, both of San Francisco; Thomas Gadek, Oakland; Rob Webb, Moss Beach, all of Calif.

[73] Assignee: Genentech, Inc., So. San Francisco, Calif.

[21] Appl. No.: 58,722

[22] Filed: May 6, 1993

Related U.S. Application Data

[60] Division of Ser. No. 866,931, Apr. 10, 1992, Pat. No. 5,250,679, which is a continuation-in-part of Ser. No. 781,477, Oct. 18, 1991, abandoned.

[51] Int. Cl.$^6$ .................... A61K 31/55; C07D 223/16
[52] U.S. Cl. .................... 514/213; 540/495; 540/506; 540/523
[58] Field of Search ................ 540/523; 514/213

[56] References Cited

U.S. PATENT DOCUMENTS

| | | | |
|---|---|---|---|
| 3,371,085 | 2/1968 | Reeder et al. | 540/504 |
| 3,374,264 | 3/1968 | Uskokovic et al. | 560/47 |
| 3,415,814 | 12/1968 | Carabateas | 540/506 |
| 3,551,414 | 12/1970 | Hawthorne et al. | 540/522 |
| 3,721,666 | 3/1973 | Weber et al. | 540/506 |

(List continued on next page.)

FOREIGN PATENT DOCUMENTS

| | | |
|---|---|---|
| 027214 | 4/1981 | European Pat. Off. |
| 158339 | 10/1985 | European Pat. Off. |
| 268148 | 5/1988 | European Pat. Off. |
| 341915 | 11/1989 | European Pat. Off. |
| 372486 | 6/1990 | European Pat. Off. |
| 381033 | 8/1990 | European Pat. Off. |
| 384362 | 8/1990 | European Pat. Off. |
| 394101 | 10/1990 | European Pat. Off. |
| 422937 | 4/1991 | European Pat. Off. |
| 425212 | 5/1991 | European Pat. Off. |
| 456835 | 12/1991 | European Pat. Off. |
| 496378 | 7/1992 | European Pat. Off. |

(List continued on next page.)

OTHER PUBLICATIONS

Kukla, M. J. et al., "Synthesis and Anti-HIV-1 Activity of 4,5,6,7-Tetrahydro-5-methylimidazo [4,5,1k][1,4]benzodiazepin-2(1H)-one(TIBO) Derivatives. 2", *J. Med. Chem.*, 34:3187–3197 (1991).

Watjen et al., "Novel Benzodiazepine Receptor Partial Agonists: Oxadiazolylimidazobenzodiazepines", *J. Med. Chem.* 3:2282–2291 (1989).

Lee, C. M. "Synthesis of 1-Methyl-3H-1,4-benzodiazepine-2,5 (1H,4H)-dione and Derivatives", *J. Heterocyclic Chem.* 1:235 (1964).

Venuti, M. C., "Isatoic Anhydride/4-Dimethylaminopyridine as Reagent for ortho-Aminobenzoylation", *Synthesis* 266–268 (1982).

CAS Substructure Search, Dec. 5, 1991.

Voorstad et al., "Comparison of the Hypolipidemic Activity of Cyclic v. Acyclic Imides", *J. Med. Chem.*, 28:9–12 (1985).

Catsoulacos, P. *Chemical Abstracts*, abstract No. 115543c, 79: 356 (1973).

(List continued on next page.)

*Primary Examiner*—Mukund J. Shah
*Assistant Examiner*—Philip I. Datlow
*Attorney, Agent, or Firm*—Daryl B. Winter

[57] ABSTRACT

A benzazepine derivative that acts as a nonpeptidyl platelet aggregation inhibitor is provided. This inhibitor potently inhibits fibrinogen binding to the GPII$_b$III$_a$ receptor and is provided in therapeutic compositions for the treatment of diseases for which blocking platelet aggregation is indicated. These nonpeptidyl inhibitors are provided in combination with thrombolytics and anticoagulants.

10 Claims, No Drawings

U.S. PATENT DOCUMENTS

| | | | |
|---|---|---|---|
| 4,689,326 | 8/1987 | Hall et al. | 514/217 |
| 5,055,464 | 10/1991 | Murakami et al. | 514/211 |
| 5,061,693 | 10/1991 | Nutt et al. | 514/17 |
| 5,063,225 | 11/1991 | Clemence et al. | 514/211 |
| 5,082,937 | 1/1992 | Calvet et al. | 540/496 |

FOREIGN PATENT DOCUMENTS

| | | |
|---|---|---|
| 059386 | 9/1992 | European Pat. Off. . |
| 1124133 | 8/1968 | United Kingdom . |
| 059390 | 9/1982 | WIPO . |
| WO90/15620 | 12/1990 | WIPO . |
| WO91/01331 | 2/1991 | WIPO . |
| WO91/07976 | 6/1991 | WIPO . |
| WO91/09024 | 6/1991 | WIPO . |
| WO91/15515 | 10/1991 | WIPO . |
| WO93/00095 | 1/1993 | WIPO . |

OTHER PUBLICATIONS

Nagarajan et al., *Chemical Abstracts*, abstract No. 136120u, 84: 423 (1974).

Oine et al., *Chemical Abstracts*, abstract no. 91597m, 84: 473 (1974).

Boehringer C. H., *Chemical Abstracts*, abstract No. 18778a, 79: 423 (1973).

Griot, Rudolf G., *Chemical Abstracts*, abstract No. 47512d, 70: 348 (1969).

Carabateas, Philip M., *Chemical Abstracts*, abstract No. 47513e, 70: 348 (1969).

Thomae, Dr. Karl, *Chemical Abstracts*, abstract No. 47516h, 70:348 (1969).

Shirai et al., *Chemical Abstracts*, abstract No. 140001r, 77: 444 (1972).

Levai et al., *Chemical Abstracts*, abstract No. 6376g, 90: 348 (1979).

Shirai et al., *Chemical Abstracts*, abstract No. 34228q, 76: 318 (1972).

Coppola, Gary M., "The Chemistry of Isatoic Anydride", *Synthesis*, ed. Verlag, Georg Thieme, pp. 505–536 (1980).

CAS Substructure Search, Dec. 12, 1991, Blackburn et al.

Kim et al., *Tetrahedron Lett.* 3183–3186 (1988).

Murai, T. et al., *Tetrahedron Lett.* 26: 5145–5148 (1985).

Bellamy et al., *Tetrahydron Lett.* 25(8): 839–842 (1984).

Kappe, T. and Stadlbauer, "Isatoic Andrides and Their Uses in Heterocyclic Synthesis", *Advances in Heterocyclic Chemistry*, 28:127–182 (1981).

Voorstad et al., *J. Med. Chem.*, 28: 9–12 (1985).

BENZAZEPINE PLATELET AGGREGATION INHIBITORS HAVING SPECIFICITY FOR THE GPII$_b$III$_a$ RECEPTOR

This application is a divisional of U.S. patent application Ser. No. 07/866,931, filed 10 Apr. 1992, now U.S. Pat. No. 5,250,679, which application is a continuation-in-part of U.S. patent application Ser. No. 07/781,477, filed 18 Oct. 1991 (now abandoned).

FIELD OF THE INVENTION

The present invention relates to nonpeptidyl inhibitors of platelet aggregation. Specifically, the invention is directed to antagonists of the final common pathway of platelet aggregation. These antagonists act as potent antithrombotics. The invention further relates to therapeutic applications of these nonpeptidyl inhibitors in diseases for which blocking platelet aggregation is indicated.

BACKGROUND OF THE INVENTION

A. Platelets

Platelets are particles found in whole blood that initiate and provide the structural basis for the hemostatic plug necessary to stop bleeding. Platelets depend on adhesive interactions with extracellular proteins and other cells for proper function (see Hawiger, J. *Atherosclerosis Reviews* 21:165-186 (1990) and Roth J. R. *Innunology Today* 13(2):100-105 (1992)). The external platelet plasma membrane surface is covered with a variety of membrane bound glycoproteins, many of which have adhesive functions. Perhaps the most abundant platelet membrane adhesive proteins belong to the integrin superfamily which include the glycoproteins; GPII$_b$III$_a$, GPI$_a$II$_a$, GPI$_c$II$_a$, GPI$_b$IX, and the fibronectin and vitronectin receptors. Each integrin receptor is an $\alpha\beta$ heterodimer displaying characteristic affinity and specificity toward various protein ligands found in serum and/or the extracellular matrix including; von Willebrand factor (vWF), collagen, entactin, tenascin, fibronectin (Fn), vitronectin (Vn), and laminin, as well as fibrinogen (Fg) and thrombospondin (see Kieffer et al., *Ann. Rev. cell Biol.* 6:329-357(1990) and Ruoslahti, *J. Clin. Invest.*, 87:1-5 (1991)). The most abundant integrin found on the surface of normal platelets is GPII$_b$III$_a$ comprising about 50,000 molecules per platelet and representing about 2% of the total platelet protein. GPII$_b$III$_a$ is a non-covalent, calcium ion dependent heterodimeric complex (Jennings, et al., *J. Biol. Chem.* 257: 10458 (1982)) that is restricted in distribution to platelets and other cells of the megakaryocytic lineage (Kieffer et al., supra). On activated platelets, GPII$_b$III$_a$ promiscously binds a number of protein ligands with varying affinities, including; fibrinogen, fibronectin, von Willebrand factor, vitronectin and thrombospondin (Plow et al., *Biochemistry of Platelets*, Phillips and Shuman eds., p. 225-256, Orlando: Academic Press [1986]). Each of these protein ligands contain at least one tripeptide sequence Arg-Gly-Asp which is commonly refered to as the "recognition sequence". It is believed the most important interactions mediating platelet aggregation involve GPII$_b$III$_a$ binding with the trinodular fibrinogen and, to a lesser extent, with the filamentous von Willebrand factor (Kieffer et al., supra and Albeda et al., *The FASEB Journal*, 4:2868-2880 [1990]).

GPII$_b$III$_a$ binding to its natural ligands can be inhibited to varying degrees by peptides and proteins containing the amino acid recognition sequences; Arg-Gly-Asp (RGD) (Ruoslahti, supra and EPO 0368486, assigned to Merck & Co.), Lys-Gly-Asp (KGD), and the fibrinogen γ-chain carboxy-terminal dodecapeptide HHLGGAKQAGDV and analogues thereof (Timmons et al., *Biochemistry*, 28:2919-2922 [1989]).

B. The Hyperthrombotic State

Many common human disorders are characteristically associated with a hyperthrombotic state leading to intravascular thrombi and emboli. These are a major cause of medical morbidity, leading to infarction, stroke and phlebitis, and of mortality from stroke and pulmonary and cardiac emboli. Patients with atherosclerosis are predisposed to arterial thromboembolic phenomena for a variety of reasons. Atherosclerotic plaques form niduses for platelet plugs and thrombi that lead to vascular narrowing and occlusion, resulting in myocardial and cerebral ischemic disease. This may happen spontaneously or following procedures such as angioplasty or endarterectomy. Thrombi that break off and are released into the circulation cause infarction of different organs, especially the brain, extremities, heart and kidneys.

In addition to being involved in arterial thrombosis, platelets may also play a role in venous thrombosis. A large percentage of such patients have no antecedent risk factors and develop venous thrombophlebitis and subsequent pulmonary emboli without a known cause. Other patients who form venous thrombi have underlying diseases known to predispose them to these syndromes. Some of these patients may have genetic or acquired deficiencies of factors that normally prevent hypercoagulability, such as antithrombin-3. Others have mechanical obstructions to venous flow, such as tumor masses, that lead to low flow states and thrombosis. Patients with malignancy have a high incidence of thrombotic phenomena for unclear reasons. Antithrombotic therapy in this situation with currently available agents is dangerous and often ineffective.

Patients whose blood flows over artificial surfaces, such as prosthetic synthetic cardiac valves or through extracorporeal perfusion devices, are also at risk for the development of platelet plugs, thrombi and emboli. It is standard practice that patients with artificial cardiac valves be treated chronically with anti-coagulants. However, in all instances, platelet activation and emboli formation may still occur despite adequate anticoagulation treatment.

Thus, a large category of patients, including those with atherosclerosis, coronary artery disease, artificial heart valves, cancer, and a history of stroke, phlebitis, or pulmonary emboli, are candidates for limited or chronic antithrombotic therapy. The number of available therapeutic agents is limited and these, for the most part, act by inhibiting or reducing levels of circulating clotting factors. These agents are frequently not effective against the patient's underlying hematologic problem, which often concerns an increased propensity for platelet aggregation and adhesion. They also cause the patient to be susceptible to abnormal bleeding. Available antiplatelet agents, such as aspirin, inhibit only part of the platelet activation process and are therefore often inadequate for therapy and also cause the patient to be susceptible to abnormal bleeding.

C. Therapeutic Agents

An agent which effectively inhibits the final common pathway of platelet activation, namely fibrinogen binding to the GP II$_b$III$_a$ receptor, should accordingly be useful in a large group of disorders characterized by a hyperthrombotic state as described above.

Such agents include anti-thrombotic peptides and pseudopeptides capable of inhibiting platelet aggregation. Ruoslahti et al. (U.S. Pat. No. 4,578,079) suggest that tetrapeptides containing the RGD sequence may be used to effect platelet aggregation. Zimmerman et al. (U.S. Pat. No. 4,683,291) disclose that positively charged amino acid residues (eg Arg and Lys) and homologues located before or toward the amino terminus of the RGD sequence are superior for inhibiting fibrinogen-platelet binding. Adams et al. (U.S. Pat. No. 4,857,508) describe superior results for in-vitro inhibition of human platelet aggregation in platelet-rich plasma for linear tetrapeptides containing O-methyl-Tyr-amide immediately following the RGD (or homo-RGD) sequence. Tjoeng et al. (U.S. Pat. No. 4,879,313) describe peptide mimetic platelet aggregation inhibitors in which the first two residues of the RGD sequence are replaced by the pseudodipeptidyl, 8-guanidino-octanoyl moiety. Other peptidomimetics in which the Arg of the RGD sequence has been altered include; WO89/07609 (homo-Arg[Har]), EP 341 915 (Har and alkyl-Arg), WO90/15620 (Har and amidino derivatives eg. imidazolinyl, imidazolyl, and substituted imidazolyl), EP 422 937 (aryl-, arylalkyl-, and cycloalkyl-amines), WO91/07976 (alkylamidino and alkylamino derivatives), and WO91/04247 (alkylamino and alkyl-guanidino proline derivatives). See also EP 384 362 (glycine derivatives) and EP 381 033.

Complete replacement of all residues in the RGD sequence has been described in EP 372 362 where platelet aggregation inhibitors that are derivatives of benzoic and phenylacetic acid are presented. A benzoic acid derivative inhibitor having a particular low IC$_{50}$ in an ELISA measurement of fibrinogen GPII$_b$III$_a$ binding is:

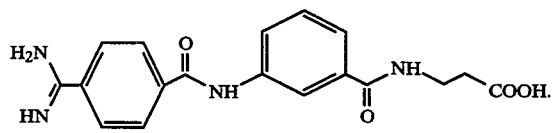

D. Benzodiazepines

It is well established that benzodiazepines and related ligands interact with a specific site commonly referred to as the "benzodiazepine receptor" that is associated with a neuro-inhibitory postsynaptic GABA receptor and a chloride ionophore channel (see eg. Watjen et al., *J. Med. Chem.* 32:2282–2291]1989]). Binding of ligands to this receptor is known to produce a wide variety of nero-physiolgical effects. Benzodiazepines have not been reported to have platelet aggregation inhibition activity. The preparation and therapeutic use of benzodiazepines is described in, for example; EP 0 059 390, EP 0 059 386, and EP 0 394 101.

Benzodiazepinediones have been employed as intmediates in the synthesis of various anti-HIV-1 compounds. For example Kukla, M. J. et al. *J. Med. Chem.* 34:3187–3197 (1991) reduce the dilactam to either the corresponding "-one" or diamine in the preparation of various TIBO derivatives having anti-HIV activity.

E. Objects

It is an object of this invention to produce nonpeptidyl compounds having potent antithrombotic activity. It is another object of the invention to produce such compounds that are essentially free of peptide bonds, substantially rigid, and stable to degradation. It is a further object to produce potent nonpeptidyl anti-thrombotics that specifically inhibit the GPII$_b$III$_a$-Fg interaction but do not strongly inhibit other RGD sensitive integrin interactions including the Vn-VnR, Fn-FnR, and GPII$_b$III$_a$-vWF interactions. It is still a further object to produce potent nonpeptidyl platelet aggregation inhibitors that do not significantly increase cutaneous bleeding time or diminish other hemodynamic factors. These and other objects of this invention will be apparent from consideration of the invention as a whole.

SUMMARY OF THE INVENTION

The objects of this invention are accomplished by providing a nonpeptidyl platelet aggregation inhibitor comprising a compound represented by structural formula I:

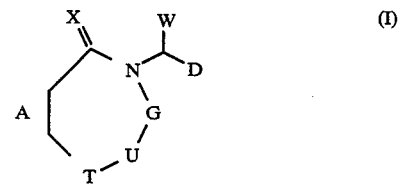

where the partial structure

represents;

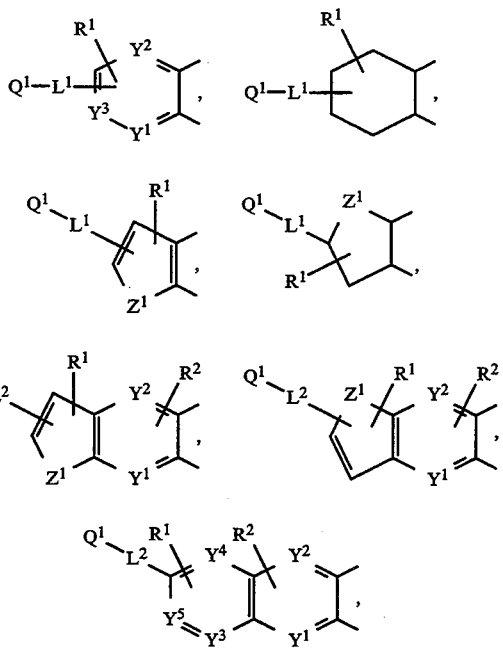

and

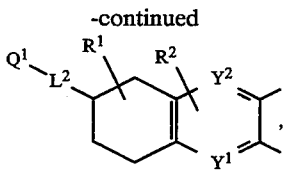

where $R^1$ and $R^2$ are one to three optional groups typically selected from; hydrogen, halo(F, Cl, Br, I), cyano, carboxamido, carbamoyloxy, formyloxy, formyl, azido, nitro, ureido, thioureido, hydroxy, mercapto, sulfonamido, and an optionally substituted radical selected from; $C_1$-$C_{12}$ alkyl, $C_2$-$C_{12}$ alkenyl, $C_3$-$C_{12}$ alkynyl, $C_3$-$C_{12}$ cycloalkyl, $C_6$-$C_{14}$ aryl, $C_6$-$C_{10}$ aryl-$C_1$-$C_8$-alkyl, $C_1$-$C_{12}$ alkyloxy, $C_6$-$C_{14}$ aryloxy, $C_1$-$C_{12}$ acylamino, N,N-di($C_1$-$C_{12}$)acylamino, N-($C_1$-$C_{12}$)alkyl-N-($C_1$-$C_{12}$)-acylamino, $C_1$-$C_{12}$ alkylsulfonamido, N-($C_1$-$C_{12}$)-alkyl-N-($C_1$-$C_{12}$)alkyl-sulfonylamino, $C_1$-$C_{12}$ alkylthiocarbonyl, $C_1$-$C_{12}$ alkylthio, $C_1$-$C_{12}$ alkylsulfinyl, $C_1$-$C_{12}$ alkylsulfonyl, $C_1$-$C_{12}$ alkylsulfonato, N-($C_1$-$C_{12}$)alkylsulfonamido, N,N-di-($C_1$-$C_{12}$) sulfonamido, N-($C_1$-$C_{12}$) alkyl-N-thioformylamino, $C_1$-$C_{12}$ thioacylamino, N-($C_1$-$C_{12}$)alkyl-N-($C_1$-$C_{12}$) thioacylamino, $C_1$-$C_{12}$ alkylsulfinamido, N-($C_1$-$C_{12}$)alkyl-N-($C_1$-$C_{12}$)alkylsulfinylamino, $C_1$-$C_{12}$ carbalkoxy, $C_1$-$C_{12}$ alkylcarbonyl, $C_1$-$C_{12}$ alkanoyloxy, N-($C_1$-$C_{12}$)alkylcarboxamido, N,N-di-($C_1$-$C_{12}$)carboxamido, N-($C_1$-$C_{12}$) alkylcarbamoyloxy, N,N-di-($C_1$-$C_{12}$)carbamoyloxy, and heterocycloalkyl or heteroaryl having from 1 to 3 rings, each ring having from 5 to 7 atoms with from 0–3 heteroatoms selected from N, O, and S, provided that at least one ring contains a heteroatom, where the substituents are typically selected from halo (F, Cl, Br, I), cyano, azido, nitro, hydroxy, mercapto, sulfonamido, ureido, thioureido, carboxamido, carbamoyloxy, formyloxy, formyl, $C_1$-$C_4$alkyl, $C_1$-$C_4$alkoxy, phenyl, and phenoxy.

$Y^1$, $Y^2$, $Y^3$, $Y^4$ and $Y^5$ are independently selected from CH, $CR^1$, $CR^2$, and N; X is O or S; and $Z^1$ is selected from $CH_2$, NH, S, and O;

$Q^1$ is a substituted or unsubstituted positively charged nitrogen-containing moiety. Preferably $Q^1$ is selected from:

(A) an amino group including;
(1) —$NH_2$,
(2) —$NR^3H$,
(3) —$NR^3R^4$, and
(4) —$NR^3R^4R^5$, where $R^3$, $R^4$, and $R^5$ are typically selected from; (i) an optionally substituted radical selected from (a) —$NR^6R^7$, (b) —C(=$NR^8$)—$NR^6R^7$, (c) —N=$CR^9$—$NR^6R^7$, (d) —$NR^{10}$—$CR^9$=$NR^8$, and (e) —$NR^{10}$—C(=$NR^8$)—$NR^6R^7$ where each $R^6$, $R^7$, $R^8$, $R^9$, and $R^{10}$ is independently selected from hydrogen, $C_1$-$C_4$ alkoxy, $C_1$-$C_4$ alkyl, and halo(F, Cl, Br, I)-$C_1$-$C_4$ alkyl, (ii) optionally substituted $C_1$-$C_{12}$ alkyl, (iii) optionally substituted $C_3$-$C_7$ alkenyl, (iv) optionally substituted $C_3$-$C_7$ alkynyl, (v) optionally substituted $C_3$-$C_{12}$ cycloalkyl, (vi) optionally substituted $C_5$-$C_{12}$ cycloalkenyl, (vii) optionally substituted $C_6$-$C_{14}$ aryl, (viii) optionally substituted $C_1$-$C_6$ alkyl-$C_6$-$C_{14}$-aryl, (ix) optionally substituted $C_3$-$C_6$ alkenyl-$C_6$-$C_{10}$ aryl, (x) optionally substituted heterocyclyl, (xi) optionally substituted $C_1$-$C_6$ alkyl-heterocyclyl, (xii) optionally substituted $C_1$-$C_8$ alkoxy, (xiii) optionally substituted $C_1$-$C_8$ thioalkoxy, (xiv) optionally substituted $C_3$-$C_{10}$ alkenoxy, and (xv) optionally substituted $C_6$-$C_{14}$ aryloxy, where the substituents are usually one to three $R^{11}$, each $R^{11}$ typically selected from (a) optionally substituted $C_6$-$C_{12}$ aryloxy, (b) optionally substituted $C_6$-$C_{12}$ arylamino, (c) optionally substituted $C_6$-$C_{12}$ aroyl, (d) optionally substituted $C_6$-$C_{12}$ arylthio, where the substituents are usually one to three $R^{12}$, each $R^{12}$ typically selected from nitro, amino, $C_1$-$C_8$ alkylamino, di-($C_1$-$C_8$) alkylamino, amidino, aminomethyleneimino, imino, imino-$C_1$-$C_4$ alkyl, iminomethyleneamino, guanidino, $C_6$-$C_{10}$ arylamino, $C_1$-$C_8$ acylamino, $C_1$-$C_4$ alkylsulfonamino, azido, cyano, hydroxy, hydroxy-$C_1$-$C_8$-alkyl, $C_1$-$C_8$-alkoxy, phenyloxy, $C_1$-$C_8$ alkanoyloxy, $C_1$-$C_8$ alkanoyl, $C_6$-$C_{12}$ aroyl, benzamido, phenyl, halo(F, Cl, Br, I), halo-$C_1$-$C_8$-alkyl, and $C_1$-$C_8$-alkyl, (e) $C_1$-$C_8$alkoxy (f) $C_1$-$C_8$alkthio (g) halo(F, Cl, Br, I), (h) hydroxy, (i) mercapto, (j) $C_1$-$C_8$ alkylcarbonyl, (k) carbamoyl (l) formyl, (m) formyloxy, (n) carboxy, (o) carbo-$C_1$-$C_8$alkyloxy, (p) $C_1$-$C_8$ alkanoyloxy, (q) N-($C_1$-$C_8$)-alkylcarboxamido, (r) N-($C_1$-$C_8$), N-($C_1$-$C_8$)-dialkylcarboxamido, (s) carbamoyloxy, (t) N-($C_1$-$C_8$) alkylcarbamoyloxy, (u) N-($C_1$-$C_8$), N-($C_1$-$C_8$-)dialkylcarbamoyloxy, (v) $C_1$-$C_8$ alkylsulfinyl, (w) $C_1$-$C_8$ alkylsulfonyl, (x) $C_1$-$C_8$ alkylsulfonato, (y) sulfo, (z) sulfonamido, (aa) N-($C_1$-$C_8$) alkylsulfonamido, (ab) N-($C_1$-$C_8$), N-($C_1$-$C_8$) dialkylsulfonamido, (ac) amino, (ad) $C_1$-$C_8$ alkylamino, (ae) $C_1$-$C_8$ dialkylamino, (af) $C_1$-$C_8$ acylamino, (ag) N-($C_1$-$C_8$), N-($C_1$-$C_8$)-diacylamino, (ah) N-($C_1$-$C_8$)-alkyl-N-($C_1$-$C_8$)-acylamino, (ai) formylamino, (aj) ureido, (ak) isothioureido, (al) amino-$C_2$-$C_8$ alkylthio, (am) amino-$C_2$-$C_8$ alkloxy, (an) amidino, (ao) guanidino, (ap) aminomethyleneimino, (aq) amino, (at) imino-$C_1$-$C_4$ alkyl, (as) iminomethyleneamino, (at) glycylamino, (au) glycyl, (av) phthalimido, (aw) succinimido, (ax) morpholino, (ay) $C_1$-$C_8$ alkylsulfonamido, (az) N-($C_1$-$C_8$)-alkyl-N-($C_1$-$C_8$) alkyl sulfonoylamino, (ba) $C_1$-$C_8$ alkylsulfinamino, (bb) N-($C_1$-$C_8$) alkyl-N-($C_1$-$C_8$) alkylsulfinamino, (bc) $C_1$-$C_8$ alkoxyamino, (bd) $C_1$-$C_8$ alkoxyamino, (be) N-($C_1$-$C_8$) alkyl-N-($C_1$-$C_8$) alkoxyamino, (bf) $C_3$-$C_7$ cycloalkyl, and (bg) heterocyclyl, optionally any one or two pairs of $R^3$-$R^{10}$ may independently be joined to form one or two optionally substituted heterocyclic rings, each ring optionally fused with one or two optionally substituted homocyclic or heterocyclic rings of from four to seven atoms where any heterocyclic ring contains from one to four heteroatoms selected from N, O, and S and where any ring may be substituted with from one to three $R^{12}$, (B) an amidino (aminoiminomethyl) group including;
(1) —C(=NH)—$NH_2$,
(2) —C(=NH)—$NHR^3$,
(3) —C(=$NR^4$)—$NHR^3$,
(4) —(=NH)—$NR^3R^4$, and
(5) —C(=$NR^5$)—$NR^3R^4$, where $R^3$, $R^4$, and $R^5$ are defined above, (C) an aminoalkyleneamino group including;
(1) —N=CH—$NH_2$,
(2) —N=CH—$NHR^3$,
(3) —N=CH—$NR^3R^4$, and
(4) —N=$CR^5$—$NR^3R^4$, where $R^3$, $R^4$, and $R^5$ are defined above, (D) an iminoalkyleneamino group, including;
(1) —NH—CH=NH,
(2) —NH—CH=$NR^3$,
(3) —NH—$CR^4$=$NR^3$, and
(4) —$NR^5$—$CR^4$=$NR^3$, where $R^3$, $R^4$, and $R^5$ are defined above, (E) a guanidino (aminoiminomethyleneamino) group including;
(1) —NH—C(=NH)—NH$_2$,
(2) —NH—C(=NH)—NR$^3$H,
(3) —NH—C(=NH)—NR$^3$R$^4$,
(4) —NH—C(=NR$^5$)—NR$^3$R$^4$,
(5) —NR$^3$—C(=NR$^3$)—NR$^3$R$^4$,
(6) —NR$^3$—C(=NH)—NR$^3$R$^4$,
(7) —NR$^3$—C(=NR$^3$)—NH$_2$,
(8) —NR$^3$—C(=NH)—NH$_2$,
(9) —NR$^3$—C(=NR$^3$)—NHR$^4$, and
(10) —NR$^3$-C(=NH)—NHR$^4$,
where R$^3$, R$^4$, and R$^5$ are defined above,
(F) an optionally substituted saturated heterocyclic group including;

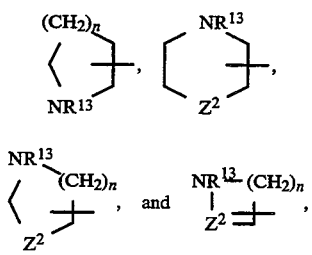

where (1) n is 0, 1, 2, or 3, (2) R$^{13}$ is selected from; R$^6$, —CR$^9$(=NR$^8$)—NR$^6$R$^7$, —C(=NR$^8$)—NR$^6$R$^7$, —N=CR$^9$—NR$^6$R$^7$, —NR$^{10}$—CR$^9$=NR$^8$, and —NR$^{10}$—(C=NR$^8$)—NR$^6$R$^7$ where R$^6$-R$^{10}$ are defined above, (3) Z$^2$ is O, S, or NR$^{13}$, and (4) the substituents are independently one to three R$^{12}$,
(G) an optionally substituted unsaturated (nonaromatic) heterocyclyl including;

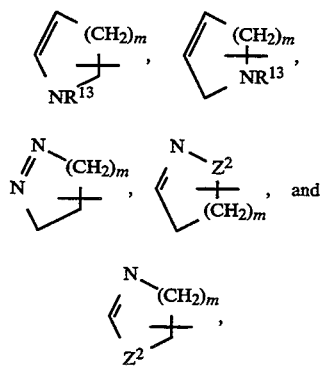

where (1) m is 1, 2, or 3, (2) Z$^2$ and R$^{13}$ are defined above, and (3) the substituents are typically one to three R$^{12}$,
(H) an optionally substituted unsaturated (aromatic) heterocyclyl including;

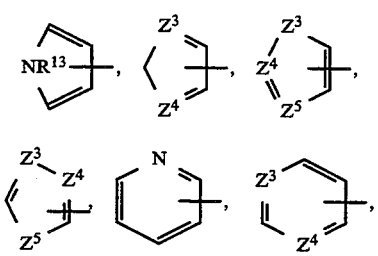

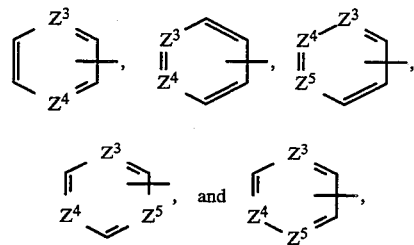

where (1) Z$^3$, Z$^4$, and Z$^5$ are typically selected from O, S, N, and NH, provided at least one Z$^3$, Z$^4$, or Z$^5$ is N or NH, (2) R$^{13}$ is defined above, and the substituents are independently one to three R$^{12}$,
(I) an optionally substituted bicycloheterocyclic group including;

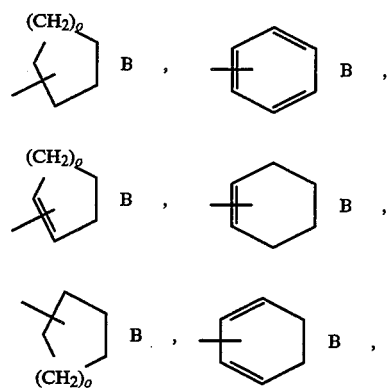

and

where the partial structure

 B represents

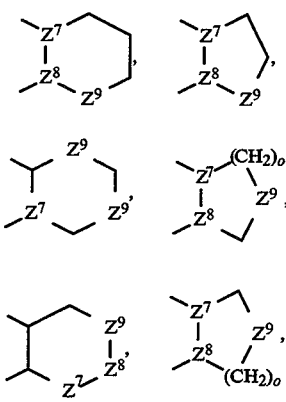

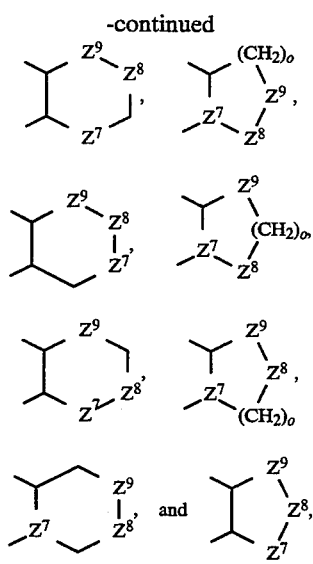

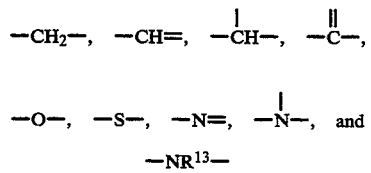

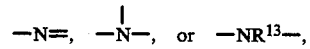

where $Z^7$, $Z^8$, and $Z^9$ are independently selected from;

$$-CH_2-,\quad -CH=,\quad -\overset{|}{C}H-,\quad -\overset{\|}{C}-,$$

$$-O-,\quad -S-,\quad -N=,\quad -\overset{|}{N}-,\text{ and}$$

$$-NR^{13}-$$

provided that at least one $Z^7$, $Z^8$, or $Z^9$ is $$-N=,\quad -\overset{|}{N}-,\quad\text{or}\quad -NR^{13}-,$$

where (1) o is 0, 1, or 2, (2) $R^{13}$ is defined above, and (3) the substituents are independently one to three $R^{12}$. Exemplary heterocyclic $Q^1$ groups include; isoindolinyl, quinuclidinyl, morpholinyl, and 1,3-diazacyclohex-4-ene. Optionally, any of the nitrogen containing heterocycles described above may be substituted with amino, imino, amidino, aminomethyleneimino, iminomethyleneamino, guanidino, $N^G$-aminoguanidino, alkylamino, dialkylamino, trialkylamino, or alkylideneamino groups.

$L^1$ is a bivalent radical containing from 3 to 9 methylene groups where any methylene group or groups may be replaced with one or more alkene, alkyne, aryl, or functional groups containing the heteroatoms selected from the group N, O, and S. Preferably, $L^1$ is a saturated or unsaturated, linear, branched, or cyclic bivalent radical separating Q from the 7 carbon of the benzodiazepinedione nucleus. Typically, the heteroatoms (N, O, and S) will comprise from 0-5 of the atoms separating Q from the benzodiazepinedione nucleus. Preferably, $L^1$ is typically an optionally substituted bivalent radical including; (A) $C_3$-$C_7$-alkylene, (B) $C_3$-$C_7$-cycloalkylene, (C) $C_3$-$C_7$-alkenylene, (D) $C_3$-$C_7$-alkadienylene, (E) $C_3$-$C_7$-alkynylene, (F) $C_4$-$C_7$-alkadiynylene, (G) $C_4$-$C_7$-alkenynylene, (H) $C_6$-$C_{14}$-arylene, (I) $C_6$-$C_{14}$-aryl-$C_2$-$C_4$-alkynylene, (J) $C_1$-$C_3$-alkyl-$C_6$-$C_{14}$-aryl-$C_2$-$C_4$-alkynylene, (K) $C_6$-$C_{14}$-aryl-$C_2$-$C_4$-alkenylene, (L) $C_1$-$C_3$-alkyl-$C_6$-$C_{14}$-arylene, (M) $C_1$-$C_3$-alkyl-$C_6$-$C_{14}$-aryl-$C_2$-$C_4$-alkenylene, (N) $C_6$-$C_{14}$-aryl-$C_1$-$C_3$-alkylene, (O) $C_6$-$C_{14}$-aryl-$C_1$-$C_3$-alkyloxyene, (P) $C_1$-$C_2$-alkyl-$C_6$-$C_{14}$-aryl-$C_1$-$C_2$-alkylene, (Q) $C_1$-$C_3$-alkyloxy-$C_6$-$C_{14}$-arylene, (R) $C_2$-$C_6$-alkyloxyene, (S) $C_1$-$C_5$-alkyloxy-$C_1$-$C_5$-alkylene, (T) $C_6$-$C_{10}$-aryloxyene, (U) $C_6$-$C_{10}$-aryloxy-$C_1$-$C_5$-alkylene, (V) $C_2$-$C_6$-alkylthioene, (W) $C_1$-$C_5$-alkylthio-$C_1$-$C_5$-alkylene, (X) $C_6$-$C_{10}$-arylthioene, (Y) $C_6$-$C_{10}$-arylthio-$C_1$-$C_5$-alkylene, (Z) $C_1$-$C_5$-alkylsulfoxide-$C_1$-$C_5$-alkylene, (AA) $C_1$-$C_5$-alkylsulfone-$C_1$-$C_5$-alkylene,

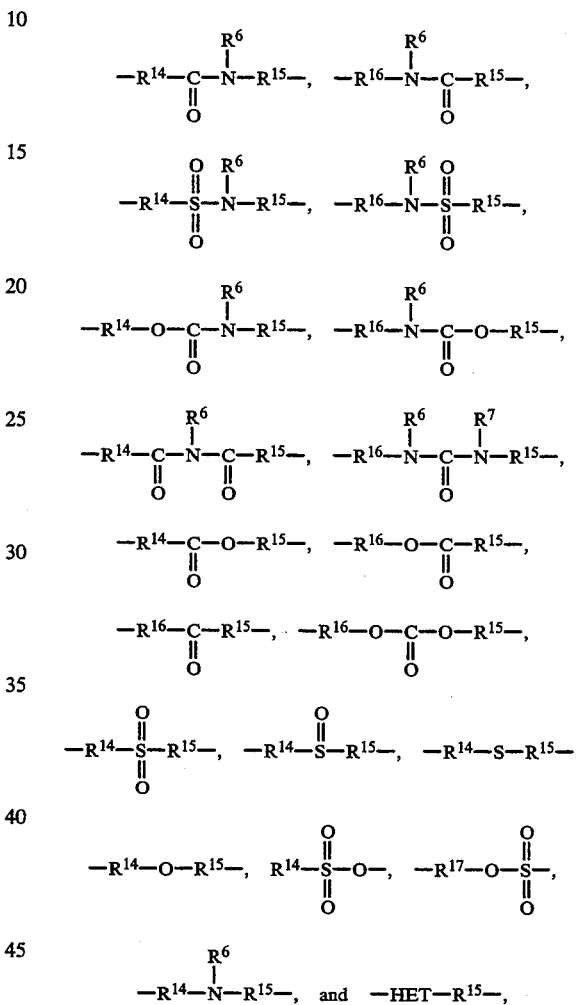

where (1) $R^{14}$ is selected from; (i) a chemical bond, (ii) $C_1$-$C_5$-alkylene, (iii) $C_3$-$C_7$-cycloalkylene, (iv) $C_2$-$C_5$-alkenylene, (v) $C_3$-$C_5$-alkynylene, (vi) $C_6$-$C_{10}$-arylene, (vii) $C_1$-$C_2$-alkyl-$C_6$-$C_{10}$-aryl-$C_1$-$C_2$-alkylene, (viii) $C_1$-$C_3$-alkyl-$C_6$-$C_{12}$-arylene, (ix) $C_6$-$C_{10}$-aryl-$C_1$-$C_2$-alkylene, (x) $C_6$-$C_{10}$-aryloxy-$C_1$-$C_2$-alkylene, and (xi) piperizinylene, (2) $R^{15}$ is selected from; (i) a chemical bond, (ii) $C_1$-$C_4$-alkylene, (iii) $C_2$-$C_4$-alkenylene, (iv) $C_2$-$C_4$-alkynylene, (v) $C_1$-$C_3$-alkyl-$C_6$-$C_{12}$-arylene, and (vi) $C_6$-$C_{10}$-arylene, (3) $R^{16}$ is selected from; (i) a chemical bond, (ii) $C_1$-$C_5$-alkylene, (iii) $C_3$-$C_7$-cycloalkylene, (iv) $C_3$-$C_5$-alkenylene, (v) $C_3$-$C_5$-alkynylene, (vi) $C_6$-$C_{10}$-arylene, (vii) $C_1$-$C_3$-alkyl-$C_6$-$C_{12}$-arylene, (viii) $C_6$-$C_{10}$-aryl-$C_1$-$C_2$-alkylene, and (ix) piperizinylene, (4) $R^{17}$ is selected from; (i) $C_3$-$C_4$-alkenylene, (ii) $C_3$-$C_4$-alkynylene, (iii) $C_6$-$C_{10}$-arylene, and (iv) benzylene, (5) HET is a saturated or unsaturated heterocycle having from 5-14 atoms in the cycle(s) and from 1-3 heteroatoms selected from N, O, and S, where the substituents are selected from one to three $R^{12}$.

$L^2$ is typically an optionally substituted bivalent radical including but not limited to;

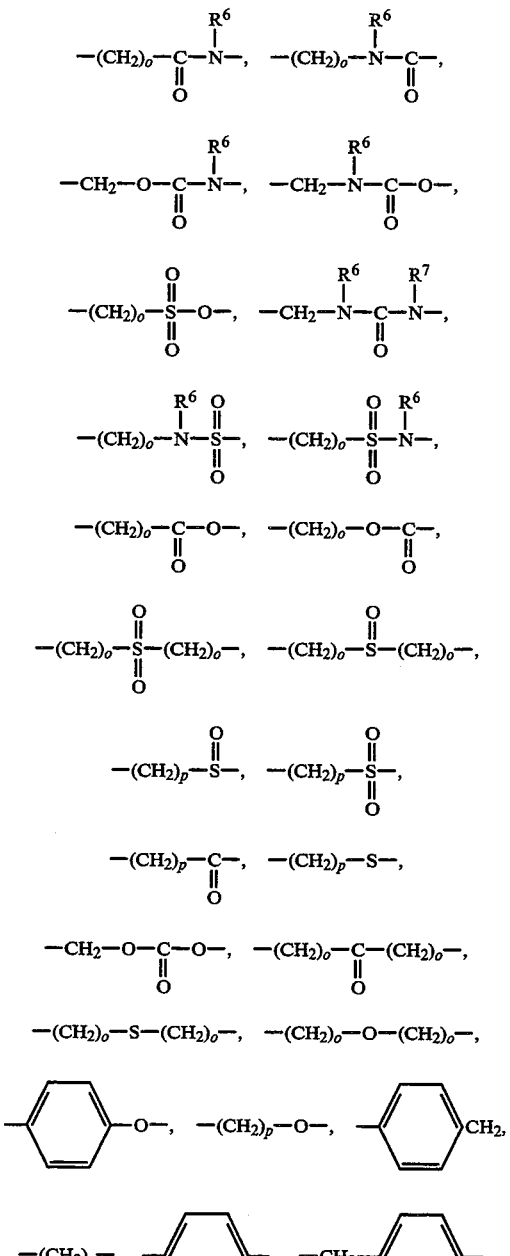

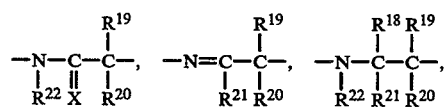

where; (1) p is 1, 2, 3 or 4, (2) $R^6$, $R^7$, o, and HET are defined above, and (3) the substituents are typically selected from one to three $R^{12}$.

T-U-G is selected from;

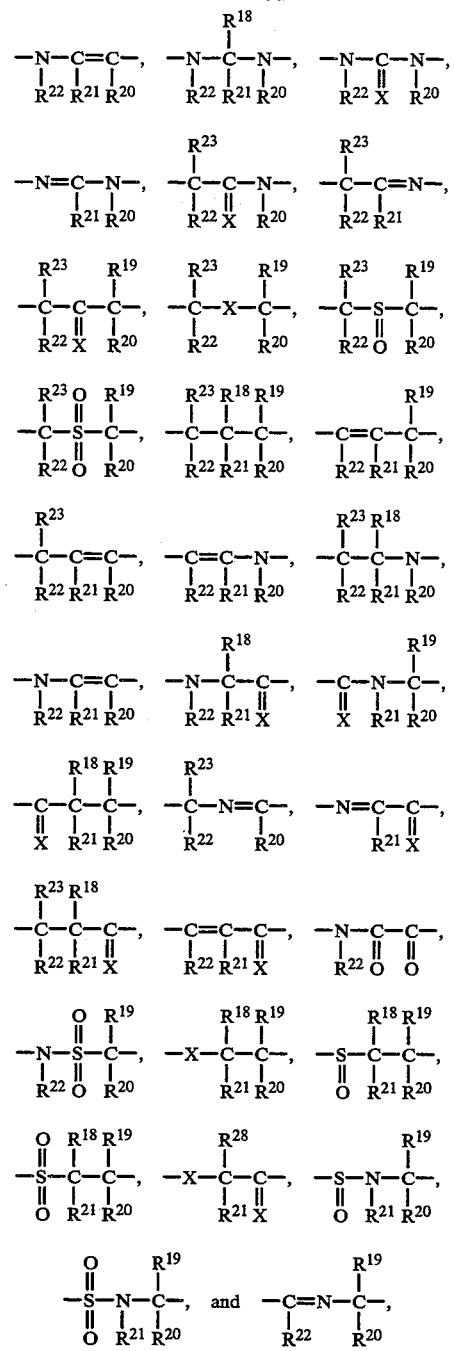

where; (1) X is defined above, (2) $R^{18}$, $R^{19}$, $R^{20}$, $R^{23}$, are typically selected from (i) hydrogen, (ii) optionally substituted $C_1$–$C_{12}$ alkyl, (iii) optionally substituted $C_3$–$C_{12}$ alkenyl, (iv) optionally substituted $C_3$–$C_{14}$ cycloalkyl, (v) optionally substituted $C_1$–$C_{12}$ alkyl-$C_6$–$C_{14}$ aryl, (vi) optionally substituted $C_6$–$C_{14}$ aryl, (vii) optionally substituted $C_1$–$C_4$ alkylphenyl, and (viii) optionally substituted $C_1$–$C_{12}$ alkoxy, (3) $R^{21}$ and $R^{22}$ are typically selected from (i) $Q^2$-$L^3$— where $Q^2$ is selected from hydrogen and $Q^1$, and $L^3$ is either a chemical bond, $L^1$ or $L^2$, (ii) optionally substituted $C_1$–$C_{12}$-alkyl, (iii) optionally substituted $C_6$–$C_{14}$-aryl, (iv) optionally substituted $C_3$–$C_{14}$-cycloalkyl, (v) optionally substituted $C_1$–$C_{12}$-alkyl-$C_6$–$C_{14}$ aryl, and (vi) optionally substituted $C_1$–$C_{12}$-alkyl-$C_3$–$C_{14}$-cycloalkyl, where the substituents are usually (a) halo (F, Cl, Br, I), (b) nitro, (c) hydroxy, (d) carboxy, (e) tetrazole, (f) hydroxamate, (g) sulfonamide, (h) trifluoroimide, (i) phosphonate, (j) $C_1$–$C_6$-alkyl, (k) $C_6$–$C_{14}$-aryl, (l) benzyl, (m) $C_3$–$C_{14}$-cycloalkyl, (n) $COR^{24}$ where $R^{24}$ is selected from $C_1$–$C_8$-alkoxy, $C_3$–$C_{12}$-alkenoxy, $C_6$–$C_{12}$-aryloxy, di-$C_1$14 $C_8$-alkylamino-$C_1$–$C_8$-alkoxy, acylamino-$C_1$–$C_8$-alkoxy selected from acetylaminoethoxy, nicotinoylaminoethoxy, succinamidoethoxy, and pivaloyloxyethoxy, and $C_6$–$C_{12}$-aryl-$C_1$–$C_8$-alkoxy where the aryl group is unsubstituted or substituted with one to three of the groups nitro, halo (F, Cl, Br, I), $C_1$–$C_4$-alkoxy, amino, hydroxy, hydroxy-$C_2$–$C_8$-alkoxy, and dihydroxy-$C_3$–$C_8$-alkoxy, and (o) $CONR^{25}R^{26}$ where $R^{25}$ and $R^{26}$ are typically selected from hydrogen, $C_1$–$C_{10}$-alkyl, $C_3$–$C_{10}$-alkenyl, $C_6$–$C_{14}$-aryl, $C_1$–$C_6$-alkyl-$C_6$–$C_{10}$-aryl. Optionally, $R^{25}$ and $R^{26}$ taken together may form trimethylene, tetramethylene, pentamethylene, and 3-oxopentamethylene. Also, optionally, $R^1$ and $R^{22}$ taken together may form an optionally substituted 5, 6, or 7 member saturated or unsaturated homocyclic or heterocyclic ring containing 0–3 heteroatoms selected from O, S, and N, where the substituents are selected from $R^{21}$.

D is typically (A) $R^{21}$, or (B) —(C=O)—Xaa, where Xaa is one to three D or L α-amino acid residues.

W is typically selected from;

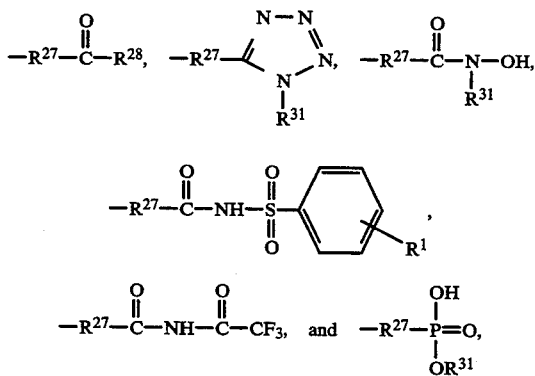

where (1) $R^{27}$ is selected from (i) a chemical bond, (ii) methylene, and (iii) ethylene, (2) $R^{28}$ is selected from the group consisting of (i) hydroxy, (ii) $C_1$–$C_8$-alkoxy, (iii) $C_3$–$C_{12}$-alkenoxy, (iv) $C_6$–$C_{12}$-aryloxy, (v) $C_1$–$C_6$-alkyl-$C_6$–$C_{12}$-aryloxy, (vi) di-$C_1$–$C_8$-alkylamino-$C_1$–$C_8$-alkoxy, (vii) acylamino-$C_1$–$C_8$-alkoxy selected from the group (a) acetylaminoethoxy, (b) nicotinoylaminoethoxy, and (c) succinamidoethoxy, (viii) $C_1$–$C_8$-alkoyloxy-$C_1$–$C_8$-alkoxy, (ix) $C_6$–$C_{12}$-aryl-$C_1$–$C_8$-alkoxy where the aryl group is unsubstituted or substituted with one to three of the groups (a) nitro, (b) halo (F, Cl, Br, I), (c) $C_1$–$C_4$-alkoxy, and (d) amino, (x) hydroxy-$C_2$–$C_8$-alkoxy, (xi) dihydroxy-$C_3$–$C_8$-alkoxy, and (xii) $NR^{29}R^{30}$ where $R^{29}$ and $R^{30}$ are independently selected from the group (a) hydrogen, (b) $C_1$–$C_8$-alkyl, (c) $C_3$–$C_8$-alkenyl, (d) $C_6$–$C_{12}$-aryl where the aryl group is unsubstituted or substituted with one to three of the groups nitro, halo (F, Cl, Br, I), $C_1$–$C_4$-alkoxy, and amino, and (e) $C_6$–$C_{12}$-aryl-$C_1$–$C_8$-alkyl where the aryl group is unsubstituted or substituted with one to three of the groups nitro, halo (F, Cl, Br, I), and $C_1$–$C_4$-alkoxy (3) $R^{31}$ is typically selected from (i) hydrogen, (ii) phenyl, (iii) $C_1$–$C_4$-alkyl, and (iv) halo(F, Cl, Br, I)-$C_1$–$C_4$-alkyl.

The invention further provides a pharmaceutical composition comprising a pharmaceutically acceptable excipient and/or pharmaceutically acceptable hydrates, solvates, and salts of I.

The invention provides a method for inhibiting platelet aggregation or reducing platelet aggregation in a mammal comprising administering a platelet aggregation inhibiting amount of the pharmaceutical composition of I. Optionally, the method includes administering the pharmaceutical composition in combination with a peptidyl antithrombotic and/or a thrombolytic agent and/or an anticoagulant.

DETAILED DESCRIPTION OF THE INVENTION

A. Definitions

Terms used in the claims and specification are defined as set forth below unless otherwise specified.

As used herein, the term "positively charged" when used to describe the moiety Q (either $Q^1$ or $Q^2$) means at least 10% of the Q groups are positively charged at physiological pH. This will normally mean that the $pK_b$ of the nitrogen containing moiety will be about 6.9 or higher.

The term "alkyl" means a branched or unbranched, saturated aliphatic hydrocarbon radical, having the number of carbon atoms specified, or if no number is specified, having up to 12 carbon atoms. Examples of alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like. The terms "lower alkyl" and "alkyl of 1 to 6 carbon atoms" are synonymous and used interchangeably.

The term "cycloalkyl" as used herein refers to a mono-, bi-, or tricyclic aliphatic ring having 3 to 14 carbon atoms and preferably 3 to 7 carbon atoms.

The term "alkenyl" means a branched or unbranched hydrocarbon radical having the number of carbon atoms designated containing one or more carbon-carbon double bonds, each double bond being independently cis, trans, or a nongeometric isomer.

The term "alkynyl" means a branched or unbranched hydrocarbon radical having the number of carbon atoms designated containing one or more carbon-carbon triple bonds, The term "aryl" when used alone means a homocyclic aromatic radical whether or not fused having the number of carbon atoms designated. Preferred aryl groups include phenyl, napthyl, biphenyl, phenanthrenyl, naphthacenyl, and the like (see e.g. *Lang's Handbook of Chemistry* (Dean, J. A., ed) 13*th* ed. Table 7-2 [1985]).

The term "arylalkyl" means one, two, or three aryl groups having the number of carbon atoms designated, appended to an alkyl radical having the number of carbon atoms designated including but not limited to; benzyl, napthylmethyl, phenethyl, benzyhydryl (diphenylmethyl), trityl, and the like.

Unless otherwise specified, the terms "heterocyclic group" or "heterocyclic" or "HET" or "heterocyclyl" are used interchangeably as used herein refer to any mono-, bi-, or tricyclic saturated, unsaturated, or aromatic ring having the number of atoms designated where at least one ring is a 5-, 6- or 7-membered ring containing from one to three heteroatoms selected from the group nitrogen, oxygen, and sulfur provided that at least one heteroatom is nitrogen (*Lang's Handbook of Chemistry*, supra). Typically, the 5-membered ring has 0 to 2 double bonds and the 6-or 7-membered ring has 0 to 3 double bonds and the nitrogen or sulfur heteroatoms may optionally be oxidized, and any nitrogen heteroatom may optionally be quarternized. Included in the definition are any bicyclic groups where any of the above heterocyclic rings are fused to a benzene ring. Heterocyclics in which nitrogen is the heteroatom are preferred.

Bivalent radicals L (either $L^1$, $L^2$, or $L^2$) whether branched or unbranched, derived from alkanes, alkenes, alkadienes, alkynes, alkadiynes, and arenes optionally containing O, N and/or S atoms, or homo- and heterocycles either aromatic or aliphatic, are designated by adding the suffix "ene" to the corresponding monovalent radical. Atoms bearing the free valences may include any C, O, N or S.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, maloneic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" as used here means a pharmacologically inactive derivative of a parent drug molecule that requires biotransformation, either spontaneous or enzymatic, within the organism to release the active drug.

B. Utility

The present invention is the result of the unexpected discovery that substituted fused 7-membered "lactam" ring compounds defined by formula I, especially including 3,4-dihydro-1H-1,4-benzodiazepine-2,5-diones (referred to hereafter as substituted benzodiazepinediones) are capable of inhibiting both platelet aggregation and binding of fibrinogen to the platelet receptor $GPII_bIII_a$ at concentrations comparable to many of the more potent antiaggregatory peptides of the prior art (see eg Ali et al. EP 341 915). Thus the compounds described in the present invention inhibit the binding of fibrinogen to its receptor on platelets, $GPII_bIII_a$, and thus prevent the aggregation of platelets and the formation of platelet plugs, emboli and thrombi in the circulatory system in mammals. Thromboembolic disorders have been shown to be directly related to the susceptibility of blood platelets to aggregate. Mammals exposed to medical procedures such as angioplasty and thrombolytic therapy are particularly susceptible to thrombus formation. The compounds of the present invention can be used to inhibit thrombus formation following angioplasty. They may also be used in combination with antithrombolytic agents such as tissue plasminogen activator and its derivatives (U.S. Pat. Nos. 4,752,603; 4,766,075; 4,777,043; EP 199,574; EP 0238,304; EP 228,862; EP 297,860; PCT WO89/04368; PCT WO89/00197), streptokinase and its derivatives, or urokinase and its derivatives to prevent arterial reocclusion following thrombolytic therapy. When used in combination with the above thrombolytic agents, the compounds of the present invention may be administered prior to, simultaneously with, or subsequent to the antithrombolytic agent. Mammals exposed to renal dialysis, blood oxygenation, cardiac catheterization and similar medical procedures as well as mammals fitted with certain prosthetic devices are also susceptible to thromboembolic disorders. Physiologic conditions, with or without known cause may also lead to thromboembolic disorders. Thus, the compounds described herein are useful in treating thromboembolic disorders in mammals. The compounds described herein may also be used as adjuncts to anticoagulant therapy, for example in combination with aspirin, heparin or warfarin and other anticoagulant agents. The application of the compounds described herein for these and related disorders will be apparent to those skilled in the art.

Compounds of this invention are also useful as intermediates generally, or as precursors of inhibitors to $GPII_bIII_a$ or other integrin receptors and thus in addition to treating cardiovascular disease, these compounds may be usefully employed in metastatic disease and bone disorders such as osteoporosis.

C. Preferred Embodiments

1. Nonpeptidyl $GPII_bIII_a$ Inhibitors

One embodiment of the invention comprises a compound represented by formula I capable of inhibiting binding of the platelet $GPII_bIII_a$ receptor to its native in vivo ligands. Prefered nonpeptidyl inhibitors include compounds represented by structural formulae II–VI:

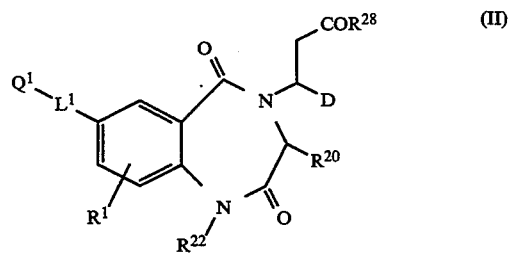

(II)

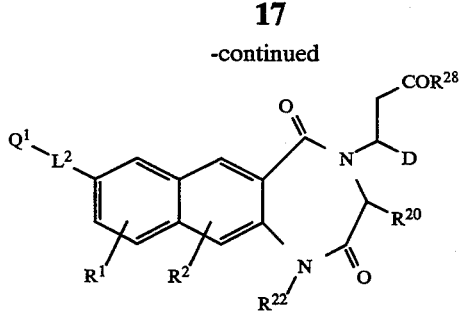

(III)

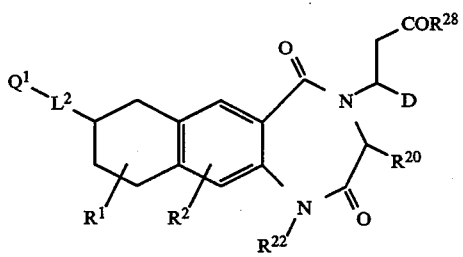

(IV)

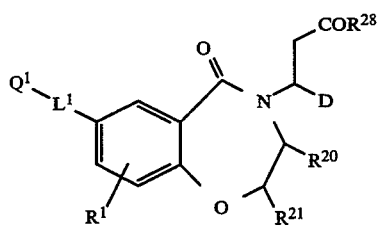

(V)

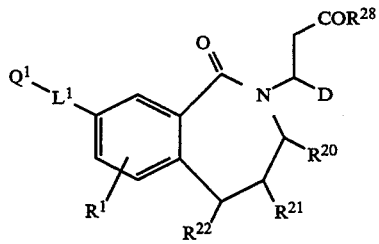

(VI)

where $R^1$, $R^2$, $R^{20}$, $R^{21}$, $R^{22}$, $R^{28}$, $Q^1$, $L^1$ and $L^2$ are defined above.

Refering to formulae I-VI the following structural features of the instant nonpeptidyl antithrombotic inhibitors can be identified:

a. The positively charged Q moiety;
b. The linking moiety L;
c. The flat (usually aromatic) ring A;
d. The 7-member "lactam" ring;
e. Substituents of T U G especially $R^{22}$;
f. The amino acid linking moiety D; and
g. The negitively charged moiety W.

a. Positively charged Q

Suitable groups Q (either $Q^1$ or $Q^2$) contain one or more nitrogen atoms and have a $pK_b$ sufficiently high so that they are at least 10% positively charged at physiological pH. Q may be one or more primary, secondary, tertiary, or quartinary amines or imines either isolated or conjugated with other nitrogen atoms to form groups including but not limited to; aminomethyleneimino, amidino, and guanidino groups and multiples thereof. Alternatively, Q may be a saturated or unsaturated (including aromatic) heterocyclic group provided the group bears a positive charge at physiological pH. In one embodiment of the invention, Q is preferably selected from; amino ($H_2N-$), imino ($=NH$), amidino ($H_2NC(=NH)-$), aminomethyleneamino ($H_2N-CH=N-$), iminomethylamino ($HN=CH-NH-$), guanidino ($H_2N-C(=NH)-NH-$), $N^G$-aminoguanidino ($H_2N-HN-C(=NH)-NH-$), alkylamino ($R^1NH-$), dialkylamino ($R^1_2N-$), trialkylamino ($R^1_3N-$), alkylideneamino ($R^1_2C=N-$), pyranyl, pyrrolyl, imadazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, B-carbolinyl, phenanthridinyl, acridinyl, perimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, and 1,3-diazacyclohex-4-ene, where $R^1$ is selected from; hydrogen, $C_1$-$C_6$-alkyl, $C_6$-$C_{10}$-aryl, and $C_3$-$C_{10}$-cycloalkyl. Optionally, any of the nitrogen containing heterocycles described above may be substituted with amino, imino, amidino, aminomethyleneamino, iminomethylamino, guanidino, $N^G$-aminoguanidino, alkylamino, dialkylamino, trialkylamino, or alkylideneamino groups.

Exemplary prefered $Q^1$ groups include the following:

(A) Amino and ammonio groups;

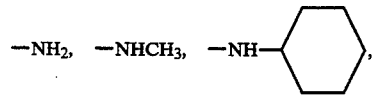

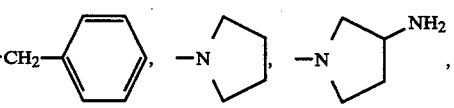

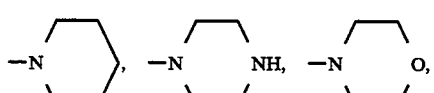

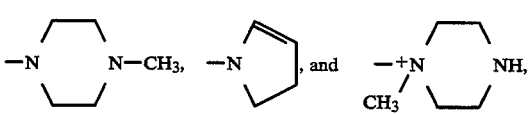

(B) Amidino groups;

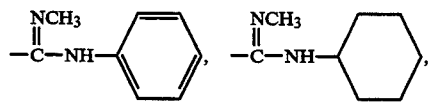

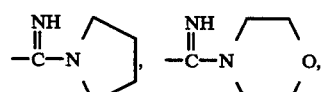

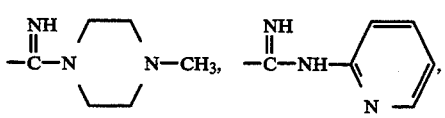

-continued
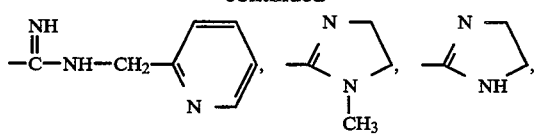
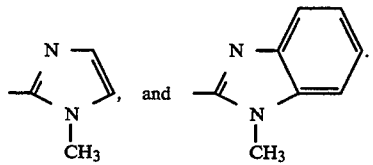
(C) Aminoalkyleneimino groups;
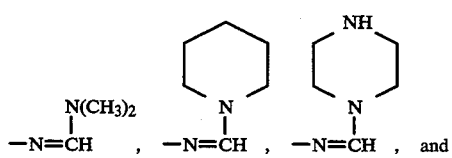
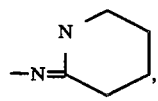
(D) Iminoalkyleneamino groups;
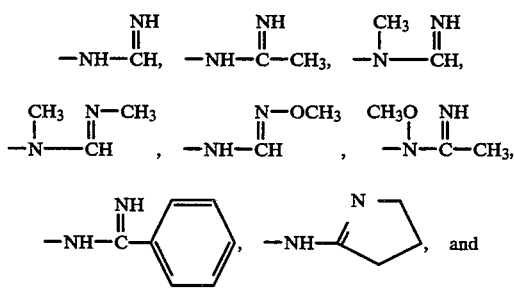
(E) Guanidino groups;
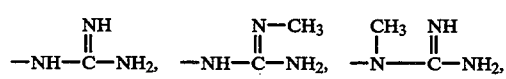
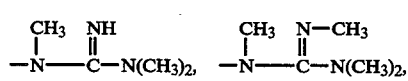
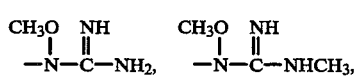
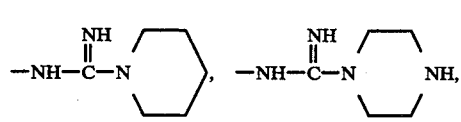
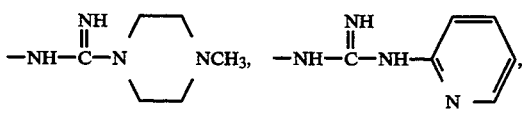
-continued
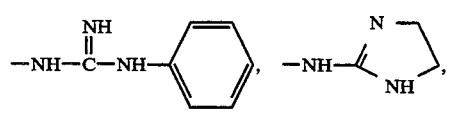
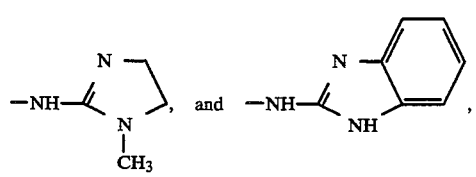
(F) Saturated heterocyclic groups;
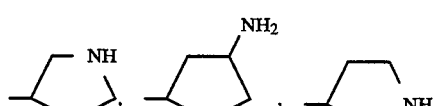
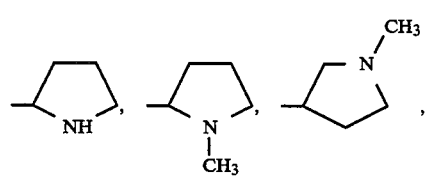
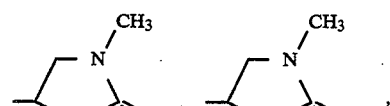
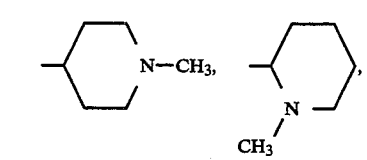
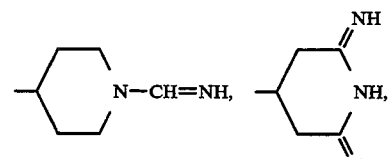
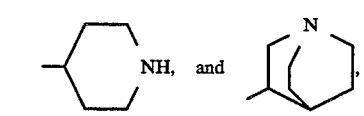
(G) Unsaturated (nonaromatic) heterocyclic groups;
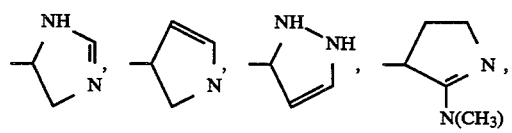
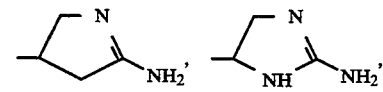

(H) Unsaturated aromatic heterocyclic groups:

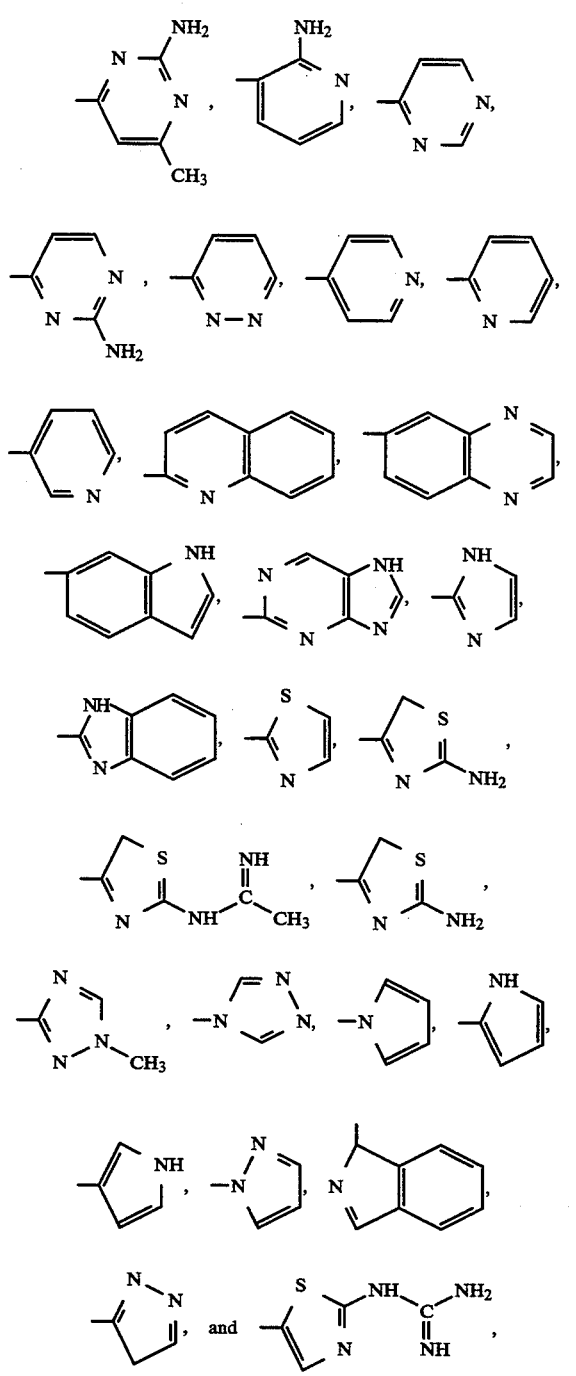

(I) Bicycloheterocyclic groups;

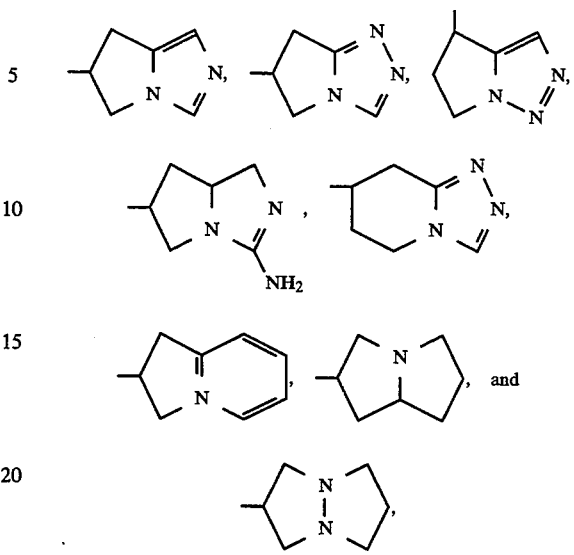

(J) Multiple amino, guanidino, and amidino groups;

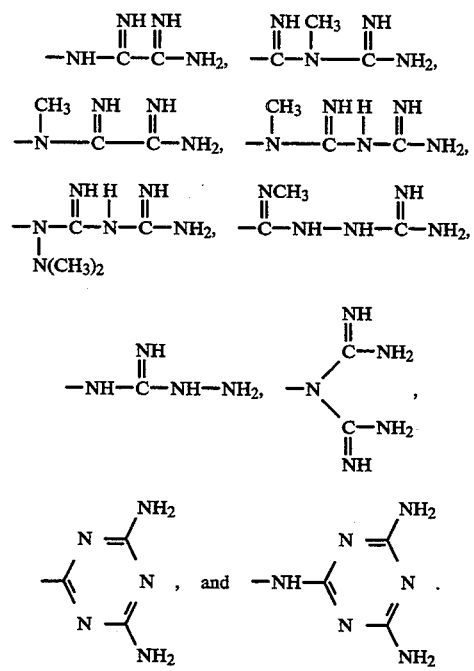

Most prefered Q groups are amino, amidino, and guanidino groups.

b. The linking group L

The length of the bivalent radical L appears to be important to biological activity. By length is meant the distance between the A ring and the first charge bearing N of substituent Q. For example, when the A moiety is a 5 or 6-member ring [e.g. the benzene moiety of the benzodiazepinedione nucleus (carbon 7 of Formula II)], suitable lengths for bivalent radical $L^1$ range from about 3 to about 9 methylene equivalents. $L^1$ is therefore a bivalent radical containing from 3 to 9 methylene groups connecting Q to the number 7 carbon of the benzodiazepinedione nucleus (or an equivalent position on other 5 or 6-member A rings) where any methylene group or groups may be replaced with one or more or a combination of; alkene, alkyne, aryl, heterocycle or a functional group or groups containing the heteroatoms N, O, and S, so long as the overall length is equivalent to from 3 to 9 methylene groups. These functional groups include one or more of the following:

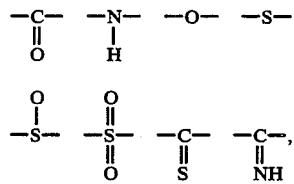

and may be isolated within the linker (e.g. forming ethers, thioethers, ketones, sulfoxides and the like) or combined in any combination, provided only that the compounds so produced are stable in aqueous solution and do not exceed the above stated length requirements. For example, combining these functional groups produces esters, amides, ureidos, carbamates, carbonates, sulfonamides, sulfoxides, sulfones, and the like. Preferred lengths for $L^1$ are from 4 to 6 while most preferred lengths are about 5 methylene equivalents. In counting atoms comprising $L^1$, only those atoms sequentially linking Q with ring A are counted except when a homo- or heterocycle comprises $L^1$ in which case the fewest number of atoms separating these moieties are counted. Furthermore, given that a bivalent radical is of appropriate length, it is preferred that it be somewhat rigid, that is, contain one or more $sp^2$ or sp atoms.

In the description that follows, the free valence to the left of the page is bonded to Q, while the free valence to the right is bonded to carbon 7 of the compound of formula II (or an equivalent position on other 5 or 6-member A rings) Preferred $L^1$'s are selected from substituted or unsubstituted; $C_3$–$C_7$-alkylene, $C_3$–$C_7$-cycloalkylene, $C_3$–$C_7$-alkenylene, $C_4$–$C_7$-cycloalkenylene, $C_5$–$C_8$-cycloalkadienylene, $C_3$–$C_7$-alkadienylene, $C_3$–$C_7$-alkynylene, $C_4$–$C_7$-alkenynylene, $C_6$–$C_{14}$-arylene, $C_6$–$C_{14}$-aryl-$C_2$–$C_4$-alkynylene, $C_1$–$C_3$-alkyl-$C_6$-$C_{14}$-aryl-$C_2$–$C_4$-alkynylene, $C_6$–$C_{14}$-aryl-$C_2$–$C_4$-alkenylene, $C_1$–$C_3$alkyl-$C_6$–$C_{14}$-arylene, $C_1$–$C_3$-alkyl-$C_6$–$C_{14}$-aryl-$C_2$–$C_4$-alkenylene, $C_6$–$C_{14}$-aryl-$C_1$–$C_3$-alkylene, $C_6$–$C_{14}$-aryl-$C_1$–$C_3$-alkyloxyene, $C_1$–$C_3$alkyl-$C_6$–$C_{14}$-aryl-$C_1$–$C_2$-alkylene, $C_1$–$C_3$-alkyloxy-$C_6$–$C_{14}$-arylene, $C_2$–$C_8$-alkyloxyene, $C_1$–$C_5$-alkyloxy-$C_1$–$C_5$-alkylene, $C_6$–$C_{10}$-aryloxyene, $C_6$–$C_{10}$-aryloxy-$C_1$–$C_5$-alkylene, $C_6$–$C_{10}$-arylthio-$C_1$–$C_5$-alkylene,

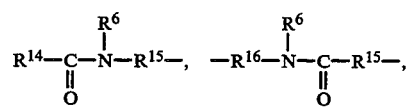

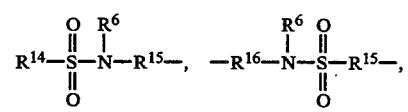

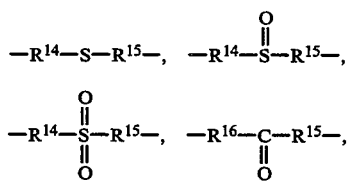

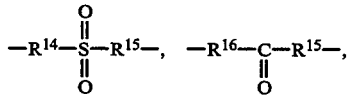

-continued

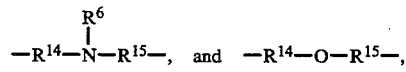

where $R^{14}$ is selected from; a chemical bond, $C_1$–$C_8$-alkyl, $C_3$–$C_7$-cycloalkyl $C_2$–$C_5$-alkenyl, $C_3$–$C_5$-alkynyl, $C_6$–$C_{10}$-aryl, $C_1$–$C_3$-alkyl-$C_6$–$C_{12}$-aryl, $C_1$–$C_2$-alkyl-$C_6$–$C_{10}$-aryl-$C_1$–$C_2$-alkyl, $C_6$–$C_{10}$-aryl-$C_1$–$C_2$-alkyl, and $C_6$–$C_{10}$-aryloxy-$C_1$–$C_2$-alkyl. $R^{15}$ is selected from; a chemical bond, $C_1$–$C_4$-alkyl, $C_2$–$C_4$-alkenyl, $C_2$–$C_4$-alkynyl, $C_6$–$C_{10}$-aryl, and $C_1$–$C_3$-alkyl-$C_6$–$C_{12}$-aryl. $R^{16}$ is selected from; a chemical bond, $C_1$–$C_5$-alkyl, $C_3$–$C_7$-cycloalkyl $C_3$–$C_5$-alkenyl, $C_3$–$C_5$-alkynyl, $C_6$–$C_{10}$-aryl, $C_1$–$C_3$alkyl-$C_6$–$C_{12}$-aryl, and $C_6$–$C_{10}$-aryl-$C_1$–$C_2$-alkyl. The substituents are preferably selected from one to three $R^{12}$ defined above.

More preferred bivalent radicals $L^1$ are selected from the following groups:

Group 1

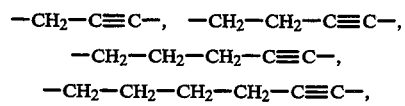

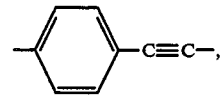

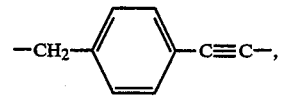

Group 2

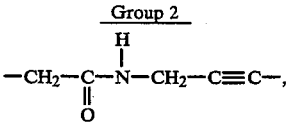

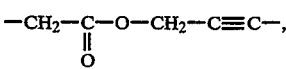

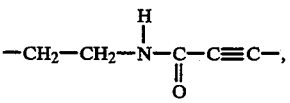

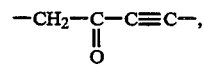

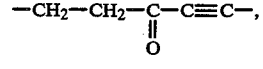

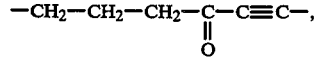

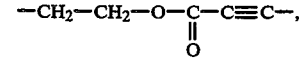

-continued
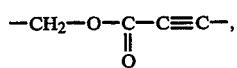
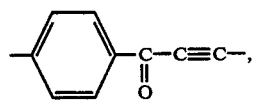
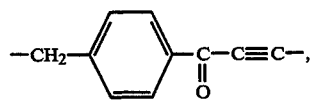
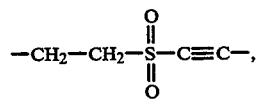
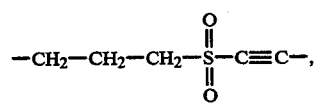
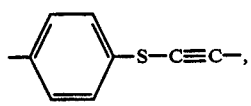
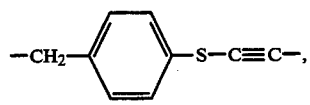
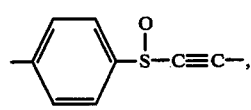
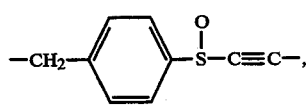
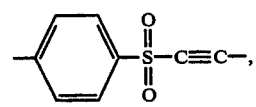
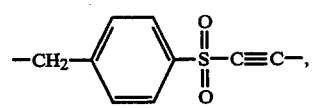
Group 3
—CH₂—CH₂—CH₂—,
—CH₂—CH₂—CH₂—CH₂—,
—CH₂—CH₂—CH₂—CH₂—CH₂—,
—CH₂—CH₂—CH₂—CH₂—CH₂—CH₂—,
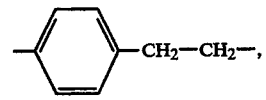
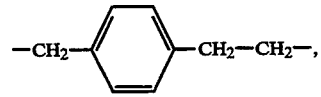
Group 4
-continued
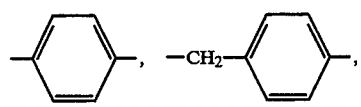
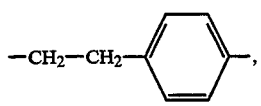
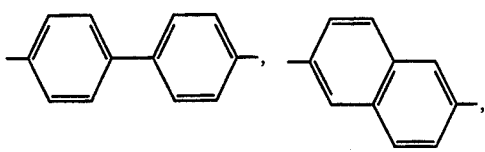
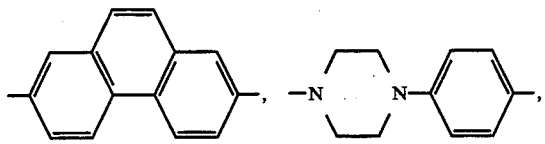
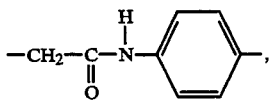
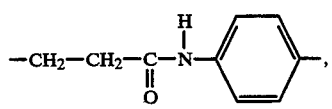
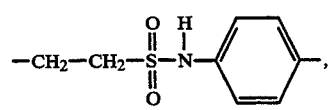
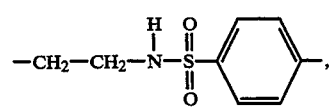
Group 5
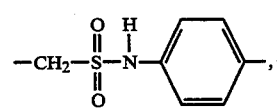
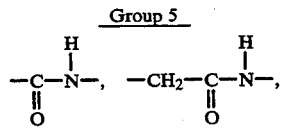
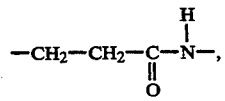
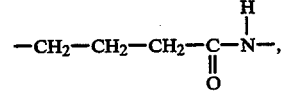
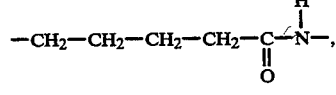

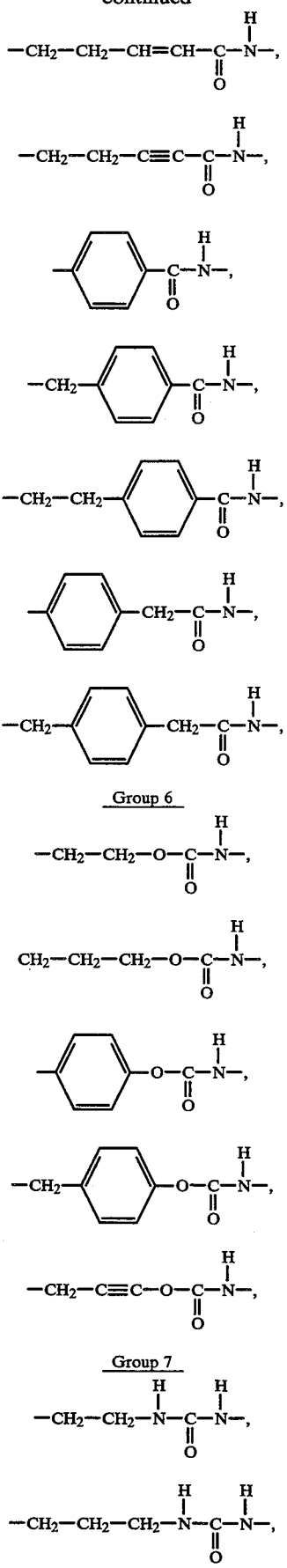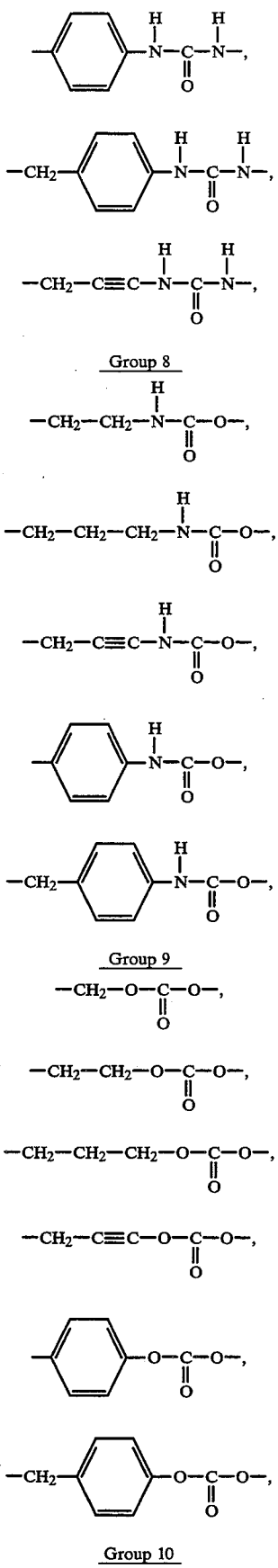

-CH₂-CH₂-NHC(O)-,

-CH₂-CH₂-CH₂-NHC(O)-,

-CH₂-CH₂-CH₂-CH₂-NHC(O)-,

-CH₂-CH=CH-CH₂-NHC(O)-,

-CH₂-C≡C-CH₂-NHC(O)-,

-C₆H₄-NHC(O)-,

-CH₂-C₆H₄-NHC(O)-,

-CH₂-CH₂-C₆H₄-NHC(O)-,

-C₆H₄-CH₂-NHC(O)-,

-CH₂-C₆H₄-CH₂-NHC(O)-,

Group 11

-CH₂-CH₂-O-C(O)-,

-CH₂-CH₂-CH₂-O-C(O)-,

-CH₂-CH=CH-CH₂-O-C(O)-,

-CH₂-C≡C-CH₂-O-C(O)-,

-C₆H₄-O-C(O)-,

-CH₂-C₆H₄-O-C(O)-,

-C₆H₄-CH₂-O-C(O)-,

-CH₂-C₆H₄-CH₂-O-C(O)-,

Group 12

-CH₂-CH₂-O-,   -CH₂-CH₂-CH₂-O-,

-C₆H₄-CH₂-O-,   -C₆H₄-CH₂-CH₂-O-,

-CH₂-C₆H₄-CH₂-O-,   -C₆H₄-O-,

-CH₂-C₆H₄-O-,   -CH₂-CH₂-C₆H₄-O-,

Group 13

-NH-S(O)₂-,   -C₆H₁₀-NH-S(O)₂-,

-C₆H₄-NH-S(O)₂-,   -CH₂-C₆H₁₀-NH-S(O)₂-,

-CH₂-C₆H₄-NH-S(O)₂-,   -NC₅H₉-NH-S(O)₂-,

-CH₂-NH-S(O)₂-,   -C₅H₈-NH-S(O)₂-,

-CH₂-CH₂-NH-S(O)₂-,   -CH₂-C≡C-CH₂-NH-S(O)₂-,

-CH₂-CH₂-CH₂-NH-S(O)₂-,

-CH₂-CH₂-CH₂-CH₂-NH-S(O)₂-,

Group 14

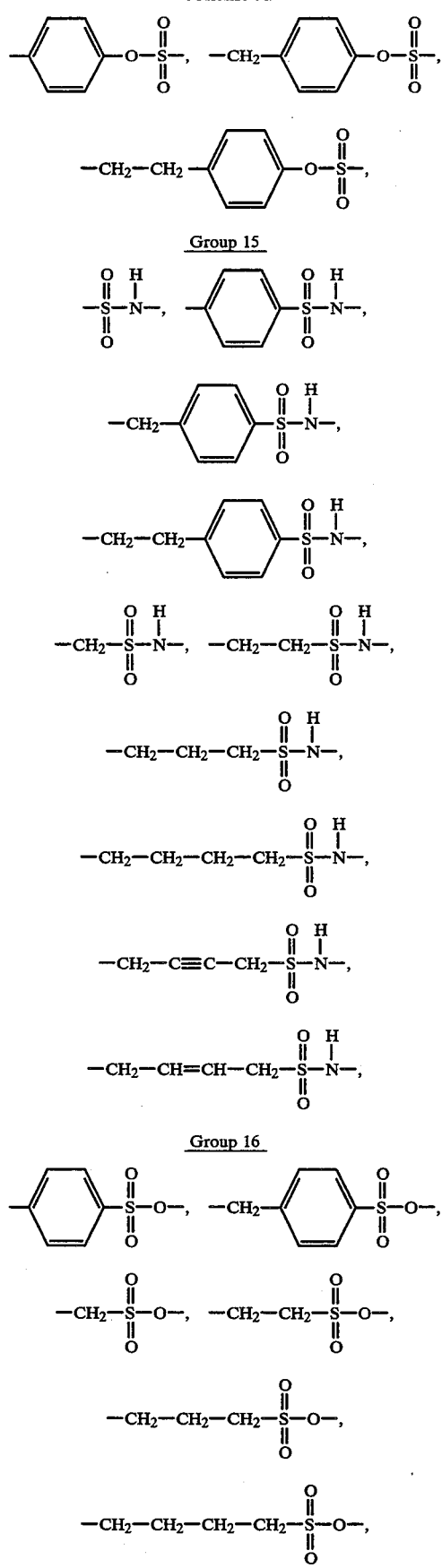
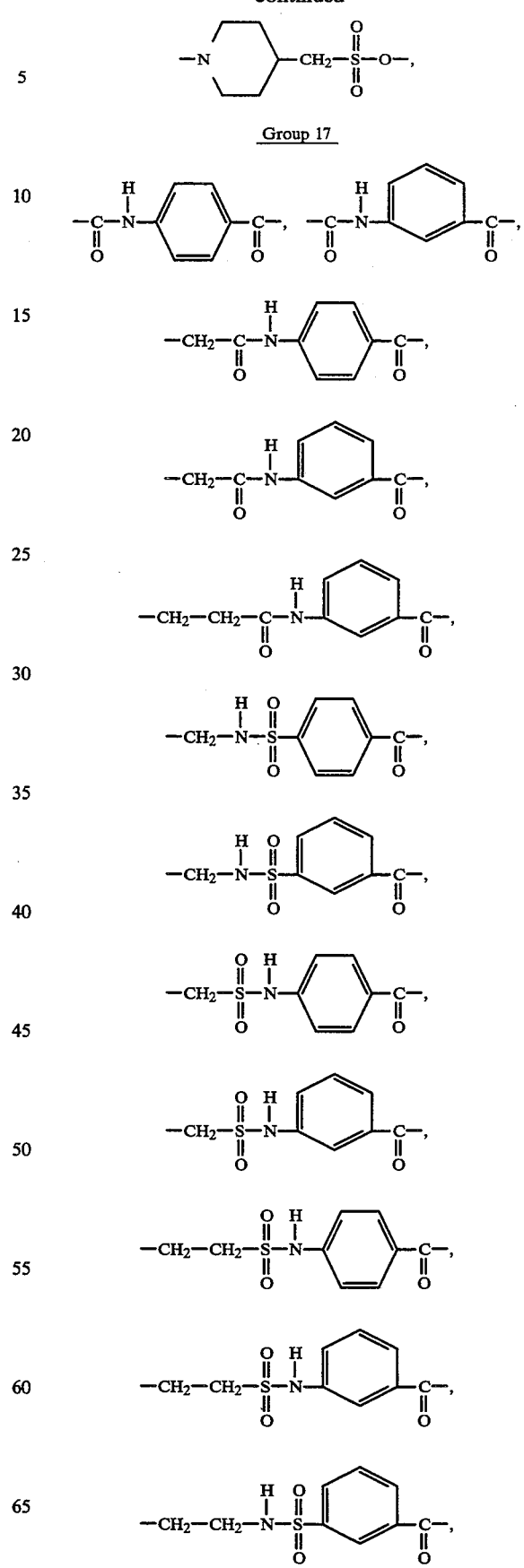

-continued

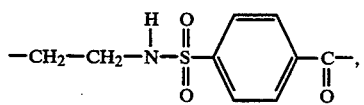

Group 18

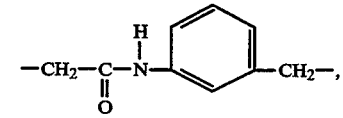

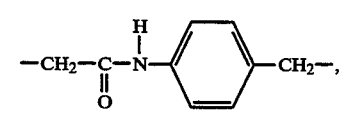

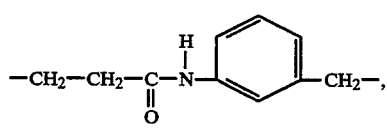

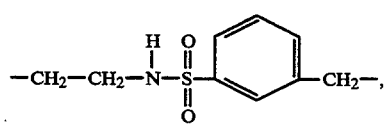

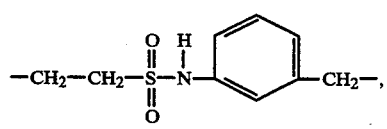

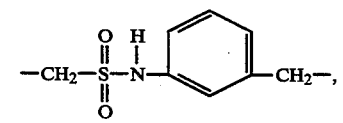

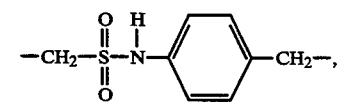

Most prefered $L^1$'s are selected from;

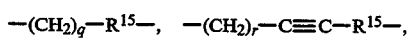

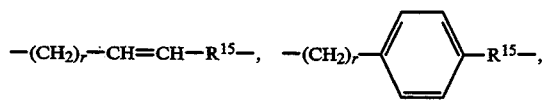

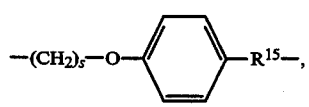

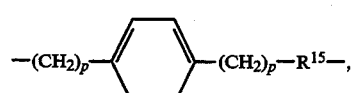

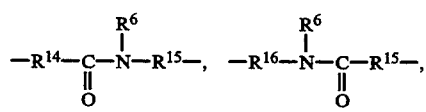

-continued

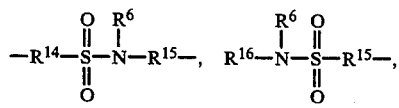

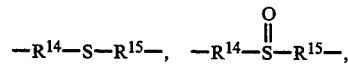

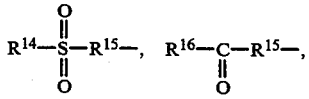

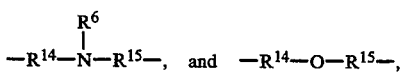

where p is 1, 2, 3, or 4; q is 3, 4, 5, 6 or 7; r is 1, 2, 3, 4, or 5; s is 2 or 3. $R^{14}$ is selected from; a chemical bond, $C_1$-$C_5$-alkyl, $C_3$-$C_7$-cycloalkyl, $C_2$-$C_5$-alkenyl, $C_3$-$C_5$-alkynyl, $C_6$-$C_{10}$-aryl, $C_1$-$C_2$-alkyl-$C_6$-$C_{12}$-aryl, $C_1$-$C_2$-alkyl-$C_6$-$C_{10}$-aryl-$C_1$-$C_2$-alkyl, $C_6$-$C_{10}$-aryl-$C_1$-$C_2$-alkyl, $C_6$-$C_{10}$-aryloxy-$C_1$-$C_2$-alkyl, and piperizinyl. $R^{15}$ is a chemical bond connecting $L^1$ to position 7 of the benzodiazepinedione. $R^{16}$ is selected from; $C_1$-$C_5$-alkyl, $C_3$-$C_7$-cycloalkyl, $C_3$-$C_5$-alkenyl, $C_3$-$C_5$-alkynyl, $C_6$-$C_{10}$-aryl, $C_1$-$C_3$-alkyl-$C_6$-$C_{12}$-aryl, $C_6$-$C_{10}$-aryl-$C_1$-$C_2$-alkyl, and piperizinyl. For the foregoing most prefered $L^1$'s $R^{14}$ and $R^{16}$ bond $L^1$ to $Q^1$.

Most prefered $Q^1$-$L^1$— combinations are selected from;

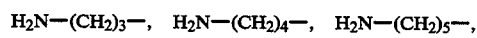

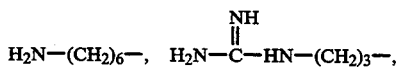

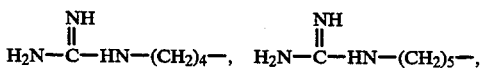

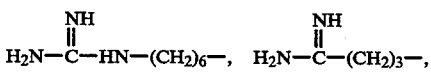

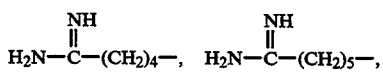

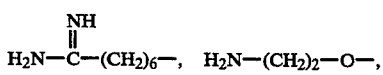

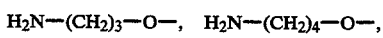

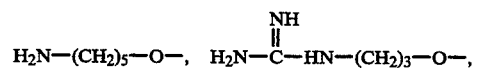

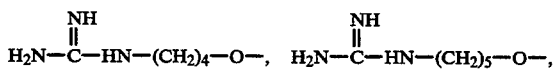

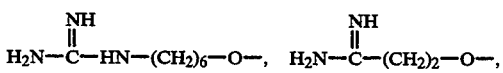

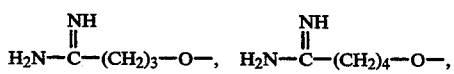

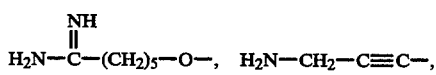

-continued
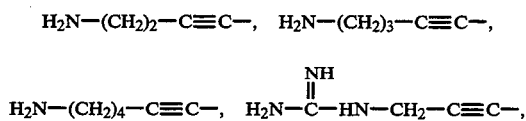
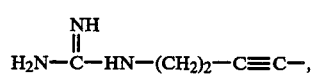
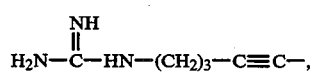
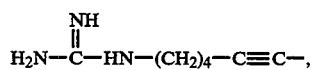
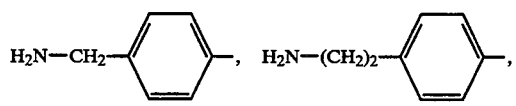
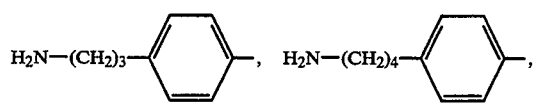
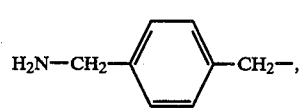
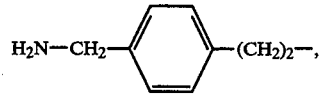
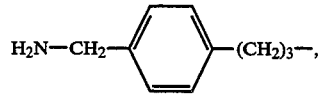
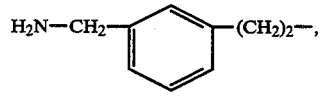
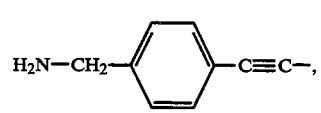
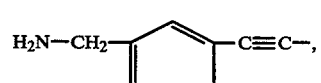
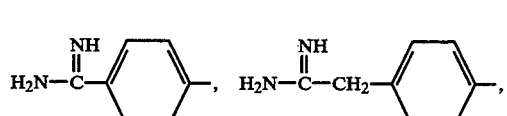
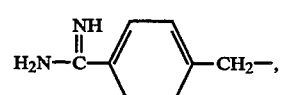
-continued
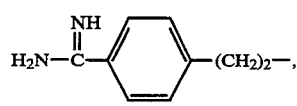
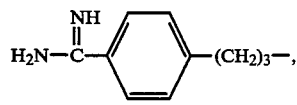
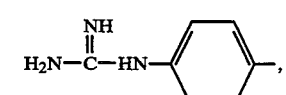
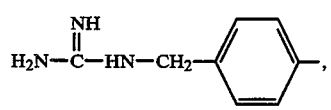
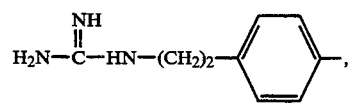
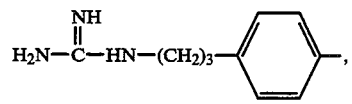
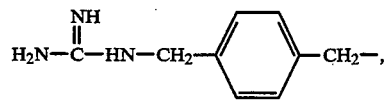
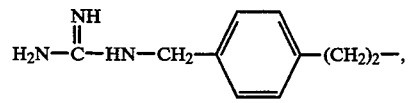
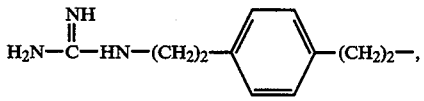
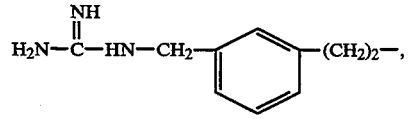
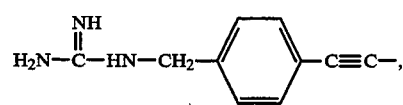
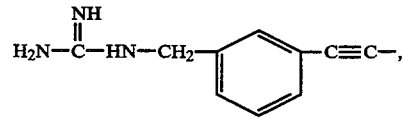
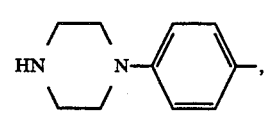

-continued
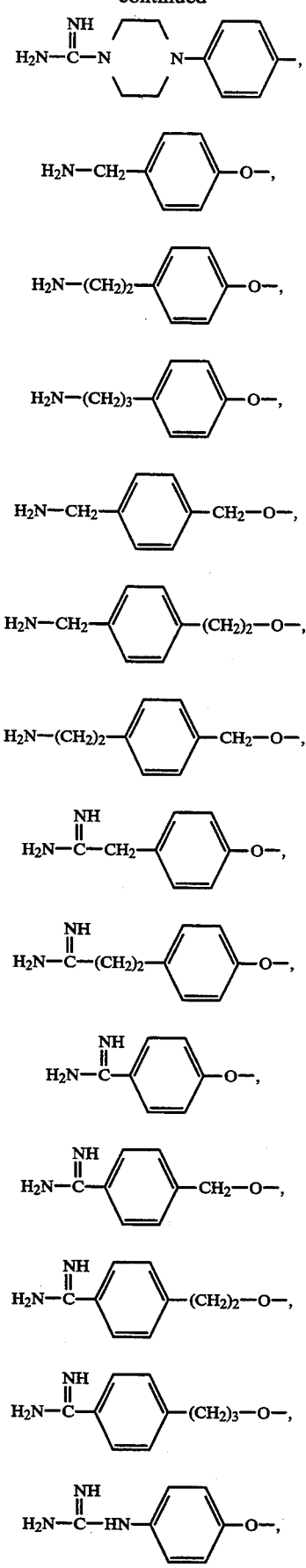
-continued
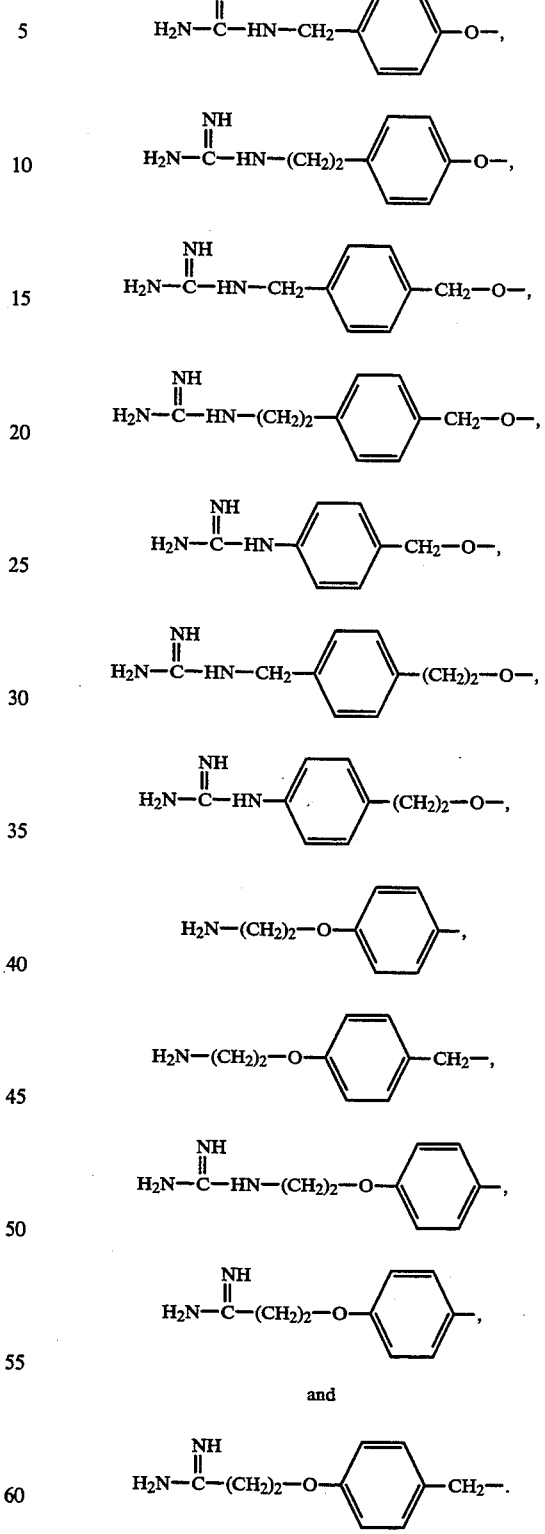
and
The length of the bivalent radical $L^2$ is also important to biological activity. Here, when the A moiety is a 10-member fused ring [e.g. the napthalene moiety of the napthadiazepinedione nucleus (carbon 8 of Formula III)], suitable lengths for bivalent radical $L^2$ range from about 1 to about 7 methylene equivalents. $L^2$ is therefore a bivalent radical containing from 1 to 7 methylene groups connecting $Q^1$ to the number 8 carbon of the napthadiazepinedione nucleus (or an equivalent position on other 10-member A rings) where any methylene group or groups may be replaced with one or more alkene, alkyne, aryl, heterocycle or functional groups containing the heteroatoms N, O, and S, so long as the overall length is equivalent to 1 to 7 methylene groups. Here, the functional groups are the same as described above for $L^1$ and may be combined in any combination provided again that the compounds produced are stable in aqueous solution and do not exceed the stated length requirements for $L^2$. Preferred lengths for $L^2$ are from 2 to 4 while most preferred lengths are about 3 methylene equivalents.

Prefered $L^2$'s are optionally substituted bivalent radicals selected from;

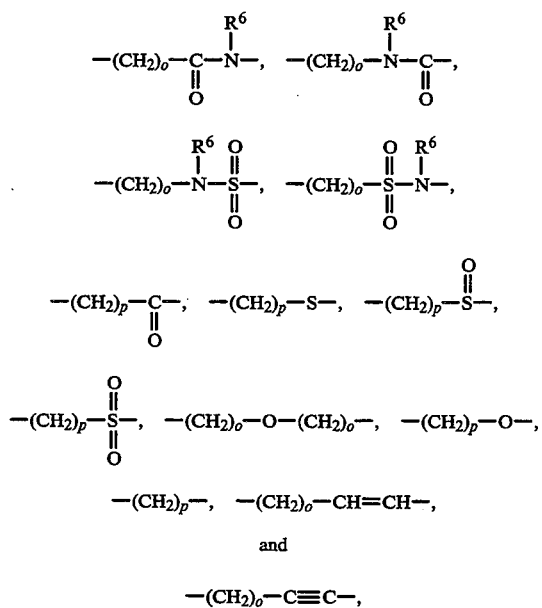

where o is 0, 1 or 2, p is 1, 2, 3 or 4, $R^6$ is defined above, and where the substituents are selected from one to three $R^{12}$ groups defined above.

c. Ring A

Prefered A rings inclued; benzene, napthalene, tetrahydronapthalene, cyclohexane, thiophene, pyridine, pyrazine, pyrimidine, quinoline, isoquinoline, quinoxaline, quinazoline, pteridine, and naphthyridine. The most prefered A ring is benzene.

d. The 7-membered "lactam" ring

Prefered seven member rings are those of formula I where T bears the substituent $R^{22}$. Thus T is preferably $sp^3$ carbon or nitrogen. Also preferably G is a methylene group. The most prefered "lactam ring" is a diazepinedione.

e. Substituents of T-U-G $R^{19}$ and $R^{20}$ are preferably hydrogen or halogen. $R^{18}$ and $R^{21}$ are preferably hydrogen or halogen or taken together form oxo. $R^{22}$ is preferably selected from; hydrogen, optionally substituted $C_1$-$C_6$-alkyl, where the substituents are selected from amino, hydroxy, halo (F, Cl, Br, I), carboxy, and $C_1$-$C_4$-alkoxycarbonyl, optionally substituted $C_6$-$C_{10}$-aryl, and optionally substituted $C_6$-$C_{12}$-aryl-$C_1$-$C_4$-alkyl, where the substituents on any aryl group are selected from amino, nitro, halo (F, Cl, Br, I), halo(F, Cl, Br, I)-$C_1$-$C_6$-alkyl, $C_1$-$C_6$-alkoxy, $C_6$-$C_{10}$-aryloxy, amino-$C_1$-$C_6$-acylamino, amino-$C_1$-$C_6$-acyl, and guanidino$C_6$-$C_{10}$-aroylamino.

f. The amino acid linking moiety D

D is preferably hydrogen, phenyl, or lower alkyl. Optionally, D is —(C=O)—Xaa, where Xaa is one to three natural, unnatural, or modified α-amino acid residues, preferably one or two naturally occurring amino acid residues, and most preferably a naturally occurring hydrophobic amino acid residue. Optionally, when Xaa is two amino acid residues, the terminal residue is Arg or Lys amide. Common naturally occurring a-amino acids are described by the standard three letter amino acid code when referring to amino acids or residues. When the three-letter code begins with a lower-case letter, it is understood the amino acid is the unnatural or D-isomeric form. Standard abbreviations are listed in The Merck Index, 10th Edition, pp Misc-2–Misc-3. Modified or unusual α-amino acids such as norleucine (Nle) and ornithine (Orn) are designated as described in U.S. Patent and Trademark Office Official Gazette 1114TMOG, May 15, 1990.

g. The negatively charged W moiety

Prefered W's are either a tetrazole or a carboxylate. Preferably these groups are represented by;

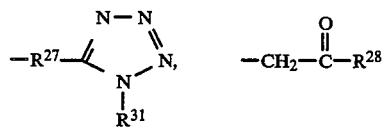

where $R^{27}$ is methylene, and $R^{28}$ and $R^{31}$ are hydroxyl and hydrogen respectively. Optionally, $R^{28}$ and $R^{31}$ are substituents that transform compounds represented by structural formulae I–VI into prodrugs. When W is a carboxylate, prefered prodrug forms include simple esters, a-acyloxyalkyl esters, and amides. Prefered esters include compounds where $R^{28}$ is selected from;

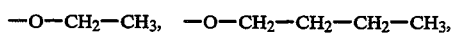

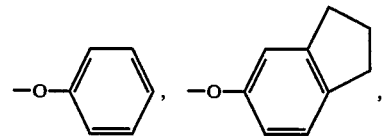

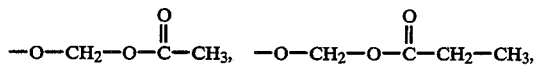

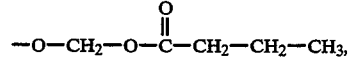

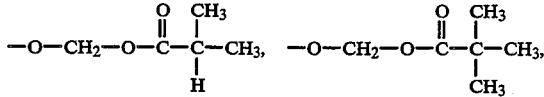

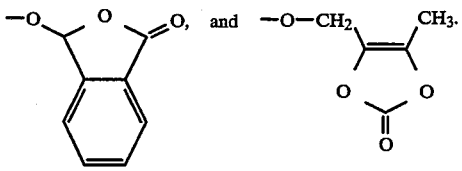

The most prefered compounds of this invention are represented by structural formula II and are selected from:

1-(4-chlorophenyl)methyl-4-(2-carboxyethyl)-7-(4-(1-piperidin)-phenyl)-3,4-dihydro-1H-1,4-benzodiazapine-2,5-dione,
1-(diphenyl)methyl-4-(2-carboxyethyl)-7-(4-(1-piperidin)-phenyl)-3,4-dihydro-1H-1,4-benzodiazapine-2,5-dione,
1-(m-trifluromethyl)phenyl-4-(2-carboxyethyl)-7-(4-(1-piperidin)-phenyl)-3,4-dihydro-1H-1,4-benzodiazapine-2,5-dione,
1-(4-chlorophenyl)methyl-4-(2-carboxyethyl)-7-(4-(2-aminoethoxy)-phenyl)-3,4-dihydro-1H-1,4-benzodiazapine-2,5-dione,
1-(diphenyl)methyl-4-(2-carboxyethyl)-7-(4-(2-aminoethoxy)-phenyl)-3,4-dihydro-1H-1,4-benzodiazapine-2,5-dione,
1-(m-trifluromethyl)phenyl-4-(2-carboxyethyl)-7-(4-(2-aminoethoxy)-phenyl)-3,4-dihydro-1H-1,4-benzodiazapine-2,5-dione,
1-(diphenyl)methyl-4-(2-carboxyethyl)-7-(6-aminohexyl)-3,4-dihydro-1H-1,4-benzodiazapine-2,5-dione,
1-(diphenyl)methyl-4-(2-carboxyethyl)-7-(6-aminohex-1-ynyl)-3,4-dihydro-1H-1,4-benzodiazapine-2,5-dione,
1-(diphenyl)methyl-4-(2-carboxyethyl)-7-(5-aminopentoxy)-3,4-dihydro-1H-1,4-benzodiazapine-2,5-dione,
1-(diphenyl)methyl-4-(2-carboxyethyl)-7-(5-guanidinopentyl)-3,4-dihydro-1H-1,4-benzodiazapine-2,5-dione,
1-(diphenyl)methyl-4-(2-carboxyethyl)-7-(4-guanidinobutoxy)-3,4-dihydro-1H-1,4-bertzodiazapine-2,5-dione,
1-(diphenyl)methyl-4-(2-carboxyethyl)-7-(5-aminopent-1-ynyl)-3,4-dihydro-1H-1,4-bertzodiazapine-2,5-dione,
1-(diphenyl)methyl-4-(2-carboxyethyl)-7-(5-guanidinopent-1-ynyl)-3,4-dihydro-1H-1,4-bertzodiazapine-2,5-dione,
1-(4-chlorophenyl)methyl-4-(2-carboxyethyl)-7-(6-aminohexyl)-3,4-dihydro-1H-1,4-benzodiazapine-2,5-dione,
1-(4-chlorophenyl)methyl-4-(2-carboxyethyl)-7-(5-aminopentoxy)-3,4-dihydro-1H-1,4-benzodiazapine-2,5-dione,
1-(2,4-diflurophenyl)methyl-4-(2-carboxyethyl)-7-(4-(1-piperidin)-phenyl)-3,4-dihydro-1H-1,4-benzodiazapine-2,5-dione,
1-(2,4-diflurophenyl)methyl-4-(2-carboxyethyl)-7-(4-(2-aminoethoxy)-phenyl)-3,4-dihydro-1H-1,4-benzodiazapine-2,5-dione,
1-(2,4-diflurophenyl)methyl-4-(2-carboxyethyl)-7-(6-aminohexyl)-3,4-dihydro-1H-1,4-benzodiazapine-2,5-dione,
1-(2,4-diflurophenyl)methyl-4-(2-carboxyethyl)-7-(5-aminopentoxy)-3,4-dihydro-1H-1,4-benzodiazapine-2,5-dione,
1-(4-chlorophenyl)methyl-4-(3-butanoyl)-7-(4-(1-piperidin)-phenyl)-3,4-dihydro-1H-1,4-benzodiazapine-2,5-dione,
1-(diphenyl)methyl-4-(3-butanoyl)-7-(4-(1-piperidin)-phenyl)-3,4-dihydro-1H-1,4-benzodiazapine-2,5-dione,
1-(diphenyl)methyl-4-(3-butanoyl)-7-(6-aminohexyl)-3,4-dihydro-1H-1,4-benzodiazapine-2,5-dione,
1-(diphenyl)methyl-4-(3-butanoyl)-7-(5-aminopentoxy)-3,4-dihydro-1H-1,4-benzodiazapine-2,5-dione,
1-(diphenyl)methyl-4-(3-butanoyl)-7-(5-guanidinopentyl)-3,4-dihydro-1H-1,4-benzodiazapine-2,5-dione,
1-(4-chlorophenyl)methyl-4-(3-butanoyl)-7-(6-aminohexyl)-3,4-dihydro-1H-1,4-bertzodiazapine-2,5-dione,
1-(2,4-diflurophenyl)methyl-4-(3-butanoyl)-7-(6-aminohexyl)-3,4-dihydro-1H-1,4-benzodiazapine-2,5-dione,
1-(4-chlorophenyl)methyl-4-(3-phenylpropion-3-yl)-7-(4-(1-piperidin)-phenyl)-3,4-dihydro-1H-1,4-benzodiazapine-2,5-dione,
1-(diphenyl)methyl4-(3-phenylpropion-3-yl)-7-(4-(1-piperidin)-phenyl)-3,4-dihydro-1H-1,4-benzodiazapine-2,5-dione,
1-(diphenyl)methyl-4-(3-phenylpropion-3-yl)-7-(6-aminohexyl)-3,4-dihydro-1H-1,4-benzodiazapine-2,5-dione,
1-(diphenyl)methyl-4-(3-phenylpropion-3-yl)-7-(5-aminopentoxy)-3,4-dihydro-1H-1,4-benzodiazapine-2,5-dione,
1-(diphenyl)methyl4-(3-phenylpropion-3-yl)-7-(5-guanidinopentyl)-3,4-dihydro-1H-1,4-benzodiazapine-2,5-dione,
1-(4-chlorophenyl)methyl-4-(3-phenylpropion-3-yl)-7-(6-aminohexyl)-3,4-dihydro-1H-1,4-benzodiazapine-2,5-dione,
1-(2,4-diflurophenyl)methyl-4-(3-phenylpropion-3-yl)-7-(6-aminohexyl)-3,4-dihydro-1H-1,4-benzodiazapine-2,5-dione,
1-(3-(butyryl)aminophenyl)methyl-4-(2-carboxyethyl)-7-(6-aminohexyl)-3,4-dihydro-1H-1,4-benzodiazapine-2,5-dione,
1-(3-(butyryl)aminophenyl)methyl-4-(2-carboxyethyl)-7-(5-guanidinopentyl)-3,4-dihydro-1H-1,4-benzodiazapine-2,5-dione,
1-(3-(4-aminobutyryl)aminophenyl)methyl-4-(2-carboxyethyl)-7-(6-aminohexyl)-3,4-dihydro-1H-1,4-benzodiazapine-2,5-dione,
1-(3-(4-guanidinobutyryl)aminophenyl)methyl-4-(2-carboxyethyl)-7-(5-guanidinopentyl)-3,4-dihydro-1H-1,4-benzodiazapine-2,5-dione,
1-(3-(6-aminohexoyl)aminophenyl)methyl4-(2-carboxyethyl)-7-(6-aminohexyl)-3,4-dihydro-1H-1,4-benzodiazapine-2,5-dione,
1-(3-(6-guanidinohexoyl)aminophenyl)methyl-4-(2-carboxyethyl)-7-(5-guanidinopentyl)-3,4-dihydro-1H-1,4-benzodiazapine-2,5-dione,
1-(3-(6-aminopentoyl)aminophenyl)methyl-4-(2-carboxyethyl)-7-(6-aminohexyl)-3,4-dihydro-1H-1,4-benzodiazapine-2,5-dione,
1-(3-(6-guanidinopentyl)aminophenyl)methyl4-(2-carboxyethyl)-7-(5-guanidinopentyl)-3,4-dihydro-1H-1,4-benzodiazapine-2,5-dione,
1-(3-(6-aminopropionyl)aminophenyl)methyl-4-(2-carboxyethyl)-7-(6-aminohexyl)-3,4-dihydro-1H-1,4-benzodiazapine-2,5-dione,
1-(3-(6-guanidinopropionyl)aminophenyl)methyl-4-(2-carboxyethyl)-7-(5-guanidinopentyl)-3,4-dihydro-1H-1,4-benzodiazapine-2,5-dione,
1-(3-(6-aminoacetyl)aminophenyl)methyl-4(2-carboxyethyl)-7-(6-aminohexyl)-3,4-dihydro-1H-1,4-benzodiazapine-2,5-dione,
1-(3-(6-guanidinoacetyl)aminophenyl)methyl-4-(2-carboxyethyl)-7-(5-guanidinopentyl)-3,4-dihydro-1H-1,4-benzodiazapine-2,5-dione,
1-(3-(4-guanidinobenzoyl)aminophenyl)methyl-4-(2-carboxyethyl)-7-(6-aminohexyl)-3,4-dihydro-1H-1,4-benzodiazapine-2,5-dione, 1-(4-(6-aminopropionyl)aminophenyl)methyl-4-(2-carboxyethyl)-7-(6-aminohexyl)-3,4-dihydro-1H-1,4-benzodiazapine-2,5-dione, 1-(3-(4-aminobutyl)phenyl)methyl-4-(2-carboxyethyl)-7-(6-aminohexyl)-3,4-dihydro-1H-1,4-benzodiazapine-2,5-dione, and 1-(4-carboxyphenyl)methyl-4-(2-carboxyethyl)-7-(6-aminohexyl)-3,4-dihydro-1H-1,4-benzodiazapine-2,5-dione.

D. Methods of Making

Compounds of the present invention can be prepared by many methods, employing standard chemical methodologies described and referenced in standard textbooks (e.g. March, J. "Advanced Organic Chemistry" McGraw-Hill, New York, 1977; Collman, J. P., Hegedus, L. S., Norton, J. R., Finke, R. G. "Principles and Applications of Organotransition Metal Chemistry" University Science, Mill Valley, 1987; Larock, R. C. "Comprehensive Organic Transformations" Verlag, New York, 1989). In the description that follows standard abbreviations as recommended by the *Journal of Organic Chemistry* (see "Guidelines for Authors" in any volume) are employed unless otherwise specified.

1. The Q Group

The nitrogen containing substituents Q or a precursor thereof may added to the linker L and the combination Q-L-, usually in protected form, may be bonded to ring A. Alternatively, Q or Q plus a portion of L may be added to L or a portion thereof after ring A and the rest of the molecule have been formed. Q itself may be prepared and bonded to ring A by standard methods published in both the scientific and patent literature (see e.g. U.S. Pat. Nos. 4,992,542, 4,997,936, 4,194,047, 5,003,076, 5,063,207, 5,063,208, and 5,079,357, and references cited therein).

In the description immediately following, addition of Q-L- to the benzene moiety of 3,4-dihydro-1H-1,4-benzodiazepine-2,5-dione is specified. It will be understood that these same procedures may be applied to other ring systems encompased by formula I.

2. The benzodiazepinedione

The key intermediate is the substituted 3,4-dihydro-1H-1,4-benzodiazepine-2,5-dione 1. The benzodiazepinedione I (R$\neq$H) may be prepared using a triply convergent approach from the isatoic anhydride 2, the $\beta$-alanine ester 3, and the $\alpha$-haloacetyl halide 4 (Scheme 1 ). The benzodiazepinedione I (R=H) may be prepared using a doubly convergent approach from the isatoic anhydride 2 (R=H) and the substituted N-carboxymethyl $\beta$-alanine ester 5 (Scheme 2).

Methods for preparation of the isatoic anhydrides 2, $\beta$-alanine esters 3, and $\alpha$-halo acetyl halides 4 (Scheme 1), are known in the art and a number of them are available from commercial sources such as Aldrich Chemical Co. A reaction sequence, similar to that shown in Scheme 1 to prepare 3,4-dihydro-1H-1,4-benzodiazepine-2,5-diones has been previously described (Lee, C. M. *J. Heterocyclic Chem.* 1964, 1, 235). Briefly, the isatoic anhydrides are converted to N-(2-aminobenzoyl)-$\beta$-alanine esters 6 by allowing 2 to react with 3, or its salt, in the presence an organic base. The isatoic anhydride 2 may be substituted or unsubstituted, but the 5-iodo isatoic anhydride is preferred (2, R$^a$=I). The $\beta$-alanine ester 3 may also be substituted or unsubstituted as the free amine or, more conveniently, as its salt (e.g. HCl). For example, the reaction may be carried out with $\beta$-alanine ethyl ester hydrochloride, ethyl 3-phenyl-3-aminopropionate p-tosylate, aspartyl-valine dibenzyl ester hydrochloride, or the like. Generally, the reaction is conducted in a dry polar aprotic solvent, such as dimethylformamide or the like, in the presence of an equimolar amount, or up to 30% excess, of a tertiary amine as the organic base, e.g. triethylamine. Alternatively, the reaction may be catalysed by dimethylaminopyridine (Venuti, M. C. *J.C.S. Chem Comm.* 1982, 266). The reaction requires between about 0.5 to 4 hours at temperatures between about room temperature and 100° C. Preferably, the reaction is conducted at 50° C. for about 2 hours in dimethylformamide as the solvent.

The products are isolated and purified by conventional methods, typically by solvent extraction into a compatible solvent. The product may be further purified by column chromatography or other appropriate methods.

If the anilino nitrogen in N-(2-aminobenzoyl)-$\beta$-alanine esters 6a is unsubstituted such that R=H, this position can be alkylated by allowing 6b (R=H) to react with a molar amount, but up to 50% excess, of an alkyl halide to produce 6 (R$\neq$H). Generally, the reaction can be accomplished in a polar aprotic solvent, in the presence of a molar amount, or up to 50% excess, of an organic base. Preferably, the reaction will be conducted in dimethylformamide as solvent and 2,6-lutidine as the organic base. The reaction is allowed to proceed at temperatures between about room temperature to 200° C. for about 0.5 hours to 2 days. Preferably, the reaction will be run at 80° C. for 16 hours. The products are isolated and purified by conventional methods, typically by solvent extraction into a compatible solvent. The product may be further purified by column chromatography or other appropriate methods.

Alternatively, 6 (R$\neq$H) may be prepared by allowing 6a to react with an aldehyde or ketone, under dehydrating conditions, in the presence of a catalytic amount of acid followed by reduction with a trialkylsilane and a strong acid. Generally, the first of these reactions can be accomplished in a non-polar aprotic solvent, such as toluene, and an organic acid, such as p-toluenesulphonic acid at temperatures between 80°-160° C. for times between 1 to 60 mins. Preferably, the reaction will be conducted at reflux for 10 mins. The product may be isolated by crystalization or carried on to reduction without further purification. Reduction can be achieved by the addition of an excess of trialkylsilane, such as triethylsilane, in the presence of an excess of a strong acid, such as trifluoroacetic acid, at temperatures between −30° to 30° C. for times between 0.5 to 48 hours with a non-reactive organic solvent, such as dichloromethane. Preferably, reduction is run at 0° C. for 2 hours with dichloromethane as a co-solvent. The products are isolated and purified by conventional methods, typically by crystalization from suitable solvents. The product may be otherwise purified by solvent extraction into a compatible solvent followed by column chromatography or other appropriate methods.

Conversion of N-(2-aminobenzoyl)-$\beta$-alanine esters 6 to the benzodiazepinedione 1 (R$\neq$H) involves first the acylation of the anilino nitrogen, followed by a base promoted ring formation. The acylation reaction can be achieved by either reaction of 6 with an $\alpha$-haloacyl halide in the presence of an equimolar amount, or up to 30% excess, of an organic base, such as triethylamine, or with an $\alpha$-haloacid in the presence of an amide coupling reagent, such as dicydohexylcarbodiimide. Acylation of 6 with an a-haloacyl halide may also be conducted in the absence of an organic base and can be run with water in a biphasic reaction system. Generally, these reactions are conducted in a pre-dried, non-reactive organic solvent, such as methylene chloride, diethyl ether, or tetrahydrofuran under a dry, inert atmosphere, such as nitrogen. Preferably, acylation with an α-halo acylhalide will be run in methylene chloride, whereas acylation with an α-halo-acid will be run in tetrahydrofuran. The reactions are allowed to run at temperatures between about 0° C. to room temperature for times between about 0.5 to 24 hours. Preferably, the reactions will be allowed to run for 2 hours at room temperature. The products are isolated and purified by conventional methods, typically by solvent extraction into a compatible solvent. Generally, further purification of the acylated products 7 is not required.

Cyclization of the acylated N-(2-acylaminobenzoyl)-β-alanine esters 7 may be achieved by reaction with a base such as an alkali metal alkoxide, hydride, or carbonate in a polar solvent at temperatures between about 0° and 100° C. for about 0.5 to 2 hours. For example, a solution of the N-(2-aminobenzoyl)-β-alanine ester 7 is commonly added over a period of approximately 15 to 60 minutes to a slurry of an alkali metal hydride in an appropriate solvent, cooled to 0° C.

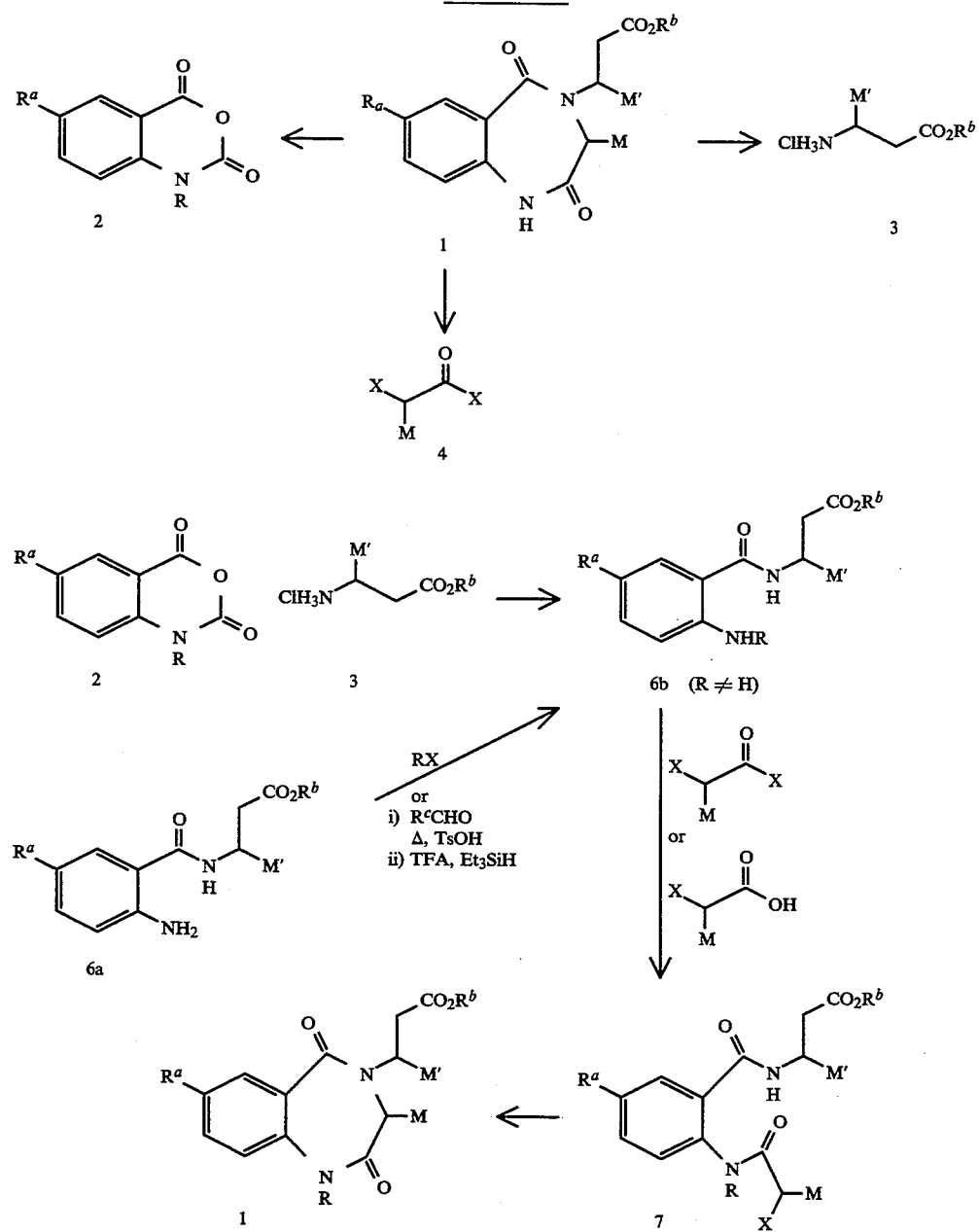

SCHEME 1

It is preferable that the solvent will be a polar aprotic solvent such as dimethylfomamide and the alkali metal hydride be sodium hydride or calcium carbonate. Once the addition is complete, the reaction mixture is generally allowed to warm to room temperature and run for an additional 60 to 105 minutes after which the reaction is neutralized by the addition of a solution of an acid, such as 10% citric acid or the like, and the solvent evaporated. The product is then isolated by solvent extraction and further purified by column chromatography.

In Scheme 2, the substituted N-carboxymethyl β-alanine esters 5 are also known in the art and may be prepared in two steps by first reaction of an acrylate ester and α-amino acid ester to give 8, followed by selective conversion of the glycine ester group to its corresponding acid. For example, allowing glycine benzyl ester to react with ethyl acrylate in an alcoholic solvent such as methanol for about 1 day yields N-(carboxymethyl benzyl ester)-β-alanine ethyl ester. Removal of the benzyl ester by hydrogenation in the presence of a catalytic amount 10% palladium on carbon provides N-carboxymethyl-β-alanine ester 5 (M'=H, $R^b$=ethyl).

Preparation of the benzodiazepinedione 1 (R=H) may be accomplished by allowing 5 to react with 2 (R=H). The reaction can be conducted in either a polar aprotic solvent, such as dimethyl sulfoxide, or weak organic base, such as pyridine, at temperatures of 100°–200° C. for about 2–86 hours. Preferably, the reaction will be run in pyridine at refluxing temperature for about 24 hours. The product is then isolated by dilution with an appropriate organic solvent, such as ethyl acetate, and washed with aqueous acid, such as 10% citric acid, and aqueous base, such as saturated sodium bicarbonate. The products can be further purified by column chromatography or crystallization from an appropriate organic solvent to provide the compounds 1 (R=H).

Reaction Scheme 3 outlines the preparation of the compounds of the present invention from compound 9 [1 ($R^a$=I)].

Conversion of the compounds having the structural formula 9 to compounds having the structural formula 10, provides those compounds classified in Groups 1 and 2. This may be accomplished by allowing 9 to react with an alkyne 11 in the presence of a palladium (II) salt, a copper (I) salt, and an organic base. Preferably, the alkyne 11 is substituted in a way such that the Y group can be synthetically converted to the positively charged Q group of structural Formula I. More preferably, the Y group is a protected form of the positively charged Q group of structural Formula I. For example, the alkyne may be a N-Boc-amino alkyne, a benzo or alkylnitrile alkyne, a nitrobenzo alkyne, or the like. L' is L less the functional groups shown below in scheme 3.

Generally, the reaction is allowed to run in a dry organic polar aprotic solvent, such as ethyl acetate or the like, to the exclusion of oxygen at temperatures between about

SCHEME 2

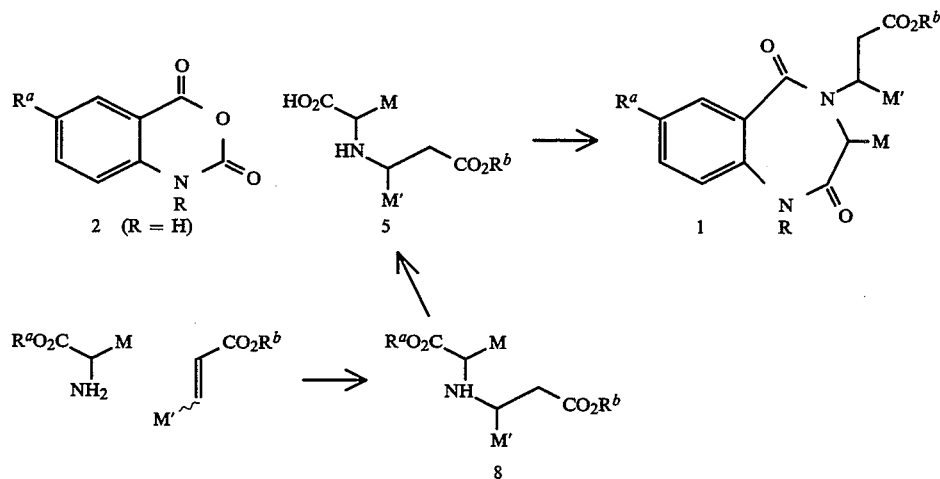

SCHEME 3

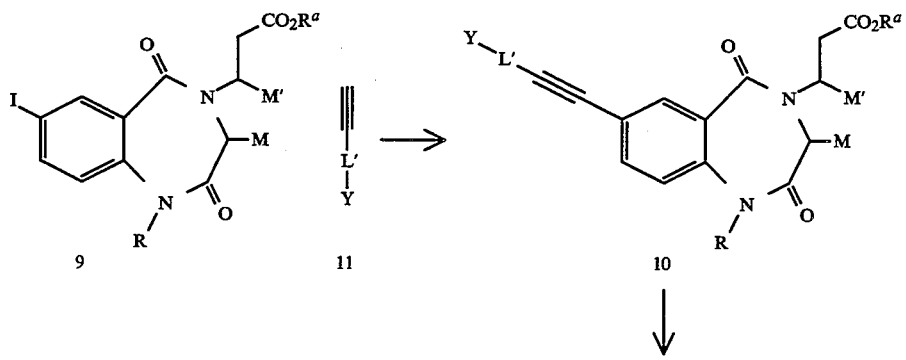

SCHEME 3
-continued

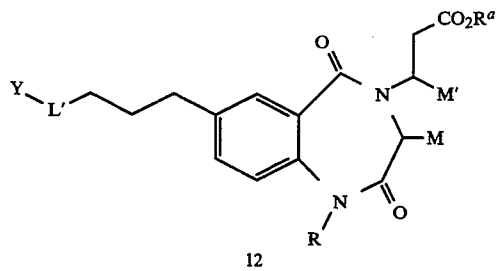

room temperature and 180° C. for times between about 2 and 48 hours. Preferably, the reaction will run with a catalytic amount of palladium(II) salt at 10 molar percent and cupric(I) salt at 5 molar percent. A 2 fold excess of the alkyne 11 and a 5 fold excess of a tertiary amine as the organic base, such as triethylamine or the like, is preferred. For example, a mixture of the iodo arene 9, a 2 fold excess of the alkyne 11, 10 molar percent of bis(triphenylphosphine)palladium dichloride, 5 molar percent cupric iodide, 5 fold excess of triethylamine, and ethyl acetate under a dry, inert atmosphere, such as nitrogen, is allowed run for about 2 hours. The product can be isolated by solvent extraction in to a suitable organic solvent, such as ethyl acetate, and washed with a solution of 10% ethylenediaminetetraacetic acid and the solvent evaporated. The products may be further purified by column chromatography.

Preparation of the compounds classified in Groups 3 and 4 may be achieved by reduction of the alkyne moiety in compounds of the general formula 10 to yield the saturated compounds 12 by allowing the alkyne to stir under an atmosphere of hydrogen in the presence of a small amount of palladium on carbon. Typically, the reaction is run in an inert solvent, such as ethyl acetate, with a 5-10 molar percent by weight of 10% palladium on carbon at temperatures between about room temperature and 50° C. for times between about 15-240 minutes. Preferably, the reaction is carried out at room temperature for 1 hour. The products are isolated by filtration of the mixture through a filter agent, such as Celite®, and evaporation of solvent.

SCHEME 3, cont.

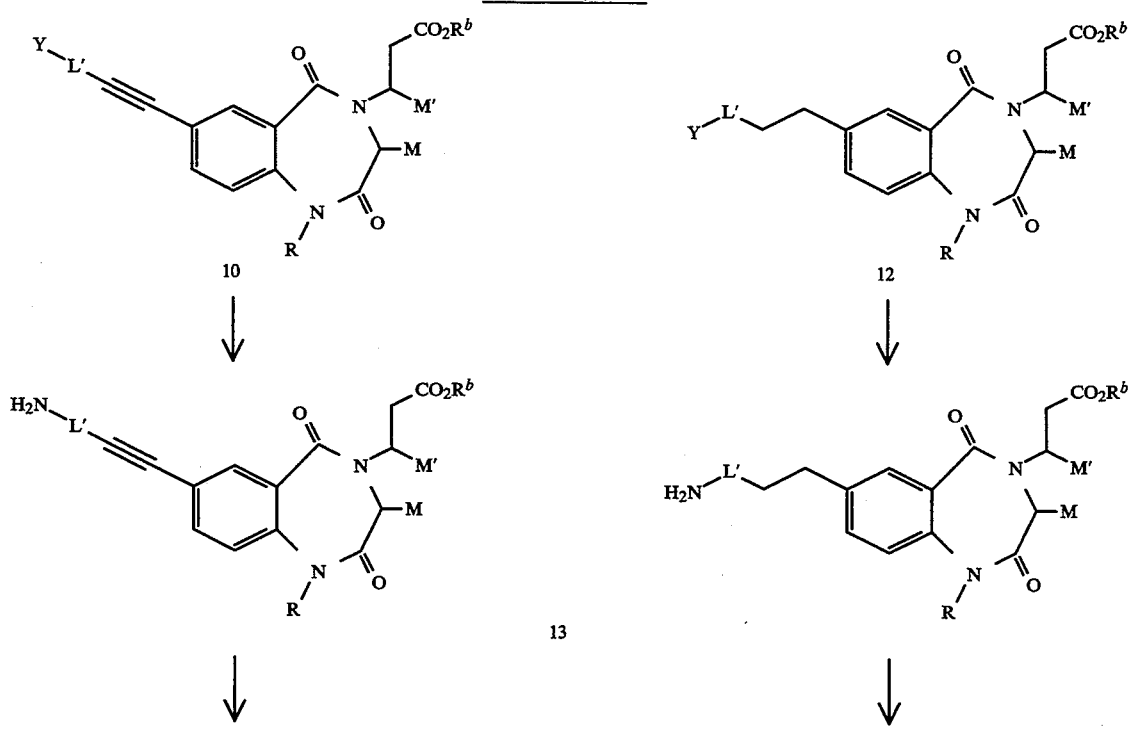

-continued
SCHEME 3, cont.

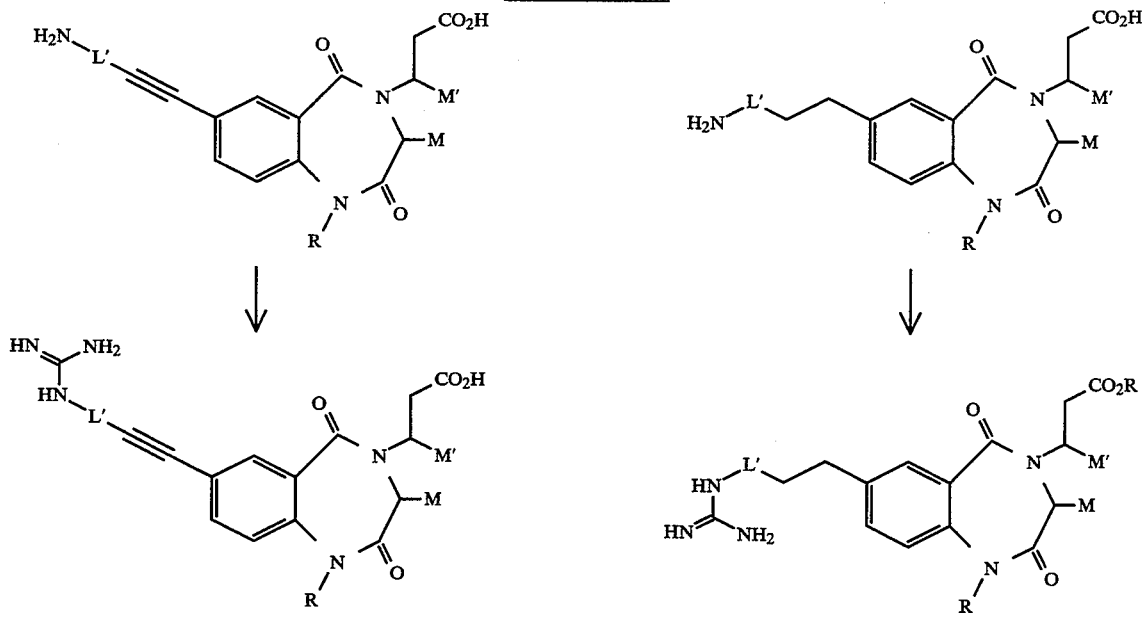

Conversion of the compounds of the general formula 10 or 12 in which Y is a N-(tert-butoxycarbonyl) amino protected moiety (N-BOC) to the amino esters 13 can be accomplished by allowing the material to react with a strong acid. Generally, the reaction is carried out by mixing the N-BOC amino ester with a large excess of concentrated solution of a strong acid, such as hydrogen chloride, dissolved in an appropriate inert solvent, such as ethyl acetate. The reaction can be conducted at a temperature between about minus 30° C. and room temperature for about 0.5 to 24 hours. The reaction can be run in the presence of a molar amount of trialkylsilane, such as triethylsilane or the like. Preferably, the reaction will be carried out at room temperature for 2 hours with a molar equivalent of triethylsilane in ethyl acetate. The solvent is evaporated and the products can be further purified by high-pressure liquid chromatography using a reverse phase column.

Conversion of the compounds of the general formula 10 or 12 in which the Y functional group is an arylnitrile to the amino esters 13 can be achieved by allowing the arylnitriles 10 or 12 to react with dicobalt octacarbonyl in the presence of trimethylsilane. The reduction of a benzonitrile to a benzylamine is a known reaction (Mural, T.; Sakane, T.; Kato, S. Tetrahedron Lett. 1985, 26, 5145-5148) and is generally carried out in an inert solvent, such as toluene or the like, at 60° C. for 20 hours with an 8 molar percent of dicobalt octacarbonyl and a 10 fold excess of trimethylsilane. The solvent is evaporated and the resulting material diluted with methanol and allowed to react with a 5 fold excess of potassium fluoride. The products are then isolated by solvent extraction and further purified by high-pressure liquid chromatography using a reverse phase column.

Conversion of the compounds of the general formula 10 or 12 in which the Y functional group is a nitroarene, to the amino ester 13 can be executed by a selective reduction (Bellamy, F. D.; Ou, K. Tetrahedron Lett. 1984, 25, 839-842). The reaction is generally run with a five molar excess of stannous chloride dihydrate in either ethyl acetate or ethanol as the solvent at temperatures between about 50° and 100° C. for times between about 15-120 minutes under an inert atmosphere, such as nitrogen. Preferably, the reaction is carried out at 70° C. in ethanol for approximately 30 minutes. The products are then isolated by solvent extraction and further purified by high-pressure liquid chromatography using a reverse phase column.

Conversion of the amino esters to their corresponding amino acids of the structural formula I involves saponification using well known conditions and reagents. For example, an aqueous solution of a strong alkali metal base, such as sodium hydroxide, lithium hydroxide or the like, is added to an alcoholic solution of the ester. Alcohols which may be used as the solvent for this reaction may include, for example, methanol, ethanol, and isopropanol, but, methanol is preferred. The preferred base is sodium hydroxide at a concentration between about 1 to 6N, though 2N is preferred. The reaction may be conducted at a temperature between about 0° to 50° C. for times between about 10 to 60 minutes. Preferably, the reaction is carried out at room temperature for 30 minutes after which the reaction is neutralized with a concentrated solution of a strong acid, such as hydrochloric acid or the like, and the solvent evaporated. The products are isolated by high-pressure liquid chromatography using a reverse phase column.

The conversion of the amino acids to their corresponding guanidino acids of the structural formula I is a known reaction (Kim, K. Lin, Y.-L.; Mosher, H. S. Tetrahedron Lett. 1988, 3183-3186). The reaction can be accomplished by allowing the amino acid to react with aminoiminomethanesulfonic acid. Generally, the reaction can be conducted with a equimolar to a 10 fold molar excess of aminoiminomethanesulfonic acid at temperatures between 0° to 50° C. for times between about 15 to 120 minutes in a polar protic solvent, such as methanol, water or the like. The solution, prior to the addition of aminoiminomethanesulfonic acid, may be made neutral or basic by the addition of weak base, such as an alkali metal carbonate. Preferably, for alkyl amines the amino acid will be allowed to react with a 5 fold excess aminoiminomethanesulfonic acid at room temperature for 30 minutes with 5% potassium bicarbonate in water as the reaction medium, whereas for aryl amines the amino acid will be allowed to react with an equimolar amount of aminoiminomethanesulfonic acid at room temperature for 1 hour in methanol. Generally, the reaction mixture will be made acidic by the addition of a dilute solution of an acid, such as acetic acid and the solvent evaporated. The products are isolated by high-pressure liquid chromatography using a reverse phase column.

Preparation of the compounds classified as Groups 4–11 may also be prepared from the key intermediate 9. Conversion of the iodoarene 9 to a synthetic precursors of those compounds found in Groups 5–11 namely compounds 15–18, may be accomplished by a multistep reaction sequence (Scheme 4). First, the iodoarene is carbonylated in an alcoholic solvent (R'OH) under a carbon monoxide atmosphere utilizing a palladium (0) catalyst. The alcoholic solvent (R'OH) must be chosen so as to allow for the selective removal of the R' group of the diester 14. For example, when R'=CH$_3$ and R$^b$=tert-butyl, the alcoholic solvent is methanol, and this methyl ester functionality in 14 can be removed by mild basic hydrolysis to afford acid 15. The treatment of 15 with a molar equivalent of diphenylphosphoryl azide and a molar equivalent of a tertiary amine such as triethylamine at room temperature in a non-protic solvent such as dichloromethane affords the isocyanate 16. This may be hydrolyzed to the amine 17 by the addition of water to a solution of 16 in tetrahydrofuran at room temperature. Finally, conversion of the aniline 17 to its corresponding diazonium salt by treatment with nitrous acid and subsequent heating of the diazonium salt in the presence of water produces the phenol 18.

SCHEME 4

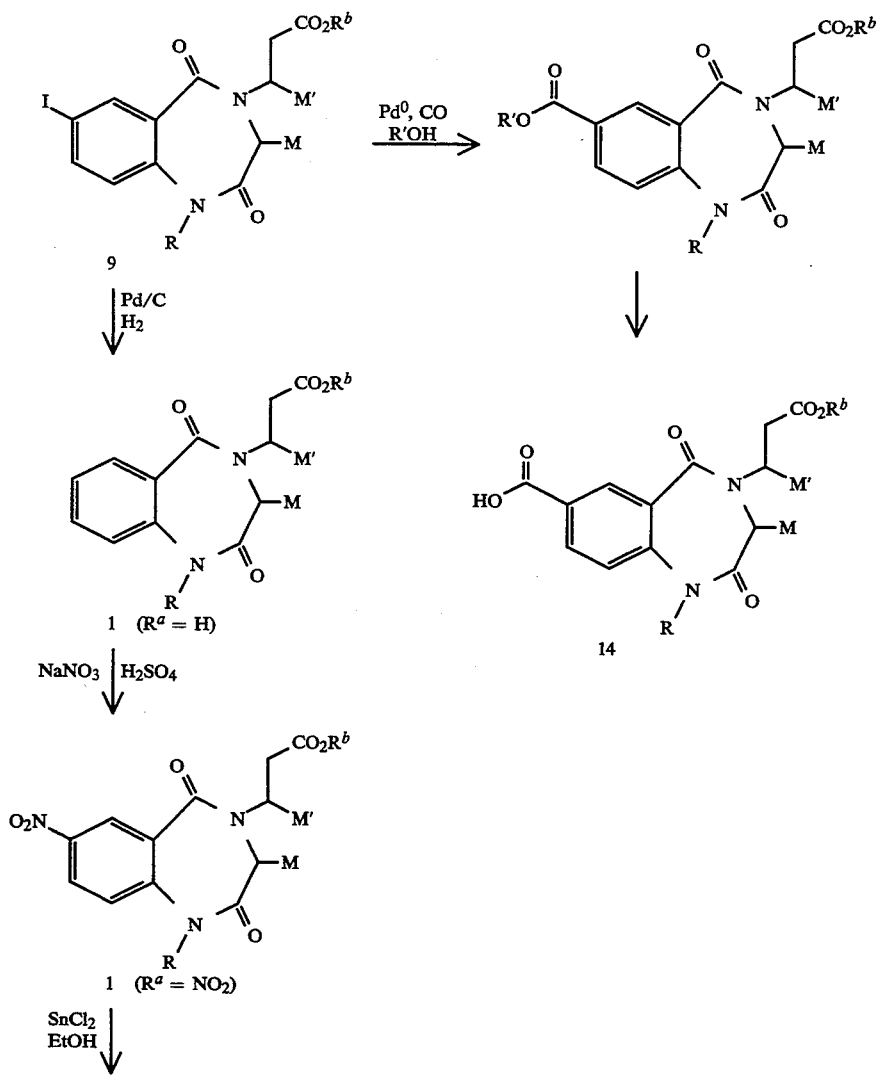

SCHEME 4

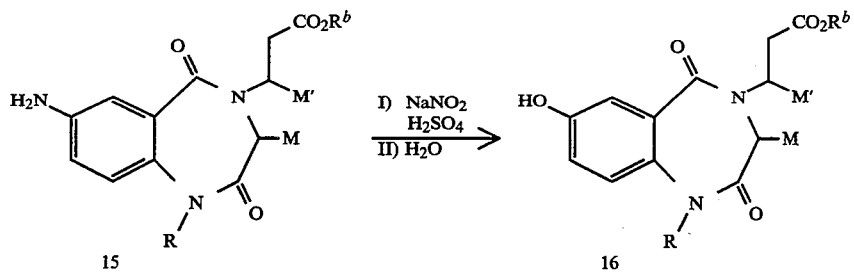

Schemes 5 and 6 depict methods that may be used to introduce the linking groups of compounds classified as Groups 4–11 onto the benzodiazepinedione nucleus. For example, preparation of the biaryl adducts 19, precursors of Group 5 type compounds, may be accomplished by allowing 9 to react with substituted aryl molecules 20, where Y and L' are defined as above, in the presence of palladium(0). Allowing the carboxylic acid 15 to react with an amine 21 or alcohol 22 in the presence of a dehydrating reagent, such as dicyclohexylcarbodiimide (DCC) or the like, will yield the amide 23 and ester 24, forerunners of Group 10 and 11 type compounds, respectively. Similarly, 25 can be prepared from the aniline 17 by reaction with a carboxylic acid 26 in the presence of a coupling reagent, such as DCC or the like. Compounds of the general formula 25 are precursors of Group 5 type compounds.

SCHEME 5

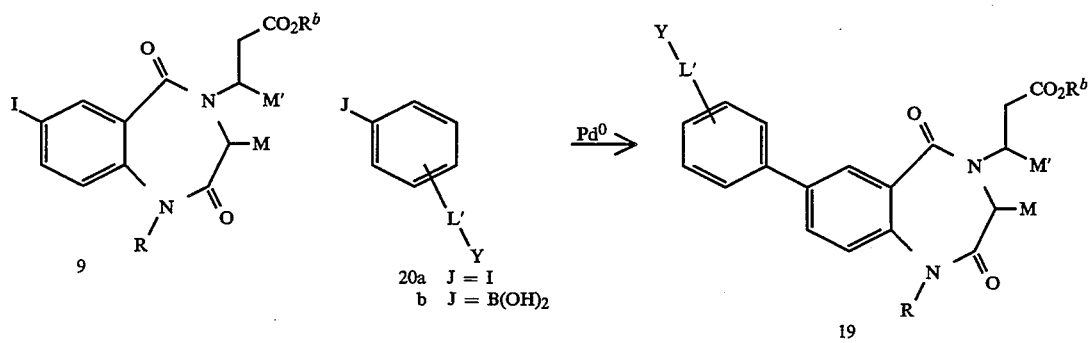

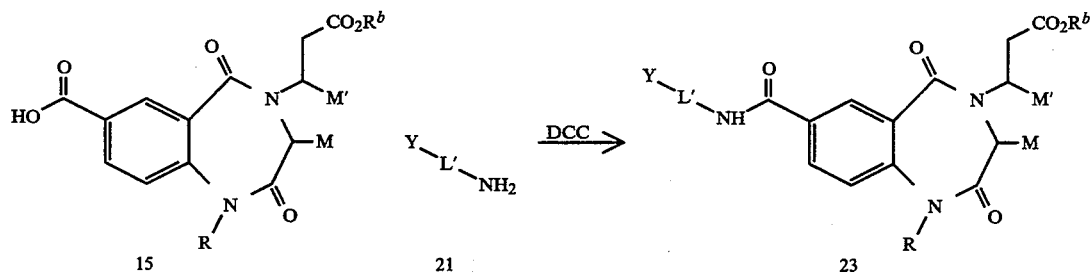

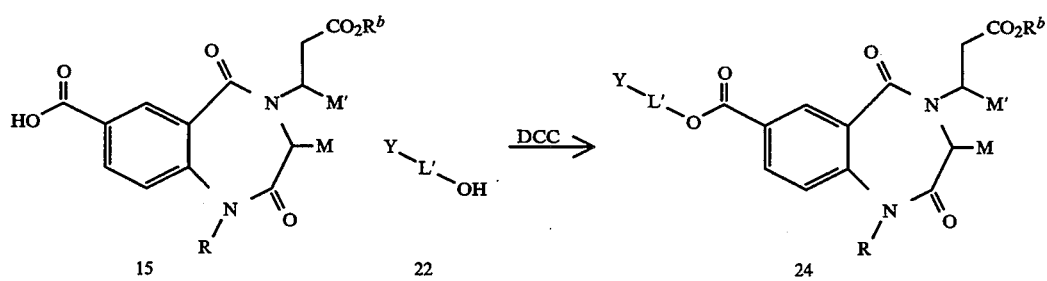

-continued
SCHEME 5

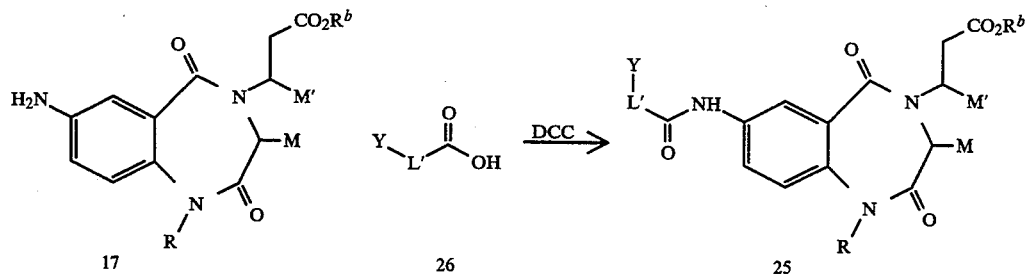

Conversion of aniline 17 into its corresponding urea 27 or carbamate 28 (Scheme 6) may be accomplished by reaction of the isocyanate 16 in the presence of an amine 21 or alcohol 22, respectively. Treatment of the phenol 18 with phosgene and an amine 21 or alcohol 22 yields the carbamate 29 and carbonate 30, respectively. Reaction of a sulfonylhalide 32 with either the aniline 17 or phenol 18 would produce the corresponding sulfonamide 33 and sufinyl ester 34, respectively. Allowing the phenol 18 to react with an alcohol 22 in the presence of diethylazodicarboxylate and triphenylphophine will furnish 31, a precursor to Group 12 type compounds. The product 27 is a synthetic precursor to those compounds classified as Group 7, product 28 is a forerunner to Group 6 type compounds, product 29 will give rise to Group 8 type compounds, whereas, product 30 is a precursor to Group 9 type compounds. Products 33 and 34 are precursors to Group 15 and 16, respectively.

SCHEME 6

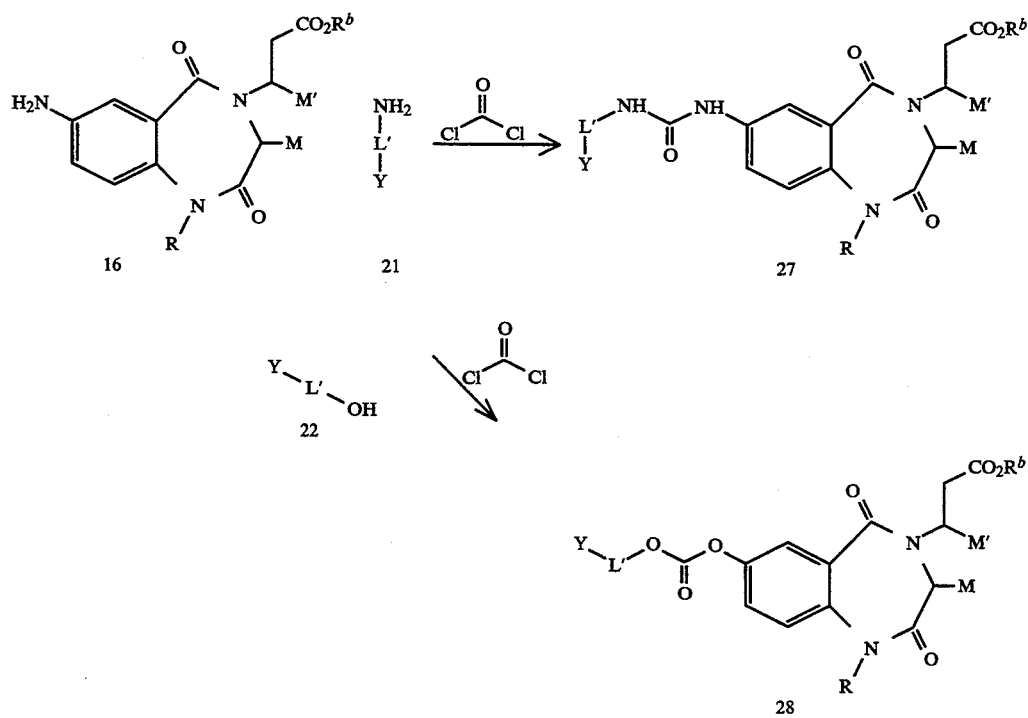

-continued
SCHEME 6

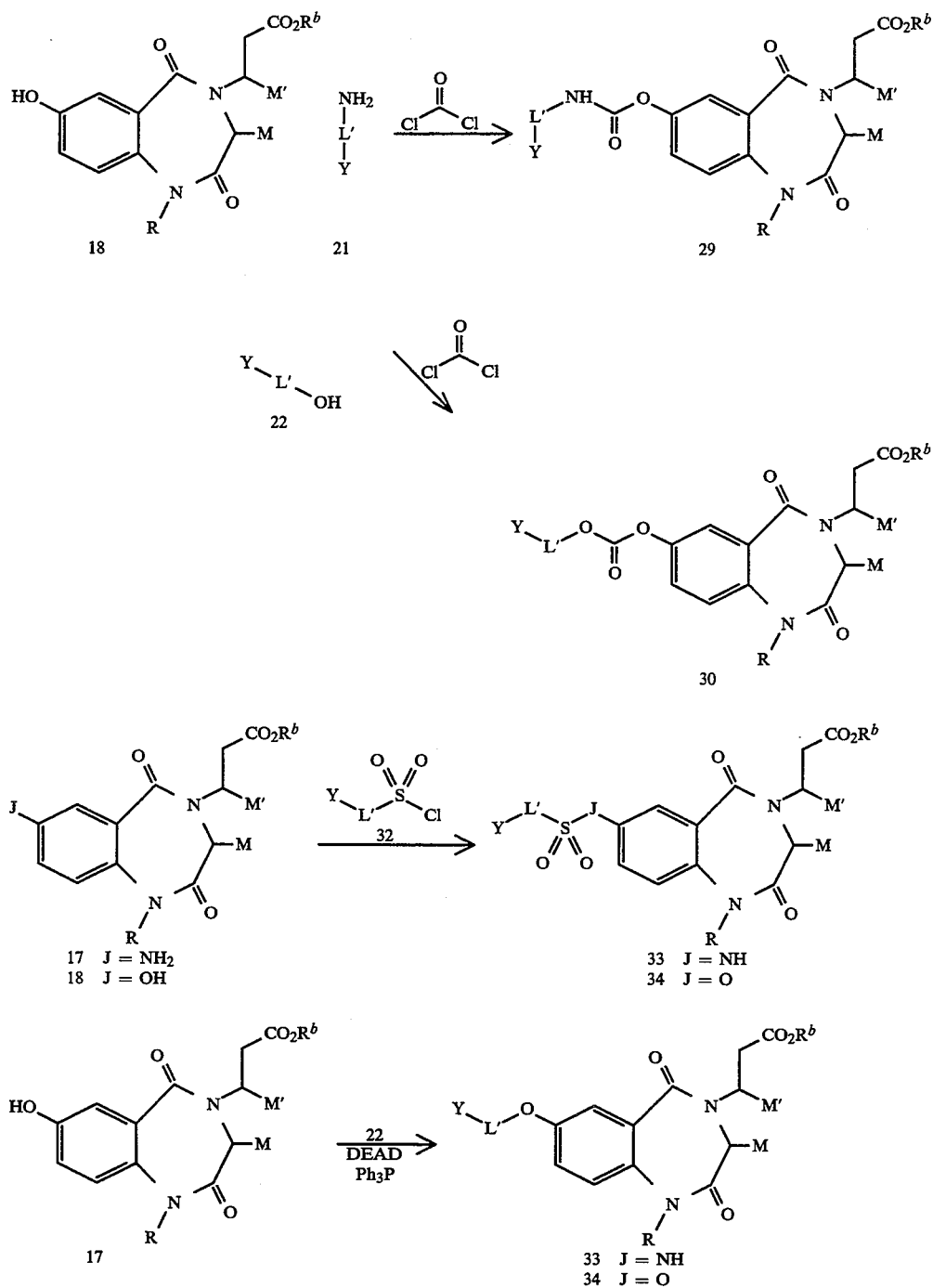

Scheme 7 depict methods that may be used in the preparation of the compounds classified as Groups 13, 14, 17 and 18. Diazotization of the aniline 17, by the reaction of 17 with nitrous acid, followed by treatment with sulfur dioxide in the presence of cupric chloride (Gilbert, *Synthesis*, 1969, 1-10) yields the sulfonyl chloride 35. Reaction of 35 with either the amine 21 or the alcohol 22 will provide the synthetic precursor to Groups 13 and 14, respectively, namely, the suphonamide 36 and sulfinyl ester 37. The diazonium salt prepared by diazotization of 17 when allowed to react with oximes in the presence of copper sulphate and sodium sufite will give the corresponding oxime 38, which can be readily hydrolyzed to yield the aryl ketone 39 (Beech, *J. Chem. Soc*, 1954, 1297). Clemmensen reduction of the ketone 39 using zinc amalgam and aqueous hydrogen chloride gives rise to the benzyl adduct 40 (Vedejs, *Org. React.* 1975, 22, 401). The products 39 and 40 are precursors to the compounds classified as Groups 17 and 18, respectively.

SCHEME 7

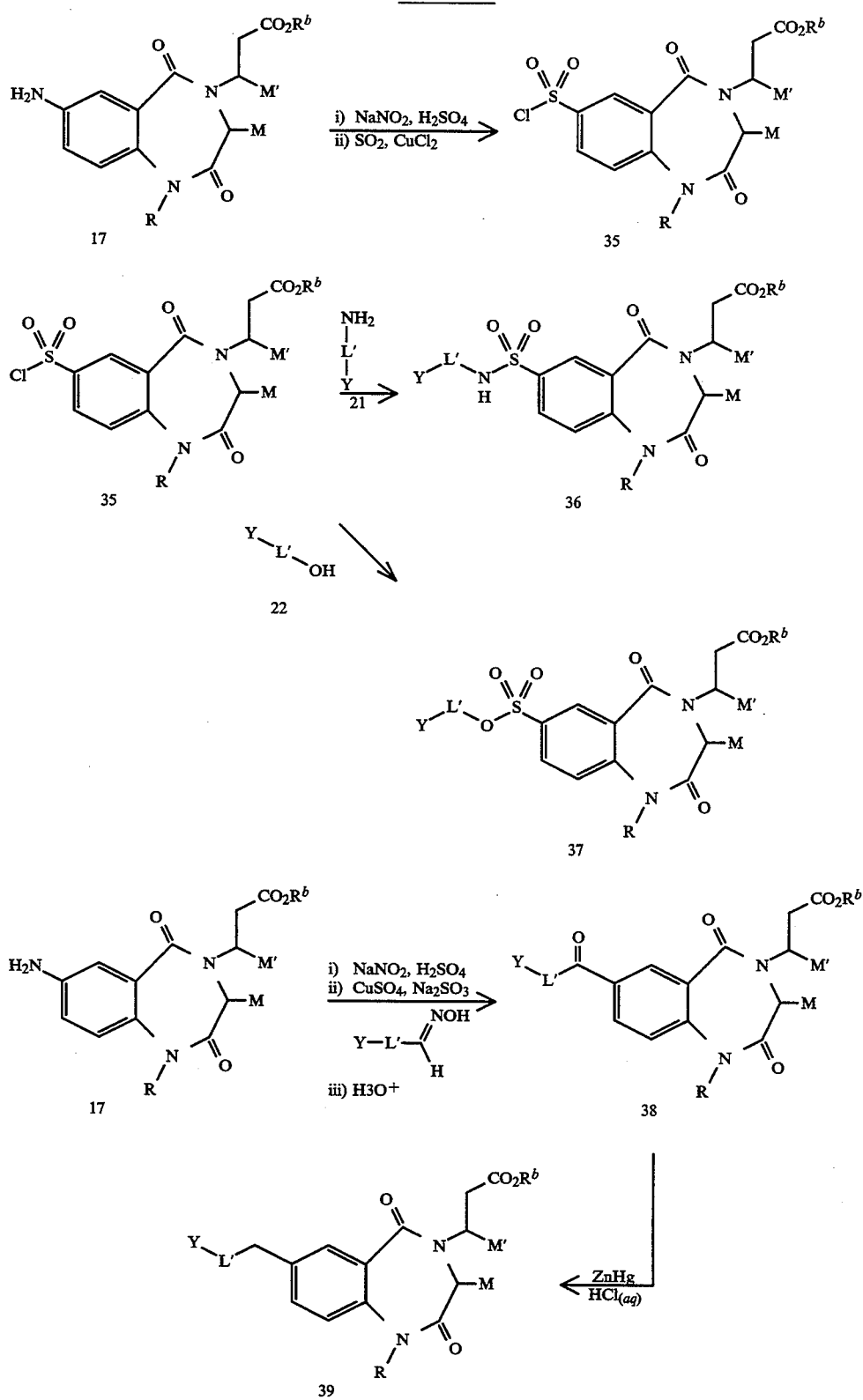

Each of the protected precursors 19, 23, 24, 25, 27, 28, 29, 30, 31, 33, 34, 36. 37, 39, and 40 may be treated in a similar way as described above for compounds 10 and 12 (Scheme 3) to prepare the compounds encompassed by this invention.

3. Other "6-7" Fused Ring Systems

Other "6-7" fused ring systems where each T, U, or G of formula I is independently selected from NH, N, NR, C=X, $CR_2$, CHR, $CH_2$, CR, CH, O, S, SO, or $SO_2$ can be prepared by methods known in the art. To provide guidence, however, specific representative synthetic routes are provided in scheme 8. It will be understood that other synthetic routes may be prefered when specific substituents or T-U-G are targeted.
SCHEME 8
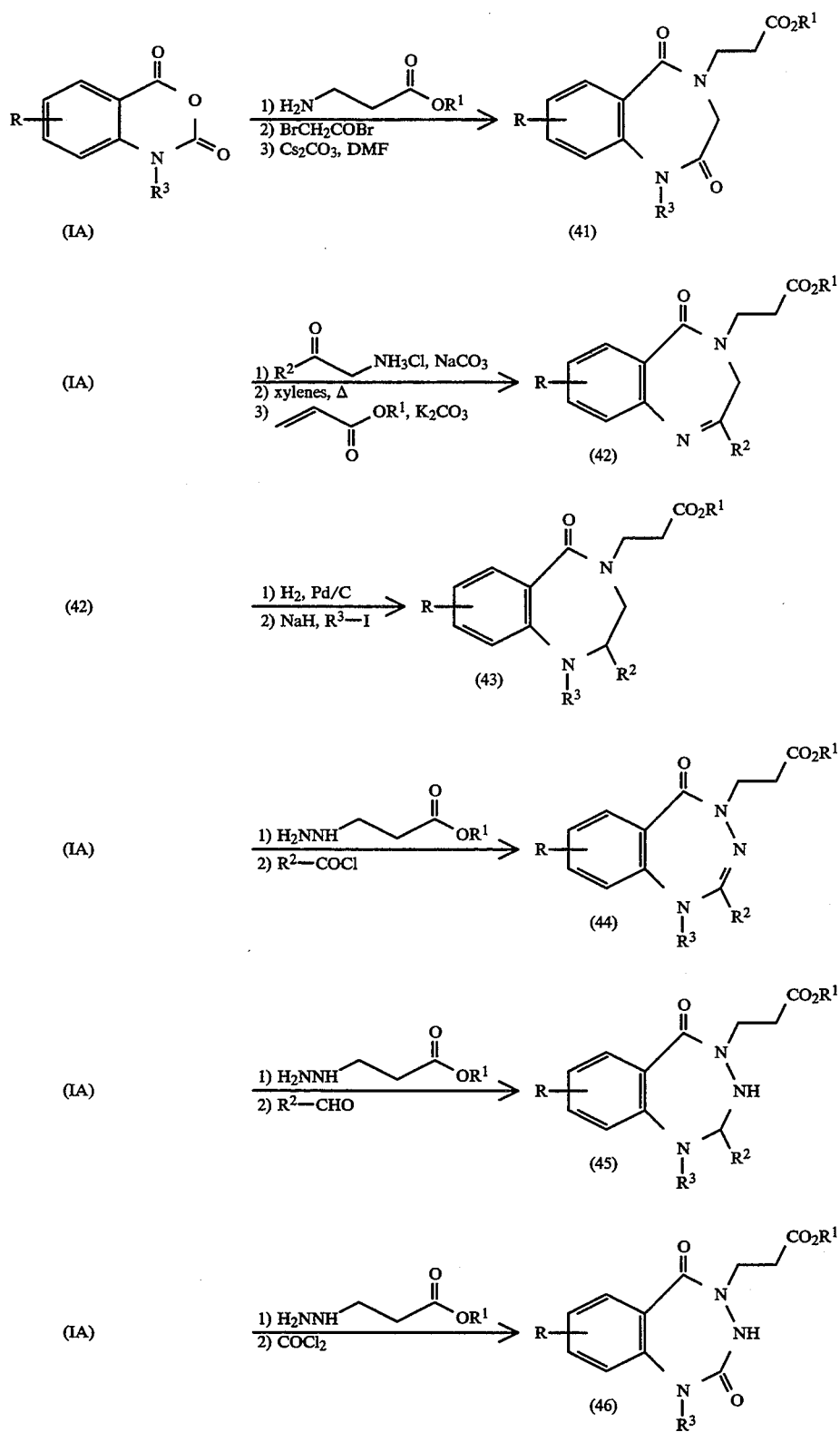

-continued
SCHEME 8
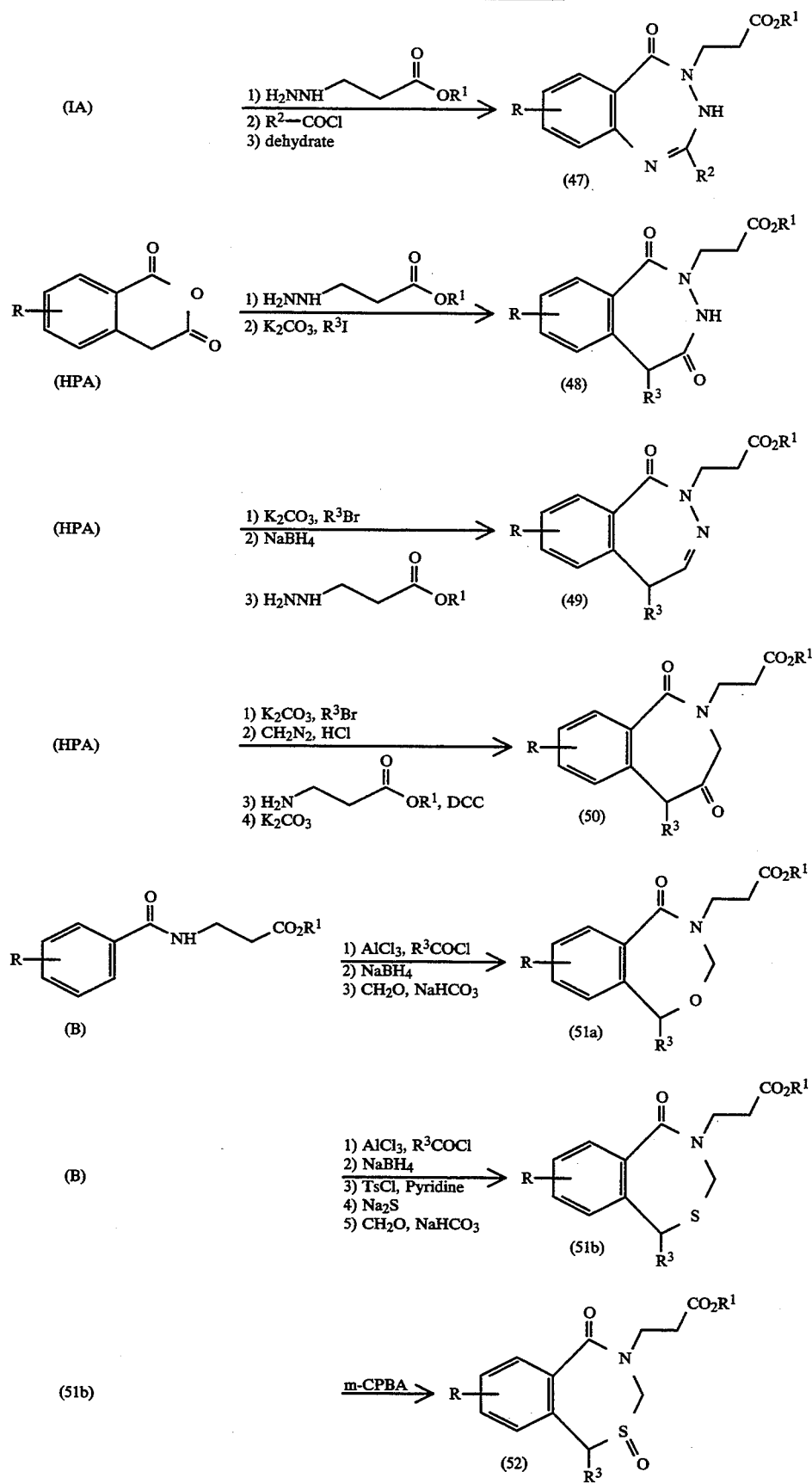

SCHEME 8
(51b) —m-CPBA→ 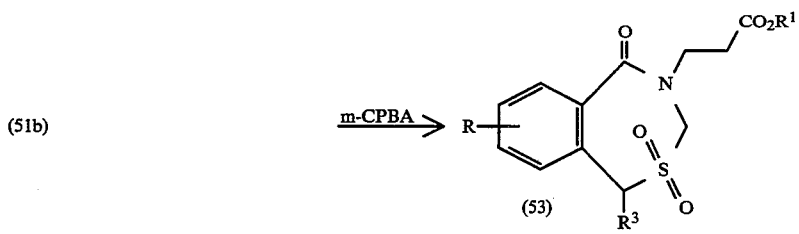
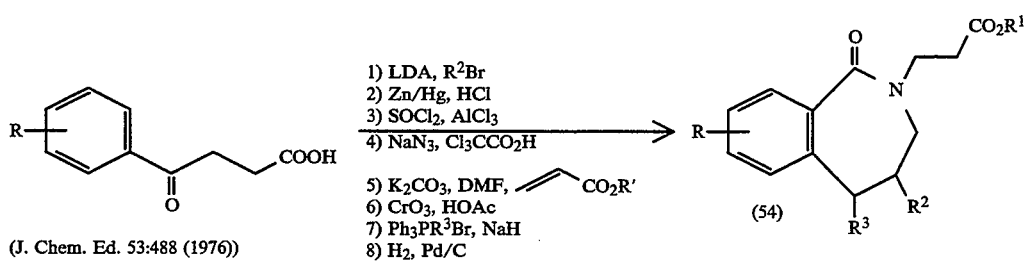
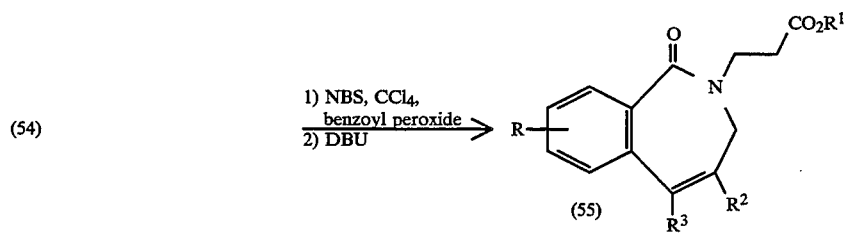
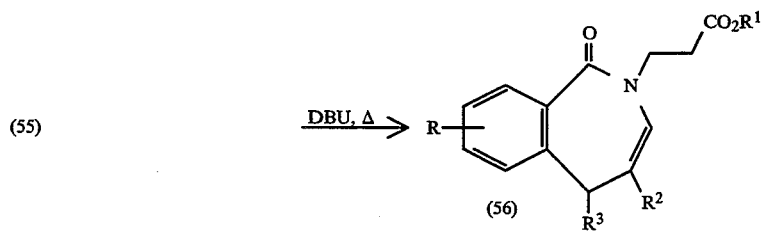
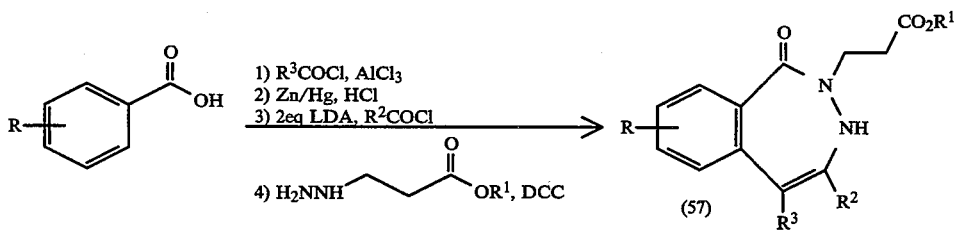
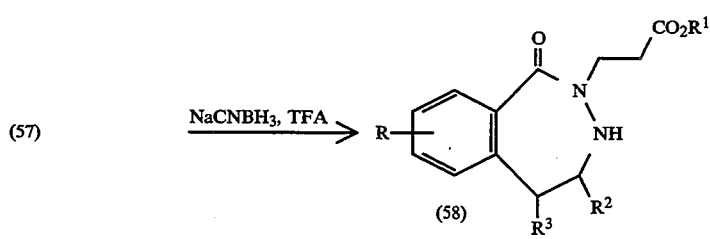

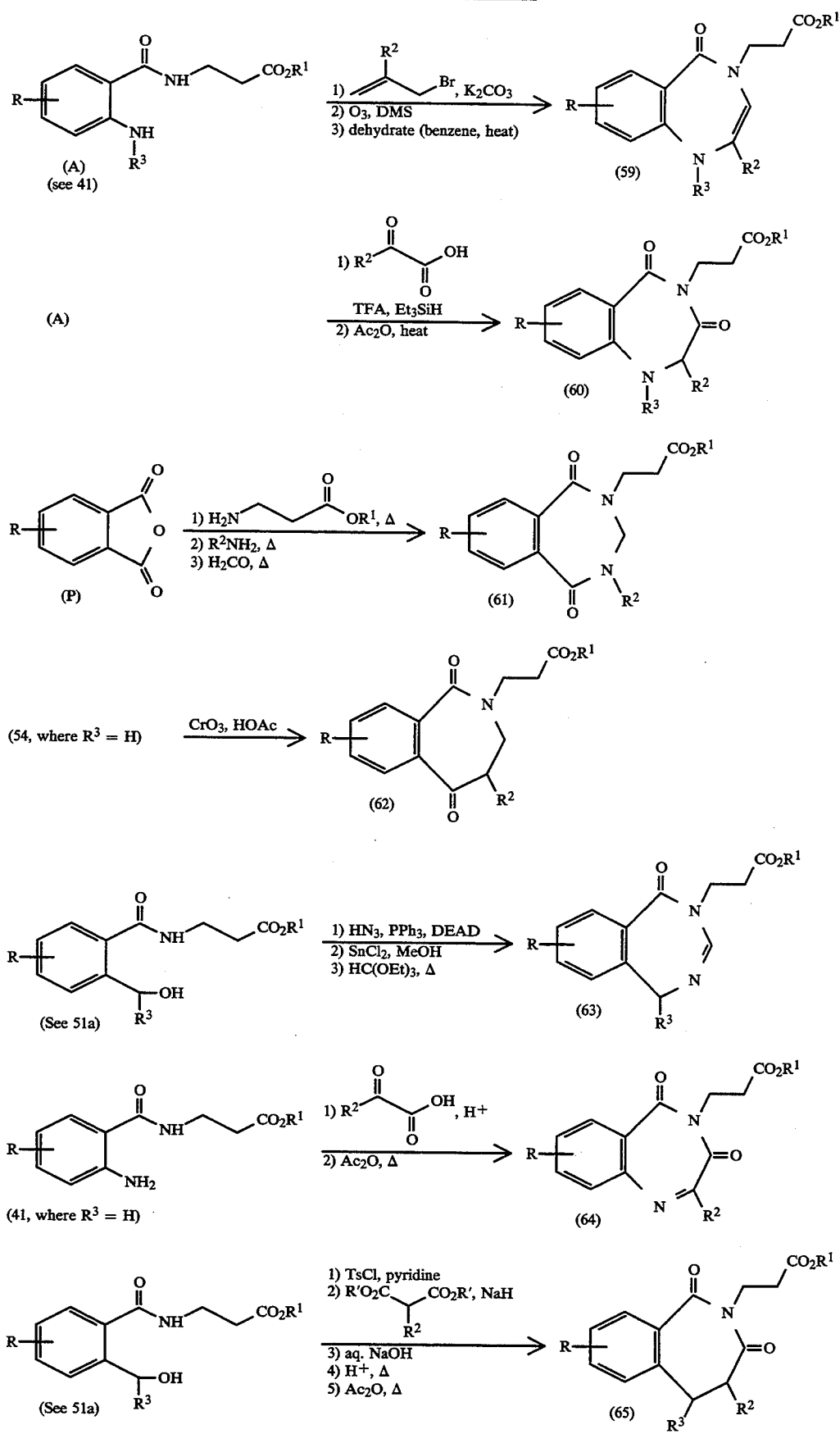

5,403,836
-continued
SCHEME 8
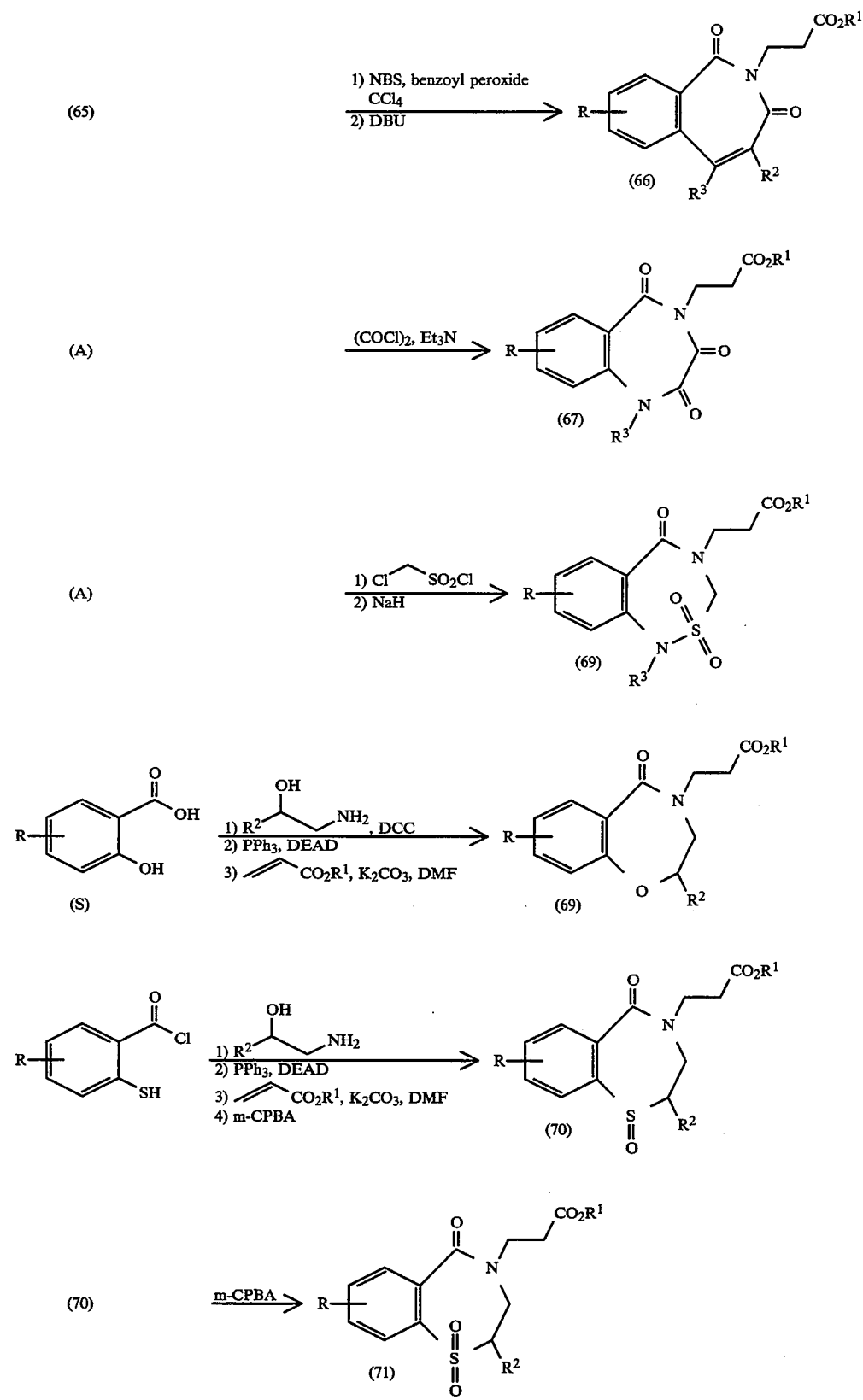

-continued
SCHEME 8

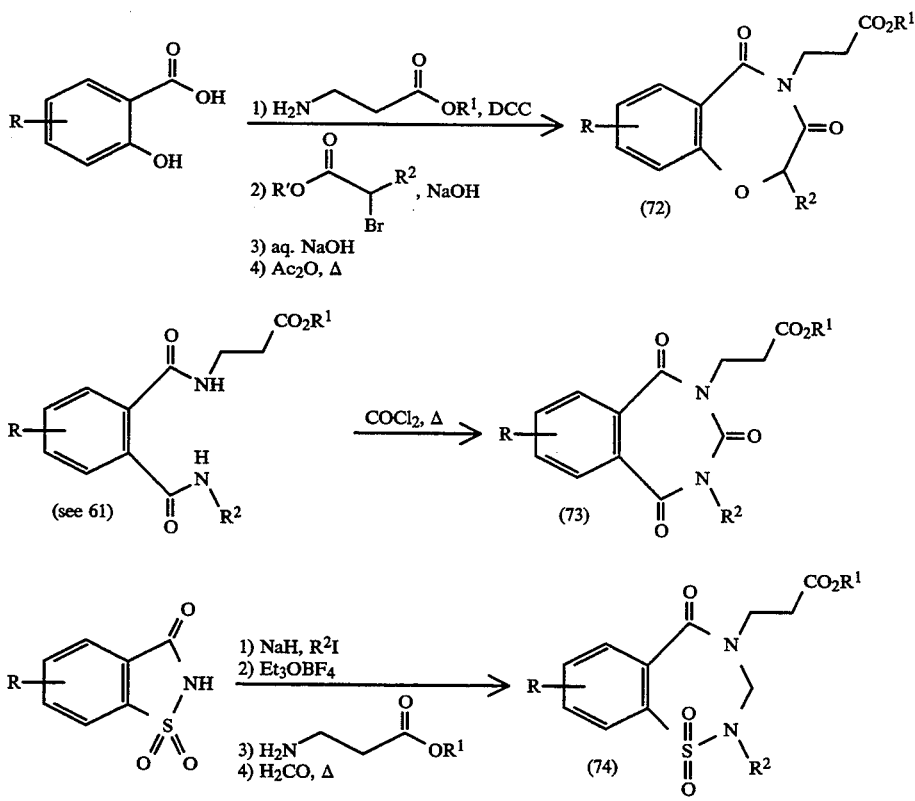

Starting reagents imployed in scheme 8 are either commercially available or readily synthesized by known procedures.

4. Isomeric Products

In products of Formula I carbon atoms bonded to four nonidentical substituents are asymmetric. Accordingly, the compounds may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present in compounds of Formula I, may be in one of two configurations (R or S) and both are within the scope of the present invention.

E. Pharmaceutical Compositions

The compounds described in this invention may be isolated as the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric and the like. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of Formula I with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

In the management of thromboembolic disorders the compounds of this invention may be utilized in compositions such as tablets, capsules or elixirs for oral administration; suppositories for rectal administration; sterile solutions or suspensions for injectable administration, and the like. Animals in need of treatment using compounds of this invention can be administered dosages that will provide optimal efficacy. The dose and method of administration will vary from animal to animal and be dependent upon such factors as weight, diet, concurrent medication and other factors which those skilled in the medical arts will recognize.

Dosage formulations of the nonpeptidyl inhibitors of the present invention are prepared for storage or administration by mixing the inhibitor having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as Tween, Pluronics or polyethyleneglycol.

Dosage formulations of the nonpeptidyl inhibitors of the present invention to be used for therapeutic administration must be sterile. Sterility is readily accomplished by filtration through sterile filtration membranes such as 0.2 micron membranes. Nonpeptidyl inhibitor formulations ordinarily will be stored in lyophilized form or as an aqueous solution. The pH of the cyclic inhibitor preparations typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by hypodermic injection needle, other methods of administration are also anticipated such as suppositories, aerosols, oral dosage formulations and topical formulations such as ointments, drops and dermal patches.

Therapeutic nonpeptidyl inhibitor formulations generally are placed into a container having a sterile access port, for example, an intravenous solution bag or vial having a stopper pierceable by hypodermic injection needle.

Therapeutically effective dosages may be determined by either in vitro or in vivo methods. For each particular nonpeptidyl inhibitor of the present invention, individual determinations may be made to determine the optimal dosage required. The range of therapeutically effective dosages will naturally be influenced by the route of administration. For injection by hypodermic needle it may be assumed the dosage is delivered into the body's fluids. For other routes of administration, the absorption efficiency must be individually determined for each inhibitor by methods well known in pharmacology.

The range of therapeutic dosages is from about 0.001 nM to 1.0 mM, more preferably from 0.1 nM to 100 mM, and most preferably from 1.0 nM to 50 mM.

Typical formulation of compounds of Formula I as pharmaceutical compositions are discussed below.

About 0.5 to 500 mg of a compound or mixture of compounds of Formula I, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

F. Platelet Inhibition Assays

Evaluation of the Formula I inhibitors of the fibrinogen-platelet interaction is guided by in vitro receptor binding assays and in vitro platelet aggregation inhibition assays.

In-vitro biological activity of the compounds of Formula I are monitored using a modified fibrinogen-GPIIbIIIa ELISA based on the method of Nachman and Leung (*J. Clin. Invest.* 69:263–269 (1982)) which measures the inhibition of fibrinogen binding to purified human platelet GPIIbIIIa receptor. Human fibrinogen is prepared by the method of Lipinska, et al. (*J. Lab. Clin. Med.* 84:509–516 (1974)). Platelet GPII$_b$III$_a$ is prepared by the method of Fitzgerald, et al., *Anal. Biochem.*, 151:169–177 (1985).

Briefly, microfiter plates are coated with fibrinogen (10 mg/ml) and then blocked with TACTS buffer containing 0.5% bovine serum albumin (BSA). (TACTS buffer contains 20 mM Tris.HCl, pH 7.5, 0.02% sodium azide, 2 mM calcium chloride, 0.05% Tween 20, 150 mM sodium chloride.) The plate is washed with phosphate buffered saline (PBS) containing 0.01% Tween 20 and the sample to be determined added, followed by addition of solubilized GP IIbIIIa receptor (40 mg/ml) in TACTS, 0.5% BSA. After incubation, the plate is washed and 1 mg/ml of murine anti-platelet monoclonal antibody AP3 (Newman et al., *Blood* 65:227–232 (1985)) is added. After another wash a goat anti-mouse IgG conjugated to horseradish peroxidase is added. A final wash is performed and developing reagent buffer (10 mg o-phenylenediamine dihydrochloride, 0.0212% hydrogen peroxide, 0.22 mM citrate, 50 mM phosphate, pH 5.0) is added and then incubated until color develops. The reaction is stopped with 1N sulfuric acid and the absorbance at 492 nm is recorded.

In addition to the GPII$_b$III$_a$ ELISA assay, platelet aggregation assays may be performed in human platelet rich plasma (PRP). Fifty milliliters of whole human blood (9 parts) is drawn on 3.6% sodium citrate (1 part) from a donor who has not taken aspirin or related medications for at least two weeks. The blood is centrifuged at 160×g for 10 min at 22° C. and then allowed to stand for 5 min after which the PRP is decanted. Platelet poor plasma (PPP) is isolated from the remaining blood after centrifugation at 2000×g for 25 min. The platelet count of the PRP is adjusted to ca. 300,000 per microliter with PPP.

A 225 mL aliquot of PRP plus 25 mL of either a dilution of the test sample or a control (PBS) is incubated for 5 rain in a Chrono-log Whole Blood Aggregometer at 25° C. An aggregating agent (collagen, 1 mg/ml; U46619, 100 ng/ml; or ADP, 8 mM) is added and the platelet aggregation recorded.

Without further description, it is believed that one of ordinary skill in the art can, using the preceding description and illustrative examples, make and utilize the present example to the fullest extent. The following working examples therefore, specifically point out preferred embodiments of the present invention, and are not to be construed as limiting in any way the remainder of the disclosure.

All references cited herein are expressly incorporated by reference.

EXAMPLES

Example 1

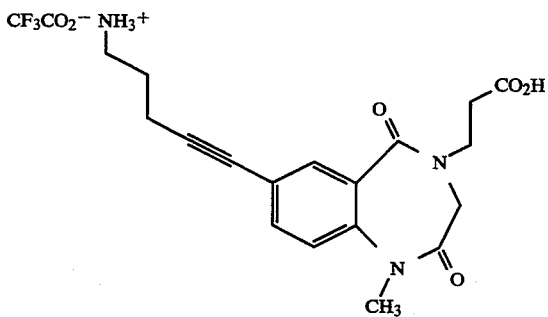

1-methyl-4-(2-carboxyethyl)-7-(5-amino-1-pentynyl)-3,4-dihydro-1H-1,4-benzodiazepine-2,5-dione trifluroacetate.

a) To a mechanically stirred solution of 26.3 grams of 5-iodo-2-amino benzoic acid (0.1 mol), 10.6 grams of sodium carbonate (0.1 mol), and 250 mL water, cooled to 0° C., was slowly added, via an addition funnel, 80 mL of a 1.93M solution of phosgene in toluene. After 2 hours, the precipitated product was isolated by filtration. The solids were washed with 200 mL water, 300 mL of a 1:1 mixture ethanol and ether, 200 mL of ether, and dried under vacuum to yield 24.3 grams (84%) of 5-iodoisatoic anhydride (264°–268° C., decomposition).

b) A magnetically stirred solution of 5 grams of 5-iodoisatoic anhydride (0.0173 mol), 5.85 grams of β-alanine benzyl ester tosylate (0.0173 mol), 35 mL pyridine, and 0.5 of dimethylaminopyridine (0.0041 mol) was heated to 80° C. for 2 hrs. The reaction mixture was allowed to cool to room temperature and concentrated in vacuo. The resulting residue was dissolved in 100mL ethyl acetate and washed 2×50 mL of 10% cupric sulfate, 1×50 mL sat. sodium bicarbonate, 1×50 mL brine, dried over sodium sulfate, filtered and concentrated in vacuo. The product was further purified by column chromatography, using silica gel, eluting with a 1:1 mixture of ethyl acetate and hexane (TLC, SIO$_2$, 1:1 EtOAc/hexane, R$_f$=0.65, vv positive) to yield 1.85 grams (25%) of N-(2-amino-5-iodobenzoyl)-β-alanine benzyl ester. $^1$H NMR (CDCl$_3$, δTMS) 7.54 (1H, d, $^4J_{HH}$=2 Hz, Ar—H o—CON), 7.42 (1H, dd, $^3J_{HH}$=9 Hz, $^4J_{HH}$=2 Hz, Ar—H p—CON), 7.38–7.32 (5H, s, ArH Ph), 6.65 (1H, bt, $^3J_{HH}$=6 Hz, CONH), 6.46 (1H, d, $^3J_{HH}$=9 Hz, Ar—H m—CON), 5.16 (2H, s, OCH$_2$), 3.68 (2H, q, $^3J_{HH}$=6 Hz, NCH$_2$), 2.69 (2H, t, $^3J_{HH}$=6 Hz, CH$_2$CO$_2$). $^{13}$C NMR (CDCl$_3$,δTMS) 172.4, 167.8, 148.2, 140.6, 135.6, 135.5, 128.7, 128.4, 128.3, 119.3, 118.1, 76.3, 66.7, 35.2, 34.0.

Using the above procedure, but substituting the appropriate 3-aminoproprionate alkyl ester for β-alanine ethyl ester and N-substituted-5-iodo-isatoic anhydride for 5-iodoisatoic arthydride there may be prepared, for example, the following compounds:

ethyl N-(2-amino-5-iodobenzoyl)-3-amino-3-methyl-propanoate,
ethyl N-(2-amino-5-iodobenzoyl)-3-amino-3-phenyl-propanoate,
ethyl N-(2-amino-5-iodobenzoyl)-3-amino-3-(3-(methoxycarbonyl)phenyl)propanoate,
t-butyl N-[N-(2-amino-5-iodobenzoyl)-L-(β-benzyl)-aspartinate,
ethyl N-[N-(2-amino-5-iodobenzoyl)-L-aspartyl-(β-benzyl ester)]-glycinate,
ethyl N-[N-(2-amino-5-iodobenzoyl)-L-aspartyl-(β-benzyl ester)]-valinate,
ethyl N-[N-(2-amino-5-iodobenzoyl)-L-aspartyl-(β-benzyl ester)]phenylalaninate,
ethyl N-(2-(N-methyl)-amino-5-iodobenzoyl)-3-amino-3-methylpropanoate,
ethyl N-(2-(N-methyl)-amino-5-iodobenzoyl)-3-amino-3-phenylpropanoate,
ethyl N-(2-(N-methyl)-amino-5-iodobenzoyl)-3-amino-3-(3-(methoxycarbonyl)phenyl)propanoate,
t-butyl N-[N-[2-(N-methyl)-amino-5-iodobenzoyl]-(±)-(β-benzyl)-aspartinate,
ethyl N-[N-(2-(N-methyl)-amino-5-iodobenzoyl)-(±)-aspartyl-(β-benzyl ester)]-glycinate,
ethyl N-[N-(2-(N-methyl)-amino-5-iodobenzoyl)-(±)-aspartyl-(β-benzyl ester)]-valinate,
ethyl N-[N-(2-(N-methyl)-amino-5-iodobenzoyl)-(±)-aspartyl-(β-benzyl ester)]-phenylalaninate,
ethyl N-(2-(N-phenyl)-amino-5-iodobenzoyl)-3-amino-3-methylpropanoate,
ethyl N-(2-(N-phenyl)-amino-5-iodobenzoyl)-3-amino-3-phenylpropanoate,
ethyl N-(2-(N-phenyl)-amino-5-iodobenzoyl)-3-amino-3-[3-(methoxycarbonyl)phenyl]propanoate,
t-butyl N-[N-[2-(N-phenyl)-amino-5-iodobenzoyl]-(±)-(β-benzyl)-aspartinate,
ethyl N-[N-(2-(N-phenyl)-amino-5-iodobenzoyl)-(±)-aspartyl-β-benzyl ester)]-glycinate,
ethyl N-[N-(2-(N-phenyl)-amino-5-iodobenzoyl)-(±)-aspartyl-(β-benzyl ester)]-valinate,
ethyl N-[N-(2-(N-phenyl)-amino-5-iodobenzoyl)-(±)-aspartyl-(β-benzyl ester)]-phenylalaninate,
ethyl N-(2-(N-benzyl)-amino-5-iodobenzoyl)-3-amino-3-methylpropanoate,
ethyl N-(2-(N-benzyl)-amino-5-iodobenzoyl)-3-amino-3-phenylpropanoate,
ethyl N-(2-(N-benzyl)-amino-5-iodobenzoyl)-3-amino-3-(3-(methoxycarbonyl)phenyl)propanoate,
t-butyl N-[N-[2-(N-benzyl)-amino-5-iodobenzoyl]-(±)-(β-benzyl)-aspartinate,
ethyl N-[N-(2-(N-benzyl)-amino-5-iodobenzoyl)-(±)-aspartyl-(β-benzyl ester)]-glycinate,
ethyl N-[N-(2-(N-benzyl)-amino-5-iodobenzoyl)-(±)-aspartyl-([β-benzyl ester)]-valinate,
ethyl N-[N-(2-(N-benzyl)-amino-5-iodobenzoyl)-(±)-aspartyl-(β-benzyl ester)]-phenylalaninate,
ethyl N-(2-(N-isopropyl)-amino-5-iodobenzoyl)-3-amino-3-methylpropanoate,
ethyl N-(2-(N-isopropyl)-amino-5-iodobenzoyl)-3-amino-3-phenylpropanoate,
ethyl N-(2-(N-isopropyl)-amino-5-iodobenzoyl)-3-amino-3-(3-(methoxycarbonyl)phenyl) propanoate,
t-butyl N-[N-[2-(N-isopropyl)-amino-5-iodobenzoyl]-(±)-(β-benzyl)-aspartinate,
ethyl N-[N-(2-(N-isopropyl)-amino-5-iodobenzoyl)-(±)-aspartyl-(β-benzyl ester)]-glycinate,
ethyl N-[N-(2-(N-isopropyl)-amino-5-iodobenzoyl)-(±)-aspartyl-(β-benzyl ester)]-valinate, ethyl N-[N-(2-(N-isopropyl)-amino-5-iodobenzoyl)-(±)-aspartyl-(β-benzyl ester)]-phenylalaninate, c) A magnetically stirred solution of 0.848 gram of N-(2-amino-5-iodobenzoyl)-β-alanine ethyl ester (2.0 mmol), 0.35 mL 2,6-lutidine (3.0 mmol), 0.19 mL methyl iodide (3.0 mmol), and 15 mL dimethylformamide was heated to 50° C. for 15 hours. The reaction mixture was allowed to cool to room temperature and concentrated in vacuo. The resulting residue was disolved in 75 mL ethyl acetate and washed 1×50 mL 10% citric acid, 1×50 mL sat. sodium bicarbonate, 1×50 mL brine, dried over magnesium sulfate, filtered and concentrated in vacuo. The resulting oil was further purified by column chromatography, using silica gel, eluting with a solvent gradient of 35/65 ethyl acetate/hexane to 65/35 ethyl acetate/hexane (TLC, $SiO_2$, 1:1 EtOAc/hexane, $R_f=0.84$, vv positive) to yield 305 mgs (35%) of N-(2-methylamino-5-iodobenzoyl)-β-alanine benzyl ester. $^1$H NMR ($CDCl_3$, δTMS) 7.56 (2H, m, Ar—H o,p—CON), 7.43 (1H, bq, $^3J_{HH}=5$ Hz, NHMe), 7.38-7.32 (5H, s, ArH Ph), 6.62 (1H, bt, $^3J_{HH}=6$ Hz, CONH), 6.42 (1H, d, $^3J_{HH}=9$ Hz, Ar—H m—CON), 5.16 (2H, s, $OCH_2$), 3.64 (2H, q, $^3J_{HH}=6$ Hz, $NCH_2$), 2.81 (3H, d, $^3J_{HH}=5$ Hz, $NCH_3$), 2.64 (2H, t, $^3J_{HH}=6$ Hz, $CH_2CO_2$). $^{13}$C NMR ($CDCl_3$, δTMS) 172.4, 168.4, 148.8, 141.0, 135.5, 128.7, 128.4, 128.3, 117.3, 113.4, 74.1, 66.7, 35.2, 34.0, 29.6.

d) To a magnetically stirred solution of 0.305 grms of N-(2-methylamino-5-iodobenzoyl)-β-alanine benzyl ester (0.69 mmol), 3 mL methylene chloride, and 0.144 mL triethylamine (1.04 mmol), cooled to −30° C. under an atmosphere of nitrogen was slowly added 0.09 mL of α-bromoacetylbromide (1.04 mmol) as a solution in 2 mL methylene chloride. The reaction mixture was allowed to warm to room temperature and stir for 2 hours. The mixture was diluted with 40 mL methylene chloride and washed with 1×50 10% citric acid, 1×50 sat. sodium bicarbonate, dried over sodium sulfate, filtered and concentrated in vacuo. The resulting residue was dissolved in 3 mL dimethylformamide and added, via an addition funnel, to a slurry of 25 mgs sodium hydride (1.04 mmol) in 2 mL dimethylformamide that was cooled to 0° C. After 2 hours, the mixture was poured over 50 mL of an ice cooled solution of 10% citric acid and extracted with 3×40 mL ethyl acetate. The combined organic layers were washed with 1×50 mL sat. sodium bicarbonate, dried over magnesium sulfate, and concentrated in vacuo. The resulting residue was further purified by column chromatography, using silica gel, eluting with a solvent gradient of 40:60 ethyl acetate/hexane to 70:30 ethyl acetate/hexane to yield 0.16 gms (49%) of 1-methyl-4-(2-carboxyethyl)-7-iodo-3,4-dihydro-1H-1,4-benzodiazepine-2,5-dione benzyl ester (TLC, $SiO_2$, 1:1 ethyl acetate/hexane, $R_f=0.48$, vv positive). $^1$H NMR ($CDCl_3$, δTMS) 8.15 (1H, d, $^4J_{HH}=2$ Hz, Ar—H o—CON), 7.78 (1H, dd, $^4J_{HH}=2$ Hz, $^3J_{HH}=9$ Hz, Ar—H p—CON), 6.90 (1H, d, $^3J_{HH}=9$ Hz, Ar—H m—CON), 5.1 (2H, s, $OCH_2$), 3.92 (1H, d, $^2J_{HH}=14$ Hz, COCHHN), 3.90 (2H, t, $^3J_{HH}=8$ Hz, $NCH_{2l}$ ),3.82 (1H, d, $^2J_{HH}=14$ Hz, COCHHN) 3.27 (3H, s, $NCH_{3l}$), 2.82 (1H, dt, $^2J_{HH}=19$ Hz, $^3J_{HH}=9$ Hz, $CHHCO_{2l}$ ), 2.68 (1H, dt, $^2J_{HH}=19$ Hz, $^3J_{HH}=9$ Hz, $CHHCO_2$).

Using the above procedure, but substituting the appropriate N-(2-amino-5-iodobenzoyl)-β-alanine alkyl ester for N-(2-methylamino-5-iodobenzoyl)-β-alanine benzyl ester and α-substituted-α-halo acetyl halide for α-bromo acetyl bromide there may be prepared, for example, the following compounds:

1-methyl-4-(3-ethoxy-1-methyl-3-oxo-1-propyl)-7-iodo-3,4-dihydro-1H-1,4-benzodiazepine-2,5-dione, 1-methyl-4-(3-ethoxy-1-phenyl-3-oxo-1-propyl)-7-iodo-3,4-dihydro-1H-benzodiazepine-2,5-dione, (±)-1-methyl-4-[2-(1-t-butoxy-4-benzyloxy)succinyl)]-7-iodo-3,4-dihydro-1H-1,4-benzodiazepine-2,5-dione, (±)-1-methyl-4-[2-(1-benzyloxyglycinyl-4-benzyloxy)succinyl)]-7-iodo-3,4-dihydro-1H-1,4-benzodiazepine-2,5-dione, (±)-1-methyl-4-[2-(1-benzyloxyvalinyl-4-benzyloxy)succinyl)]-7-iodo-3,4-dihydro-1H-1,4-benzodiazepine-2,5-dione, (±)-1-methyl-4-[2-(1-benzyloxyphenylalanyl-4-benzyloxy)succinyl)]-7-iodo-3,4-dihydro-1H-1,4-benzodiazepine-2,5-dione, 1-phenyl-4-(3-ethoxy-1-methyl-3-oxo-1-propyl)-7-iodo-3,4-dihydro-1H-1,4-benzodiazepine-2,5-dione, 1-phenyl-4-(3-ethoxy-1-phenyl-3-oxo-1-propyl)-7-iodo-3,4-dihydro-1H-1,4-benzodiazepine-2,5-dione, (±)-1-phenyl-4-[2-(1-t-butoxy-4-benzyloxy)succinyl)]-7-iodo-3,4-dihydro-1H-1,4-benzodiazepine-2,5-dione, (±)-1-phenyl-4-[2-(1-benzyloxyglycinyl-4-benzyloxy)succinyl)]-7-iodo-3,4-dihydro-1H-1,4-benzodiazepine-2,5-dione, (±)-1-phenyl-4-[2-(1-benzyloxyvalinyl-4-benzyloxy)succinyl)]-7-iodo-3,4-dihydro-1H-1,4-benzodiazepine-2,5-dione, (±)-1-phenyl-4-[2-(1-benzyloxyphenylalanyl-4-benzyloxy)succinyl)]-7-iodo-3,4-dihydro-1H-1,4-benzodiazepine-2,5-dione, 1-benzyl-4-(3-ethoxy-1-methyl-3-oxo-1-propyl)-7-iodo-3,4-dihydro-1H-1,4-benzodiazepine-2,5-dione, 1-benzyl-4-(3-ethoxy-1-phenyl-3-oxo-1-propyl)-7-iodo-3,4-dihydro-1H-1,4-benzodiazepine-2,5-dione, (±)-1-benzyl-4-[2-(1-t-butoxy-4-benzyloxy)succinyl)]-7-iodo-3,4-dihydro-1H-1,4-benzodiazepine-2,5-dione, (±)-1-benzyl-4-[2-(1-benzyloxyglycinyl-4-benzyloxy)succinyl)]-7-iodo-3,4-dihydro-1H-1,4-benzodiazepine-2,5-dione, (±)-1-benzyl-4-[2-(1-benzyloxyvalinyl-4-benzyloxy)succinyl)]-7-iodo-3,4-dihydro-1H-1,4-benzodiazepine-2,5-dione, (±)-1-benzyl-4-[2-(1-benzyloxyphenylalanyl-4-benzyloxy)succinyl)]-7-iodo-3,4-dihydro-1H-1,4-benzodiazepine-2,5-dione, 1-isopropyl-4-(3-ethoxy-1-methyl-3-oxo-1-propyl)-7-iodo-3,4-dihydro-1H-1,4-benzodiazepine-2,5-dione, 1-isopropyl-4-(3-ethoxy-1-phenyl-3-oxo-1-propyl)-7-iodo-3,4-dihydro-1H-1,4-benzodiazepine-2,5-dione, (±)-1-isopropyl-4-[2-(1-t-butoxy-4-benzyloxy)succinyl)]-7-iodo-3,4-dihydro-1H-1,4-benzodiazepine-2,5-dione, (±)-1-isopropyl-4-[2-(1-benzyloxyglycinyl-4-benzyloxy)succinyl)]-7-iodo-3,4-dihydro-1H-1,4-benzodiazepine-2,5-dione, (±)-1-isopropyl-4-[2-(1-benzyloxyvalinyl-4-benzyloxy)succinyl)]-7-iodo-3,4-dihydro-1H-1,4-benzodiazepine-2,5-dione, (±)-1-isopropyl-4-[2-(1-benzyloxyphenylalanyl-4-benzyloxy)succinyl)]-7-iodo-3,4-dihydro-1H-1,4-benzodiazepine-2,5-dione, 1-methyl-3-phenyl-4-(3-ethoxy-1-methyl-3-oxo-1-propyl)-7-iodo-3,4-dihydro-1H-1,4-benzodiazepine-2,5-dione, 1-methyl-3-phenyl-4-(3-ethoxy-1-phenyl-3-oxo-1-propyl)-7-iodo-3,4-dihydro-1H-1,4-benzodiazepine-2,5-dione, (±)-1-methyl-3-phenyl-4-[2-(1-t-butoxy-4-benzyloxy)succinyl)]-7-iodo-3,4-dihydro-1H-1,4-benzodiazepine-2,5-dione, (±)-1-methyl-3-phenyl-4-[2-(1-benzyloxyglycinyl-4-benzyloxy)succinyl)]-7-iodo-3,4-dihydro-1H-1,4-benzodiazepine-2,5-dione, (±)-1-methyl-3-phenyl-4-[2-(1-benzyloxyvalinyl-4-benzyloxy)succinyl)]-7-iodo-3,4-dihydro-3-phenyl-1H-1,4-benzodiazepine-2,5-dione, (±)-1-methyl-3-phenyl-4-[2-(1-benzyloxyphenylalanyl-4-benzyloxy)succinyl)]-7-iodo-3,4-dihydro-1H-1,4-benzodiazepine-2,5-dione, 1,3-diphenyl-4-(3-ethoxy-1-methyl-3-oxo-1-propyl)-7-iodo-3,4-dihydro-1H-1,4-benzodiazepine-2,5-dione, 1,3-diphenyl-4-(3-ethoxy-1-phenyl-3-oxo-1-propyl)-7-iodo-3,4-dihydro-1H-1,4-benzodiazepine-2,5-dione, (±)-1,3-diphenyl-4-[2-(1-t-butoxy-4-benzyloxy)succinyl)]-7-iodo-3,4-dihydro-1H-1,4-benzodiazepine-2,5-dione, (±)-1,3-diphenyl-4-[2-(1-benzyloxyglycinyl-4-benzyloxy)succinyl)]-7-iodo-3,4-dihydro-1H-1,4-benzodiazepine-2,5-dione, (±)-1,3-diphenyl-4-[2-(1-benzyloxyvalinyl-4-benzyloxy)succinyl)]-7-iodo-3,4-dihydro-1H-1,4-benzodiazepine-2,5-dione, (±)-1,3-diphenyl-4-[2-(1-benzyloxyphenylalanyl-4-benzyloxy)succinyl)]-7-iodo-3,4-dihydro-1H-1,4-benzodiazepine-2,5-dione, 1-benzyl-3-phenyl-4-(3-ethoxy-1-methyl-3-oxo-1-propyl)-7-iodo-3,4-dihydro-1H-1,4-benzodiazepine-2,5-dione, 1-benzyl-3-phenyl-4-(3-ethoxy-1-phenyl-3-oxo-1-propyl)-7-iodo-3,4-dihydro-1H-1,4-benzodiazepine-2,5-dione, (±)-1-benzyl-3-phenyl-4-[2-(1-t-butoxy-4-benzyloxy)succinyl)]-7-iodo-3,4-dihydro-1H-1,4-benzodiazepine-2,5-dione, (±)-1-benzyl-3-phenyl-4-[2-(1-benzyloxyglycinyl-4-benzyloxy)succinyl)]-7-iodo-3,4-dihydro-1H-1,4-benzodiazepine-2,5-dione, (±)-1-benzyl-3-phenyl-4-[2-(1-benzyloxyvalinyl-4-benzyloxy)succinyl)]-7-iodo-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-iodo-3,4-dihydro-1H-1,4-benzodiazepine-2,5-dione, 1-isopropyl-3-phenyl-4-(3-ethoxy-1-methyl-3-oxo-1-propyl)-7-iodo-3,4-dihydro-1H-1,4-benzodiazepine-2,5-dione, 1-isopropyl-3-phenyl-4-(3-ethoxy-1-phenyl-3-oxo-1-propyl)-7-iodo-3,4-dihydro-1H-1,4-benzodiazepine-2,5-dione, (±)-1-isopropyl-3-phenyl-4-[2-(1-t-butoxy-4-benzyloxy)succinyl)]-7-iodo-3,4-dihydro-1H-1,4-benzodiazepine-2,5-dione, (±)-1-isopropyl-3-phenyl-4-[2-(1-benzyloxyglycinyl-4-benzyloxy)succinyl)]-7-iodo-3,4-dihydro-1H-1,4-benzodiazepine-2,5-dione, (±)-1-isopropyl-3-phenyl-4-[2-(1-benzyloxyvalinyl-4-benzyloxy)succinyl)]-7-iodo-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-iodo-3,4-dihydro-1H-1,4-benzodiazepine-2,5-dione, e) To a magnetically stirred solution of 9.13 grams hex-5-ynoic acid (0.081 mol), 7.12 mL triethylamine (0.051 mol), 30 mL tert-butanol, was added 17.7 mL diphenylphosphoryl azide (0.082 mol) and the mixture heated to reflux for 3 hours. The reaction mixture was allowed to cool to room temperature and poured over a biphasic mixture of 200 mL water and 200 mL ether. The layers were separated and the organic layer was washed 1×50 mL 5% ethylene-diaminetetraacetic acid disodium salt, 1×50 mL 10% sodium bicarbonate, 1×50 mL brine, dried over magnesium sulfate and activated carbon, filtered and concentrated in vacuo. The resulting residue was further purified by column chromatography, using silica gel, eluting with 1:1 ether/hexane (TLC, $SiO_2$, 1:3 ethyl acetate/hexane, $R_f=0.18$, ninhydrin char) to yield 3.8 grams (25%) N-boc-5-amino-1-pentyne. $^1$H NMR ($CDCl_3$, δTMS) 4.65 (1H, bs, NH), 3.22 (2H, q, $^3J_{HH}=6$ Hz, $NCH_{2l}$), 2.23 (2H, dt, $^3J_{HH}=6$ Hz, $^4J_{HH}=3$ Hz, $CH_2ClC$), 1.98 (1H, t, $^4J_{HH}=3$ Hz, ClCH), 1.73 (2H, p, $^3J_{HH}=6$ Hz, $CH_{2l}$), 1.42 (9H, s, t—Bu)

f) To a magnetically stirred solution of 160 mgs 1-methyl-2-(carboxyethyl)-7-iodo-3,4-dihydro-1H-1,4-benzodiazepine-2,5-dione benzyl ester (0.335 mmol) in 5 mL ethyl acetate, degassed of oxygen, under an atmosphere of nitrogen was added 123 mgs N-boc-5-amino-1-pentyne (0.67 mmol), 10 mgs bis-triphenylphosphine palladium dichloride (0.014 mmol), 5 mgs cuprous iodide (0.026 mmol) and 0.233 mL triethylamine (1.675 mmol). After 2 hours, the reaction mixture was diluted with 50 mL ethyl acetate and washed 2×50 mL 10% citric acid, 2×50 mL sat. sodium bicarbonate, dried over magnesium sulfate, filtered, and concentrated in vacuo. The resulting residue was further purified by column chromatography, using silica gel, eluting with a solvent gradient of 50:50 ethyl acetate/hexane to 75:25 ethyl acetate/hexane (TLC, $SiO_2$, 1:1 ethyl acetate/hexane, $R_f=0.39$, uv positive) to yield 90 mgs (50%) 1-methyl-4-(2-carboxyethyl)-7-(N-boc-5-amino-1-pentynyl)-3,4-dihydro-1H-1,4-benzodiazepine-2,5-dione ethyl ester. $^1$H NMR ($CDCl_3$, δTMS) 7.85 (1H, d, $^4J_{HH}=2$ Hz, Ar—H o—CON), 7.48 (1H, dd, $^4J_{HH}=2$ Hz, $^3J_{HH}=8$ Hz, Ar—H p—CON), 7.32 (5H, s, Ph), 7.06 (1H, d, $^3J_{HH}=8$ Hz, Ar—H m—CON), 5.10 (2H, s, $OCH_{2l}$), 4.67 (1H, bs, NH), 3.95 (1H, d, $^2J_{HH}=15$ Hz, NCHHCO), 3.91 (2H, t, $^3J_{HH}=7$ Hz, $NCH_2$), 3.81 (1H, d, $^2J_{HH}=15$ Hz, NCHHCO), 3.29 (3H, s, $NCH_3$), 3.26 (2H, q, $^3J_{HH}=7$ Hz, $BocNHCH_{2l}$), 2.82 (1H, dt, $^2J_{HH}=16$ Hz, $^3J_{HH}=8$ Hz, $CHHCO_{2l}$), 2.69 (1H, dt, $^2J_{HH}=16$ Hz, $^3J_{HH}=8$ Hz, $CHHCO_{2l}$), 2.46 (2H, t, $^3J_{HH}=7$ Hz, $C\!\!\int CCH_2$), 1.78 (2H, p, $^3J_{HH}=7$ Hz, $CH_2CH_2CH_2$).

Using the above procedure, but substituting the appropriate 7-iodo-3,4-dihydro-1H-1,4-benzodiazepine-2,5-dione for 1-methyl-2-(carboxyethyl)-7-iodo-3,4-dihydro-1H-1,4-benzodiazepine-2,5-dione benzyl ester and alkyne for N-boc-5-amino-1-pentyne there may be prepared, for example, the following compounds:

1-methyl-4-(3-ethoxy-1-methyl-3-oxo-1-propyl)-7-[5-(N-Boc)-amino-1-pentyne]-3,4-dihydro-1H-1,4-benzodiazepine-2,5-dione, 1-methyl-4-(3-ethoxy-1-phenyl-3-oxo-1-propyl)-7-[5-(N-Boc)-amino-1-pentyne]-3,4-dihydro-1H-1,4-benzodiazepine-2,5-dione, (±)-1-methyl-4-[2-(1-t-butoxy-4-benzyloxy)succinyl)]-7-[5-(N-Boc)-amino-1-pentyne]-3,4-dihydro-1H-1,4-benzodiazepine-2,5-dione, (±)-1-methyl-4-[2-(1-benzyloxyglycinyl-4-benzyloxy)succinyl)]-7-[5-(N-Boc)-amino-1-pentyne]-3,4-dihydro-1H-1,4-benzodiazepine-2,5-dione, (±)-1-methyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione, (±)-1-methyl-4-[2-(1-benzyloxyphenylalanyl-4-benzyloxy)succinyl)]-7-[5-(N-Boc)-amino-1-pentyne]-3,4-dihydro-1H-1,4-benzodiazepine-2,5-dione, 1-phenyl-4-(3-ethoxy-1-methyl-3-oxo-1-propyl)-7-[5-(N-Boc)-amino-1-pentyne]-3,4-dihydro-1H-1,4-benzodiazepine-2,5-dione, 1-phenyl-4-(3-ethoxy-1-phenyl-3-oxo-1-propyl)-7-[5-(N-Boc)-amino-1-pentyne]-3,4-dihydro-1H-1,4-benzodiazepine-2,5-dione, (±)-1-phenyl-4-[2-(1-t-butoxy-4-benzyloxy)succinyl)]-7-[5-(N-Boc)-amino-1-pentyne]-3,4-dihydro-1H-1,4-benzodiazepine-2,5-dione, (±)-1-phenyl-4-[2-(1-benzyloxyglycinyl-4-benzyloxy)succinyl)]-7-[5-(N-Boc)-amino-1-pentyne]-3,4-dihydro-1H-1,4-benzodiazepine-2,5-dione, (±)-1-phenyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione, (±)-1-phenyl-4-[2-(1-benzyloxyphenylalanyl-4-benzyloxy)succinyl)]-7-[5-(N-Boc)-amino-1-pentyne]-3,4-dihydro-1H-1,4-benzodiazepine-2,5-dione, 1-benzyl-4-(3-ethoxy-1-methyl-3-oxo-1-propyl)-7-[5-(N-Boc)-amino-1-pentyne]-3,4-dihydro-1H-1,4-benzodiazepine-2,5-dione, 1-benzyl-4-(3-ethoxy-1-phenyl-3-oxo-1-propyl)-7-[5-(N-Boc)-amino-1-pentyne]-3,4-dihydro-1H-1,4-benzodiazepine-2,5-dione, (±)-1-benzyl-4-[2-(1-t-butoxy-4-benzyloxy)succinyl)]-7-[5-(N-Boc)-amino-1-pentyne]-3,4-dihydro-1H-1,4-benzodiazepine-2,5-dione, (±)-1-benzyl-4-[2-(1-benzyloxyglycinyl-4-benzyloxy)succinyl)]-7-[5-N-Boc)-amino-1-pentyne]-3,4-dihydro-1H-1,4-benzodiazepine-2,5-dione, (±)-1-benzyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione, (±)-1-benzyl-4-[2-(1-benzyloxyphenylalanyl-4-benzyloxy)succinyl)]-7-[5-(N-Boc)-amino-1-pentyne]-3,4-dihydro-1H-1,4-benzodiazepine-2,5-dione, 1-isopropyl-4-(3-ethoxy-1-methyl-3-oxo-1-propyl)-7-[5-(N-Boc)-amino-1-pentyne]-3,4-dihydro-1H-1,4-benzodiazepine-2,5-dione, 1-isopropyl-4-(3-ethoxy-1-phenyl-3-oxo-1-propyl)-7-[5-(N-Boc)-amino-1-pentyne]-3,4-dihydro-1H-1,4-benzodiazepine-2,5-dione, (±)-1-isopropyl-4-[2-(1-t-butoxy-4-benzyloxy)succinyl)]-7-[5-(N-Boc)-amino-1-pentyne]-3,4-dihydro-1H-1,4-benzodiazepine-2,5-dione, (±)-1-isopropyl-4-[2-(1-benzyloxyglycinyl-4-benzyloxy)succinyl)]-7-[5-(N-Boc)-amino-1-pentyne]-3,4-dihydro-1H-1,4-benzodiazepine-2,5-dione, (±)-1-isopropyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione, (±)-1-isopropyl-4-[2-(1-benzyloxyphenylalanyl-4-benzyloxy)succinyl)]-7-[5-(N-Boc)-amino-1-pentyne]-3,4-dihydro-1H-1,4-benzodiazepine-2,5-dione, 1-methyl-4-(3-ethoxy-1-methyl-3-oxo-1-propyl)-7-[5-cyano-1-pentyne]-3,4-dihydro-1H-1,4-benzodiazepine-2,5-dione, 1-methyl-4-(3-ethoxy-1-phenyl-3-oxo-1-propyl)-7-[5-cyano-1-pentyne]-3,4-dihydro-1H-1,4-benzodiazepine-2,5-dione, (±)-1-methyl-4-[2-(1-t-butoxy-4-benzyloxy)succinyl)]-7-[5-cyano-1-pentyne]-3,4-dihydro-1H-1,4-benzodiazepine-2,5-dione, (±)-1-methyl-4-[2-(1-benzyloxyglycinyl-4-benzyloxy)succinyl)]-7-[5-cyano-1-pentyne]-3,4-dihydro-1H-1,4-benzodiazepine-2,5-dione, (±)-1-methyl-4-[2-(1-benzyloxyvalinyl-4-benzyloxy)succinyl)]-7-[5-cyano-1-pentyne]-3,4-dihydro-1H-1,4-benzodiazepine-2,5-dione, (±)-1-methyl-4-[2-(1-benzyloxyphenylalanyl-4-benzyloxy)succinyl)]-7-[5-cyano-1-pentyne]-3,4-dihydro-1H-1,4-benzodiazepine-2,5-dione, 1-phenyl-4-(3-ethoxy-1-methyl-3-oxo-1-propyl)-7-[5-cyano-1-pentyne]-3,4-dihydro-1H-1,4-benzodiazepine-2,5-dione, 1-phenyl-4-(3-ethoxy-1-phenyl-3-oxo-1-propyl)-7-[5-cyano-1-pentyne]-3,4-dihydro-1H-1,4-benzodiazepine-2,5-dione, (±)-1-phenyl-4-[2-(1-t-butoxy-4-benzyloxy)succinyl)]-7-[5-cyano-1-pentyne]-3,4-dihydro-1H-1,4-benzodiazepine-2,5-dione, (±)-1-phenyl-4-[2-(1-benzyloxyglycinyl-4-benzyloxy)succinyl)]-7-[5-cyano-1-pentyne]-3,4-dihydro-1H-1,4-benzodiazepine-2,5-dione, (±)-1-phenyl-4-[2-(1-benzyloxyvalinyl-4-benzyloxy)succinyl)]-7-[5-cyano-1-pentyne]-3,4-dihydro-1H-1,4-benzodiazepine-2,5-dione, (±)-1-phenyl-4-[2-(1-benzyloxyphenylalanyl-4-benzyloxy)succinyl)]-7-[5-cyano-1-pentyne]-3,4-dihydro-1H-1,4-benzodiazepine-2,5-dione, 1-benzyl-4-(3-ethoxy-1-methyl-3-oxo-1-propyl)-7-[5-cyano-1-pentyne]-3,4-dihydro-1H-1,4-benzodiazepine-2,5-dione, 1-benzyl-4-(3-ethoxy-1-phenyl-3-oxo-1-propyl)-7-[5-cyano-1-pentyne]-3,4-dihydro-1H-1,4-benzodiazepine-2,5-dione, (±)-1-benzyl-4-[2-(1-t-butoxy-4-benzyloxy)succinyl)]-7-[5-cyano-1-pentyne]-3,4-dihydro-1H-1,4-benzodiazepine-2,5-dione, (±)-1-benzyl-4-[2-(1-benzyloxyglycinyl-4-benzyloxy)succinyl)]-7-[5-cyano-1-pentyne]-3,4-dihydro-1H-1,4-benzodiazepine-2,5-dione, (±)-1-benzyl-4-[2-(1-benzyloxyvalinyl-4-benzyloxy)succinyl)]-7-[5-cyano-1-pentyne]-3,4-dihydro-1H-1,4-benzodiazepine-2,5-dione, (±)-1-benzyl-4-[2-(1-benzyloxyphenylalanyl-4-benzyloxy)succinyl)]-7-[5-cyano-1-pentyne]-3,4-dihydro-1H-1,4-benzodiazepine-2,5-dione, 1-isopropyl-4-(3-ethoxy-1-methyl-3-oxo-1-propyl)-7-[5-cyano-1-pentyne]-3,4-dihydro-1H-1,4-benzodiazepine-2,5-dione, 1-isopropyl-4-(3-ethoxy-1-phenyl-3-oxo-1-propyl)-7-[5-cyano-1-pentyne]-3,4-dihydro-1H-1,4-benzodiazepine-2,5-dione, (±)-1-isopropyl-4-[2-(1-t-butoxy-4-benzyloxy)succinyl)]-7-[5-cyano-1-pentyne]-3,4-dihydro-1H-1,4-benzodiazepine-2,5-dione, (±)-1-isopropyl-4-[2-(1-benzyloxyglycinyl-4-benzyloxy)succinyl)]-7-[5-cyano-1-pentyne]-3,4-dihydro-1H-1,4-benzodiazepine-2,5-dione, (±)-1-isopropyl-4-[2-(1-benzyloxyvalinyl-4-benzyloxy)succinyl)]-7-[5-cyano-1-pentyne]-3,4-dihydro-1H-1,4-benzodiazepine-2,5-dione, (±)-1-isopropyl-4-[2-(1-benzyloxyphenylalanyl-4-benzyloxy)succinyl)]-7-[5-cyano-1-pentyne]-3,4-dihydro-1H-1,4-benzodiazepine-2,5-dione, 1-methyl-4-(3-ethoxy-1-methyl-3-oxo-1-propyl)-7-[2-(3-cyanophenyl)-1-ethyne]-3,4-dihydro-1H-1,4-benzodiazepine-2,5-dione, 1-methyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-methyl-4-[2-(1-t-butoxy-4-benzyloxy)succinyl)]-7-[2-(3-cyanophenyl)-1-ethyne]-3,4-dihydro-1H-1,4-benzodiazepine-2,5-dione, (±)-1-methyl-4-[2-(1-benzyloxyglycinyl-4-benzyloxy)succinyl)]-7-[2-(3-cyanophenyl)-1-ethyne]-3,4-dihydro-1H-1,4-benzodiazepine-2,5-dione, (±)-1-methyl-4-[2-(1-benzyloxyvalinyl-4-benzyloxy)succinyl)]-7-[2-(3-cyanophenyl)-1-ethyne]-3,4-dihydro-1H-1,4-benzodiazepine-2,5-dione, (±)-1-methyl -4-[2-(1-benzyloxyphenylalanyl-4-benzyloxy)succinyl)]-7-[2-(3-cyanophenyl)-1-ethyne]-3,4-dihydro-1H-1,4-benzodiazepine-2,5-dione, 1-phenyl-4-(3-ethoxy-1-methyl-3-oxo-1-propyl)-7-[2-(3-cyanophenyl)-1-ethyne]-3,4-dihydro-1H-1,4-benzodiazepine-2,5-dione, 1-phenyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-phenyl-4-[2-(1-t-butoxy-4-benzyloxy)succinyl)]-7-[2-(3-cyanophenyl)-1-ethyne]-3,4-dihydro-1H-1,4-benzodiazepine-2,5-dione, (±)-1-phenyl-4-[2-(1-benzyloxyglycinyl-4-benzyloxy)succinyl)]-7-[2-(3-cyanophenyl)-1-ethyne]-3,4-dihydro-1H-1,4-benzodiazepine-2,5-dione, (±)-1-phenyl-4-[2-(1-benzyloxyvalinyl-4-benzyloxy)succinyl)]-7-[2-(3-cyanophenyl)-1-ethyne]-3,4-dihydro-1H-1,4-benzodiazepine-2,5-dione, (±)-1-phenyl-4-[2-(1-benzyloxyphenylalanyl-4-benzyloxy)succinyl)]-7-[2-(3-cyanophenyl)-1-ethyne]-3,4-dihydro-1H-1,4-benzodiazepine-2,5-dione, 1-benzyl-4-(3-ethoxy-1-methyl-3-oxo-1-propyl)-7-[2-(3-cyanophenyl)-1-ethyne]-3,4-dihydro-1H-1,4-benzodiazepine-2,5-dione, 1-benzyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-benzyl-4-[2-(1-t-butoxy-4-benzyloxy)succinyl)]-7-[2-(3-cyanophenyl)-1-ethyne]-3,4-dihydro-1H-1,4-benzodiazepine-2,5-dione, (±)-1-benzyl-4-[2-(1-benzyloxyglycinyl-4-benzyloxy)succinyl)]-7-[2-(3-cyanophenyl)-1-ethyne]-3,4-dihydro-1H-1,4-benzodiazepine-2,5-dione, (±)-1-benzyl-4-[2-(1-benzyloxyvalinyl-4-benzyloxy)succinyl)]-7-[2-(3-cyanophenyl)-1-ethyne]-3,4-dihydro-1H-1,4-benzodiazepine-2,5-dione, (±)-1-benzyl-4-[2-(1-benzyloxyphenylalanyl-4-benzyloxy)succinyl)]-7-[2-(3 -cyanophenyl)-1-ethyne]-3,4-dihydro-1H-1,4-benzodiazepine-2,5-dione, 1-isopropyl-4-(3-ethoxy-1-methyl-3-oxo-1-propyl)-7-[2-(3-cyanophenyl)-1-ethyne]-3,4-dihydro-1H-1,4-benzodiazepine-2,5-dione, 1-isopropyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-isopropyl-4-[2-(1-t-butoxy-4-benzyloxy)succinyl)]-7-[2-(3-cyanophenyl)-1-ethyne]-3,4-dihydro-1H-1,4-benzodiazepine-2,5-dione, (±)-1-isopropyl-4-[2-(1-benzyloxyglycinyl-4-benzyloxy)succinyl)]-7-[2-(3-cyanophenyl)-1-ethyne]-3,4-dihydro-1H-1,4-benzodiazepine-2,5-dione, (±)-1-isopropyl-4-[2-(1-benzyloxyvalinyl-4-benzyloxy)succinyl)]-7-[2-(3cyanophenyl)-1-ethyne]-3,4-dihydro-1H-1,4-benzodiazepine-2,5-dione, (±)-1-isopropyl-4-[2-(1-benzyloxyphenylalanyl-4-benzyloxy)succinyl)]-7-[2-(3-cyanophenyl)-1-ethyne]-3,4-dihydro-1H-1,4-benzodiazepine-2,5-dione, 1-methyl-4-(3-ethoxy-1-methyl-3-oxo-1-propyl)-7-[2-(4-nitrophenyl)-1-ethyne]-3,4-dihydro-1H-1,4-benzodiazepine-2,5-dione, 1-methyl-4-(3-ethoxy-1-phenyl-3-oxo-1-propyl)-7-[2-(4-nitrophenyl)-1-ethyne]-3,4-dihydro-1H-1,4-benzodiazepine-2,5-dione, (±)-1-methyl-4-[2-(1-t-butoxy-4-benzyloxy)succinyl)]-7-[2-(4-nitrophenyl)-1-ethyne]-3,4-dihydro-1H-1,4-benzodiazepine-2,5-dione, (±)-1-methyl-4-[2-(1-benzyloxyglycinyl-4-benzyloxy)succinyl)]-7-[2-(4-nitrophenyl)-1-ethyne]-3,4-dihydro-1H-1,4-benzodiazepine-2,5-dione, (±)-1-methyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1-methyl -4-[2-(1-benzyloxyphenylalanyl -4-benzyloxy)succinyl)]-7-[2-(4-nitrophenyl)-1-ethyne]-3,4-dihydro-1H-1,4-benzodiazepine-2,5-dione, 1-phenyl-4-(3-ethoxy-1-methyl-3-oxo-1-propyl)-7-[2-(4-nitrophenyl)-1-ethyne]-3,4-dihydro-1H-1,4-benzodiazepine-2,5-dione, 1-phenyl-4-(3-ethoxy-1-phenyl-3-oxo-1-propyl)-7-[2-(4-nitrophenyl)-1-ethyne]-3,4-dihydro-1H-1,4-benzodiazepine-2,5-dione, (±)-1-phenyl-4-[2-(1-t-butoxy-4-benzyloxy)succinyl)]-7-[2-(4-nitrophenyl)-1-ethyne]-3,4-dihydro-1H-1,4-benzodiazepine-2,5-dione, (±)-1-phenyl-4-[2-(1-benzyloxyglycinyl-4-benzyloxy)succinyl)]-7-[2-(4-nitrophenyl)-1-ethyne]-3,4-dihydro-1H-1,4-benzodiazepine-2,5-dione, (±)-1-phenyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1-phenyl-4-[2-(1-benzyloxyphenylalanyl-4-benzyloxy)succinyl)]-7-[2-(4-nitrophenyl)-1-ethyne]-3,4-dihydro-1H-1,4-benzodiazepine-2,5-dione, 1-benzyl-4-(3-ethoxy-1-methyl-3-oxo-1-propyl)-7-[2-(4-nitrophenyl)-1-ethyne]-3,4-dihydro-1H-1,4-benzodiazepine-2,5-dione, 1-benzyl-4-(3-ethoxy-1-phenyl-3-oxo-1-propyl)-7-[2-(4-nitrophenyl)-1-ethyne]-3,4-dihydro-1H-1,4-benzodiazepine-2,5-dione, (±)-1-benzyl-4-[2-(1-t-butoxy-4-benzyloxy)succinyl)]-7-[2-(4-nitrophenyl)-1-ethyne]-3,4-dihydro-1H-1,4-benzodiazepine-2,5-dione, (±)-1-benzyl-4-[2-(1-benzyloxyglycinyl-4-benzyloxy)succinyl)]-7-[2-(4-nitrophenyl)-1-ethyne]-3,4-dihydro-1H-1,4-benzodiazepine-2,5-dione, (±)-1-benzyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1-benzyl-4-[2-(1-benzyloxyphenylalanyl-4-benzyloxy)succinyl)]-7-[2-(4-nitrophenyl)-1-ethyne]-3,4-dihydro-1H-1,4-benzodiazepine-2,5-dione, 1-isopropyl-4-(3-ethoxy-1-methyl-3-oxo-1-propyl)-7-[2-(4-nitrophenyl)-1-ethyne]-3,4-dihydro-1H-1,4-benzodiazepine-2,5-dione, 1-isopropyl-4-(3-ethoxy-1-phenyl-3-oxo-1-propyl)-7-[2-(4-nitrophenyl)-1-ethyne]-3,4-dihydro-1H-1,4-benzodiazepine-2,5-dione,
(±)-1-isopropyl-4-[2-(1-t-butoxy-4-benzyloxy)succinyl)]-7-[2-(4-nitrophenyl)-1-ethyne]-3,4-dihydro-1H-1,4-benzodiazepine-2,5-dione,
(±)-1-isopropyl-4-[2-(1-benzyloxyglycinyl-4-benzyloxy)succinyl)]-7-[2-(4-nitrophenyl)-1-ethyne]-3,4-dihydro-1H-1,4-benzodiazepine-2,5-dione,
(±)-1-isopropyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione,
(±)-1-isopropyl-4-[2-(1-benzyloxyphenylalanyl-4-benzyloxy)succinyl)]-7-[2-(4-nitrophenyl)-1-ethyne]-3,4-dihydro-1H-1,4-benzodiazepine-2,5-dione,
1-methyl-4-(3-ethoxy-1-methyl-3-oxo-1-propyl)-7-[N-[2-(N-Boc)-aminoethane]-3-keto-1-propyn-3-amine]-3,4-dihydro-1H-1,4-benzodiazepine-2,5-dione,
1-methyl-4-(3-ethoxy-1-phenyl-3-oxo-1-propyl)-7-[N-[2-(N-Boc)-aminoethane]-3-keto-1-propyn-3-amine]-3,4-dihydro-1H-1,4-benzodiazepine-2,5-dione,
(±)-1-methyl-4-[2-(1-t-butoxy-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-methyl-4-[2-(1-benzyloxyglycinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-methyl-4-[2-(1-benzyloxyvalinyl-4-benzyloxy)succinyl)]-7-[N-[2-(N-Boc)-aminoethanethane]-3-keto-1-propyn-3-amine]-3,4-dihydro-1H-1,4-benzodiazepine-2,5-dione,
(±)-1-methyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
1-phenyl-4-(3-ethoxy-1-methyl-3-oxo-1-propyl)-7-[N-[2-(N-Boc)-aminoethane]-3-keto-1-propyn-3-amine]-3,4-dihydro-1H-1,4-benzodiazepine-2,5-dione,
1-phenyl-4-(3-ethoxy-1-phenyl-3-oxo-1-propyl)-7-[N-[2-(N-Boc)-aminoethane]-3-keto-1-propyn-3-amine]-3,4-dihydro-1H-1,4-benzodiazepine-2,5-dione,
(±)-1-phenyl-4-[2-(1-t-butoxy-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-phenyl-4-[2-(1-benzyloxyglycinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-phenyl-4-[2-(1-benzyloxyvalinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-phenyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
1-benzyl-4-(3-ethoxy-1-methyl-3-oxo-1-propyl)-7-[N-[2-(N-Boc)-aminoethane]-3-keto-1-propyn-3-amine]-3,4-dihydro-1H-1,4-benzodiazepine-2,5-dione,
1-benzyl-4-(3-ethoxy-1-phenyl-3-oxo-1-propyl)-7-[N-[2-(N-Boc)-aminoethane]-3-keto-1-propyn-3-amine]-3,4-dihydro-1H-1,4-benzodiazepine-2,5-dione,
(±)-1-benzyl-4-[2-(1-t-butoxy-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-benzyl-4-[2-(1-benzyloxyglycinyl-4-benzyloxy)succinyl)]-7-[N-[2-(N-Boc)aminoethane]-3-keto-1-propyn-3-amine]-3,4-dihydro-1H-1,4-benzodiazepine-2,5-dione,
(±)-1-benzyl-4-[2-(1-benzyloxyvalinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-benzyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
1-isopropyl-4-(3-ethoxy-1-methyl-3-oxo-1-propyl)-7-[N-[2-(N-Boc)-aminoethane]-3-keto-1-propyn-3-amine]-3,4-dihydro-1H-1,4-benzodiazepine-2,5-dione,
1-isopropyl-4-(3-ethoxy-1-phenyl-3-oxo-1-propyl)-7-[N-[2-(N-Boc)-aminoethane]-3-keto-1-propyn-3-amine]-3,4-dihydro-1H-1,4-benzodiazepine-2,5-dione,
(±)-1-isopropyl-4-[2-(1-t-butoxy-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-isopropyl-4-[2-(1-benzyloxyglycinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-isopropyl-4-[2-(1-benzyloxyvalinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
(±)-1-isopropyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4-benzodiazepine-2,5-dione,
1-methyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5-dione,
1-methyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5-dione,
(±)-1-methyl-4-[2-(1-t-butoxy-4-benzyloxy)succinyl)]-7-[3-keto-1-propyn-3-[4-(N-Boc)-1-piperizine]]-3,4-dihydro-1H-1,4-benzodiazepine-2,5-dione,
(±)-1-methyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione,
(±)-1-methyl-4-[2-(1-benzyloxyvalinyl-4-benzyloxy)succinyl)]-7-[3-keto-1-propyn-3-[4-(N-Boc)-1-piperizine]]-3,4-dihydro-1H-1,4-benzodiazepine-2,5-dione,
(±)-1-methyl-4-[2-(1-benzoyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione,
1-phenyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5-dione,
1-phenyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5-dione,
(±)-1-phenyl-4-[2-(1-t-butoxy-4-benzyloxy)succinyl)]-7-[3-keto-1-propyn-3-[4-(N-Boc)-1-piperizine]]-3,4-dihydro-1H-1,4-benzodiazepine-2,5-dione,
(±)-1-phenyl4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione,
(±)-1-phenyl-4-[2-(1-benzyloxyvalinyl-4-benzyloxy)succinyl)]-7-[3-keto-1-propyn-3-[4-(N-Boc)-1- piperizine]]-3,4-dihydro-1H-1,4-benzodiazepine-2,5-dione, (±)-1-phenyl-4-[2-(1-benzyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione, 1-benzyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5-dione, 1-benzyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5-dione, (±)-1-benzyl-4-[2-(1-t-butoxy-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-benzyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-benzyl-4-[2-(1-benzyloxyvalinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-benzyl-4-[2-(1-benzyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione, 1-isopropyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5-dione, 1-isopropyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5-dione, (±)-1-isopropyl-4-[2-(1-t-butoxy-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-isopropyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-isopropyl-4-[2-(1-benzyloxyvalinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-isopropyl-4-[2-(1-benzyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione, 1-methyl-4-(3-ethoxy-1-methyl-3-oxo-1-propyl)-7-[2-[2-(N-Boc)aminoethanethiol]-1-ethyne]-3,4-dihydro-1H-1,4-benzodiazepine-2,5-dione, 1-methyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1-methyl-4-[2-(1-t-butoxy-4-benzyloxy)succinyl)]-7-[2-[2-(N-Boc)aminoethanethiol]-1-ethyne]-3,4-dihydro-1H-1,4-benzodiazepine-2,5-dione, (±)-1-methyl-4-[2-(1-benzyloxyglycinyl-4-benzyloxy)succinyl)]-7-[2-[2-(N-Boc)aminoethanethiol]-1ethyne]-3,4-dihydro-1H-1,4-benzodiazepine-2,5-dione, (±)-1-methyl-4-[2-(1-benzyloxyvalinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-methyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, 1-phenyl-4-(3-ethoxy-1-methyl-3-oxo-1-propyl)-7-[2-[2-(N-Boc)aminoethanethiol]-1-ethyne]-3,4-dihydro-1H-1,4-benzodiazepine-2,5-dione, 1-phenyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1-phenyl-4-[2-(1-t-butoxy-4-benzyloxy)succinyl)]-7-[2-[2-(N-Boc)aminoethanethiol]-1-ethyne]-3,4-dihydro-1H-1,4-benzodiazepine-2,5-dione, (±)-1-phenyl-4-[2-(1-benzyloxyglycinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-phenyl-4-[2-(1-benzyloxyvalinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-phenyl-4-[2-(1-benzyloxyphenylalanyl-4-benzyloxy)succinyl)]-7-[2-[2-(N-Boc))aminoethanethiol]-1-ethyne]-3,4-dihydro-1H-1,4-benzodiazepine-2,5-dione, 1-benzyl-4-(3-ethoxy-1-methyl-3-oxo-1-propyl)-7-[2-[2-(N-Boc)a -1-ethyne]-3,4-dihydro-1H-1,4-benzodiazepine-2,5-dione, 1-benzyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1-benzyl-4-[2-(1-t-butoxy-4-benzyloxy)succinyl)]-7-[2-[2-(N-Boc)aminoethanethiol]-1-ethyne]-3,4-dihydro-1H-1,4-benzodiazepine-2,5-dione, (±)-1-benzyl-4-[2-(1-benzyloxyglycinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-benzyl-4-[2-(1-benzyloxyvalinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-benzyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, 1-isopropyl-4-(3-ethoxy-1-methyl-3-oxo-1-propyl)-7-[2-[2-(N-Boc)aminoethanethiol]-1-ethyne]-3,4-dihydro-1H-1,4-benzodiazepine-2,5-dione, 1-isopropyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1-isopropyl-4-[2-(1-t-butoxy-4-benzyloxy)succinyl)]-7-[2-[2-(N-Boc)aminoethanethiol]-1-ethyne]-3,4-dihydro-1H-1,4-benzodiazepine-2,5-dione, (±)-1-isopropyl-4-[2-(1-benzyloxyglycinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-isopropyl-4-[2-(1-benzyloxyvalinyl-4-benzyloxy)succinyl)]-7-[2-[2(N-Boc)aminoethanethiol]-1-ethyne]-3,4-dihydro-1H-1,4-benzodiazepine-2,5-dione, (±)-1-isopropyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, 1-methyl-4-(3-ethoxy-1-methyl-3-oxo-1-propyl)-7-[2-(4-cyanothiophenol)-1-ethyne]-3,4-dihydro-1H-1,4-benzodiazepine-2,5-dione, 1-methyl4-(3-ethoxy-1-phenyl-3-oxo-1-propyl)-7-[2-(4-cyanothiophenol)-1-ethyne]-3,4-dihydro-1H-1,4-benzodiazepine-2,5-dione, (±)-1-methyl-4-[2-(1-t-butoxy-4-benzyloxy)succinyl)]-7-[2-(4-cyanothiophenol)-1-ethyne]-3,4-dihydro-1H-1,4-benzodiazepine-2,5-dione, (±)-1-methyl-4-[2-(1-benzyloxyglycinyl-4-benzyloxy)succinyl)]-7-[2-(4cyanothiophenol)-1-ethyne]-3,4-dihydro-1H-1,4-benzodiazepine-2,5-dione, (±)-1-methyl-4-[2-(1-benzyloxyvalinyl-4-benzyloxy)succinyl)]-7-[2-(4-cyanothiophenol)-1-ethyne]-3,4-dihydro-1H-1,4-benzodiazepine-2,5-dione, (±)-1-methyl-4-[2-(1-benzyloxyphenylalanyl-4-benzyloxy)succinyl)]-7-[2-(4-cyanothiophenol)-1-ethyne]-3,4-dihydro-1H-1,4-benzodiazepine-2,5-dione, 1-phenyl-4-(3-ethoxy-1-methyl-3-oxo-1-propyl)-7-[2-(4-cyanothiophenol)-1-ethyne]-3,4-dihydro-1H-1,4-benzodiazepine-2,5-dione, 1-phenyl-4-(3-ethoxy-1-phenyl-3-oxo-1-propyl)-7-[2-(4-cyanothiophenol)-1-ethyne]-3,4-dihydro-1H-1,4-benzodiazepine-2,5-dione, (±)-1-phenyl-4-[2-(1-t-butoxy-4-benzyloxy)succinyl)]-7-[2-(4-cyanothiophenol)-1-ethyne]-3,4-dihydro-1H-1,4-benzodiazepine-2,5-dione, (±)-1-phenyl-4-[2-(1-benzyloxyglycinyl-4-benzyloxy)succinyl)]-7-[2-(4cyanothiophenol)-1-ethyne]-3,4-dihydro-1H-1,4-benzodiazepine-2,5-dione, (±)-1-phenyl-4-[2-(1-benzyloxyvalinyl-4-benzyloxy)succinyl)]-7-[2-(4cyanothiophenol)-1-ethyne]-3,4-dihydro-1H-1,4-benzodiazepine-2,5-dione, (±)-1-phenyl-4-[2-(1-benzyloxyphenylalanyl-4-benzyloxy)succinyl)]-7-[2-(4cyanothiophenol)-1-ethyne]-3,4-dihydro-1H-1,4-benzodiazepine-2,5-dione, 1-benzyl-4-(3-ethoxy-1-methyl-3-oxo-1-propyl)-7-[2-(4-cyanothiophenol)-1ethyne]-3,4-dihydro-1H-1,4-benzodiazepine-2,5-dione, 1-benzyl-4-(3-ethoxy-1-phenyl-3-oxo-1-propyl)-7-[2-(4-cyanothiophenol)-1-ethyne]-3,4-dihydro-1H-1,4-benzodiazepine-2,5-dione, (±)-1-benzyl-4-[2-(1-t-butoxy-4-benzyloxy)succinyl)]-7-[2-(4-cyanothiophenol)-1-ethyne]-3,4-dihydro-1H-1,4-benzodiazepine-2,5-dione, (±)-1-benzyl-4-[2-(1-benzyloxyglycinyl-4-benzyloxy)succinyl)]-7-[2-(4-cyanothiophenol)-1-ethyne]-3,4-dihydro-1H-1,4-benzodiazepine-2,5-dione, (±)-1-benzyl-4-[2-(1-benzyloxyvalinyl-4-benzyloxy)succinyl)]-7-[2-(4cyanothiophenol)-1-ethyne]-3,4-dihydro-1H-1,4-benzodiazepine-2,5-dione, (±)-1-benzyl-4-[2-(1-benzyloxyphenylalanyl-4-benzyloxy)succinyl)]-7-[2-(4-cyanothiophenol)-1-ethyne]-3,4-dihydro-1H-1,4-benzodiazepine-2,5-dione, 1-isopropyl-4-(3-ethoxy-1-methyl-3-oxo-1-propyl)-7-[2-(4-cyanothiophenol-1-ethyne]-3,4-dihydro-1H-1,4-benzodiazepine-2,5-dione, 1-isopropyl-4-(3-ethoxy-1-phenyl-3-oxo-1-propyl)-7-[2-(4-cyanothiophenol)-1-ethyne]-3,4-dihydro-1H-1,4-benzodiazepine-2,5-dione, (±)-1-isopropyl-4-[2-(1-t-butoxy-4-benzyloxy)succinyl)]-7-[2-(4-cyanothiophenol)-1-ethyne]-3,4-dihydro-1H-1,4-benzodiazepine-2,5-dione, (±)-1-isopropyl-4-[2-(1-benzyloxyglycinyl-4-benzyloxy)succinyl)]-7-[2-(4cyanothiophenol)-1-ethyne]-3,4-dihydro-1H-1,4-benzodiazepine-2,5-dione, (±)-1-isopropyl-4-[2-(1-benzyloxyvalinyl-4-benzyloxy)succinyl)]-7-[2-4-cyanothiophenol)-1-ethyne]-3,4-dihydro-1H-1,4-benzodiazepine-2,5-dione, (±)-1-isopropyl-4-[2-(1-benzyloxyphenylalanyl-4-benzyloxy)succinyl)]-7-[2-(4cyanothiophenol)-1-ethyne ]-3,4-dihydro-1H-1,4-benzodiazepine-2,5-dione, 1-methyl-4-(3-ethoxy-1-methyl-3-oxo-1-propyl)-7-[4-[2-(N-Boc)amino-6-methylpyrimidine-4-yl ]-4-oxa-1-butyne]-3,4-dihy dro- 1H- 1,4-benzodiazepine-2,5-dione, 1-methyl-4-(3-ethoxy-1-phenyl-3-oxo-1-propyl)-7-[4-[2-(N-Boc)amino-6-methylpyrimidine-4-yl]-4-oxo-1-butyne]-3,4-dihydro-1H-1,4-benzodiazepine-2,5-dione, (±)-1-methyl-4-[2-(1-t-butoxy-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)- 1-methyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro- 1H-1,4-benzodiazepine-2,5-dione, (±)-1-methyl-4-[2-(1-benzyloxyvalinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-methyl-4-[2-(1-benzyloxyphenylalanyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, 1-phenyl-4-(3-ethoxy-1-methyl-3-oxo-1-propyl)-7-[4-[2-(N-Boc)amino-6-ethylpyrimidine-4-yl]-4-oxa-1-butyne]-3,4-dihydro-1H-1,4-benzodiazepine-2,5-dione, 1-phenyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro-1H-1,4-benzodiazepine2,5-dione, (±)-1-phenyl-4-[2-(1-t-butoxy-4-benzyloxy)succinyl)]-7-[4-[2-(N-Boc)amino-6-methylpyrimidine-4-yl]-4-oxa-1-butyne]-3,4-dihydro-1H-1,4-benzodiazepine2,5-dione, (±)-1-phenyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-phenyl-4-[2-(1-benzyloxyvalinyl-4-benzyloxy)succinyl)]-7-[4-[2-(N-Boc)amino-6-methylpyrimidine-4-yl]-4-oxa-1-butyne ]-3,4-dihydro-1H-1,4-benzodiazepine-2,5-dione, (±)-1-phenyl-4-[2-(1-benzyloxyphenylalanyl-4-benzyloxy)succinyl)]-7-[4-[2-(N-Boc)amino-6-methylpyrimidine-4-yl]-4-oxa-1-butyne ]-3,4-dihydro- 1H-1,4-benzodiazepine-2,5-dione, 1-benzyl-4-(3-ethoxy-1-methyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, 1-benzyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro- 1H-1,4-benzodiazepine-2,5-dione, (±)-1-benzyl-4-[2-(1-t-butoxy-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-4-[2-(1-benzyloxyvalinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-4-[2-(1-benzyloxyphenylalanyl-4-benzyloxy)succinyl)]-7-[4-[2-(N-Boc)amino-6-methylpyrimidine-4-yl]-4-oxa-1-butyne ]-3,4-dihydro-1H-1,4-benzodiazepine-2,5-dione, 1-isopropyl-4-(3-ethoxy-1-methyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, 1-isopropyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1-isopropyl-4-[2-(1-t-butoxy-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-isopropyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro- 1H-1,4-benzodiazepine-2,5-dione, (±)-1-isopropyl-4-[2-(1-benzyloxyvalinyl-4-bertzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-isopropyl-4-[2-(1-bertzyloxyphenylalanyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, 1-methyl-4-(3-ethoxy-1-methyl-3-oxo-1-propyl)-7-[5-[2-(N-Boc)aminopyridine-3-yl]-5-oxa-1-pentyne]-3,4-dihydro-H-1,4-benzodiazepine-2,5-dione, 1-methyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-methyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-methyl-4-[2-(1-benzyloxyglycinyl-4-benzyloxy)succinyl)]-7-[5-[2-(N-Boc)aminopyridine-3-yl ]-5-oxa-1-pentyne]-3,4-dihydro-1H-1,4-benzodiazepine-2,5-dione, (±)-1-methyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-methyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, 1-phenyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, 1-phenyl-4-(3-ethoxy-1-phenyl-3-oxo-1-propyl)-7-[5-[2-(N-Box)aminopyridine-3-yl]-5-oxa-1-pentyne]-3,4-dihydro-1H-1,4-benzodiazepine-2,5-dione, (±)-1-phenyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-phenyl-4-[2-(1-benzyloxyglycinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-phenyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-phenyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, 1-benzyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, 1-benzyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-benzyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-benzyl-4-[2-(1-benzyloxyglycinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-benzyl-4-[2-(1-benzyloxyvalinyl4-benzyloxy)succinyl)]-7-[5-[2-(N-Boc)aminopyridine-3-yl]-5-oxa-1-pentyne]-3,4-dihydro-1 H-1,4-benzodiazepine-2,5-dione, (±)-1-benzyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, 1-isopropyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, 1-isopropyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-isopropyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-isopropyl-4-[2-(1-benzyloxyglycinyl-4-benzyloxy)succinyl)]-7-[5-[2-(N-Boc)aminopyridine-3-yl]-5-oxa-1-pentyne]-3,4-dihydro-1H- 1,4-benzodiazepine-2,5-dione, (±)-1-isopropyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-isopropyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-methyl-3-phenyl-4-(3-ethoxy-1-methyl-3-oxo-1-propyl)-7-[5-(N-Boc)-amino-1-pentyne]-3,4-dihydro-1H-1,4-benzodiazepine-2,5-dione, (±)-1-methyl-3-phenyl-4-(3-ethoxy-1-phenyl-3-oxo-1-propyl )-7-[5-(N-Boc)-amino-1-pentyne]-3,4-dihydro-1H-1,4-benzodiazepine-2,5-dione, (±)-1-methyl-3-phenyl-4-[2-(1-t-butoxy-4-benzyloxy)succinyl)]-7-[5-(N-Boc)-amino-1-pentyne]-3,4-dihydro-1H-1,4-benzodiazepine-2,5-dione, (±)-1-methyl-3-phenyl-4-[2-(1-benzyloxyglycinyl-4-benzyloxy)succinyl)]-7-[5-(N-Boc)-amino-1-pentyne]-3,4-dihydro-1H-1,4-benzodiaze pine-2,5-dione, (±)-1-methyl-3-phenyl-4-[2-(1-benzyloxyvalinyl-4-benzyloxy)succinyl)]-7-[5-(N-Boc)-amino--1pentyne]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[5-(N-Boc )-amino-1-pentyne]-3,4-dihydro-1H-1,4-benzodiazepine-2,5-dione, (±)-1,3-diphenyl-4-(3-ethoxy-1-methyl-3-oxo-1-propyl)-7-[5-(N-Boc)-amino-1-pentyne]-3,4-dihydro-1H-1,4-benzodiazepine-2,5-dione,
(±)-1,3-diphenyl-4-(3-ethoxy-1-phenyl-3-oxo-1-propyl)-7-[5-(N-Boc)-amino-1-pentyne]-3,4-dihydro-1H-1,4-benzodiazepine-2,5-dione,
(±)-1,3-diphenyl-4-[2-(1-t-butoxy-4-bertzyloxy)succinyl)]-7-[5-(N-Boc)-amino-1-pentyne]-3,4-dihydro-1H-1,4-benzodiazepine-2,5-dione,
(±)-1,3-diphenyl-4-[2-(1-benzyloxyglycinylat-benzyloxy)succinyl)]-7-[5-(N-Boc)-amino-1-pentyne]-3,4-dihydro-1H-1,4-benzodiazepine-2,5-dione,
(±)-1,3-diphenyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione,
(±)-1,3-diphenyl-4-[2-(1-benzyloxyphenylalanyl-4-benzyloxy)succinyl)]-7-[5-(N-Boc)-amino--pentyne]-3,4-dihydro-1H-1,4-benzodiazepine-2,5-dione,
(±)-1-benzyl-3-phenyl-4-(3-ethoxy-1-methyl-3-oxo-1-propyl)-7-[5-(N-Boc)-amino-1-pentyne]-3,4-dihydro-1H-1,4-benzodiazepine-2,5-dione,
(±)-1-benzyl-3-phenyl-4-(3-ethoxy-1-phenyl-3-oxo-1-propyl)-7-[5-(N-Boc)-amino-1-pentyne]-3,4-dihydro-1H-1,4-benzodiazepine-2,5-dione,
(±)-1-benzyl-3-phenyl-4-[2-(1-t-butoxy-4-benzyloxy)-succinyl)]-7-[5-(N-Boc)-amino-1-pentyne]-3,4-dihydro-1H-1,4-benzodiazepine-2,5-dione,
(±)-1-benzyl-3-phenyl-4-[2-(1-benzyloxyglycinyl-4-benzyloxy)succinyl)]-7-[5-(N-Boc)-amino-1-pentyne]-3,4-dihydro-1H-1,4-benzodiazepine-2,5-dione,
(+)-1-benzyl-3-phenyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione,
(±)-1-benzyl-3-phenyl-4-[2-(1-benzyloxyphenylalanyl-4-benzyloxy)succinyl)]-7-[5-(N-Boc )-amino-1-pentyne]-3,4-dihydro-1H-1,4-benzodiazepine-2,5-dione,
(±)-1-isopropyl-3-phenyl-4-(3-ethoxy-1-methyl-3-oxo-1-propyl)-7-[5-(N-amino-1-pentyne]-3,4-dihydro-1H-1,4-benzodiazepine-2,5-dione,
(±)-1-isopropyl-3-phenyl-4-(3-ethoxy-1-phenyl-3-oxo-1-propyl)-7-[5-(N-Boc)-amino-1-pentyne]-3,4-dihydro-1H-1,4-benzodiazepine-2,5-dione,
(±)-1-isopropyl-3-phenyl-4-[2-(1-t-butoxy-4-benzyloxy)succinyl)]-7-[5-(N-Boc)-amino-1-pentyne]-3,4-dihydro-1H-1,4-benzodiazepine-2,5-dione,
(±)-1-isopropyl-3-phenyl-4-[2-(1-benzyloxyglycinyl-4-benzyloxy)succinyl)]-7-[5-(N-Boc)-amino-1-pentyne]-3,4-dihydro-1H-1,4-benzodiazepine-2,5-dione,
(±)-1-isopropyl-3-phenyl-4-[2-(1-benzyloxyvalinyl-4-benzyloxy)succinyl)]-7-[5-(N-Boc)-amino-1-pentyne]-3,4-dihydro-1H-1,4-benzodiazepine-2,5-dione,
(±)-1-isopropyl-3-phenyl-4-[2-(1-benzyloxyphenylalanyl-4-benzyloxy)succinyl)]7-[5-(N-Boc)-amino-1-pentyne[-3,4-dihydro-1H-1,4-benzodiazepine-2,5-dione,
(±)-1-methyl-3-phenyl-4-(3-ethoxy-1-methyl-3-oxo-1-propyl)-7-[5-cyano-1-pentyne]-3,4-dihydro-1H-1,4-benzodiazepine-2,5-dione,
(±)-1-methyl-3-phenyl-4-(3-ethoxy-1-phenyl-3-oxo-1-propyl)-7-[5-cyano-1-pentyne]-3,4-dihydro-1H-1,4-benzodiazepine-2,5-dione,
(±)-1-methyl-3-phenyl-4-[2-(1-t-butoxy-4-benzyloxy)-succinyl)]-7-[5-cyano-1-pentyne]-3,4-dihydro-1H-1,4-benzodiazepine-2,5-dione,
(±)-1-methyl-3-phenyl-4-[2-(1-benzyloxyglycinyl-4-benzyloxy)succinyl)]-7-[5-cyano-1-pentyne]-3,4-dihydro-1H-1,4-benzodiazepine-2,5-dione,
(±)-1-methyl-3-phenyl-4-[2-(1-benzyloxyv alinyl-4-benzyloxy)succinyl)]-7-[5-cyano-1-pentyne]-3,4-dihydro-1H-1,4-benzodiazepine-2,5-dione,
(±)-1-methyl-3-phenyl-4-[2-(1-benzyloxyphenylalanyl-4-benzyloxy)succinyl)]-7-[5-cyano-1-pentyne]-3,4-dihydro-1H-1,4-benzodiazepine-2,5-dione,
(±)-1,3-diphenyl-4-(3-ethoxy-1-methyl-3-oxo-1-propyl)-7-[5-cyano-1-pentyne]-3,4-dihydro-1H-1,4-benzodiazepine-2,5-dione,
(±)-1,3-diphenyl-4-(3-ethoxy-1-phenyl-3-oxo-1-propyl)-7-[5-cyano-1-pentyne]-3,4-dihydro-1H-1,4-benzodiazepine-2,5-dione,
(±)-1,3-diphenyl-4-[2-(1-t-butoxy-4-benzyloxy)succinyl)]-7-[5-cyano-1 -pentyne]-3,4-dihydro-1H-1,4-benzodiazepine-2,5-dione,
(±)-1,3-diphenyl-4-[2-(1-benzyloxyglycinyl-4-benzyloxy)succinyl)]-7-[5-cyano-1-pentyne]-3,4-dihydro-1H-1,4-benzodiazepine-2,5-dione,
(±)-1,3-diphenyl-4-[2-(1-benzyloxyvalinyl-4-benzyloxy)succinyl)]-7-[5-cyano-1-pentyne]-3,4-dihydro-1H-1,4-benzodiazepine-2,5-dione,
(±)-1,3-diphenyl-4-[2-(1-benzyloxyphenylalanyl-4-benzyloxy)succinyl)]-7-[5-cyano-1-pentyne]-3,4-dihydro-1H-1,4-benzodiazepine-2,5-dione,
(±)-1-benzyl-3-phenyl-4-(3-ethoxy-1-methyl-3-oxo-1-propyl)-7-[5-cyano-1pentyne]-3,4-dihydro-1H-1,4-benzodiazepine-2,5-dione,
(±)-1-benzyl-3-phenyl-4-(3-ethoxy-1-phenyl-3-oxo-1-propyl)-7-[5-cyano-1-pentyne]-3,4-dihydro-1H-1,4-benzodiazepine-2,5-dione,
(±)-1-benzyl-3-phenyl-4-[2-(1-t-butoxy-4-benzyloxy)-succinyl)]-7-[5-cyano-1pentyne]-3,4-dihydro-1H-1,4-benzodiazepine-2,5-dione,
(±)-1-benzyl-3-phenyl-4-[2-(1-benzyloxyglycinyl-4-benzyloxy)succinyl)]-7-[5-cyano-1-pentyne]-3,4-dihydro-1H-1,4-benzodiazepine-2,5-dione,
(±)-1-benzyl-3-phenyl-4-[2-(1-benzyloxyvalinyl-4-benzyloxy)succinyl)-7-[5-cyano-1-pentyne]-3,4-dihydro-1H-1,4-benzodiazepine-2,5-dione,
(±)-1-benzyl-3-phenyl-4-[2-(1-benzyloxyphenylalanyl-4-benzyloxy)succinyl)]-7-[5-cyano-1-pentyne]-3,4-dihydro-1H-1,4-benzodiazepine-2,5-dione,
(±)-1-isopropyl-3-phenyl-4-(3-ethoxy-1-methyl-3-oxo-1-propyl)-7-[5-cyano-1-pentyne]-3,4-dihydro-1H-1,4-benzodiazepine-2,5-dione,
(±)-1-isopropyl-3-phenyl-4-(3-ethoxy-1-phenyl-3-oxo-1-propyl )-7-[5-cyano-1-pentyne]-3,4-dihydro-1H-1,4-benzodiazepine-2,5-dione,
(±)-1-isopropyl-3-phenyl-4-[2-(1-t-butoxy-4-benzyloxy)succinyl)]-7-[5-cyano-1-pentyne]-3,4-dihydro-1H-1,4-benzodiazepine-2,5-dione,
(±)-1-isopropyl-3-phenyl-4-[2-(1-benzyloxyglycinyl-4-benzyloxy)succinyl)]-7-[5-cyano-1-pentyne]-3,4-dihydro-1H-1,4-benzodiazepine-2,5-dione,
(±)-1-isopropyl-3-phenyl-4-[2-(1-benzyloxyvalinyl-4-benzyloxy)succinyl)]-7-[5-cyano-1-pentyne]-3,4-dihydro-1H-1,4-benzodiazep ine-2,5-dione,
(±)-1-isopropyl-3-phenyl-4-[2-(1-benzyloxyphenylalanyl-4-benzyloxy)succinyl)]-7-[5-cyano-1-pentyne]-3,4-dihydro-1H-1,4-benzodiazepine-2,5-dione,
(±)-1-methyl-3-phenyl-4-(3-ethoxy-1-methyl-3-oxo-1-propyl)-7-[2-(3-cyanophenyl)-1-ethyne]-3,4-dihydro-1H-1,4-benzodiazepine-2,5-dione,
(±)-1-methyl-3-phenyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-methyl-3-phenyl-4-[2-(1-t-butoxy-4-benzyloxy)-succinyl)]-7-[2-(3-cyanophenyl)-1-ethyne]-3,4-dihydro-1H-1,4-benzodiazepine-2,5-dione, (±)-1-methyl-3-phenyl-4-[2-(1-benzyloxyglycinyl-4-benzyloxy)succinyl)]-7-[2-(3-cyanophenyl)-1-ethyne]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-(3-cyanopheyl)-1-ethyne]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[2-(3-cyanophenyl)-1-ethyne]-3,4-dihydro-1H-1,4-benzodiazepine-2,5-dione, (±)- 1,3-diphenyl -4-(3-ethoxy-1-methyl-3-oxo-1-propyl)-7-[2-(3cyanophenyl)-1-ethyne]-3,4-dihydro-1H-1,4-benzodiazepine-2,5-dione, (±)-1,3-diphenyl-4-(3-ethoxy-1-phenyl-3-oxo-1-propyl)-7-[2-(3-cyanophenyl )-1-ethyne]-3,4-dihydro-1H-1,4-benzodiazepine-2,5-dione, (±)-1,3-diphenyl-4-[2-(1-t-butoxy-4-benzyloxy)succinyl)]-7-[2-(3-cyanophenyl)-1-ethyne]-3,4-dihydro-1H- 1,4-benzodiazepine-2,5-dione, (±)-1,3-diphenyl-4-[2-(1-benzyloxyglycinyl-4-benzyloxy)succinyl)]-7-[2-(3-cyanophenyl)-1-ethyne]-3,4-dihydro-1H-1,4-benzodiaze p ine-2,5-dione, (±)-1,3-diphenyl-4-[2-(1-benzyloxyvalinyl-4-benzyloxy)succinyl)]-7-[2-(3-cyanophenyl)-1-ethyne]-3,4-dihydro-1H-1,4-benzodiazepine-2,5-dione, (±)-1,3-diphenyl-4-[2-(1-benzyloxyphenylalanyl-4-benzyloxy)succinyl)]-7-[2-(3-cyanopyl)-1-ethyne]-3,4-dihydro-1H-1,4-benzodiazepine-2,5-dione, (±)-1 -benzyl-3-phenyl-4-(3-ethoxy-1-methyl-3-oxo-1-propyl)-7-[2-(3-cyanophenyl)-1-ethyne]-3,4-dihydro-1H-1,4-benzodiazepine-2,5-dione, (±)-1 -benzyl-3-phenyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-benzyl-3-phenyl-4-[2-(1-t-butoxy -4-benzyloxy)succinyl)]-7-[2-(3-cyanophenyl)-1-ethyne]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[2-(3-cyanophenyl)-1-ethyne]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[2-(3-cyanophenyl)-1-ethyne]-3,4-dihydro-1H-1,4-bertzodiazepine-2,5-dione, (±)-1-benzyl-3-phenyl-4-[2-(1-benzyloxyphenylalanyl-4-benzyloxy)succinyl)]-7-[2-(3-cyanophenyl)-1-ethyne]-3,4-dihydro-1H-1,4-benzodiazepine-2,5-dione, (±)-1-isopropyl-3-phenyl-4-(3-ethoxy-1-methyl-3-oxo-1-propyl)-7-[2-(3-cyanophenyl)-1-ethyne]-3,4-dihydro-1H-1,4-benzodiazepine-2,5-dione, (±)-1-isopropyl-3-phenyl-4-(3-ethoxy-1-phenyl-3-oxo-1-propyl)-7-[2-(3-cyanophenyl)-1-ethyne]-3,4-dihydro-1H-1,4-benzodiazepine-2,5-dione, (±)-1-isopropyl-3-phenyl-4-[2-(1-t-butoxy-4-benzyloxy)succinyl)]-7-[2-(3-cyanophenyl)-1-ethyne]-3,4-dihydro-1H-1,4-benzodiazepine-2,5-dione, (±)-1-isopropyl-3-phenyl-4-[2-(1-benzyloxyglycinyl-4-bertzyloxy)succinyl)]-7-[2-(3-cyanophenyl)-1-ethyne]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[2-(3-cyanophenyl)-1-ethyne]-3,4-dihydro-1H-1,4-bertzodiazepine-2,5-dione, (±)-1-isopropyl-3-phenyl-4-[2-(1-benzyloxyphenylalanyl-4-benzyloxy)succinyl)]-7-[2-(3-cyanophenyl)-1-ethyne]-3,4-dihydro-1 H- 1,4-benzodiazepine-2,5-dione, (±)-1-methyl-3-phenyl-4-(3-ethoxy-1-methyl-3-oxo-1-propyl)-7-[2-(4-nitrophenyl)-1-ethyne]-3,4-dihydro-1H-1,4-benzodiazepine-2,5-dione, (±)-1-methyl-3-phenyl-4-(3-ethoxy-1-phenyl-3-oxo-1-propyl)-7-[2-(4-nitrophenyl)-1-ethyne]-3,4-dihydro-1H-1,4-benzodi aze pine-2,5-dione, (±)-1-methyl-3-phenyl-4-[2-(1-t-butoxy-4-benzyloxy)succinyl)]-7-[2-(4-nitrophenyl)-1-ethyne]-3,4-dihydro-1H-1,4-bertzodiazepine-2,5-dione, (±)-1-methyl-3-phenyl-4-[2-(1-benzyloxyglycinyl-4-benzyloxy)succinyl)]-7-[2-(4-nitrophenyl)-1-ethyne]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[2-(4-nitrophenyl)-1-ethyne]-3,4-dihydro-1H-1,4-benzodiazepine-2,5-dione, (±)-1,3-diphenyl-4-(3-ethoxy-1-methyl-3-oxo-1-propyl)-7-[2-(4-nitrophenyl)-1-ethyne]-3,4-dihydro-1H-1,4-benzodiazepine-2,5-dione, (±)-1,3-diphenyl-4-(3-ethoxy-1-phenyl-3-oxo-1-propyl)-7-[2-(4-nitrophenyl)-1-ethyne]-3,4-dihydro-1H-1,4-benzodiazepine-2,5-dione, (±)-1,3-diphenyl-4-[2-(1-t-butoxy-4-benzyloxy)succinyl)]-7-[2-(4-nitrophenyl)-1-ethyne]-3,4-dihydro-1H-1,4-benzodiazepine-2,5-dione, (±)-1,3-diphenyl-4-[2-(1-benzyloxyglycinyl-4-bertzyloxy)succinyl)]-7-[2-(4-nitrophenyl)-1-ethyne]-3,4-dihydro-1H-1,4-benzodiazepine-2,5-dione, (±)- 1,3-diphenyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1,3-diphenyl-4-[2-(1-bertzyloxyphenylalanyl-4-benzyloxy)succinyl) ]-7-[2-(4-nitrophenyl)-1-ethyne]-3,4-dihydro-1H-1,4-benzodiazepine-2,5-dione, (±)-1-benzyl-3-phenyl-4-(3-ethoxy-1-methyl-3-oxo-1-propyl)-7-[2-(4-nitrophenyl)-1-ethyne]-3,4-dihydro-1H-1,4-benzodiazepine-2,5-dione, (±)-1-benzyl-3-phenyl-4-(3-ethoxy-1-phenyl-3-oxo-1-propyl)-7-[2-(4-nitrophenyl)-1-ethyne]-3,4-dihydro-1H-1,4-benzodiazepine-2,5-dione, (±)-1-bertzyl-3-phenyl4-[2-(1-t-butoxy-4-benzyloxy)-succinyl)]-7-[2-(4-nitrophenyl)-1-ethyne]-3,4-dihydro-1H-1,4-bertzodiazepine-2,5-dione, (±)-1-benzyl-3-phenyl-4-[2-(1-benzyloxyglycinyl-4-benzyloxy)succinyl)]-7-[2-(4-nitrophenyl)-1-ethyne]-3,4-dihydro-1H-1,4-bertzodiazepine-2,5-dione, (±)-1-bertzyl-3-phenyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1-benzyl-3-phenyl-4-[2-(1-benzyloxyphenylalanyl-4-bertzyloxy)succinyl)]-7-[2-(4-nitrophenyl)-1-ethyne]-3,4-dihydro-1H-1,4-benzodiazepine-2,5-dione, (±)-1-isopropyl-3-phenyl-4-(3-ethoxy-1-methyl-3-oxo-1-propyl)-7-[2-(4-nitrophenyl)-1-ethyne]-3,4-dihydro-1H-1,4-benzodiazepine-2,5-dione, (±)-1-isopropyl-3-phenyl-4-(3-ethoxy-1-phenyl-3-oxo-1-propyl)-7-[2-(4-nitrophenyl)-1-ethyne]-3,4-dihydro-1H-1,4-benzodiazepine-2,5-dione, (±)-1-isopropyl-3-phenyl-4-[2-(1-t-butoxy-4-benzyloxy)succinyl)]-7-[2-(4-nitrophenyl)-1-ethyne]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[2-(4-nitrophenyl)-1-ethyne]-3,4-dihydro-1H-1,4-bertzodiazepine-2,5-dione, (±)-1-isopropyl-3-phenyl-4-[2-(1-benzyloxyvalinyl-4-benzyloxy)succinyl)]-7-[2-(4-nitrophenyl)-1-ethyne]-3,4-dihydro-1H-1,4-benzodiazepine-2,5-dione, (±)-1-isopropyl-3-phenyl-4-[2-(1-benzyloxyphenylalanyl-4-bertzyloxy)succinyl)]-7-[2-(4-nitrophenyl)-1-ethyne]-3,4-dihydro-1H-1,4-benzodiazepine-2,5-dione, (±)-1-methyl-3-phenyl-4-(3-ethoxy-1methyl-3-oxo-1-propyl)-7-[N-[2-(N-Boc)aminoethane]-3-keto-1-propyn-3-amine]-3,4-dihydro-1H-1,4-benzodiazepine-2,5-dione, (±)-1-methyl-3-phenyl-4-(3-ethoxy-1-phenyl-3-oxo-1-propyl)-7-[N-[2-(N-Boc)aminoethane]-3-keto-1-propyn-3-amine]-3,4-dihydro-1H-1,4-benzodiazepine-2,5-dione, (±)-1-methyl-3-phenyl-4-[2-(1-t-butoxy-4-benzyloxy)succinyl)]-7-[N-[2-(N-Boc)aminoethane]-3-keto-1-propyn-3-amine]-3,4-dihydro-1H-1,4-benzodiazepine-2,5-dione, (±)-1-methyl-3-phenyl-4-[2-(1-benzyloxyglycinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-methyl-3-phenyl-4-[2-(1-benzyloxyvalinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4benzodiazepine-2,5-dione, (±)-1,3-diphenyl-4-(3-ethoxy-1-methyl-3-oxo-1-propyl)-7-[N-[2-(N-Boc)aminoethane]-3-keto-1-propyn-3-amine]-3,4-dihydro-1H-1,4-benzodiazepine-2,5-dione, (±)-1,3-diphenyl 4-(3-ethoxy-1-phenyl-3-oxo-1-propyl)-7-[N-[2-(N-Boc)-aminoethane]-3-keto-1-propyn-3-amine]-3,4-dihydro-1H-1,4-benzodiazepine-2,5-dione, (±)-1,3-diphenyl-4-[2-(1-t-butoxy-4-hertzyloxy)succinyl)]-7-[N-[2-(N-Boc)-aminoethane]-3-keto-1-propyn-3-amine]-3,4-dihydro-1H-1,4-benzodiazepine-2,5-dione, (±)-1,3-diphenyl-4-[2-(1-benzyloxyglycinyl-4-benzyloxy)succinyl)]-7-[N-[2-(N-Boc)-aminoethane]-3-keto-1-ptopyn-3-amine]-3,4-dihydro-1H-1,4-benzodiazepine-2,5-dione, (±)-1,3-diphenyl-4-[2-(1-benzyloxyvalinyl-4-benzyloxy)succinyl)]-7-[N-[2-(N-Box)-aminoethane]-3-keto-1-propyn-3-amine]-3,4-dihydro-1H-1,4-benzodiazepine-2,5-dione, (±)-1,3-diphenyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-bertzyl-3-phenyl-4-(3-ethoxy-1-methyl-3-oxo-1-propyl)-7-[N-[2-(N-Boc)aminoethane]-3-keto-1-propyn-3-amine]-3,4-dihydro-1H-1,4-benzodiazepine-2,5-dione, (±)-1-benzyl-3-phenyl-4-(3-ethoxy-1-phenyl-3-oxo-1-propyl)-7-[N-[2-(N-Boc)-aminoethane]-3-keto-1-propyn-3-amine]-3,4-dihydro-1H-1,4-benzodiazepine-2,5-dione, (±)-1-benzyl-3-phenyl-4-[2-(1-t-butoxy-4-benzyloxy)succinyl)]-7-[N-[2-(N-Boc)]-3-keto-1-propyn-3-amine]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[N-[-2-(N-Boc)-aminoethane]-3-keto-1-propyn-3-amine]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4benzodiazepine-2,5-dione, (±)-1-isopropyl-3-phenyl-4-(3-ethoxy-1-methyl-3-oxo-1-propyl)-7-[N-[2-(N-Boc)-aminoethane]-3-keto-1-propyn-3-amine]-3,4-dihydro-1H-1,4-benzodiazepine-2,5-dione, (±)-1-isopropyl-3-phenyl-4-(3-ethoxy-1-phenyl-3-oxo-1-propyl)-7-[N-[2-(N-Boc)aminoethane]-3-keto-1-propyn-3-amine]-3,4-dihydro-1H-1,4-benzodiazepine-2,5-dione, (±)-1-isopropyl-3-phenyl-4-[2-(1-t-butoxy-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[N-[-2-(N-Boc)-aminoethane]-3-keto-1-propyn-3-amine]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[N-[2-(N-Boc)-aminoethane]-3-keto-1-propyn-3-amine]-3,4-dihydro-1H-1,4-benzodiazepine-2,5-dione, (±)-1-methyl-3-phenyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5dione, (±)-1-methyl-3-phenyl 4-(3-ethoxy-1-phenyl-3-oxo-1-propyl)-7-[3-keto-1-pyopyn-3-[4-(N-Boc)-1-piperizine]]-3,4-dihydro-1H-1,4-bertzodiazepine-2,5-dione, (±)-1-methyl-3-phenyl-4-[2-(1-t-butoxy -4-benzyloxy)succinyl)]-7-[3-keto-1-propyn-3-[4-(N-Boc)-1-piperizine]]-3,4-dihydro-1H-1,4-benzodiazepine-2,5-dione, (±)-1-methyl-3-phenyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-methyl-3-phenyl-4-[2-(1-benzyloxyvalinyl-4-bertzyloxy)succinyl)]-7-[3-keto-1-propyn-3-[4-(N-Boc)-1-piperizine]]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-3-keto-1-propyn-3-[4-(N-Boc)-1-piperizine]]-3,4-dihydro-1H-1,4-benzodiazepine-2,5-dione, (±)-1,3-diphenyl-4-(3-ethoxy-1-methyl-3-oxo-1-propyl)-7-[3-keto-1-propyn-3-[4-(N-Boc)-1- piperizine]]-3,4-dihydro-1H-1,4-benzodiazepine-2,5-dione, (±)-1,3-diphenyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5-dione, (±)-1,3-diphenyl-4-[2-(1-t-butoxy-4-benzyloxy)succinyl)]-7-[3-keto-1-propyn-3-[4-(N-Boc)-1-piperizine]]-3,4-dihydro-1H-1,4-benzodiazepine-2,5-dione, (±)-1,3-diphenyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1,3-diphenyl-4-[2-(1-benzyloxyvalinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1,3-diphenyl-4-[2-(1-benzyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-benzyl-3-phenyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5-dione, (±)-1-benzyl-3-phenyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5-dione, (±)-1-benzyl-3-phenyl-4-[2-(1-t-butoxy-4-benzyloxy)succinyl)]-7-[3-keto-1-propyn-3-[4-(N-Boc)-1-piperizine]]-3,4-dihydro-1H-1,4-benzodiazepine-2,5-dione (±)-1-benzyl-3-phenyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-isopropyl-3-phenyl-4-(3-ethoxy-1-methyl-3-oxo-1-propyl)-7-[3-keto-1-propyn-3-[4-(N-Boc)-1-piperizine]]-3,4-dihydro-1H-1,4-benzodiazepine-2,5-dione, (±)-1-isopropyl-3-phenyl-4-(3-ethoxy-1-phenyl-3-oxo-1-propyl)-7-[3-keto-1-propyn-3-[4-(N-Boc)-1-piperizine]]-3,4-dihydro-1H-1,4-benzodiazepine-2,5dione, (±)-1-isopropyl-3-phenyl-4-[2-(1-t-butoxy -4-benzyloxy)succinyl)]-7-[3-keto-1-propyn-3-[4-(N-Boc)-1-piperizine]]-3,4-dihydro-1H-1,4-benzodiazepine-2,5dione, (±)-1-isopropyl-3-phenyl-4-[2-(1-benzyloxyglycinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-isopropyl-3-phenyl-4-[2-(1-bertzyloxyphenylalanyl-4-benzyloxy)succinyl)]-7-[3-keto-1-propyn-3-[4-(N-Boc)-1-piperizine]]-3,4-dihydro-1H-1,4-benzodiazepine-2,5-dione, (±)-1-methyl-3-phenyl-4-(3-ethoxy-1-methyl-3-oxo-1-propyl)-7-[2-[2-(N-Boc)aminoethanethiol]-1-ethyne]-3,4-dihydro-1H-1,4-benzodiazepine-2,5-dione, (±)-1-methyl-3-phenyl-4-(3-ethoxy-1-phenyl-3-oxo-1-propyl)-7-[2-[2-(N-Boc)aminoethanethiol]- 1-ethyne]-3,4-dihydro-1H-1,4-benzodiazepine-2,5-dione, (±)-1-methyl-3-phenyl-4-[2-(1-t-butoxy-4-benzyloxy)succinyl)]-7-[2-[2-(N-Boc)aminyoethanenthiyol]-1-ethyne]-3,4-dihydro-1H-1,4-benzodiazepine-2,5dione, (±)-1-methyl-3-phenyl-4-[2-(1-benzyloxyglycinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, (±)-1,3-diphenyl-4-(3-ethoxy-1-methyl-3-oxo-1-propyl)-7-[2-[2-(N-Boc)aminoethanethiol]-1-ethyne]-3,4-dihydro-1H-1,4-benzodiazepine-2,5-dione, (±)- 1,3-diphenyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1,3-diphenyl-4-[2-(1-t-butoxy-4-benzyloxy)succinyl)]-7-[2-[2-(N-Boc)aminoethanethiyol-1-ethyne]-3,4-dihydro-1H-1,4-benzodiazepine-2,5-dione, (±)-1,3-diphenyl-4-[2-(1-benzyloxyglycinyl-4-benzyloxy)succinyl)]-7-[2-[2-(N-Boc)aminoethanethiol]-1-ethyne]-3,4-dihydro-1H-1,4-benzodiazepine-2,5-dione, (±)-1,3-diphenyl-4-[2-(1-benzyloxyvalinyl -4-benzyloxy)succinyl)]-7-[2-[2-(N-Boc)aminoethanethiol]-1-ethyne]-3,4-dihydro-1H-1,4-benzodiazepine-2,5-dione, (±)-1,3-diphenyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, (±)-1-benzyl-3-phenyl-4-(3-ethoxy-1-methyl-3-oxo-1-propyl)-7-[2-[2-(N-Boc)aminoethanethiol]-1-ethyne]-3,4-dihydro-1H-1,4-benzodiazepine-2,5-dione, (±)- 1-benzyl-3-phenyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1-benzyl-3-phenyl-4-[2-(1-t-butoxy-4-benzyloxy)succinyl)]-7-[2-[2-(N-Boc)aminoethanethiol]-1-ethyne]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[2-[2(N-Boc)aminoethanethiol]-1-ethyne]-3,4-dihydro-1H-1,4-benzodiazepine-2,5-dione, (±)-1-benyl-3-phenyl-4-[2-(1-benzyloxyvalinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, (±)-1-isopropyl-3-phenyl-4-(3-ethoxy-1-methyl-3-oxo-1-propyl)-7-[2-[2-(N-Boc)aminoethanethiol]-1- ethyne]-3,4-dihydro-1H-1,4-benzodiazepine-2,5-dione, (±)-1-isopropyl-3-phenyl-4-(3-ethoxy-1-phenyl-3-oxo-1-propyl)-7-[2-[2-(N-Boc)aminoethanethiol]-1-ethyne]-3,4-dihydro-1H-1,4-benzodiazepine-2,5-dione, (±)-1-isopropyl-3-phenyl-4-[2-(1-t-butoxy-4-benzyloxy)succinyl)]-7-[2-[2-(N-Bocy)aminoethanethiol]-1-ethyne]-3,4-dihydro-1H-1,4-benzodiazepine-2,5-dione, (±)-1-isopropyl-3-phenyl-4-[2-(1-bertzyloxyglycinyl-4-benzyloxy)succinyl)]-7-[2-[2-(N-Boc)aminoethanethiol]-1-ethyne]-3,4-dihydro-1H-1,4-benzodiazepine-2,5-dione, (±)-1-isopropyl-3-phenyl-4-[2-(1-bertzyloxyvalinyl4-benzyloxy)succinyl)]-7-[2-[2-(N-Boc)aminoethanethiol]-1-ethyne]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[2-[2-(N-Boc)aminoethanethiol]-1-ethyne]-3,4-dihydro-1H-1,4-benzodiazepine-2,5-dione, (±)-1-methyl-3-phenyl-4-(3-ethoxy-1-methyl-3-oxo-1-propyl)-7-[2-(4-cyanothiophenol)-1-ethyne]-3,4-dihydro-1H-1,4-benzodiazepine-2,5-dione, (±)-1-methyl-3-phenyl-4-(3-ethoxy-1-phenyl-3-oxo-1-propyl)-7-[2-(4cyanothiophenol)-1-ethyne]-3,4-dihydro-1H-1,4-benzodiazepine-2,5-dione, (±)-1-methyl-3-phenyl-4-[2-(1-t-butoxy-4-benzyloxy)succinyl)]-7-[2-(4-cyanothiophenol)-1-ethyne]-3,4-dihydro-1H-1,4-benzodiazepine-2,5-dione, (±)-1-methyl-3-phenyl-4-[2-(1-benzyloxyglycinyl-4-benzyloxy)succinyl)]-7-[2-(4-cyanothiophenol)-1-ethyne]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-(4-cyanothiophenol)-1-ethyne]-3,4-dihydro-1H-1,4-benzodiazepine-2,5-dione, (±)-1-methyl-3-phenyl-4-[2-(1-benzyloxyphenylalanyl4-benzyloxy)succinyl)]-7-[2-(4-cyanothiophenol)-1-ethyne]-3,4-dihydro-1H-1,4-benzodiazepine-2,5-dione, (±)-1,3-diphenyl-4-(3-ethoxy-1-methyl-3-oxo-1-propyl)-7-[2-(4-cyanothiophenol)-1-ethyne]-3,4-dihydro-1H-1,4-benzodiazepine-2,5-dione, (±)-1,3-diphenyl-4-(3-ethoxy-1-phenyl-3-oxo-1-propyl)-7-[2-(4-cyanothiophenol)-1-ethyne]-3,4-dihydro-1H-1,4-benzodiaze pine-2,5-dione, (±)-1,3-diphenyl-4-[2-(1-t-butoxy-4-bertzyloxy)succinyl)]-7-[2-(4-cyanothiophenol)-1-ethyne]-3,4-dihydro-1H-1,4-benzodiazepine-2,5-dione, (±)-1,3-diphenyl4-[2-(1-benzyloxyglycinyl-4-benzyloxy)succinyl)]-7-[2-(4-cyanothiophenol)-1-ethyne]-3,4-dihydro-1H-1,4-benzodiazepine-2,5-dione, (±)-1,3-diphenyl-4-[2-(1-benzyloxyvalinyl-4-benzyloxy)succinyl)]-7-[2-(4-cyanothiophenol)-1-ethyne]-3,4-dihydro-1H-1,4-benzodiazepine-2,5-dione, (±)-1,3-diphenyl-4-[2-(1-benzyloxyphenylalanyl-4-benzyloxy)succinyl)]-7-[2-(4-cyanothiophenol)-1-ethyne]-3,4-dihydro-1H-1,4-benzodiazepine-2,5-dione, (±)-1-benzyl-3-phenyl-4-(3-ethoxy-1-methyl-3-oxo-1-propyl)-7-[2-(4-cyanothiophenol)-1-ethyne]-3,4-dihydro-1H-1,4-benzodiazepine-2,5-dione, (±)-1-benzyl-3-phenyl-4-(3-ethoxy-1-phenyl-3-oxo-1-propyl)-7-[2-(4-cyanothiophenol)-1-ethyne]-3,4-dihy-dro-1H-1,4-bertzodiazepine-2,5-dione, (±)-1-benzyl-3-phenyl-4-[2-(1-t-butoxy -4-benzyloxy)succinyl)]-7-[2-(Y4-cyanothiophenol)-1-ethyne]-3,4-dihydro-1H-1,4-benzodiazepine-2,5-dione, (±)-1benzyl-3-phenyl-4-[2-(1-benzyloxyglycinyl-4-benzyloxy)succinyl)]-7-[2-(4-cyanothiophenol)-1-ethyne]-3,4-dihydro-1H-1,4-bertzodiazepine-2,5-dione, (±)-1-benzyl-3-phenyl-4-[2-(1-benzyloxyvalinyl-4-benzyloxy)succinyl)]-7-[2-(4-cyanothiophenol)-1-ethyne]-3,4-dihydro-1H-1,4-benzodiazepine-2,5-dione, (±)-1-benzyl-3-phenyl-4-[2-(1-benzyloxyphenylalanyl-4-bertzyloxy)succinyl)]-7-[2-(4-cyanothiophenol)-1-ethyne]-3,4-dihydro-1H-1,4-benzodiazepine-2,5-dione, (±)-1-isopropyl-3-phenyl-4-(3-ethoxy-1-methyl-3-oxo-1-propyl)-7-[2-(4-cyanothiophenol)-1-ethyne]-3,4-dihydro-1H-1,4-benzodiazepine-2,5-dione, (±)-1-isopropyl-3-phenyl-4-(3-ethoxy-1-phenyl-3-oxo-1-propyl)-7-[2-(4-cyanothiophenol)-1-ethyne]-3,4-dihydro-1H-1,4-benzodiazepine-2,5-dione, (±)- 1-isopropyl-3-phenyl-4-[2-(1-t-butoxy-4-benzyloxy)succinyl)]-7-[2-(4-cyanothiophenol)-1-ethyne]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[2(4-cyanothiophenol)-1-ethyne]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[2(4-cyanothiophenol)-1-ethyne]-3,4-dihydro-1H-1,4-benzodiazepine-2,5-dione, (±)-1-isopropyl-3-phenyl-4-[2-(1-benzyloxyphenylalanyl-4-benzyloxy)succinyl)]7-[2-(4-cyanothiophenol)-1-ethyne]-3,4-dihydro-1H-1,4-benzodiazepine-2,5-dione, (±)-1-methyl-3-phenyl-4-(3-ethoxy-1-methyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1-methyl-3-phenyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro- 1H-1,4-benzodiazepine-2,5-dione, (±)-1-methyl-3-phenyl-4-[2-(1-t-butoxy-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-methyl-3-phenyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-(N-Boc)amino-6-methylpyrimidine-4-yl]-4-oxa-1-butyne]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[4-[2-(N-Boc)amino-6-methylpyrimidine-4-yl]-4-oxa-1-butyne]-3,4-dihydr01H,1,4-benzodiazepine-2,5-dione, 1(±)-,3-diphenyl-4-(3-ethoxy-1-methyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1,3-diphenyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1,3-diphenyl-4-[2-(1-t-butoxy-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1,3-diphenyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1,3-diphenyl-4-[2-(1-benzyloxyvalinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1,3-diphenyl-4-[2-(1-benzyloxyphenylalanyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-3-phenyl-4-(3-ethoxy-1-methyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-3-phenyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro-1H-1,4benzodiazepine-2,5-dione, (±)-1-benzyl-3-phenyl-4-[2-(1-t-butoxy-4-benzyloxy)succinyl)]-7-[4-[2-(N-Boc)amino-6-methylpyrimidine-4-yl ]-4-oxa-1-butyne]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[4-[2-(N-Boc)amino-6-methylpyrimidine-4-yl]-4-oxa-1-butyne]-3,4-dihydro-1H-1,4-benzodiaze pine-2,5-dione, (±)-1-isopropyl-3-phenyl-4-(3-ethoxy-1-methyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1-isopropyl-3-phenyl-4-(3-ethoxy-1-phenyl-3-oxo-1-propyl)-7-[4-[2-(N-Boc)amino-6-methylpyrimidine-4-yl]-4-oxa-1-butyne]-3,4-dihydro-1H-1,4-benzodiazepine-2,5-dione, (±)-1-isopropyl-3-phenyl-4-[2-(1-t-butoxy-4-benzyloxy)succinyl)]-7-[4-[2(N-Boc)amino-6-methylpyrimidine-4-yl]-4-oxa-1-butyne ]-3,4-dihydro-1H-1,4-benzodiazepine-2,5-di one, (±)-1-isopropyl-3-phenyl-4-[2-(1-benzyloxyglycinyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-isopropyl-3-phenyl 4-[2-(1-benzyloxyvalinyl-4-benzyloxy)succinyl)]-7-[4-[2-(N-Boc)amino-6-methylpyrimidine-4-yl]-4-oxa-1-butyne]-3,4-dihydro-1H-4-benzodiazepine-2,5-dione, (±)-1-isopropyl-3-phenyl-4-[2-(1-benzyloxyphenylalanyl-4-benzyloxy)succinyl)]-7-[4-[2-(N-Boc)amino-6-methylpyrimidine-4-yl]-4-oxa-1-butyne]-3,4-dihydro-1H-1,4-benzodiazepine-2,5-dione, (±)-1-methyl-3-phenyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-methyl-3-phenyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-methyl-3-phenyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-methyl-3-phenyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-methyl-3-phenyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1,3-diphenyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1,3-diphenyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1,3-diphenyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1,3-diphenyl-4-[2-(1-benzyloxyglycinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1,3-diphenyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1,3-diphenyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-benzyl-3-phenyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-benzyl-3-phenyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-benzyl-3-phenyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-isopropyl-3-phenyl-4-(3-ethoxy-1-methyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-isopropyl-3-phenyl-4-(3-ethoxy-1-phenyl-3-oxo-1-propyl)-7-[5-[2-(N-Boc)aminopyridine-3-yl]-5-oxa-1-pentyne]-3,4-dihydro-1H-1,4-benzodiazepine-2,5-dione, (±)-1-isopropyl-3-phenyl-4-[2-(1-t-butoxy-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[5-[2-(N-Boc)aminopyridine-3-yl]-5-oxa-1-pentyne]-3,4-dihydro-1H-1,4-benzodiazepine-2,5-dione, g) To a solution of 22 mgs 1-methyl-4-(2-carboxyethyl)-7-(N-boc-5-amino-1-pentynyl)-3,4-dihydro-1H-1,4-benzodiazepine-2,5-dione benzyl ester (0.0412 mmol) in 0.5 mL ethyl acetate was added 3 mL sat. HCl in ethyl acetate. After 1 hour, the mixture was concentrated in vacuo and diluted with 2 mL methanol. To the methanolic solution was added 0.5mL 2N sodium hydroxide. After 1 hour, the reaction was quenched with 3 mL acetic acid, concentrated in vacuo, diluted with 3 mL water and purified by high pressure liquid chromatography, using a ½" C-18 reverse-phase column, eluting with a solvent gradient of 10:90 methanol(0.1% trifluroacetic acid)/water (0.1% trifluroacetic acid), time 0 to 10 min, to 50:50 methanol(0.1% trifluroacetic acid)/water (0.1% trifluroacetic acid), time 10 min to 40 min, flow=10 ml/min ($R_t$=33.1 min, un detection 254 nm) to yield 13 mgs (92%) 1-methyl-4-(2-carboxyethyl)-7-(5-amino-1-pentynyl)-3,4-dihydro-1H-1,4-benzodiazepine-2,5-dione trifluroacetate. HRMS (FAB) molecular ion m/z=344.1626 ( cald. $C_{18}H_{22}N_3O_4$, 344.1610). $^1$H NMR ($D_2O$) 7.63 (1H, d, $^4J_{HH}$, Ar-H o-CON), 7.54 (1H, dd, $^4J_{HH}$=2Hz, $^3J_{HH}$=8Hz, Ar-H p-CON), 7.20 (1H, d, $^3J_{HH}$=8Hz, Ar-H m-CON), 4.05 (1H, d, $^2J_{HH}$=14Hz, NCHHCO), 4.0 (1H, m, NCHHCH$_2$), 3.74 (1H, d, $^2J_{HH}$=14Hz, NCHHCO), 3.59 (1H, m, NCHHCH$_2$), 3.20 (3H, s, NCH$_3$), 3.03 (2H, t, $^3J_{HH}$=7Hz, NCH$_2$), 2.59 (2H, m, CH$_2$CO$_2$), 2.42 (2H, t, $^3J_{HH}$=7Hz, C∫CCH$_2$), 1.82 (2H, p, $^3J_{HH}$=7Hz, CH$_2$CH$_2$CH$_2$).

Using the above procedure, but substituting the appropriate 3,4-dihydro-1H-1,4-benzodiazepine-2,5-dione for 1-methyl-4-(2-carboxyethyl)-7-(N-boc-5-amino-1-pentynyl)-3,4-dihydro-1H-1,4-benzodiazepine-2,5-dione benzyl ester there may be prepared, for example, the following compounds: 1-methyl-4-(2-carboxy-1-methylethyl)-7-(5-amino-1-pentyne)-3,4-dihydro-1H-1,4-benzodiazepine-2,5-dione trifluroacetate, 1-methyl-4-(2-carboxy-1-phenylethyl)-7-(5-amino-1-pentyne)-3,4-dihydro-1H-1,4-benzodiazepine-2,5-dione trifluroacetate, (±)-1-methyl-4-[succin-2-yl-(1-t-butoxy)]-7-(5-amino-1-pentyne)-3,4-dihydro-1H-1,4-benzodiazepine-2,5-dione trifluroacetate, (±)-1-methyl-4-[succin-2-yl-(1-glycine)]-7-(5-amino-1-pentyne)-3,4-dihydro-1H-1,4-benzodiazepine-2,5-dione trifluroacetate, (±)-1-methyl-4-[succin-2-yl-(1-valine)]-7-(5-amino-1-pentyne)-3,4-dihydro-1H-1,4-benzodiazepine-2,5-dione trifluroacetate, (±)-1-methyl-4-[succin-2-yl-(1-phenylalanine)]-7-(5-amino-1-pentyne)-3,4-dihydro-1H-1,4-benzodiazepine-2,5-dione trifluroacetate, 1-phenyl-4-(2-carboxy-1-methylethyl)-7-(5-amino-1-pentyne)-3,4-dihydro-1H-1,4-benzodiazepine-2,5-dione trifluroacetate, 1-phenyl-4-(2-carboxy-1-phenylethyl)-7-(5-amino-1-pentyne)-3,4-dihydro-1H-1,4-benzodiazepine-2,5-dione trifluroacetate, (±)-1-phenyl-4-[succin-2-yl-(1-t-butoxy)]-7-(5-amino-1-pentyne)-3,4-dihydro-1H-1,4-benzodiazepine-2,5-dione trifluroacetate, (±)-1-phenyl-4-[succin-2-yl-(1-glycine)]-7-(5-amino-1-pentyne )-3,4-dihydro-1H-1,4-benzodiazepine-2,5-dione trifluroacetate, (±)-1-phenyl-4-[succin-2-yl-(1-valine)]-7-(5-amino-1-pentyne)-3,4-dihydro-1H-1,4-benzodiazepine-2,5-dione trifluroacetate, (±)-1-phenyl-4-[succin-2-yl-(1-phenylalanine)]-7-(5-amino-1-pentyne)-3,4-dihydro-1H-1,4-benzodiazepine-2,5-dione trifluroacetate, 1-benzyl-4-(2-carboxy-1-methylethyl)-7-(5-amino-1-pentyne)-3,4-dihydro-1H-1,4-benzodiazepine-2,5-dione trifluroacetate, 1-benzyl-4-(2-carboxy-1-phenylethyl)-7-(5-amino-1-pentyne)-3,4-dihydro-1H-1,4-benzodiazepine-2,5-dione trifluroacetate, (±)-1-benzyl-4-[succin-2-yl-(1-t-butoxy)]-7-(5-amino-1-pentyne)-3,4-dihydro-1H-1,4-benzodiazepine-2,5-dione trifluroacetate, (±)-1-benzyl-4-[succin-2-yl-(1-glycine)]-7-(5-amino-1-pentyne)-3,4-dihydro-1H-1,4-benzodiazepine-2,5-dione trifluroacetate, (±)-1-benzyl-4-[succin-2-yl-(1-valine)]-7-(5-amino-1-pentyne)-3,4-dihydro-1H-1,4-benzodiazepine-2,5-dione trifluroacetate, (±)-1-benzyl-4-[succin-2-yl-(1-phenylalanine)]-7-(5-amino-1-pentyne)-3,4-dihydro-1H-1,4-benzodiazepine-2,5-dione trifluroacetate, 1-isopropyl-4-(2-carboxy-1-methylethyl)-7-(5-amino-1-pentyne)-3,4-dihydro-1H-1,4-benzodiazepine-2,5-dione trifluroacetate, 1-isopropyl-4-(2-carboxy-1-phenylethyl)-7-(5-amino-1-pentyne)-3,4-dihydro-1H-1,4-benzodiazepine-2,5-dione trifluroacetate, (±)-1-isopropyl-4-[succin-2-yl-(1-t-butoxy)]-7-(5-amino-1-pentyne )-3,4-dihydro-1H-1,4-benzodiazepine-2,5-dione trifluroacetate, (±)-1-isopropyl-4-[succin-2-yl-(1-glycine)]-7-(5-amino-1-pentyne)-3,4-dihydro-1H-1,4-benzodiazepine-2,5-dione trifluroacetate, (±)-1-isopropyl-4-[succin-2-yl-(1-valine)]-7-(5-amino-1-pentyne)-3,4-dihydro-1H-1,4-benzodiazepine-2,5-dione trifluroacetate, (±)-1-isopropyl-4-[succin-2-yl-(1-phenylalanine)]-7-(5-amino-1-pentyne )-3,4-dihydro-1H-1,4-benzodiazepine-2,5-dione trifluroacetate, 1-methyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-methyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-phenyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-phenyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-benzyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-benzyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-isopropyl-4-(2-carboxy-1-methylethyl)-7-[N-(2-aminoethane )-3-keto-1-propyn-3-amine]-3,4-dihydro-1H-1,4-benzodiazepine-2,5-dione trifluroacetate, 1-isopropyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-methyl -4-(2-carboxy-1-methylethyl)-7-[3-keto-1-propyn-3-(1-piperizine)]-3,4-dihydro-1H-1,4-benzodiazepine-2,5-dione trifluroacetate, 1-methyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-methyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-methyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-methyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-methyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-phenyl-4-(2-carboxy-1-methylethyl)-7-[3-keto-1-propyn-3-(1-piperizine)]-3,4-dihydro-1H-1,4-benzodiazepine-2,5-dione trifluroacetate, 1-phenyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-benzyl-4-(2-carboxy-1-methylethyl)-7-[3-keto-1-propyn-3-(1-piperizine)]-3,4-dihydro-1H-1,4-benzodiazepine-2,5-dione trifluroacetate, 1-benzyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-isopropyl-4-(2-carboxy-1-methylethyl)-7-[3-keto-1-propyn-3-(1-piperizine)]-3,4-dihydro-1H-1,4-benzodiazepine-2,5-dione trifluroacetate, 1-isopropyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-glycine )]-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-methyl-4-(2-carboxy-1-methylethyl)-7-[2-(2-aminoethanethiol)-1-ethyne]-3,4-dihydro-1H-1,4-benzodiazepine-2,5-dione trifluroacetate, 1-methyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1-methyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-methyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1-methyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1-methyl-4-[succin-2-yl-(1-phenylalanine)]-7-[2-(2-aminoethanethiol)-1-ethyne]-3,4-dihydro-1H-1,4-benzodiazepine-2,5-dione trifluroacetate, 1-phenyl-4-(2-carboxy-1-methylethyl)-7-[2-(2-aminoethanethiol)-1-ethyne]-3,4-dihydro-1H-1,4-benzodiazepine-2,5-dione trifluroacetate, 1-phenyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1-phenyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-phenyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1-phenyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1-phenyl-4-[succin-2-yl-(1-phenylalanine)]-7-[2-(2-aminoethanethiol )-1-ethyne]-3,4-dihydro-1H-1,4-benzodiazepine-2,5-dione trifluroacetate, 1-benzyl-4-(2-carboxy-1-methylethyl)-7-[2-(2-aminoethanethiol)-1-ethyne]-3,4-dihydro-1H-1,4-benzodiazepine-2,5-dione trifluroacetate, 1-benzyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1-benzyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-benzyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1-benzyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1-benzyl-4-[succin-2-yl-(1-phenylalanine)]-7-[2-(2-aminoethanethiol)-1-ethyne]-3,4-dihydro-1H-1,4-benzodiazepine-2,5-dione trifluroacetate, 1-isopropyl-4-(2-carboxy-1-methylethyl)-7-[2-(2-aminoethanethiol)-1-ethyne]-3,4-dihydro-1H-1,4-benzodiazepine-2,5-dione trifluroacetate, 1-isopropyl-4-(2-carboxy-1-phenylethyl )-7-[2-(2-aminoethanethiol )-1-ethyne]-3,4-dihydro-1H-1,4-benzodiazepine-2,5-dione trifluroacetate, (±)-1-isopropyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-isopropyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1-isopropyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1-isopropyl-4-[succin-2-yl-(1-phenylalanine)]-7-[2-(2-aminoethanethiol)-1-ethyne]-3,4-dihydro-1H-1,4-benzodiazepine-2,5-dione trifluroacetate, 1-methyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, 1-methyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-4-[succin-2-yl-(1-t-butoxy)]-7-[4-(2-amino-6-methylpyrimidine-4-yl)-4-yl)-4-oxa-1-butyne]-3,4-dihydro-1H-1,4-benzodiazepine-2,5-dione trifluroacetate, (±)-1-methyl-4-[succin-2-yl-(1-glycine)]-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, 1-phenyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, 1-phenyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-phenyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1-phenyl-4-[succin-2-yl-(1-glycine)]-7-[4-(2-amino-6-methylpyrimidine-4-yl)-4-oxa-1-butyne]-3,4-dihydro-1H-1,4-benzodiazepine-2,5-dione trifluroacetate, (±)-1-phenyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-phenyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, 1-benzyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, 1-benzyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-4-[succin-2-yl-(1-glycine)]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, 1-isopropyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, 1-isopropyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-4-[succin-2-yl-(1-glycine)]-7-[4-(2-amino-6-methylpyrimidine-4-yl)]-4-oxa-1-butyne]-3,4-dihydro-1H-1,4-benzodiazepine-2,5-dione trifluroacetate, (±)-1-isopropyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, 1-methyl-4-(2-carboxy-1-methylethyl)-7-[5-(2-aminopyridine-3-yl)-5-oxa-1-pentyne]-3,4-dihydro-1H-1,4-benzodiazepine-2,5-dione trifluroacetate, 1-methyl-4-(2-carboxy-1-phenylethyl)-7-[5-(2-aminopyridine-3-yl )-5-oxa-1-pentyne]-3,4-dihydro-1H-1,4-benzodiazepine-2,5-dione trifluroacetate, (±)-1-methyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1-methyl-4-[succin-2-yl-(1-glycine)]-7-[5-(2-aminopyridine-3-yl)-5-yl)-5-oxa-1-pentyne]-3,4-dihydro-1H-1,4-benzodiazepine-2,5-dione trifluroacetate, (±)-1-methyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-methyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate, 1-phenyl-4-(2-carboxy-1-methylethyl)-7-[5-(2-aminopyridine-3-yl)-5-oxa-1-pentyne]-3,4-dihydro-1H-1,4-benzodiazepine-2,5-dione trifluroacetate, 1-phenyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1-phenyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1-phenyl-4-[succin-2-yl-(1-glycine)]-7-[5-(2-aminopyridine-3-yl )-5-oxa-1-pentyne]-3,4-dihydro-1H-1,4-benzodiazepine-2,5-dione trifluroacetate, (±)-1-phenyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-phenyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate, 1-benzyl-4-(2-carboxy-1-methylethyl)-7-[5-(2-aminopyridine-3-yl)-5-oxa-1--pentyne]-3,4-dihydro-1H-1,4-benzodiazepine-2,5--dione, 1-benzyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1-benzyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1-benzyl-4-[succin-2-yl-(1-glycine)]-7-[5-(2-aminopyridine-3-yl)-5-oxa-1-pentyne]-3,4-dihydro-1H-1,4-benzodiazepine-2,5-dione trifluroacetate, (±)-1-benzyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-benzyl-4-[succin-2-yl-(1-phenylalanine )]-7-[5-(2-aminopyridine-3-yl)-5-oxa-1-pentyne]-3,4-dihydro-1H-1,4-benzodiazepine-2,5-dione trifluroacetate, 1-isopropyl-4-(2-carboxy-1-methylethyl)-7-[5-(2-aminopyridine-3-yl)-5-oxa-1-pentyne]-3,4-dihydro-1H-1,4-benzodiazepine-2,5-dione trifluroacetate, 1-isopropyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1-isopropyl-4[-succin-2-yl-(1t-butoxy)]-7-[5-(2-aminopyridine-3-yl)-5-oxa-1-pentyne]-3,4-dihydro-1H-1,4-benzodiazepine-2,5-dione trifluroacetate, (±)-1-isopropyl-4-[succin-2-yl-(1-glycine)]-7-[5-(2-aminopyridine-3-yl)-5-oxa-1-pentyne]-3,4-dihydro-1H-1,4-benzodiazepine-2,5-dione trifluroacetate, (±)-1-isopropyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-isopropyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate, (±)-1-methyl-3-phenyl-4-(2-carboxy-1-methylethyl)-7-(5-amino-1-pentyne)-3,4-dihydro-1H-1,4-benzodiazepine-2,5-dione trifluroacetate, (±)-1-methyl-3-phenyl-4-(2-carboxy-1-phenylethyl)-7-(5-amino-1-pentyne)-3,4-dihydro-1H-1,4-benzodiazepine-2,5-dione trifluroacetate, (±)-1-methyl-3-phenyl-4-[succin-2-yl-(1-t-butoxy)]-7-(5-amino-1-pentyne)-3,4-dihydro-1H-1,4-benzodiazepine-2,5-dione trifluroacetate, (±)-1-methyl-3-phenyl-4-[succin-2-yl-(1-glycine )]-7-(5-amino-1-pentyne)-3,4-dihydro-1H-1,4-benzodiazepine-2,5-dione trifluroacetate, (±)-1-methyl-3-phenyl-4-[succin-2-yl-(1-valine)]-7-(5-amino-1-pentyne )-3,4-dihydro-1H-1,4-benzodiazepine-2,5-dione trifluroacetate, (±)-1-methyl-3-phenyl-4-[succin-2-yl-(1-phenylalanine)]-7-(5-amino-1-pentyne)-3,4-dihydro-1H-1,4-benzodiazepine-2,5-dione trifluroacetate, (±)-1,3-diphenyl-4-(2-carboxy-1-methylethyl)-7-(5-amino-1-pentyne )-3,4-dihydro-1H-1,4-benzodiazepine-2,5-dione trifluroacetate, (±)-1,3-diphenyl-4-(2-carboxy-1-phenylethyl)-7-(5-amino-1-pentyne)-3,4-dihydro-1H-1,4-benzodiazepine-2,5-dione trifluroacetate, (±)-1,3-diphenyl-4-[succin-2-yl-(1-t-butoxy)]-7-(5-amino-1-pentyne)-3,4-dihydro-1H-1,4-benzodiazepine-2,5-dione trifluroacetate, (±)-1,3-diphenyl-4-[succin-2-yl-(1-glycine)]-7-(5-amino-1-pentyne)-3,4-dihydro-1H-1,4-benzodiazepine-2,5-dione trifluroacetate, (±)-1,3-diphenyl-4-[succin-2-yl-(1-valine)]-7-(5-amino-1-pentyne)-3,4-dihydro-1H-1,4-benzodiazepine-2,5-dione trifluroacetate, (±)-1,3-diphenyl-4-[succin-2-yl-(1-phenylalanine)]-7-(5-amino-1-pentyne)-3,4-dihydro-1H-1,4-benzodiazepine-2,5-dione trifluroacetate, (±)-1-benzyl-3-phenyl-4-(2-carboxy-1-methylethyl)-7-(5-amino-1-pentyne)-3,4-dihydro-1H-1,4-benzodiazepine-2,5-dione trifluroacetate, (±)-1-benzyl-3-phenyl-4-(2-carboxy-1-phenylethyl)-7-(5-amino-1-pentyne)-3,4-dihydro-1H-1,4-benzodiazepine-2,5-dione trifluroacetate, (±)-1-benzyl-3-phenyl-4-[succin-2-yl-(1-t-butoxy)]-7-(5-amino-1-pentyne)-3,4-dihydro-1H-1,4-benzodiazepine-2,5-dione trifluroacetate, (±)-1-benzyl-3-phenyl-4-[succin-2-yl-(1-glycine)]-7-(5-amino-1-pentyne)-3,4-dihydro-1H-1,4-benzodiazepine-2,5-dione trifluroacetate, (±)-1-benzyl-3-phenyl-4-[succin-2-yl-(1-valine)]-7-(5-amino-1-pentyne)-3,4-dihydro-1H-1,4-benzodiazepine-2,5-dione trifluroacetate, (±)-1-benzyl-3-phenyl-4-[succin-2-yl-(1-phenylalanine)]-7-(5-amino-1-pentyne)-3,4-dihydro-1H-1,4-benzodiazepine-2,5-dione trifluroacetate, (±)-1-isopropyl-3-phenyl-4-(2-carboxy-1-methylethyl)-7-(5-amino-1-pentyne)-3,4-dihydro-1H-1,4-benzodiazepine-2,5-dione trifluroacetate, (±)-1-isopropyl-3-phenyl-4-(2-carboxy-1-phenylethyl)-7-(5-amino-1-pentyne)-3,4-dihydro-1H-1,4-benzodiazepine-2,5-dione trifluroacetate, (±)-1-isopropyl-3-phenyl-4-[succin-2-yl-(1-t-butoxy)]-7-(5-amino-1-pentyne)-3,4-dihydro-1H-1,4-benzodiazepine-2,5-dione trifluroacetate, (±)-1-isopropyl-3-phenyl-4-[succin-2-yl-(1-glycine)]-7-(5-amino-1-pentyne)-3,4-dihydro-1H-1,4-benzodiazepine-2,5-dione trifluroacetate, (±)-1-isopropyl-3-phenyl-4-[succin-2-yl-(1-valine)]-7-(5-amino-1-pentyne)-3,4-dihydro-1H-1,4-benzodiazepine-2,5-dione trifluroacetate, (±)-1-isopropyl-3-phenyl-4-[succin-2-yl-(1-phenylalanine)]-7-(5-amino-1-pentyne)-3,4-dihydro-1H-1,4-benzodiazepine-2,5-dione trifluroacetate, (±)-1-methyl-3-phenyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, (±)-1-methyl-3-phenyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-methyl-3-phenyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-methyl-3-phenyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-methyl-3-phenyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-methyl-3-phenyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, (±)-1,3-diphenyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, (±)-1,3-diphenyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1,3-diphenyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1,3-diphenyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1,3-diphenyl-4-[succin-2-yl-(1-valine)]-7-[N-(2-aminoethane)-3-keto-1-propyn-3-amine]-3,4-dihydro-1H-1,4-benzodiazepine-2,5,-dione trifluroacetate, (±)-1,3-diphenyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, (±)-1-benzyl-3-phenyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, (±)-1-benzyl-3-phenyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-benzyl-3-phenyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-benzyl-3-phenyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-benzyl-3-phenyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-benzyl-3-phenyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, (±)-1-isopropyl-3-phenyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, (±)-1-isopropyl-3-phenyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-isopropyl-3-phenyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-isopropyl-3-phenyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-isopropyl-3-phenyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-isopropyl-3-phenyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, (±)-1-methyl-3-phenyl-4-(2-carboxy-1-methylethyl)-7-[3-keto-1-propyn-3-(1-piperizine)]-3,4-dihydro-1H-1,4-benzodiazepine-2,5-dione trifluroacetate, (±)-1-methyl-3-phenyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-methyl-3-phenyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-methyl-3-phenyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-methyl-3-phenyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-methyl-3-phenyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, (±)-1,3-diphenyl-4-(2-carboxy-1-methylethyl)-7-[3-keto-1-propyn-3-(1-piperizine)]-3,4-dihydro-1H-1,4-benzodiazepine-2,5-dione trifluroacetate, (±)-1,3-diphenyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1,3-diphenyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1,3-diphenyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1,3-diphenyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1,3-diphenyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, (±)-1-benzyl-3-phenyl-4-(2-carboxy-1-methylethyl)-7-[3-keto-1-propyn-3-(1-piperizine)]-3,4-dihydro-1H-1,4-benzodiazepine-2,5-dione trifluroacetate, (±)-1-benzyl-3-phenyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-benzyl-3-phenyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-benzyl-3-phenyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-benzyl-3-phenyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-benzyl-3-phenyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, (±)-1-isopropyl-3-phenyl-4-(2-carboxy-1-methylethyl)-7-[3-keto-1-propyn-3-(1-piperizine)]-3,4-dihydro-1H-1,4-benzodiazepine-2,5-dione trifluroacetate, (±)-1-isopropyl-3-phenyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-isopropyl-3-phenyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-isopropyl-3-phenyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-isopropyl-3-phenyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-isopropyl-3-phenyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, (±)-1-methyl-3-phenyl-4-(2-carboxy-1-methylethyl)-7-[2-(2-aminoethanethiol)-1-ethyne]-3,4-dihydro-1H-1,4-benzodiazepine-2,5-dione trifluroacetate, (±)-1-methyl-3-phenyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1-methyl-3-phenyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-methyl-3-phenyl-4-[succin-2-yl-(1-glycine)]-7-[2-(2-aminoethanethiol)-1ethyne]-3,4-dihydro-1H-1,4-benzodiazepine-2,5-dione trifluroacetate, (±)-1-methyl-3-phenyl-4-[succin-2-yl-(1-valine)]-7-[2-(2-aminoethanethiol)-1ethyne]-3,4-dihydro-1H-1,4-benzodiazepine-2,5-dione trifluroacetate, (±)-1-methyl-3-phenyl-4-[succin-2-yl-(1-phenylalanine)]-7-[2-(2-aminoethanethiol)-1-ethyne]-3,4-dihydro-1H-1,4-benzodiazepine-2,5-dione trifluroacetate, (±)-1,3-diphenyl-4-(2-carboxy-1-methylethyl)-7-[2-(2-aminoethanethiol)-1-ethyne]-3,4-dihydro-1H-1,4-benzodiazepine-2,5-dione trifluroacetate, (±)-1,3-diphenyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1,3-diphenyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1,3-diphenyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1,3-diphenyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1,3-diphenyl-4-[succin-2-yl-(1-phenylalanine)]-7-[2-(2-aminoethanethiol)-1-ethyne]-3,4-dihydro-1H-1,4-benzodiazepine-2,5-dione trifluroacetate, (±)-1-benzyl-3-phenyl-4-(2-carboxy-1-methylethyl)-7-[2-(2-aminoethanethiol)-1-ethyne]-3,4-dihydro-1H-1,4-benzodiazepine-2,5-dione trifluroacetate, (±)-1-benzyl-3-phenyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1-benzyl-3-phenyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-benzyl-3-phenyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1-benzyl-3-phenyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1-benzyl-3-phenyl-4-[succin-2-yl-(1-phenylalanine)]-7-[2-(2-aminoethanethiol)-1-ethyne]-3,4-dihydro-1H-1,4-benzodiazepine-2,5-dione trifluroacetate, (±)-1-isopropyl-3-phenyl-4-(2-carboxy-1-methylethyl)-7-[2-(2-aminoethanethiol)-1-ethyne]-3,4-dihydro-1H-1,4-benzodiazepine-2,5-dione trifluroacetate, (±)-1-isopropyl-3-phenyl-4-(2-carboxy-1-phenylethyl)-7-[2-(2-aminoethanethiol)-1-ethyne]-3,4-dihydro-1H-1,4-benzodiazepine-2,5-dione trifluroacetate, (±)-1-isopropyl-3-phenyl-4-[succin-2-yl-(1-t-butoxy)]-7-[2-(2-aminoethanethiol)-1-ethyne]-3,4-dihydro-1H-1,4-benzodiazepine-2,5-dione trifluroacetate, (±)-1-isopropyl-3-phenyl-4-[succin-2-yl-(1-glycine)]-7-[2-(2-aminoethanethiol)-1-ethyne]-3,4-dihydro-1H-1,4-benzodiazepine-2,5-dione trifluroacetate, (±)-1-isopropyl-3-phenyl-4-[succin-2-yl-(1-valine)]-7-[2-(2-aminoethanethiol)-1-ethyne]-3,4-dihydro-1H-1,4-benzodiazepine-2,5-dione trifluroacetate, (±)-1-isopropyl-3-phenyl-4-[succin-2-yl-(1-phenylalanine)]-7-[2-(2-aminoethanethiol)-1-ethyne]-

3,4-dihydro-1H-1,4-benzodiazepine-2,5-dione trifluroacetate, (±)-1-methyl-3-phenyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-3-phenyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-3-phenyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-3-phenyl-4-[succin-2-yl-(1-glycine)]-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-3-phenyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-3-phenyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, (±)-1,3-diphenyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1,3-diphenyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1,3-diphenyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1,3-diphenyl-4-[succin-2-yl-(1-glycine)]-7-[4-(2-amino-6-methylpyrimidine-4-yl)-4-oxa-1-butyne]-3,4-dihydro-1H-1,4-benzodiazepine-2,5-dione trifluroacetate, (±)-1,3-diphenyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1,3-diphenyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-3-phenyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-3-phenyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-3-phenyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-3-phenyl-4-[succin-2-yl-(1-glycine(]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-3-phenyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-benzyl-3-phenyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-3-phenyl-4-(2-carboxy-1-methylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-3-phenyl-4-(2-carboxy-1-phenylethyl)-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-3-phenyl-4-[succin-2-yl-(1-t-butoxy)]-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-3-phenyl-4-[succin-2-yl-(1-glycine)]-7-[4-(2-amino-6-methylpyrimidine4-yl)]-4-oxa-1-butyne]-3,4-dihydro-1H-1,4-benzodiazepine-2,5-dione trifluroacetate, (±)-1-isopropyl-3-phenyl-4-[succin-2-yl-(1-valine)]-7-[4-(2-amino-6-methylpyrimidine-4-yl)-4-oxa-1-butyne]-3,4-dihydro-1H-1,4-benzodiazepine-2,5-dione trifluroacetate, (±)-1-isopropyl-3-phenyl-4-[succin-2-yl-(1-phenylalanine)]-7-[4-(2-amino-6-methylpyrimidine-4-yl)-4-oxa-1-butyne]-3,4-dihydro-1H-1,4-benzodiazepine-2,5-dione trifluroacetate, (±)-1-methyl-3-phenyl-4-(2-carboxy-1-methylethyl)-7-[5-(2-aminopyridine-3-yl)-5-oxa-1-pentyne]-3,4-dihydro-1H-1,4-benzodiazepine-2,5-dione trifluroacetate, (±)-1-methyl-3-phenyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1-methyl-3-phenyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1-methyl-3-phenyl-4-[succin-2-yl-(1-glycine)]-7-[5-(2-aminopyridine-3-yl)-5-oxa-1-pentyne]-3,4-dihydro-1H-1,4-benzodiazepine-2,5-dione trifluroacetate, (±)-1-methyl-3-phenyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-methyl-3-phenyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate, (±)-1,3-diphenyl-4-(2-carboxy-1-methylethyl)-7-[5-(2-aminopyridine-3-yl)-5-oxa-1-pentyne]-3,4-dihydro-1H-1,4-benzodiazepine-2,5-dione trifluroacetate, (±)-1,3-diphenyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1,3-diphenyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1,3-diphenyl-4-[succin-2-yl-(1-glycine)]-7-[5-(2-aminopyridine-3-yl)-5-oxa-1-pentyne]-3,4-dihydro-1H-1,4-benzodiazepine-2,5-dione trifluroacetate, (±)-1,3-diphenyl4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1,3-diphenyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate, (±)-1-benzyl-3-phenyl-4-(2-carboxy-1-methylethyl)-7-[5-(2-aminopyridine-3-yl)-5-oxa-1-pentyne]-3,4-dihydro-1H-1,4-benzodiazepine-2,5-dione, (±)-1-benzyl-3-phenyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1-benzyl-3-phenyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1-benzyl-3-phenyl-4-[succin-2-yl-(1-glycine)]-7-[5-(2-aminopyridine-3-yl)-5-oxa-1-pentyne]-3,4-dihydro-1H-1,4-benzodiazepine-2,5-dione trifluroacetate, (±)-1-benzyl-3-phenyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-benzyl-3-phenyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate, (±)-1-isopropyl-3-phenyl-4-(2-carboxy-1-methylethyl)-7-[5-(2-aminopyridine-3-yl)-5-oxa-1-pentyne]-3,4-dihydro-1H-1,4-benzodiazepine-2,5-dione trifluroacetate, (±)-1-isopropyl-3-phenyl-4-(2-carboxy-1-phenylethyl)-7-[5-(2-aminopyridine-3-yl)-5-oxa-1-pentyne]-3,4-dihydro-1H-1,4-benzodiazepine-2,5-dione trifluroacetate, (±)-1-isopropyl-3-phenyl-4-[succin-2-yl-(1-t-butoxy)]-7-[5-(2-aminopyridine-3-yl)-5-oxa-1-pentyne]-3,4-dihydro-1H-1,4-benzodiazepine-2,5-dione trifluroacetate, (±)-1-isopropyl-3-phenyl-4-[succin-2-yl-(1-glycine)]-7-[5-(2-aminopyridine-3-yl)-5-oxa-1-pentyne]-3,4-dihydro-1H-1,4-benzodiazepine-2,5-dione trifluroacetate, (±)-1-isopropyl-3-phenyl-4-[succin-2-yl-(1-valine)]-7-[5-(2-aminopyridine-3-yl)-5-oxa-1-pentyne]-3,4-dihydro-1H-1,4-benzodiazepine-2,5-dione trifluroacetate, (±)-1-isopropyl-3-phenyl-4-[succin-2-yl-(1-phenylalanine)]-7-[5-(2-aminopyridine-3-yl)-5-oxa-1-pentyne]-3,4-dihydro-1H-1,4-benzodiazepine-2,5-dione trifluroacetate.

EXAMPLE 2

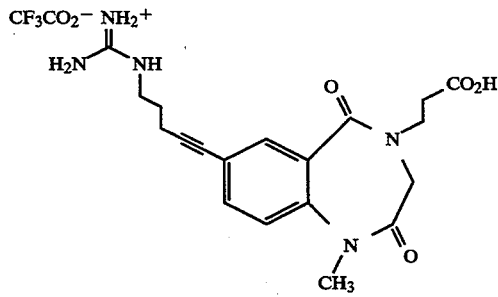

1-methyl-4-(2-carboxyethyl)-7-(5-guanidino-1-pentynyl)-3,4-dihydro-1H-1,4-benzodiazepine-2,5-dione trifluroacetate.

To a magnetically stirred solution of 6 mgs of 1-methyl-4-(2-carboxyethyl)-7-(5-amino-1-pentynyl)-3,4-dihydro-1H-1,4-benzodiazepine-2,5-dione trifluroacetate (0.017 mmol) in 1.0 mL 10% potassium bicarbonate was added 31.0 mgs of formamidine sulfonic acid (0.25 mmol). After 30 minutes, the reaction mixture was quenched with 0.5 mL acetic acid and concentrated in vacuo. The resulting residue was diluted with 2 mL water and purified by high pressure liquid chromatography, using a ½" C-18 reverse-phase column, eluting with a solvent gradient of 10:90 methanol(0.1% trifluroacetic acid)/water (0.1% trifluroacetic acid), time 0 to 10 min, to 50:50 methanol(0.1% trifluroacetic acid)/water (0.1% trifluroacetic acid), time 10 min to 40 min, flow=10 ml/min ($R_t$=36.8 min, un detection 254 nm) to yield 4.5 mgs (67%) 1-methyl-4-(2-carboxyethyl)-7-(5-guanidino-1-pentynyl)-3,4-dihydro-1H-1,4-benzodiazepine-2,5-dione trifluroacetate. HRMS (FAB) molecular ion m/z=386.1823 (cald. $C_{19}H_{24}N_5O_4$, 386.1829). $^1$H NMR ($D_2O$) 7.60 (1H, d, $^4J_{HH}$, Ar-H o-CON), 7.51 (1H, dd, $^4J_{HH}$=2 Hz, $^3J_{HH}$=8 Hz, Ar-H p-CON), 7.20 (1H, d, $^3J_{HH}$=8 Hz, Ar-H m-CON), 4.05 (1H, d, $^2J_{HH}$=14 Hz, NCHHCO), 3.92 (1H, m, NCHHCH$_2$), 3.72 (1H, d, $^2J_{HH}$=14 Hz, NCHHCO), 3.40 (1H, m, NCHHCH$_2$), 3.23-3.15 (5H, NCH$_3$, H$_2$NC(=NH$_2$)NHCH$_2$), 2.58 (2H, m, CH$_2$CO$_2$), 2.38 (2H, t, $^3J_{HH}$=7 Hz, C∫CCH$_2$), 1.76 (2H, p, $^3J_{HH}$=7 Hz, CH$_2$CH$_2$CH$_2$).

Using the above procedure, but substituting the appropriate amino acid for 1-methyl-4-(2-carboxyethyl)-7-(5-amino-1-pentynyl)-3,4-dihydro-1H-1,4-benzodiazepine-2,5-dione trifluroacetate there may be prepared, for example, the following compounds:

1-methyl-4-(2-carboxy-1-methylethyl)-7-(5-guanidino-1-pentyne)-3,4-dihydro-1H-1,4-benzodiazepine-2,5-dione trifluroacetate, 1-methyl-4-(2-carboxy-1-phenylethyl)-7-(5-guanidino-1-pentyne)-3,4-dihydro-1H-1,4-benzodiazepine-2,5-dione trifluroacetate, (±)-1-methyl-4-[succin-2-yl-(1-t-butoxy)]-7-(5-guanidino-1-pentyne)-3,4-dihydro-1H-1,4-benzodiazepine-2,5-dione trifluroacetate, (±)-1-methyl-4-[succin-2-yl-(1-glycine)]-7-(5-guanidino-1-pentyne)-3,4-dihydro-1H-1,4-benzodiazepine-2,5-dione trifluroacetate, (±)-1-methyl-4-[succin-2-yl-(1-valine)]-7-(5-guanidino-1-pentyne)-3,4-dihydro-1H-1,4-benzodiazepine-2,5-dione trifluroacetate, (±)-1-methyl-4-[succin-2-yl-(1-phenylalanine)]-7-(5-guanidino-1-pentyne)-3,4-dihydro-1H-1,4-benzodiazepine-2,5-dione trifluroacetate, 1-phenyl-4-(2-carboxy-1-methylethyl)-7-(5-guanidino-1-pentyne)-3,4-dihydro-1H-1,4-benzodiazepine-2,5-dione trifluroacetate, 1-phenyl-4-(2-carboxy-1-phenylethyl)-7-(5-guanidino-1-pentyne)-3,4-dihydro-1H-1,4-benzodiazepine-2,5-dione trifluroacetate, (±)-1-phenyl-4-[succin-2-yl-(1-t-butoxy)]-7-(5-guanidino-1-pentyne)-3,4-dihydro-1H-1,4-benzodiazepine-2,5-dione trifluroacetate, (±)-1-phenyl-4-[succin-2-yl-(1-glycine)]-7-(5-guanidino-1-pentyne)-3,4-dihydro-1H-1,4-benzodiazepine-2,5-dione trifluroacetate, (±)-1-phenyl-4-[succin-2-yl-(1-valine)]-7-(5-guanidino-1-pentyne)-3,4-dihydro-1H-1,4-benzodiazepine-2,5-dione trifluroacetate, (±)-1-phenyl-4-[succin-2-yl-(1-phenylalanine)]-7-(5-guanidino-1-pentyne)-3,4-dihydro-1H-1,4-benzodiazepine-2,5-dione trifluroacetate, 1-benzyl-4-(2-carboxy-1-methylethyl)-7-(5-guanidino-1-pentyne)-3,4-dihydro-1H-1,4-benzodiazepine-2,5-dione trifluroacetate, 1-benzyl-4-(2-carboxy-1-phenylethyl)-7-(5-guanidino-1-pentyne)-3,4-dihydro-1H-1,4-benzodiazepine-2,5-dione trifluroacetate, (±)-1-benzyl-4-[succin-2-yl-(1-t-butoxy)]-7-(5-guanidino-1-pentyne)-3,4-dihydro-1H-1,4-benzodiazepine-2,5-dione trifluroacetate, (±)-1-benzyl-4-[succin-2-yl-(1-glycine)]-7-(5-guanidino-1-pentyne)-3,4-dihydro-1H-1,4-benzodiazepine-2,5-dione trifluroacetate, (±)-1-benzyl-4-[succin-2-yl-(1-valine)]-7-(5-guanidino-1-pentyne)-3,4-dihydro-1H-1,4-benzodiazepine-2,5-dione trifluroacetate, (±)-1-benzyl-4-[succin-2-yl-(1-phenylalanine)]-7-(5-guanidino-1-pentyne)-3,4-dihydro-1H-1,4-benzodiazepine-2,5-dione trifluroacetate, 1-isopropyl-4-(2-carboxy-1-methylethyl)-7-(5-guanidino-1-pentyne)-3,4-dihydro-1H-1,4-benzodiazepine-2,5-dione trifluroacetate, 1-isopropyl-4-(2-carboxy-1-phenylethyl)-7-(5-guanidino-1-pentyne)-3,4-dihydro-1H-1,4-benzodiazepine-2,5-dione trifluroacetate, (±)-1-isopropyl-4-[succin-2-yl-(1-t-butoxy)]-7-(5-guanidino-1-pentyne)-3,4-dihydro-1H-1,4-benzodiazepine-2,5-dione trifluroacetate, (±)-1-isopropyl-4-[succin-2-yl-(1-glycine)]-7-(5-guanidino-1-pentyne)-3,4-dihydro-1H-1,4-benzodiazepine-2,5-dione trifluroacetate, (±)-1-isopropyl-4-[succin-2-yl-(1-valine)]-7-(5-guanidino-1-pentyne)-3,4-dihydro-1H-1,4-benzodiazepine-2,5-dione trifluroacetate, (±)-1-isopropyl-4-[succin-2-yl-(1-phenylalanine)]-7-(5-guanidino-1-pentyne)-3,4-dihydro-1H-1,4-benzodiazepine-2,5-dione trifluroacetate, 1-methyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate, 1-methyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate, (±)-1-methyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate, (±)-1-methyl-4-[succin-2-yl-(1-glycine)]-7-[N-(2-guanidinoethane)-3-keto-1-propyn-3-amine]-3,4-dihydro-1H-1,4-benzodiazepine-2,5-dione trifluroacetate, (±)-1-methyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate, (±)-1-methyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate, 1-phenyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate, 1-phenyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate, (±)-1-phenyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate, (±)-1-phenyl-4-[succin-2-yl-(1-glycine)]-7-[N-(2-guanidinoethane)-3-keto-1-propyn-3-amine]-3,4-dihydro-1H-1,4-benzodiazepine-2,5-dione trifluroacetate, (±)-1-phenyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate, (±)-1-phenyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate, 1-benzyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate, 1-benzyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate, (±)-1-benzyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate, (±)-1-benzyl-4-[succin-2-yl-(1-glycine)]-7-[N-(2-guanidinoethane)-3-keto-1-propyn-3-amine]-3,4-dihydro-1H-1,4-benzodiazepine-2,5-dione trifluroacetate, (±)-1-benzyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate, (±)-1-benzyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate, 1-isopropyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate, 1-isopropyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate, (±)-1-isopropyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate, (±)-1-isopropyl-4-[succin-2-yl-(1-glycine)]-7-[N-(2-guanidinoethane)-3-keto1-propyn-3-amine]-3,4-dihydro-1H-1,4-benzodiazepine-2,5-dione trifluroacetate, (±)-1-isopropyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate, (±)-1-isopropyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate, 1-methyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, 1-methyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-methyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-methyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-methyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-methyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluroacetate, 1-phenyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, 1-phenyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-phenyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-phenyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-phenyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-phenyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluroacetate, 1-benzyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, 1-benzyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-benzyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-benzyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-benzyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-benzyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluroacetate, 1-isopropyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, 1-isopropyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-isopropyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-isopropyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-isopropyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-isopropyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluroacetate, 1-methyl-4-(2-carboxy-1-methylethyl)-7-[2-(2-guanidinoethanethiol)-1-ethyne]-3,4-dihydro-1H-1,4-benzodiazepine-2,5-dione trifluroacetate, 1-methyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1-methyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1-methyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1-methyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1-methyl-4-[succin-2-yl-(1-phenylalanine)]-7-[2-(2-guanidinoethanethiol)-1-ethyne]-3,4-dihydro-1H-1,4-benzodiazepine-2,5-dione trifluroacetate, 1-phenyl-4-(2-carboxy-1-methylethyl)-7-[2-(2-guanidinoethanethiol)-1-ethyne]-3,4-dihydro-1H-1,4-benzodiazepine-2,5-dione trifluroacetate, 1-phenyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1-phenyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1-phenyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1-phenyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1-phenyl-4-[succin-2-yl-(1-phenylalanine)]-7-[2-(2-guanidinoethanethiol)-1-ethyne]-3,4-dihydro-1H-1,4-benzodiazepine-2,5-dione trifluroacetate, 1-benzyl-4-(2-carboxy-1-methylethyl)-7-[2-(2-guanidinoethanethiol)-1-ethyne]-3,4-dihydro-1H-1,4-benzodiazepine-2,5-dione trifluroacetate, 1-benzyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1-benzyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1-benzyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1-benzyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1-benzyl-4-[succin-2-yl-(1-phenylalanine)]-7-[2-(2-guanidinoethanethiol)-1-ethyne]-3,4-dihydro-1H-1,4-benzodiazepine-2,5-dione trifluroacetate, 1-isopropyl-4-(2-carboxy-1-methylethyl)-7-[2-(2-guanidinoethanethiol)-1-ethyne]-3,4-dihydro-1H-1,4-benzodiazepine-2,5-dione trifluroacetate, 1-isopropyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1-isopropyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1-isopropyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1-isopropyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1-isopropyl-4-[succin-2-yl-(1-phenylalanine)]-7-[2-(2-guanidinoethanethiol)-1-ethyne]-3,4-dihydro-1H-1,4-benzodiazepine-2,5-dione trifluroacetate, (±)-1-methyl-3-phenyl-4-(2-carboxy-1-methylethyl)-7-(5-guanidino-1-pentyne)-3,4-dihydro-1H-1,4-benzodiazepine-2,5-dione trifluroacetate, (±)-1-methyl-3-phenyl-4-(2-carboxy-1-phenylethyl)-7-(5-guanidino-1-pentyne)-3,4-dihydro-1H-1,4-benzodiazepine-2,5-dione trifluroacetate, (±)-1-methyl-3-phenyl-4-[succin-2-yl-(1-t-butoxy)]-7-(5-guanidino-1-pentyne)-3,4-dihydro-1H-1,4-benzodiazepine-2,5-dione trifluroacetate, (±)-1-methyl-3-phenyl-4-[succin-2-yl-(1-glycine)]-7-(5-guanidino-1-pentyne)-3,4-dihydro-1H-1,4-benzodiazepine-2,5-dione trifluroacetate, (±)-1-methyl-3-phenyl-4-[succin-2-yl-(1-valine)]-7-(5-guanidino-1-pentyne)-3,4-dihydro-1H-1,4-benzodiazepine-2,5-dione trifluroacetate, (±)-1-methyl-3-phenyl-4-[succin-2-yl-(1-phenylalanine)]-7-(5-guanidino-1-pentyne)-3,4-dihydro-1H-1,4-benzodiazepine-2,5-dione trifluroacetate, (±)-1,3-diphenyl-4-(2-carboxy-1-methylethyl)-7-(5-guanidino-1-pentyne)-3,4-dihydro-1H-1,4-benzodiazepine-2,5-dione trifluroacetate,
(±)-1,3-diphenyl-4-(2-carboxy-1-phenylethyl)-7-(5-guanidino-1-pentyne)-3,4-dihydro-1H-1,4-benzodiazepine-2,5-dione trifluroacetate,
(±)-1,3-diphenyl-4-[succin-2-yl-(1-t-butoxy)]-7-(5-guanidino-1-pentyne)-3,4-dihydro-1H-1,4-benzodiazepine-2,5-dione trifluroacetate,
(±)-1,3-diphenyl-4-[succin-2-yl-(1-glycine)]-7-(5-guanidino-1-pentyne)-3,4-dihydro-1H-1,4-benzodiazepine-2,5-dione trifluroacetate,
(±)-1,3-diphenyl-4-[succin-2-yl-(1-valine)]-7-(5-guanidino-1-pentyne)-3,4-dihydro-1H-1,4-benzodiazepine-2,5-dione trifluroacetate,
(±)-1,3-diphenyl-4-[succin-2-yl-(1-phenylalanine)]-7-(5-guanidino-1-pentyne)-3,4-dihydro-1H-1,4-benzodiazepine-2,5-dione trifluroacetate,
(±)-1-benzyl-3-phenyl-4-(2-carboxy-1-methylethyl)-7-(5-guanidino-1-pentyne)-3,4-dihydro-1H-1,4-benzodiazepine-2,5-dione trifluroacetate,
(±)-1-benzyl-3-phenyl-4-(2-carboxy-1-phenylethyl)-7-(5-guanidino-1-pentyne)-3,4-dihydro-1H-1,4-benzodiazepine-2,5-dione trifluroacetate,
(±)-1-benzyl-3-phenyl-4-[succin-2-yl-(1-t-butoxy)]-7-(5-guanidino-1-pentyne)-3,4-dihydro-1H-1,4-benzodiazepine-2,5-dione trifluroacetate,
(±)-1-benzyl-3-phenyl-4-[succin-2-yl-(1-glycine)]-7-(5-guanidino-1-pentyne)-3,4-dihydro-1H-1,4-benzodiazepine-2,5-dione trifluroacetate,
(±)-1-benzyl-3-phenyl-4-[succin-2-yl-(1-valine)]-7-(5-guanidino-1-pentyne)-3,4-dihydro-1H-1,4-benzodiazepine-2,5-dione trifluroacetate,
(±)-1-benzyl-3-phenyl-4-[succin-2-yl-(1-phenylalanine)]-7-(5-guanidino-1-pentyne)-3,4-dihydro-1H-1,4-benzodiazepine-2,5-dione trifluroacetate,
(±)-1-isopropyl-3-phenyl-4-(2-carboxy-1-methylethyl)-7-(5-guanidino-1-pentyne)-3,4-dihydro-1H-1,4-benzodiazepine-2,5-dione trifluroacetate,
(±)-1-isopropyl-3-phenyl-4-(2-carboxy-1-phenylethyl)-7-(5-guanidino-1-pentyne)-3,4-dihydro-1H-1,4-benzodiazepine-2,5-dione trifluroacetate,
(±)-1-isopropyl-3-phenyl-4-[succin-2-yl-(1-t-butoxy)]-7-(5-guanidino-1-pentyne)-3,4-dihydro-1H-1,4-benzodiazepine-2,5-dione trifluroacetate,
(±)-1-isopropyl-3-phenyl-4-[succin-2-yl-(1-glycine)]-7-(5-guanidino-1-pentyne)-3,4-dihydro-1H-1,4-benzodiazepine-2,5-dione trifluroacetate,
(±)-1-isopropyl-3-phenyl-4-[succin-2-yl-(1-valine)]-7-(5-guanidino-1-pentyne)-3,4-dihydro-1H-1,4-benzodiazepine-2,5-dione trifluroacetate,
(±)-1-isopropyl-3-phenyl-4-[succin-2-yl-(1-phenylalanine)]-7-(5-guanidino-1-pentyne)-3,4-dihydro-1H-1,4-benzodiazepine-2,5-dione trifluroacetate,
(±)-1-methyl-3-phenyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate,
(±)-1-methyl-3-phenyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate,
(±)-1-methyl-3-phenyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate,
(±)-1-methyl-3-phenyl-4-[succin-2-yl-(1-glycine)]-7-[N-(2-guanidinoethane)-3-keto-1-propyn-3-amine]-3,4-dihydro-1H-1,4-benzodiazepine-2,5-dione trifluroacetate,
(±)-1-methyl-3-phenyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate,
(±)-1-methyl-3-phenyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate,
(±)-1,3-diphenyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate,
(±)-1,3-diphenyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate,
(±)-1,3-diphenyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate,
(±)-1,3-diphenyl-4-[succin-2-yl-(1-glycine)]-7-[N-(2-guanidinoethane)-3-keto-1-propyn-3-amine]-3,4-dihydro-1H-1,4-benzodiazepine-2,5-dione trifluroacetate,
(±)-1,3-diphenyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate,
(±)-1,3-diphenyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate,
(±)-1-benzyl-3-phenyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate,
(±)-1-benzyl-3-phenyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate,
(±)-1-benzyl-3-phenyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate,
(±)-1-benzyl-3-phenyl-4-[succin-2-yl-(1-glycine)]-7-[N-(2-guanidinoethane)-3-keto-1-propyn-3-amine]-3,4-dihydro-1H-1,4-benzodiazepine-2,5-dione trifluroacetate,
(±)-1-benzyl-3-phenyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate,
(±)-1-benzyl-3-phenyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate,
(±)-1-isopropyl-3-phenyl-4-(2-carboxy-1-methylethyl)-7-[N-(2-guanidinoethane)-3-keto-1-propyn-3-amine]-3,4-dihydro-1H-1,4-benzodiazepine-2,5-dione trifluroacetate,
(±)-1-isopropyl-3-phenyl-4-(2-carboxy-1-phenylethyl)-7-[N-(2-guanidinoethane)-3-keto-1-propyn-3-amine]-3,4-dihydro-1H-1,4-benzodiazepine-2,5-dione trifluroacetate,
(±)-1-isopropyl-3-phenyl-4-[succin-2-yl-(1-t-butoxy)]-7-[N-(2-guanidinoethane)-3-keto-1-propyn-3-amine]-3,4-dihydro-1H-1,4-benzodiazepine-2,5-dione trifluroacetate,
(±)-1-isopropyl-3-phenyl-4-[succin-2-yl-(1-glycine)]-7-[N-(2-guanidinoethane)-3-keto-1-propyn-3-amine]-

3,4-dihydro-1H-1,4-benzodiazepine-2,5-dione trifluroacetate, (±)-1-isopropyl-3-phenyl-4-[succin-2-yl-(1-valine)]-7-[N-(2-guanidinoethane)-3-keto-1-propyn-3-amine]-3,4-dihydro-1H-1,4-benzodiazepine-2,5-dione trifluroacetate, (±)-1-isopropyl-3-phenyl-4-[succin-2-yl-(1-phenylalanine)]-7-[N-(2-guanidinoethane)-3-keto-1-propyn-3-amine]-3,4-dihydro-1H-1,4-benzodiazepine-2,5-dione trifluroacetate, (±)-1-methyl-3-phenyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, (±)-1-methyl-3-phenyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-methyl-3-phenyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-methyl-3-phenyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-methyl-3-phenyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-methyl-3-phenyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluoracetate, (±)-1,3-diphenyl-4-(2-carboxy-1-methylethyl)-7-[3-keto-1-propyn-3-(4-amidino-1-piperizine)]-3,4-dihydro-1H-1,4-benzodiazepine-2,5-dione trifluoracetate, (±)-1,3-diphenyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1,3-diphenyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1,3-diphenyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1,3-diphenyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1,3-diphenyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluroacetate, (±)-1-benzyl-3-phenyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, (±)-1-benzyl-3-phenyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-benzyl-3-phenyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-benzyl-3-phenyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-benzyl-3-phenyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-benzyl-3-phenyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluoracetate, (±)-1-isopropyl-3-phenyl-4-(2-carboxy-1-methylethyl)-7-[3-keto-1-propyn-3-(4-amidino-1-piperizine)]-3,4-dihydro-1H-1,4-benzodiazepine-2,5-dione trifluroacetate, (±)-1-isopropyl-3-phenyl-4-(2-carboxy-1-phenylethyl)-7-[3-keto-1-propyn-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-t-butoxy)]-7-[3-keto-1-propyn-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-glycine)]-7-[3-keto-1-propyn-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-valine)]-7-[3-keto-1-propyn-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-phenylalanine)]-7-[3-keto-1-propyn-3-(4-amidino-1-piperizine)]-3,4-dihydro-1H-1,4-benzodiazepine-2,5-dione trifluoracetate, (±)-1-methyl-3-phenyl-4-(2-carboxy-1-methylethyl)-7-[2-(2-guanidinoethanethiol)-1-ethyne]-3,4-dihydro-1H-1,4-benzodiazepine-2,5-dione trifluoracetate, (±)-1-methyl-3-phenyl-4-(2-carboxy-1-phenylethyl)-7-[2-(2-guanidinoethanethiol)-1-ethyne]-3,4-dihydro-1H-1,4-benzodiazepine-2,5-dione trifluoracetate, (±)-1-methyl-3-phenyl-4-[succin-2-yl-(1-t-butoxy)]-7-[2-(2-guanidinoethanethiol)-1-ethyne]-3,4-dihydro-1H-1,4-benzodiazepine-2,5-dione trifluoracetate, (±)-1-methyl-3-phenyl-4-[succin-2-yl-(1-glycine)]-7-[2-(2-guanidinoethanethiol)-1-ethyne]-3,4-dihydro-1H-1,4-benzodiazepine-2,5-dione trifluoracetate, (±)-1-methyl-3-phenyl-4-[succin-2-yl-(1-valine)]-7-[2-(2-guanidinoethanethiol)-1-ethyne]-3,4-dihydro-1H-1,4-benzodiazepine-2,5-dione trifluoracetate, (±)-1-methyl-3-phenyl-4-[succin-2-yl-(1-phenylalanine)]-7-[2-(2-guanidinoethanethiol)-1-ethyne]-3,4-dihydro-1H-1,4-benzodiazepine-2,5-dione trifluoracetate, (±)-1,3-diphenyl-4-(2-carboxy-1-methylethyl)-7-[2-(2-guanidinoethanethiol)-1-ethyne]-3,4-dihydro-1H-1,4-benzodiazepine-2,5-dione trifluroacetate, (±)-1,3-diphenyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1,3-diphenyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1,3-diphenyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1,3-diphenyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1,3-diphenyl-4-[succin-2-yl-(1-phenylalanine)]-7-[2-(2-guanidinoethanethiol)-1-ethyne]-3,4-dihydro-1H-1,4-benzodiazepine-2,5-dione trifluoracetate, (±)-1-benzyl-3-phenyl-4-(2-carboxy-1-methylethyl)-7-[2-(2-guanidinoethanethiol)-1-ethyne]-3,4-dihydro-1H-1,4-benzodiazepine-2,5-dione trifluroacetate, (±)-1-benzyl-3-phenyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1-benzyl-3-phenyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1-benzyl-3-phenyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1-benzyl-3-phenyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1-benzyl-3-phenyl-4-[succin-2-yl-(1-phenylalanine)]-7-[2-(2-guanidinoethanethiol)-1-ethyne]-3,4-dihydro-1H-1,4-benzodiazepine-2,5-dione trifluroacetate, (±)-1-isopropyl-3-phenyl-4-(2-carboxy-1-methylethyl)-7-[2-(2-guanidinoethanethiol)-1-ethyne]-3,4-dihydro-1H-1,4-benzodiazepine-2,5-dione trifluroacetate, (±)-1-isopropyl-3-phenyl-4-(2-carboxy-1-phenylethyl)-7-[2-(2-guanidinoethanethiol)-1-ethyne]-3,4-dihydro-1H-1,4-benzodiazepine-2,5-dione trifluroacetate, (±)-1-isopropyl-3-phenyl-4-[succin-2-yl-(1-t-butoxy)]-7-[2-(2-guanidinoethanethiol)-1-ethyne]-3,4-dihydro-1H-1,4-benzodiazepine-2,5-dione trifluroacetate, (±)-1-isopropyl-3-phenyl-4-[succin-2-yl-(1-glycine)]-7-[2-(2-guanidinoethanethiol)-1-ethyne]-3,4-dihydro-1H-1,4-benzodiazepine-2,5-dione trifluroacetate, (±)-1-isopropyl-3-phenyl-4-[succin-2-yl-(1-valine)]-7-[2-(2-guanidinoethanethiol)-1-ethyne]-3,4-dihydro-1H-1,4-benzodiazepine-2,5-dione trifluroacetate, (±)-1-isopropyl-3-phenyl-4-[succin-2-yl-(1-phenylalanine)]-7-[2-(2-guanidinoethanethiol)-1-ethyne]-3,4-dihydro-1H-1,4-benzodiazepine-2,5-dione trifluroacetate.

EXAMPLE 3

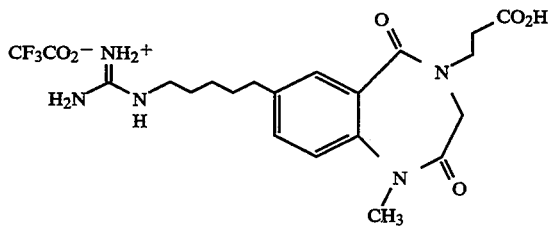

1-methyl-4-(2-carboxyethyl)-7-(5-guanidino-1-pentyl)-3,4-dihydro-1H-1,4-benzodiazepine-2,5-dione trifluroacetate.

a) A magnetically stirred slurry of 45 mgs 1-methyl-4-(2-carboxyethyl)-7-(N-boc-5-amino-1-pentynyl)-3,4-dihydro-1H-1,4-benzodiazepine-2,5-dione benzyl ester (0.0924 mmol) in 2.0 mL ethyl acetate and 10 mgs of 10% palladium on carbon was stirred under an atmosphere of hydrogen for 3 hours. The mixture was filtered, washing the solids with ethyl acetate, and concentrated in vacuo to yield 45 mgs (99%) 1-methyl-4-(2-carboxyethyl)-7-(N-boc-5-amino-1-pentyl)-3,4-dihydro-1H-1,4-benzodiazepine-2,5-dione benzyl ester. $^1$H NMR (CDCl$_3$, dTMS) 7.63 (1H, d, $^4J_{HH}$=2 Hz, Ar-H o-CON), 7.35-7.27 (6H, Ph, p-CON), 7.06 (1H, d, $^3J_{HH}$=8 Hz, m-CON), 5.11 (2H, s, OCH$_2$), 4.55 (1H, bs, BocNH), 3.98 (1H, d, $^2J_{HH}$=15 Hz, NCHHCO), 3.94 (2H, q, $^3J_{HH}$=7 Hz, NCH$_2$), 3.80 (1H, d, $^2J_{HH}$=15 Hz, NCHHCO), 3.35 (3H, s, NCH$_3$), 3.08 (2H, q, $^3J_{HH}$=6.5 Hz, BocNHCH$_2$), 2.88-2.67 (2H, m, CH$_2$CO$_2$), 2.62 (2H, t, $^3J_{HH}$=8 Hz, ArCH$_2$), 1.65 (2H, p, $^3J_{HH}$=8 Hz), 1.49 (2H, p, $^3J_{HH}$=8 Hz), 1.42 (9H, s, t-Bu), 1.35 (2H, p, $^3J_{HH}$=8 Hz). $^{13}$C NMR (CDCl$_3$, δTMS) 171.2, 168.9, 167.3, 140.1, 138.8, 135.6, 132.2, 130.2, 128.5, 128.4, 128.3, 120.9, 66.6, 52.3, 45.1, 40.4, 34.9, 34.8, 32.9, 30.7, 29.9, 28.4, 26.4.

Using the above procedure, but substituting the appropriate 7-alkynyl-3,4-dihydro-1H-1,4-benzodiazepine-2,5-dione for 1-methyl-4-(2-carboxyethyl)-7-(N-boc-5-amino-1-pentynyl)-3,4-dihydro-1H-1,4-benzodiazepine-2,5-dione benzyl ester there may be prepared, for example, the following compounds:

1-methyl-4-(3-ethoxy-1-methyl-3-oxo-1-propyl)-7-[5-(N-Boc)-amino-1-pentyl]-3,4-dihydro-1H-1,4-benzodiazepine-2,5-dione, 1-methyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1-methyl-4-[2-(1-t-butoxy-4-benzyloxy)succinyl)]-7-[5-(N-Boc)-amino-1-pentyl]-3,4-dihydro-1H-1,4-benzodiazepine-2,5-dione, (±)-1-methyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione, (±)-1-methyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1-methyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, 1-phenyl-4-(3-ethoxy-1-methyl-3-oxo-1-propyl)-7-[5-(N-Boc)-amino-1-pentyl]-3,4-dihydro-1H-1,4-benzodiazepine-2,5-dione, 1-phenyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1-phenyl-4-[2-(1-t-butoxy-4-benzyloxy)succinyl)]-7-[5-(N-Boc)-amino-1-pentyl]-3,4-dihydro-1H-1,4-benzodiazepine-2,5-dione, (±)-1-phenyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione, (±)-1-phenyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1-phenyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, 1-benzyl-4-(3-ethoxy-1-methyl-3-oxo-1-propyl)-7-[5-(N-Boc)-amino-1-pentyl]-3,4-dihydro-1H-1,4-benzodiazepine-2,5-dione, 1-benzyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1-benzyl-4-[2-(1-t-butoxy-4-benzyloxy)succinyl)]-7-[5-(N-Boc)-amino-1-pentyl]-3,4-dihydro-1H-1,4-benzodiazepine-2,5-dione, (±)-1-benzyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione, (±)-1-benzyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1-benzyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, 1-isopropyl-4-(3-ethoxy-1-methyl-3-oxo-1-propyl)-7-[5-(N-Boc)-amino-1-pentyl]-3,4-dihydro-1H-1,4-benzodiazepine-2,5-dione,
1-isopropyl-4-(3-ethoxy-1-phenyl-3-oxo-1-propyl)-7-[5-(N-Boc)-amino-1-pentyl]-3,4-dihydro-1H-1,4-benzodiazepine-2,5-dione,
(±)-1-isopropyl-4-[2-(1-t-butoxy-4-benzyloxy)succinyl)]-7-[5-(N-Boc)-amino-1-pentyl]-3,4-dihydro-1H-1,4-benzodiazepine-2,5-dione,
(±)-1-isopropyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione,
(±)-1-isopropyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione,
(±)-1-isopropyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione,
1-methyl-4-(3-ethoxy-1-methyl-3-oxo-1-propyl)-7-[5-cyano-1-pentyl]-3,4-dihydro-1H-1,4-benzodiazepine-2,5-dione,
1-methyl-4-(3-ethoxy-1-phenyl-3-oxo-1-propyl)-7-[5-cyano-1-pentyl]-3,4-dihydro-1H-1,4-benzodiazepine-2,5-dione,
(±)-1-methyl-4-[2-(1-t-butoxy-4-benzyloxy)succinyl)]-7-[5-cyano-1-pentyl]-3,4-dihydro-1H-1,4-benzodiazepine-2,5-dione,
(±)-1-methyl-4-[2-(1-benzyloxyglycinyl-4-benzyloxy)succinyl)]-7-[5-cyano-1-pentyl]-3,4-dihydro-1H-1,4-benzodiazepine-2,5-dione,
(±)-1-methyl-4-[2-(1-benzyloxyvalinyl-4-benzyloxy)succinyl)]-7-[5-cyano-1-pentyl]-3,4-dihydro-1H-1,4-benzodiazepine-2,5-dione,
(±)-1-methyl-4-[2-(1-benzyloxyphenylalanyl-4-benzyloxy)succinyl)]-7-[5-cyano-1-pentyl]-3,4-dihydro-1H-1,4-benzodiazepine-2,5-dione,
1-phenyl-4-(3-ethoxy-1-methyl-3-oxo-1-propyl)-7-[5-cyano-1-pentyl]-3,4-dihydro-1H-1,4-benzodiazepine-2,5-dione,
1-phenyl-4-(3-ethoxy-1-phenyl-3-oxo-1-propyl)-7-[5-cyano-1-pentyl]-3,4-dihydro-1H-1,4-benzodiazepine-2,5-dione,
(±)-1-phenyl-4-[2-(1-t-butoxy-4-benzyloxy)succinyl)]-7-[5-cyano-1-pentyl]-3,4-dihydro-1H-1,4-benzodiazepine-2,5-dione,
(±)-1-phenyl-4-[2-(1-benzyloxyglycinyl-4-benzyloxy)succinyl)]-7-[5-cyano-1-pentyl]-3,4-dihydro-1H-1,4-benzodiazepine-2,5-dione,
(±)-1-phenyl-4-[2-(1-benzyloxyvalinyl-4-benzyloxy)succinyl)]-7-[5-cyano-1-1-pentyl]-3,4-dihydro-1H-1,4-benzodiazepine-2,5-dione,
(±)-1-phenyl-4-[2-(1-benzyloxyphenylalanyl-4-benzyloxy)succinyl)]-7-[5-cyano-1-pentyl]-3,4-dihydro-1H-1,4-benzodiazepine-2,5-dione,
1-benzyl-4-(3-ethoxy-1-methyl-3-oxo-1-propyl)-7-[5-cyano-1-pentyl]-3,4-dihydro-1H-1,4-benzodiazepine-2,5-dione,
1-benzyl-4-(3-ethoxy-1-phenyl-3-oxo-1-propyl)-7-[5-cyano-1-pentyl]-3,4-dihydro-1H-1,4-benzodiazepine-2,5-dione,
(±)-1-benzyl-4-[2-(1-t-butoxy-4-benzyloxy)succinyl)]-7-[5-cyano-1-pentyl]-3,4-dihydro-1H-1,4-benzodiazepine-2,5-dione,
(±)-1-benzyl-4-[2-(1-benzyloxyglycinyl-4-benzyloxy)succinyl)]-7-[5-cyano-1-pentyl]-3,4-dihydro-1H-1,4-benzodiazepine-2,5-dione,
(±)-1-benzyl-4-[2-(1-benzyloxyvalinyl-4-benzyloxy)succinyl)]-7-[5-cyano-1-penyl]-3,4-dihydro-1H-1,4-benzodiazepine-2,5-dione,
(±)-1-benzyl-4-[2-(1-benzyloxyphenylalanyl-4-benzyloxy)succinyl)]-7-[5-cyano-1-pentyl]-3,4-dihydro-1H-1,4-benzodiazepine-2,5-dione,
1-isopropyl-4-(3-ethoxy-1-methyl-3-oxo-1-propyl)-7-[5-cyano-1-pentyl]-3,4-dihydro-1H-1,4-benzodiazepine-2,5-dione,
1-isopropyl-4-(3-ethoxy-1-phenyl-3-oxo-1-propyl)-7-[5-cyano-1-pentyl]-3,4dihydro-1H- 1,4-benzodiaze pine-2,5-dione,
(±)-1-isopropyl-4-[2-(1-t-butoxy-4-benzyloxy)succinyl)]-7-[5-cyano-1-pentyl]-3,4-dihydro-1H-1,4-benzodiazepihe-2,5-dione,
(±)-1-isopropyl-4-[2-(1-benzyloxyglycinyl-4-benzyloxy)succinyl)]-7-[5-cyano-1-pentyl]-3,4-dihydro-1H-1,4-benzodiazepine-2,5-dione,
(±)-1-isopropyl-4-[2-(1-benzyloxyvalinyl-4-benzyloxy)succinyl)]-7-[5-cyano-1-pentyl]-3,4-dihydro-1H-1,4-benzodiazepine-2,5-dione,
(±)-1-isopropyl-4-[2-(1-benzyloxyphenylalanyl-4-benzyloxy)succinyl)]-7-[5-cyano-1-pentyl]-3,4-dihydro-1H-1,4-benzodiazepine-2,5-dione,
1-methyl-4-(3-ethoxy-1-methyl-3-oxo-1-propyl)-7-[2-(3-cyanophenyl)-1-ethyl]-3,4-dihydro-1H-1,4-benzodiazepine-2,5-dione,
1-methyl-4-(3-ethoxy-1-phenyl-3-oxo-1-propyl)-7-[2-(3-cyanophenyl)-1-ethyl]-3,4-dihydro-1H-1,4oben-zodiazepine-2,5-dione,
(±)-1-methyl-4-[2-(1-t-butoxy-4-benzyloxy)succinyl)]-7-[2-(3-cyanophenyl)-1-ethyl]-3,4-dihydro-1H-1,4-benzodiazepine-2,5-dione,
(±)-1-methyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5-dione,
(±)-1-methyl-4-[2-(1-benzyloxyvalinyl-4-benzyloxy)succinyl)]-7-[2-(3-cyanophenyl)-1-ethyl]-3,4-dihydro-1H-1,4-benzodiazepine-2,5-dione,
(±)-1-methyl-4-[2-(1-benzyloxyphenylalanyl-4-benzyloxy)succinyl)]-7-[2-(3-cyanophenyl)-1-ethyl]-3,4-dihydro-1H-1,4-benzodiazepine-2,5-dione,
1-phenyl-4-(3-ethoxy-1-methyl-3-oxo-1-propyl)-7-[2-(3-cyanophenyl)-1-ethyl]-3,4-dihydro-1H-1,4-benzodiazepine-2,5-dione,
1-phenyl-4-(3-ethoxy-1-phenyl-3-oxo-1-propyl)-7-[2-(3-cyanophenyl)-1-ethyl]-3,4-dihydro-1H-1,4-benzodiazepine-2,5-dione,
(±)-1-phenyl-4-[2-(1-t-butoxy-4-benzyloxy)succinyl)]-7-[2-(3-cyanophenyl)-1-ethyl]-3,4-dihydro-1H-1,4-benzodiazepine-2,5-dione,
(±)-1-phenyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5-dione,
(±)-1-phenyl-4-[2-(1-benzyloxyvalinyl-4-benzyloxy)succinyl)]-7-[2-(3-cyanophenyl)-1-ethyl]-3,4-dihydro-1H-1,4-benzodiazepine-2,5-dione,
(±)-1-phenyl-4-[2-(1-benzyloxyphenylalanyl-4-benzyloxy)succinyl)]-7-[2-(3-cyanophenyl)-1-ethyl]-3,4-dihydro-1H-1,4-benzodiazepine-2,5-dione,
1-benzyl-4-(3-ethoxy-1-methyl-3-oxo-1-propyl)-7-[2-(3-cyanophenyl)-1-ethyl]-3,4-dihydro-1H-1,4-benzodiazepine-2,5-dione,
1-benzyl-4-(3-ethoxy-1-phenyl-3-oxo-1-propyl)-7-[2-(3-cyanophenyl)-1-ethyl]-3,4-dihydro-1H-1,4-benzodiazepine-2,5-dione, (±)-1-benzyl-4-[2-(1-t-butoxy-4-benzyloxy)succinyl)]-7-[2-(3-cyanophenyl)-1-ethyl]-3,4-dihydro-1H-1,4-benzodiazepine-2,5-dione, (±)-1-benzyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5,dione, (±)-1-benzyl-4-[2-(1-benzyloxyvalinyl-4-benzyloxy)-succinyl)]-7-[2-(3-cyanophenyl)-1-ethyl]-3,4-dihydro-1H-1,4-benzodiazepine-2,5-dione, (±)-1-benzyl-4-[2-(1 -benzyloxyphenylalanyl-4-benzyloxy)succinyl)]-7-[2-(3-cyanophenyl)-1-ethyl]-3,4-dihydro-1H-1,4-benzodiazepine-2,5-dione, 1-isopropyl-4-(3-ethoxy-1-methyl-3-oxo- 1-propyl)-7-[2-(3-cyanophenyl)-1-ethyl]-3,4-dihydro-1H-1,4-benzodiazepine-2,5-dione, 1-isopropyl-4-(3-ethoxy-1-phenyl-3-oxo-1-propyl)-7-[2-(3-cyanophenyl)-1-ethyl]-3,4-dihydro-1H-1,4-benzodiazepine-2,5-dione, (±)-1-isopropyl-4-[2-(1-t-butoxy-4-benzyloxy)succinyl)]-7-[2-(3-cyanophenyl)-1-ethyl]-3,4-dihydro-1H-1,4-benzodiazepine-2,5-dione, (±)-1-isopropyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5-dione, (±)- 1-isopropyl-4-[2-(1-benzyloxyvalinyl-4-benzyloxy)succinyl) ]-7-[2-(3-cyanophenyl)-1-ethyl]-3,4-dihydro-1H-1,4-benzodiazepine-2,5-dione, (±)-1-isopropyl-4-[2-(1-benzyloxyphenylalanyl-4-benzyloxy)succinyl)]-7-[2-(3-cyanophenyl)-1-ethyl]-3,4-dihydro-1H-1,4-benzodiazepine-2,5-dione, 1-methyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione, 1-methyl-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione, (±)-1-methyl-4-[2-(1-t-butoxy-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-methyl-4-[2-(1-benzyloxyglycinyl-4-benzyloxy)succinyl)]-7-[N-[2-(N-Boc)-]-3-keto-1-propyl-3-amine]-3,4-dihydro-1H-1,4-benzodiazepine-2,5-dione, (±)-1-methyl-4-[2-(1-benzyloxyvalinyl-4-benzyloxy)-succinyl)]-7-[N-[2-(N-Boc)-aminoethane]-3-keto-1-propyl-3-amine]-3,4-dihydro-1H-1,4-benzodiazepine-2,5-dione, (±)-1-methyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H- 1,4-benzodiazepine-2,5-dione, 1-phenyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione, 1-phenyl-4-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione, (±)-1-phenyl-4-[2-(1-t-butoxy-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1 -phenyl-4-[2-(1 -bertzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)- 1-phenyl-4-[2-(1-benzyloxyvalinyl-4-benzyloxy)-succinyl)]-7-[N-[2-(N-Boc)-aminoethane]-3-keto-1-propyl-3-amine]-3,4-dihydro-1H-1,4-benzodiazepine-2,5-dione, (±)-1-phenyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione 1-benzyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione, 1-benzyl-4-(3-ethoxy-1-phenyl-3-oxo-1-propyl)-7-[N-[2-(N- Boc)-aminoethane]-3-keto-1-propyl-3-amine]-3,4-dihydro-1H-1,4-benzodiazepine-2,5-dione, (±)-1-benzyl-4-[2-(1-t-butoxy-4-benzyloxy)succinyl)]-7-[N-[2-(N-Boc)-aminoehane]-3-keto-1-propyl-3-amine]-3,4-dihydro-1H-1,4-benzodiazepine-2,5-dione, (±)-1-benzyl-4-[2-(1 -benzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-benzyl-4-[2-(1-benzyloxyvalinyl-4-benzyloxy)succinyl) ]-7-[N-[2-(N-Boc)-aminoethane]-3-keto-1-propyl-3-amine]-3,4-dihydro-1H-1,4-benzodiazepine-2,5-dione, (±)-1-benzyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, 1-isopropyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione, 1-isopropyl-4-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione, (±)-1-isopropyl-4-[2-( 1-t-butoxy-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl-4-[2-(1-benzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl -4-[2-(1-benzyloxyvalinyl -4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, 1-methyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione, 1-methyl-4-(3-ethoxy-1-phenyl-3-oxo-1-propyl)-7-[3-keto-1-propyl-3-[4-(N-Boc)-1-piperizine]]-3,4-dihydro-1H-1,4-benzodiazepine-2,5-dione, (±)-1-methyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5-dione, 1-phenyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione, 1-phenyl-4-(3-ethoxy-1-phenyl-3-oxo-1-propyl)-7-[3-keto-1-propyl-3-keto-1-propyl-3-[4-(N-Boc)-1-piperizine]]-3,4-dihydro-1H-1,4-benzodiazepine-2,5-dione, (±)-1-phenyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-phenyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-phenyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione (±)-1-phenyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5dione, 1-benzyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione, 1-benzyl-4-(3-ethoxy-1-phenyl-3-oxo-1-propyl)-7-[3-keto-1-propyl-3-[4-(N-Boc)-1-piperizine]]-3,4-dihydro-1H-1,4-bertzodiaze pine- 2,5-dione, (±)-1-benzyl-4-[2-(1-t-butoxy-4-benzyloxy)succinyl)]-7-[3-keto-1-propyl-3-[4-(N-Boc)-1- piperizine]]-3,4-dihydro-1H-1,4-benzodiazep ine-2,5-dione, (±)-1-benzyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-benzyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-benzyl-4-[2-(1-benzyloxyphenylalanyl-4-bertzyloxy)succinyl)]-7-[3-keto-1-proyl-3-[4-(N-Boc)-1-piperizine]]-3,4-dihydro-1H-1,4-benzodiazepine-2,5-dione, 1-isopropyl-4-(3-ethoxy- 1-methyl-3-oxo-1-propyl)-7-[3-keto-1-propyl-3-[4-(N-Boc)-1-piperizine]]-3,4-dihydro-1H-1,4-benzodiazepine-2,5-dione, 1-isopropyl-4-(3-ethoxy-1-phenyl-3-oxo-1-propyl )-7-[3-keto-1-propyl-3-[4-(N-Boc)-1-piperizine]]-3,4-dihydro-1H-1,4-benzodiazepine-2,5-dione, (±)-1-isopropyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiaze pine-2,5-dione, (±)-1-isopropyl-4-[2-(1-benzyloxyglycinyl-4-benzyloxy)succinyl)-7-[3-keto-1-propyl-3-[4-(N-Boc )-1-piperizine]]-3,4-dihydro-1H-1,4-benzodiazepine-2,5-dione, (±)-1-isopropyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-isopropyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5-dione, 1-methyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, 1-methyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1-methyl-4-[2-(1-t-butoxy-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl-4-[2-(1-benzyloxyvalinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl4-[2-(1 -benzyloxyphenylalanyl-4-benzyloxy)succinyl)]-7-[2-[2-(N-Boc)aminoethanethiol]-1-ethyl]-3,4-dihydro-1H-1,4-bertzodiazepine-2,5-dione, 1-phenyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, 1-phenyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1-phenyl-4-[2-(1-t-butoxy-4-benzyloxy)succinyl)]-7-[2-[2-(N-Boc)aminoethanethiol]-1-ethyl]-3,4-dihydro-1H-1,4-bertzodiazepine-2,5-dione, (±)-1-phenyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-phenyl-4-[2-(1-benzyloxyvalinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-phenyl-4-[2-(1-benzyloxyphenylalanyl-4-benzyloxy)succinyl)]-7-[2-[2(N-Boc)aminoethanethiol]-1-ethyl]-3,4-dihydro-1H-1,4-benzodi azepine-2,5-dione, 1-benzyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, 1-benzyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1-benzyl-4-[2-(1-t-butoxy-4-benzyloxy )succinyl )]-7-[2-[2-(N-Boc)aminoethanethiol]-1-ethyl]-3,4-dihydro-1H-1,4-benzodiazepine-2,5-dione, (+)-1-benzyl-4-[2-(1-benzyloxyglycinyl-4-bertzyloxy)succinyl)]-7-[2-[2-(N-Boc)aminoetanethiol]-1-ethyl]-3,4-dihydro-1H-1,4-benzodiazepine-2,5-dione, (±)-1-benzyl-4-[2-(1-benzyloxyvalinyl-4-benzyloxy)succinyl)]-7-[2-[2-(N-Boc)aminoethanethiol]-1-ethyl]-3,4-dihydro-1H- 1,4-benzodi aze p ine-2,5-dione, (±)-1-benzyl-4-[2-(1-benzyloxyphenylalanyl-4-bertzyloxy)succinyl)]-7-[2-[2-(N-Boc)aminoethanethiol]-1-ethyl]-3,4-dihydro-1H-1,4-benzodiazepine-2,5-dione, 1-isopropyl-4-(3-ethoxy-1-methyl-3-oxo-1-propyl)-7-[2-[2-(N-Boc)aminoethanethiol]-1-ethyl]-3,4-dihydro-1H-1,4-benzodiaze p ine-2,5-dione, 1-isopropyl-4-(3-ethoxy-1-phenyl-3-oxo-1-propyl )-7-[2-[2-(N-Boc)aminoethanethiol]-1-ethyl]-3,4-dihydro-1H-1,4-benzodiazepine-2,5-dione, (±)-1-isopropyl-4-[2-(1-t-butoxy-4-benzyloxy)succinyl)]-7-[2-[2-(N-Boc)aminoethanethiol]-1-ethyl]-3,4-dihydro-1 H-1,4-benzodiazepine-2,5-dione, (±)-1-isopropyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-isopropyl-4-[2-(1-benzyloxyvalinyl-4-benzyloxy)succinyl)]-7-[2-[2-(N-Boc)aminoethanethiol]-1-ethyl]-3,4-dihydro- 1 H- 1,4-benzodiazepine-2,5-dione, (±)-1-isopropyl-4-[2-(1-benzyloxyphenylalany14-benzyloxy)succinyl)]-7-[2-[2-(N-Boc)aminoethanethiol]-1-ethyl]-3,4-dihydro-1H-1,4-benzodiazepine-2,5-dione, 1-methyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, 1-methyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1-methyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1-methyl-4-[2-(1-benzyloxyglycinyl-4-benzyloxy)succinyl)]-7-[2-(4-cyanothiophenol)-1-ethyl]-3,4-dihydro-1H-1,4-benzodi azepine-2,5-dione, (±)-1-methyl -4-[2-(1-benzyloxyvalinyl-4-benzyloxy)succinyl) ]-7-[2-(4-cyanothiophenol)-1-ethyl]-3,4-dihydro-1H-1,4-benzodiazepine-2,5-dione, (±)-1-methyl-4-[2-(1 -benzyloxyphenylalanyl-4-benzyloxy)succinyl)]-7-[2-(4-cyanothiophenol)-1-ethyl]-3,4-dihydro-1H-1,4-benzodiazepine-2,5-dione, 1-phenyl-4-(3-ethoxy-1-methyl-3-oxo-1-propyl )-7-[2-(4-cyanothiophenol)- 1-ethyl]-3,4-dihydro-1H-1,4-benzodiazepine-2,5-dione, 1-phenyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1-phenyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1-phenyl-4-[2-(1-benzyloxyglycinyl-4-benzyloxy)succinyl)]-7-[2-(4-cyanothiophenol)-1-ethyl]-3,4-dihydro-1H-1,4-benzodiazepine-2,5-dione, (±)-1-phenyl-4-[2-(1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1-phenyl-4-[2-(1-benzyloxyphenylalanyl-4-benzyloxy)succinyl)]-7-[2-(4-cyanothiophenol)-1-ethyl]-3,4-dihydro-1H-1,4-benzodiazepine-2,5-dione, 1-benzyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, 1-benzyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)1-benzyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1-benzyl-4-[2-(1-benzyloxyglycinyl-4-benzyloxy)succinyl)]-7-[2-(4-cyanothiophenol)-1-ethyl]-3,4-dihydro-1H-1,4-benzodiazepine-2,5-dione, (±)-1-benzyl-4-[2-(1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1-benzyl-4-[2-(1-benzyloxyphenylalanyl-4-benzyloxy)succinyl)]-7-[2-(4-cyanothiophenol)-1-ethyl]-3,4-dihydro-1H-1,4-benzodiazepine-2,5-dione, 1-isopropyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, 1-isopropyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1-isopropyl-4-[2-(1-t-butoxy -4-benzyloxy)succinyl)]-7-[2-(4-cyanothiophenol)-1-ethyl]-3,4-dihydro-1H-1,4-benzodiazepine-2,5-dione, (±)-1-isopropyl-4-[2-(1-benzyfoxyglycinyl-4-benzyloxy)succinyl)]-7-[2-(4-cyanothiophenol)-1-ethyl]-3,4-dihydro-1H-1,4-benzodiazepine-2,5-dione, (±)-1-isopropyl-4-[2-( 1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1-isopropyl-4-[2-(1-benzyloxyphenylalanyl-4-benzyloxy)succinyl)]-7-[2-(4-cyanothiophenol)-1-ethyl]-3,4-dihydro-1H-1,4-benzodiaze pine-2,5-dione, 1-methyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, 1-methyl-4-(3-ethoxy-1-phenyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-4-[2-(1-benzyloxyglycinyl-4-benzyloxy)succinyl) ]-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-4-[2-(1-benzyloxyvalinyl-4-benzyloxy)succinyl)]-7-[4-[2-(N-Boc)amino-6-methylpyrimidine-4-yl]-4-oxa- 1-b utyl ]-3,4-dihydro-1H-1,4-benzodiazepine-2,5-dione, (±)-1-methyl-4-[2-(1-benzyloxyphenylalanyl-4-benzyloxy)succinyl)]-7-[4-[2-(N-Boc)amino-6-methylpyrimidine-4-yl ]-4-oxa-1-butyl]-3,4-dihydro-1H-1,4-benzodiazepine-2,5-dione, 1-phenyl-4-(3-ethoxy-1-methyl-3-oxo-1-propyl)-7-[4-[2-(N-Boc)amino-6-methylpyrimidine-4-yl]-4-oxa-1 -butyl]-3,4-dihydro-1H-1,4-benzodiazepine-2,5-dione, 1-phenyl-4-(3-ethoxy-1-phenyl-3-oxo-1-propyl)-7-[4-[2-(N-Boc )amino-6-methylpyrimidine-4-yl]-4-oxa-1-butyl]-3,4-dihydro-1H-1,4-benzodiazepine-2,5-dione, (±)-1-phenyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-phenyl-4-[2-(1-benzyloxyglycinyl-4-benzyloxy)succinyl)]-7-[4-[2-(N-Boc)amino-6-methylpyrimidine-4-yl]-4-oxa-1-b utyl ]-3,4-dihydro-1H-1,4-benzodiazepine-2,5-dione, (±)-1-phenyl-4-[2-(1-benzyloxyvalinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-phenyl-4-[2-(1-benzyloxyphenylalanyl-4-benzyloxy)succinyl)]-7-[4-[2-(N-Boc)amino-6-methylpyrimidine-4-yl]-4-oxa-1-butyl]-3,4-dihydro-1H-1,4benzodiazepine-2,5-dione, 1-benzyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, 1-benzyl-4-(3-ethoxy-1-phenyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-4-[2-(1-benzyloxyglycinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-4-[2-(1-benzyloxyvalinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-4-[2-(1-benzyloxyphenylalanyl-4-bertzyloxy)succinyl)]-7-[4-[2-(N-Boc)amino-6-methylpyrimidine-4-yl]4-oxa-1-butyl]-3,4-dihydro-1H-1,4-benzodiazepine-2,5-dione, 1-isopropyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, 1-isopropyl-4-(3-ethoxy-1-phenyl-3-oxo-1-propyl)-7-[4-[2-(N-Boc )amino-6-methylpyrimidine-4-yl]-4-oxa-1-butyl]-3,4-dihydro-1H-1,4-benzodiazepine-2,5-dione, (±)-1-isopropyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-4-[2-(1-benzyloxyglycinyl-4-benzyloxy)succinyl )]-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-4-[2-(1-benzyloxyvalinyl-4-benzyloxy)succinyl)]-7-[4-[2(N-Boc)amino-6-methylpyrimidine-4-yl]-4-oxa-1-butyl]-3,4-dihydro-1H-1,4-benzodiazepine-2,5-dione, (±)-1-isopropyl-4-[2-(1-benzyloxyphenylalanyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, 1-methyl-4-(3-ethoxy-1-methyl-3-oxo-1-propyl)-7-[5-[2-(N-Boc)aminopyridine-3-yl]-5-oxa-1-pentyl]-3,4-dihydro-1H-1,4-benzodiazepine-2,5-dione, 1-methyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-methyl-4-[2-(1-t-butoxy-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-methyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-methyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)- 1-methyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, 1-phenyl-4-(3-ethoxy-1-methyl-3-oxo-1-propyl)-7-[5-[2-(N-Boc)aminopyridine-3- yl]-5-oxa-1-pentyl]-3,4-dihydro-1H-1,4-benzodiazepine-2,5-dione, 1-phenyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-phenyl-4-[2-(1-t-butoxy-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-phenyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-phenyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H- 1,4-benzodiazepine-2,5-dione, (±)-1-phenyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, 1-benzyl-4-(3-ethoxy-1-methyl-3-oxo-1-propyl)-7-[5-[2-(N-Boc)aminopyridine-3-yl]-5-oxa-1-pentyl]-3,4-dihydro-1H-1,4-benzodiazepine-2,5-dione, 1-benzyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-benzyl-4-[2-(1-t-butoxy-4-benzyloxy)succinyl)]-7-[5-[2-(N-Boc)aminopyridine-3-yl]-5-oxa-1-pentyl]-3,4-dihydro- 1H-1,4-benzodiazepine-2,5-dione, (±)-1-benzyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-benzyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-benzyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, 1-isopropyl-4-(3-ethoxy-1-methyl-3-oxo- 1-propyl)-7-[5-[2-(N-Boc)aminopyridine-3-yl]-5-oxa-1-pentyl]-3,4-dihydro-1H-1,4-benzodiazepine-2,5-dione, 1-isopropyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-isopropyl-4-[2-(1-t-butoxy-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-isopropyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-isopropyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-isopropyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-methyl-3-phenyl-4-(3-ethoxy-1-methyl-3-oxo-1-propyl)-7-[5-(N-Boc)-amino-1-pentyl]-3,4-dihydro-1H-1,4-benzodiazepine-2,5-dione, (±)-1-methyl-3-phenyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1-methyl-3-phenyl-4-[2-(1-t-butoxy-4-benzyloxy)succinyl)]-7-[5-(N-Boc)-amino-1-pentyl]-3,4-dihydro-1H-1,4-benzodiazepine-2,5-dione, (±)-1-methyl-3-phenyl-4-[2-(1 -benzyloxyglycinyl-4-benzyloxy)succinyl)]-7-[5-(N-Boc)-amino-1-pentyl]-3,4-dihydro-1H-1,4-benzodiazepine-2,5-dione, (±)-1-methyl-3-phenyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, (±)-1,3-diphenyl-4-(3-ethoxy-1-methyl-3-oxo-1-propyl)-7-[5-(N-Boc)-amino-1-pentyl]-3,4-dihydro-1H-1,4-benzodiazepine-2,5-dione, (±)-1,3-diphenyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1,3-diphenyl-4-[2-(1-t-butoxy-4-benzyloxy)succinyl)]-7-[5-(N-Boc)-amino-1-pentyl]-3,4-dihydro-1H-1,4-benzodiazepine-2,5-dione, (±)-1,3-diphenyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione, (±)-1,3-diphenyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1,3-diphenyl -4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, (±)-1-benzyl-3-phenyl-4-(3-ethoxy-1 -methyl-3-oxo-1-propyl)-7-[5-(N-Boc)-amino-1-pentyl]-3,4-dihydro-1H-1,4-benzodiazepine-2,5-dione, (±)-1-benzyl-3-phenyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1-benzyl-3-phenyl-4-[2-(1-t-butoxy-4-benzyloxy)-succinyl)]-7-[5-(N-Boc)-amino-1-pentyl]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione, (±)-1-benzyl-3-phenyl-4-[2-( 1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, (±)-1-isopropyl-3-phenyl-4-(3-ethoxy-1-methyl-3-oxo-1-propyl)-7-[5-(N-Boc)-amino-1-pentyl]-3,4-dihydro-1H-1,4-benzodiazepine-2,5-dione, (±)-1-isopropyl-3-phenyl-4-(3-ethoxy-1-phenyl-3-oxo-1-propyl)-7-[5-(N-Boc)-amino-1-pentyl]-3,4-dihydro-1H-1,4-benzodiazepine-2,5-dione, (±)-1-isopropyl-3-phenyl-4-[2-(1-t-butoxy-4-benzyloxy)succinyl)]-7-[5-(N-Boc)-amino-1-pentyl]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[5-(N-Boc)-amino-1-pentyl]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[5-(N-Boc)-amino-1-pentyl]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[5-(N-Boc)-amino-1-pentyl]-3,4-dihydro-1H-1,4-benzodiazepine-2,5-dione, (±)-1-methyl-3-phenyl-4-(3-ethoxy-1-methyl-3-oxo-1-propyl)-7-[5-cyano-1-pentyl]-3,4-dihydro-1H-1,4-benzodiazepine-2,5-dione, (±)-1-methyl-3-phenyl-4-(3-ethoxy-1-phenyl-3-oxo-1-propyl)-7-[5-cyano-1-pentyl]-3,4-dihydro-1H-1,4-benzodiazepine-2,5-dione, (±)- 1-methyl-3-phenyl-4-[2-(1-t-butoxy-4-benzyloxy)succinyl)]-7-[5-cyano-1-pentyl]-3,4-dihydro-1H-1,4-benzodiazepine-2,5-dione, (±)-1-methyl-3-phenyl-4-[2-(1-benzyloxyglycinyl-4-benzyloxy)succinyl)]-7-[5-cyano-1-pentyl]-3,4-dihydro-1H-1,4-benzodiazepine-2,5-dione, (±)-1-methyl-3-phenyl-4-[2-(1-benzyloxyvalinyl-4-benzyloxy)succinyl)]-7-[5-cyano-1-pentyl]-3,4-dihydro-1H-1,4-benzodiazepine-2,5-dione, (-±)-1-methyl-3-phenyl-4-[2-(1-benzyloxyphenylalanyl-4-benzyloxy)succinyl)]-7-[5-cyano-1-pentyl]-3,4-dihydro-1H-1,4-benzodiazepine-2,5-dione, (±)-1,3-diphenyl-4-(3-ethoxy-1-methyl-3-oxo-1-propyl)-7-[5-cyano-1-pentyl]-3,4-dihydro-1H-1,4-benzodiazepine-2,5-dione, (±)-1,3-diphenyl-4-(3-ethoxy-1-phenyl-3-oxo-1-propyl)-7-[5-cyano-1-pentyl]-3,4-dihydro-1H-1,4-benzodiazepine-2,5-dione, (±)-1,3-diphenyl-4-[2-(1-t-butoxy-4-benzyloxy)succinyl)]-7-[5-cyano-1-pentyl]-3,4-dihydro-1H-1,4-benzodiazepine-2,5-dione, (±)-1,3-diphenyl-4-[2-(1-benzyloxyglycinyl-4-benzyloxy)succinyl)]-7-[5-cyano-1-pentyl]-3,4-dihydro-1H-1,4-benzodiazepine-2,5-dione, (±)-1,3-diphenyl-4-[2-(1-benzyloxyvalinyl-4-benzyloxy)succinyl)]-7-[5-cyano-1-pentyl]-3,4-dihydro-1H-1,4-benzodiazepine-2,5-dione, (±)-1,3-diphenyl-4-[2-(1-benzyloxyphenylalanyl-4-benzyloxy)succinyl)]-7-[5-cyano-1-pentyl]-3,4-dihydro-1H-1,4-benzodiazepine-2,5-dione, (±)-1-benzyl-3-phenyl-4-(3-ethoxy-1-methyl-3-oxo-1-propyl)-7-[5-cyano-1-pentyl]-3,4-dihydro-1H-1,4-benzodiazepine-2,5-dione, (±)-1-benzyl-3-phenyl-4-(3-ethoxy-1-phenyl-3-oxo-1-propyl)-7-[5-cyano-1-pentyl]-3,4-dihydro-1H-1,4-benzodiazepine-2,5-dione, (±)- 1-benzyl-3-phenyl-4-[2-(1-t-butoxy-4-benzyloxy)succinyl)]-7-[5-cyano-1-pentyl]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[5-cyano-1-pentyl]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[5-cyano-1-pentyl]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[5-cyano-1-pentyl]-3,4-dihydro-1H-1,4-benzodiazepine-2,5-dione, (±)-1-isopropyl-3-phenyl-4-(3-ethoxy-1-methyl-3-oxo-1-propyl)-7-[5-cyano-1]-3,4-dihydro-1H-1,4-benzodiazepine-2,5-dione, (±)- 1-isopropyl-3-phenyl-4-(3-ethoxy-1-phenyl-3-oxo-1-propyl)-7-[5-cyano-1-pentyl]-3,4-dihydro-1H-1,4-benzodiazepine-2,5-dione, (±)-1-isopropyl-3-phenyl-4-[2-(1-t-butoxy-4-benzyloxy)succinyl)]-7-[5-cyano-1]-3,4-dihydro-1H-1,4-benzodiazepine-2,5-dione, (±)-1-isopropyl-3-phenyl-4-[2-(1-benzyloxyglydnyl-4-benzyloxy)succinyl)]-7-[5-cyano-1-pentyl]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[5-cyano-1-pentyl]-3,4-dihydro-1H-1,4-benzodiazepine-2,5-dione, (±)-1-isopropyl-3-phenyl-4-[2-(1-benzyloxyphenylalanyl-4-benzyloxy)succinyl)]7-[5-cyano-1-pentyl]-3,4-dihydro-1H-1,4-benzodiazepine-2,5-dione, (±)-1-methyl-3-phenyl-4-(3-ethoxy-1-methyl-3-oxo-1-propyl)-7-[2-(3-cyanophenyl)-1-ethyl]-3,4-dihydro-1H-1,4-benzodiazepine-2,5-dione, (±)-1-methyl-3-phenyl-4-(3-ethoxy-1-phenyl-3-oxo-1-propyl)-7-[2-(3-cyanophenyl)-1 -ethyl]-3,4-dihydro-1H-1,4-benzodiazepine-2,5-dione, (±)-1-methyl-3-phenyl-4-[2-(1-t-butoxy-4-benzyloxy)-succinyl)]-7-[2-(3-cyanophenyl)-1-ethyl]-3,4-dihydro-1H-1,4-benzodiazepine-2,5-dione,
(±)-1-methyl-3-phenyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5-dione,
(±)-1-methyl-3-phenyl-4-[2-(1-benzyloxyvalinyl-4-benzyloxy)succinyl)]-7-[2-(3-cyanophenyl)-1-ethyl]-3,4-dihydro-1H-1,4-benzodiazepine-2,5-dione,
(±)-1-methyl-3-phenyl-4-[2-(1-benzyloxyphenylalanyl-4-benzyloxy)succinyl)]-7-[2-(3-cyanophenyl)-1-ethyl]-3,4-dihydro-1H-1,4-benzodiazepine-2,5-dione,
(±)-1,3-diphenyl-4-(3-ethoxy-1-methyl-3-oxo-1-propyl)-7-[2-(3-cyanophenyl)-1-ethyl]-3,4-dihydro-1H-1,4-benzodiazepine-2,5-dione,
(±)-1,3-diphenyl-4-(3-ethoxy-1-phenyl-3-oxo-1-propyl)-7-[2-(3-cyanophenyl)-1-ethyl]-3,4-dihydro-1H-1,4-benzodiazepine-2,5-dione,
(±)-1,3-diphenyl-4-[2-(1-t-butoxy -4-benzyloxy)succinyl)]-7-[2-(3-cyanophenyl)-1-ethyl]-3,4-dihydro-1H-1,4-benzodiazepine-2,5-dione,
(±)-1,3-diphenyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5-dione,
(±)-1,3-diphenyl-4-[2-(1-benzyloxyvalinyl-4-benzyloxy)succinyl)]-7-[2-(3-cyanophenyl)-1-ethyl]-3,4-dihydro-1H-1,4-benzodiazepine-2,5-dione,
(±)-1,3-diphenyl-4-[2-(1-benzyloxyphenylalanyl-4-bertzyloxy)succinyl)]-7-[2-(3-cyanophenyl)-1-ethyl]-3,4-dihydro-1H-1,4-benzodiazepine-2,5-dione,
(±)-1-benzyl-3-phenyl-4-(3-ethoxy-1-methyl-3-oxo-1-propyl)-7-[2-(3-cyanophenyl)-1-ethyl]-3,4-dihydro-1H-1,4-bertzodiazepine-2,5-dione,
(±)-1-benzyl-3-phenyl-4-(3-ethoxy-1-phenyl-3-oxo-1-propyl)-7-[2-(3-cyanophenyl)-1-ethyl]-3,4-dihydro-1H-1,4-benzodiazepine-2,5-dione,
(±)-1-benzyl-3-phenyl-4-[2-(1-t-butoxy -4-benzyloxy)succinyl)]-7-[2-(3-cyanophenyl)-1-ethyl]-3,4-dihydro-1H-1,4-benzodiazepine-2,5-dione,
(±)-1-benzyl-3-phenyl-4-[2-(1-benzyloxyglycinyl-4-benzyloxy)succinyl)]-7-[2-(3-cyanophenyl)-1-ethyl]-3,4-dihydro-1H-1,4-benzodiazepine-2,5-dione,
(±)-1-benzyl-3-phenyl-4-[2-(1-benzyloxyvalinyl-4-benzyloxy)succinyl)]-7-[2-(3-cyanophenyl)-1-ethyl]-3,4-dihydro-1H-1,4-benzodiazepine-2,5-dione,
(±)-1-benzyl-3-phenyl-4-[2-(1-benzyloxyphenylalanyl-4-benzyloxy)succinyl)]-7-[2-(3-cyanophenyl)-1-ethyl]-3,4-dihydro-1H-1,4-benzodiazepine-2,5-dione,
(±)-1-isopropyl-3-phenyl-4-(3-ethoxy-1-methyl-3-oxo-1-propyl)-7-[2-(3-cyanophenyl)-1-ethyl]-3,4-dihydro-1H-1,4-benzodiazepine-2,5-dione,
(±)-1-isopropyl-3-phenyl-4-(3-ethoxy-1-phenyl-3-oxo-1-propyl)-7-[2-(3-cyanophenyl)-1-ethyl]-3,4-dihydro-1H-1,4-benzodiazepine-2,5-dione,
(±)-1-isopropyl-3-phenyl-4-[2-(1-t-butoxy-4-benzyloxy)succinyl)]-7-[2-(3-cyanophenyl)-1-ethyl]-3,4-dihydro-1H-1,4-benzodiazepine-2,5-dione,
(±)-1-isopropyl-3-phenyl-4-[2-( 1-benzyloxy glycinyl-4-bertzyloxy)succinyl)]-7-[2(3-cyanophenyl)-1-ethyl]-3,4-dihydro-1H-1,4-benzodiazepine-2,5-dione,
(±)-1-isopropyl-3-phenyl-4-[2-(1-benzyloxyvalinyl-4-benzyloxy)succinyl)]-7-[2-(3-cyanophenyl)-1-ethyl]-3,4-dihydro-1H-1,4-benzodiazepine-2,5-dione,
(±)-1-isopropyl-3-phenyl-4-[2-(1-benzyloxyphenylalanyl-4-benzyloxy)succinyl)]-7-[2-(3-cyanophenyl)-1-ethyl]-3,4-dihydro-1H-1,4-benzodiazepine-2,5-dione,
(±)-1-methyl-3-phenyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione,
(±)-1-methyl-3-phenyl-4-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione,
(±)-1-methyl-3-phenyl-4-[2-(1-t-butoxy4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-methyl-3-phenyl-4-[2-(1-benzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-methyl-3-phenyl-4-[2-(1-benzyloxyvalinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-methyl-3-phenyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1,3-diphenyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione,
(±)-1,3-diphenyl-4-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione,
(±)-1,3-diphenyl-4-[2-(1-t-butoxy-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1,3-diphenyl-4-[2-(1-benzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1,3-diphenyl-4-[2-(1-benzyloxyvalinyl-4-benzyloxy)succinyl) ]-7-[N-[2-(N-Boc)-aminoethane]-3-keto-1-propyl-3-amine]-3,4-dihydro-1H-1,4-benzodiazepine-2,5-dione,
(±)-1,3-diphenyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-benzyl-3-phenyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione,
(±)-1-benzyl-3-phenyl-4-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione,
(±)-1-benzyl-3-phenyl-4-[2-(1-t-butoxy-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-benzyl-3-phenyl-4-[2-(1-benzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-benzyl-3-phenyl-4-[2-(1-benzyloxyvalinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione,
(±)-1-benzyl-3-phenyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl-3-phenyl-4-(3-ethoxy-1-methyl-3-oxo-1-propyl)-7-[N-[2-(N-Boc)-aminoethane]-3-keto-1-propyl-3-amine]-3,4-dihydro-1H-1,4-benzodiazepine-2,5-dione, (±)-1-isopropyl-3-phenyl-4-(3-ethoxy-1-phenyl-3-oxo-1-propyl)-7-[N-[2-(N-Boc)-aminoethane]-3-keto-1-propyl-3-amine]-3,4-dihydro-1H-1,4-benzodiazepine-2,5-dione, (±)-1-isopropyl-3-phenyl-4-[2-(1-t-butoxy-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[N-[2-(N-Boc)-aminoethane]-3-keto-1-propyl-3-amine]-3,4-dihydro-1H-1,4-benzodiazepine-2,5-dione, (±)-1-methyl-3-phenyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione, (±)-1-methyl-3-phenyl-4-(3-ethoxy-1-phenyl-3-oxo-1-propyl)-7-[3-keto-1-propyl-3-[4-(N-Boc)-1-piperizine]]-3,4-dihydro-1H-1,4-benzodiazepine-2,5-dione, (±)-1-methyl-3-phenyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-3-phenyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-3-phenyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1,3-diphenyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione, (±)-1,3-diphenyl-4-(3-ethoxy-1-phenyl-3-oxo-1-propyl)-7-[3-keto-1-propyl-3-[4-(N-Boc)-1-piperizine]]-3,4-dihydro-1H-1,4-benzodiazepine-2,5-dione, (±)-1,3-diphenyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiazepine-2,5-dione, (±)-1,3-diphenyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1,3-diphenyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1,3-diphenyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-benzyl-3-phenyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione, (±)-1-benzyl-3-phenyl-4-(3-ethoxy-1-phenyl-3-oxo-1-propyl)-7-[3-keto-1-propyl-3-[4-(N-Boc)-1-piperizine]]-3,4-dihydro-1H-1,4-benzodiazepine-2,5-dione, (±)-1-benzyl-3-phenyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiazepine-2,5dione, (±)-1-benzyl-3-phenyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-isopropyl-3-phenyl-4-(3-ethoxy-1-methyl-3-oxo-1-propyl)-7-[3-keto-1-propyl-3-[4-(N-Boc)-1-piperizine]]-3,4-dihydro-1H-1,4-benzodiazepine-2,5-dione (±)-1-isopropyl-3-phenyl-4-(3-ethoxy-1-phenyl-3-oxo-1-propyl)-7-[3-keto-1-propyl-3-[4-(N-Boc)-1-piperizine]]-3,4-dihydro-1H-1,4-benzodiazepine-2,5-dione, (±)-1-isopropyl-3-phenyl-4-[2-(1-t-butoxy-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[3-keto-1-propyl-3-[4-(N-Boc)-1-piperizine]]-3,4-dihydro-1H-1,4-benzodiazepine-2,5-dione, (±)-1-methyl-3-phenyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, (±)-1-methyl-3-phenyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1-methyl-3-phenyl-4-[2-(1-t-butoxy-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl-3-phenyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[2-[2-(N-Boc)aminoethanethiol]-1-ethyl]-3,4-dihydro-1H-1,4-benzodiazepine-2,5-dione, (±)-1,3-diphenyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, (±)-1,3-diphenyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1,3-diphenyl-4-[2-(1-t-butoxy-4-benzyloxy)succinyl)]-7-[2-[2-(N-Boc)aminoethanethiol]-1-ethyl]-3,4-dihydro-1H-1,4-benzodiazepine-2,5-dione, (±)-1,3-diphenyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione, (±)-1,3-diphenyl-4-[2-(1-benzyloxyvalinyl-4-benzyloxy)succinyl)]-7-[2-[2-(N-Boc)aminoethanethiol]-1-ethyl]-3,4-dihydro-1H-1,4-benzodiazepine-2,5-dione, (±)-1,3-diphenyl-4-[2-(1-benzyloxyphenylalanyl-4-benzyloxy)succinyl)]-7-[2-[2-(N-Boc)aminoethanethiol]-1-ethyl]-3,4-dihydro-1H-1,4-benzodiazepine-2,5-dione, (±)-1-benzyl-3-phenyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, (±)-1-benzyl-3-phenyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1-benzyl-3-phenyl-4-[2-(1-t-butoxy-4-benzyloxy)succinyl)]-7-[2-[2-(N-Boc)aminoethanethiol]-1-ethyl]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[2-[2-(N-Boc)aminoethanethiol]-1-ethyl]-3,4-dihydro-1H-1,4-benzodiazepine-2,5-dione, (±)-1-isopropyl-3-phenyl-4-(3-ethoxy-1-methyl-3-oxo-1-propyl)-7-[2-[2-(N-Boc)aminoethanethiol]-1-ethyl]-3,4-dihydro-1H-1,4-benzodiazepine-2,5-dione, (±)-1-isopropyl-3-phenyl-4-(3-ethoxy-1-phenyl-3-oxo-1-propyl)-7-[2-[2-(N-Boc)aminoethanethiol]-1-ethyl]-3,4-dihydro-1H-1,4-benzodiazepine-2,5-dione, (±)-1-isopropyl-3-phenyl-4-[2-(1-t-butoxy-4-benzyloxy)succinyl)]-7-[2-[2-(N-Boc)aminoethanethiol]-1-ethyl]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[2-[2-(N-Boc)aminoethanethiol]-1-ethyl]-3,4-dihydro-1H-1,4-benzodiazepine-2,5-dione (±)-1-isopropyl-3-phenyl-4-[2-(1-benzyloxyvalinyl-4-benzyloxy)succinyl)]-7-[2-[2-(N-Boc)aminoethanethiol]-1-ethyl]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[2-[2-(N-Boc)aminoethanethiol]-1-ethyl]-3,4-dihydro-1H-1,4-benzodiazepine-2,5-dione, (±)-1-methyl-3-phenyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, (±)-1-methyl-3-phenyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1-methyl-3-phenyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1-methyl-3-phenyl-4-[2-(1-benzyloxyglycinyl-4-benzyloxy)succinyl)]-7-[2-(4-cyanothiophenol)-1-ethyl]-3,4-dihydro-1H-1,4-benzodiazepine-2,5-dione, (±)-1-methyl-3-phenyl-4-[2-(1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[2-(4-cyanothiophenol)-1-ethyl]-3,4-dihydro-1H-1,4-benzodiazepine-2,5-dione, (±)-1,3-diphenyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, (±)-1,3-diphenyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1,3-diphenyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1,3-diphenyl-4-[2-(1-benzyloxyglycinyl-4-benzyloxy)succinyl)]-7-[2-(4-cyanothiophenol)-1-ethyl]-3,4-dihydro-1H-1,4-benzodiazepine-2,5-dione, (±)-1,3-diphenyl-4-[2-(1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1,3-diphenyl-4-[2-(1-benzyloxyphenylalanyl-4-benzyloxy)succinyl)]-7-[2-(4-cyanothiophenol)-1-ethyl]-3,4-dihydro-1H-1,4-benzodiazepine-2,5-dione, (±)-1-benzyl-3-phenyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, (±)-1-benzyl-3-phenyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1-benzyl-3-phenyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[2-(4-cyanothiophenol)-1-ethyl]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[2-(4-cyanothiophenol)-1-ethyl]-3,4-dihydro-1H-1,4-benzodiazepine-2,5-dione, (±)-1-isopropyl-3-phenyl-4-(3-ethoxy-1-methyl-3-oxo-1-propyl)-7-[2-(4-cyanothiophenol)-1-ethyl]-3,4-dihydro-1H-1,4-benzodiazepine-2,5-dione, (±)-1-isopropyl-3-phenyl-4-(3-ethoxy-1-phenyl-3-oxo-1-propyl)-7-[2-(4-cyanothiophenol)-1-ethyl]-3,4-dihydro-1H-1,4-benzodiazepine-2,5-dione, (±)-1-isopropyl-3-phenyl-4-[2-(1-t-butoxy-4-benzyloxy)succinyl)]-7-[2-(4-cyanothiophenol)-1-ethyl]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[2-(4-cyanothiophenol)-1-ethyl]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[2-(4-cyanothiophenol)-1-ethyl]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[2-(4-cyanothiophenol)-1-ethyl]-3,4-dihydro-1H-1,4-benzodiazepine-2,5-dione, (±)-1-methyl-3-phenyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-3-phenyl-4-(3-ethoxy-1-phenyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-3-phenyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-3-phenyl-4-[2-(1-benzyloxyglycinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-3-phenyl-4-[2-(1-benzyloxyvalinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1,3-diphenyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1,3-diphenyl-4-(3-ethoxy-1-phenyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1,3-diphenyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1,3-diphenyl-4-[2-(1-benzyloxyglycinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1,3-diphenyl-4-[2-(1-benzyloxyvalinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1,3-diphenyl-4-[2-(1-benzyloxyphenylalanyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-3-phenyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-3-phenyl-4-(3-ethoxy-1-phenyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-3-phenyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-3-phenyl-4-(3-ethoxy-1-methyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-3-phenyl-4-(3-ethoxy-1-phenyl-3-oxo-1-propyl)-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-3-phenyl-4-[2-(1-t-butoxy-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-3-phenyl-4-[2-(1-benzyloxyglycinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[4-[2-(N-Boc)amino-6-methylpyrimidine-4-yl]-4-oxa-1-butyl]-3,4-dihydro-1H-1,4-benzodiazepine-2,5-dione, (±)-1-methyl-3-phenyl-4-(3-ethoxy-1-methyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-methyl-3-phenyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-methyl-3-phenyl-4-[2-(1-t-butoxy-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-methyl-3-phenyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-methyl-3-phenyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-methyl-3-phenyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1,3-diphenyl-4-(3-ethoxy-1-methyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1,3-diphenyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1,3-diphenyl-4-[2-(1-t-butoxy-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1,3-diphenyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1,3-diphenyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1,3-diphenyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-benzyl-3-phenyl-4-(3-ethoxy-1-methyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-benzyl-3-phenyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-benzyl-3-phenyl-4-[2-(1-t-butoxy-4-benzyloxy)-succinyl)]-7-[5-[2-(N-Boc)aminopyridine-3-yl]-5-oxa-1-pentyl]-3,4-dihydro-1H-1,4-benzodiazepine-2,5-dione, (±)-1-benzyl-3-phenyl-4-[2-(1-benzyloxyglycinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-benzyl-3-phenyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-benzyl-3-phenyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-isopropyl-3-phenyl-4-(3-ethoxy-1-methyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-isopropyl-3-phenyl-4-(3-ethoxy-1-phenyl-3-oxo-1-propyl)-7-[5-[2-(N-Boc)aminopyridine-3-yl]-5-oxa-1-pentyl]-3,4-dihydro-1H-1,4-benzodiazepine-2,5-dione, (±)-1-isopropyl-3-phenyl-4-[2-(1-t-butoxy-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-isopropyl-3-phenyl-4-[2-(1-benzyloxyglycinyl-4-benzyloxy)succinyl)-7-[5-[2-(N-Boc)aminopyridine-3-yl]-5-oxa-1-pentyl]-3,4-dihydro-1H-1,4-benzodiazepine-2,5-dione, (±)-1-isopropyl-3-phenyl-4-[2-(1-benzyloxyvalinyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, (±)-1-isopropyl-3-phenyl-4-[2-(1-benzyloxyphenylalanyl-4-benzyloxy)succinyl)]-7-[5-[2-(N-Boc)aminopyridine-3-yl]-5-oxa-1-pentyl]-3,4-dihydro-1H-1,4-benzodiazepine-2,5-dione, b) 1-methyl-4-(2-carboxyethyl)-7-(5-amino-1-pentyl)-3,4-dihydro-1H-1,4-benzodiazepine-2,5-dione trifluroacetate was prepared using the method described in part (g) of example 1. Thus, 45 mgs 1-methyl-4-(2-carboxyethyl)-7-(N-boc-5-amino-1-pentyl)-3,4-dihydro-1H-1,4-benzodiazepine-2,5-dione benzyl ester yielded 36 mgs (93%) 1-methyl-4-(2-carboxyethyl)-7-(5-amino-1-pentyl)-3,4-dihydro-1H-1,4-benzodiazepine-2,5-dione trifluoroacetate (½" C-18 reverse-phase column, eluting with a solvent gradient of 10:90 acetonitrile (0.1% trifluoroacetic acid)/water (0.1% trifluoroacetic acid), time 0 to 10 min, to 50:50 acetonitrile (0.1% trifluoroacetic acid)/water (0.1% trifluoroacetic acid), time 10 min to 40 min, flow=10 ml/min, $R_t$=30.3 min, uv detection 254 nm). HRMS (FAB) molecular ion m/z=348.1931 (cald. $C_{18}H_{25}N_3O_4$, 348.1923) $^1$H NMR (CDCl$_3$, δTMS) 7.39 (1H, bs, Ar-H o-CON), 7.34 (1H, d, $^3J_{HH}$=8Hz, p-CON), 7.16 (1H, d, $^3J_{HH}$=8Hz, m-CON), 4.00–3.90 (2H, m, NCHHCO, NCHHCH$_2$), 3.67 (1H, d, $^2J_{HH}$=16Hz, NCHHCO), 3.56 (1H, dt, $^2J_{HH}$=14Hz, $^3J_{HH}$=6Hz, NCHHCH$_2$) 3.17 (3H, s, NCH$_3$), 2.82 (2H, t, $^3J_{HH}$=7Hz, H$_3$NCH$_2$), 2.67–2.47 (4H, m, CH$_2$CO$_2$, ArCH$_2$), 1.57–1.42 (4H, bs), 1.16 (2H, p, $^3J_{HH}$=7Hz).

Using the above procedure, but substituting the appropriate 3,4-dihydro-1H-1,4-benzodiazepine-2,5-dione for 1-methyl-4-(2-carboxyethyl)-7-(N-boc-5-amino-1-pentyl)-3,4-dihydro-1H-1,4-benzodiazepine-2,5-dione benzyl ester there could be prepared, for example, the following compounds:

1-methyl-4-(2-carboxy-1-methylethyl)-7-(5-amino-1-pentyl)-3,4-dihydro-1H-1,4-benzodiazepine-2,5-dione trifluroacetate, 1-methyl-4-(2-carboxy-1-phenylethyl)-7-(5-amino-1-pentyl)-3,4-dihydro-1H-1,4-benzodiazepine-2,5-dione trifluroacetate, (±)-1-methyl-4-[succin-2-yl-(1-t-butoxy)]-7-(5-amino-1-pentyl)-3,4-dihydro-1H-1,4-benzodiazepine-2,5-dione trifluroacetate, (±)-1-methyl-4-[succin-2-yl-(1-glycine)]-7-(5-amino-1-pentyl)-3,4-dihydro-1H-1,4-benzodiazepine-2,5-dione trifluroacetate, (±)-1-methyl-4-[succin-2-yl-(1-valine)]-7-(5-amino-1-pentyl)-3,4-dihydro-1H-1,4-benzodiazepine-2,5-dione trifluroacetate, (±)-1-methyl-4-[succin-2-yl-(1-phenylalanine)]-7-(5-amino-1-pentyl)-3,4-dihydro-1H-1,4-benzodiazepine-2,5-dione trifluroacetate, 1-phenyl-4-(2-carboxy-1-methylethyl)-7-(5-amino-1-pentyl)-3,4-dihydro-1H-1,4-benzodiazepine-2,5-dione trifluroacetate, 1-phenyl-4-(2-carboxy-1-phenylethyl)-7-(5-amino-1-pentyl)-3,4-dihydro-1H-1,4-benzodiazepine-2,5-dione trifluroacetate, (±)-1-phenyl-4-[succin-2-yl-(1-t-butoxy)]-7-(5-amino-1-pentyl)-3,4-dihydro-1H-1,4-benzodiazepine-2,5-dione trifluroacetate, (±)-1-phenyl-4-[succin-2-yl-(1-glycine)]-7-(5-amino-1-pentyl)-3,4-dihydro-1H-1,4-benzodiazepine-2,5-dione trifluroacetate, (±)-1-phenyl-4-[succin-2-yl-(1-valine)]-7-(5-amino-1-pentyl)-3,4-dihydro-1H-1,4-benzodiazepine-2,5-dione trifluroacetate, (±)-1-phenyl-4-[succin-2-yl-(1-phenylalanine)]-7-(5-amino-1-pentyl)-3,4-dihydro-1H-1,4-benzodiazepine-2,5-dione trifluroacetate, 1-benzyl-4-(2-carboxy-1-methylethyl)-7-(5-amino-1-pentyl)-3,4-dihydro-1H-1,4-benzodiazepine-2,5-dione trifluroacetate, 1-benzyl-4-(2-carboxy-1-phenylethyl)-7-(5-amino-1-pentyl)-3,4-dihydro-1H-1,4-benzodiazepine-2,5-dione trifluroacetate, (±)-1-benzyl-4-[succin-2-yl-(1-t-butoxy)]-7-(5-amino-1-pentyl)-3,4-dihydro-1H-1,4-benzodiazepine-2,5-dione trifluroacetate, (±)-1-benzyl-4-[succin-2-yl-(1-glycine)]-7-(5-amino-1-pentyl)-3,4-dihydro-1H-1,4-benzodiazepine-2,5-dione trifluroacetate, (±)-1-benzyl-4-[succin-2-yl-(1-valine)]-7-(5-amino-1-pentyl)-3,4-dihydro-1H-1,4-benzodiazepine-2,5-dione trifluroacetate, (±)-1-benzyl-4-[succin-2-yl-(1-phenylalanine)]-7-(5-amino-1-pentyl)-3,4-dihydro-1H-1,4-benzodiazepine-2,5-dione trifluroacetate, 1-isopropyl-4-(2-carboxy-1-methylethyl)-7-(5-amino-1-pentyl)-3,4-dihydro-1H-1,4-benzodiazepine-2,5-dione trifluroacetate, 1-isopropyl-4-(2-carboxy-1-phenylethyl)-7-(5-amino-1-pentyl)-3,4-dihydro-1H-1,4-benzodiazepine-2,5-dione trifluroacetate, (±)-1-isopropyl-4-[succin-2-yl-(1-t-butoxy)]-7-(5-amino-1-pentyl)-3,4-dihydro-1H-1,4-benzodiazepine-2,5-dione trifluroacetate, (±)-1-isopropyl-4-[succin-2-yl-(1-glycine)]-7-(5-amino-1-pentyl)-3,4-dihydro-1,4-benzodiazepine-2,5-dione trifluroacetate, (±)-1-isopropyl-4-[succin-2-yl-(1-valine)]-7-(5-amino-1-pentyl)-3,4-dihydro-1,4-benzodiazepine-2,5-dione trifluroacetate, (±)-1-isopropyl-4-[succin-2-yl-(1-phenylalanine)]-7-(5-amino-1-pentyl)-3,4-dihydro-1H-1,4-benzodiazepine-2,5-dione trifluroacetate, 1-methyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-methyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-methyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-phenyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-phenyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-phenyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-benzyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-benzyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-benzyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-isopropyl-4-(2-carboxy-1-methylethyl)-7-[N-(2-aminoethane)-3-keto-1-propyn-3-amine]-3,4-dihydro-1H-1,4-benzodiazepine-2,5-dione trifluroacetate, 1-isopropyl-4-(2-carboxy-1-phenylethyl)-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-t-butoxy)]-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-glycine)]-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-valine)]-7-[N-(2-aminoethane)-3-keto-1-propyn-3-amine]-3,4-dihydro-1H-1,4-benzodiazepine-2,5-dione trifluroacetate, (±)-1-isopropyl-4-[succin-2-yl-(1-phenylalanine)]-7-[N-(2-aminoethane)-3-keto-1-propyn-3-amine]-3,4-dihydro-1H-1,4-benzodiazepine-2,5-dione trifluroacetate, 1-methyl-4-(2-carboxy-1-methylethyl)-7-[3-keto-1-propyn-3-(1-piperizine)]-3,4-dihydro-1H-1,4-benzodiazepine-2,5-dione trifluroacetate, 1-methyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-methyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-methyl-4-[succin-2-yl-(1-glycine)]-7-[3-keto-1-propyn-3-(1-piperazine)]-3,4-dihydro-1H-1,4-benzodiazepine-2,5-dione trifluroacetate, (±)-1-methyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-methyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-phenyl-4-(2-carboxy-1-methylethyl)-7-[3-keto-1-propyn-3-(1-piperizine)]-3,4-dihydro-1H-1,4-benzodiazepine-2,5-dione trifluroacetate, 1-phenyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-phenyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-benzyl-4-(2-carboxy-1-methylethyl)-7-[3-keto-1-propyn-3-(1-piperizine)]-3,4-dihydro-1H-1,4-benzodiazepine-2,5-dione trifluroacetate, 1-benzyl-4-(2-carboxy-1-phenylethyl)-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-benzyl-4-[succin-2-yl-(1-phenylalanine)]-7-[3-keto-1-propyn-3-(1-piperazine)]-3,4-dihydro-1H-1,4-benzodiazepine-2,5-dione trifluroacetate, 1-isopropyl-4-(2-carboxy-1-methylethyl)-7-[3-keto-1-propyn-3-(1-piperizine)]-3,4-dihydro-1H-1,4-benzodiazepine-2,5-dione trifluroacetate, 1-isopropyl-4-(2-carboxy-1-phenylethyl)-7-[3-keto-1-propyn-3-(1-piperazine)]-3,4-dihydro-1H-1,4-benzodiazepine-2,5-dione trifluroacetate, (±)-1-isopropyl-4-[succin-2-yl-(1-t-butoxy)]-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-glycine)]-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-valine)]-7-[3-keto-1-propyn-3-(1-piperizine)]-3,4-dihydro-1H-1,4-benzodiazepine-2,5-dione trifluroacetate, (±)-1-isopropyl-4-[succin-2-yl-(1-phenylalanine)]-7-[3-keto-1-propyn-3-(1-piperizine)]-3,4-dihydro-1H-1,4-benzodiazepine-2,5-dione trifluroacetate, 1-methyl-4-(2-carboxy-1-methylethyl)-7-[2-(2-aminoethanethiol)-1-ethyl]-3,4-dihydro-1H-1,4-benzodiazepine-2,5-dione trifluroacetate, 1-methyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1-methyl-4-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1-methyl-4-[succin-2-yl-(1-glycine)]-7-[2-(2-aminoethanethiol)-1-ethyl]-3,4-dihydro-1H-1,4-benzodiazepine-2,5-dione trifluroacetate, (±)-1-methyl-4-[succin-2-yl-(1-valine)]-7-[2-(2-aminoethanethiol)-1-ethyl]-3,4-dihydro-1H-1,4-benzodiazepine-2,5-dione trifluroacetate, (±)-1-methyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, 1-phenyl-4-(2-carboxy-1-methylethyl)-7-[2-(2-aminoethanethiol)-1-ethyl]-3,4-dihydro-1H-1,4-benzodiazepine-2,5-dione trifluroacetate, 1-phenyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1-phenyl-4-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1-phenyl-4-[succin-2-yl-(1-glycine)]-7-[2-(2-aminoethanethiol)-1-ethyl]-3,4-dihydro-1H-1,4-benzodiazepine-2,5-dione trifluroacetate, (±)-1-phenyl-4-[succin-2-yl-(1-valine)]-7-[2-(2-aminoethanethiol)-1-ethyl]-3,4-dihydro-1H-1,4-benzodiazepine-2,5-dione trifluroacetate, (±)-1-phenyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, 1-benzyl-4-(2-carboxy-1-methylethyl)-7-[2-(2-aminoethanethiol)-1-ethyl]-3,4-dihydro-1H-1,4-benzodiazepine-2,5-dione trifluroacetate, 1-benzyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1-benzyl-4-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1-benzyl-4-[succin-2-yl-(1-glycine)]-7-[2-(2-aminoethanethiol)-1-ethyl]-3,4-dihydro-1H-1,4-benzodiazepine-2,5-dione trifluroacetate, (±)-1-benzyl-4-[succin-2-yl-(1-valine)]-7-[2-(2-aminoethanethiol)-1-ethyl]-3,4-dihydro-1H-1,4-benzodiazepine-2,5-dione trifluroacetate, (±)-1-benzyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, 1-isopropyl-4-(2-carboxy-1-methylethyl)-7-[2-(2-aminoethanethiol)-1-ethyl]-3,4-dihydro-1H-1,4-benzodiazepine-2,5-dione trifluroacetate, 1-isopropyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1-isopropyl-4-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1-isopropyl-4-[succin-2-yl-(1-glycine)]-7-[2-(2-aminoethanethiol)-1-ethyl]-3,4-dihydro-1H-1,4-benzodiazepine-2,5-dione trifluroacetate, (±)-1-isopropyl-4-[succin-2-yl-(1-valine)]-7-[2-(2-aminoethanethiol)-1-ethyl]-3,4-dihydro-1H-1,4-benzodiazepine-2,5-dione trifluroacetate, (±)-1-isopropyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, 1-methyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, 1-methyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-4-[succin-2-yl-(1-t-butoxy)]-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-4-[succin-2-yl-(1-glycine)]-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-4-[succin-2-yl-(1-valine)]-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, 1-phenyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, 1-phenyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-phenyl-4-[succin-2-yl-(1-t-butoxy)]-7-[4-(2-amino-6-methylpyrimidine-4-yl)-4-oxa-1-butyl]-3,4-dihydro-1H-1,4-benzodiazepine-2,5-dione trifluroacetate, (±)-1-phenyl-4-[succin-2-yl-(1-glycine)]-7-[4-(2-amino-6-methylpyrimidine-4-yl)-4-oxa-1-butyl]-3,4-dihydro-1H-1,4-benzodiazepine-2,5-dione trifluroacetate, (±)-1-phenyl-4-[succin-2-yl-(1-valine)]-7-[4-(2-amino-6-methylpyrimidine-4-yl)-4-oxa-1-butyl]-3,4-dihydro-1H-1,4-benzodiazepine-2,5-dione trifluroacetate, (±)-1-phenyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, 1-benzyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, 1-benzyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-benzyl-4-[succin-2-yl-(1-t-butoxy)]-7-[4-(2-amino-6-methylpyrimidine-4-yl)-4-oxa-1-butyl]-3,4-dihydro-1H-1,4-benzodiazepine-2,5-dione trifluroacetate, (±)-1-benzyl-4-[succin-2-yl-(1-glycine)]-7-[4-(2-amino-6-methylpyrimidine-4-oxa-1-butyl]-3,4-dihydro-1H-1,4-benzodiazepine-2,5-dione trifluroacetate, (±)-1-benzyl-4-[succin-2-yl-(1-valine)]-7-[4-(2-amino-6-methylpyrimidine-4-oxa-1-butyl]-3,4-dihydro-1H-1,4-benzodiazepine-2,5-dione trifluroacetate, (±)-1-benzyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, 1-isopropyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, 1-isopropyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-isopropyl-4-[succin-2-yl-(1-t-butoxy)]-7-[4-(2-amino-6-methylpyrimidine-4-yl)-4-oxa-1-butyl]-3,4-dihydro-1H-1,4-benzodiazepine-2,5-dione trifluroacetate, (±)-1-isopropyl-4-[succin-2-yl-(1-glycine)]-7-[4-(2-amino-6-methylpyrimidine-4-yl)-4-oxa-1-butyl]-3,4-dihydro-1H-1,4-benzodiazepine-2,5-dione trifluroacetate, (±)-1-isopropyl-4-[succin-2-yl-(1-valine)]-7-[4-(2-amino-6-methylpyrimidine-4-yl)-4-oxa-1-butyl]-3,4-dihydro-1H-1,4-benzodiazepine-2,5-dione trifluroacetate, (±)-1-isopropyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, 1-methyl-4-(2-carboxy-1-methylethyl)-7-[5-(2-aminopyridine-3-yl)-5-oxa-1-pentyl]-3,4-dihydro-1H-1,4-benzodiazepine-2,5-dione trifluroacetate, 1-methyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1-methyl-4-[succin-2-yl-(1-t-butoxy)]-7-[5-(2-aminopyridine-3-yl)-5-oxa-1-pentyl]-3,4-dihydro-1H-1,4-benzodiazepine-2,5-dione trifluroacetate, (±)-1-methyl-4-[succin-2-yl-(1-glycine)]-7-[5-(2-aminopyridine-3-yl)-5-oxa-1-pentyl]-3,4-dihydro-1H-1,4-benzodiazepine-2,5-dione trifluroacetate, (±)-1-methyl-4-[succin-2-yl-(1-valine)]-7-[5-(2-aminopyridine-3-yl)-5-oxa-1-pentyl]-3,4-dihydro-1H-1,4-benzodiazepine-2,5-dione trifluroacetate, (±)-1-methyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, 1-phenyl-4-(2-carboxy-1-methylethyl)-7-[5-(2-aminopyridine-3-yl)-5-oxa-1-pentyl]-3,4-dihydro-1H-1,4-benzodiazepine-2,5-dione trifluroacetate, 1-phenyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1-phenyl-4-[succin-2-yl-(1-t-butoxy)]-7-[5-(2-aminopyridine-3-yl)-5-oxa-1-pentyl]-3,4-dihydro-1H-1,4-benzodiazepine-2,5-dione trifluroacetate, (±)-1-phenyl-4-[succin-2-yl-(1-glycine)]-7-[5-(2-aminopyridine-3-yl)-5-oxa-1-pentyl]-3,4-dihydro-1H-1,4-benzodiazepine-2,5-dione trifluroacetate, (±)-1-phenyl-4-[succin-2-yl-(1-valine)]-7-[5-(2-aminopyridine-3-yl)-5-oxa-1-pentyl]-3,4-dihydro-1H-1,4-benzodiazepine-2,5-dione trifluroacetate, (±)-1-phenyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, 1-benzyl-4-(2-carboxy-1-methylethyl)-7-[5-(2-aminopyridine-3-yl)-5-oxa-1-pentyl]-3,4-dihydro-1H-1,4-benzodiazepine-2,5-dione, 1-benzyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1-benzyl-4-[succin-2-yl-(1-t-butoxy)]-7-[5-(2-aminopyridine-3-yl)-5oxa-1-pentyl]-3,4-dihydro-1H-1,4-benzodiazepine-2,5-dione trifluroacetate, (±)-1-benzyl-4-[succin-2-yl-(1-glycine)]-7-[5-(2-aminopyridine-3-yl)-5-oxa-1-pentyl]-3,4-dihydro-1H-1,4-benzodiazepine-2,5-dione trifluroacetate, (±)-1-benzyl-4-[succin-2-yl-(1-valine)]-7-[5-(2-aminopyridine-3-yl)-5-oxa-1-pentyl]-3,4-dihydro-1H-1,4-benzodiazepine-2,5-dione trifluroacetate, (±)-1-benzyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, 1-isopropyl-4-(2-carboxy-1-methylethyl)-7-[5-(2-aminopyridine-3-yl)-5-oxa-1-pentyl]-3,4-dihydro-1H-1,4-benzodiazepine-2,5-dione trifluroacetate, 1-isopropyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1-isopropyl-4-[succin-2-yl-(1-t-butoxy)]-7-[5-(2-aminopyridine-3-yl)-5-oxa-1-pentyl]-3,4-dihydro-1H-1,4-benzodiazepine-2,5-dione trifluroacetate, (±)-1-isopropyl-4-[succin-2-yl-(1-glycine)]-7-[5-(2-aminopyridine-3-yl)-5-oxa-1-pentyl]-3,4-dihydro-1H-1,4-benzodiazepine-2,5-dione trifluroacetate, (±)-1-isopropyl-4-[succin-2-yl-(1-valine)]-7-[5-(2-aminopyridine-3-yl)-5-oxa-1-pentyl]-3,4-dihydro-1H-1,4-benzodiazepine-2,5-dione trifluroacetate, (±)-1-isopropyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, (±)-1-methyl-3-phenyl-4-(2-carboxy-1-methylethyl)-7-(5-amino-1-pentyl)-3,4-dihydro-1H-1,4-benzodiazepine-2,5-dione trifluroacetate,
(±)-1-methyl-3-phenyl-4-(2-carboxy-1-phenylethyl)-7-(5-amino-1-pentyl)-3,4-dihydro-1H-1,4-benzodiazepine-2,5-dione trifluroacetate,
(±)-1-methyl-3-phenyl-4-[succin-2-yl-(1-t-butoxy)]-7-(5-amino-1-pentyl)-3,4-dihydro-1H-1,4-benzodiazepine-2,5-dione trifluroacetate,
(±)-1-methyl-3-phenyl-4-[succin-2-yl-(1-glycine)]-7-(5-amino-1-pentyl)-3,4-dihydro-1H-1,4-benzodiazepine-2,5-dione trifluroacetate,
(±)-1-methyl-3-phenyl-4-[succin-2-yl-(1-valine)]-7-(5-amino-1-pentyl)-3,4-dihydro-1H-1,4-benzodiazepine-2,5-dione trifluroacetate,
(±)-1-methyl-3-phenyl-4-[succin-2-yl-(1-phenylalanine)]-7-(5-amino-1-pentyl)-3,4-dihydro-1H-1,4-benzodiazepine-2,5-dione trifluroacetate,
(±)-1,3-diphenyl-4-(2-carboxy-1-methylethyl)-7-(5-amino-1-pentyl)-3,4-dihydro-1H-1,4-benzodiazepine-2,5-dione trifluroacetate,
(±)-1,3-diphenyl-4-(2-carboxy-1-phenylethyl)-7-(5-amino-1-pentyl)-3,4-dihydro-1H-1,4-benzodiazepine-2,5-dione trifluroacetate,
(±)-1,3-diphenyl-4-[succin-2-yl-(1-t-butoxy)]-7-(5-amino-1-pentyl)-3,4-dihydro-1H-1,4-benzodiazepine-2,5-dione trifluroacetate,
(±)-1,3-diphenyl-4-[succin-2-yl-(1-glycine)]-7-(5-amino-1-pentyl)-3,4-dihydro-1H-1,4-benzodiazepine-2,5-dione trifluroacetate,
(±)-1,3-diphenyl-4-[succin-2-yl-(1-valine)]-7-(5-amino-1-pentyl)-3,4-dihydro-1H-1,4-benzodiazepine-2,5-dione trifluroacetate,
(±)-1,3-diphenyl-4-[succin-2-yl-(1-phenylalanine)]-7-(5-amino-1-pentyl)-3,4-dihydro-1H-1,4-benzodiazepine-2,5-dione trifluroacetate,
(±)-1-benzyl-3-phenyl-4-(2-carboxy-1-methylethyl)-7-(5-amino-1-pentyl)-3,4-dihydro-1H-1,4-benzodiazepine-2,5-dione trifluroacetate,
(±)-1-benzyl-3-phenyl-4-(2-carboxy-1-phenylethyl)-7-(5-amino-1-pentyl)-3,4-dihydro-1H-1,4-benzodiazepine-2,5-dione trifluroacetate,
(±)-1-benzyl-3-phenyl-4-[succin-2-yl-(1-t-butoxy)]-7-(5-amino-1-pentyl)-3,4-dihydro-1H-1,4-benzodiazepine-2,5-dione trifluroacetate,
(±)-1-benzyl-3-phenyl-4-[succin-2-yl-(1-glycine)]-7-(5-amino-1-pentyl)-3,4-dihydro-1H-1,4-benzodiazepine-2,5-dione trifluroacetate,
(±)-1-benzyl-3-phenyl-4-[succin-2-yl-(1-valine)]-7-(5-amino-1-pentyl)-3,4-dihydro-1H-1,4-benzodiazepine-2,5-dione trifluroacetate,
(±)-1-benzyl-3-phenyl-4-[succin-2-yl-(1-phenylalanine)]-7-(5-amino-1-pentyl)-3,4-dihydro-1H-1,4-benzodiazepine-2,5-dione trifluroacetate,
(±)-1-isopropyl-3-phenyl-4-(2-carboxy-1-methylethyl)-7-(5-amino-1-pentyl)-3,4-dihydro-1H-1,4-benzodiazepine-2,5-dione trifluroacetate,
(±)-1-isopropyl-3-phenyl-4-(2-carboxy-1-phenylethyl)-7-(5-amino-1-pentyl)-3,4-dihydro-1H-1,4-benzodiazepine-2,5-dione trifluroacetate,
(±)-1-isopropyl-3-phenyl-4-[succin-2-yl-(1-t-butoxy)]-7-(5-amino-1-pentyl)-3,4-dihydro-1H-1,4-benzodiazepine-2,5-dione trifluroacetate,
(±)-1-isopropyl-3-phenyl-4-[succin-2-yl-(1-glycine)]-7-(5-amino-1-pentyl)-3,4-dihydro-1H-1,4-benzodiazepine-2,5-dione trifluroacetate,
(±)-1-isopropyl-3-phenyl-4-[succin-2-yl-(1-valine)]-7-(5-amino-1-pentyl)-3,4-dihydro-1H-1,4-benzodiazepine-2,5-dione trifluroacetate,
(±)-1-isopropyl-3-phenyl-4-[succin-2-yl-(1-phenylalanine)]-7-(5-amino-1-pentyl)-3,4-dihydro-1H-1,4-benzodiazepine-2,5-dione trifluroacetate,
(±)-1-methyl-3-phenyl-4-(2-carboxy-1-methylethyl)-7-[N-(2-aminoethane)-3-keto-1-propyl-3-amine]-3,4-dihydro-1H-1,4-benzodiazepine-2,5-dione trifluroacetate,
(±)-1-methyl-3-phenyl-4-(2-carboxy-1-phenylethyl)-7-[N-(2-aminoethane)-3-keto-1-propyl-3-amine]-3,4-dihydro-1H-1,4-benzodiazepine-2,5-dione trifluroacetate,
(±)-1-methyl-3-phenyl-4-[succin-2-yl-(1-t-butoxy)]-7-[N-(2-aminoethane)-3-keto-1-propyl-3-amine]-3,4-dihydro-1H-1,4-benzodiazepine-2,5-dione trifluroacetate,
(±)-1-methyl-3-phenyl-4-[succin-2-yl-(1-glycine)]-7-[N-(2-aminoethane)-3-keto-1-propyl-3-amine]-3,4-dihydro-1H-1,4-benzodiazepine-2,5-dione trifluroacetate,
(±)-1-methyl-3-phenyl-4-[succin-2-yl-(1-valine)]-7-[N-(2-aminoethane)-3-keto-1-propyl-3-amine]-3,4-dihydro-1H-1,4-benzodiazepine-2,5-dione trifluroacetate,
(±)-1-methyl-3-phenyl-4-[succin-2-yl-(1-phenylalanine)]-7-[N-(2-aminoethane)-3-keto-1-propyl-3-amine]-3,4-dihydro-1H-1,4-benzodiazepine-2,5-dione trifluroacetate,
(±)-1,3-diphenyl-4-(2-carboxy-1-methylethyl)-7-[N-(2-aminoethane)-3-keto-1-propyl-3-amine]-3,4-dihydro-1H-1,4-benzodiazepine-2,5-dione trifluroacetate,
(±)-1,3-diphenyl-4-(2-carboxy-1-phenylethyl)-7-[N-(2-aminoethane)-3-keto-1-propyl-3-amine]-3,4-dihydro-1H-1,4-benzodiazepine-2,5-dione trifluroacetate,
(±)-1,3-diphenyl-4-[succin-2-yl-(1-t-butoxy)]-7-[N-(2-aminoethane)-3-keto-1-propyl-3-amine]-3,4-dihydro-1H-1,4-benzodiazepine-2,5-dione trifluroacetate,
(±)-1,3-diphenyl-4-[succin-2-yl-(1-glycine)]-7-[N-(2-aminoethane)-3-keto-1-propyl-3-amine]-3,4-dihydro-1H-1,4-benzodiazepine-2,5-dione trifluroacetate,
(±)-1,3-diphenyl-4-[succin-2-yl-(1-valine)]-7-[N-(2-aminoethane)-3-keto-1-propyl-3-amine]-3,4-dihydro-1H-1,4-benzodiazepine-2,5-dione trifluroacetate,
(±)-1,3-diphenyl-4-[succin-2-yl-(1-phenylalanine)]-7-[N-(2-aminoethane)-3-keto-1-propyl-3-amine]-3,4-dihydro-1H-1,4-benzodiazepine-2,5-dione trifluroacetate,
(±)-1-benzyl-3-phenyl-4-(2-carboxy-1-methylethyl)-7-[N-(2-aminoethane)-3-keto-1-propyl-3-amine]-3,4-dihydro-1H-1,4-benzodiazepine-2,5-dione trifluroacetate,
(±)-1-benzyl-3-phenyl-4-(2-carboxy-1-phenylethyl)-7-[N-(2-aminoethane)-3-keto-1-propyl-3-amine]-3,4-dihydro-1H-1,4-benzodiazepine-2,5-dione trifluroacetate,
(±)-1-benzyl-3-phenyl-4-[succin-2-yl-( 1-t-butoxy)]-7-[N-(2-aminoethane)-3-keto-1-propyl-3-amine]-3,4-dihydro-1H-1,4-benzodiazepine-2,5-dione trifluroacetate,
(±)-1 -benzyl-3-phenyl-4-[succin-2-yl-(1-glycine)]-7-[N-(2-aminoethane)-3-keto-1-propyl-3-amine ]-3,4-dihydro-1 H-1,4-benzodiazepine-2,5-dione trifluroacetate,
(±)-1-benzyl-3-phenyl-4-[succin-2-yl-(1-valine)]-7-[N-(2-aminoethane)-3-keto-1-propyl-3-amine]-3,4-dihydro-1H-1,4-benzodiazepine-2,5-dione trifluroacetate, (±)-1-benzyl-3-phenyl-4-[succin-2-yl-(1-phenylalanine)]-7-[N-(2-aminoethane)-3-keto-1-propyl-3-amine]-3,4-dihydro-1H-1,4-benzodiazepine-2,5-dione trifluroacetate, (±)-1-isopropyl-3-phenyl-4-(2-carboxy-1-methylethyl)-7-[N-(2-aminoethane)-3-keto-1-propyl-3-amine]-3,4-dihydro-1H-1,4-benzodiazepine-2,5-dione trifluroacetate, (±)-1-isopropyl-3-phenyl-4-(2-carboxy-1-phenylethyl)-7-[N-(2-aminoethane)-3-keto-1-propyl-3-amine]-3,4-dihydro-1H-1,4-benzodiazepine-2,5-dione trifluroacetate, (±)-1-isopropyl-3-phenyl-4-[succin-2-yl-( 1-t-butoxy )]-7-[N-(2-aminoethane)-3- keto-1-propyl-3-amine]-3,4-dihydro-1H-1,4-benzodiazepine-2,5-dione trifluroacetate, (±)-1-isopropyl-3-phenyl-4-[succin-2-yl-(1-glycine)]-7-[N-(2-aminoethane)-3-keto-1-propyl-3-amine]-3,4-dihydro-1H-1,4-benzodiazepine-2,5-dione trifluroacetate, (±)-1-isopropyl-3-phenyl-4-[succin-2-yl-(1-valine) ]-7-[N-(2-aminoethane)-3-keto-1-propyl-3-amine]-3,4-dihydro-1H-1,4-benzodiazepine-2,5-dione trifluroacetate, (±)-1-isopropyl-3-phenyl-4-[succin-2-yl-(1-phenylalanine)]-7-[N-(2aminoethane)-3-keto-1-propyl-3-amine]-3,4-dihydro-1H-1,4-benzodiazepine-2,5-dione trifluoracetate, (±)-1-methyl-3-phenyl-4-(2-carboxy-1-methylethyl)-7-[3-keto-1-propyl-3-(1-piperizine)]-3,4-dihydro-1H-1,4-benzodiazepine-2,5-dione trifluroacetate, (±)-1 -methyl-3-phenyl-4-(2-carboxy-1-phenylethyl)-7-[3-keto-1-propyl-3-(1-piperizine)]-3,4-dihydro-1H-1,4-benzodiazepine-2,5-dione trifluroacetate, (±)-1-methyl-3-phenyl-4-[succin-2-yl-(1-t-butoxy)]-7-[3-keto-1-propyl-3-(1-piperizine)]-3,4-dihydro-1H-1,4-benzodiazepine-2,5-dione trifluroacetate, (±)-1-methyl-3-phenyl-4-[succin-2-yl-(1-glycine)]-7-[3-keto-1-propyl-3-(1-piperizine)]-3,4-dihydro-1H-1,4-benzodiazepine-2,5-dione trifluroacetate, (±)-1-methyl-3-phenyl-4-[succin-2-yl-(1-valine)]-7-[3-keto-1-propyl-3-(1-piperizine)]-3,4-dihydro-1H-1,4-benzodiazepine-2,5-dione trifluroacetate, (±)-1-methyl-3-phenyl-4-[succin-2-yl-(1-phenylalanine)]-7-[3-keto-1-propyl-3-(1-piperizine)]-3,4-dihydro-1H-1,4-benzodiazepine-2,5-dione trifluroacetate, (±)-1,3-diphenyl-4-(2-carboxy-1-methylethyl)-7-[3-keto-1-propyl-3-(1-piperizine)]-3,4-dihydro-1H-1,4-benzodiazepine-2,5-dione trifluroacetate, (±)-1,3-diphenyl-4-(2-carboxy-1-phenylethyl)-7-[3-keto-1-propyl-3-(1-piperizine)]-3,4-dihydro-1H-1,4-benzodiazepine-2,5-dione trifluroacetate, (±)-1,3-diphenyl-4-[succin-2-yl-(1-t-butoxy)]-7-[3-keto-1-propyl-3-(1-piperizine)]-3,4-dihydro-1H-1,4-benzodiazepine-2,5-dione trifluroacetate, (±)-1,3-diphenyl-4-[succin-2-yl-(1-glycine)]-7-[3-keto-1-propyl-3-(1-piperizine)]-3,4-dihydro-1H-1,4-benzodiazepine-2,5-dione trifluroacetate, (±)-3-diphenyl-4-[succin-2-yl-(1-valine)]-7-[3-keto-1-propyl-3-(1-piperizine)]-3,4-dihydro-1H-1,4-benzodiazepine-2,5-dione trifluroacetate, (±)-1,3-diphenyl-4-[succin-2-yl-(1-phenylalanine)]-7-[3-keto-1-propyl-3-(1-piperizine)]-3,4-dihydro-1H-1,4-benzodiazepine-2,5-dione trifluroacetate, (±)-1-benzyl-3-phenyl-4-(2-carboxy-1-methylethyl)-7-[3-keto-1-propyl-3-(1-piperizine)]-3,4-dihydro-1H-1,4-benzodiazepine-2,5-dione trifluroacetate, (±)-1-benzyl-3-phenyl-4-(2-carboxy-1-phenylethyl)-7-[3-keto-1-propyl-3-(1-piperizine)]-3,4-dihydro-1H-1,4-benzodiazepine-2,5-dione trifluroacetate, (±)-1-benzyl-3-phenyl-4-[succin-2-yl-(1-t-butoxy)]-7-[3-keto-1-propyl-3-(1piperizine)]-3,4-dihydro-1H-1,4-benzodiazepine-2,5-dione trifluroacetate, (±)-1-benzyl-3-phenyl-4-[succin-2-yl-(1-glycine )]-7-[3-keto-1-propyl-3-(1-piperizine)]-3,4-dihydro-1H-1,4-benzodiazepine-2,5-dione trifluroacetate, (±)-1-benzyl-3-phenyl-[succin-2-yl-(1-valine)]-7-[3-keto-1-propyl-3-(1-piperizine)]-3,4-dihydro-1H-1,4-benzodiazepine-2,5-dione trifluroacetate, (±)-1-benzyl-3-phenyl-4-[succin-2-yl-(1-phenylalanine)]-7-[3-keto-1-propyl-3-(1-piperizine)]-3,4-dihydro-1H-1,4-benzodiazepine-2,5-dione trifluroacetate, (±)-1-isopropyl-3-phenyl-4-(2-carboxy-1-methylethyl)-7-[3-keto-1-propyl-3-(1-piperizine)]-3,4-dihydro-1H-1,4-benzodiazepine-2,5-dione trifluoracetate, (±)-1-isopropyl-3-phenyl-4-(2-carboxy-1-phenylethyl)-7-[3-keto-1-propyl-3-(1piperizine)]-3,4-dihydro-1H-1,4-benzodiazepine-2,5-dione trifluroacetate, (±)-1-isopropyl-3-phenyl-4-[succin-2-yl-(1-t-butoxy)]-7-[3-keto-1-propyl-3-(1-piperizine)]-3,4-dihydro-1H-1,4-benzodiazepine-2,5-dione trifluroacetate, (±)-1-isopropyl-3-phenyl-4-[succin-2-yl-(1-glycine)]-7-[3-keto-1-propyl-3-(1piperizine)]-3,4-dihydro-1H-1,4-benzodiazepine-2,5-dione trifluroacetate, (±)- 1-isopropyl-3-phenyl -4-[succin-2-yl-(1-valine)]-7-[3-keto-1-propyl-3-(1-piperizine)]-3,4-dihydro-1H-1,4-benzodiazepine-2,5-dione trifluroacetate, (±)-1-isopropyl-3-phenyl-4-[succin-2-yl-(1-phenylalanine)]-7-[3-keto-1-propyl-3-(1-piperizine)]-3,4-dihydro-1H-1,4-benzodiazepine-2,5-dione trifluroacetate, (±)-1-methyl-3-phenyl-4-(2-carboxy-1-methylethyl)-7-[2-(2-aminoethanethiol)-1-ethyl]-3,4-dihydro-1H-1,4-benzodiazepine-2,5-dione trifluoracetate, (±)-1-methyl-3-phenyl-4-(2-carboxy-1-phenylethyl)-7-[2-(2-aminoethanethiol)-1-ethyl]-3,4-dihydro-1H-1,4-benzodiazepine-2,5-dione trifluoracetate, (±)-1-methyl-3-phenyl-4-[succin-2-yl-(1-t-butoxy)]-7-[2-(2-aminoethanethiol)-1-ethyl]-3,4-dihydro-1H-1,4-benzodiazepine-2,5-dione trifluoracetate, (±)-1-methyl-3-phenyl-4-[succin-2-yl-(1-glycine)]-7-[2-(2-aminoethanethiol)-1-ethyl]-3,4-dihydro-1H-1,4-benzodiazepine-2,5-dione trifluoracetate, (±)-1-methyl-3-phenyl-4-[succin-2-yl-(1-valine)]-7-[2-(2-aminoethanethiol)-1-ethyl]-3,4-dihydro-1H-1,4-benzodiazepine-2,5-dione trifluoracetate, (±)-1-methyl-3-phenyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, (±)-1,3-diphenyl-4-(2-carboxy-1-methylethyl)-7-[2-(2-aminoethanethiol)-1-ethyl]-3,4-dihydro-1H-1,4-benzodiazepine-2,5-dione trifluroacetate, (±)-1,3-diphenyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1,3-diphenyl-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1,3-diphenyl-4-[succin-2-yl-(1-glycine)]-7-[2-( 2-aminoethanethiol)-1-ethyl]-3,4-dihydro-1H-1,4-benzodiazepine-2,5-dione trifluroacetate, (±)-1,3-diphenyl-4-[succin-2-yl-(1-valine)]-7-[2-(2-aminoethanethiol)-3,4-dihydro-1H-1,4-benzodiazepine-2,5-dione trifluroacetate, (±)-1,3-diphenyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, (±)-1-benzyl-3-phenyl-4-(2-carboxy-1-methylethyl )-7-[2-(2-aminoethanethiol)-1-ethyl]-3,4-dihydro-1H-1,4-benzodiazepine-2,5-dione trifluroacetate, (±)-1-benzyl-3-phenyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1-benzyl-3-phenyl-4-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1-benzyl-3-phenyl-4-[succin-2-yl-(1-glycine)]-7-[2-(2-aminoethanethiol)-1-ethyl]-3,4-dihydro-1H-1,4-benzodiazepine-2,5-dione trifluroacetate, (±)-1 -benzyl-3-phenyl-4-[succin-2-yl-(1-valine) ]-7-[2-(2-aminoethanethiol)-1-ethyl]-3,4-dihydro-1H-1,4-benzodiazepine-2,5-dione trifluroacetate, (±)-1 -benzyl-3-phenyl-4-[succin-2-yl-(1-phenylalanine)]-7-[2-(2-aminoethanethiol-1-ethyl]-3,4-dihydro-1H-1,4-benzodiazepine-2,5-dione trifluroacetate, (±)-1-isopropyl-3-phenyl-4-(2-carboxy-1-methylethyl)-7-[2-(2-aminoethanethiol)-1-ethyl]-3,4-dihydro-1H-1,4-benzodiazepine-2,5-dione trifluroacetate, (±)-1-isopropyl-3-phenyl-4-(2-carboxy-1-phenylethyl)-7-[2-(2-aminoethanethiol)-1-ethyl]-3,4-dihydro-1H-1,4-benzodiazepine-2,5-dione trifluroacetate, (±)-1-isopropyl-3-phenyl-4-[succin-2-yl-(1-t-butoxy)]-7-[2-(2-aminoethanethiol)-1-ethyl]-3,4-dihydro-1H-1,4-benzodiazepine-2,5-dione trifluroacetate, (±)-1-isopropyl-3-phenyl-4-[succin-2-yl-(1-glycine)]-7-[2-(2-aminoethanethiol)-1-ethyl]-3,4-dihydro-1H-1,4-benzodiazepine-2,5-dione trifluroacetate, (±)-1-isopropyl-3-phenyl-4-[succin-2-yl-(1-valine)]-7-[2-(2-aminoethanethiol)-1-ethyl]-3,4-dihydro-1H-1,4-benzodiazepine-2,5-dione trifluroacetate, (±)-1-isopropyl-3-phenyl-4-[succin-2-yl-(1-phenylalanine)]-7-[2-(2-aminoethanethiol)-1-ethyl]-3,4-dihydro-1H-1,4-benzodiazepine-2,5-dione trifluroacetate, (±)-1-methyl-3-phenyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-3-phenyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-3-phenyl-4-[succin-2-yl-(1-t-butoxy)]-7-[4-(2-amino-6-methylpyrimidine-4-yl )-4-oxa-1-butyl]-3,4-dihydro- 1 H- 1,4-benzodiazepine-2,5-dione trifluroacetate, (±)-1-methyl-3-phenyl-4-[succin-2-yl-(1-glycine)]-7-[4-(2-amino-6- methylpyrimidine-4-yl)-4-oxa-1-butyl]-3,4-dihydro-1H-1,4-benzodiazepine-2,5-dione trifluroacetate, (±)-1-methyl-3-phenyl-4-[succin-2-yl-( 1-valine ) ]-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-3-phenyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, (±)-1,3-diphenyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1,3-diphenyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1,3-diphenyl-4-[succin-2-yl-(1-t-butoxy)]-7-[4-(2-amino-6methylpyrimidine-4-yl)-4-oxa-1-butyl]-3,4-dihydro-1H-1,4-benzodiazepine-2,5-dione trifluroacetate, (±)-1,3-diphenyl-4-[succin-2-yl-(1-glycine)]-7-[4-(2-amino-6-methylpyrimidine-4-yl)-4-oxa-1-butyl ]-3,4-dihydro-1H-1,4-benzodiazepine-2,5-dione trifluroacetate, (±)-1,3-diphenyl-4-[succin-2-yl-(1-valine)]-7-[4-(2-amino-6-methylpyrimidine-4-yl )-4-oxa-1-butyl]-3,4-dihydro-1H-1,4-benzodiazepine-2,5-dione trifluroacetate, (±)-1,3-diphenyl-4-[succin-2-yl-(1-phenylalanine)]-7-[4-(2-amino-6-methylpyrimidine-4-yl)-4-oxa-1-buryl]-3,4-dihydro-1 H- 1,4-benzodiazepine-2,5-dione trifluroacetate, (±)-1 -benzyl-3-phenyl-4-(2-carboxy-1-methylethyl)-7-[4-(2-amino-6-methylpyrimidine-4-yl)-4-oxa-1-butyl]-3,4-dihydro-1H- 1,4-benzodiazepine-2,5-dione trifluroacetate, (±)-1 -benzyl-3-phenyl-4-(2-carboxy-1-phenylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-benzyl-3-phenyl-4-[succin-2-yl-(1-t-butoxy)]-7-[4-(2-amino-6-methylpyrimidine-4-yl)-4-oxa-1-butyl]-3,4-dihydro-1H-1,4-benzodiazepine-2,5-dione trifluroacetate, (±)-1-benzyl-3-phenyl-4-[succin-2-yl-(1-glycine)]-7-[4-(2-methylpyrimidine-4-yl)-4-oxa-1-butyl]-3,4-dihydro-1H-1,4-benzodiazepine-2,5-dione trifluoroacetate, (±)-1-benzyl-3-phenyl-4-[succin-2-yl-(1-valine)]-7-[4-(2-amino-6-methylpyrimidine-4-yl)-4-oxa-1-butyl ]-3,4-dihydro- 1 H- 1,4-benzodiazepine-2,5-dione trifluoroacetate, (±)-1-benzyl-3-phenyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, (±)-1-isopropyl-3-phenyl-4-(2-carboxy-1-methylethyl)-7-[4-(2-amino-6-methylpyrimidine-4-yl)-4-oxa-1-butyl]-3,4-dihydro-1H-1,4-benzodiazepine-2,5-dione trifluroacetate, (±)-1-isopropyl-3-phenyl-4-(2-carboxy-1-phenylethyl)-7-[4-(2-amino-6-methylpyrimidine-4-yl )-4-oxa-1-butyl]-3,4-dihydro-1H-1,4-benzodiazepine-2,5-dione trifluroacetate, (±)-1-isopropyl-3-phenyl-4-[succin-2-yl-(1-t-butoxy)]-7-[4-(2-amino-6-methylpyrimidine-4-yl)-4-oxa-1-butyl]-3,4-dihydro-1H-1,4-benzodiazepine-2,5-dione trifluoroacetate, (±)-1-isopropyl-3-phenyl-4-[succin-2-yl-(1-glycine)]-7-[4-(2-amino-6-methylpyrimidine-4-yl)]-4-oxa-1-butyl]-3,4-dihydro-1H-1,4-benzodiazepine-2,5-dione trifluroacetate, (±)-1-isopropyl-3-phenyl-4-[succin-2-yl -(1-valine)]-7-[4-(2-amino-6-methylpyrimidine-4-yl)-4-oxa-1-butyl ]-3,4-dihydro-1H-1,4-benzodiazepine-2,5-dione trifluroacetate, (±)-1-isopropyl-3-phenyl-4-[succin-2-yl-(1-phenylalanine)]-7-[4-(2-amino-6-methylpyrimidine-4-yl)-4-oxa-1-butyl]-3,4-dihydro-1H-1,4-benzodiazepine-2,5-dione trifluroacetate, (±)-1-methyl-3-phenyl-4-(2-carboxy-1-methylethyl)-7-[5-(2-aminopyridine-3-yl)-5-oxa-1-pentyl ]-3,4-dihydro-1H-1,4-benzodiazepine-2,5-dione trifluroacetate, (±)-1-methyl-3-phenyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluoroacetate, (±)-1-methyl-3-phenyl-4-[succin-2-yl-(1-t-butoxy)]-7-[5-(2-aminopyridine-3-yl)5-oxa-1-pentyl]-3,4-dihydro-1H-1,4-benzodiazepine-2,5-dione trifluoroacetate, (±)-1-methyl-3-phenyl-4-[succin-2-yl-(1-glycine) ]-7-[5-(2-aminopyridine-3-yl )-5-oxa-1-pentyl]-3,4-dihydro-1H-1,4-benzodiazepine-2,5-dione trifluroacetate, (±)-1-methyl-3-phenyl-4-[succin-2-yl-(1-valine)]-7-[5-(2-aminopyridine-3-yl)-5-oxa-1-pentyl]-3,4-dihydro-1H-1,4-benzodiazepine-2,5-dione trifluroacetate, (±)-1-methyl-3-phenyl-4-[succin-2-yl-( 1-phenylalanine )]-7-[5-(2aminopyridine-3-yl )-5-oxa-1-pentyl]-3,4-dihydro-1H-1,4-benzodiazepine-2,5-dione trifluroacetate, (±)-1,3-diphenyl-4-(2-carboxy-1-methylethyl)-7-[5-(2-aminopyridine-3-yl)-5-oxa-1-pentyl]-3,4-dihydro-1H-1,4-benzodiazepine-2,5-dione trifluroacetate, (±)-1,3-diphenyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1,3-diphenyl-4-[succin-2-yl-(1-t-butoxy)]-7-[5-(2-aminopyridine-3-yl)-1-pentyl]-3,4-dihydro-1H-1,4-benzodiazepine-2,5-dione trifluroacetate, (±)-1,3-diphenyl-4-[succin-2-yl-(1-glycine)]-7-[5-(2-aminopyridine-3-yl)-5-oxa-1-pentyl]-3,4-dihydro-1H-1,4-benzodiazepine-2,5-dione trifluroacetate, (±)-1,3-diphenyl-4-[succin-2-yl-(1-valine)]-7-[5-(2-aminopyridine-3-yl)-5-oxa-1-pentyl-3,4-dihydro-1H-1,4-benzodiazepine-2,5-dione trifluroacetate, (±)-1,3-diphenyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, (±)-1-benzyl-3-phenyl-4-(2-carboxy-1-methylethyl)-7-[5-(2-aminopyridine-3-yl)-5-oxa-1-pentyl]-3,4-dihydro-1H-1,4-benzodiazepine-2,5-dione, (±)-1-benzyl-3-phenyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1-benzyl-3-phenyl-4-[succin-2-yl-(1-t-butoxy)]-7-[5-(2-aminopyridine-3-yl)-5- oxa-1-pentyl]-3,4-dihydro-1H-1,4-benzodiazepine-2,5-dione trifluroacetate, (±)-1-benzyl-3-phenyl-4-[succin-2-yl-(1-glycine)]-7-[5-(2-aminopyridine-3-yl)-5-oxa-1-pentyl]-3,4-dihydro-1 H-1,4-benzodiazepine-2,5-dione trifluroacetate, (±)-1-benzyl-3-phenyl-4-[succin-2-yl-( 1-valine)]-7-[5-(2-aminopyridine-3-yl)-5-oxa-1-pentyl]-3,4-dihydro-1H-1,4-benzodiazepine-2,5-dione trifluroacetate, (±)-1-benzyl-3-phenyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, (±)-1-isopropyl-3-phenyl-4-(2-carboxy-1-methylethyl)-7-[5-(2-aminopyridine-3-yl)-5-oxa-1-pentyl]-3,4-dihydro-1H-1,4-benzodiazepine-2,5-dione trifluroacetate, (±)-1-isopropyl-3-phenyl-4-(2-carboxy-1-phenylethyl)-7-[5-(2-aminopyridine-3-yl)-5-oxa-1-pentyl]-3,4-dihydro-1H-1,4-benzodiazepine-2,5-dione trifluroacetate, (±)-1-isopropyl-3-phenyl-4-[succin-2-yl-(1-t-butoxy)]-7-[5-( 2-aminopyridine-3-yl(-5-oxa- 1-pentyl]-3,4-dihydro-1H-1,4-benzodiazepine-2,5-dione trifluroacetate, (±)-1-isopropyl-3-phenyl-4-[succin-2-yl-(1-glycine)]-7-[5-( 2-aminopyridine-3-yl)-5-oxa-1-pentyl]-3,4-dihydro-1H-1,4-benzodiazepine-2,5-dione trifluroacetate, (±)-1-isopropyl-3-phenyl-4-[succin-2-yl-( 1-valine) ]-7-[5-(2-aminopyridine-3-yl)-5-oxa-1-pentyl]-3,4-dihydro-1H-1,4-benzodiazepine-2,5-dione trifluroacetate, (±)-1-isopropyl-3-phenyl-4-[succin-2-yl-(1-phenylalanine)]-7-[5-(2-aminopyridine-3-yl)-5-oxa-1-pentyl]-3,4-dihydro-1H-1,4-benzodiazepine-2,5-dione trifluroacetate, c) 1-methyl-4-(2-carboxyethyl)-7-(5-guanidino-1-pentyl)-3,4-dihydro-1H-1,4-benzodiazepine-2,5-dione was prepared by the method described in example 2.

Thus, 18 mgs 1-methyl-4-(2-carboxyethyl)-7-(5-amino-1-pentyl)-3,4-dihydro-1H-1,4-benzodiazepine-2,5-dione yielded 17 mgs (87%) 1-methyl-4-(2carboxyethyl)-7-(5-guanidino-1-pentyl)-3,4-dihydro-1H-1,4-benzodiazepine-2,5-dione trifluoroacetate ($\frac{1}{2}''$ C-18 reverse-phase column, eluting with a solvent gradient of 10:90 methanol(0.1% trifluoroacetic acid)/water (0.1% trifluoroacetic acid), time 0 to 10 min, to 50:50 methanol(0.1% trifluoroacetic acid)/water (0.1% trifluoroacetic acid), time 10 min to 40 rain, flow=10 ml/min, $R_t$=38.5 min, vv detection 254 nm). HRMS (FAB) molecular ion m/z =390.2132 (cald. $C_{19}H_{27}N_5O_4$, 390.2182)

Using the above procedure, but substituting the appropriate amino acid for 1-methyl-4-(2-carboxyethyl)-7-(5-amino-1-pentyl)-3,4-dihydro-1H- 1,4-benzodiazepine-2,5-dione there may be prepared, for example, the following compounds:

1-methyl-4-(2-carboxy-1-methylethyl)-7-(5-guanidino-1-pentyl)-3,4-dihydro-1H-1,4-benzodiazepine-2,5-dione trifluroacetate, 1-methyl-4-(2-carboxy-1-phenylethyl)-7-(5-guanidino-1-pentyl)-3,4-dihydro-1H-1,4-benzodiazepine-2,5-dione trifluroacetate, (±)-1-methyl-4-[succin-2-yl-(1-t-butoxy)]-7-(5-guanidino-1-pentyl)-3,4-dihydro-1H-1,4-benzodiazepine-2,5-dione trifluroacetate, (±)-1-methyl-4-[succin-2-yl-(1-glycine)]-7-(5-guanidino-1-pentyl)-3,4-dihydro-1H-1,4-benzodiazepine-2,5-dione trifluroacetate, (±)-1-methyl-4-[succin-2-yl-(1-valine)]-7-(5-guanidino-1-pentyl)-3,4-dihydro-1H-1,4-benzodiazepine-2,5-dione trifluroacetate, (±)-1-methyl-4-[succin-2-yl-( 1-phenylalanine)]-7-(5-guanidino-1-pentyl )-3,4-dihydro-1H-1,4-benzodiazepine-2,5-dione trifluroacetate, (±)- 1-phenyl-4-(2-carboxy-1-methylethyl)-7-(5-guanidino-1-pentyl)-3,4-dihydro-1H-1,4-benzodiazepine-2,5-dione trifluroacetate, (±)-1-phenyl-4-(2-carboxy-1-phenylethyl)-7-(5-guanidino-1-pentyl)-3,4-dihydro-1H-1,4-benzodiazepine-2,5-dione trifluroacetate, (±)-1-phenyl-4-[succin-2-yl-(1-t-butoxy)]-7-(5-guanidino-1-pentyl)-3,4-dihydro-1H-1,4-benzodiazepine-2,5-dione trifluroacetate, (±)- 1-phenyl-4-[succin-2-yl-(1-glycine)]-7-(5-guanidino-1-pentyl)-3,4-dihydro-1H-1,4-benzodiazepine-2,5-dione trifluroacetate, (±)-1-phenyl-4-[succin-2-yl-(1-valine)]-7-(5-guanidino-1-pentyl )-3,4-dihydro-1H-1,4-benzodiazepine-2,5-dione trifluroacetate, (±)-1-phenyl-4-[succin-2-yl-(1-phenylalanine)]-7-(5-guanidino-1-pentyl)-3,4-dihydro-1H-1,4-benzodiazepine-2,5-dione trifluroacetate, 1-benzyl-4-(2-carboxy-1-methylethyl)-7-(5-guanidino-1-pentyl)-3,4-dihydro-1H-1,4-benzodiazepine-2,5-dione trifluroacetate, 1-benzyl-4-(2-carboxy-1-phenylethyl)-7-(5-guanidino-1-pentyl)-3,4-dihydro-1H-1,4-benzodiazepine-2,5-dione trifluroacetate, (±)-1-benzyl-4-[succin-2-yl-(1-t-butoxy)]-7-(5-guanidino-1-pentyl)-3,4-dihydro-1H-1,4-benzodiazepine-2,5-dione trifluroacetate, (±)-1-benzyl-4-[succin-2-yl-(1-glycine)]-7-(5-guanidino-1-pentyl)-3,4-dihydro-1H-1,4-benzodiazepine-2,5-dione trifluroacetate, (±)-1-benzyl-4-[succin-2-yl-(1-valine)]-7-(5-guanidino-1-pentyl)-3,4-dihydro-1,4-benzodiazepine-2,5-dione trifluroacetate, (±)-1-benzyl-4-[succin-2-yl-(1-phenylalanine)]-7-(5-guanidino-1-pentyl)-3,4-dihydro-1H-1,4-benzodiazepine-2,5-dione trifluroacetate, 1-isopropyl-4-(2-carboxy-1-methylethyl)-7-(5-guanidino-1-pentyl)-3,4-dihydro-1H-1,4-benzodiazepine-2,5-dione trifluroacetate, 1-isopropyl-4-(2-carboxy-1-phenylethyl)-7-(5-guanidino-1-pentyl)-3,4-dihydro-1H-1,4-benzodiazepine-2,5-dione trifluroacetate, (±)-1-isopropyl-4-[succin-2-yl-(1-t-butoxy)]-7-(5-guanidino-1-pentyl)-3,4-dihydro-1H-1,4-benzodiazepine-2,5-dione trifluroacetate, (±)-1-isopropyl-4-[succin-2-yl-(1-glycine)]-7-(5-guanidino-1-pentyl)-1H-1,4-benzodiazepine-2,5-dione trifluoacetate, (±)-1-isopropyl-4-[succin-2-yl-(1-valine)]-7-(5-guanidino-1-pentyl)-3,4-dihydro-1H-1,4-benzodiazepine-2,5-dione trifluroacetate, (±)-1-isopropyl-4-[succin-2-yl-(1-phenylalanine)]-7-(5-guanidino-1-pentyl)-3,4-dihydro-1H-1,4-benzodiazepine-2,5-dione trifluroacetate, 1-methyl-4-(2-carboxy-1-methylethyl)-7-[N-(2-guanidinoethane)-3-keto-1-propyl-3-amine]-3,4-dihydro-1H-1,4-benzodiazepine-2,5-dione trifluroacetate, 1-methyl-4-(2-carboxy-1-phenylethyl)-7-[N-(2-guanidinoethane)-3-keto-1-propyl-3-amine]-3,4-dihydro-1H-1,4-benzodiazepine-2,5-dione trifluroacetate, (±)-1-methyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate, (±)-1-methyl-4-[succin-2-yl-(1-glycine)]-7-[N-(2-guanidinoethane)-3-keto-1-propyl-3-amine]-3,4-dihydro-1H-1,4-benzodiazepine-2,5-dione trifluroacetate, (±)-1-methyl-4-[succin-2-yl-(1-valine)]-7-[N-(2-guanidinoethane)-3-keto-1-propyl-3-amine]-3,4-dihydro-1H-1,4-benzodiazepine-2,5-dione trifluroacetate, (±)-1-methyl-4-[succin-2-yl-(1-phenylalanine)]-7-[N-(2-guanidinoethane)-3-keto-1-propyl-3-amine]-3,4-dihydro-1H-1,4-benzodiazepine-2,5-dione trifluroacetate, 1-phenyl-4-(2-carboxy-1-methylethyl)-7-[N-(2-guanidinoethane)-3-keto-1-propyl-3-amine]-3,4-dihydro-1H-1,4-benzodiazepine-2,5-dione trifluroacetate, 1-phenyl-4-(2-carboxy-1-phenylethyl)-7-[N-(2-guanidinoethane)-3-keto-1-propyl-3-amine]-3,4-dihydro-1H-1,4-benzodiazepine-2,5-dione trifluroacetate, (±)-1-phenyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate, (±)-1-phenyl-4-[succin-2-yl-(1-glycine)]-7-[N-(2-guanidinoethane)-3-keto-1propyl-3-amine]-3,4-dihydro-1H-1,4-benzodiazepine-2,5-dione trifluroacetate, (±)-1-phenyl-4-[succin-2-yl-(1-valine)]-7-[N-(2-guanidinoethane)-3-propyl-3-amine]-3,4-dihydro-1H-1,4-benzodiazepine-2,5-dione trifluroacetate, (±)-1-phenyl-4-[succin-2-yl-(1-phenylalanine)]-7-[N-(2-guanidinoethane)-3-keto-1-propyl-3-amine]-3,4-dihydro-1H-1,4-benzodiazepine-2,5-dione trifluroacetate, 1-benzyl-4-(2-carboxy-1-methylethyl)-7-[N-(2-guanidinoethane)-3-keto-1-propyl-3-amine]-3,4-dihydro-1H-1,4-benzodiazepine-2,5-dione trifluroacetate, 1-benzyl-4-(2-carboxy-1-phenylethyl)-7-[N-(2-guanidinoethane)-3-keto-1-propyl-3-amine]-3,4-dihydro-1H-1,4-benzodiazepine-2,5-dione trifluroacetate, (±)-1-benzyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate, (±)-1-benzyl-4-[succin-2-yl-(1-glycine)]-7-[N-(2-guanidinoethane)-3-keto-1-propyl-3-amine]-3,4-dihydro-1H-1,4-benzodiazepine-2,5-dione trifluroacetate, (±)-1-benzyl-4-[succin-2-yl-(1-valine)]-7-N-(2-guanidinoethane)-3-keto-1-propyl-3-amine]-3,4-dihydro-1H-1,4-benzodiazepine-2,5-dione trifluroacetate, (±)-1-benzyl-4-[succin-2-yl-(1-phenylalanine)]-7-[N-(2-guanidinoethane)-3-keto-1-propyl-3-amine]-3,4-dihydro-1H-1,4-benzodiazepine-2,5-dione trifluroacetate, 1-isopropyl-4-(2-carboxy-1-methylethyl)-7-[N-(2-guanidinoethane)-3-keto-1-propyl-3-amine]-3,4-dihydro-1H-1,4-benzodiazepine-2,5-dione trifluroacetate, 1-isopropyl-4-(2-carboxy-1-phenylethyl)-7-[N-(2-guanidinoethane)-3-keto-1-propyl-3-amine]-3,4-dihydro-1H-1,4-benzodiazepine-2,5-dione trifluroacetate, (±)-1-isopropyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate, (±)-1-isopropyl-4-[succin-2-yl-(1-glycine)]-7-[N-(2-guanidinoethane)-3-keto-1-propyl-3-amine]-3,4-dihydro-1H-1,4-benzodiazepine-2,5-dione trifluroacetate, (±)-1-isopropyl-4-[succin-2-yl-(1-valine)]-7-[N-(2-guanidinoethane)-3-keto-1-propyl-3-amine]-3,4-dihydro-1H-1,4-benzodiazepine-2,5-dione trifluroacetate, (±)-1-isopropyl-4-[succin-2-yl-(1-phenylalanine)]-7-[N-(2-guanidinoethane)-3-keto-1-propyl-3-amine]-3,4-dihydro-1H-1,4-benzodiazepine-2,5-dione trifluroacetate, 1-methyl-4-(2-carboxy-1-methylethyl)-7-[3-keto-1-propyl-3-(4-amidino-1piperizine)]-3,4-dihydro-1H-1,4-benzodiazepine-2,5-dione trifluroacetate, 1-methyl-4-(2-carboxy-1-phenylethyl)-7-[3-keto-1-propyl-3-(4-amidino-1-piperizine)]-3,4-dihydro-1H-1,4-benzodiazepine-2,5-dione trifluroacetate, (±)-1-methyl-4-[succin-2-yl-(1-t-butoxy)]-7-[3-keto-1-propyl-3-(4-amidino-1-piperizine)]-3,4-dihydro-1H-1,4-benzodiazepine-2,5-dione trifluroacetate, (±)-1-methyl-4-[succin-2-yl-(1-glycine)]-7-[3-keto-1-propyl-3-(4-amidino-1-3,4-dihydro-1H-1,4-benzodiazepine-2,5-dione trifluroacetate, (±)-1-methyl-4-[succin-2-yl-(1-valine)]-7-[3-keto-1-propyl-3-(4-amidino-1-piperizine)]-3,4-dihydro-1H-1,4-benzodiazepine-2,5-dione trifluroacetate, (±)-1-methyl-4-[succin-2-yl-(1-phenylalanine)]-7-[3-keto-1-propyl-3-(4-amidino-1-piperizine)]-3,4-dihydro-1H-1,4-benzodiazepine-2,5-dione trifluroacetate, 1-phenyl-4-(2-carboxy-1-methylethyl)-7-[3-keto-1-propyl-3-(4-amidino-1-piperizine]-3,4-dihydro-1H-1,4-benzodiazepine-2,5-dione trifluroacetate, 1-phenyl-4-(2-carboxy-1-phenylethyl)-7-[3-keto-1-propyl-3-(4-amidino-1-piperizine)]-3,4-dihydro-1H-1,4-benzodiazepine-2,5-dione trifluroacetate, (±)-1-phenyl-4-[succin-2-yl-(1-t-butoxy )]-7-[3-keto-1-propyl-3-(4-amidino-1-3,4-dihydro-1H-1,4-benzodiazepine-2,5-dione trifluroacetate, (±)-1-phenyl-4-[succin-2-yl-(1-glycine)]-7-[3-keto-1-propyl-3-(4-amidino-1-3,4-dihydro-1H-1,4-benzodiazepine-2,5-dione trifluroacetate, (±)-1-phenyl-4-[succin-2-yl-(1-valine)]-7-[3-keto-1-propyl-3-(4-amidino-1piperizine)]-3,4-dihydro-1H-1,4-benzodiazepine-2,5-dione trifluroacetate, (±)-1-phenyl-4-[succin-2-yl-( 1-phenylalanine ) ]-7-[3-keto-1-propyl-3-(4-amidino-1-piperizine)]-3,4-dihydro-1H-1,4-benzodiazepine-2,5-dione trifluroacetate, 1-benzyl-4-(2-carboxy-1-methylethyl)-7-[3-keto-1-propyl-3-(4-amidino-1piperizine(]-3,4-dihydro-1H-1,4-benzodiazepine-2,5-dione trifluroacetate, 1-benzyl-4-(2-carboxy-1-phenylethyl)-7-[3-keto-1-propyl-3-(4-amidino-1-piperizine)]-3,4-dihydro-1H-1,4-benzodiazepine-2,5-dione trifluroacetate, (±)-1-benzyl-4-[succin-2-yl-(1-t-butoxy)]-7-[3-keto-1-propyl-3-(4-amidino-1-piperizine) -3,4-dihydro-1H-1,4-benzodiazepine-2,5-dione trifluroacetate, (±)-1-benzyl-4-[succin-2-yl-( 1-glycine )]-7-[3-keto-1-propyl-3-(4-amidino-1-piperizine)]-3,4-dihydro-1H-1,4-benzodiazepine-2,5-dione trifluroacetate, (±)-1-benzyl-4-[succin-2-yl-( 1-valine)]-7-[3-keto-1-propyl-3-(4-amidino-1-piperizine)]-3,4-dihydro-1H-1,4-benzodiazepine-2,5-dione trifluroacetate, (±)-1-benzyl-4-[succin-2-yl-(1-phenylalanine)]-7-[3-keto-1-propyl-3-(4-amidino-1-piperizine)]-3,4-dihydro-1H-1,4-benzodiazepine-2,5-dione trifluroacetate, 1-isopropyl-4-(2-carboxy-1-methylethyl)-7-[3-keto-1-propyl-3-(4-amidino-1-3,4-dihydro-1H-1,4-benzodiazepine-2,5-dione trifluroacetate, 1-isopropyl-4-(2-carboxy-1-phenylethyl)-7-[3-keto- 1-propyl-3-(4-amidino-1-piperizine) -3,4-dihydro-1H-1,4-benzodiazepine-2,5-dione trifluroacetate, (±)- 1 -isopropyl-4-[succin-2-yl-(1-t-butoxy)]-7-[3-keto-1-propyl-3-(4-amidino-1-piperizine)]-3,4-dihydro-1H-1,4-benzodiazepine-2,5-dione trifluroacetate, (±)-1-isopropyl-4-[succin-2-yl-(1-glycine)]-7-[3-keto-1-propyl-3-(4-amidino-1-piperizine)]-3,4-dihydro-1H-1,4-benzodiazepine-2,5-dione trifluroacetate, (±)-1 -isopropyl-4-[succin-2-yl-( 1-valine)]-7-[3-keto-1-propyl-3-(4-amidino-1-piperizine)]-3,4-dihydro-1H-1,4-benzodiazepine-2,5-dione trifluroacetate, (±)-1-isopropyl-4-[succin-2-yl-(1-phenylalanine)]-7-[3-keto-1-propyl-3-(4-amidino-1-piperizine)]-3,4-dihydro-1H-1,4-benzodiazepine-2,5-dione trifluroacetate, 1-methyl-4-(2-carboxy-1-methylethyl)-7-[2-(2-guanidinoethanethiol)-1-ethyl]-3,4-dihydro-1H-1,4-benzodiazepine-2,5-dione trifluoroacetate, 1-methyl-4-(2-carboxy-1-phenylethyl )-7-[2-(2-guanidinoethanethiol)-1-ethyl]-3,4-dihydro-1H-1,4-benzodiazepine-2,5-dione trifluroacetate, (±)-1-methyl-4-[succin-2-yl-(1-t-butoxy)]-7-[2-(2-guanidinoethanethiol)-1-ethyl]-3,4-dihydro-1H-1,4-benzodiazepine-2,5-dione trifluroacetate, (±)-1-methyl-4-[succin-2-yl-(1-glycine)]-7-[2-(2-guanidinoethanethiol)-1-ethyl]-3,4-dihydro-1H-1,4-benzodiazepine-2,5-dione trifluroacetate, (±)-1-methyl-4-[succin-2-yl-(1-valine)]-7-[2-(2-guanidinoethanethiol)-1-ethyl]-3,4-dihydro-1H-1,4-benzodiazepine-2,5-dione trifluroacetate, (±)-1-methyl-4-[succin-2-yl-( 1-phenylalanine )]-7-[2-(2-guanidinoethanethiol)-1-ethyl]-3,4-dihydro- 1H-1,4-benzodiazepine-2,5-dione trifluroacetate, 1-phenyl-4-(2-carboxy-1-methylethyl)-7-[2-(2-guanidinoethanethiol)-1-ethyl]-3,4-dihydro-1H-1,4-benzodiazepine-2,5-dione trifluroacetate, 1-phenyl-4-(2-carboxy-1-phenylethyl)-7-[2-(2-guanidinoethanethiol)-1-ethyl]-3,4-dihydro-1H-1,4-benzodiazepine-2,5-dione trifluroacetate, (±)-1-phenyl-4-[succin-2-yl-(1-t-butoxy)]-7-[2-(2-guanidinoethanethiol)-1-ethyl]-3,4-dihydro-1H-1,4-benzodiazepine-2,5-dione trifluroacetate, (±)-1-phenyl-4-[succin-2-yl-(1-glycine )]-7-[2-(2-guanidinoethanethiol)-1-ethyl]-3,4-dihydro-1H-1,4-benzodiazepine-2,5-dione trifluroacetate, (±)-1-phenyl-4-[succin-2-yl-(1-valine)]-7-[2-( 2-guanidinoethanethiol)-1-ethyl]-3,4-dihydro-1H-1,4-benzodiazepine-2,5-dione trifluroacetate, (±)-1-phenyl-4-[succin-2-yl-(1-phenylalanine)]-7-[2-(2-guanidinoethanethiol)-1-ethyl]-3,4-dihydro-1H-1,4-benzodiazepine-2,5-dione trifluroacetate, 1-benzyl-4-(2-carboxy-1-methylethyl)-7-[2-(2-guanidinoethanethiol)-1-ethyl]-3,4-dihydro-1H-1,4-benzodiazepine-2,5-dione trifluroacetate, 1-benzyl-4-(2-carboxy-1-phenylethyl)-7-[2-(2-guanidinoethanethiol)-1-ethyl]-3,4-dihydro-1H-1,4-benzodiazepine-2,5-dione trifluroacetate, (±)-1-benzyl-4-[succin-2-yl-(1-t-butoxy)]-7-[2-(2-guanidinoethanethiol)-1-ethyl]-3,4-dihydro-1H-1,4-benzodiazepine-2,5-dione trifluroacetate, (±)-1-benzyl-4-[succin-2-yl-(1-glycine)]-7-[2-(2-guanidinoethanethiol)-1-ethyl]-3,4-dihydro-1H-1,4-benzodiazepine-2,5-dione trifluroacetate, (±)-1 -benzyl-4-[succin-2-yl-(1-valine)]-7-[2-(2-guanidinoethanethiol)-1-ethyl]-3,4-dihydro-1H-1,4-benzodiazepine-2,5-dione trifluroacetate, (±)-1-benzyl-4-[succin-2-yl-(1-phenylalanine)]-7-[2-(2-guanidinoethanethiol)-1-ethyl]-3,4-dihydro-1H-1,4-benzodiazepine-2,5-dione trifluroacetate, 1-isopropyl-4-(2-carboxy-1-methylethyl)-7-[2-(2-guanidinoethanethiol)-1-ethyl]-3,4-dihydro-1H-1,4-benzodiazepine-2,5-dione trifluroacetate, 1-isopropyl-4-(2-carboxy-1-phenylethyl)-7-[2-(2-guanidinoethanethiol)-1-ethyl]-3,4-dihydro-1H-1,4-benzodiazepine-2,5-dione trifluroacetate, (±)-1-isopropyl-4-[succin-2-yl-(1-1-butoxy)]-7-[2-(2-guanidinoethanethiol)-1-ethyl]-3,4-dihydro-1H-1,4-benzodiazepine-2,5-dione trifluroacetate, (±)-1-isopropyl-4-[succin-2-yl-(1-glycine)]-7-[2-(2-guanidinoethanethiol)-1-ethyl]-3,4-dihydro-1H-1,4-benzodiazepine-2,5-dione trifluroacetate, (±)-1-isopropyl-4-[succin-2-yl-(1-valine)]-7-[2-(2-guanidinoethanethiol)-1-ethyl]-3,4-dihydro-1H-1,4-benzodiazepine-2,5-dione trifluroacetate, (±)-1-isopropyl-4-[succin-2-yl-(1-phenylalanine)]-7-[2-(2-guanidinoethanethiol)-1-ethyl]-3,4-dihydro-1H-1,4-benzodiazepine-2,5-dione trifluroacetate, (±)-1-methyl-3-phenyl-4-(2-carboxy-1-methylethyl)-7-(5-guanidino-1-pentyl)-3,4-dihydro-1H-1,4-benzodiazepine-2,5-dione trifluroacetate, (±)-1-methyl-3-phenyl-4-(2-carboxy-1-phenylethyl)-7-(5-guanidino-1-pentyl)-3,4-dihydro- 1H-1,4-benzodiazepine-2,5-dione trifluroacetate, (±)-1-methyl-3-phenyl-4-[succin-2-yl-(1-t-butoxy)]-7-(5-guanidino-1-pentyl)-3,4dihydro-1H-1,4-benzodiazepine-2,5-dione trifluroacetate,
(±)-1-methyl-3-phenyl-4-[succin-2-yl-(1-glycine)]-7-(5-guanidino-1-pentyl)-3,4-dihydro-1H-1,4-benzodiazepine-2,5-dione trifluroacetate,
(±)-1-methyl-3-phenyl-4-[succin-2-yl-( 1-valine )]-7-(5-guanidino-1-pentyl)-3,4-dihydro-1H-1,4-benzodiazepine-2,5-dione trifluroacetate,
(±)-1-methyl-3-phenyl-4-[succin-2-yl-(1-phenylalanine)]-7-(5-guanidino-1-pentyl)-3,4-dihydro-1H-1,4-benzodiazepine-2,5-dione trifluroacetate,
(±)-1,3-diphenyl-4-(2-carboxy-1-methylethyl)-7-(5-guanidino-1-pentyl)-3,4-dihydro-1H-1,4-benzodiazepine-2,5-dione trifluroacetate,
(±)-1,3-diphenyl-4-(2-carboxy-1-phenylethyl)-7-(5-guanidino-1-pentyl )-3,4-dihydro-1H-1,4-benzodiazepine-2,5-dione trifluroacetate,
(±)-1,3-diphenyl-4-[succin-2-yl-(1-t-butoxy)]-7-(5-guanidino-1-pentyl)-3,4-dihydro-1H-1,4-benzodiazepine-2,5-dione trifluroacetate,
(±)-1,3-diphenyl-4-[succin-2-yl-(1-glycine)]-7-(5-guanidino-1-pentyl)-3,4-dihydro-1H-1,4-benzodiazepine-2,5-dione trifluroacetate,
(±)-1,3-diphenyl-4-[succin-2-yl-(1-valine)]-7-(5-guanidino-1-pentyl)-3,4-dihydro-1H-1,4-benzodiazepine-2,5-dione trifluroacetate,
(±)-1,3-diphenyl-4-[succin-2-yl-(1-phenylalanine)]-7-(5-guanidino-1--pentyl )-3,4-dihydro-1H-1,4-benzodiazepine-2,5-dione trifluroacetate,
(±)-1-benzyl-3-phenyl-4-(2-carboxy-1-methylethyl)-7-(5-guanidino-1-pentyl)-3,4-dihydro-1H-1,4-benzodiazepine-2,5-dione trifluroacetate,
(±)-1-benzyl-3-phenyl-4-(2-carboxy-1-phenylethyl)-7-(5-guanidino-1-pentyl)-3,4-dihydro-1H-1,4-benzodiazepine-2,5-dione trifluroacetate,
(±)-1-benzyl-3-phenyl-4-[succin-2-yl-(1-t-butoxy)]-7-(5-guanidino-1-pentyl)-3,4-dihydro-1H-1,4-benzodiazepine-2,5-dione trifluroacetate,
(±)-1-benzyl-3-phenyl-4-[succin-2-yl-(1-glycine)]-7-(5-guanidino-1-pentyl)-3,4-dihydro-1H-1,4-benzodiazepine-2,5-dione trifluroacetate,
(±)-1-benzyl-3-phenyl-4-[succin-2-yl-(1-valine)]-7-(5-guanidino-1-pentyl )-3,4-dihydro-1H-1,4-benzodiazepine-2,5-dione trifluroacetate,
(±)-1-benzyl-3-phenyl-4-[succin-2-yl-(1-phenylalanine)]-7-(5-guanidino-1-pentyl)-3,4-dihydro-1H-1,4-benzodiazepine-2,5-dione trifluroacetate,
(±)-1-isopropyl-3-phenyl-4-(2-carboxy-1-methylethyl)-7-(5-guanidino-1-pentyl)3,4-dihydro-1H-1,4-benzodiazepine-2,5-dione trifluroacetate,
(±)-1-isopropyl-3-phenyl-4-(2-carboxy-1-phenylethyl)-7-(5-guanidino-1-pentyl)3,4-dihydro-1H-1,4-benzodiazepine-2,5-dione trifluroacetate,
(±)-1-isopropyl-3-phenyl-4-[succin-2-yl-(1-t-butoxy)]-7-(5-guanidino-1-pentyl)-3,4-dihydro-1H-1,4-benzodiazepine-2,5-dione trifluroacetate,
(±)-1-isopropyl-3-phenyl-4-[succin-2-yl-(1-glycine) ]-7-(5-guanidino-1-pentyl)-3,4-dihydro-1H-1,4-benzodiazepine-2,5-dione trifluroacetate,
(±)-1-isopropyl-3-phenyl-4-[succin-2-yl-(1-valine) ]-7-(5-guanidino-1-pentyl)-3,4-dihydro-1H-1,4-benzodiazepine-2,5-dione trifluroacetate,
(±)-1-isopropyl-3-phenyl-4-[succin-2-yl-( 1-phenylalanine )]-7-(5-guanidino-1-pentyl)-3,4-dihydro-1H-1,4-benzodiazepine-2,5-dione trifluroacetate,
(±)-1-methyl-3-phenyl-4-(2-carboxy- 1-methylethyl )-7-[N-(2-guanidinoethane)-3-keto-1-propyl-3-amine ]-3,4-dihydro-1H-1,4-benzodiazepine-2,5-dione trifluroacetate,
(±)-1-methyl-3-phenyl-4-(2-carboxy-1-phenylethyl)-7-[N-(2-guanidinoethane)-3-keto-1-propyl-3-amine ]-3,4-dihydro-1H-1,4-benzodiazepine-2,5-dione trifluroacetate,
(±)-1-methyl-3-phenyl-4-[succin-2-yl-( 1-t-butoxy)]-7-[N-(2-guanidinoethane)-3-keto-1-propyl-3-amine]-3,4-dihydro-1H-1,4-benzodiazepine-2,5-dione trifluroacetate,
(±)-1-methyl-3-phenyl-4-[succin-2-yl-( 1-glycine)]-7-[N-(2-guanidinoethane)-3-keto-1-propyl-3-amine ]-3,4-dihydro-1H-1,4-benzodiazepine-2,5-dione trifluroacetate,
(±)-1-methyl-3-phenyl-4-[succin-2-yl-(1-valine)]-7-[N-(2-guanidinoethane)-3-keto-1-propyl-3-amine ]-3,4-dihydro-1H-1,4-benzodiazepine-2,5-dione trifluroacetate,
(±)-1-methyl-3-phenyl-4-[succin-2-yl-(1-phenylalanine)]-7-[N-(2-guanidinoethane)-3-keto-1-propyl-3-amine]-3,4-dihydro-1H-1,4-benzodiazepine-2,5-dione trifluroacetate,
(±)-1,3-diphenyl-4-(2-carboxy-1-methylethyl)-7-[N-(2-guanidinoethane)-3-keto-1-propyl-3-amine ]-3,4-dihydro-1H-1,4-benzodiazepine-2,5-dione trifluroacetate,
(±)-1,3-diphenyl-4-(2-carboxy-1-phenylethyl )-7-[N-(2-guanidinoethane )-3-keto-1-propyl-3-amine]-3,4-dihydro-1H-1,4-benzodiazepine-2,5-dione trifluroacetate,
(±)-1,3-diphenyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate,
(±)-1,3-diphenyl-4-[succin-2-yl-(1-glycine)]-7-[N-(2-guanidinoethane)-3-keto-1-propyl-3-amine]-3,4-dihydro-1H-1,4-benzodiazepine-2,5-dione trifluroacetate,
(±)-1,3-diphenyl-4-[succin-2-yl-(1-valine)]-7-[N-(2-guanidinoethane)-3-keto-1-propyl-3-amine]-3,4-dihydro-1H-1,4-benzodiazepine-2,5-dione trifluroacetate,
(±)-1,3-diphenyl -4-[succin-2-yl-( 1-phenylalanine )]-7-[N-(2-guanidinoethane)-3-keto-1-propyl-3-amine ]-3,4-dihydro-1H-1,4-benzodiazepine-2,5-dione trifluoroacetate,
(±)-1 -benzyl-3-phenyl-4-(2-carboxy-1-methylethyl)-7-[N-(2-guanidinoethane)-3-keto-1-propyl-3-amine]-3,4-dihydro-1H-1,4-benzodiazepine-2,5-dione trifluroacetate,
(±)-1-benzyl-3-phenyl-4-(2-carboxy-1-phenylethyl)-7-[N-(2-guanidinoethane)-3-keto-1-propyl-3-amine]-3,4-dihydro-1H-1,4-benzodiazepine-2,5-dione trifluroacetate,
(±)- 1-benzyl-3-phenyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate,
(±)-1-benzyl-3-phenyl-4-[succin-2-yl -(1-glycine)]-7-[N-(2-guanidinoethane)-3-keto-1-propyl-3-amine]-3,4-dihydro-1H-1,4-benzodiazepine-2,5-dione trifluroacetate,
(±)-1-benzyl-3-phenyl-4-[succin-2-yl-(1-valine)]-7-[N-(2-guanidinoethane)-3-keto-1-propyl-3-amine]-3,4-dihydro-1H-1,4-benzodiazepine-2,5-dione trifluroacetate,
(±)-1-benzyl-3-phenyl-4-[succin-2-yl-(1-phenylalanine)]-7-[N-(2-guanidinoethane)-3-keto-1-propyl-3-amine ]-3,4-dihydro-1 H- 1,4-benzodiazepine-2,5-dione trifluroacetate,
(±)-1-isopropyl-3-phenyl-4-(2-carboxy-1-methylethyl)-7-[N-(2-guanidinoethane)-3-keto-1-propyl-3-amine]-

3,4-dihydro-1H-1,4-benzodiazepine-2,5-dione trifluroacetate, (±)-1-isopropyl-3-phenyl 4-(2-carboxy-1-phenylethyl)-7-[N-(2-guanidinoethane)-3-keto-1-propyl-3-amine ]-3,4-dihydro-1H-1,4-benzodiazepine-2,5-dione trifluroacetate, (±)-1-isopropyl-3-phenyl-4-[succin-2-yl-(1-t-butoxy)]-7-[N-(2-guanidinoethane)-3-keto-1-propyl-3-amine]-3,4-dihydro-1H-1,4-benzodiazepine-2,5-dione trifluroacetate, (±)-1-isopropyl-3-phenyl-4-[succin-2-yl-(1-glycine)]-7-[N-(2-guanidinoethane)-3-keto-1-propyl-3-amine]-3,4-dihydro-1H-1,4-benzodiazepine-2,5-dione trifluroacetate, (±)-1-isopropyl-3-phenyl-4-[succin-2-yl-(1-valine)]-7-[N-(2-guanidinoethane)-3-keto-1-propyl-3-amine ]-3,4-dihydro- 1H-1,4-benzodiazepine-2,5-dione trifluroacetate, (±)-1-isopropyl-3-phenyl-4-[succin-2-yl-(1-phenylalanine)]-7-[N-(2guanidinoethane)-3-keto-1-propyl-3-amine ]-3,4-dihydro-1H-1,4-benzodiazepine-2,5-dione trifluroacetate, (±)-1-methyl-3-phenyl-4-(2-carboxy-1-methylethyl)-7-[3-keto-1-propyl-3-(4-amidino-1-piperizine)]-3,4-dihydro-1H-1,4-benzodiazepine-2,5-dione trifluroacetate, (±)-1-methyl-3-phenyl-4-(2-carboxy-1-phenylethyl)-7-[3-keto-1-propyl-3-(4-amidino-1-piperizine)]-3,4-dihydro-1H-1,4-benzodiazepine-2,5-dione trifluroacetate, (±)-1-methyl-3-phenyl-4-[succin-2-yl-(1-t-butoxy)]-7-[3-keto-1-propyl-3-(4-amidino-1-piperizine)]-3,4-dihydro-1H-1,4-benzodiazepine-2,5-dione trifluroacetate, (±)-1-methyl-3-phenyl-4-[succin-2-yl-(1-glycine) ]-7-[3-keto-1-propyl-3-(4-amidino-1-piperizine)]-3,4-dihydro-1H-1,4-benzodiazepine-2,5-dione trifluroacetate, (±)-1-methyl-3-phenyl-4-[succin-2-yl-(1-valine)]-7-[3-keto-1-propyl-3-(4-amidino-1-piperizine)]-3,4-dihydro-1H-1,4-benzodiazepine-2,5-dione trifluroacetate, (±)-1-methyl-3-phenyl-4-[succin-2-yl-(1-phenylalanine)]-7-[3-keto-1-propyl-3-(4-amidino-1-piperizine)]-3,4-dihydro-1H-1,4-benzodiazepine-2,5-dione trifluroacetate, (±)-1,3-diphenyl-4-(2-carboxy-1-methylethyl)-7-[3-keto-1-propyl-3-(4-amidino-1-piperizine ) ]-3,4-dihydro-1 H-1,4-benzodiazepine-2,5-dione trifluroacetate, (±)-1,3-diphenyl-4-(2-carboxy-1-phenylethyl)-7-[3-keto-1-propyl-3-(4-amidino1-piperizine)]-3,4-dihydro-1H-1,4-benzodiazepine-2,5-dione trifluroacetate, (±)-1,3-diphenyl-4-[succin-2-yl-(1-t-butoxy)]-7-[3-keto-1-propyl-3-(4-amidino-1piperizine)]-3,4-dihydro-1H-1,4-benzodiazepine-2,5-dione trifluroacetate, (±)-1,3-diphenyl-4-[succin-2-yl-(1-glycine)]-7-[3-keto-1 -propyl-3-(4amidino-1-piperizine)]-3,4-dihydro-1H-1,4-benzodiazepine-2,5-dione trifluroacetate, (±)-1,3-diphenyl-4-[succin-2-yl-(1-valine)]-7-[3-keto-1-propyl-3-(4-amidino-1-piperizine)]-3,4-dihydro-1H-1,4-benzodiazepine-2,5-dione trifluroacetate, (±)-1,3-diphenyl-4-[succin-2-yl-(1-phenylalanine) ]-7-[3-keto-1-propyl-3-(4-amidino-1-piperizine)]-3,4-dihydro-1H-1,4-benzodiazepine-2,5-dione trifluroacetate, (±)-1-benzyl-3-phenyl-4-(2-carboxy-1-methylethyl)-7-[3-keto-1-propyl-3-(4-amidino-1-piperizine)]-3,4-dihydro-1H-1,4-benzodiazepine-2,5-dione trifluroacetate, (±)-1-benzyl-3-phenyl-4-(2-carboxy-1-phenylethyl)-7-[3-keto-1-propyl-3-(4-amidino-1-piperizine)]-3,4-dihydro-1H-1,4-benzodiazepine-2,5-dione trifluroacetate, (±)-1-benzyl-3-phenyl-4-[succin-2-yl-(1-t-butoxy)]-7-[3-keto-1-proyl-3-(4-amidino-1-piperizine)]-3,4-dihydro-1H-1,4-benzodiazepine-2,5-dione trifluroacetate, (±)-1-benzyl-3-phenyl-4-[succin-2-yl-(1-glycine)]-7-[3-keto- 1-propyl-3-(4-amidino-1-piperizine)]-3,4-dihydro-1H-1,4-benzodiazepine-2,5-dione trifluroacetate, (±)-1-benzyl-3-phenyl-4-[succin-2-yl-(1-valine)]-7-[3-keto-1-propyl-3-(4-amidino-1-piperizine)]-3,4-dihydro-1H-1,4-benzodiazepine-2,5-dione trifluroacetate, (±)-1-benzyl-3-phenyl-4-[succin-2-yl-(1-phenylalanine)]-7-[3-keto-1-propyl-3-(4-amidino-1-piperizine)]-3,4-dihydro-1H-1,4-benzodiazepine-2,5-dione trifluoroacetate, (±)-1-isopropyl-3-phenyl-4-(2-carboxy-1-methylethyl)-7-[3-keto-1-propyl-3-(4-amidino-1-piperizine)]-3,4-dihydro-1H-1,4-benzodiazepine-2,5-dione trifluroacetate, (±)-1-isopropyl-3-phenyl-4-(2-carboxy-1-phenylethyl)-7-[3-keto-1-propyl-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-t-butoxy)]-7-[3-keto-1-propyl-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-glycine)]-7-[3-keto-1-propyl-3-(4-amidino-1-piperizine)]-3,4-dihydro-1H-1,4-benzodiazepine-2,5-dione trifluroacetate, (±)-1-isopropyl -3-phenyl-4-[succin-2-yl-(1-valine)]-7-[3-keto-1-propyl-3-(4-amidino-1-piperizine)]-3,4-dihydro-1H-1,4-benzodiazepine-2,5-dione trifluroacetate, (±)-1-isopropyl-3-phenyl-4-[succin-2-yl-(1-phenylalanine)]-7-[3-keto-1-propyl-3-(4-amidino-1-piperizine)]-3,4-dihydro-1H-1,4-benzodiazepine-2,5-dione trifluroacetate, (±)-1-methyl-3-phenyl-4-(2-carboxy-1-methylethyl)-7-[2-(2-guanidinoethanethiol)-1-ethyl]-3,4-dihydro-1H-1,4-benzodiazepine-2,5-dione trifluroacetate, (±)-1-methyl-3-phenyl-4-(2-carboxy-1-phenylethyl)-7-[2-(2-guanidinoethanethiol)-1-ethyl]-3,4-dihydro-1H-1,4-benzodiazepine-2,5-dione trifluroacetate, (±)-1-methyl-3-phenyl-4-[succin-2-yl-(1-t-butoxy)]-7-[2-(2-guanidinoethanethiol)-1-ethyl ]-3,4-dihydro-1H-1,4-benzodiazepine-2,5-dione trifluroacetate, (±)-1-methyl-3-phenyl-4-[succin-2-yl-(1-glycine)]-7-[2-(2-guanidinoethanethiol)-1-ethyl]-3,4-dihydro-1H-1,4-benzodiazepine-2,5-dione trifluroacetate, (±)-1-methyl-3-phenyl-4-[succin-2-yl-(1-valine)]-7-[2-(2-guanidinoethanethiol)-1-ethyl]-3,4-dihydro-1H-1,4-benzodiazepine-2,5-dione trifluroacetate, (±)-1-methyl-3-phenyl-4-[succin-2-yl-(1-phenylalanine)]-7-[2-(2-guanidinoethanethiol)-1-ethyl]-3,4-dihydro-1H-1,4-benzodiazepine-2,5-dione trifluroacetate, (±)-1,3-diphenyl-4-(2-carboxy-1-methylethyl)-7-[2-(2-guanidinoethanethiol)-1-ethyl]-3,4-dihydro-1H-1,4-benzodiazepine-2,5-dione trifluroacetate, (±)-1,3-diphenyl-4-(2-carboxy-1-phenylethyl)-7-[2-(2-guanidinoethanethiol )-1ethyl]-3,4-dihydro-1H-1,4-benzodiazepine-2,5-dione trifluroacetate, (±)-1,3-diphenyl-4-[succin-2-yl-( 1-t-butoxy ) ]-7-[2-(2-guanidinoethanethiol)-1-3,4-dihydro-1H-1,4-benzodiazepine-2,5-dione trifluroacetate, (±)-1,3-diphenyl-4-[succin-2-yl-( 1-glycine)]-7-[2-(2-guanidinoethanethiol)-1-ethyl]-3,4-dihydro-1H-1,4-benzodiazepine-2,5-dione trifluroacetate, (±)-1,3-diphenyl-4-[succin-2-yl-(1-valine)]-7- [2-( 2-guanidinoethanethiol)-1-ethyl]-3,4-dihydro-1H-1,4-benzodiazepine-2,5-dione trifluroacetate, (±)-1,3-diphenyl-4-[succin-2-yl-(1-phenylalanine )]-7-[2-(2-guanidinoethanethiol)-1-ethyl]-3,4-dihydro-1H-1,4-benzodiazepine-2,5-dione trifluroacetate, (±)-1-benzyl-3-phenyl -4-(2-carboxy-1-methylethyl)-7-[2-(2- guanidinoethanethiol)-1-ethyl]-3,4-dihydro-1H-1,4-benzodiazepine-2,5-dione trifluroacetate, (±)-1-benzyl-3-phenyl-4-(2-carboxy-1-phenylethyl)-7-[2-(2-guanidinoethanethiol)-1-ethyl]-3,4-dihydro-1H-1,4-benzodiazepine-2,5-dione trifluroacetate, (±)-1-benzyl-3-phenyl -4-[succin-2-yl-(1-t-butoxy)]-7-[2-(2-guanidinoethanethiol)-1-ethyl]-3,4-dihydro-1H-1,4-benzodiazepine-2,5-dione trifluroacetate, (±)-1-benzyl-3-phenyl-4-[succin-2-yl-(1-glycine)]-7-[2-(2-guanidinoethanethiol)-1-ethyl]-3,4-dihydro-1H-1,4-benzodiazepine-2,5-dione trifluroacetate, (±)-1-benzyl-3-phenyl-4-[succin-2-yl-(1-valine)]-7-[2-(2-guanidinoethanethiol)-1-ethyl]-3,4-dihydro-1H-1,4-benzodiazepine-2,5-dione trifluroacetate, (±)-1-benzyl-3-phenyl-4-[succin-2-yl-(1-phenylalanine)]-7-[2-(2-guanidinoethanethiol)-1-ethyl]-3,4-dihydro-1H-1,4-benzodiazepine-2,5-dione trifluroacetate, (±)-1-isopropyl-3-phenyl-4-(2-carboxy-1-methylethyl)-7-[2-(2- guanidinoethanethiol)-1-ethyl]-3,4-dihydro-1H-1,4-benzodiazepine-2,5-dione trifluroacetate, (±)-1-isopropyl-3-phenyl-4-(2-carboxy-1-phenylethyl)-7-[2-(2- guanidinoethanethiol)-1-ethyl]-3,4-dihydro-1H-1,4-benzodiazepine-2,5-dione trifluroacetate, (±)-1-isopropyl-3-phenyl-4-[succin-2-yl-(1-t-butoxy)]-7-[2-(2- guanidinoethanethiol)-1-ethyl]-3,4-dihydro-1H-1,4-benzodiazepine-2,5-dione trifluroacetate, (±)-1-isopropyl-3-phenyl-4-[succin-2-yl-(1-glycine)]-7-[2-(2- guanidinoethanethiol)-1-ethyl]-3,4-dihydro-1H-1,4-benzodiazepine-2,5-dione trifluroacetate, (±)-1-isopropyl-3-phenyl-4-[succin-2-yl-(1-valine)]-7-[2-(2-guanidinoethanethiol)-1-ethyl]-3,4-dihydro-1H-1,4-benzodiazepine-2,5-dione trifluroacetate, (±)-1-isopropyl-3-phenyl-4-[succin-2-yl-(1-phenylalanine)]-7-[2-(2-guanidinoethanethiol)-1-ethyl]-3,4-dihydro-1H-1,4-benzodiazepine-2,5-dione trifluroacetate.

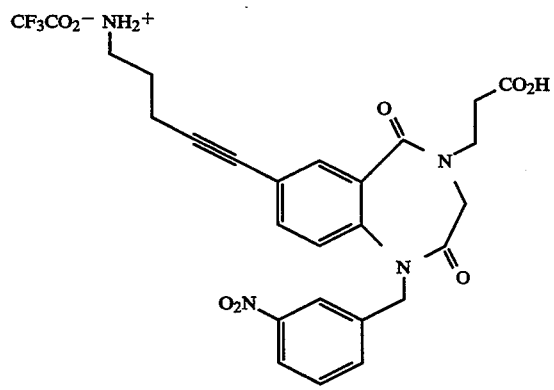

1-(3-nitrobenzyl)-4-(2-carboxyethyl)-7-(5-amino-1-pentynyl)-3,4-dihydro-1H-1, 4-benzodiazepine-2,5-dione trifluroacetate.

a) N-(2-amino-5-iodobenzoyl)-b-alanine ethyl ester was prepared using the method described in part (b) of example 1. Thus, from 21.0 grams of 6-iodoisatoic anhydride (0.73 mol) and 11.3 grams of β-alanine ethyl ester hydrogenchloride (0.73 mol) was prepared 9.1 grams (35%) N-(2-amino-5-iodobenzoyl)-β-alanine ethyl ester (mp=83°-85° C., TLC, SiO$_2$, 1:1 EtOAc/hexane, R$_f$=0.46, uv positive). $^1$H NMR (CDCl$_3$, dTMS) 7.57 (1H, d, $^4$JHH =2 Hz, Ar-H o-CON), 7.42 (1H, dd, $^3$JHH=9 Hz, $^4$JHH=2 Hz, Ar-H p-CON), 6.63 (1H, bs, CONH), 6.44 (1H, d, $^3$JHH=9 Hz, Ar-H m-CON), 5.57 (2H, bs, NH$_2$), 4.10 (2H, q, $^3$JHH=7 Hz, OCH$_2$), 3.63 (2H, q, $^3$JHH=6 Hz, NCH$_2$), 2.63 (2H, t, $^3$JHH=6 Hz, CH$_2$CO$_2$), 1.14 (3H, t, $^3$JHH=7 Hz, CH$_3$).

b) A magnetically stirred solution of 1.2 grams N-(2-amino-5-iodobenzoyl)-b-alanine ethyl ester (3.35 mmol), 0.43 mL 2,6-lutidine (3.7 mmol), 0.713 grams 3-nitrobenyl bromide (3.3 mmol), and 20 mL dimethylformamide, under an atmosphere of nitrogen, was heated to 50° C. for 24 hours. The reaction mixture was allowed to cool to room temperature, poured over 100 mL 10% citric acid, and extracted 3×75 mL ether. The combined organics were dried over magnesium sulfate, filtered and concentrated in vacuo. The resulting residue was purified by column chromatography, using silica gel, eluting with a solvent gradient of 1:4 ethyl acetate/hexane to 1:1 ethyl acetate/hexane isolating the yellow band (TLC, SiO$_2$, 1:1 ethyl acetate/hexane, R$_f$=0.66, uv positive) characterized as N-[2-(3- nitrobenzyl)-5-iodobenzoyl]-β-alanine ethyl ester (1.1 grams, 66%,mp=104°-105° C.).

c) To a magnetically stirred solution of 1.0 grams N-[2-(3-nitrobenzyl)-5-iodobenzoyl]-b-alanine ethyl ester (2.0 mmol), 5 mL methylene chloride, 0.56 mL triethylamine (4.0 mmol) at −30° C. under an atmosphere of nitrogen was slowly added, via an addition funnel, 0.26 mL α-bromoacetylbromide (3.0 mmol) as a solution in 4 mL methylene chloride. After 2 hours, the mixture was diluted with 35 mL methylene chloride and washed 2×75 mL 10% citric acid, 2×75 mL sat. sodium bicarbonate, dried over magnesium sulfate, filtered and concentrated in vacuo. The resulting residue was dissolved in 5 mL dimethylformamide and added, via an addition funnel, to a slurry of 72 mgs sodium hydride (3.0 mmol) in 1.0 mL dimethylformamide cooled to 0° C. The reaction was allowed to warm to room temperature, After 2 hours, the mixture was poured over 100 mL of an ice cooled solution of 10% citric acid and extracted 3×75 mL ethyl acetate. The combined organics were washed with 1×50 mL sat. sodium bicarbonate, dried over magnesium sulfate, and concentrated in vacuo. The resulting residue was further purified by column chromatography, using silica gel, eluting with a solvent gradient of 40:60 ethyl acetate/hexane to 70:30 ethyl acetate/hexane to yield 0.45 grams (55%) 1-(3-nitrobenzyl)-4-(2-carboxyethyl)-7-iodo-3,4-dihydro-1H-1,4-benzodiazepine-2,5-dione ethyl ester (TLC, SiO$_2$, 1:1 ethyl acetate/hexane, R$_f$=0.39, un positive) and 0.18 grams of recovered N-[2-(3-nitrobenzyl)-5-iodobenzoyl]-β-alanine ethyl ester. $^1$H NMR (CDCl$_3$, dTMS) 8.09 (1H, d, $^4$JHH=2 Hz, o-CON), 8.06 [1H, dt, $^3J_{HH}=7$ Hz, $^4J_{HH}=2$ Hz, NCH$_2$(C4-Ar-H)], 8.00 [1H, bs, NCH$_2$(C2-Ar-H)], 7.73 (1H, dd, $^3J_{HH}=9$ Hz, $^4J_{HH}=2$ Hz, Ar-H p-CON), 7.5–7.4 [2H, m, NCH$_2$(C5, C6-Ar-H)], 6.88 (1H, d, $^3J_{HH}=9$ Hz, Ar-H m-CON), 5.20 (1H, d, $^2J_{HH}=16$ Hz, NCHHAr), 5.03 (1H, d, $^2J_{HH}=16$ Hz, NCHHAr), 4.15 (1H, d, $^2J_{HH}=15$ Hz, NCHHCO), 4.10 (2H, q, $^3J_{HH}=7$ Hz, OCH$_2$), 3.96 (1H, d, $^2J_{HH}=15$ Hz, NCHHCO), 3.98–3.92 (2H, m, NCH$_2$CH$_2$), 2.71 (1H, dt, $^2J_{HH}=16$ Hz, $^3J_{HH}=8$ Hz, CHHCO2), 2.63 (1H, dt, $^2J_{HH}=16$ Hz, $^3J_{HH}=8$ Hz, CHHCO2), 1.22 (3H, t, $^3J_{HH}=7$ Hz, CH$_3$). $^{13}$C NMR (CDCl$_3$, dTMS) 171.2, 168.3, 165.3, 148.4, 141.0, 139.7, 139.0, 138.5, 132.8, 131.1, 129.9, 122.9, 122.8, 121.9, 90.5, 60.8, 52.1, 50.3, 45.2, 32.7, 14.1.

d) 1-(3-nitrobenzyl)-4-(2-carboxyethyl)-7-(N-boc-5-amino-1-pentynyl)-3,4-dihydro-1H-1,4-benzodiazepine 2,5-dione ethyl ester was prepared using the method described in part (f) of example 1. Thus, from 0.205 grams of 1-(3-nitrobenzyl)-4-(2-carboxyethyl)-7-iodo-3,4-dihydro-1H-1,4-benzodiazepine-2, 5-dione ethyl ester was prepared 168.2 mgs (57%) 1-(3-nitrobenzyl)-4-(2-carboxyethyl)-7-(N-boc-5-amino-1-pentynyl)-3,4-dihydro-1H-1,4-benzodiazepine-2, 5-dione ethyl ester (TLC, SIO$_2$, 1:1 ethyl acetate/hexane, R$_f$=0.36, uv positive). $^1$H NMR (CDCl$_3$, dTMS) 8.09 [1H, dt, $^3J_{HH}=7$ Hz, $^4J_{HH}=2$ Hz, NCH$_2$(C4-Ar-H)], 8.02 [1H, bs, NCH$_2$(C2-Ar-H)], 7.81 (1H, d, $^4J_{HH}=2$Hz,o-CON), 7.50–7.35 [3H, m, NCH$_2$(C5,C6-Ar-H), Ar-H p-CON], 7.04 (1H, d, $^3J_{HH}=9$ Hz, Ar-H m-CON), 5.22 (1H, d, $^2J_{HH}=16$ Hz, NCHHAr), 5.04 (1H, d, $^2J_{HH}=16$ Hz, NCHHAr), 4.70 (1H, bs, BocNH), 4.40 (1H, d, $^2J_{HH}=12$ Hz, NCHHCO), 4.12 (2H, q, $^3J_{HH}=7$ Hz, OCH$_2$), 3.96 (1H, d, $^2J_{HH}=12$ Hz, NCHHCO), 4.0–3.8 (2H, m, NCH$_2$CH$_2$), 3.23 (2H, q, $^3J_{HH}=6$ Hz, BocNHCH$_2$), 2.72 (1H, dt, $^2J_{HH}=17$ Hz, $^3J_{HH}=8$ Hz, CHHCO2), 2.62 (1H, dt, $^2J_{HH}=17$ Hz, $^3J_{HH}=8$ Hz, CHHCO2), 2.41 (2H, t, $^3J_{HH}=7$ Hz, C∫CCH$_2$), 1.74 (2H, p, $^3J_{HH}=7$ Hz, CH$_2$CH$_2$CH$_2$), 1.40 (9H, s, t-Bu), 1.24 (3H, t, $^3J_{HH}=7$ Hz, CH$_3$). $^{13}$C NMR (CDCl$_3$, δTMS) 171.2, 168.4, 166.2, 155.9, 148.4, 138.6, 138.2, 134.9, 134.2, 132.8, 129.9, 129.5, 122.7, 122.4, 122.0, 121.2, 91.4, 79.2, 60.8, 52.2, 50.4, 45.2, 39.8, 32.7, 28.7, 28.4, 16.8, 14.1.

e) 1-(3-nitrobenzyl)-4-(2-carboxyethyl)-7-(5-amino-1-pentynyl)-3,4-dihydro-1H-1,4-benzodiazepine-2,5-dione trifluroacetate was prepared using the method described in part (g) of example 1. Thus, 84 mgs 1-(3-nitrobenzyl)-4- (2-carboxyethyl)-7-(N-boc-5-amino-1-pentynyl)-3,4-dihydro-1H- 1,4-benzodiazepine-2, 5-dione ethyl ester (0.142 mmol) yielded 75 mgs (91%) 1-(3- nitrobenzyl )-4-(2-carboxyethyl)-7-(5-amino-1-pentynyl)-3,4-dihydro-1H-1, 4-benzodiazepine-2,5-dione trifluroacetate (½″ C-18 reverse-phase column, eluting with a solvent gradient of 10:90 methanol(0.1% trifluroacetic acid)/water (0.1% trifluroacetic acid), time 0 to 10 min, to 50:50 methanol(0.1% trifluroacetic acid)/water (0.1% trifluroacetic acid), time 10 min to 40 min, flow=10 ml/min, R$_t$=45.1 min, uv detection 254 nm). HRMS (FAB) molecular ion m/z=465.1744 (cald. C$_{24}$H$_{25}$N$_4$O$_6$, 465.1774) $^1$H NMR (CD$_3$ CN, δTMS) 8.07 [1H, dt, $^4J_{HH}=2$ Hz, $^3J_{HH}=7$ Hz, NCH$_2$(C4-Ar-H)], 8.02 [1H, bs, NCH$_2$(C2-Ar-H)], 7.73 (1H, d, $^4J_{HH}=2$ Hz,o-CON), 7.60–7.50 [3H, m, NCH$_2$(C5,C6-Ar-H), Ar-H p-CON], 7.25 (1H, d, $^3J_{HH}=9$ Hz, Ar-H m-CON), 5.40 (1H, d, $^2J_{HH}=15$ Hz, NCHHAr), 5.00 (1H, d, $^2J_{HH}=15$ Hz, NCHHAr), 4.13 (1H, d, $^2J_{HH}=12$ Hz, NCHHCO), 4.0–3.6 (3H, m, NCHHCO, NCH$_2$CH$_2$), 3.1 (2H, bs, NH$_3$CH$_2$), 2.65 (2H, t, $^3J_{HH}=7$ Hz, CH$_2$CO$_2$), 2.41 (2H, t, $^3J_{HH}=7$ Hz, C∫CCH$_2$), 1.9 (2H, p, $^3J_{HH}=7$ Hz, CH$_2$CH$_2$CH$_2$).

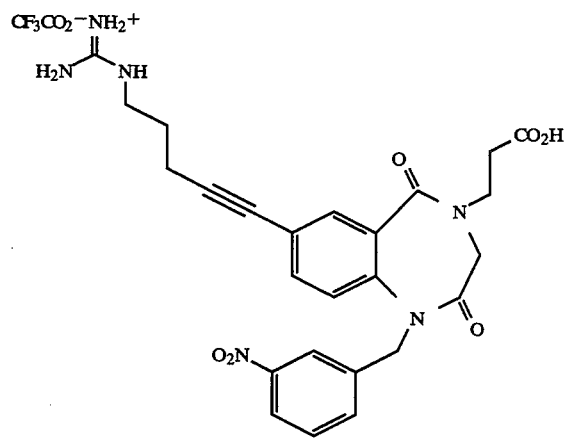

1-(3-nitrobenzyl)-4-(2-carboxyethyl)-7-(5-guanidino-1-pentynyl)-3,4-dihydro-1H-1,4-benzodiazepine-2,5-dione trifluroacetate.

1-(3-nitrobenzyl)-4-(2-carboxyethyl)-7-(5-guanidino-1-pentynyl)-3,4-dihydro-1H-1,4-benzodiazepine-2,5-dione trifluroacetate was prepared using the method described in example 2. Thus, 30 mgs of 1-(3-nitrobenzyl)-4-(2- carboxyethyl)-7-(5-amino-1-pentynyl)-3,4-dihydro-1H-1,4-benzodiazepine-2,5-dione trifluroacetate yielded 14 mgs (44%) of 1-(3-nitrobenzyl)-4-(2-carboxyethyl) -7-(5-guanidino-1-pentynyl)-3,4-dihydro-1H-1,4-benzodiazepine-2, 5-dione trifluroacetate (½″ C-18 reverse-phase column, eluting with a solvent gradient of 20:80 methanol(0.1% trifluroacetic acid)/water (0.1% trifluroacetic acid), time 0 to 10 min, to 70:30 methanol(0.1% trifluroacetic acid)/water (0.1% trifluroacetic acid), time 10 min to 40 min, flow=10 ml/min, R$_t$=33.8 min, uv detection 254 nm). HRMS (FAB) molecular ion m/z=507.2007 (cald. C$_{25}$H$_{27}$N$_6$O$_6$, 507.1992) $^1$H NMR (CD$_3$ CN/CD$_3$OD, dTMS) 8.04 [1H, d, $^3J_{HH}=7$ Hz, NCH$_2$(C4-Ar-H)], 7.98 [1H, bs, NCH$_2$(C2-Ar-H)], 7.68 (1H, d, $^4J_{HH}=2$ Hz,o-CON), 7.60–7.40 [3H, m, NCH$_2$(C5,C6-Ar-H), Ar-H p-CON], 7.25 (1H, d, $^3J_{HH}=9$ Hz, Ar-H m-CON), 5.37 (1H, d, $^2J_{HH}=15$ Hz, NCHHAr), 5.00 (1H, d, $^2J_{HH}=15$ Hz, NCHHAr), 4.13 (1H, d, $^2J_{HH}=12$ Hz, NCHHCO), 4.0–3.6 (3H, m, NCHHCO, NCH$_2$CH$_2$), 3.24 (2H, bs, H$_2$N(H$_2$N=)NHCH$_2$), 2.65 (2H, t, CH$_2$CO$_2$), 2.41 (2H, t, C∫CCH2), 1.9 (2H, p, $^3J_{HH}=7$ Hz, CH$_2$CH$_2$CH$_2$).

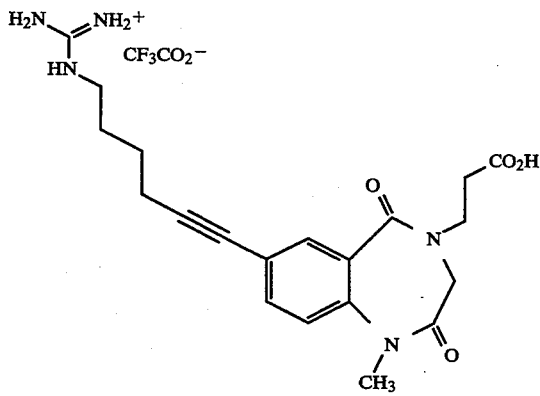

1-(methyl)-4-(2-carboxyethyl)-7-(6-guanidino-1-hexynyl)-3,4-dihydro-1H-1, 4-benzodiazepine-2,5-dione trifluoroacetate.

a) N-(2-methylamino-5-iodobenzoyl)-β-alanine ethyl ester was prepared using the method described in part (c) of example 1. Thus, 0.5 grams N-(2-amino-5-iodobenzoyl)-β-alanine ethyl ester yielded 204.5 mgs (39%) of N-(2-methylamino-5-iodobenzoyl)-β-alanine ethyl ester (TLC, SiO$_2$, 1:1 ethyl acetate/hexane R$_f$=0.67) and 253.2 mgs of a 7:1 mixture of N-(2-amino-5-iodobenzoyl)-β-alanine ethyl ester and N-(2-dimethylamino-5-iodobenzoyl)-β-alanine ethyl ester (TLC, SiO$_2$, 1:1 ethyl acetate/hexane R$_f$=0.46, uv positive). $^1$H NMR (CDCl$_3$, δTMS) 7.6–7.5 (2H, m, Ar-H o,p-CON), 7.43 (1H, bs, NHMe), 6.62 (1H, bt, CONH), 6.42 (1H, d, $^3$JHH=9 Hz, Ar-H m-CON), 4.18 (2H, q, $^3$JHH=7 Hz, OCH$_2$), 3.63 (2H, q, $^3$JHH=6 Hz, NCH$_2$), 2.81 (3H, d, $^3$JHH=5 Hz, NCH$_3$), 2.61 (2H, t, $^3$JHH=6 Hz, CH$_2$CO$_2$), 1.28 (3H, t, $^3$JHH=7 Hz, CH$_3$).

b) 1-methyl-4-(2-carboxyethyl)-7-iodo-3,4-dihydro-1H-1,4-benzodiazepine-2, 5-dione ethyl ester was prepared using the method described in part (d) of example 1. Thus, 1.9 grams of N-(2-methylamino-5-iodobenzoyl)-b-alanine ethyl ester yielded 0.91 grams (43%) of 1-methyl-4-(2-carboxyethyl)-7-iodo-3,4-dihydro-1H-1,4-benzodiazepine-2,5-dione ethyl ester (TLC, SiO$_2$, 1:1 ethyl acetate/hexane R$_f$=0.36, uv positive). $^1$H NMR (CDCl$_3$, δTMS) 8.14 (1H, d, $^4$JHH=2 Hz, Ar-H o-CON), 7.79 (1H, dd, $^4$JHH=2 Hz, $^3$JHH=9 Hz, Ar-H p-CON), 6.92 (1H, d, $^3$JHH=9 Hz, Ar-H m-CON), 4.13 (2H, q, $^3$JHH=7 Hz, OCH$_2$), 4.01 (1H, d, $^2$JHH=15 Hz, COCHHN), 3.90 (2H, dt, $^3$JHH=8 Hz, JHH=2 Hz, NCH$_2$), 3.87 (1H, d, $^2$JHH=15 Hz, COCHHN), 3.34 (3H, s, NCH$_3$), 2.74 (1H, dt, $^2$JHH=17 Hz, $^3$JHH=7 Hz, CHHCO$_2$), 2.63 (1H, dt, $^2$JHH=17 Hz, $^3$JHH=7 Hz, CHHCO$_2$), 1.24 (3H, t, $^3$JHH=7 Hz, CH$_3$).

c) To a magnetically stirred slurry of 2.94 grams lithium aluminum hydride (0.077 mol) in 150 mL ether cooled to 0° C. was slowly added, via an addition funnel, 6 grams of 5-cyano-1-pentyne (0.065 mol) in 15 mL ether. The reaction mixture was allowed to warm to room temperature. After 1 hour, the reaction was cooled to 0° C. and quenched with 3.1 mL water, 2.33 mL 20% sodium hydroxide, 10.83 mL water added in succession. After an additional 30 minutes, the slurry was filtered, washing the salts with 40 mL ether. The ether was distilled at atmospheric pressure to leave an oil, which was further purified by Kugelrohr distillation (oven temp.ca. 145° C.) to yield 3.99 grams 6-amino-1-hexyne (64%).

d) To a magnetically stirred solution of 3.99 grams of 6-amino-1-hexyne (0.0413 mol) in 50 mL tetrahydrofuran was added 9.1 grams of di-tert-butyl dicarbonate (0.042 mol). After 2 hours, the reaction mixture was concentrated in vacuo and the resulting residue chromatographed, using silica gel, eluting with 1:1 ether/hexane to yield 3.4 grams (42%) N-boc-6-amino-1-hexyne (TLC, SiO$_2$, 1:1 ether/hexane, R$_f$=0.5, ninhydrin char). $^1$H NMR (CDCl$_3$, δTMS) 4.55 (1H, bs, BocNH), 3.13 (2H, bq, $^3$JHH=5 Hz, BocNHCH$_2$), 2.21 (2H, dt, $^4$JHH=3 Hz, $^3$JHH=7 Hz, C∫CCH$_2$), 1.95 (1H, t, $^4$JHH=3 Hz, C∫CH), 1.6 (4H, m, CH$_2$CH$_2$CH$_2$CH$_2$), 1.42 (9H, s, t-Bu).

e) 1-(methyl)-4-(2-carboxyethyl)-7-(N-boc-6-amino-1-hexynyl)-3,4-dihydro-1H-1,4-benzodiazepine-2,5-dione ethyl ester was prepared using the method described in part (f) of example 1. Thus, 0.126 grams of 1-methyl-4-(2-carboxyethyl)-7-iodo-3, 4-dihydro-1H-1,4-benzodiazepine-2,5-dione ethyl ester and 0.119 grams of N-boc-6-amino-1-hexyne yielded 0.124 grams (84%) 1-(methyl)-4-(2-carboxyethyl )-7-(N-boc-6-amino-1-hexynyl)-3,4-dihydro-1H-1, 4-benzodiazepine-2,5-dione ethyl ester (TLC, SiO$_2$, 1:1 ethyl acetate/hexane, R$_f$=0.36, uv positive). $^1$H NMR (CDCl$_3$, δTMS) 7.84 (1H, d, $^4$JHH=2 Hz, Ar-H o-(CON), 7.47 (1H, dd, $^4$JHH=2 Hz, $^3$JHH=9 Hz, Ar-H p-CON), 7.07 (1H, d, $^3$JHH=9 Hz, Ar-H m-CON), 4.60 (1H, bs, NH), 4.12 (2H, q, $^3$JHH=7 Hz, OCH$_2$), 4.0 (1H, d, $^2$JHH=15 Hz, NCHHCO), 3.90 (2H, t, $^3$JHH=7 Hz, NCH$_2$), 3.84 (1H, d, $^2$JHH=15 Hz, NCHHCO), 3.26 (3H, s, NCH$_3$), 3.15 (2H, q, $^3$JHH=7 Hz, BocNHCH$_2$), 2.73 (1H, dt, $^2$JHH=16 Hz, $^3$JHH=9 Hz, CHHCO$_2$), 2.63 (1H, dt, $^2$JHH=16 Hz, $^3$JHH=9 Hz, CHHCO$_2$), 2.40 (2H, t, $^3$JHH=6 Hz, C∫CCH$_2$), 1.62 (4H, m, CH$_2$CH$_2$CH$_2$CH$_2$), 1.24 (3H, t, $^3$JHH=7 Hz, CH$_3$).

f) 1-(methyl)-4-(2-carboxyethyl)-7-(6-amino-1-hexynyl)-3, 4-dihydro-1H-1,4-benzodiazepine-2,5-dione trifluroacetate was prepared using the method described in part (g) of example 1. Thus, 62 mgs of 1-(methyl)-4-(2-carboxyethyl)-7- (N-boc-6-amino-1-hexynyl)-3,4-dihydro-1H-1,4-benzodiazepine-2, 5-dione ethyl ester yielded 50 mgs (83%) 1-(methyl)-4-(2- carboxyethyl)-7-(6-amino- 1-hexynyl)-3,4-dihydro-1H-1,4-benzodiazepine-2,5-dione trifluroacetate (⅜" C-18 reverse-phase column, eluting with a solvent gradient of 20:80 methanol(0.1% trifluroacetic acid)/water (0.1% trifluroacetic acid), time 0 to 10 rain, to 70:30 methanol(0.1% trifluroacetic acid)/water (0.1% trifluroacetic acid), time 10 min to 40 min, flow=10 ml/min, R$_t$=26.2 min, uv detection 254 nm). HRMS (FAB) molecular ion m/z=358.1761 (cald. C$_{19}$H$_{24}$N$_3$O$_4$, 358.1767). $^1$H NMR (D$_2$O,) 7.47 (1H, d, $^4$JHH=2 Hz, Ar-H o-CON), 7.37 (1H, dd, $^4$JHH=2 Hz, $^3$JHH=9 Hz, Ar-H p-CON), 7.12 (1H, d, $^3$JHH=9 Hz, Ar-H m-CON), 3.95–3.8 (2H, m, NCHHCO, NCHHCH$_2$), 3.63 (1H, d, $^2$JHH=15 Hz, NCHHCO), 3.52 (1H, dr, $^2$JHH=15 Hz, $^3$JHH=5 Hz, NCHHCO$_2$), 3.16 (3H, s, NCH$_3$), 2.85 (2H, t, $^3$JHH=7 Hz, NH$_3$CH$_2$), 2.6–2.4 (2H, m, CH$_2$CO$_2$), 2.28 (2H, t, $^3$JHH=6 Hz, C∫CCH$_2$), 1.62 & 1.47 (each 2H, p, $^3$JHH=6 Hz, CH$_2$CH$_2$CH$_2$CH$_2$).

g) 1-(methyl)-4-(2-carboxyethyl)-7-(6-guanidino-1-hexynyl)-3,4-dihydro-1H-1,4-benzodiazepine-2,5-dione trifluroacetate was prepared by the method described in example 2. Thus, from 25 mgs 1-(methyl)-4-(2-carboxyethyl)-7-(6-amino-1-hexynyl)-3,4-dihydro-1H-1,4-benzodiazepine-2,5-dione trifluroacetate was prepared 22 mgs (71%) of 1-(methyl)-4-(2-carboxyethyl)-7-(6-guanidino-1-hexynyl)-3, 4-dihydro-1H-1,4-benzodiazepine-2,5-dione trifluroacetate (½" C-18 reverse-phase column, eluting with a solvent gradient of 20:80 methanol(0.1% trifluroacetic acid)/water (0.1% trifluroacetic acid), time 0 to 10 min, to 70:30 methanol(0.1% trifluroacetic acid)/water (0.1% trifluoroacetic acid), time 10 min to 40 rain, flow=10 ml/min, $R_f$=28.6 min, un detection 254 nm). HRMS (FAB) molecular ion m/z=400.1956 (cald. $C_{20}H_{26}N_5O_4$, 400.1985). $^1$H NMR ($D_2O$,) 7.58 (1H, d, $^4$JHH=2 Hz, Ar-H o-CON), 7.43 (1H, dd, $^4$JHH=2 Hz, $^3$JHH=9 Hz, Ar-H p-CON), 7.20 (1H, d, $^3$JHH=9 Hz, Ar-H m-CON), 4.05–3.95 (2H, m, NCHHCO$_2$, NCHHCH$_2$), 3.71 (1H, d, $^2$JHH=15 Hz, NCHHCO), 3.56 (1H, dr, $^2$JHH=15 Hz, $^3$JHH=5 Hz, NCHHCO$_2$), 3.19 (3H, s, NCH$_3$), 3.06 (2H, t, $^3$JHH=7 Hz, H$_2$N(H$_2$N=)CNHCH$_2$), 2.7–2.5 (2H, m, CH$_2$CO$_2$), 2.32 (2H, t $^3$JHH=6 Hz, C∫CCH$_2$), 1.60 & 1.49 (each 2H, p, $^3$JHH=6 Hz, CH$_2$CH$_2$CH$_2$CH$_2$).

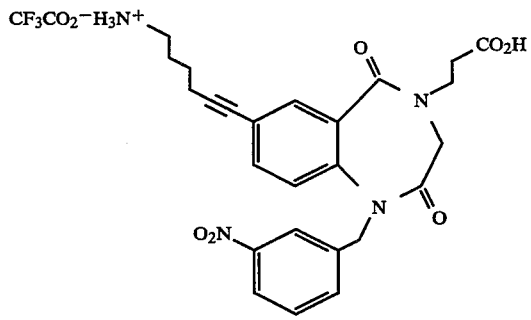

1-(3-nitrobenzyl)-4-(2-carboxyethyl)-7-(6-amino-1-hexynyl)-3,4-dihydro-1H-1, 4-benzodiazepine-2,5-dione trifuroacetate.

a) 1-(3-nitrobenzyl)-4-(2-carboxyethyl)-7-(N-boc-6-amino-1-hexynyl)-3, 4-dihydro-1H-1,4-benzodiazepine-2,5-dione ethyl ester was prepared using the method described in part (f) of example 1. Thus, from 0.26 grams of 1-(3nitrobenzyl)-4-(2-carboxyethyl)-7-iodo-3,4-dihydro-1H-1,4-benzodiazepine-2, 5-ethyl ester and 0.19 grams of N-boc-6-amino-1-hexyne was prepared 226.3 mgs (78%) 1-(3-nitrobenzyl)-4-(2-carboxyethyl)-7-(N-boc-6-amino-1-hexynyl)-3, 4-dihydro-1H-1,4-benzodiazepine-2,5-dione ethyl ester (TLC, SiO$_2$, 1:1 ethyl acetate/hexane, $R_f$=0.34, uv positive). $^1$H NMR (CDCl$_3$, δTMS) 8.09 [1H, dt, $^3$JHH=7 Hz, $^4$JHH=2 Hz, NCH$_2$(C4-Ar-H)], 8.02 [1H, bs, NCH$_2$(C2-Ar-H)], 7.83 (1H, d, $^4$JHH=2 Hz,o-CON), 7.50–7.35 [3H, m, NCH$_2$(C5,C6-Ar-H), Ar-H p-CON], 7.05 (1H, d, $^3$JHH=8 Hz, Ar-H m-CON), 5.22 (1H, d, $^2$JHH=16 Hz, NCHHAr), 5.02 (1H, d, $^2$JHH=16 Hz, NCHHAr), 4.60 (1H, bs, BocNH), 4.20–4.08 (3H, m, NCHHCO, OCH$_2$), 4.0–3.8 (3H, m, NCH$_2$CH$_2$, NCHHCO), 3.16 (2H, q, $^3$JHH=6 Hz, BocNHCH$_2$), 2.72 (1H, dr, $^2$JHH=16 Hz, $^3$JHH=8 Hz, CHHCO$_2$), 2.62 (1H, dt, $^2$JHH=16 Hz, $^3$JHH=8 Hz, CHHCO$_2$), 2.39 (2H, t, 3JHH=6 Hz, C∫CCH$_2$), 1.60 (4H, bs, CH$_2$CH$_2$CH$_2$CH$_2$), 1.41 (9H, s, t-Bu), 1.24 (3H, t, $^3$JHH=7 Hz, CH$_3$).

b) 1-(3-nitrobenzyl)-4-(2-carboxyethyl)-7-(6-amino-1-hexynyl)-3,4-dihydro-1H-1,4-benzodiazepine-2,5-dione trifluroacetate was prepared using the method described in part (g) of example 1. Thus, from 0.11 grams of 1-(3-nitrobenzyl)-4-(2-carboxyethyl)-7-(N-boc-6-amino-1-hexynyl)-3,4-dihydro-1H-1,4-benzodiazepine-2,5-dione ethyl ester was prepared 90 mgs (79%) of 1-(3-nitrobenzyl)-4-(2-carboxyethyl)-7-(6-amino-1-hexynyl)-3,4-dihydro-1H-1,4-benzodiazepine-2, 5-dione trifluroacetate (½" C-18 reverse-phase column, eluting with a solvent gradient of 20:80 methanol(0.1% trifluroacetic acid)/water (0.1% trifluroacetic acid), time 0 to 10 rain, to 70:30 methanol(0.1% trifluroacetic acid)/water (0.1% trifluroacetic add), time 10 rain to 40 min, flow=10 ml/min, $R_f$=39.2 rain, un detection 254 nm). HRMS (FAB) molecular ion m/z=479.1911 (cald. $C_{25}H_{27}N_4O_6$, 479.1931). $^1$H NMR (D$_2$O) 7.7 [1H, bd, $^3$JHH=8 Hz, NCH$_2$(C4-Ar-H)], 7.58 [1H, bs, NCH$_2$(C2-Ar-H)], 7.41 (1H, d, $^4$JHH=2 Hz,o-CON), 7.25–7.05 [3H, m, NCH$_2$(C5,C6-Ar-H), Ar-H p-CON], 7.01 (1H, d, $^3$JHH=9 Hz, Ar-H m-CON), 5.09 (1H, d, $^2$JHH=16 Hz, NCHHAr), 4.8 (1H, d, NCHHAr, overlapping with HOD), 4.00 (1H, d, $^2$JHH=14 Hz, NCHHCO), 3.9–3.65 (2H, m, NCHHCO, NCHHCH$_2$), 3.6–3.5 (1H, m, NCHHCH$_2$), 2.83 (2H, t, $^3$JHH=7 Hz, NH$_3$CH$_2$), 2.51 (2H, t, $^3$JHH=7 Hz, CH$_2$CO$_2$), 2.17 (2H, t, $^3$JHH=7 Hz, C∫CCH$_2$), 1.57 & 1.40 (each 2H, p, $^3$JHH=7 Hz, CH$_2$CH$_2$CH$_2$CH$_2$).

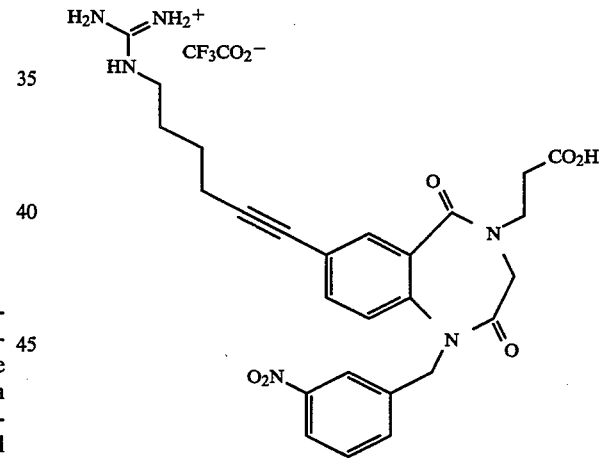

1-(3-nitrobenzyl)-4-(2-carboxyethyl)-7-(6-guanidino-1-hexynyl)-3,4-dihydro-1-H-1,4-benzodiazepine-2,5-dione trifluroacetate.

1-(3-nitrobenzyl)-4-(2-carboxyethyl)-7-(6-guanidino-1-hexynyl)-3,4-dihydro-1-H-1,4-benzodiazepine-2,5-dione trifluroacetate was prepared using the method described in example 2. Thus, 45 mgs of 1-(3-nitrobenzyl)-4-(2-carboxyethyl)-7-(6-amino-1-hexynyl )-3,4-dihydro-1H- 1,4-benzodiazepine-2,5-dione trifluroacetate yielded 25 mgs (52%) of 1-(3-nitrobenzyl)-4-(2-carboxyethyl)-7-(6-guanidino-1-hexynyl)-3,4-dihydro-1H-1,4-benzodiazepine-2,5-dione trifluroacetate (½" C-18 reverse-phase column, eluting with a solvent gradient of 20:80 methanol(0.1% trifluroacetic acid)/water (0.1% trifluroacetic acid), time 0 to 10 min, to 70:30 methanol(0.1% trifluroacetic acid)/water (0.1% trifluoroacetic acid), time 10 rain to 40 min, flow=10 ml/min, R$_t$=41.3 min, uv detection 254 nm). HRMS (FAB) molecular ion m/z=521.2161 (cald. C$_{26}$H$_{28}$N$_6$O$_6$, 521.2148). $^1$H NMR (D$_2$O) 7.86 [1H, dt, $^4$JHH=3 Hz, $^3$JHH=6 Hz, NCH$_2$(C4-Ar-H)], 7.64 [1H, bs, NCH$_2$(C2-Ar-H)], 7.46 (1H, d, $^4$JHH=2 Hz,o-CON) 7.30–7.23 [3H, m, NCH$_2$(C5,C6-Ar-H), Ar-H p-CON], 7.18 (1H, d, $^3$JHH=8 Hz, Ar-H m-CON), 5.30 (1H, d, $^2$JHH=16 Hz, NCHHAr), 4.7 (1H, NCHHAr, overlapping with HOD), 4.03 (1H, d, $^2$JHH=14 Hz, NCHHCO), 3.85 (1H, dr, $^2$JHH=14 Hz, $^3$JHH=7 Hz, NCHHCH$_2$), 3.74 (1H, d, $^2$JHH=14 Hz, NCHHCO), 3.55 (1H, dt, $^2$JHH=14 Hz, $^3$JHH=7 Hz, NCHHCH$_2$), 2.97 (2H, t, $^3$JHH=7 Hz, H$_2$N(H$_2$N=)NHCH$_2$), 2.49 (2H, t, $^3$JHH=7 Hz, CH$_2$CO$_2$), 2.21 (2H, t, $^3$JHH=7 Hz, C∫CCH$_2$), 1.48 & 1.38 (each 2H, p, $^3$JHH=7 Hz, CH$_2$CH$_2$CH$_2$CH$_2$).

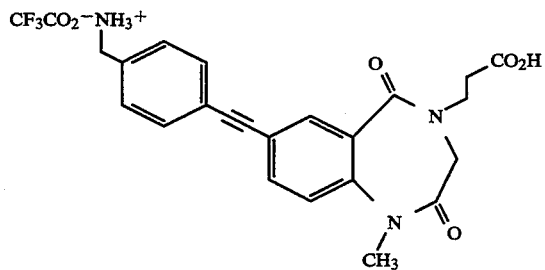

1-(methyl)-4-(2-carboxyethyl)-7-[4-(aminomethyl)-phenyl]ethynyl-3,4-dihydro-1H-1,4-benzodiazepine-2,5-dione trifluroacetate.

a) 1-(methyl)-4-(2-carboxyethyl)-7-(4-cyanophenyl)ethynyl-3,4-dihydro-1H-1, 4-benzodiazepine-2,5-dione ethyl ester was prepared using the method employed in part (f) of example 1. Thus, from 0.41 grams of 1-methyl-2-(carboxyethyl)-7-iodo-3, 4-dihydro-1H-1,4-benzodiazepine-2,5-dione ethyl ester and 0.127 grams of (4-cyanophenyl)ethyne (Gilbert, J. C.; Weerasooriya, U. *J. Org. Chem.* 1979, 44, 4997–98) was prepared 0.205 grams of 1-(methyl)-4-(2-carboxyethyl )-7-(4-cyanophenyl )ethynyl-3,4-dihydro-1H-1,4-benzodiazepine-2, 5-dione ethyl ester (mp=160°–161° C., TLC, SiO2, 1:1 ethyl acetate/hexane, Rf=0.30, uv positive). $^1$H NMR (CDCl$_3$, δTMS) 7.98 (1H, d, $^4$JHH=2 Hz, Ar-Ho-CON), 7.65–7.50 (5H, m, Ar-H p-CON, Ar-H o,p-CN), 7.17 (1H, d, $^3$JHH=9 Hz, m-CON), 4.09 (2H, q, $^3$JHH=7 Hz, OCH$_2$), 4.02 (1H, d, $^2$JHH=15 Hz, NCHHCO), 3.89 (2H, t, $^3$JHH=7 Hz, NCH$_2$CH$_2$), 3.86 (1H, d, $^2$JHH=15 Hz, NCHHCO), 3.34 (3H, s, NCH$_3$), 2.72 (1H, dt, $^2$JHH=16 Hz, $^3$JHH=7 Hz, CHHCO$_2$), 2.62 (1H, dt, $^2$JHH=16 Hz, $^3$JHH=7 Hz, CHHCO$_2$), 1.20 (3H, t, $^3$JHH=7 Hz, CH$_3$). $^{13}$C NMR (CDCl$_3$, δTMS) 171.2, 168.6, 166.2, 141.0, 134.8, 134.4, 132.0, 128.8, 127.5, 121.1, 119.7, 118.3, 111.8, 91.7, 88.9, 60.3, 52.1, 45.1, 32.7, 31.5, 14.1.

b) A magnetically stirred solution of 3 mL toluene, 6.8 mgs dicobalt octacarbonyl (0.02 mmol) cooled to −20° C. was saturated with triethylsilane via a gas bubbler. 0.1 grams of 1-(methyl)-4-(2-carboxyethyl)-7-(4-cyanophenyl) ethynyl-3,4-dihydro-1H-1,4-benzodiazepine-2,5-dione ethyl ester 5 (0.24 mmol) was added as a solution in 0.5 mL toluene and the reaction mixture heated to 60° C. for 20 hours (Murai, T. et al., *Tetrahedron Lett.* 1985, 26, 5145–48). The mixture was allowed to cool to room temperature and concentrated in vacuo. The resulting residue was diluted with methanol and 2 mL of 2N sodium hydroxide was added. After 30 minutes, the mixture was neutralized with 2 mL acetic acid, concentrated in vacuo, diluted with 2 mL of a 1:1 methanol/water solution and purified by high-pressure liquid chromatography (½" C-18 reverse-phase column, eluting with a solvent gradient of 20:80 methanol(0.1% trifluroacetic acid)/water (0.1% trifluroacetic acid), time 0 to 10 mtn, to 70:30 methanol(0.1% trifluroacetic acid)/water (0.1% trifluroacetic acid), time 10 min to 40 min, flow=10 ml/min, R$_t$=36.8 min, un detection 254 nm) to yield 30.0 mgs (25%) of 1-(methyl)-4-(2-carboxyethyl)-7-[4-(aminomethyl)phenyl]ethynyl-3,4-dihydro-1H-1,4-benzodiazepine-2,5-dione trifluoroacetate. $^1$H NMR (CD$_3$OD) 7.68 (1H, d, $^4$JHH=2 Hz, Ar-Ho-CON), 7.48 (1H, dd, $^4$JHH=2 Hz, $^3$JHH=9 Hz, Ar-H p-CON) 7.4–7.3 (4H, m, Ar-H o,p-CN), 7.17 (1H, d, m-CON), 4.02 (2H, s, ArCH$_2$N), 4.0–3.7 (4H, m, NCH$_2$CO, NCH$_2$CH$_2$), 3.0 (3H, s, NCH$_3$) 2.6 (2H, m, CH$_2$CO$_2$).

Using the above procedure, but substituting the appropriate 3,4-dihydro-1H-1,4-benzodiazepine-2,5-dione nitrile for 1-(methyl)-4-(2carboxyethyl) -7-(4-cyanophenyl)ethynyl-3,4-dihydro-1H-1,4-benzodiazepine2,5-dione ethyl ester there may be prepared, for example, the following compounds:

1-methyl -4-(2-carboxy-1-methylethyl)-7-[2-(3-aminomethylphenyl)-1-ethyne]-3,4-dihydro-1H-1,4-benzodiazepine-2,5-dione, 1-methyl-4-(2-carboxy-1-phenylethyl)-7-[2-(3-aminomethylphenyl)-1-ethyne]-3,4-dihydro-1H-1,4-benzodiazepine-2,5-dione trifluroacetate, (±)-1-methyl -4-[succin-2-yl-(1-t-butoxy )]-7-[2-(3-aminomethylphenyl)-1-ethyne]-3,4-dihydro-1H-1,4-benzodiazepine-2,5-dione trifluroacetate, (±)-1-methyl-4-[succin-2-yl-(1-glycine)]-7-[2-(3-aminomethylphenyl)-1-ethyne]-3,4-dihydro-1H-1,4-benzodiazepine-2,5-dione trifluroacetate, (±)-1-methyl-4-[succin-2- yl-(1-valine )]- 7-[2-(3-aminomethylphenyl)-1-ethyne]-3,4-dihydro-1H-1,4-benzodiazepine-2,5-dione trifluroacetate, (±)-1-methyl -4-[succin-2-yl-(1-phenylalanine)]-7-[2-(3-aminomethyl)-1-ethyne]-3,4-dihydro-1H-1,4-benzodiazepine-2,5-dione trifluroacetate, 1-phenyl-4-(2-carboxy-1-methylethyl)-7-[2-(3-aminomethylphenyl)-1-ethyne]-3,4-dihydro-1H-1,4-benzodiazepine-2,5-dione trifluroacetate, 1-phenyl -4-(2-carboxy-1-phenylethyl)-7-[2-(3-aminomethylphenyl)-1-ethyne]-3,4-dihydro-1H-1,4-benzodiazepine-2,5-dione trifluroacetate, (±)-1-phenyl-4-[succin-2-yl-(1-t-butoxy)]-7-[2-(3-aminomethylphenyl)-1ethyne]-3,4-dihydro-1H-1,4-benzodiazepine-2,5-dione trifluroacetate, (±)- b 1-phenyl-4-[succin-2-yl-(1-glycine)]-7-[2-(3-aminomethylphenyl)-1-ethyne]-3,4-dihydro-1H-1,4-benzodiazepine-2,5-dione trifluroacetate, (±)-1-phenyl-4-[succin-2-yl-(1-valine)]-7-[2-(3-aminomethylphenyl)-1-ethyne]-3,4-dihydro-1H-1,4-benzodiazepine-2,5-dione trifluroacetate, (±)-1-phenyl-4-[succin-2-yl-(1-phenylalanine)]-7-[2-(3-aminomethylphenyl)-1-ethyne]-3,4-dihydro-1H-1,4-benzodiazepine-2,5-dione trifluroacetate, 1-benzyl-4-(2-carboxy-1-methylethyl)-7-[2-(3-aminomethylphenyl)-1-ethyne]-3,4-dihydro-1H-1,4-benzodiazepine-2,5-dione trifluroacetate, 1-benzyl-4-(2-carboxy-1-phenylethyl)-7-[2-(3-aminomethylphenyl)-1-ethyne]-3,4-dihydro-1H-1,4-benzodiazepine-2,5-dione trifluroacetate, (±)-1-benzyl-4-[succin-2-yl-(1-t-butoxy)]-7-[2-(3-aminomethylphenyl)-1-ethyne]-3,4-dihydro-1H-1,4-benzodiazepine-2,5-dione trifluroacetate, (±)-1-benzyl-4-[succin-2-yl-(1-glycine)]-7-[2-(3-aminomethylphenyl)-1-ethyne]-3,4-dihydro-1H-1,4-benzodiazepine-2,5-dione trifluroacetate, (±)-1-benzyl-4-[succin-2-yl-(1-valine)]-7-[2-(3-aminomethylphenyl)-1-ethyne]-3,4-dihydro-1H-1,4-benzodiazepine-2,5-dione trifluroacetate, (±)-1-benzyl-4-[succin-2-yl-(1-phenylalanine)]-7-[2-(3-aminomethylphenyl)-1-ethyne]-3,4-dihydro-1H-1,4-benzodiazepine-2,5-dione trifluroacetate, 1-isopropyl-4-(2-carboxy-1-methylethyl)-7-[2-(3-aminomethylphenyl)-1-ethyne]-3,4-dihydro-1H-1,4-benzodiazepine-2,5-dione trifluroacetate, 1-isopropyl-4-(2-carboxy-1-phenylethyl)-7-[2-(3-aminomethylphenyl)-1-ethyne]-3,4-dihydro-1H-1,4-benzodiazepine-2,5-dione trifluroacetate, (±)-1-isopropyl-4-[succin-2-yl-(1-t-butoxy)]-7-[2-(3-aminomethylphenyl)-1-ethyne]-3,4-dihydro-1H-1,4-benzodiazepine-2,5-dione trifluroacetate, (±)-1-isopropyl-4-[succin-2-yl-(1-glycine)]-7-[2-(3-aminomethylphenyl)-1-ethyne]-3,4-dihydro-1H-1,4-benzodiazepine-2,5-dione trifluroacetate, (±)-1-isopropyl-4-[succin-2-yl-(1-valine)]-7-[2-(3-aminomethylphenyl)-1-ethyne]-3,4-dihydro-1H-1,4-benzodiazepine-2,5-dione trifluroacetate, (±)-1-isopropyl-4-[succin-2-yl-(1-phenylalanine)]-7-[2-(3-aminomethylphenyl)-1-ethyne]-3,4-dihydro-1H-1,4-benzodiazepine-2,5-dione trifluroacetate, 1-methyl-4-(2-carboxy-1-methylethyl)-7-[2-(4-aminomethylthiophenol)-1-ethyne]-3,4-dihydro-1H-1,4-benzodiazepine-2,5-dione trifluroacetate, 1-methyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1-methyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1-methyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1-methyl-4-[succin-2-yl-(1-valine)]-7-[2-(4-aminomethylthiophenol)-1-ethyne]-3,4-dihydro-1H-1,4-benzodiazepine-2,5-dione trifluroacetate, (±)-1-methyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate, 1-phenyl-4-(2-carboxy-1-methylethyl)-7-[2-(4-aminomethylthiophenol)-1-ethyne]-3,4-dihydro-1H-1,4-benzodiazepine-2,5-dione trifluroacetate, 1-phenyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1-phenyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1-phenyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1-phenyl-4-[succin-2-yl-(1-valine)]-7-[2-(4-aminomethylthiophenol)-1-ethyne]-3,4-dihydro-1H-1,4-benzodiazepine-2,5-dione trifluroacetate, (±)-1-phenyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate, 1-benzyl-4-(2-carboxy-1-methylethyl)-7-[2-(4-aminomethylthiophenol)-1-ethyne]-3,4-dihydro-1H-1,4-benzodiazepine-2,5-dione trifluroacetate, 1-benzyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1-benzyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1-benzyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1-benzyl-4-[succin-2-yl-(1-valine)]-7-[2-(4-aminomethylthiophenol)-1-ethyne]-3,4-dihydro-1H-1,4-benzodiazepine-2,5-dione trifluroacetate, (±)-1-benzyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate, 1-isopropyl-4-(2-carboxy-1-methylethyl)-7-[2-(4-aminomethylthiophenol)-1-ethyne]-3,4-dihydro-1H-1,4-benzodiazepine-2,5-dione trifluroacetate, 1-isopropyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1-isopropyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1-isopropyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1-isopropyl-4-[succin-2-yl-(1-valine)]-7-[2-(4-aminomethylthiophenol)-1-ethyne]-3,4-dihydro-1H-1,4-benzodiazepine-2,5-dione trifluroacetate, (±)-1-isopropyl-4-[succin-2-yl-(1-phenylalanine)]-7-[2-(4aminomethylthiophenol)-1-ethyne]-3,4-dihydro-1H-1,4-benzodiaze pine-2,5-dione trifluroacetate, (±)-1-methyl-3-phenyl-4-(2-carboxy-1-methylethyl)-7-[2-(3-aminomethylphenyl)-1-ethyne]-3,4-dihydro-1H-1,4-benzodiazepine-2,5-dione trifluroacetate, (±)-1-methyl-3-phenyl-4-(2-carboxy-1-phenylethyl)-7-[2-(3-aminomethylphenyl)-1-ethyne]-3,4-dihydro-1H-1,4-benzodiazepine-2,5-dione trifluroacetate, (±)-1-methyl-3-phenyl-4-[succin-2-yl-(1-t-butoxy)]-7-[2-(3-aminomethylphenyl)-1-ethyne]-3,4-dihydro-1H-1,4-benzodiazepine-2,5-dione trifluroacetate, (±)-1-methyl-3-phenyl-4-[succin-2-yl-(1-glycine)]-7-[2-(3-aminomethylphenyl)-1-ethyne]-3,4-dihydro-1H-1,4-benzodiazepine-2,5-dione trifluroacetate, (±)-1-methyl-3-phenyl-4-[succin-2-yl-(1-valine)]-7-[2-(3-aminomethylphenyl)-1-ethyne]-3,4-dihydro-1H-1,4-benzodiazepine-2,5-dione trifluroacetate, (±)-1-methyl-3-phenyl-4-[succin-2-yl-(1-phenylanine)]-7-[2-(3-aminomethylphenyl)-1-ethyne]-3,4-dihydro-1H-1,4-benzodiazepine-2,5-dione trifluroacetate, (±)-1,3-diphenyl-4-(2-carboxy-1-methylethyl)-7-[2-(3-aminomethylphenyl)-1-ethyne]-3,4-dihydro-1H-1,4-benzodiazepine-2,5-dione trifluroacetate, (±)-1,3-diphenyl-4-(2-carboxy-1-phenylethyl)-7-[2-(3-aminomethylphenyl)-1-ethyne]-3,4-dihydro-1H-1,4-benzodiazepine-2,5-dione trifluroacetate, (±)-1,3-diphenyl-4-[succin-2-yl-(1-t-butoxy)]-7-[2-(3-aminomethylphenyl)-1-ethyne]-3,4-dihydro-1H-1,4-benzodiazepine-2,5-dione trifluroacetate, (±)-1,3-diphenyl-4-[succin-2-yl-(1-glycine)]-7-[2-(3-aminomethylphenyl)-1-ethyne]-3,4-dihydro-1H-1,4-benzodiazepine-2,5-dione trifluroacetate, (±)-1,3-diphenyl-4-[succin-2-yl-(1-valine)]-7-[2-(3-aminomethylphenyl)-1-ethyne]-3,4-dihydro-1H-1,4-benzodiazepine-2,5-dione trifluroacetate, (±)-1,3-diphenyl-4-[succin-2-yl-(1-phenylalanine)]-7-[2-(3-aminomethylphenyl) -1-ethyne]-3,4-dihydro-1H-1,4-benzodiazepine-2,5-dione trifluroacetate, (±)-1-benzyl-3-phenyl-4-(2-carboxy-1-methylethyl)-7-[2-(3-aminomethylphenyl) -1-ethyne]-3,4-dihydro-1H-1,4-benzodiazepine-2,5-dione trifluroacetate, (±)-1-benzyl-3-phenyl -4-(2-carboxy-1-phenylethyl)-7-[2-(3-aminomethylphenyl) -1-ethyne]-3,4-dihydro-1H-1,4-benzodiazepine-2,5-dione trifluroacetate, (±)-1-benzyl-3-phenyl-4-[succin-2-yl-(1-t-butoxy)]-7-[2-(3-aminomethylphenyl) -1-ethyne]-3,4-dihydro-1H-1,4-benzodiazepine-2,5-dione trifluroacetate, (±)-1-benzyl-3-phenyl-4-[succin-2-yl-(1-glycine)]-7-[2-(3-aminomethylphenyl) -1-ethyne]-3,4-dihydro-1H-1,4-benzodiazepine-2,5-dione trifluroacetate, (±)-1-benzyl-3-phenyl-4-[succin-2-yl-(1-valine)]-7-[2-(3-aminomethylphenyl) -1-ethyne]-3,4-dihydro-1H-1,4-benzodiazepine-2,5-dione trifluroacetate, (±)-1-benzyl-3-phenyl-4-[succin-2-yl-(1-phenylalanine)]-7-[2-(3-aminomethylphenyl) -1-ethyne]-3,4-dihydro-1H-1,4-benzodiazepine-2,5-dione trifluroacetate, (±)-1-isopropyl-3-phenyl-4-(2-carboxy-1-methylethyl)-7-[2-(3-aminomethylphenyl) -1-ethyne]-3,4-dihydro-1H-1,4-benzodiazepine-2,5-dione trifluroacetate, (±)-1-isopropyl-3-phenyl-4-(2-carboxy-1-phenylethyl)-7-[2-(3-aminomethylphenyl) -1-ethyne]-3,4-dihydro-1H-1,4-benzodiazepine-2,5-dione trifluroacetate, (±)-1-isopropyl-3-phenyl -4-[succin-2-yl-(1-t-butoxy)]-7-[2-(3-aminomethylphenyl) -1-ethyne]-3,4-dihydro-1H-1,4-benzodiazepine-2,5-dione trifluroacetate, (±)-1-isopropyl-3-phenyl-4-[succin-2-yl-(1-glycine)]-7-[2-(3-aminomethylphenyl) -1-ethyne]-3,4-dihydro-1H-1,4-benzodiazepine-2,5-dione trifluroacetate, (±)-1-isopropyl-3-phenyl-4-[succin-2-yl-(1-valine)]-7-[2-(3-aminomethylphenyl) -1-ethyne]-3,4-dihydro-1H-1,4-benzodiazepine-2,5-dione trifluroacetate, (±)-1-isopropyl-3-phenyl-4-[succin-2-yl-(1-phenylalanine)]-7-[2-(3-aminomethylphenyl)-1-ethyne]-3,4-dihydro-1H-1,4-benzodiazepine-2,5-dione trifluroacetate, (±)-1-methyl-3-phenyl-4-(2-carboxy-1-methylethyl)-7-[2-(4-aminomethylthiophenol) -1-ethyne]-3,4-dihydro-1H-1,4-benzodiazepine-2,5-dione trifluroacetate, (±)-1-methyl-3-phenyl-4-(2-carboxy-1-phenylethyl)-7-[2-(4-aminomethylthiophenol) -1-ethyne]-3,4-dihydro-1H-1,4-benzodiazepine-2,5-dione trifluroacetate, (±)-1-methyl-3-phenyl-4-[succin-2-yl-(1-t-butoxy)]-7-[2-(4-aminomethylthiophenol) -1-ethyne]-3,4-dihydro-1H-1,4-benzodiazepine-2,5-dione trifluroacetate, (±)-1-methyl-3-phenyl-4-[succin-2-yl-(1-glycine)]-7-[2-(4-aminomethylthiophenol) -1-ethyne]-3,4-dihydro-1H-1,4-benzodiazepine-2,5-dione trifluroacetate, (±)-1-methyl-3-phenyl-4-[succin-2-yl-(1-valine)]-7-[2-(4-aminomethylthiophenol) -1-ethyne]-3,4-dihydro-1H-1,4-benzodiazepine-2,5-dione trifluroacetate, (±)-1-methyl-3-phenyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate, (±)-1,3-diphenyl-4-(2-carboxy-1-methylethyl)-7-[2-(4-aminomethylthiophenol)-1-ethyne]-3,4-dihydro-1H-1,4-benzodiazepine-2,5-dione trifluroacetate, (±)-1,3-diphenyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1,3-diphenyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1,3-diphenyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1,3-diphenyl-4-[succin-2-yl-(1-valine)]-7-[2-(4-aminomethylthiophenol)-1-ethyne]-3,4-dihydro-,1H-1,4-benzodiazepine-2,5-dione trifluroacetate, (±)-1,3-diphenyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate, (±)-1-benzyl-3-phenyl-4-(2-carboxy-1-methylethyl)-7-[2-(4-aminomethylthiophenol)-1-ethyne]-3,4-dihydro-1H-1,4-benzodiazepine-2,5-dione trifluroacetate, (±)-1-benzyl-3-phenyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1-benzyl-3-phenyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1-benzyl-3-phenyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1-benzyl-3-phenyl-4-[succin-2-yl-(1-valine)]-7-[2-(4-aminomethylthiophenol)-1-ethyne]-3,4-dihydro-1H-1,4-benzodiazepine-2,5-dione trifluroacetate, (±)-1-benzyl-3-phenyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate, (±)-1-isopropyl-3-phenyl-4-(2-carboxy-1-methylethyl)-7-[2-(4-aminomethylthiophenol)-1-ethyne]-3,4-dihydro-1H-1,4-benzodiazepine-2,5-dione trifluroacetate, (±)-1-isopropyl-3-phenyl-4-(2-carboxy-1-phenylethyl)-7-[2-(4-aminomethylthiophenol)-1-ethyne]-3,4-dihydro-1H-1,4-benzodiazepine-2,5-dione trifluroacetate, (±)-1-isopropyl-3-phenyl-4-[succin-2-yl-(1-t-butoxy)]-7-[2-(4-aminomethylthiophenol)-1-ethyne]-3,4-dihydro-1H-1,4-benzodiazepine-2,5-dione trifluroacetate, (±)-1-isopropyl-3-phenyl-4-[succin-2-yl-(1-glycine)]-7-[2-(4-aminomethylthiophenol)-1-ethyne]-3,4-dihydro-1H-1,4-benzodiazepine-2,5-dione trifluroacetate, (±)-1-isopropyl-3-phenyl-4-[succin-2-yl-(1-valine)]-7-[2-(4-aminomethylthiophenol)-1-ethyne]-3,4-dihydro-1H-1,4-benzodiazepine-2,5-dione trifluroacetate, (±)-1-isopropyl-3-phenyl-4-[succin-2-yl-(1-phenylalanine)]-7-[2-(4-aminomethylthiophenol)-1-ethyne]-3,4-dihydro-1H-1,4-benzodiazepine-2,5-dione trifluroacetate.

EXAMPLE 10

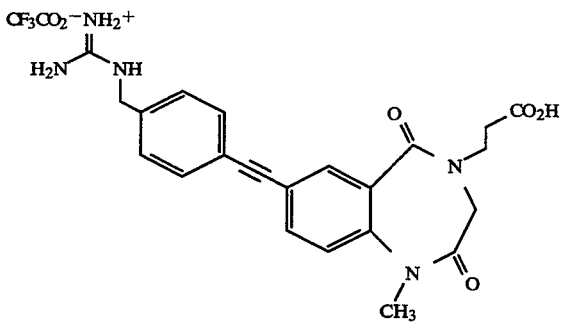

1-(methyl)-4-(2-carboxyethyl)-7-[4-(guanidinomethyl)-phenyl]ethynyl-3,4-dihydro-1H-1,4-benzodiazepine-2,5-dione trifluroacetate.

1-(methyl)-4-(2-carboxyethyl)-7-[4-(guanidinomethyl)-phenyl]ethynyl-3,4-dihydro-1H-1,4-benzodiazepine-2,5-dione trifluroacetate was prepared using the method described in example 2. Thus, from 15 mgs of 1-(methyl)-4-(2-carboxyethyl)-7-[4-(aminomethyl)phenyl]ethynyl-3,4-dihydro-1H-1,4-benzodiazepine-2,5-dione trifluroacetate was prepared 7 mgs (37%) of 1-(methyl)-4-(2-carboxyethyl)-7-[4-(guanidinomethyl)phenyl]ethynyl-3,4-dihydro-1H-1,4-benzodiazepine-2,5-dione trifluroacetate ($\frac{1}{2}''$ C-18 reverse-phase column, eluting with a solvent gradient of 20:80 methanol(0.1% trifluroacetic acid)/water (0.1% trifluroacetic acid), time 0 to 10 min, to 70:30 methanol(0.1% trifluroacetic acid)/water (0.1% trifluroacetic acid), time 10 min to 40 min, flow=10 ml/min, $R_t$=39.6 min, un detection 254 nm). $^1$H NMR (CD$_3$OD, D$_2$O) 7.50 (1H, d, $^4$JHH=2 Hz, Ar—Ho—CON), 7.38 (1H, bd, $^3$JHH=9 Hz, Ar—H p—CON) 7.20 (1H, d, $^3$JHH=9 Hz, m-CON), 7.15–7.0 (4H, m, Ar—H o,p—CN), 4.23 (2H, s, ArCH$_2$NHC(=NH$_2$)NH$_2$), 3.9-3.8 (2H, m, NCHHCO, NCHHCH$_2$), 3.72 (1H, d, 2JHH=16 Hz, NCHHCO), 3.58 (1H, m, NCHHCH$_2$), 3.12 (3H, s, NCH$_3$) 2.53 (2H, m, CH$_2$CO$_2$).

Using the above procedure, but substituting the appropriate amino acid for 1-(methyl)-4-(2-carboxyethyl)-7-[4-(aminomethyl)phenyl]ethynyl-3,4-dihydro-1H-1,4-benzodiazepine-2,5-dione trifluroacetate there may be prepared, for example, the following compounds:

1-methyl-4-(2-carboxy-1-methylethyl)-7-[2-(3-guanidinomethylphenyl)-1-ethyne]3,4-dihydro-1H-1,4-benzodiazepine-2,5-dione,
1-methyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-methyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1-methyl-4-[succin-2-yl-(1-glycine)]-7-[2-(3-guanidinomethylphenyl)-1-ethyne]-3,4-dihydro-1H-1,4-benzodiazepine-2,5-dione trifluroacetate,
(±)-1-methyl-4-[succin-2-yl-(1-valine)]-7-[2-(3-guanidinomethylphenyl)-1-ethyne]-3,4-dihydro-1H-1,4-benzodiazepine-2,5-dione trifluroacetate,
(±)-1-methyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
1-phenyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
1-phenyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-phenyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate, (±)-1-phenyl-4-[succin-2-yl-(1-glycine)]-7-[2-(3-guanidinomethylphenyl)-1-ethyne]-3,4-dihydro-1H-1,4-benzodiazepine-2,5-dione trifluroacetate,
(±)-1-phenyl-4-[succin-2-yl-(1-valine)]-7-[2-(3-guanidinomethylphenyl)-1-ethyne]-3,4-dihydro-1H-1,4-benzodiazepine-2,5-dione trifluroacetate,
(±)-1-phenyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
1-benzyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
1-benzyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-benzyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1-benzyl-4-[succin-2-yl-(1-glycine)]-7-[2-(3-guanidinomethylphenyl)-1-ethyne]-3,4-dihydro-1H-1,4-benzodiazepine-2,5-dione trifluroacetate, (±)-1-benzyl-4-[succin-2-yl-(1-valine)]-7-[2-(3-guanidinomethylphenyl)-1-ethyne]-3,4-dihydro-1H-1,4-benzodiazepine-2,5-dione trifluroacetate, (±)-1-benzyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
1-isopropyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
1-isopropyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-isopropyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1-isopropyl-4-[succin-2-yl-(1-glycine)]-7-[2-(3-guanidinomethylphenyl)1-3,4-dihydro-1H-1,4-benzodiazepine-2,5-dione trifluroacetate, (±)-1-isopropyl-4-[succin-2-yl-(1-valine)]-7-[2-(3-guanidinomethylphenyl)-1-3,4-dihydro-1H-1,4-benzodiazepine-2,5-dione trifluroacetate, (±)-1-isopropyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
1-methyl-4-(2-carboxy-1-methylethyl)-7-[2-(4-guanidinomethylthiophenol)-1-ethyne]-3,4-dihydro-1H-1,4-benzodiazepine-2,5-dione trifluroacetate,
1-methyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate,
(±)-1-methyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate,
(±)-1-methyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate,
(±)-1-methyl-4-[succin-2-yl-(1-valine)]-7-[2-(4-guanidinomethylthiophenol)-1-ethyne]-3,4-dihydro-1H-1,4-benzodiazepine-2,5-dione trifluroacetate, (±)-1-methyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate,
1-phenyl-4-(2-carboxy-1-methylethyl)-7-[2-(4-guanidinomethylthiophenol)-1-ethyne]-3,4-dihydro-1H-1,4-benzodiazepine-2,5-dione trifluroacetate,
1-phenyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate,
(±)-1-phenyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate,
(±)-1-phenyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate,
(±)-1-phenyl-4-[succin-2-yl-(1-valine)]-7-[2-(4-guanidinomethylthiophenol)-1-ethyne]-3,4-dihydro-1H-1,4-benzodiazepine-2,5-dione trifluroacetate,
(±)-1-phenyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate,
1-benzyl-4-(2-carboxy-1-methylethyl)-7-[2-(4-guanidinomethylthiophenol)-1-ethyne]-3,4-dihydro-1H-1,4-benzodiazepine-2,5-dione trifluroacetate,
1-benzyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate,
(±)-1-benzyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate,
(±)-1-benzyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate,
(±)-1-benzyl-4-[succin-2-yl-(1-valine)]-7-[2-(4-guanidinomethylthiophenol)-1-ethyne]-3,4-dihydro-1H-1,4-benzodiazepine-2,5-dione trifluroacetate,
(±)-1-benzyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate,
1-isopropyl-4-(2-carboxy-1-methylethyl)-7-[2-(4-guanidinomethylthiophenol)-1-ethyne]-3,4-dihydro-1H-1,4-benzodiazepine-2,5-dione trifluroacetate,
1-isopropyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate,
(±)-1-isopropyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate,
(±)-1-isopropyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate,
(±)-1-isopropyl-4-[succin-2-yl-(1-valine)]-7-[2-(4-guanidinomethylthiophenol)-1-ethyne]-3,4-dihydro-1H-1,4-benzodiazepine-2,5-dione trifluroacetate,
(±)-1-isopropyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate,
(±)-1-methyl-3-phenyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
(±)-1-methyl-3-phenyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-methyl-3-phenyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1-methyl-3-phenyl-4-[succin-2-yl-(1-glycine)]-7-[2-(3-guanidinomethylphenyl)-1-ethyne]-3,4-dihydro-1H-1,4-benzodiazepine-2,5-dione trifluroacetate,
(±)-1-methyl-3-phenyl-4-[succin-2-yl-(1-valine)]-7-[2-(3-guanidinomethylphenyl)-1-ethyne]-3,4-dihydro-1H-1,4-benzodiazepine-2,5-dione trifluroacetate,
(±)-1-methyl-3-phenyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
(±)-1,3-diphenyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
(±)-1,3-diphenyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1,3-diphenyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1,3-diphenyl-4-[succin-2-yl-(1-glycine)]-7-[2-(3-guanidinomethylphenyl)-1-ethyne]-3,4-dihydro-1H-1,4-benzodiazepine-2,5-dione trifluroacetate,
(±)-1,3-diphenyl-4-[succin-2-yl-(1-valine)]-7-[2-(3-guanidinomethylphenyl)-1-ethyne]-3,4-dihydro-1H-1,4-benzodiazepine-2,5-dione trifluroacetate,
(±)-1,3-diphenyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
(±)-1-benzyl-3-phenyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
(±)-1-benzyl-3-phenyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-benzyl-3-phenyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1-benzyl-3-phenyl-4-[succin-2-yl-(1-glycine)]-7-[2-(3-guanidinomethylphenyl)-1-ethyne]-3,4-dihydro-1H-1,4-benzodiazepine-2,5-dione trifluroacetate,
(±)-1-benzyl-3-phenyl-4-[succin-2-yl-(1-valine)]-7-[2-(3-guanidinomethylphenyl)-1-ethyne]-3,4-dihydro-1H-1,4-benzodiazepine-2,5-dione trifluroacetate,
(±)-1-benzyl-3-phenyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
(±)-1-isopropyl-3-phenyl-4-(2-carboxy-1-methylethyl)-7-[2-(3-guanidinomethylphenyl)-1-ethyne]-3,4-dihydro-1H-1,4-benzodiazepine-2,5-dione trifluroacetate,
(±)-1-isopropyl-3-phenyl-4-(2-carboxy-1-phenylethyl)-7-[2-(3-guanidinomethylphenyl)-1-ethyne]-3,4-dihydro-1H-1,4-benzodiazepine-2,5-dione trifluroacetate,
(±)-1-isopropyl-3-phenyl-4-[succin-2-yl-(1-t-butoxy)]-7-[2-(3-guanidinomethylphenyl)-1-ethyne]-3,4-dihydro-1H-1,4-benzodiazepine-2,5-dione trifluroacetate,
(±)-1-isopropyl-3-phenyl-4-[succin-2-yl-(1-glycine)]-7-[2-(3-guanidinomethylphenyl)-1-ethyne]-3,4-dihydro-1H-1,4-benzodiazepine-2,5-dione trifluroacetate,
(±)-1-isopropyl-3-phenyl-4-[succin-2-yl-(1-valine)]-7-[2-(3-guanidinomethylphenyl)-1-ethyne]-3,4-dihydro-1H-1,4-benzodiazepine-2,5-dione trifluroacetate,
(±)-1-isopropyl-3-phenyl-4-[succin-2-yl-(1-phenylalanine)]-7-[2-(3-guanidinomethylphenyl)-1-ethyne]-3,4-dihydro-1H-1,4-benzodiazepine-2,5-dione trifluroacetate,
(±)-1-methyl-3-phenyl-4-(2-carboxy-1-methylethyl)-7-[2-(4-guanidinomethylthiophenol)-1-ethyne]-3,4- dihydro-1H-1,4-benzodiazepine-2,5-dione trifluroacetate, (35)-1-methyl-3-phenyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate, (±)-1-methyl-3-phenyl4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate, (±)-1-methyl-3-phenyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate, (±)-1-methyl-3-phenyl-4-[succin-2-yl-(1-valine)]-7-[2-(4-guanidinomethylthiophenol)-1-ethyne]-3,4-dihydro-1H-1,4-benzodiazepine-2,5-dione trifluroacetate, (±)-1-methyl-3-phenyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate, (±)-1,3-diphenyl-4-(2-carboxy-1-methylethyl)-7-[2-(4-guanidinomethylthiophenol)-1-ethyne]-3,4-dihydro-1H-1,4-benzodiazepine-2,5-dione trifluroacetate, (±)-1,3-diphenyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate, (±)-1,3-diphenyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate, (±)-1,3-diphenyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate, (±)-1,3-diphenyl-4-[succin-2-yl-(1-valine)]-7-[2-(4-guanidinomethylthiophenol)-1-ethyne]-3,4-dihydro-1H-1,4-benzodiazepine-2,5-dione trifluroacetate, (±)-1,3-diphenyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate, (±)-1-benzyl-3-phenyl-4-(2-carboxy-1-methylethyl)-7-[2-(4-guanidinomethylthiophenol)-1-ethyne]-3,4-dihydro-1H-1,4-benzodiazepine-2,5-dione trifluroacetate, (±)-1-benzyl-3-phenyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate, (±)-1-benzyl-3-phenyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate, (±)-1-benzyl-3-phenyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate, (±)-1-benzyl-3-phenyl-4-[succin-2-yl-(1-valine)]-7-[2-(4-guanidinomethylthiophenol)-1-ethyne]-3,4-dihydro-1H-1,4-benzodiazepine-2,5-dione trifluroacetate, (±)-1-benzyl-3-phenyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate, (±)-1-isopropyl-3-phenyl-4-(2-carboxy-1-methylethyl)-7-[2-(4-guanidinomethylthiophenol)-1-ethyne]-3,4-dihydro-1H-1,4-benzodiazepine-2,5-dione trifluroacetate, (±)-1-isopropyl-3-phenyl-4-(2-carboxy-1-phenylethyl)-7-[2-(4-guanidinomethylthiophenol)-1-ethyne]-3,4-dihydro-1H-1,4-benzodiazepine-2,5-dione trifluroacetate, (±)-1-isopropyl-3-phenyl-4-[succin-2-yl-(1-t-butoxy)]-7-[2-(4-guanidinomethylthiophenol)-1-ethyne]-3,4-dihydro-1H-1,4-benzodiazepine-2,5-dione trifluroacetate, (±)-1-isopropyl-3-phenyl-4-[succin-2-yl-(1-glycine)]-7-[2-(4-guanidinomethylthiophenol)-1-ethyne]-3,4-dihydro-1H-1,4-benzodiazepine-2,5-dione trifluroacetate, (±)-1-isopropyl-3-phenyl-4-[succin-2-yl-(1-valine)]-7-[2-(4-guanidinomethylthiophenol)-1-ethyne]-3,4-dihydro-1H-1,4-benzodiazepine-2,5-dione trifluroacetate, (±)-1-isopropyl-3-phenyl-4-[succin-2-yl-(1-phenylalanine)]-7-[2-(4-guanidinomethylthiophenol)-1-ethyne]-3,4-dihydro-1H-1,4-benzodiazepine-2,5-dione trifluroacetate.

EXAMPLE 11

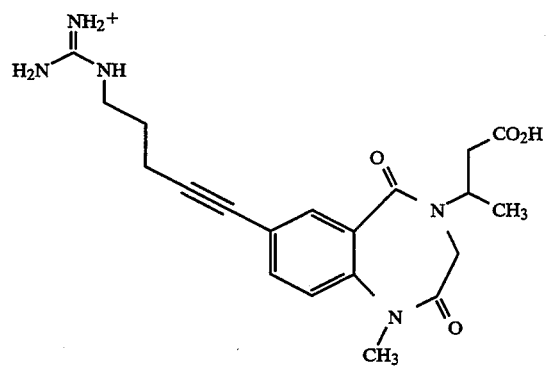

1-methyl-4-(2-carboxy-1-methylethyl)-7-(5-guanidino-1-pentynyl)-3,4-dihydro-1H-1,4,benzodiazepine-2,5-dione trifluroacetate.

a) Methyl N-(2-amino-5-iodobenzoyl)-3-amino-3-methylpropanate was prepared using the method described in part (b) of example 1. Thus, 1.72 grams of 5-iodoisatoic anhydride and 1.73 grams of methyl 3-aminobutanoate p-tosylate yielded 0.65 grams (30%) methyl N-(2-amino-5-iodobenzoyl)-3-aminobutanoate (TLC, SiO2, 1:1 EtOAc/hexane, $R_f$=0.63, uv positive).

b) Methyl N-(2-methylamino-5-iodobenzoyl)-3-amino-3-methylpropanoate was prepared using the method described in part (c) of example 1. Thus, 0.32 grams of methyl N-(2-amino-5-iodobenzoyl)-3-aminobutanoate yielded 0.14 grams (43%) of methyl N-(2-methylamino-5-iodobenzoyl)-3-aminobutanoate (TLC, SiO2, 1:1 EtOAc/hexane, $R_f$=0.85, uv positive).

c) 1-methyl-4-(3-methoxy-3-oxobutan-2-yl)-7-iodo-3,4-dihydro-1H-1,4-benzo-diazapine-2,5-dione was prepared using the method described in part (d) of example 1. Thus, 0.25 grams of N-(2-methylamino-5-iodobenzoyl)-3-aminobutanoate yielded 0.08 grams (29%) of 1-methyl-4-(3-methoxy-3-oxobutan-2-yl)-7-iodo-3,4-dihydro-1H-1,4-benzo-diazapine-2,5-dione (TLC, SiO2, 1:1 EtOAc/hexane, $R_f$=0.33, uv positive).

d) 1-methyl-4-(3-methoxy-3-oxobutan-2-yl)-7-[5-(N-Boc)-amino-1-pentyne]-3,4-dihydro-1H-1,4-benzodiazepine-2,5-dione was prepared using the method described in part (f) of example 1. Thus, 0.08 grams of 1-methyl-4-(3-methoxy-3-oxobutan-2-yl)-7-iodo-3,4-dihydro-1H-1,4-benzo-diazapine-2,5-dione yielded 0.061 grams (68%) of 1-methyl-4-(3-methoxy-3-oxobutan-2-yl)-7-[5-(N-Boc)-amino-1-pentyne]-3,4-dihydro- 1H-1,4-benzodiazepine-2,5-dione (TLC, SiO$_2$, 1:1 EtOAc/hexane, R$_f$=0.24, un positive).

e) 1-methyl-4-(2-carboxy-1-methylethyl)-7-(5-amino-1-pentyne)-3,4-dihydro-1H-1,4-benzodiazepine-2,5-dione trifluroacetate was prepared using the method described in part (g) of example 1. Thus, 61 mgs of 1-methyl-4-(3-methoxy-3-oxobutan-2-yl)-7-[5-(N-Boc)-amino-1-pentyne]-3,4-dihydro-1H-1,4-benzodiazepine-2,5-dione yielded 40 mgs (87%) of 1-methyl-4-(2-carboxy-1-methylethyl)-7-(5-amino-1-pentyne)-3,4-dihydro-1H-1,4-benzodiazepine-2,5-dione trifluoroacetate ($\frac{1}{2}$″ C-18 reverse-phase column, eluting with a solvent gradient of 10:90 methanol (0.1% trifluroacetic acid)/water(0.1% trifluroacetic acid), time 0 to 10 min, to 50:50 methanol(0.1% trifluroacetic acid)/water(0.1% trifluroacetic acid), time 10 min to 40 min, flow 10ml/min, R$_t$=31.2 min, uv detection 254 nM). HRMS (FAB) molecular ion m/z=358.1765 (cald. C$_{19}$H$_{24}$N$_3$O$_4$, 358.1767)

f) 1-methyl-4-(2-carboxy-1-methylethyl)-7-(5-guanidino-1-pentyne)-3,4-dihydro-1H-1,4-benzodiazepine-2,5-dione trifluroacetate was prepared using the method described in example 2. Thus, 15 mgs of 1-methyl-4-(2-carboxy-1-methylethyl)-7-(5-amino-1-pentyne)-3,4-dihydro-1H-1,4-benzodiazepine-2,5-dione trifluoroacetate yielded 10mgs (67%) of 1-methyl-4-(2-carboxy-1-methylethyl)-7-(5-guanidino-1-pentyne)-3,4-dihydro-1H-1,4-benzodiazepine-2,5-dione trifluoroacetate ($\frac{1}{2}$″ C-18 reverse-phase column, eluting with a solvent gradient of 10:90 methanol(0.1% trifluroacetic acid)/water(0.1% trifluroacetic acid), time 0 to 10 min, to 50:50 methanol(0.1% trifluroacetic acid)/water(0.1% trifluroacetic acid), time 10 min to 40 min, flow 10ml/min, R$_t$=36.9 min, uv detection 254nM). HRMS (FAB) molecular ion m/z=400.1999 (cald. C$_{20}$H$_{26}$N$_5$O$_4$, 400.1986).

EXAMPLE 12

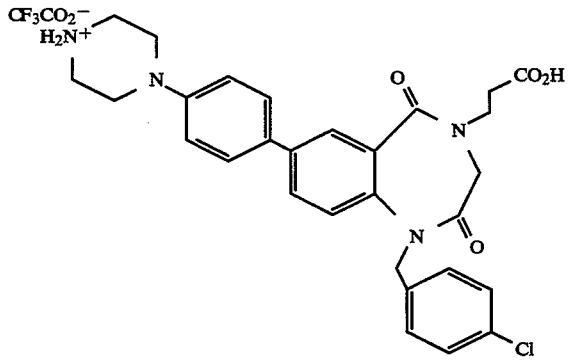

1-(4-chlorophenyl)methyl-4-(2-carboxyethyl)-7-(4-(1-piperidin)-phenyl)-3,4-dihydro-1H-1,4-benzodiazapine-2,5-dione trifluroacetate.

a) Over a period of 15 minutes samples of iodine (8.62 grams, 0.034mol) and silver benzoate (7.78 grams, 0.034 mol) were added in portions to a magnetically stirred solution of 5 grams of 1-phenylpiperazine in 80 mL acetic acid. The mixture stirred for 1 hour. The solvent was evaporated and the residue partioned between 150 mL diethyl ether and 150 mL 2N sodium hydroxide. The organic layer was washed with 100 mL water, 100 mL brine, then dried over potassium carbonate and concentrated in vacuo to yield 1.0 gram (11%)of 1-(4-iodophenyl)-piperzine (110°-115° C.). The material obtained was used without further purification. $^1$H NMR (CDCl$_3$, dTMS) 7.51 (2 H, d, $^3$JHH=9 Hz, m-ArH), 6.69 (2H, d, $^3$JHH=9 Hz, o-ArH), 3.17 (4H, m), 3.04 (4H, m). $^{13}$C NMR (CDCl$_3$) 151.36, 137.73, 118.05, 81.35, 49.92, 45.95.

b) The crude material obtained from part (a) (1 gram, 3.47 mmol) was dissolved in dry THF (10 mL) and a catalytic amount of dimethylaminopyridine (100 mgs) and di-tert-butyl dicarbonate (0.9 grams, 4.1 mmol, 1.2 molar excess) were added, monitoring the reaction by TLC (SiO$_2$, 1:1 EtOAc/hexane, R$_f$(product)=0.88). After 12 hours (overnight) the reaction was diluted with diethyl ether and extracted 1×75 mL water, 1×75 mL 1N HCl, 1×75 mL sat. sodium bicarbonate, 1×75 mL brine, dried over potassium carbonate, filtered and concentrated in vacuo. The material was further purified by filtering through a packet of SiO$_2$ using 1:1 diethyl ether/hexane as the eluting solvent to yield 1-(4-iodophenyl)-4-(N-Boc)-piperzine (1 grm, 77%, 142°-143° C.). $^1$H NMR (CDCl$_3$, dTMS) 7.54 (2 H, d, $^3$JHH=8 Hz, m-ArH), 6.69 (2 H, d, $^3$JHH=8 Hz, o-ArH), 3.58 (4 H, t, $^3$JHH=5 Hz), 3.04 (4 H, t, $^3$JHH=5 Hz) 1.48 (9 H, s, Bu$^t$).

c) A magnetically stirred solution of N-(2-amino-5-iodobenzoyl)-3-aminoproprionate (8.8 grams, 23.4 mmol), prepared using the procedure shown in part (b) of example 1, dimethylformamide, 2,6-lutidine (1.5 molar equiv., 35.1 mmol, 4.25 mL) and 4-chlorobenzyl chloride (1.5 molar equiv., 35.1 mmol, 5.96 grams) was heated to 100° C. for 24 hours. The mixture was allowed to cool to room temperature and concentrated in vacuo. The resulting residue was dissolved in 150 mL methylene chloride and washed with 2×100 mL 10% citric acid, 1×100 mL water, dried over sodium sulfate, filtered and concentrated in vacuo. The solid obtained was dissolved in a minimum volume of methylene chloride and a 5 fold excess of hexanes added. The solution was allowed to stand overnight in the refrigerator (5°-7° C.) to yield 7.56 grams of N-(2-(p-chlorobenzyl)amino-5-iodobenzoyl)-3-aminoproprionate (153°-155° C.). Concentration of the mother liquor and repeating the steps for crystalization yielded a second crop (3.32 grams) for a total 92% isolated yield of the desired product. $^1$H NMR (CDCl$_3$, dTMS) 8.10 (1H, bt, $^3$JHH=5 Hz, NH), 7.60 (1H, d, $^4$JHH=2 Hz, C6-H), 7.44 (1H, dd, $^3$JHH=9 Hz, $^4$JHH=2 Hz, C8-H), 7.29 (4H, m, p-ClC6H4), 6.72 (1H, bt, $^3$JHH=6 Hz, NH), 6.34 (1H, d, $^3$JHH=9 Hz, C9-H), 4.35 (2H, d, $^3$JHH=9 Hz, NCH$_2$Ar), 4.20 (2H, q, $^3$JHH=7 Hz, OCH$_2$), 3.68 (2H, q, JHH=6 Hz, NCH$_2$), 2.65 (2H, t, $^3$JHH=6, CH$_2$CO$_2$), 1.31 (3H, t, $^3$JHH=7 Hz, CH$_2$CH$_3$). $^{13}$C NMR (CDCl$_3$) 172.6, 168.3, 148.6, 141.0, 137.0, 135.6, 128.8, 128.3, 117.6, 114.3, 75.1, 60.9, 46.3, 35.1, 33.9, 14.2 d) To a magnetically stirred biphasic solution of N-(2-(p-chlorobenzyl)amino-5-iodobenzoyl)-3-aminoproprionate (10 grams, 20.57 mmol), 200 mL methylene chloride, and 200 mL water was added, at room temperature, α-bromoacetyl bromide (24.7 mmol, 1.2 molar equiv., 2.15 mL), monitoring the reaction by TLC (SiO$_2$, 1:1 EtOAc/hexane). The reaction was complete 6 hours. The layers were separated, washing the aqueous layer with 75 mL methylene chloride. The combined organics were washed 1×100 mL sat. sodium bicarbonate, 1×100 mL Brine, dried over sodium sulfate, filtered and concentrated in vacuo. The resulting residue was dissolved in 50 mL dimethylformamide and added, v/a an addition funnel, over a period of 30 minutes to a slurry of sodium hydride (1.2 molar equiv., 24.7 mmol, 0.60 grams) in 10 mL dimethylformamide cooled to 0° C. under an atmosphere of nitrogen. The reaction was stirred for an additional 1 hour and then poured over an ice-cold 10% citric acid solution. The cloudy mixture was extracted 3×100 mL EtOAc. The combined organics were dried over magnesium sulfate, filtered, and concentrated in vacuo. Purification was achieved by column chromatography (SiO$_2$, 600 mL, using 30%EtOAc/70% hexane to 60%EtOAc/40% hexane as the eluting solvent gradient) to yield 6.5 grams (63%) of 1-(p-chlorobenzyl)-7-iodo-4-(2-carboxyethyl)-3,4-dihydro-1H-1,4-benzodiazpine-2,4-dione ethyl ester. $^1$H NMR (CDCl$_3$, dTMS) 8.11 (1H, d, $^3$JHH=2 Hz, C6-H), 6.68 (1H, dd, $^4$JHH=2 Hz, $^3$JHH=9 Hz, C8-H), 7.23 (2H, d, $^3$JHH=8 Hz, ArH), 7.03 (2H, d, $^3$JHH=8 Hz, ArH), 6.87 (1H, d, $^3$JHH=9 Hz, C9-H), 5.05 (1 H, d, $^2$JHH=16 Hz, NCHHAr), 4.95 (1H, d, 2JHH=16 Hz, NCHHAr), 4.1 (3H, m, OCH2, C3-H), 3.93 (1H, d, $^2$JHH=15 Hz, C3-H), 3.9 (2 H, m, NCH$_2$CH$_2$), 2.65 (2H, m, CH$_2$CO$_2$), 1.25 (3H, t, $^3$JHH=7 Hz, OCH$_2$CH$_3$)

e) To a magnetically stirred solution of 1-(4-iodophenyl)-4-(N-Boc)-piperzine (0.5 grams, 1.29mmol) in 0.65mL THF at −78° C. under an atmosphere of nitrogen was added n-BuLi as a 2.5M solution in hexane (1.42 mmol, 1.1 molar equiv., 0.57 mL) over a 5 minute period. The mixture was stirred for 15 minutes at −78° C. and the treated with triisopropylborate (3 molar equiv., 3.9 mmol, 0.9 mL). The mixture was allowed to warm to room temperature and stirred overnight (ca. 12 hours). The mixture was cooled to 0° C. and acidified to pH 6.5 with 5% aq. HCl and extracted with CH$_2$Cl$_2$ (50 mL). The organic layer was washed with brine, dried over sodium sulfate, decanted and concentrated in vacuo. The resulting residue, in a minimum volume of ethanol, was added to a prestirred (10 mins) mixture of tetrakistriphenylphosphine palladium (0.03 molar equiv., 0.026 mmol, 30 mgs), and 0.447 grams of 1-(p-chlorobenzyl)-7-iodo-4-(2-carboxyethyl)-3,4-dihydro-1H-1,4-benzodiazpine-2,4-dione ethyl ester (0.85 mmol) in 0.5 mL dimethylformamide at room temperature. 1.3 mL of a 2M solution of sodium carbonate (2 equiv.) was added and the reaction mixture heated to 80° C. for 6 hours. The mixture was allowed to cool to room temperature and is quenched with 1N HCl (25 mL) and extracted 3×50 mL ethyl acetate. The combined organics were washed 1×50 mL sat NaHCO$_3$, brine, dried over Na$_2$SO$_4$, decanted and concentrated in vacuo. The resulting residue was chromatographed (SiO$_2$, 1:1 EtOAc/hexane to 9:1 EtOAc/hexane as the eluting solvent) to yield 1-(p-chlorobenzyl)-7-[4-(4-N-Boc-1-piperazine)phenyl]-4-(2-carboxyethyl)-3,4-dihydro-1H-1,4-benzodiazpine-2,4-dione ethyl ester (0.137 grams, 24%, R$_f$(SiO$_2$, 1:1 EtOAc/hexane)=0.15, mu and ninhydrin positive). $^1$H NMR (CDCl$_3$, dTMS) 8.00 (1H, d, $^4$JHH=2 Hz, C6-H), 7.59 (1H, dd, $^4$JHH=2 Hz, $^3$JHH=9 Hz, C8-H), 7.50 (2H, d, $^3$JHH=9 Hz, C7-o-ArH), 7.23 (2H, d, $^3$JHH=8 Hz, CH$_2$-m-ArH), 7.16 (1H, d, $^3$JHH=9 Hz, C9-H), 7.10 (2H, d, $^3$JHH=9 Hz, CH$_2$-o-ArH), 6.95 (2H, d, $^3$JHH=8 Hz, C7-m-ArH), 5.08 (1H, d, $^2$JHH=16 Hz, NCHHAr), 4.99 (1H, d, $^2$JHH=16 Hz, NCHHAr), 4.18 (1H, d, $^2$JHH=15 Hz, C3-H), 4.13 (2H,q, $^3$JHH=7 Hz, OCH$_2$), 3.92 (2H, m, NCH$_2$CH$_2$), 3.92 (1H, d, $^2$JHH=15 Hz, C3-H), 3.58 (4H, t, $^3$JHH=5 Hz, NCH$_2$CH$_2$NH), 3.18 (4H, t, $^3$JHH=5 Hz, NCH$_2$NCH$_2$NH), 2.68 (2H, m, CH$_2$CO$_2$), 1.47 (9H, s, Bu$^t$), 1.25 (3 H, t, $^3$JHH=7 Hz). 13 C NMR 171.3, 168.5, 167.1, 154.7, 150.9, 138.6, 138.0, 135.2, 133.3, 132.1,130.9, 129.9, 129.7, 128.9, 128.4, 127.5, 121.9, 116.4, 79.9, 60.8, 52.4, 50.6, 48.8, 45.1, 32.8, 28.4, 14.2.

Using the above procedure, but substituting the appropriate 7-iodo-3,4-dihydro-1H-1,4-benzodiazpine-2,4-dione alkyl ester for 1-(p-chlorobenzyl)-7-iodo-4-(2-carboxyethyl)-3,4-dihydro-1H-1,4-benzodiazpine-2,4-dione ethyl ester and substituting the appropriate iodoarene for 1-(4-iodophenyl)-4-(N-Boc)-piperzine there may be prepared, for example, the following compounds:

1-methyl-7-[4-(4-N-Boc-1-piperazine)phenyl]-4-(2-carboxyethyl)-3,4-dihydro-1H-1,4-benzodiazpine-2,4-dione ethyl ester, 1-(diphenylmethyl)-7-[4-(4-N-Boc-1-piperazine)phenyl]-4-(2-carboxyethyl)-3,4-dihydro-1H-1,4-benzodiazpine-2,4-dione ethyl ester, 1-(2-napthyl)methyl-7-[4-(4-N-Boc-1-piperazine)phenyl]-4-(2-carboxyethyl)-3,4-dihydro-1H-1,4-benzodiazpine-2,4-dione ethyl ester, (±)-1-methyl-7-[4-(4-N-Boc-1-piperazine)phenyl]-4-(3-phenyl-3-proprionate)-3,4-dihydro-1H-1,4-benzodiazpine-2,4-dione methyl ester, (±)-1-(2-napthyl)methyl-7-[4-(4-N-Boc-1-piperazine)phenyl]-4-(3-phenyl-3-proprionate)-3,4-dihydro-1H-1,4-benzodiazpine-2,4-dione methyl ester, 1-(p-chlorobenzyl)-7-[4-(2-(N-Boc)-aminoethoxy)phenyl]-4-(2-carboxyethyl)-3,4-dihydro-1H-1,4-benzodiazpine-2,4-dione ethyl ester 1-methyl-7-[4-(2-(N-Boc)-aminoethoxy)phenyl]-4-(2-carboxyethyl)-3,4-dihydro-1H-1,4-benzodiazpine-2,4-dione ethyl ester, 1-(diphenylmethyl)-7-[4-(2-(N-Boc)-aminoethoxy)phenyl]-4-(2-carboxyethyl)-3,4-dihydro-1H-1,4-benzodiazpine-2,4-dione ethyl ester, 1-(2-napthyl)methyl-7-[4-(2-(N-Boc)-aminoethoxy)phenyl]-4-(2-carboxyethyl)-3,4-dihydro-1H-1,4-benzodiazpine-2,4-dione ethyl ester, (±)-1-methyl-7-[4-(2-(N-Boc)-aminoethoxy)phenyl]-4-(3-phenyl-3-proprionate)-3,4-dihydro-1H-1,4-benzodiazpine-2,4-dione methyl ester, (±)-1-(2-napthyl)methyl-7-[4-(2-(N-Boc)-aminoethoxy)phenyl]-4-(3-proprionate)-3,4-dihydro-1H-1,4-benzodiazpine-2,4-dione methyl ester, 1-(p-chlorobenzyl)-7-[4-(N-Boc-aminomethyl)phenyl]-4-(2-carboxyethyl)-3,4-dihydro-1H-1,4-benzodiazpine-2,4-dione ethyl ester 1-methyl-7-[4-(N-Boc-aminomethyl)phenyl]-4-(2-carboxyethyl)-3,4-dihydro-1H-1,4-benzodiazpine-2,4-dione ethyl ester, 1-(diphenylmethyl)-7-4-(N-Boc-aminomethyl)phenyl]-4-(2-carboxyethyl)-3,4-dihydro-1H-1,4-benzodiazpine-2,4-dione ethyl ester, 1-(2-napthyl)methyl-7-[4-(N-Boc-aminomethyl)phenyl]-4-(2-carboxyethyl)-3,4-dihydro-1H-1,4-benzodiazpine-2,4-dione ethyl ester, (±)-1-methyl-7-[4-(N-Boc-aminomethyl)phenyl]-4-(3-phenyl-3-proprionate)-3,4-dihydro-1H-1,4-benzodiazpine-2,4-dione methyl ester, (±)-1-(2-napthyl)methyl-7-[4-(N-Boc-aminomethyl)phenyl]-4-(3-phenyl-3-proprionate)-3,4-dihydro-1H-1,4-benzodiazpine-2,4-dione methyl ester.

f) 1-(p-chlorobenzyl)-7-[4-(1-piperazine)phenyl]-4-(2-carboxyethyl)-3,4-dihydro-1H-1,4-benzodiazpine-2,4-dione trifluroacetate was prepared using the method described in part (c) of example 1. Thus, 34 mgs (0.052 mmol) 1-(p-chlorobenzyl)-7-[4-(4-N-Boc-1-piperazine)-phenyl]-4-(2-carboxyethyl)-3,4-dihydro-1H-1,4-benzodiazpine-2,4-dione ethyl ester yielded 25 mgs (90%) of 1-(p-chlorobenzyl)-7-[4-(1-piperazine)phenyl]-4-(2-carboxyethyl)-3,4-dihydro-1H-1,4-benzodiazpine-2,4-dione trifluroacetate ($\frac{1}{2}''$ C-18 reverse-phase column, eluting with a solvent gradient of 1:9 acetonitrile(0.1%TFA)/water (0.1% TFA) time 0 to 10 minutes, to 1:1 acetonitrile(0.1%TFA)/water (0.1% TFA) time 10 to 40 minutes, flow 10mL/min, $R_t$=34.9 min, mu detection 254 nM). HRMS (FAB) molecular ion m/z=533.1950 (cald. C29H30N4O4Cl, 533.1956). $^1$H NMR (D$_2$O,10%CD$_3$OD) 7.61 (1H, d, $^4$JHH=2 Hz, C6-H), 7.43 (1H, dd, $^4$JHH=2 Hz $^3$JHH=8 Hz, C8-H), 7.28 (2H, d, C7-o-ArH), 7.10 (1H, d, $^3$JHH=8 Hz, C9-H), 6.98 (2H, d, 3JHH=7 Hz, CH$_2$-m-ArH), 6.87 (2H, d, $^3$JHH=7 Hz, CH$_2$-o-ArH), 6.80 (2H, d, $^3$JHH=8 Hz, C7-m-ArH), 5.20 (1H, d, $^2$JHH=16 Hz, NCHHAr), 3.95 (1H, d, $^2$JHH=14 Hz, C3-H), 3.84 (1H, dr, NCHHCH$_2$), 3.72 (1H, d, $^2$JHH=14 Hz, C3-H), 3.58 (1H, dt, C3-H), 3.23 (4H, bs, NCH$_2$CH$_2$NH), 3.18 (4H, bs, NCH$_2$CH$_2$NH), 2.58 (2H, t, 3JHH=7 Hz, CH$_2$CO$_2$).

Using the above procedure, but substituting the appropriate 7-aryl-3,4-dihydro-1H-1,4-benzodiazpine-2,4-dione N-Boc amino alkyl ester for 1-(p-chlorobenzyl)-7-[4-(4-N-Boc-1-piperazine)phenyl]-4-(2-carboxyethyl)-3,4-dihydro-1H-1,4-benzodiazpine-2,4-dione ethyl ester there may be prepared, for example, the following compounds:

1-methyl-7-[4-(1-piperazine)phenyl]-4-(2-carboxyethyl)-3,4-dihydro-1H-1,4-benzodiazpine-2,4-dione trifluoroacetate, 1-(diphenylmethyl)-7-[4-(1-piperazine)phenyl]-4-(2-carboxyethyl)-3,4-dihydro-1H-1,4-benzodiazpine-2,4-dione trifluoroacetate, 1-(2-napthyl)methyl-7-[4-(1-piperazine)phenyl]-4-(2-carboxyethyl)-3,4-dihydro-1H-1,4-benzodiazpine-2,4-dione trifluoroacetate, (±)-1-methyl-7-[4-(1-piperazine)phenyl]-4-(3-phenyl-3-proprionate)-3,4-dihydro-1H-1,4-benzodiazpine-2,4-dione trifluoroacetate, (±)-1-(2-napthyl)methyl-7-[4-(1-piperazine)phenyl]-4-(3-phenyl-3-proprionate)-3,4-dihydro-1H-1,4-benzodiazpine-2,4-dione trifluoroacetate, 1-(p-chlorobenzyl)-7-[4-(2-aminoethoxy)phenyl]-4-(2-carboxyethyl)-3,4-dihydro-1H-1,4-benzodiazpine-2,4-dione trifluoroacetate, 1-methyl-7-[4-(2-aminoethoxy)phenyl]-4-(2-carboxyethyl)-3,4-dihydro-1H-1,4-benzodiazpine-2,4-dione trifluoroacetate, 1-(diphenylmethyl)-7-[4-(2-aminoethoxy)phenyl]-4-(2-carboxyethyl)-3,4-dihydro-1H-1,4-benzodiazpine-2,4-dione trifluoroacetate, 1-(2-napthyl)methyl-7-[4-(2-aminoethoxy)phenyl]-4-(2-carboxyethyl)-3,4-dihydro-1H-1,4-benzodiazpine-2,4-dione trifluoroacetate, (±)-1-methyl-7-[4-(2-aminoethoxy)phenyl]-4-(3-phenyl-3-proprionate)-3,4-dihydro-1H-1,4-benzodiazpine-2,4-dione trifluoroacetate, (±)-1-(2-napthyl)methyl-7-[4-(2-aminoethoxy)phenyl]-4-(3-phenyl-3-proprionate)-3,4-dihydro-1H-1,4-benzodiazpine-2,4-dione trifluoroacetate, 1-(p-chlorobenzyl)-7-[4-(aminomethyl)phenyl]-4-(2-carboxyethyl)-3,4-dihydro-1H-1,4-benzodiazpine-2,4-dione trifluoroacetate, 1-methyl-7-[4-(aminomethyl)phenyl]-4-(2-carboxyethyl)-3,4-dihydro-1H-1,4-benzodiazpine-2,4-dione trifluoroacetate, 1-(diphenylmethyl)-7-4-(aminomethyl)phenyl]-4-(2-carboxyethyl)-3,4-dihydro-1H-1,4-benzodiazpine-2,4-dione trifluoroacetate, 1-(2-napthyl)methyl-7-[4-(aminomethyl)phenyl]-4-(2-carboxyethyl)-3,4-dihydro-1H-1,4-benzodiazpine-2,4-dione trifluoroacetate, (±)-1-methyl-7-[4-(aminomethyl)phenyl]-4-(3-phenyl-3-proprionate)-3,4-dihydro-1H-1,4-benzodiazpine-2,4-dione trifluoroacetate, (±)-1-(2-napthyl)methyl-7-[4-(aminomethyl)phenyl]-4-(3-phenyl-3-proprionate)-3,4-dihydro-1H-1,4-benzodiazpine-2,4-dione trifluoroacetate.

EXAMPLE 13

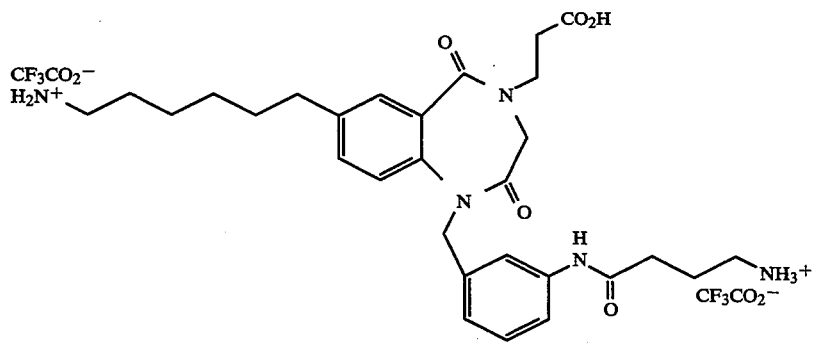

1-[3-(N-(4-aminobuturyl))aminophenyl)methyl-4-(2-carboxyethyl)-7-(6-aminohexyl)-3,4-dihydro-1H-1,4-benzodiazapine-2,5-dione bistrifluoroacetate.

a) 1-(3-nitrophenyl)methyl-4-(2-carboxyethyl)-7-(N-Boc-6-aminohexynyl)-3,4-dihydro-1H-1,4-benzodiazapine-2,5-dione ethyl ester (110 mgs, 0.18 mmol) was reduced under an atmosphere of nitrogen in 4 mL ethyl acetate in the presence of a catalytic amount of 10% Pd on carbon (25 mgs), monitoring the reaction by TLC (SiO$_2$, 1:1 ethyl acetate/hexane, $R_f$(starting material)=0.33, $R_f$(product)=0.15, mu and ninhydrin positive). After 3 hours, the reaction was filtered through Celite ®, washing with ethyl acetate, and concentrated in vacuo to yield 97 mgs (92%) of 1-(3-aminophenyl)-methyl-4-(2-carboxyethyl)-7-(N-Boc-6-aminohexyl)-3,4-dihydro-1H-1,4-benzodiazapine-2,5-dione ethyl ester. 1H NMR (CDCl$_3$, dTMS) 7.58 (1H, d, $^4$J$_{HH}$=2 Hz, C6-H), 7.18 (1H, dd, $^4$J$_{HH}$=2 Hz, $^3$J$_{HH}$=8 Hz, C8-H), 7.09 (1H, d, $^3$J$_{HH}$=9 Hz, CH$_2$ArH), 7.04 (1H, t, 3JHH=8 Hz, CH$_2$ArH), 6.54 (1H, bd, CH$_2$ArH), 6.48 (1H, bs, CH2ArH), 4.99 (1H, d, $^2$J$_{HH}$=16 Hz, CHHAr), 4.90 (1H, d, $^2$J$_{HH}$=16 Hz, CHHAr), 4.53 (1H, vbs, NHBoc), 4.20-3.96 (4H, m, OCH$_2$, C3-H, NCHHCH$_2$), 3.92-3.80 (2H, m, C3-H, NCHHCH$_2$), 3.55 (2H, bs, NH$_2$), 3.06 (2H, bq, $^3J_{HH}$=6Hz, CH2NHBoc), 2.72 (2H, m, CH2CO2), 2.56 (2H, t, $^3J_{HH}$=7Hz), 1.66–1.20 (20H, m, (CH2)4, Bu$^t$, OCH2CH3). 13C NMR (CDCl3) 171.4, 168.5, 167.4, 146.3, 140.7, 138.1, 137.9, 132.2, 130.1, 129.6, 129.0, 121.6, 117.4, 114.5, 113.6, 79.0, 60.8, 52.4, 51.1, 45.1 40.5, 34.9, 32.8, 30.8, 29.9, 28.8, 28.4, 26.5, 14.2.

Using the above procedure, but substituting the appropriate 7-alkyl or aryl-3,4-dihydro-1H-1,4-benzodiazpine-2,4-dione N-Boc amino alkyl ester for 1-(3-nitrophenyl)methyl-4-(2-carboxyethyl)-7-(N-Boc-6-aminohexynyl)-3,4-dihydro-1H-1,4-benzodiazapine-2,5-dione ethyl ester there may be prepared, for example, the following compounds:

1-(2-aminophenyl)methyl-4-(2-carboxyethyl)-7-(N-Boc-6-aminohexyl)-3,4-dihydro-1H-1,4-benzodiazapine-2,5-dione ethyl ester, 1-(4-aminophenyl)methyl-4-(2-carboxyethyl)-7-(N-Boc-6-aminohexyl)-3,4-dihydro-1H-1,4-benzodiazapine-2,5-dione ethyl ester, 1-(3-aminophenyl)methyl-4-(2-carboxyethyl)-7-[4-(4-N-Boc-1-piperazine)phenyl]-3,4-dihydro-1H-1,4-benzodiazapine-2,5-dione ethyl ester, 1-(2-aminophenyl)methyl-4-(3-phenyl-3-proprionate)-7-[4-(4-N-Boc-1-piperazine)phenyl]-3,4-dihydro-1H-1,4-benzodiazapine-2,5-dione ethyl ester, 1-(3-aminophenyl)methyl-4-(3-phenyl-3-proprionate)-7-(N-Boc-6-aminohexyl)-3,4-dihydro-1H-1,4-benzodiazapine-2,5-dione ethyl ester, b) A solution of the aniline 1-(3-aminophenyl)methyl-4-(2-carboxyethyl)-7-(N-Boc-6-aminohexyl)-3,4-dihydro-1H-1,4-benzodiazapine-2,5-dione ethyl ester (50 mgs, 0.09 mmol) and 0.5 mL dimethylacetamide was added to a prestirred solution of N-Boc-4-aminobutyric acid (0.16 mmol, 32.5 mgs), 0.5 mL dimethylacetamide, 0.5 mL pyridine, and benztriazol-1-yl-oxy-tris-(dimethyamino)phosphonium hexafluorophosphate (BOP Reagent) and a catalytic amount of dimethylaminopyridine (DMAP, 5 mgs), monitoring by TLC (8:2 ethyl acetate/hexane). After 6 hours, the reaction was poured over 50 mL 1N HCl and extracted 2×50 mL ethyl acetate. The combined organics was dried over sodium sulfate, decanted, and concentrated in vacuo. The resulting residue was purified by column chromatography, SiO2, using 7:3 ethyl acetate/hexane to 9:1 ethyl acetate/hexane, R$_f$(8:2 ethyl acetae/hexane, product)=0.15, to yield 59 mgs (86%) of 1-[3-(4-N-Boc-aminobutyryl)aminophenyl]methyl-4-(2-carboxyethyl)-7-(N-Boc-6-aminohexyl)-3,4-dihydro-1H-1,4-benzodiazapine-2,5-dione ethyl ester. $^1$H NMR (CDCl3, dTMS) 8.78 (1H, bs, ArNHCO), 7.56 (1H, d, $^4J_{HH}$=2Hz, C6-H), 7.44 (1H, bd, $^3J_{HH}$=8Hz, C8-H), 7.36 (1H, bs, CH2ArH), 7.17 (2H, m, CH2ArH), 7.09 (1H, t, $^3J_{HH}$=8Hz, CH2ArH), 6.81 (1H, bd, $^3J_{HH}$=8Hz, C9-H), 5.1–4.9 (3H, m, NHBoc, CH2Ar), 4.58 (1H, bs, NHBoc), 4.20–4.05 (4H, m, OCH2, C3-H, NCHHCH2), 3.87 (1H, d, $^2J_{HH}$=15Hz, C3-H), 3.80 (1H, dt, NCHHCH2), 3.16 (2H, bq, $^3J_{HH}$=6Hz, CH2NHBoc), 3.04 (2H, bq, $^3J_{HH}$=6Hz, CH2NHBoc), 2.71 (2H, m, CH2CO2), 2.54 (2H, t, $^3J_{HH}$=7 Hz, NCOCH2), 2.32 (2H, t, $^3J_{HH}$=7Hz, ArCH2), 1.82 (2H, p, $^3J_{HH}$=7Hz, NCOCH2CH2), 1.6–1.2 (20H, m, (CH2)4, Bu$^t$, OCH2CH3).

Using the above procedure, but substituting the appropriate 7-alkyl or aryl-3,4-dihydro-1H-1,4-benzodiazpine-2,4-dione N-Boc amino alkyl ester for 1-(3-aminophenyl)methyl-4-(2-carboxyethyl)-7-(N-Boc-6-aminohexyl)-3,4-dihydro-1H-1,4-benzodiazapine-2,5-dione ethyl ester there may be prepared, for example, the following compounds:

1-[2-(4-N-Boc-aminobutyryl)aminophenyl]methyl-4-(2-carboxyethyl)-7-(N-Boc-6-aminohexyl)-3,4-dihydro-1H-1,4-benzodiazapine-2,5-dione ethyl ester, 1-(4-(4-N-Boc-aminobutyryl)aminophenyl)methyl-4-(2-carboxyethyl)-7-(N-Boc-6-aminohexyl)-3,4-dihydro-1H-1,4-benzodiazapine-2,5-dione ethyl ester, 1-(3-(4-N-Boc-aminobutyryl)aminophenyl)methyl-4-(2-carboxyethyl)-7-[4-(4-N-Boc-1-piperazine)phenyl]-3,4-dihydro-1H-1,4-benzodiazapine-2,5-dione ethyl ester, 1-(3-(4-N-Boc-aminobutyryl)aminophenyl)methyl-4-(3-phenyl-3-proprionate)-7-[4-(4-N-Boc-1-piperazine)phenyl]-3,4-dihydro-1H-1,4-benzodiazapine-2,5-dione ethyl ester, 1-(3-(4-N-Boc-aminobutyryl)aminophenyl)methyl-4-(3-phenyl-3-proprionate)-7-(N-Boc-6-aminohexyl)-3,4-dihydro-1H-1,4-benzodiazapine-2,5-dione ethyl ester, 1-[3-(3-N-Boc-aminopropionyl)aminophenyl]methyl-4-(2-carboxyethyl)-7-(N-Boc-6-aminohexyl)-3,4-dihydro-1H-1,4-benzodiazapine-2,5-dione ethyl ester, 1-[2-(3-N-Boc-aminopropionyl)aminophenyl]methyl-4-(2-carboxyethyl)-7-(N-Boc-6-aminohexyl)-3,4-dihydro-1H-1,4-benzodiazapine-2,5-dione ethyl ester, 1-(4-(3-N-Boc-aminopropionyl)aminophenyl)methyl-4-(2-carboxyethyl)-7-(N-Boc-6-aminohexyl)-3,4-dihydro-1H-1,4-benzodiazapine-2,5-dione ethyl ester, 1-(3-(3-N-Boc-aminopropionyl)aminophenyl)methyl-4-(2-carboxyethyl)-7-[4-(4-N-Boc-1-piperazine)phenyl]-3,4-dihydro-1H-1,4-benzodiazapine-2,5-dione ethyl ester, 1-(3-(3-N-Boc-aminopropionyl)aminophenyl)methyl-4-(3-phenyl-3-proprionate)-7-[4-(4-N-Boc-1-piperazine)phenyl]-3,4-dihydro-1H-1,4-benzodiazapine-2,5-dione ethyl ester, 1-(3-(3-N-Boc-aminopropionyl)aminophenyl)methyl-4-(3-phenyl-3-proprionate)-7-(N-Boc-6-aminohexyl)-3,4-dihydro-1H-1,4-benzodiazapine-2,5-dione ethyl ester.

c) 1-[3-(N-(4-aminobuturyl))aminophenyl]methyl-4-(2-carboxyethyl)-7-(6-aminohexyl)-3,4-dihydro-1H-1,4-benzodiazapine-2,5-dione trifluoroacetate was prepared using the method described in part (c) of example 1. Thus, 59 mgs (0.074 mmol) 1-[3-(4-N-Boc-aminobutyryl)aminophenyl]methyl-4-(2-carboxyethyl)-7-(N-Boc-6-aminohexyl)-3,4-dihydro-1H-1,4-benzodiazapine-2,5-dione ethyl ester yielded 50 mgs (99%) of 1-[3-(N-(4aminobuturyl))aminophenyl]methyl-4-(2-carboxyethyl)-7-(6-aminohexyl)-3,4-dihydro-1H-1,4-benzodiazapine-2,5-dione trifluoroacetate ($\frac{1}{2}$"C-18 reverse-phase column, eluting with a solvent gradient of 1:9 acetonitrile(0.1%TFA)/water (0.1% TFA) time 0 to 10 minutes, to 1:1 acetonitrile(0.1%TFA)/water (0.1% TFA) time 10 to 40 minutes, flow 10 mL/min, R$_t$=30.5 min, mu detection 254nM). HRMS (FAB) molecular ion m/z=538.3032 (cald. C$_{29}$H$_{39}$N$_5$O$_5$, 538.3030). $^1$H NMR (D2O) 7.21 (1H, bs, C6-H), 7.05–6.85 (5H, m, CH2ArH, C8-H), 6.52 (1H, bd, 3J$_{HH}$=8Hz, C9-H), 5.03 (1H,d, $^2J_{HH}$=16Hz, CHHAr), 4.47 (1H, d, 2J$_{HH}$=16Hz, CHHAr), 3.86 (1H, d, $^2J_{HH}$=15Hz, C3-H), 3.80 (1H, dt, $^3J_{HH}$=7Hz, $^2J_{HH}$=15Hz, NCHHCH2), 3.63 (1H, d, $^2J_{HH}$=15Hz, C3-H), 3.51 (1H, dt, $^3J_{HH}$=7Hz, $^2J_{HH}$=15Hz, NCHHCH2), 2.83 (2H, t, $^3J_{HH}$=8Hz, CH2NH2), 2.68 (2H, t, $^3J_{HH}$=8Hz, CH2NH2 ), 2.43 (2H, t, $^3J_{HH}$=7Hz), 2.3–2.2 (4H, m), 1.76 (2H, p, $^3J_{HH}$=7Hz, NCOCH$_2$CH$_2$), 1.35 (2H, p, $^3J_{HH}$=7Hz), 1.22 (2H, p, $^3J_{HH}$=7Hz), 1.1–0.9 (4H, m).

Using the above procedure, but substituting the appropriate 7-alkyl or aryl-3,4-dihydro-1H-1,4-benzodiazpine-2,4-dione bis-N-Boc diamino alkyl ester for 1-[3-(4-N-Boc-aminobutyryl)aminophenyl]methyl-4-(2-carboxyethyl)-7-(N-Boc-6-aminohexyl)-3,4-dihydro-1H-1,4-benzodiazapine-2,5-dione ethyl ester there may be prepared, for example, the following compounds:

1-[2-(4-aminobutyryl)aminophenyl]methyl-4-(2-carboxyethyl)-7-(6-aminohexyl)-3,4-dihydro-1H-1,4-benzodiazapine-2,5-dione bistrifluoroacetate,
1-(4-(4-aminobutyryl)aminophenyl)methyl-4-(2-carboxyethyl)-7-(6-aminohexyl)-3,4-dihydro-1H-1,4-benzodiazapine-2,5-dione bistrifluoroacetate,
1-(3-(4-aminobutyryl)aminophenyl)methyl-4-(2-carboxyethyl)-7-[4-(1-piperazine)phenyl]-3,4-dihydro-1H-1,4-benzodiazapine-2,5-dione bistrifluoroacetate,
1-(3-(4-aminobutyryl)aminophenyl)methyl-4-(3-phenyl-3-proprionate)-7-[4-(1-piperazine)phenyl]-3,4-dihydro-1H-1,4-benzodiazapine-2,5-dione bistrifluoroacetate,
1-(3-(4-aminobutyryl)aminophenyl)methyl-4-(3-phenyl-3-proprionate)-7-(6-aminohexyl)-3,4-dihydro-1H-1,4-benzodiazapine-2,5-dione bistrifluoroacetate,
1-[3-(3-aminopropionyl)aminophenyl]methyl-4-(2-carboxyethyl)-7-(6-aminohexyl)-3,4-dihydro-1H-1,4-benzodiazapine-2,5-dione bistrifluoroacetate,
1-[2-(3-aminopropionyl)aminophenyl]methyl-4-(2-carboxyethyl)-7-(6-aminohexyl)-3,4-dihydro-1H-1,4-benzodiazapine-2,5-dione bistrifluoroacetate,
1-(4-(3-aminopropionyl)aminophenyl)methyl-4-(2-carboxyethyl)-7-(6-aminohexyl)-3,4-dihydro-1H-1,4-benzodiazapine-2,5-dione bistrifluoroacetate,
1-(3-(3-aminopropionyl)aminophenyl)methyl-4-(2-carboxyethyl)-7-[4-(1-piperazine)phenyl]-3,4-dihydro-1H-1,4-benzodiazapine-2,5-dione bistrifluoroacetate,
1-(3-(3-aminopropionyl)aminophenyl)methyl-4-(3-phenyl-3-proprionate)-7-[4-(4-(1-piperazine)phenyl]-3,4-dihydro-1H-1,4-benzodiazapine-2,5-dione bistrifluoroacetate,
1-(3-(3-aminopropionyl)aminophenyl)methyl-4-(3-phenyl-3-proprionate)-7-(6-aminohexyl)-3,4-dihydro-1H-1,4-benzodiazapine-2,5-dione bistrifluoroacetate.

EXAMPLE 14

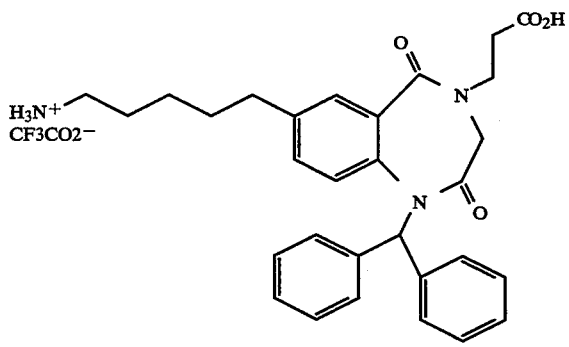

1-(diphenylmethyl)-4-(2-carboxyethyl)-7-(5-aminopentyl)-3,4-dihydro-1H-1,4-benzodiazepine-2,5-dione trifluoroacetate a) A magnetically stirred solution of 1.1 gram of N-(2-amino-5-iodobenzoyl)-B-alanine ethyl ester (3.1 mmol), prepared by the method shown in part (b) of example 1, 0.48 mL of 2,6-lutidine (4.1 mmol), 1.2 grams of chlorodiphenylmethane (4.7 mmol), and 10 mL of dimethylformamide was heated to 50° C. for 1 hour. The reaction mixture was allowed to cool to room temperature and concentrated in vacuo. The resulting oil was dissolved in 35 mL of methylene chloride and washed with 2×50 mL 10% citric acid, 1×50 mL water, dried over sodium sulfate, decanted and concentrated in vacuo. The resulting oil was further purified by column chromatography, using silica gel, eluting with a solvent gradient of 10/90 ethyl acetate/hexane to 25/75 ethyl acetate/hexane (TLC, SiO$_2$, 1:1 EtOAc/hexane, R$_f$=0.82, uv positive) to yield 0.92 gram (56%) of N-(2-diphenylmethylamino-5-iodobenzoyl)-b-alanine ethyl ester. $^1$H NMR (CDCl$_3$, dTMS) 8.40 (1H, d, $^3J_{HH}$=5Hz, NHCHAr$_2$), 7.56 (1H, d, $^3J_{HH}$=2Hz, ArH o-CON), 7.18–7.36 (11H, m, $^4J_{HH}$=2Hz, ArH Ph, ArH p-CON), 6.73 (1H, t, $^3J_{HH}$=6Hz, NHCH$_2$), 6.29 (1H, d, $^3J_{HH}$=9Hz, ArH m-CON), 5.52 (1H, d, $^3J_{HH}$=5Hz, CHNH), 4.15 (2H, q, $^3J_{HH}$=7Hz, OCH$_2$), 3.61 (2H, q, $^3J_{HH}$=6Hz, CH$_2$NH), 2.58 (2H, t, $^3J_{HH}$=6Hz, CH$_2$CO), 1.25 (3H, t, $^3J_{HH}$=6Hz, CH$_3$CH$_2$O).

Using the above procedure, but substituting the appropriate alkyl or aryl halide there may be prepared, for example, the following compounds:

N-(2-(1-napthyl)methylamino-5-iodobenzoyl)-B-alanine ethyl ester,
N-(2-(2-napthyl)methylamino-5-iodobenzoyl)-b-alanine ethyl ester,
N-(2-(p-phenoxybenzyl)amino-5-iodobenzoyl)-b-alanine ethyl ester,
N-(2-(m-phenoxybenzyl)amino-5-iodobenzoyl)-b-alanine ethyl ester,
N-(2-(p-trifluoromethylbenzyl)amino-5-iodobenzoyl)-b-alanine ethyl ester,
N-(2-(ethyl-5-valeroyl)amino-5-iodobenzoyl)-b-alanine ethyl ester,
N-(2-(p-methoxybenzyl)amino-5-iodobenzoyl)-b-alanine ethyl ester,
Methyl 3(S)-N-(2-(2-methylnapthyl)amino-5-iodobenzoyl)-3-amino-3-methylpropionate,
Methyl 3(R)-N-(2-(2-napthyl)methylamino-5-iodobenzoyl)-3-amino-3-methylpropionate,
Methyl (+/−)-N-(2-(2-napthyl)methylamino-5-iodobenzoyl)-3-amino-3-methylpropionate,
Methyl 3(S)-N-(2-(2-napthyl)methylamino-5-iodobenzoyl)-3-amino-3-phenyl propionate,
Methyl 3(R)-N-(2-(2-napthyl)methylamino-5-iodobenzoyl)-3-amino-3-phenylpropionate,
Methyl (+/−)-N-(2-(2-napthyl)methylamino-5-iodobenzoyl)-3-amino-3-phenylpropionate, b) To a magnetically stirred solution of 0.93 gram of N-(2-diphenylmethylamino-5-iodobenzoyl)-B-alanine ethyl ester (1.8 mmol) in 15 mL of methylene chloride and 15 mL water, was added 183 mL A-bromoacetylbromide (2.1 mmol). The reaction mixture was stirred overnight. The layers were separated, the aqueous fraction was washed 1×15 mL methylene chloride, and the two methylene chloride fractions were combined and washed with 1×20 mL of saturated sodium bicarbonate, dried over sodium sulfate, filtered and concentrated in vacuo. The resulting residue was dissolved in 7 mL of dimethylformamide and added, via an addition funnel, to a slurry of 57 mgs of 95% sodium hydride (2.2 mmol) in 5 mL dimethylformamide that was cooled at 0° C. After 2 hours, the mixture was poured over 40 mL of ice cooled 10% citric acid and extracted 3×40 mL methylene chloride. The combined organic layers were washed with 2×50 mL of 10% citric acid and 1×50 mL water, dried over sodium sulfate, decanted, concentrated in vacuo and further purified by column chromatography, using silica gel, eluting with a 1:1 mixture of ethyl acetate and hexane (TLC, SiO$_2$, 1:1 EtOAc/hexane, R$_f$=0.61, uv positive) to yield 474 mgs (48%) of 1-(diphenylmethyl)-4-(2-carboxyethyl)-8-iodo-3,4-dihydro-1H-1,4-benzodiazepine-2,5-dione ethyl ester. $^1$H NMR (CDCl$_3$, dTMS) 8.03 (1H, d, $^3J_{HH}$=2Hz, ArH o-CON), 7.45 (1H, dd, $^3J_{HH}$=2Hz, $^3J_{HH}$=9Hz, ArH p-CON), 7.1–7.4 (1H, m, $^4J_{HH}$=2Hz, ArH Ph), 6.79 (1H, d, $^3J_{HH}$=9Hz, ArH m-CON), 6.70 (1H, s), 4.13 (2H, q, $^3J_{HH}$=7Hz, OCH$_2$), 3.98 (2H, dd, $^3J_{HH}$=100Hz, $^3J_{HH}$=15Hz, COCH$_2$N), 3.86 (2H, dm, $^3J_{HH}$=62Hz, $^3J_{HH}$=8Hz, CH$_2$N), 2.58 (2H, dm, $^3J_{HH}$=40Hz, $^3J_{HH}$=8Hz, CH$_2$CO), 1.27 (3H, t, $^3J_{HH}$=7Hz, CH$_3$CH$_2$O). $^{13}$C NMR (CDCl$_3$) 171.2, 168.0, 165.6, 139.9, 139.3, 138.8, 138.1, 137.5, 132.0, 129.1, 128.5, 128.4, 128.0, 128.0, 128.0, 127.9, 127.6, 125.4, 90.6, 67.2, 60.8, 53.1, 45.0, 32.6, 14.2.

Using the above procedure, but substituting the appropriate N-(2-amino-5-iodobenzoyl)-B-alanine ethyl ester for N-(2-diphenylmethylamino-5-iodobenzoyl)-B-alanine ethyl ester there may be prepared, for example, the following compounds:

1-(1-napthyl)methyl-4-(2-carboxyethyl)-7-iodo-3,4-dihydro-1H-1,4-benzodiazepine-2,5-dione ethyl ester,
1-(2-napthyl)methyl-4-(2-carboxyethyl)-7-iodo-3,4-dihydro-1H-1,4-benzodiazepine-2,5-dione ethyl ester,
1-(m-phenoxybenzyl)-4-(2-carboxyethyl)-7-iodo-3,4-dihydro-1H-1,4-benzodiazepine-2,5-dione ethyl ester,
1-(p-phenoxybenzyl)-4-(2-carboxyethyl)-7-iodo-3,4-dihydro-1H-1,4-benzodiazepine-2,5-dione ethyl ester,
1-(p-trifluoromethylbenzyl)-4-(2-carboxyethyl)-7-iodo-3,4-dihydro-1H-1,4-benzodiazepine-2,5-dione ethyl ester,
1-(ethyl-5-valeroyl)-4-(2-carboxyethyl)-7-iodo-3,4-dihydro-1H-1,4-benzodiazepine-2,5-dione ethyl ester,
1-(p-methoxybenzyl)-4-(2-carboxyethyl)-7-iodo-3,4-dihydro-1H-1,4-benzodiazepine-2,5-dione ethyl ester,
1-(p-methylmethylbenzoyl)-4-(2-carboxyethyl)-7-iodo-3,4-dihydro-1H-1,4-benzodiazepine-2,5-dione ethyl ester,
1-(2-napthyl)methyl-4-(3(S)-butanoate)-7-iodo-3,4-dihydro-1H-1,4-benzodiazepine-2,5-dione methyl ester,
1-(2-napthyl)methyl-4-(3(R)-butanoate)-7-iodo-3,4-dihydro-1H-1,4-benzodiazepine-2,5-dione methyl ester,
1-(2-napthyl)methyl-4-((+/−)3-butanoate)-7-iodo-3,4-dihydro-1H-1,4-benzodiazepine-2,5-dione methyl ester,
1-(2-napthyl)methyl-4-(3(S)-phenyl-3-proprionate)-7-iodo-3,4-dihydro-1H-1,4-benzodiazepine-2,5-dione methyl ester,
1-(2-napthyl)methyl-4-(3(R)-phenyl-3-proprionate)-7-iodo-3,4-dihydro-1H-1,4-benzodiazepine-2,5-dione methyl ester,
1-(2-napthyl)methyl-4-((+/−)3-phenyl-3-proprionate)-7-iodo-3,4-dihydro-1H-1,4-benzodiazepine-2,5-dione methyl ester.

c) To a magnetically stirred solution of 208 mgs of 1-(diphenylmethyl)-4-(2-carboxyethyl)-7-iodo-3,4-dihydro-1H-1,4-benzodiazepine-2,5-dione ethyl ester (0.37 mmol) in 6 mL ethyl acetate, degassed of oxygen, under an atmosphere of nitrogen, was added 134 mgs of N-boc-5-amino-1-pentyne (0.74 mmol), prepared as described in part (e) of example 1, 10 mgs of bistriphenylphosphite palladium dichloride (0.014 mmol), 5 mgs of cuprous iodide (0.026 mmol) and 250 uL of triethylamine (1.75 mmol). After 1.5 hours, the reaction mixture was diluted with 35 mL of ethyl acetate and washed with 1×15 mL 5% EDTA.Na$_2$, dried over sodium sulfate, decanted, concentrated in vacuo, and further purified by column chromatography, using silica gel, eluting with a 1:1 mixture of ethyl acetate and hexane (TLC, SiO$_2$, 1:1 EtOAc/hexane, R$_f$=0.46, uv positive) to yield 131 mgs (60%) of 1-(diphenylmethyl)-4-(2-carboxyethyl)-8-(N-boc-5-amino-1-pentynl)-3,4-dihydro-1H-1,4-benzodiazepine-2,5-dione ethyl ester. $^1$H NMR (CDCl$_3$, TMS) 7.71 (1H, d, $^4J_{HH}$=2Hz, ArH o-CON), 7.10–7.36 (1 1H, m, $^3J_{HH}$=2Hz, ArH Ph, ArH p-CON), 6.94 (1H, d, $^4J_{HH}$=9Hz, ArH p-CON), 6.67 (1H, s, CHAr$_2$), 4.78 (1H, s, NHBoc), 4.10 (2H, q, $^3J_{HH}$=7Hz, CH$_2$O) 3.95 (2H, dd, $^2J_{HH}$=106Hz, $^2J_{HH}$=15Hz, COCH$_2$CN), 3.82 (2H, dm, $^{2,3}J_{HH}$=7Hz, $^{2,3}J_{HH}$=59Hz, CH$_2$N), 3.19 (2H, q, $^3J_{HH}$=3Hz, CH$_2$NHBoc), 2.54 (2H, dm, $^3J_{HH}$=7Hz, $^3J_{HH}$=21Hz, CH$_2$CO), 2.37 (2H, t, $^3J_{HH}$=7Hz, CH$_2$CC), 1.71 (2H, m, $^3J_{HH}$=7Hz, CH$_2$CH$_2$CH$_2$), 1.38 (9H), s, CH$_3$ Boc), 1.22 (3H, t, $^3J_{HH}$=7Hz, CH$_3$CH$_2$O).

Using the above procedure, but substituting the appropriate 7-iodo-3,4-dihydro-1H-1,4-benzodiazepine-2,5-dione for 1-(diphenylmethyl)-4-(2-carboxyethyl)-7-iodo-3,4-dihydro-1H-1,4-benzodiazepine-2,5-dione ethyl ester and alkyne for N-boc-5-amino-1-pentyne there may be prepared, for example, the following compounds:

1-(diphenylmethyl)-4-(2-carboxyethyl)-7-(N-boc-6-amino-1-hexynl)-3,4-dihydro-1H-1,4-benzodiazepine-2,5-dione ethyl ester,
1-(diphenylmethyl)-4-(2-carboxyethyl)-7-(N-boc-4-amino-1-butynl)-3,4-dihydro-1H-1,4-benzodiazepine-2,5-dione ethyl ester,
1-(1-napthyl)methyl-4-(2-carboxyethyl)-7-(N-boc-5-amino-1-pentynl)-3,4-dihydro-1H-1,4-benzodiazepine-2,5-dione ethyl ester,
1-(1-napthyl)methyl-4-(2-carboxyethyl)-7-(N-boc-6-amino-1-hexynl)-3,4-dihydro-1H-1,4-benzodiazepine-2,5-dione ethyl ester,
1-(2-napthyl)methyl-4-(2-carboxyethyl)-7-(N-boc-5-amino-1-pentynl)-3,4-dihydro-1H-1,4-benzodiazepine-2,5-dione ethyl ester,
1-(2-napthyl)methyl-4-(2-carboxyethyl)-7-(N-boc-6-amino-1-hexynl)-3,4-dihydro-1H-1,4-benzodiazepine-2,5-dione ethyl ester,
1-(p-phenoxybenzl)-4-(2-carboxyethyl)-7-(N-boc-5-amino-1-pentynl)-3,4-dihydro-1H-1,4-benzodiazepine-2,5-dione ethyl ester,
1-(p-phenoxybenzyl)-4-(2-carboxyethyl)-7-(N-boc-6-amino-1-hexynl)-3,4-dihydro-1H-1,4-benzodiazepine-2,5-dione ethyl ester,
1-(m-phenoxybenzyl)-4-(2-carboxyethyl)-7-(N-boc-5-amino-1-pentynl)-3,4-dihydro-1H-1,4-benzodiazepine-2,5-dione ethyl ester,
1-(m-phenoxybenzyl)-4-(2-carboxyethyl)-7-(N-boc-6-amino-1-hexynl)-3,4-dihydro-1H-1,4-benzodiazepine-2,5-dione ethyl ester,
1-(p-trifluoromethylbenzyl)-4-(2-carboxyethyl)-7-(N-boc-5-amino-1-pentynl)-3,4-dihydro-1H-1,4-benzodiazepine-2,5-dione ethyl ester,
1-(p-trifluoromethylbenzyl)-4-(2-carboxyethyl)-7-(N-boc-6-amino-1-hexynl)-3,4-dihydro-1H-1,4-benzodiazepine-2,5-dione ethyl ester,
1-(ethyl-5-valeroyl)-4-(2-carboxyethyl)-7-(N-boc-5-amino-1-pentynl)-3,4-dihydro-1H-1,4-benzodiazepine-2,5-dione ethyl ester, 1-(ethyl-5-valeroyl)-4-(2-carboxyethyl)-7-(N-boc-6-amino-1-hexyl)-3,4-dihydro-1H-1,4-benzodiazepine-2,5-dione ethyl ester, 1-(p-methoxybenzyl)-4-(2-carboxyethyl)-7-(N-boc-5-amino-1-pentynl)-3,4-dihydro-1H-1,4-benzodiazepine-2,5-dione ethyl ester, 1-(p-methoxybenzyl)-4-(2-carboxyethyl)-7-(N-boc-6-amino-1-hexynl)-3,4-dihydro-1H-1,4-benzodiazepine-2,5-dione ethyl ester, 1-(p-methylmethylbenzoyl)-4-(2-carboxyethyl)-7-(N-boc-5-amino-1-pentynl)-3,4-dihydro-1H-1,4-benzodiazepine-2,5-dione ethyl ester, 1-(p-methylmethylbenzoyl)-4-(2-carboxyethyl)-7-(N-boc-6-amino-1-hexynl)-3,4-dihydro-1H-1,4-benzodiazepine-2,5-dione ethyl ester, 1-(2-napthyl)methyl-4-(3(S)-butanoate)-7-(N-boc-5-amino-1-pentynl)-3,4-dihydro-1H-1,4-benzodiazepine-2,5-dione methyl ester, 1-(2-napthyl)methyl-4-(3(S)-butanoate)-7-(N-boc-6-amino-1-hexyl)-3,4-dihydro-1H-1,4-benzodiazepine-2,5-dione methyl ester, 1-(2-napthyl)methyl-4-(3(R)-butanoate)-7-(N-boc-5-amino-1-pentynl)-3,4-dihydro-1H-1,4-benzodiazepine-2,5-dione methyl ester, 1-(2-napthyl)methyl-4-(3(R)-butanoate)-7-(N-boc-6-amino-1-hexynl)-3,4-dihydro-1H-1,4-benzodiazepine-2,5-dione methyl ester, 1-(2-napthyl)methyl-4-((+/−)3-butanoate)-7-(N-boc-5-amino-1-pentynl)-3,4-dihydro-1H-1,4-benzodiazepine-2,5-dione methyl ester, 1-(2-napthyl)methyl-4-((+/−)3-butanoate)-7-(N-boc-6-amino-1-hexynl)-3,4-dihydro-1H-1,4-benzodiazepine-2,5-dione methyl ester, 1-(2-napthyl)methyl-4-(3(S)-phenyl-3-proprionate)-7-(N-boc-5-amino-1-pentynl)-3,4-dihydro-1H-1,4-benzodiazepine-2,5-dione methyl ester, 1-(2-napthyl)methyl-4-(3(S)-phenyl-3-proprionate)-7-(N-boc-6-amino-1-hexynl)-3,4-dihydro-1H-1,4-benzodiazepine-2,5-dione methyl ester, 1-(2-napthyl)methyl-4-(3(R)-phenyl-3-proprionate)-7-(N-boc-5-amino-1-pentynl)-3,4-dihydro-1H-1,4-benzodiazepine-2,5-dione methyl ester, 1-(2-napthyl)methyl-4-(3(R)-phenyl-3-proprionate)-7-(N-boc-6-amino-1-hexynl)-3,4-dihydro-1H-1,4-benzodiazepine-2,5-dione methyl ester, 1-(2-napthyl)methyl-4-((+/−)3-phenyl-3-proprionate)-7-(N-boc-5-amino-1-pentynl)-3,4-dihydro-1H-1,4-benzodiazepine-2,5-dione methyl ester, 1-(2-napthyl)methyl-4-((+/−)3-phenyl-3-proprionate)-7-(N-boc-6-amino-1-hexynl)-3,4-dihydro-1H-1,4-benzodiazepine-2,5-dione methyl ester.

d) To a magnetically stirred solution of 66 mgs of 1-(diphenylmethyl)-4-(2-carboxyethyl)-8-(N-boc-5-amino-1-pentynl)-3,4-dihydro-1H-1,4-benzodiazepine-2,5-dione ethyl ester (0.11 mmol) in 2 mL ethyl acetate, covered with an atmosphere of hydrogen, was added 23 mgs of palladium/carbon catalyst. The mixture was stirred for 1 hr. before filtering the mixture through Celite® and concentrating in vacuo to yield quantitative yield of 1-(diphenylmethyl)-4-(2-carboxyethyl)-8-(N-boc-5-aminopentyl)-3,4-dihydro-1H-1,4-benzodiazepine-2,5-dione ethyl ester. $^1$H NMR (CDCl$_3$, dTMS) 7.54 (1H, d, $^4J_{HH}$=2Hz, Ar-H o-CON), 6.90–7.38 (12H, m, $^3J_{HH}$=2Hz, Ar-H Ph, ArH p-CON, ArH m-CON), 6.54 (1H, s, NCHAr$_2$), 4.64 (1H, s, NHBoc), 4.12 (2H, q, $^3J_{HH}$=7Hz, CH$_2$O) 3.97 (2H, dd, $^2J_{HH}$=129Hz, $^2J_{HH}$=15Hz, COCH$_2$CN), 3.82 (2H, dm, $^{2,3}J_{HH}$=6Hz, $^{2,3}J_{HH}$=75Hz, CH$_2$N), 3.07 (2H, q, $^3J_{HH}$=3Hz, CH$_2$NHBoc), 2.55 (4H, dm, t, $^3J_{HH}$=7Hz, $^3J_{HH}$=30Hz, $^3J_{HH}$=7Hz, CH$_2$CO, CH$_2$Ar), 1.3–1.6 (4H, m, m, $^3J_{HH}$=7Hz, $^3J_{HH}$=7Hz, CH$_2$CH$_2$Ar, CH$_2$CH$_2$NHBoc), 1.1–1.3 (14H, s, m, t, $^3J_{HH}$=7Hz, $^3J_{HH}$=7Hz, CH$_3$ Boc, CH$_2$CH$_2$CH$_2$NHBoc, CH$_3$CH$_2$).

Using the above procedure, but substituting the appropriate 4-(2-carboxyethyl)-7-(N-boc-amino-1-alkynl)-3,4-dihydro-1H-1,4-benzodiazepine-2,5-dione ethyl ester for 1-(diphenylmethyl)-4-(2-carboxyethyl)-7-(N-boc-5-amino-1-pentynl)-3,4-dihydro-1H-1,4-benzodiazepine-2,5-dione ethyl ester there may be prepared, for example, the following compounds:

1-(diphenylmethyl)-4-(2-carboxyethyl)-7-(N-boc-6-aminohexyl)-3,4-dihydro-1H-1,4-benzodiazepine-2,5-dione ethyl ester, 1-(diphenylmethyl)-4-(2-carboxyethyl)-7-(N-boc-4-aminobutyl)-3,4-dihydro-1H-1,4-benzodiazepine-2,5-dione ethyl ester, 1-(1-napthyl)methyl-4-(2-carboxyethyl)-7-(N-boc-5-aminopentyl)-3,4-dihydro-1H-1,4-benzodiazepine-2,5-dione ethyl ester, 1-(1-napthyl)methyl-4-(2-carboxyethyl)-7-(N-boc-6-aminohexyl)-3,4-dihydro-1H-1,4-benzodiazepine-2,5-dione ethyl ester, 1-(2-napthyl)methyl-4-(2-carboxyethyl)-7-(N-boc-5-aminopentyl)-3,4-dihydro-1H-1,4-benzodiazepine-2,5-dione ethyl ester, 1-(2-napthyl)methyl-4-(2-carboxyethyl)-7-(N-boc-6-aminohexyl)-3,4-dihydro-1H-1,4-benzodiazepine-2,5-dione ethyl ester, 1-(p-phenoxybenzyl)-4-(2-carboxyethyl)-7-(N-boc-5-aminopentyl)-3,4-dihydro-1H-1,4-benzodiazepine-2,5-dione ethyl ester, 1-(p-phenoxybenzyl)-4-(2-carboxyethyl)-7-(N-boc-6-aminohexyl)-3,4-dihydro-1H-1,4-benzodiazepine-2,5-dione ethyl ester, 1-(m-phenoxybenzyl)-4-(2-carboxyethyl)-7-(N-boc-5-aminopentyl)-3,4-dihydro-1H-1,4-benzodiazepine-2,5-dione ethyl ester, 1-(m-phenoxybenzyl)-4-(2-carboxyethyl)-7-(N-boc-6-aminohexyl)-3,4-dihydro-1H-1,4-benzodiazepine-2,5-dione ethyl ester, 1-(p-trifluoromethylbenzyl)-4-(2-carboxyethyl)-7-(N-boc-5-aminopentyl)-3,4-dihydro-1H-1,4-benzodiazepine-2,5-dione ethyl ester, 1-(p-trifluoromethylbenzyl)-4-(2-carboxyethyl)-7-(N-boc-6-amino hexyl)-3,4-dihydro-1H-1,4-benzodiazepine-2,5-dione ethyl ester, 1-(ethyl-5-valeroyl)-4-(2-carboxyethyl)-7-(N-boc-5-aminopentyl)-3,4-dihydro-1H-1,4-benzodiazepine-2,5-dione ethyl ester, 1-(ethyl-5-valeroyl)4-(2-carboxyethyl)-7-(N-boc-6-aminohexy l)-3,4-dihydro-1H-1,4-benzodiazepine-2,5-dione ethyl ester, 1-(p-methoxybenzyl)-4-(2-carboxyethyl)-7-(N-boc-5-aminopentyl)-3,4-dihydro-1H-1,4-benzodiazepine-2,5-dione ethyl ester, 1-(p-methoxybenzyl)-4-(2-carboxyethyl)-7-(N-boc-6-aminohexyl)-3,4-dihydro-1H-1,4-benzodiazepine-2,5-dione ethyl ester, 1-(p-methylmethylbenzoyl)-4-(2-carboxyethyl)-7-(N-boc-5-aminopentyl)-3,4-dihydro-1H-1,4-benzodiazepine-2,5-dione ethyl ester, 1-(p-methylmethylbenzoyl)-4-(2-carboxyethyl)-7-(N-boc-6-amino hexyl)-3,4-dihydro-1H-1,4-benzodiazepine-2,5-dione ethyl ester, 1-(2-napthyl)methyl-4-(3(S)-butanoate)-7-(N-boc-5-amino-1-pentyl)-3,4-dihydro-1H-1,4-benzodiazepine-2,5-dione methyl ester, 1-(2-napthyl)methyl-4-(3(S)-butanoate)-7-(N-boc-6-amino-1-hexyl)-3,4-dihydro-1H-1,4-benzodiazepine-2,5-dione methyl ester, 1-(2-napthyl)methyl-4-(3(R)-butanoate)-7-(N-boc-5-amino-1-pentyl)-3,4-dihydro-1H-1,4-benzodiazepine-2,5-dione methyl ester, 1-(2-napthyl)methyl-4-(3(R)-butanoate)-7-(N-boc-6-amino-1-hexyl)-3,4-dihydro-1H-1,4-benzodiazepine-2,5-dione methyl ester, 1-(2-napthyl)methyl-4-((+/−)3-butanoate)-7-(N-boc-5-amino-1-pentyl)-3,4-dihydro-1H-1,4-benzodiazepine-2,5-dione methyl ester, 1-(2-napthyl)methyl-4-((+/−)3-butanoate)-7-(N-boc-6-amino-1-hexyl)-3,4-dihydro-1H-1,4-benzodiazepine-2,5-dione methyl ester, 1-(2-napthyl)methyl-4-(3(S)-phenyl-3-proprionate)-7-(N-boc-5-amino-1-pentyl)-3,4-dihydro-1H-1,4-benzodiazepine-2,5-dione methyl ester, 1-(2-napthyl)methyl-4-(3(S)-phenyl-3-proprionate)-7-(N-boc-6-amino-1-hexyl)-3,4-dihydro-1H-1,4-benzodiazepine-2,5-dione methyl ester, 1-(2-napthyl)methyl-4-(3(R)-phenyl-3-proprionate)-7-(N-boc-5-amino-1-pentyl)-3,4-dihydro-1H-1,4-benzodiazepine-2,5-dione methyl ester, 1-(2-napthyl)methyl-4-(3(R)-phenyl-3-proprionate)-7-(N-boc-6-amino-1-hexyl)-3,4-dihydro-1H-1,4-benzodiazepine-2,5-dione methyl ester, 1-(2-napthyl)methyl-1((+/−)3-phenyl-3-proprionate)-7-(N-boc-5-amino-1-pentyl)-3,4-dihydro-1H-1,4-benzodiazepine-2,5-dione methyl ester, 1-(2-napthyl)methyl-4-((+/−)3-phenyl-3-proprionate)-7-(N-boc-6-amino-1-hexyl)-3,4-dihydro-1H-1,4-benzodiazepine-2,5-dione methyl ester.

e) To a solution of 33 mgs of 1-(diphenylmethyl)-4-(2-carboxyethyl)-7-(N-boc-5-aminopentyl)-3,4-dihydro-1H-1,4-benzodiazepine-2,5-dione ethyl ester (0.05 mmol) in 2 mL ethyl acetate was added 0.4 mL triethylsilane (2.5 mmol) and 6 mL of saturated HCl/ethyl acetate at 5° C. After 1 hour at 5° C. the mixture was concentrated in vacuo and diluted with 2 mL of methanol. To the methanolic solution was added 2 mL of 2N sodium hydroxide. After 1 hour, the reaction was quenched with ½ mL of acetic acid, concentrated in vacuo, diluted with 5 mL of methanol and water and purified by high pressure liquid chromatography, using a ½" C-18 reverse phase column, eluting with a solvent gradient of 30:70 methanol (0.1% trifluoroacetic acid)/water (0.1% trifluoroacetic acid), time 0 to 10 minutes, to 70:30 methanol (0.1% trifluoroacetic acid)/water (0.1% trifluoroacetic acid), time 10 minutes to 40 minutes, flow=10 mL/min. ($R_t$=37.5 min., uv detection 254 nm) to yield 14 mgs (46%)of 1-(diphenylmethyl)-4-(2-carboxyethyl)-7-(5-aminopentyl)-3,4-dihydro-1H-1,4-benxodiazepine-2,5-dione trifluoroacetate. HRMS (FAB) molecular ion m/z=500.2529 (calc. $C_{30}N_3O_4H_{33}$, 500.2549). $^1$H NMR (CDCl$_3$, TMS) 6.60–7.20 (13H, m, $^3J_{HH}$=2Hz, ArH Ph, ArH p-CON, ArH o-CON, ArH m-CON), 6.33 (1H, s, NCH-Ar$_2$), 3.65 (2H, dd, $^2J_{HH}$=113Hz, $^2J_{HH}$=15Hz, COCH$_2$CN), 3.50 (2H, dm, $^{2,3}J_{HH}$=7Hz, $^{2,3}J_{HH}$=59Hz, CH$_2$N), 2.66 (2H, t, $^3J_{HH}$=8Hz, CH$_2$NH$_2$) 2.22–2.39 (4H, m, t, $^3J_{HH}$=6Hz, $^3J_{HH}$=8Hz, CH$_2$CO, CH$_2$Ar), 1.20–1.33 (4H, m, m, $^3J_{HH}$=7Hz, CH$_2$CH$_2$Ar, CH$_2$CH$_2$NH$_2$), 1.0 (2H, m, $^3J_{HH}$=7Hz, CH$_2$CH$_2$CH$_2$NH$_2$).

Using the above procedure, but substituting the appropriate 3,4-dihydro-1H-1,4-benzodiazepine-2,5-dione for 1-(diphenylmethyl)-4-(2-carboxyethyl)-7-(N-boc-5-aminopentyl)-3,4-dihydro-1H-1,4-benzodiazepine- 2,5-dione ethyl ester there may be prepared, for example, the following compounds:

1-(diphenylmethyl)-4-(2-carboxyethyl)-7-(6-aminohexyl)-3,4-dihydro-1H-1,4-benzodiazepine-2,5-dione trifluoroacetate, 1-(diphenylmethyl)-4-(2-carboxyethyl)-7-(4-aminobutyl)-3,4-dihydro-1H-1,4-benzodiazepine-2,5-dione trifluoroacetate, 1-(1-napthyl)methyl-4-(2-carboxyethyl)-7-(5-aminopentyl)-3,4-dihydro-1H-1,4-benzodiazepine-2,5-dione trifluoroacetate, 1-(1-napthyl)methyl-4-(2-carboxyethyl)-7-(6-aminohexyl)-3,4-dihydro-1H-1,4-benzodiazepine-2,5-dione trifluoroacetate, 1-(2-napthyl)methyl-4-(2-carboxyethyl)-7-(5-aminopentyl)-3,4-dihydro-1H-1,4-benzodiazepine-2,5-dione trifluoroacetate, 1-(2-napthyl)methyl-4-(2-carboxyethyl)-7-(6-aminohexyl)-3,4-dihydro-1H-1,4-benzodiazepine-2,5-dione trifluoroacetate, 1-(p-phenoxybenzyl)-4-(2-carboxyethyl)-7-(5-aminopentyl)-3,4-dihydro-1H-1,4-benzodiazepine-2,5-dione trifluoroacetate, 1-(p-phenoxybenzyl)-4-(2-carboxyethyl)-7-(6-aminohexyl)-3,4-dihydro-1H-1,4-benzodiazepine-2,5-dione trifluoroacetate, 1-(m-phenoxybenzyl)-4-(2-carboxyethyl)-7-(5-aminopentyl)-3,4-dihydro-1H-1,4-benzodiazepine-2,5-dione trifluoroacetate, 1-(m-phenoxybenzyl)-4-(2-carboxyethyl)-7-(6-aminohexyl)-3,4-dihydro-1H-1,4-benzodiazepine-2,5-dione trifluoroacetate, 1-(p-trifluoromethylbenzyl)-4-(2-carboxyethyl)-7-(5-aminopentyl)-3,4-dihydro-1H-1,4-benzodiazepine-2,5-dione trifluoroacetate, 1-(p-trifluoromethylbenzyl)-4-(2-carboxyethyl)-7-(6-aminohexyl)-3,4-dihydro-1H-1,4-benzodiazepine-2,5-dione trifluoroacetate, 1-(ethyl-5-valeroyl)-4-(2-carboxyethyl)-7-(5-aminopentyl)-3,4-dihydro-1H-1,4-benzodiazepine-2,5-dione trifluoroacetate, 1-(ethyl-5-valeroyl)-4-(2-carboxyethyl)-7-(6-aminohexyl)-3,4-dihydro-1H-1,4-benzodiazepine-2,5-dione trifluoroacetate, 1-(p-methoxybenzyl)-4-(2-carboxyethyl)-7-(5-aminopentyl)-3,4-dihydro-1H-1,4-benzodiazepine-2,5-dione trifluoroacetate, 1-(p-methoxybenzyl)-4-(2-carboxyethyl)-7-(6-aminohexyl)-3,4-dihydro-1H-1,4-benzodiazepine-2,5-dione trifluoroacetate, 1-(p-methylmethylbenzoyl)-4-(2-carboxyethyl)-7-(5-aminopentyl)-3,4-dihydro-1H-1,4-benzodiazepine-2,5-dione trifluoroacetate, 1-(p-methylmethylbenzoyl)-4-(2-carboxyethyl)-7-(6-aminohexyl)-3,4-dihydro-1H-1,4-benzodiazepine-2,5-dione trifluoroacetate, 1-(diphenylmethyl)-4-(2-carboxyethyl)-7-(6-amino-1-hexynl)-3,4-dihydro-1H-1,4-benzodiazepine-2,5-dione trifluoroacetate, 1-(diphenylmethyl)-4-(2-carboxyethyl)-7-(4-amino-1-butynl)-3,4-dihydro-1H-1,4-benzodiazepine-2,5-dione trifluoroacetate, 1-(1-napthyl)methyl-4-(2-carboxyethyl)-7-(5-amino-1-pentynl)-3,4-dihydro-1H-1,4-benzodiazepine-2,5-dione trifluoroacetate,
1-(1-napthyl)methyl-4-(2-carboxyethyl)-7-(6-amino-1-hexynl)-3,4-dihydro-1H-1,4-benzodiazepine-2,5-dione trifluoroacetate,
1-(2-napthyl)methyl-4-(2-carboxyethyl)-7-(5-amino-1-pentynl)-3,4-dihydro-1H-1,4-benzodiazepine-2,5-dione trifluoroacetate,
1-(2-napthyl)methyl-4-(2-carboxyethyl)-7-(6-amino-1-hexynl)-3,4-dihydro-1H-1,4-benzodiazepine-2,5-dione trifluoroacetate,
1-(p-phenoxybenzyl)-4-(2-carboxyethyl)-7-(5-amino-1-pentynl)-3,4-dihydro-1H-1,4-benzodiazepine-2,5-dione trifluoroacetate,
1-(p-phenoxybenzyl)-4-(2-carboxyethyl)-7-(6-amino-1-hexynl)-3,4-dihydro-1H-1,4-benzodiazepine-2,5-dione trifluoroacetate,
1-(m-phenoxybenzyl)-4-(2-carboxyethyl)-7-(5-amino-1-pentynl)-3,4-dihydro-1H-1,4-benzodiazepine-2,5-dione trifluoroacetate,
1-(m-phenoxybenzyl)-4-(2-carboxyethyl)-7-(6-amino-1-hexynl)-3,4-dihydro-1H-1,4-benzodiazepine-2,5-dione trifluoroacetate,
1-(p-trifluoromethylbenzyl)-4-(2-carboxyethyl)-7-(5-amino-1-pentynl)-3,4-dihydro-1H-1,4-benzodiazepine-2,5-dione trifluoroacetate,
1-(p-trifluoromethylbenzyl)-4-(2-carboxyethyl)-7-(6-amino-1-hexynl)-3,4-dihydro-1H-1,4-benzodiazepine-2,5-dione trifluoroacetate,
1-(ethyl-5-valeroyl)-4-(2-carboxyethyl)-7-(5-amino-1-pentynl)-3,4-dihydro-1H-1,4-benzodiazepine-2,5-dione trifluoroacetate,
1-(ethyl-5-valeroyl)-4-(2-carboxyethyl)-7-(6-amino-1-hexynl)-3,4-dihydro-1H-1,4-benzodiazepine-2,5-dione trifluoroacetate,
1-(p-methoxybenzyl)-4-(2-carboxyethyl)-7-(5-amino-1-pentynl)-3,4-dihydro-1H-1,4-benzodiazepine-2,5-dione trifluoroacetate,
1-(p-methoxybenzyl)-4-(2-carboxyethyl)-7-(6-amino-1-hexynl)-3,4-dihydro-1H-1,4-benzodiazepine-2,5-dione trifluoroacetate,
1-(p-methylmethylbenzoyl)-4-(2-carboxyethyl)-7-(5-amino-1-pentynl)-3,4-dihydro-1H-1,4-benzodiazepine-2,5-dione trifluoroacetate,
1-(p-methylmethylbenzoyl)-4-(2-carboxyethyl)-7-(6-amino-1-hexynl)-3,4-dihydro-1H-1,4-benzodiazepine-2,5-dione trifluoroacetate,
1-(2-napthyl)methyl-4-(3(S)-butanoate)-7-(5-amine-1-pentyl)-3,4-dihydro-1H-1,4-benzodiazepine-2,5-dione trifluoroacetate,
1-(2-napthyl)methyl-4-(3(S)-butanoate)-7-(6-amino-1-hexyl)-3,4-dihydro-1H-1,4-benzodiazepine-2,5-dione-trifluoroacetate,
1-(2-napthyl)methyl-4-(3(R)-butanoate)-7-(5-amino-1-pentyl)-3,4-dihydro-1H-1,4-benzodiazepine-2,5-dionetrifluoroacetate,
1-(2-napthyl)methyl-4-(3(R)-butanoate)-7-(6-amino-1-hexyl)-3,4-dihydro-1H-1,4-benzodiazepine-2,5-dione trifluoroacetate,
1-(2-napthyl)methyl-4-((+/−)3-butanoate)-7-(5-amino-1-pentyl)-3,4-dihydro-1H-1,4-benzodiazepine-2,5-dione trifluoroacetate,
1-(2-napthyl)methyl-4-((+/−)3-butanoate)-7-(6-amino-1-hexyl)-3,4-dihydro-1H-1,4-benzodiazepine-2,5-dione trifluoroacetate,
1-(2-napthyl)methyl-4-(3(S)-phenyl-3-proprionate)-7-(5-amino-1-pentyl)-3,4-dihydro-1H-1,4-benzodiazepine-2,5-dione trifluoroacetate,
1-(2-napthyl)methyl-4-(3(S)-phenyl-3-proprionate)-7-(6-amino-1-hexyl)-3,4-dihydro-1H-1,4-benzodiazepine-2,5-dione trifluoroacetate,
1-(2-napthyl)methyl-4-(3(R)-phenyl-3-proprionate)-7-(5-amino-1-pentyl)-3,4-dihydro-1H-1,4-benzodiazepine-2,5-dione trifluoroacetate,
1-(2-napthyl)methyl-4-(3(R)-phenyl-3-proprionate)-7-(6-amino-1-hexyl)-3,4-dihydro-1H-1,4-benzodiazepine-2,5-dione trifluoroacetate,
1-(2-napthyl)methyl-4-((+/−)3-phenyl-3-proprionate)-7-(5-amino-1-pentyl)-3,4-dihydro-1H-1,4-benzodiazepine-2,5-dione trifluoroacetate,
1-(2-napthyl)methyl-4-((+/−)3-phenyl-3-proprionate)-7-(6-amino-1-hexyl)-3,4-dihydro-1H-1,4-benzodiazepine-2,5-dione trifluoroacetate,
1-(2-napthyl)methyl-4-(3(S)-butanoate)-7-(5-amino-1-pentynl)-3,4-dihydro-1,4-benzodiazepine-2,5-dione trifluoroacetate,
1-(2-napthyl)methyl-4-(3(S)-butanoate)-7-(6-amino-1-hexynl)-3,4-dihydro-1H-1,4-benzodiazepine-2,5-dione trifluoroacetate,
1-(2-napthyl)methyl-4-(3(R)-butanoate)-7-(5-amino-1-pentynl)-3,4-dihydro-1H-1,4-benzodiazepine-2,5-dione trifluoroacetate,
1-(2-napthyl)methyl-4-(3(R)-butanoate)-7-(6-amino-1-hexynl)-3,4-dihydro-1H-1,4-benzodiazepine-2,5-dione trifluoroacetate,
1-(2-napthyl)methyl-4-((+/−)3-butanoate)-7-(5-amino-1-pentynl)-3,4-dihydro-1H-1,4-benzodiazepine-2,5-dione trifluoroacetate,
1-(2-napthyl)methyl-4-((+/−)3-butanoate)-7-(6-amino-1-hexynl)-3,4-dihydro-1H-1,4-benzodiazepine-2,5-dione trifluoroacetate,
1-(2-napthyl)methyl-4-(3(S)-phenyl-3-proprionate)-7-(5-amino-1-pentynl)-3,4-dihydro-1H-1,4-benzodiazepine-2,5-dione trifluoroacetate,
1-(2-napthyl)methyl-4-(3(S)-phenyl-3-proprionate)-7-(6-amino-1-hexynl)-3,4-dihydro-1H-1,4-benzodiazepine-2,5-dione trifluoroacetate,
1-(2-napthyl)methyl-4-(3(R)-phenyl-3-proprionate)-7-(5-amino-1-pentynl)-3,4-dihydro-1H-1,4-benzodiazepine-2,5-dione trifluoroacetate,
1-(2-napthyl)methyl-4-(3(R)-phenyl-3-proprionate)-7-(6-amino-1-hexynl)-3,4-dihydro-1H-1,4-benzodiazepine-2,5-dione trifluoroacetate,
1-(2-napthyl)methyl-4-((+/−)3-phenyl-3-proprionate)-7-(5-amino-1-pentynl)-3,4-dihydro-1H-1,4-benzodiazepine-2,5-dione trifluoroacetate,
1-(2-napthyl)methyl-4-((+/−)3-phenyl-3-proprionate)-7-(6-amino-1-hexynl)-3,4-dihydro-1H-1,4-benzodiazepine-2,5-dione trifluoroacetate.

EXAMPLE 15

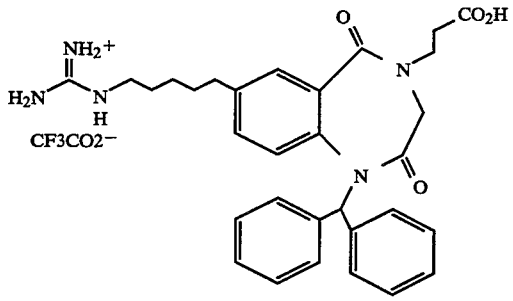

1-(diphenylmethyl)-4-(2-carboxyethyl)-7-(5-guanidinopentyl)-3,4-dihydro-1H-1,4-benxodiazepine-2,5-dione trifluoroacetate a) To a solution of 11 mgs of 1-(diphenylmethyl)-4-(2-carboxyethyl)-7-(5-aminopentyl)-3,4-dihydro-1H-1,4-benxodiazepine-2,5-dione trifluoroacetate (0.02 mmol) in 2 mL of methanol was added 1 mL of 5% potassium bicarbonate and 17 mgs of aminoiminomethanesulfonic acid (0.12 mmol). After 30 minutes, the reaction mixture was quenched with 0.5 mL of acetic acid and concentrated in vacuo. The resulting residue was diluted with 5 mL of water and methanol and purified by high pressure liquid chromatography, using a ½" C-18 reverse phase column, eluting with a solvent gradient of 30:70 methanol (0.1% trifluoroacetic acid)/water (0.1% trifluoroacetic acid), time 0 to 10 minutes, to 70:30 methanol (0.1% trifluoroacetic acid)/water (0.1% trifluoroacetic acid), time 10 minutes to 40 minutes, flow=10 mL/min. ($R_t$=40.5 min., uv detection 254nm) to yield 9.3 mg (71%) of 1-(diphenylmethyl)-4-(2-carboxyethyl)-7-(5-guanidinopentyl)-3,4-dihydro-1H-1,4-benzodiazepine-2,5-dione trifluoroacetate. HRMS (FAB) molecular ion m/z=542.2750 (calc. $C_{31}N_5O_4H_{35}$, 542.2767). $^1$H NMR ($CDCl_3$, dTMS) 6.78–7.22 (13H, m, $^3J_{HH}$=2Hz, ArH Ph, ArH p-CON, ArH o-CON, ArH m-CON), 6.45 (1H, s, NCHAr$_2$), 3.83 (2H, dd, $^2J_{HH}$=113Hz, $^2J_{HH}$=15Hz, COCH$_2$CN), 3.65 (2H, dm, $^{2,3}J_{HH}$=7Hz, $^{2,3}J_{HH}$=59Hz, CH$_2$N), 2.85 (2H, t, $^3J_{HH}$=8Hz, CH$_2$NH$_2$) 2.25–2.45 (4H, t, t, CH$_2$CO, CH$_2$Ar), 1.31 (4H, m, m, $^3J_{HH}$=7Hz, CH$_2$CH$_2$Ar, CH$_2$CH$_2$NH$_2$), 0.98 (2H, m, $^3J_{HH}$=7Hz, CH$_2$CH$_2$CH$_2$NH$_2$).

Using the above procedure, but substituting the appropriate amino acid for 1-(diphenylmethyl)-4-(2-carboxyethyl)-7-(5-aminopentyl)-3,4-dihydro-1H-1,4-benxodiazepine-2,5-dione trifluoroacetate there may be prepared, for example, the following compounds:

1-(diphenylmethyl)-4-(2-carboxyethyl)-7-(6-guanidinohexyl)-3,4-dihydro-1H-1,4-benzodiazepine-2,5-dione trifluoroacetate, 1-(diphenylmethyl)-4-(2-carboxyethyl)-7-(4-guanidinobutyl)-3,4-dihydro-1H-1,4-benzodiazepine-2,5-dione trifluoroacetate, 1-(1-napthyl)methyl-4-(2-carboxyethyl)-7-(5-guanidinopentyl)-3,4-dihydro-1H-1,4-benzodiazepine-2,5-dione trifluoroacetate, 1-(1-napthyl)methyl-4-(2-carboxyethyl)-7-(6-guanidinohexyl)-3,4-dihydro-1H-1,4-benzodiazepine-2,5-dione trifluoroacetate, 1-(2-napthyl)methyl-4-(2-carboxyethyl)-7-(5-guanidinopentyl)-3,4-dihydro-1H-1,4-benzodiazepine-2,5-dione trifluoroacetate, 1-(2-napthyl)methyl-4-(2-carboxyethyl)-7-(6-guanidinohexyl)-3,4-dihydo-1H-1,4-benzodiazepine-2,5-dione trifluoroacetate, 1-(p-phenoxybenzyl)-4-(2-carboxyethyl)-7-(5-guanidinopentyl)-3,4-dihydro-1H-1,4-benzodiazepine-2,5-dione trifluoroacetate, 1-(p-phenoxybenzyl)-4-(2-carboxyethyl)-7-(6-guanidinohexyl)-3,4-dihydro-1H-1,4-benzodiazepine-2,5-dione trifluoroacetate, 1-(m-phenoxybenzyl)-4-(2-carboxyethyl)-7-(5-guanidinopentyl)-3,4-dihydro-1H-1,4-benzodiazepine-2,5-dione trifluoroacetate, 1-(m-phenoxybenzyl)-4-(2-carboxyethyl)-7-(6-guanidinohexyl)-3,4-dihydro-1H-1,4-benzodiazepine-2,5-dione trifluoroacetate, 1-(p-trifluoromethylbenzyl)-4-(2-carboxyethyl)-7-(5-guanidinopentyl)-3,4-dihydro-1H-1,4-benzodiazepine-2,5-dione trifluoroacetate, 1-(p-trifluoromethylbenzyl)-4-(2-carboxyethyl)-7-(6-guanidinohexyl)-3,4-dihydro-1H-1,4-benzodiazepine-2,5-dione trifluoroacetate, 1-(ethyl-5-valeroyl)-4-(2-carboxyethyl)-7-(5-guanidinopentyl)-3,4-dihydro-1H-1,4-benzodiazepine-2,5-dione trifluoroacetate, 1-(ethyl-5-valeroyl)-4-(2-carboxyethyl)-7-(6-guanidinohexyl)-3,4-dihydro-1H-1,4-benzodiazepine-2,5-dione trifluoroacetate, 1-(p-methoxybenzyl)-4-(2-carboxyethyl)-7-(5-guanidinopentyl)-3,4-dihydro-1H-1,4-benzodiazepine-2,5-dione trifluoroacetate, 1-(p-methoxybenzyl)-4-(2-carboxyethyl)-7-(6-guanidinohexyl)-3,4-dihydro-1H-1,4-benzodiazepine-2,5-dione trifluoroacetate, 1-(p-methylmethylbenzoyl)-4-(2-carboxyethyl)-7-(5-guanidinopentyl)-3,4-dihydro-1H-1,4-benzodiazepine-2,5-dione trifluoroacetate, 1-(p-methylmethylbenzoyl)-4-(2-carboxyethyl)-7-(6-guanidinohexyl)-3,4-dihydro-1H-1,4-benzodiazepine-2,5-dione trifluoroacetate, 1-(diphenylmethyl)-4-(2-carboxyethyl)-7-(6-guanidino-1-hexynl)-3,4-dihydro-1H-1,4-benzodiazepine-2,5-dione trifluoroacetate, 1-(diphenylmethyl)-4-(2-carboxyethyl)-7-(4-guanidino-1-butynl)-3,4-dihydro-1H-1,4-benzodiazepine-2,5-dione trifluoroacetate, 1-(1-napthyl)methyl-4-(2-carboxyethyl)-7-(5-guanidino-1-pentynl)-3,4-dihydro-1H-1,4-benzodiazepine-2,5-dione trifluoroacetate, 1-(1-napthyl)methyl-4-(2-carboxyethyl)-7-(6-guanidino-1-hexynl)-3,4-dihydro-1H-1,4-benzodiazepine-2,5-dione trifluoroacetate, 1-(2-napthyl)methyl-4-(2-carboxyethyl)-7-(5-guanidino-1-pentynl)-3,4-dihydro-1H-1,4-benzodiazepine-2,5-dione trifluoroacetate, 1-(2-napthyl)methyl-4-(2-carboxyethyl)-7-(6-guanidino-1-hexynl)-3,4-dihydro-1H-1,4-benzodiazepine-2,5-dione trifluoroacetate, 1-(p-phenoxybertzyl)-4-(2-carboxyethyl)-7-(5-guanidino-1-pentynl)-3,4-dihydro-1H-1,4-benzodiazepine-2,5-dione trifluoroacetate, 1-(p-phenoxybenzyl)-4-(2-carboxyethyl)-7-(6-guanidino-1-hexynl)-3,4-dihydro-1H-1,4-benzodiazepine-2,5-dione trifluoroacetate, 1-(m-phenoxybenzyl)-4-(2-carboxyethyl)-7-(5-guanidino-1-pentynl)-3,4-dihydro-1H-1,4-benzodiazepine-2,5-dione trifluoroacetate, 1-(m-phenoxybenzyl)-4-(2-carboxyethyl)-7-(6-guanidino-1-hexynl)-3,4-dihydro-1H-1,4-benzodiazepine-2,5-dione trifluoroacetate, 1-(p-trifluoromethylbenzyl)-4-(2-carboxyethyl)-7-(5-guanidino-1-pentynl)-3,4-dihydro-1H-1,4-benzodiazepine-2,5-dione trifluoroacetate, 1-(p-trifluoromethylbenzyl)-4-(2-carboxyethyl)-7-(6-guanidino-1-hexynl)-3,4-dihydro-1H-1,4-benzodiazepine-2,5-dione trifluoroacetate, 1-(ethyl-5-valeroyl)-4-(2-carboxyethyl)-7-(5-guanidino-1-pentynl)-3,4-dihydro-1H-1,4-benzodiazepine-2,5-dione trifluoroacetate, 1-(ethyl-5-valeroyl)-4-(2-carboxyethyl)-7-(6-guanidino-1-hexynl )-3,4-dihydro-1H-1,4-benzodiazepine-2,5-dione trifluoroacetate, 1-(p-methoxybenzyl)-4-(2-carboxyethyl)-7-(5-guanidino-1-pentynl)-3,4-dihydro-1H-1,4-benzodiazepine-2,5-dione trifluoroacetate, 1-(p-methoxybenzyl)-4-(2-carboxyethyl)-7-(6-guanidino-1-hexynl)-3,4-dihydro-1H-1,4-benzodiazepine-2,5-dione trifluoroacetate, 1-(p-methylmethylbenzoyl)-4-(2-carboxyethyl)-7-(5-guanidino-1-pentynl)-3,4-dihydro-1H-1,4-benzodiazepine-2,5-dione trifluoroacetate, 1-(p-methylmethylbenzoyl)-4-(2-carboxyethyl)-7-(6-guanidino-1-hexynl)-3,4-dihydro-1H-1,4-benzodiazepine-2,5-dione trifluoroacetate, 1-(2-napthyl)methyl-4-(3(S)-butanoate)-7-(5-guanidino-1-pentyl)-3,4-dihydro-1H-1,4-benzodiazepine-2,5-dione trifluoroacetate, 1-(2-napthyl)methyl-4-(3(S)-butanoate)-7-(6-guanidino-1-hexyl)-3,4-dihydro-1H-1,4-benzodiazepine-2,5-dionetrifluoroacetate, 1-(2-napthyl)methyl-4-(3(R)-butanoate)-7-(5-guanidino-1-pentyl)-3,4-dihydro-1H-1,4-benzodiazepine-2,5-dionetrifluoroacetate, 1-(2-napthyl)methyl-4-(3(R)-butanoate)-7-(6-guanidino-1-hexyl)-3,4-dihydro-1H-1,4-benzodiazepine-2,5-dione trifluoroacetate, 1-(2-napthyl)methyl-4-((+/−)3-butanoate)-7-(5-guanidino-1-pentyl)-3,4-dihydro-1H-1,4-benzodiazepine-2,5-dione trifluoroacetate, 1-(2-napthyl)methyl-4-((+/−)3-butanoate)-7-(6-guanidino-1-hexyl)-3,4-dihydro-1H-1,4-benzodiazepine-2,5-dione trifluoroacetate, 1-(2-napthyl)methyl-4-(3(S)-phenyl-3-proprionate)-7-(5-guanidino-1-pentyl)-3,4-dihydro-1H-1,4-benzodiazepine-2,5-dione trifluoroacetate, 1-(2-napthyl)methyl-4-(3(S)-phenyl-3-proprionate)-7-(6-guanidino-1-hexyl)-3,4-dihydro-1H-1,4-benzodiazepine-2,5-dione trifluoroacetate, 1-(2-naphthyl)methyl-4-(3(R)-phenyl-3-proprionate)-7-(5-guanidino-1-pentyl)-3,4-dihydro-1H-1,4-benzodiazepine-2,5-dione trifluoroacetate, 1-(2-napthyl)methyl-4-(3(R)-phenyl-3-proprionate)-7-(6-guanidino-1-hexyl)-3,4-dihydro-1H-1,4-benzodiazepine-2,5-dione trifluoroacetate, 1-(2-napthyl)methyl-4-((+/−)3-phenyl-3-proprionate)-7-(5-guanidino-1-pentyl)-3,4-dihydro-1H-1,4-benzodiazepine-2,5-dione trifluoroacetate, 1-(2-napthyl)methyl-4-((+/−)3-phenyl-3-proprionate)-7-(6-guanidino-1-hexyl)-3,4-dihydro-1H-1,4-benzodiazepine-2,5-dione trifluoroacetate, 1-(2-napthyl)methyl-4-(3(S)-butanoate)-7-(5-guanidino-1-pentynl)-3,4-dihydro-1H-1,4-benzodiazepine-2,5-dione trifluoroacetate, 1-(2-napthyl)methyl-4-(3(S)-butanoate)-7-(6-guanidino-1-hexynl)-3,4-dihydro-1H-1,4-benzodiazepine-2,5-dione trifluoroacetate, 1-(2-napthyl)methyl-4-(3(R)-butanoate)-7-(5-guanidino-1-pentynl)-3,4-dihydro-1H-1,4-benzodiazepine-2,5-dione trifluoroacetate, 1-(2-napthyl)methyl-4-(3(R)-butanoate)-7-(6-guanidino-1-hexynl)-3,4-dihydro-1H-1,4-benzodiazepine-2,5-dione trifluoroacetate, 1-(2-napthyl)methyl-4-((+/−)3-butanoate)-7-(5-guanidino-1-pentynl)-3,4-dihydro-1H-1,4-benzodiazepine-2,5-dione trifluoroacetate, 1-(2-naphthyl)methyl-4-((+/−)3-butanoate)-7-(6-guanidino-1-hexynl)-3,4-dihydro-1H-1,4-benzodiazepine-2,5-dione trifluoroacetate, 1-(2-napthyl)methyl-4-(3(S)-phenyl-3-proprionate)-7-(5-guanidino-1-pentynl)-3,4-dihydro-1H-1,4-benzodiazepine-2,5-dione trifluoroacetate, 1-(2-napthyl)methyl-4-(3(S)-phenyl-3-proprionate)-7-(6-guanidino-1-hexynl)-3,4-dihydro-1H-1,4-benzodiazepine-2,5-dione trifluoroacetate, 1-(2-napthyl)methyl-4-(3(R)-phenyl-3-proprionate)-7-(5-guanidino-1-pentynl)-3,4-dihydro-1H-1,4-benzodiazepine-2,5-dione trifluoroacetate, 1-(2-napthyl)methyl-4-(3(R)-phenyl-3-proprionate)-7-(6-guanidino-1-hexynl)-3,4-dihydro-1H-1,4-benzodiazepine-2,5-dione trifluoroacetate, 1-(2-napthyl)methyl-4-((+/−)3-phenyl-3-proprionate)-7-(5-guanidino-1-pentynl)-3,4-dihydro-1H-1,4-benzodiazepine-2,5-dione trifluoroacetate, 1-(2-napthyl)methyl-4-((+/−)3-phenyl-3-proprionate)-7-(6-guanidino-1-hexynl)-3,4-dihydro-1H-1,4-benzodiazepine-2,5-dione trifluoroacetate.

EXAMPLE 16

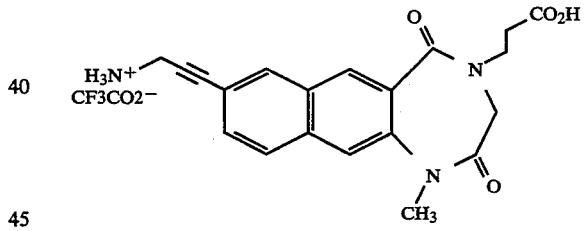

1-methyl-4-(2-carboxyethyl)-8-(3-amino-1-propynyl)-3,4-dihydro 1H-1,4-napthodiazepine-2,4-dione trifluoracetate a) [4,5]-Benzoisatoic anhydride was prepared according to the method described in part (a) of example 1. Thus, 35 g of 3-amino-2-naphthoic acid (187 mMol) was dissolved in 500 mL of water containing 20 g of potassium carbonate. A solution of phosgene in toluene (1.93M, 290 mL) was added slowly with vigorous stirring. A precipitate appeared along with evolution of gas. Stirring was continued for 30 min after complete addition of the phosgene. The precipitate was collected by suction filtration. The solid material was washed thoroughly with water and hexane and air dried yielding 37.7 g (95%) of [4,5]-benzoisatoic anhydride. M.p. >400° C.

$^1$H NMR (CDCL$_3$): 12.0, s, 1H; 8.95, s, 1H; 8.3, d, J=7Hz, 1H; 8.15, d, J=7 Hz, 1H, 7.85, t, J=7Hz, 1H; 7.7, t, J=7 Hz, 1H; 7,7, s, 1H.

b) 10.3 g (48.3 mMol) of [4,5]-benzoisatoic anhydride was dissolved in 50 mL of anhydrous N,N-dimethylformamide (DMF) and added dropwise to an ice-cooled suspension of sodium hydride (97%, 1.25 g) in 50 mL of DMF with gas evolution. After stirring an additional 30 min, 3.16 mL (105 mol %) of methyl iodide was added to the solution. After one hour, the reaction mixture was poured over ice and the precipitated product was collected by suction filtration and air dried, yielding 9.3 g (85%) of N-methyl-[4,5]-benzoisatoic anhydride, a tan solid. M.p. 219°–222° C.

$^1$H NMR (d$^6$-DMSO): 8.8, s, 1H; 8.15, d, J=7 Hz, 1H; 8.0, d, J=7 Hz, 1H; 7.85, s, 1H; 7.7, t, J=7 Hz, 1H; 7.55, t, J=7 Hz, 1H; 3.35, s, 3H.

Using the above procedure, but substituting the appropriate alkyl halide for methyl iodide there may be prepared, for example, the following compounds:
N-benzyl-[4,5]-benzoisatoic anhydride, N-(2,4-diflurobenzyl)-[4,5]-benzoisatoic anhydride, N-(B-napthyl)methyl-[4,5]-benzoisatoic anhydride.

c) A solution of 20.0 g (89 mMol) of N-methyl-[4,5]-benzoisatoic anhydride, 20.5 g (133.5 mMol) of the hydrochloride salt of ethyl 3-aminopropionate, and 18.6 mL (133.5 mMol) of triethylamine in 100 mL of DMF was stirred at 80° C. for four hr. The reaction mixture was then poured over ice containing citric acid and the precipitated product was collected by suction filtration. The crude product was recrystallized from benzene/hexane, yielding 24 g (60%) of 3-(N-methylamino)-2-[N-(2-carboxyethyl)]-naphthocarboxamide ethyl ester, a yellow crystalline solid. MS (FAB) 300.1.

$^1$H NMR (CDCL$_3$): 7.8, s, 1H; 7.65, d, J=7 Hz, 1H; 7.6, d, J=7 Hz, 1H; 7.4, t, J=7 Hz, 1H; 7.2, t, J=7 Hz, 1H; 6.9, br s, 1H; 6.8, s, 1H; 4.2, q, J=7 Hz, 2H; 3.75, q, J=5 Hz, 2H; 2.95, s, 3H; 2.65, t, J=5 Hz, 2H; 1.3, t, J=7 Hz, 3H.

Using the above procedure, but substituting the appropriate 3-aminopropionate for ethyl 3-aminopropionate there may be prepared, for example, the following compounds:

(±)-3-(N-methyl)amino-2-[N-(3-butanoate)]-naphthocarboxamide ethyl ester,
(±)-3-(N-methyl)amino-2-[N-(3-phenyl-3-proprionate)]-naphthocarboxamide ethyl ester,
(±)-3-(N-benzyl)amino-2-[N-(3-butanoate)]-naphthocarboxamide ethyl ester,
(±)-3-(N-benzyl)amino-2-[N-(3-phenyl-3-proprionate)]-naphthocarboxamide ethyl ester,
(±)-3-(N-2,4-diflurobenzyl)amino-2-[N-(3-butanoate)]-naphthocarboxamide ethyl ester,
(±)-3-(N-2,4-diflurobenzyl)amino-2-[N-(3-phenyl-3-proprionate)]naphthocarboxamide ethyl ester,
(±)-3-(N-(B-napthyl)methyl)amino-2-[N-(3-butanoate)]-naphthocarboxamide ethyl ester,
(±)-3-(N-(B-napthyl)methyl)amino-2-[N-(3-phenyl-3-proprionate)]naphthocarboxamide ethyl ester.

d) To an ice-cooled solution of 5.0 g (17.5 mMol) of 3-(N-methyl)amino-2-[N-(2-carboxyethyl)]-naphthocarboxamide ethyl ester and 2.68 mL (19 mMol) of triethylamine in 50 mL of methylene chloride was added dropwise a solution of 1.59 mL 19(mMol) of bromoacetyl bromide. After warming to room temperature, the solution was washed with aqueous citric acid and aqueous sodium bicarbonate solution, dried over sodium sulfate and evaporated. This material was dissolved in DMF (20 mL) and added dropwise to a suspension of 97% sodium hydride (462mg, 19 mMol) at −15° C. After warming to room temperature the solution was poured over ice/citric acid and extracted into ether. 3.1 g (52%) of 1-methyl-4-(carboxyethyl)-3,4-dihydro-1H-1,4-naphthodiazepine-2,5-dione ethyl ester, a yellow oil, was obtained after column chromatography on silica gel. MS (FAB) 341.

$^1$H NMR (CDCL$_3$): 8.4, s, 1H; 7.9, d, J=8.5, 1H; 7.8, d, J=8.5, 1H; 7.6, s, 1H; 7.45–7.6, m, 2H; 4.15, q, J=7Hz, 2H; 4.1, d, J=14 Hz, 1H; 3.95, t, J=7 Hz, 2H; 3.85, d, J=14 Hz, 1H; 3.5, s, 3H; 2.75, m, 2H; 1.25, t, J=7 Hz, 3H.

Using the above procedure, but substituting the appropriate naphthocarboxamide for 3-(N-methyl)amino-2-[N-(2-carboxyethyl)]naphthocarboxamide ethyl ester there may be prepared, for example, the following compounds:

1-benzyl-4-(carboxyethyl)-3,4-dihydro-1H-1,4-naphthodiazepine-2,5-dione ethyl ester
1-(2,4-diflurobenzyl)-4-(carboxyethyl)-3,4-dihydro-1H-1,4-naphthodiazepine-2,5-dione ethyl ester
1-(p-napthyl)methyl-4-(carboxyethyl)-3,4-dihydro-1H-1,4-naphthodiazepine-2,5-dione ethyl ester
(±)-1-methyl-4-(3-butanoate)-3,4-dihydro-1H-1,4-naphthodiazepine-2,5-dione ethyl ester,
(±)-1-methyl-4-(3-phenyl-3-proprionate)-3,4-dihydro-1H-1,4-naphthodiazepine-2,5-dione ethyl ester,
(±) -1-benzyl-2-(3-butanoate)-3,4-dihydro-1H-1,4-naphthodiazepine-2,5-dione ethyl ester,
(±)-1-benzyl-2-(3-phenyl-3-proprionate)-3,4-dihydro-1H-1,4-naphthodiazepine-2,5-dione ethyl ester,
(±)-1-(2,4-diflurobenzyl)-2-(3-butanoate)-3,4-dihydro-1H-1,4-naphthodiazepine-2,5-dione ethyl ester,
(±)-1-(2,4-diflurobenzyl)-2-(3-phenyl-3-proprionate)-3,4-dihydro-1 H-1,4-naphthodiazepine-2,5-dione ethyl ester,
(±)-1-(B-napthyl)methyl-2-(3-butanoate)-3,4-dihydro-1 H-1,4-naphthodiazepine-2,5-dione ethyl ester,
(±)-1-(B-napthyl)methyl-4-(3-phenyl-3-proprionate)-3,4-dihydro-1H-1,4-naphthodiazepine-2,5-dione ethyl ester.

e) 1-Methyl-4-(ethoxycarbonylethyl)-3,4-dihydro-1H-1,4-naphthodiazepine-2,5-dione (3.1 g, 9.1 mMol) was placed in an ice bath and 4 mL of fuming nitric acid was added. After stirring for 1 hr at 0° C. the reaction was allowed to warm to room temperature and stirred for an additional 2 hr. The reaction mixture was poured into ice water and extracted with ethyl acetate, dried (sodium sulfate) and evaporated to yield a yellow solid. Thin layer chromatography (TLC) and $^1$H NMR analysis indicated a mixture of nitrated products. The crude mixture was purified by column chromatography (SiO$_2$) to yield 600 mgs (17%) of 8-Nitro-1-methyl-4-(ethoxycarbonylethyl)-3,4-dihydro-1H-1,4-naphthodiazepine-2,5-dione.

$^1$H NMR (CDCl$_3$, dTMS) 8.8 (1H, d, $^4$]HH=2 Hz), 8.6 (1H, s), 8.3 (1H, dd, $^2$J$_{HH}$=9 Hz, $^4$J$_{HH}$=2 Hz), 7.95 (1H, d, $^3$J$_{HH}$=9 Hz), 7.7 (1H, s), 4.15 (2H, q, $^3$J$_{HH}$=8 Hz), 4.1 (1H, d, $^2$J$_{HH}$=14 Hz), 4.0 (2H, t, $^3$J$_{HH}$=7 Hz), 3.95 (1H, $^2$J$_{HH}$=14 Hz), 3.5 (3H, s), 2.75 (2H, m), 1.25 (3H, t, $^3$J$_{HH}$=8 Hz).

Using the above procedure, but substituting the appropriate naphthocarboxamide for 3-(N-methyl)amino-2-[N-(2-carboxyethyl)]naphthocarboxamide ethyl ester there may be prepared, for example, the following compounds:

1-(2,4-diflurobenzyl)-4-(carboxyethyl)-8-nitro-3,4-dihydro-1H-1,4-naphthodiazepine-2,5-dione ethyl ester,
(±)-1-methyl-4-(3-butanoate)-8-nitro-3,4-dihydro-1H-1,4-naphthodiazepine-2,5-dione ethyl ester, (±)-1-(2,4-diflurobenzyl)-2-(3-butanoate)-8-nitro-3,4-dihydro-1H-1,4-naphthodiazepine-2,5-dione ethyl ester.

f) 1-Methyl-4-(carboxylethyl)-8-nitro-3,4-dihydro-1H-1,4-naphthodiazepine-2,5-dione ethyl ester (600 mg, 1.56 mMol) was hydrogenated in ethanol with 200 mg of 10% palladium on carbon catalyst at 50 psi hydrogen for 24 hr after which time tlc indicated that reduction was complete. The catalyst was removed by filtration through Celite ®, and the filtrate was evaporated yielding ca. 500 mg of 1-methyl-4-(carboxylethyl)-8-amino-3,4-dihydro-1H-1,4-naphthodiazepine-2,5-dione ethyl ester.

$^1$H NMR (CDCL$_3$): 8.1, s, 1H; 7.6, d, J=9.5 Hz, 1H; 7.45, s, 1H; 7.15, s, 1H; 7.1, d, J=9.5 Hz, 1H; 4.15, q, J=8 Hz, 2H; 4.1, d, J=14 Hz, 1H; 3.95, t, J=7 Hz, 2H; 3.8, d, J=14 Hz, 1H; 3.4, s, 3H; 2.7, m, 2H; 1.2, t, J=8 Hz. This material was dissolved in 4 mL of water containing 117 mL of concentrated sulfuric acid and cooled to 0° C. with an ice bath. Sodium nitrite (97 mg, 1.5 mMol) in 2 mL of water was added to the solution dropwise, and the temperature of the solution was allowed to rise to room temperature over one hour. 2.6 g (14 mMol) of potassium iodide was added to the solution and stirring was continued for 24 hr. The reaction mixture was diluted with water and extracted with ethyl acetate, and the ethyl acetate was dried (sodium sulfate) and evaporated. Chromatography on silica gel yielded ca. 240 mg of 8-Iodo-1-methyl-4-(ethoxycarbonylethyl)-3,4-dihydro-1H-1,4-naphthodiazepine-2,5-dione as an amber oil. MS (FAB) 466.9.

$^1$H NMR (CDCL$_3$): 8.3, s, 2H; 7.8, dd, J=8.5 Hz, J'=1.5 Hz, 1H; 7.55, s, 1H; 7.55, d, J=8.5 Hz, 1H; 4.15, q, J=7 Hz, 2H; 4.1, d, J=14 Hz, 1H; 3.95, t, J=7 Hz, 2H; 3.9, d, J=14 Hz, 1H; 3.5, s, 3H; 2.75, m, 2H; 1.25, t, J=7 Hz.

Using the above procedure, but substituting the appropriate 8-nitro-3,4-dihydro-1H-1,4-naphthodiazepine-2,5-dione for 1-methyl-4-(2-carboxylethyl)-8-nitro-3,4-dihydro-1H-1,4-naphthodiazepine-2,5-dione ethyl ester there may be prepared, for example, the following compounds:

1-(2,4-diflurobenzyl)-4-(carboxyethyl)-8-iodo-3,4-dihydro-1H-1,4-naphthodiazepine-2,5-dione ethyl ester,
(±)-1-methyl-4-(3-butanoate)-8-iodo-3,4-dihydro-1H-1,4-naphthodiazepine-2,5-dione ethyl ester,
(±)-1-(2,4-diflurobenzyl)-2-(3-butanoate)-8-iodo-3,4-dihydro-1H-1,4-naphthodiazepine-2,5-dione ethyl ester.

g) 1-Methyl-4-(ethoxycarbonylethyl)-8-Iodo-3,4-dihydro-1H-1,4-naphthodiazepine-2,5-dione (100 mg, 215 mM) was combined in 1 mL of ethyl acetate with 166 mg (500 m %) of N-t-butoxycarbonylpropargyl amine, 15 mg (10 mol %) of bistriphenylphosphine palladium dichloride, and 299 mL (10X excess) of triethylamine. The apparatus was degassed and an atmosphere of nitrogen was introduced. 8.2mg (20 mol %) of cuprous iodide was added and the solution was again degassed and nitrogen atmosphere was replaced. After 24 hr the reaction mixture was diluted with ethyl acetate and washed succesively with aqueous citric acid and aqueous sodium bicarbonate, dried (sodium sulfate) and evaporated. The residue was chromatographed on silica gel, yielding 110 mg of 1-methyl-4-(crboxylethyl)-8-(3-t-butyloxycarbonylamino-1-propynyl)-3,4-dihydro-1H-1,4-naphthodiazepine-2,5-dione. MS (FAB) 494.1.

$^1$H NMR (CDCL$_3$): 8.35, s, 1H; 7.95, s, 1H; 7.75, d, J=8.5 Hz, 1H; 7.55, s, 1H; 7.5, d, J=8.5 Hz, 1H; 4.9, br s, 1H; 4.2, br s, 2H; 4.2, q, J=7 Hz, 2H; 4.1, d, J=14 Hz, 1H; 4.0, t, J=7 Hz, 2H; 3.9, d, J=7 Hz, 1H; 3.5; s, 3H; 2.75, m, 2H; 1.5, s, 9H; 1.25, t, J=7 Hz, 3H.

Using the above procedure, but substituting the appropriate 8-iodo-3,4-dihydro-1H-1,4-naphthodiazepine-2,5-dione for 1-methyl-4-(2-carboxylethyl)-8-iodo-3,4-dihydro-1H-1,4-naphthodiazepine-2,5-dione ethyl ester there may be prepared, for example, the following compounds:

1-(2,4-diflurobenzyl)-4-(carboxyethyl)-8-(3- t-butyloxycarbonylamino-1-propynyl)-3,4-dihydro-1H-1,4-naphthodiazepine-2,5-dione ethyl ester,
(±)1-methyl-4-(3-butanoate)-8-(3-t-butyloxycarbonylamino-1-propynyl)-3,4-dihydro-1H-1,4-naphthodiazepine-2,5-dione ethyl ester,
(±)-1-(2,4-diflurobenzyl)-2-(3-butanoate)-8-(3-t -butyloxycarbonylamino-1-propynyl)-3,4-dihydro-1 H-1,4-naphthodiazepine-2,5-dione ethyl ester,
1-(2,4-diflurobenzyl)-4-( carboxyethyl)-8-(4-t-butyloxycarbonylamino-1-butynyl)-3,4-dihydro-1H-1,4-naphthodiazepine-2,5-dione ethyl ester,
(±)-1-methyl-4-(3-butanoate)-8-(4-t-butyloxycarbonylamino-1-butynyl)-3,4-dihydro-1H-1,4-naphthodiazepine-2,5-dione ethyl ester,
(±)-1-(2,4-diflurobenzyl)-2-(3-butanoate)-8-(4-t-butyloxycarbonylamino-1-butynyl)-3,4-dihydro-1H-1,4-naphthodiazepine-2,5-dione ethyl ester.

h) To a stirred solution of 1-methyl-4-(carboxyethyl)-8-(3-t-butyloxycarbonylamino-1-propynyl)-3,4-dihydro-1H-1,4-naphthodiazepine-2,5-dione ethyl ester (110 mg, 0.22 mMol) in 8 mL of methanol was added 1 mL of 1N sodium hydroxide solution. After 4 hr no more starting material was detected by tlc. The solvent was removed in vacuo and the residue was treated with 10 mL of 4N HCl in dioxane. After 2 hr the solvent was removed in vacuo and the residue was purified by reverse phase HPLC, yielding 25 mg of 1-methyl-4-(carboxyethyl)-8-(3-amino-1-propynyl)-3,4-dihydro-1H-1,4-naphthodiazepine-2,5-dione.

HRMS (FAB) molecular ion m/z=366.1454 (cald. $C_{20}H_{20}N_3O_4$, 366.4004).

$^1$H NMR (CD$_3$OD): 7.9, s, 1H; 7.7, s, 1H; 7.55, d, J=8 Hz, 1H; 7.45, s, 1H; 7.2, d, J=8 Hz, 1H; 3.75, d, J=14 Hz, 1H; 3.65, s, 2H; 3.55, d, J=14 Hz, 1H; 3.5, m, 2H; 3.05, s, 3H; 2.2, q, J=7 Hz, 2H.

Using the above procedure, but substituting the appropriate 8-(t-butyloxycarbonylamino-1-alkynyl)-3,4-dihydro-1H-1,4-naphthodiazepine-2,5-dione for 1-methyl-4-(carboxyethyl)-8-(3-t-butyloxycarbonylamino-1-propynyl)-3,4-dihydro-1H-1,4-naphthodiazepine-2,5-dione ethyl ester there may be prepared, for example, the following compounds:

1-(2,4-diflurobenzyl)-4-(carboxyethyl)-8-(3-amino-1-propynyl)-3,4-dihydro-1H-1,4-naphthodiazepine-2,5-dione,
(±)-1-methyl-4-(3-butanoate)-8-(3-amino-1-propynyl)-3,4-dihydro-1H-1,4-naphthodiazepine-2,5-dione,
(±)-1-(2,4-diflurobenzyl)-4-(3-butanoate)-8-(3-amino-1-propynyl)-3,4-dihydro-1H-1,4-naphthodiazepine-2,5-dione,
1-(2,4-diflurobenzyl)-4-(carboxyethyl)-8-(4-amino-1-butynyl)-3,4-dihydro-1H-1,4-naphthodiazepine-2,5-dione,
(±)-1-methyl-4-(3-butanoate)-8-(4-amino-1-butynyl)-3,4-dihydro-1H-1,4-naphthodiazepine-2,5-dione, (±)-1-(2,4-diflurobenzyl)-4-(3-butanoate)-8-(4-amino-1-butynyl)-3,4-dihydro-1H-1,4-naphthodiazepine-2,5-dione.

EXAMPLE 17

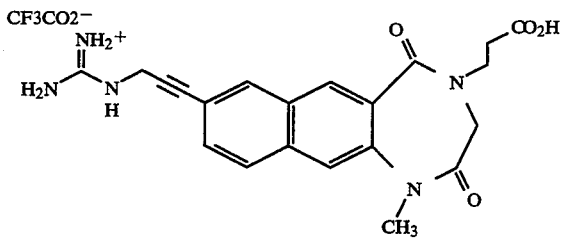

1-Methyl-4-(carboxyethyl)-8-(3-guanidino-1-propynyl)-3,4-dihydro-1H-1,4-naphthodiazepine-2,5-dione The title compound was prepared from 1-methyl-4-(carboxyethyl)-8-(3-amino-1-propynyl)-3,4-dihydro-1H-1,4-naphthodiazepine-2,5-dione (50 mg) according to the procedure described in Example 2.

HRMS (FAB) molecular ion m/z=408.1672 (cald. $C_{21}H_{22}N_5O_4$, 408.1672).

$^1$H NMR (CD$_3$OD): 7.9, s, 1H; 7.7, s, 1H; 7.55, d, J=8 Hz, 1H; 7.45, s, 1H; 7.2, d, J=8 Hz, 1H; 3.75, d, J=14 Hz, 1H; 3.65, s, 2H; 3.55, d, J=14 Hz, 1H; 3.5, m, 2H; 3.05, s, 3H; 2.2, q, J=7 Hz, 2H.

Using the above procedure, but substituting the appropriate 8-(amino-1-alkynyl)-3,4-dihydro-1H-1,4-naphthodiazepine-2,5-dione for 1-methyl-4-(carboxyethyl)-8-(3-amino-1-propynyl)-3,4-dihydro-1H-1,4-naphthodiazepine-2,5-dione there may be prepared, for example, the following compounds:

1-(2,4-diflurobenzyl)-4-(carboxyethyl)-8-(3-guanidino-1-propynyl)-3,4-dihydro-1H-1,4-naphthodiazepine-2,5-dione, (±)-1-methyl-4-(3-butanoate)-8-(3-guanidino-1-propynyl)-3,4-dihydro-1H-1,4-naphthodiazepine-2,5-dione, (±)-1-(2,4-diflurobenzyl)-2-(3-butanoate)-8-(3-guanidino-1-propynyl)-3,4-dihydro-1H-1,4-naphthodiazepine-2,5-dione, 1-(2,4-diflurobenzyl)4-(carboxyethyl)-8-(4-guanidino-1-butynyl)-3,4-dihydro-1H-1,4-naphthodiazepine-2,5-dione, (±)-1-methyl-4-(3-butanoate)-8-(4-guanidino-1-butynyl)-3,4-dihydro-1H-1,4-naphthodiazepine-2,5-dione, (±)-1-(2,4-diflurobenzyl)-2-(3-butanoate)-8-(4-guanidino-1-butynyl)-3,4-dihydro-1H-1,4-naphthodiazepine-2,5-dione.

EXAMPLE 18

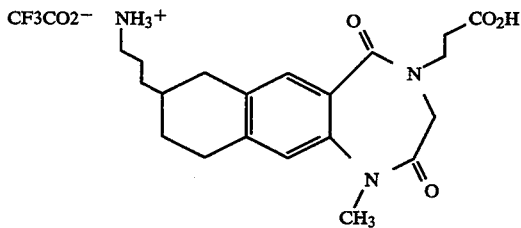

1-Methyl-4-(carboxyethyl)-8-(3-amino-1-propyl)-3,4,7,8,9,10-hexahydrohydro-1H-1,4-naphthodiazepine-2,5-dione 1-Methyl-4-(carboxyethyl)-8-(3-amino-1-propynyl)-3,4-dihydro-1H-1,4-naphthodiazepine-2,5-dione (50 mg) was reduced with 10mg of 10% Pd/C in 10 mL of 5:1 water ethanol at 45 psi of hydrogen in a Parr hydrogenation apparatus for 24 hr yielding, after filtration through Celite® and purification by reverse phase HPLC, the title compound.

MS (FAB) 374.1.

$^1$H NMR (CD$_3$OD): 7.4, s, 1H; 7.0, s, 1H; 3.95, d, J=14 Hz, 1H; 3.8, d, J=14 Hz, 1H; 3.6, m, 2H; 3.2, s, 3H; 2.85, t, J=7 Hz, 2H; 2.4, t, J=7 Hz, 2H; 1.9, m, 1H; 1.65, m, 4H; 1.4, m, 4H.

Using the above procedure, but substituting the appropriate 8-(amino-1-alkynyl)-3,4-dihydro-1H-1,4-naphthodiazepine-2,5-dione for 1-methyl-4-(carboxyethyl)-8-(3-amino-1-propynyl)-3,4,7,8,9,10-hexahydrohydro-1H-1,4-naphthodiazepine-2,5-dione there may be prepared, for example, the following compounds:

1-(2,4-diflurobenzyl)-4-(carboxyethyl)-8-(3-guanidino-1-propynyl)-3,4,7,8,9,10-hexahydrohydro-1H-1,4-naphthodiazepine-2,5-dione, (±)-1-methyl-4-(3-butanoate)-8-(3-guanidino-1-propynyl)-3,4,7,8,9,10-hexahydrohydro-1H-1,4-naphthodiazepine-2,5-dione, (±)-1-(2,4-diflurobenzyl)-2-(3-butanoate)-8-(3-guanidino-1-propynyl)-3,4,7,8,9,10-hexahydrohydro-1H-1,4-naphthodiazepine-2,5-dione,

EXAMPLE 19

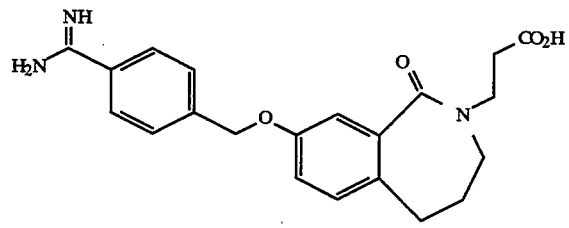

2-(2-carboxyethyl)-8-(4-amidinobenzyloxy)-2,3,4,5-tetrahydro-1H-2-benzazepin-1-one trifluoroacetate a) A solution of 7-methoxytetralone (Fluka Chemical, 100.0 g, 0.567 mol) in dry pyridine (600 mL) was treated with hydroxylamine hydrochloride (Fluka, 3.0 g, 0.618 mol) and the resulting dark yellow solution was stirred at room temperature for 1 hour. The solution was then concentrated in vacuo, and azeotroped with several volumes of toluene, then partitioned between ethyl acetate and brine. The combined organic layers were dried (K$_2$CO$_3$), filtered, and concentrated in vacuo. The residue was crystallized from ethyl acetate/hexanes to yield 88 g (81%) of the oxime as a waxy solid.

b) Following a procedure of Tomita, et. al., *J. Chem. Soc. C* 1969, 183, 7-methoxytetralone oxime (45.0 g, 0.235 mol) was mixed with solid trichloroacetic acid (150 g), and the resulting suspension heated to ca. 80 C., at which time a violent exotherm ensued, yielding a black solid mixture. The residue was cooled, partitioned between ethyl acetate and saturated aqueous sodium bicarbonate solution, and the combined organic layers were concentrated in vacuo. The residue was purified by chromatography over silica gel to yield 10.0 g (22%)

of 8-methoxy-2,3,4,5-tetrahydro-1H-2-benzazepin-1-one. An analytical sample was obtained by recrystallization from CH$_2$Cl$_2$/hexanes to yield colorless crystals: mp. 99°–101° C. (lit. (see above) 100°–101° C.);

$^1$H NMR(CDCl$_3$) d7.35(brs, 1H), 7.30(d, J=3 Hz, 1H), 7.10(d, J=9 Hz, 1H), 6.9 5 (dd, J=3, 9 Hz, 1H, 3.82(s, 3H), 3.10(q, J=6 Hz, 2H), 2.80(t, J=6 Hz, 2H), 1.98(m, 2H).

c) A solution of 8-methoxy-2,3,4,5-tetrahydro-1H-2-benzazepin-1-one (10.0 g, 0.052 mol) in N,N-dimethylformamide (30 mL) and allylbromide (23 mL, 0.260 mL) was treated with NaH (60% by wt. dispersion in oil, 2.50 g, 0.063 mol) and the resulting grey suspension stirred at room temperature under an atmosphere of argon. Gas evolution was noted. After 15 minutes, the solution was diluted with brine and partitioned between ethyl acetate and brine. The combined organic layers were concentrated in vacuo and purified by chromatography over silica gel eluting with a gradient of hexane to 1:1 ethyl acetate/hexane to yield 8 g (83%) of 2-allyl-8-methoxy-2,3,4,5-tetrahydro-1H-2-benzazepin-1-one as a colorless oil:

$^1$H NMR (CDCl$_3$) d7.23(m, 1H), 7.03(d, J=9 Hz, 1H), 6.90(dd, J=3, 9 Hz, 1H), 5.91(m, 1H), 5.23(m, 2H), 4.20(d, J=6 Hz, 2H), 3.82(s, 3H), 3.18(t, J=6 Hz, 2H), 2.72(t, J=6 Hz, 2H), 1.96(pentet, J=6 Hz, 2H);

$^{13}$C NMR(CDCl$_3$) d170.59(C̲O), 158.42(NC̲O), 136.88, 133.81,129.43, 129.35, 129.33, 117.56, 117.54, 112.98, 55.26, 49.43, 45.37, 29.57, 29.22; MS(FAB) m/z=232.1(MH+).

d) A solution of 2-allyl-8-methoxy-2,3,4,5-tetrahydro-1H-2-benzazepin-1-one (8.0 g, 0.043 mol) in dry tetrahydrofuran (40 mL) was treated with 9-borabicyclononane (1.0M in THF) and the resulting mixture was stirred for 18 hours at room temperature. The solution was then diluted with EtOH (50 mL), cooled to 0° C. (ice bath), and treated with 15% aqueous NaOH (15 mL) followed by 30% aqueous H$_2$O$_2$ (10 mL). The resulting mixture was stirred for 1 hour at 0° C., then treated cautiously with saturated aqueous sodium thiosulfate (50 mL). The mixture was partitioned between ethyl acetate and brine, and the combined organic layers were concentrated in vacuo, and the residue was purified by chromatography over silica gel eluting with ethyl acetate to yield 6.5 g (60%) of 2-(3-hydroxypropyl)-8-methoxy-2,3,4,5-tetrahydro-1H-2-benzazepin-1-one as a colorless oil;

$^1$H NMR (CDCl$_3$) d7.19(s, 1H), 7.06(d, J=9 Hz, 1H, 6.92(dd, J=3, 9 Hz, 1H), 4.30(brs, 1H), 3.82(s, 3H), 3.71 (t, J=6 Hz, 2H), 3.61(brs, 2H), 3.18(t, J=6 Hz, 2H), 2.72(t, J=6 Hz, 2H), 2.0(pentet, J=6 Hz, 2H), 1.79(pentet, J=6 Hz, 2H);

$^{13}$C NMR(CDCl$_3$) d172.25(C̲O), 158.51(NC̲O), 136.34, 129.53, 117.46, 112.94, 58.19, 55.42, 46.16, 43.30, 30.91, 29.45, 29.12;

MS (FAB) m/z=250.1(MH+); HRMS (FAB, MH+) m/z=249.1364 (calcd C$_{14}$H$_{19}$NO$_3$: 249.1364).

e) A solution of 2-(3-hydroxypropyl)-8-methoxy-2,3,4,5-tetrahydro-1H-2-benzazepin-1-one (6.50 g, 0.026 mol) in CH$_2$Cl$_2$ was added, at −78° C. (CO$_2$/acetone), to a solution of (COCl)$_2$ (4.50 mL, 0.052 mol) and DMSO (7.4 mL, 0.104 mol) in CH$_2$Cl$_2$ (100 mL) at −78° C. After stirring for 15 minutes at −78° C., the mixture was treated with NEt$_3$ (30 mL, 0.208 mol), and the bath removed. The CH$_2$Cl$_2$ solution was washed with brine, dried (MgSO$_4$) and concentrated in vacuo. The residue was immediately dissolved in N,N-dimethylformamide (30 mL) and MeOH (30 mL), and treated, in portions, with pyridinium dichromate (30 g total). After stirring for 24 hours, the dark brown suspension was diluted with ethyl acetate and filtered, and the filtrate was partitioned between ethyl acetate and brine. The combined organic layers were washed with water, brine, dried (MgSO$_4$) and concentrated in vacuo. The residue was purified by chromatography over silica gel eluting with a gradient of 10% ethyl acetate/hexane to 100% ethyl acetate to yield 2.5 g (35%) of 2-(2-carboxyethyl)-8-methoxy-2,3,4,5-tetrahydro-1H-2-benzazepin-1-one methyl ester as a colorless oil;

$^1$H NMR(CDCl$_3$) d7.18(d, J=3 Hz, 1H), 7.02(d, J=9 Hz, 1H), 6.88(dd, J=3, 9 Hz, 1H), 3.83(t, J=6 Hz, 2H), 3.80(s, 3H), 3.69(s, 3H), 3.23(t, J=6 Hz, 2H), 2.78(t, J=6 Hz, 2H), 2.67(t, J=6 Hz, 2H), 1.96(m, 2H);

$^{13}$C NMR(CDCl$_3$) d172.41(C̲O), 171.15(C̲O), 158.50, 136.80, 129.58, 129.40, 117.3̲4, 112.86, 5̲5.42, 51.78, 47.37, 44.13, 33.64, 29.85, 29.14;

MS(FAB) m/z=278.1 (MH+); HRMS(FAB, MH+) m/z=278.1392 (cald for C$_{15}$H$_{19}$NO$_4$: 277.1313).

f) A solution of 2-(2-carboxyethyl)-8-methoxy-2,3,4,5-tetrahydro-1H-2-benzazepin-1-one methyl ester (3.20 g, 0.011 mol) in CH$_2$Cl$_2$ was added to a suspension of AlCl$_3$ (4.70 g, 0.034 mol) and n-propanethiol (5.3 mL, 0.057 mol) at 0° C. (ice bath), and the resulting mixture stirred for 10 minutes at room temperature. The mixture was diluted with saturated aqueous sodium bicarbonate (50 mL), and the resulting white suspension stirred for 1 hour. The gelatinous mixture was filtered, and the filtrate was dried (MgSO$_4$) and concentrated in vacuo to yield 2.0 g (85%) of 2-(2-carboxyethyl)-8-hydroxy-2,3,4,5-tetrahydro-1H-2-benzazepin-1-one methyl ester as a colorless oil;

$^1$H NMR(CD$_3$OD) d7.08(d, J=9 Hz, 1H, 7.02(d, J=3Hz, 1H), 6.87(dd, J=3, 9 Hz, 1H), 3.05(t, J=6 Hz, 2H), 2.72(t, J=6 Hz, 2H), 1.97(t, J=6 Hz, 2H).

g) A suspension of 2-(2-carboxyethyl)-8-hydroxy-2,3,4,5-tetrahydro-1H-2-benzazepin-1-one methyl ester (250 mg, 0.950 mmol), p-cyanobenzylbromide (186 mg, 0.950 mmol) and K$_2$CO$_3$ (500 mg) in N,N-dimethylformamide (20 mL) was stirred vigorously at room temperature under an atmosphere of argon. After 1 hour, the suspension was diluted with ethyl acetate (100 mL), washed with water and brine, dried (Na$_2$SO$_4$) and concentrated in vacuo. The residue was purified by chromatography over silica gel to yield 150 mg (40%) of 2-(2-carboxyethyl)-8-(4-cyanobenzyloxy)-2,3,4,5-tetrahydro-1H-2-benzazepin-1-one methyl ester as a colorless oil;

$^1$H NMR(CDCl$_3$) d7.66(d, J=6Hz, 1H), 7.54(d, J=6Hz, 1H), 7.00(dd, J=3, 9 Hz, 1H), 5.13(s, 2H), 3.84(t, J=6 Hz, 2H), 3.70(s, 3H), 3.24(t, J=6 Hz, 2H), 2.72(m, 4H), 1.98(pentet, J=6 Hz, 2H);

$^{13}$C NMR(CDCl$_3$) d172.27(C̲O), 170.82(C̲O), 157.05, 142.32, 137.01, 132.39, 132.3̲2, 130.45, 129.63, 127.52, 118.66, 117.83,.113.98, 111.53, 68.90, 51.76, 47.31, 44.14, 33.58, 29.76, 29.13; MS(FAB) m/z=379.1(MH+).

h) A solution of 2-(2-carboxyethyl)-8-(4-cyanobenzyloxy)-2,3,4,5-tetrahydro-1H-2-benzazepin-1-one methyl ester (150 mg, 0.400 mmol) in 50 mL of 1:1 pyridine-NEt$_3$ was saturated with H$_2$S, and heated at 50° C. under argon. After 1 hour, the solvents were removed in vacuo. The residue was dissolved in CH$_2$Cl$_2$ (20 mL) and treated with iodomethane (4 mL), and the resulting mixture heated at reflux for 1 hour. The solvents were removed in vacuo, and the residue was dissolved in MeOH and treated with an excess of NH$_4$OAc (1 g). The resulting suspension was stirred for 15 minutes at 60° C. The MeOH was then removed, and the residue was treated with 50% NaOH (3 mL) in tetrahydrofuran (20 mL), and stirred for 15 minutes at room temperature. The mixture was then diluted with trifluoroacetic acid, and the volatiles were removed in vacuo. The residue was purified by HPLC (½" C-18 reverse-phase column, eluting with a solvent gradient of 1:9 acetonitrile (0.1% TFA)/water (0.1% TFA) time 0 to 10 minutes, to 1:1 acetonitrile (0.1%TFA)/water (0.1% TFA) time 10 to 40 minutes, flow 10 mL/min, $R_t$=30.5 min, mu detection 254 nM), to give 18.5 mg (9 %) of 2-(2-carboxyethyl)-8-(4-amidinobenzyloxy)-2,3,4,5-tetrahydro-1H-2-benzazepin-1-one trifluoroacetate as a yellowish-brown solid after lyophilization;

$^1$H NMR(CD$_3$OD) d7.66(d, J=6 Hz, 1H), 7.54(d, J=6 Hz, 1H), 7.00(dd, J=3, 9 Hz, 1H), 5.13(s, 2H), 3.84(t, J=6 Hz, 2H), 3.70(s, 3H), 3.24(t, J=6 Hz, 2H), 2.72(m, 4H), 1.98(m, J=6 Hz, 2H); MS(FAB) m/z=381.1688 (MH+).

EXAMPLE 20

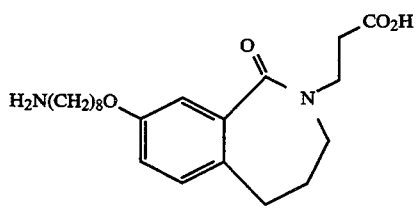

2-(2-carboxyethyl)-8-(8-aminooctyloxy)-2,3,4,5-tetrahydro-1H-2-benzazepin-1-one trifluoroacetate a) A solution of 2-allyl-8-methoxy-2,3,4,5-tetrahydro-1H-2-benzazepin-1-one (1.10 g, 0.0047 mol) in CH$_2$Cl$_2$ (20 mL) was treated at 0° C. with BBr$_3$ (1M in CH$_2$Cl$_2$, 9.50 mL), and the resulting mixture stirred at 0° C. for 30 minutes. The solution was poured over ice, NaHCO$_3$ was added, and the solution was extracted with CH$_2$Cl$_2$. The combined organic layers were dried (MgSO$_4$), filtered, and concentrated in vacuo to yield ca. 1.0 g (100%) of 2-allyl-8-hydroxy-2,3,4,5-tetrahydro-1H-2-benzazepin-1-one as a colorless oil;

$^1$H NMR(CDCl$_3$) d8.2(brs, 1H), 7.47(s, 1H), 6.95(d, J=6 Hz, 1H), 6.84(dd, J=3, 6 Hz, 1H), 5.89(m, 1H), 5.22(m, complex, 2H), 4.20(d, J=6 Hz, 2H), 3.18(t, J=6 Hz, 2H), 2.66(t, J=6 Hz, 2H), 2.15(s, 1H), 1.96(m, 2H);

$^{13}$C NMR(CDCl$_3$) d171.65(CO), 156.01,135.68, 133.27, 129.55, 128.46, 11831, 118.05, 115.91, 53.46, 49.81, 45.83, 30.87, 29.76, 29.12.

b) A suspension of 2-allyl-8-hydroxy-2,3,4,5-tetrahydro-1H-2-benzazepin-1-one (1.0 g, 0.0049 mol), 8-azido-1-(toluenesulfonyloxy)octane (1.50 g, 0.0049 mol) and K$_2$CO$_3$ in N,N-dimethylformamide (20 mL) was stirred vigorously under argon, and heated at 65° C. for 18 hours. The solution was then partitioned between ethyl acetate and brine, and the combined organic layers were washed with water, dried (K$_2$CO$_3$), filtered, and concentrated in vacuo. The residue was purified by chromatography over silica gel to yield 920 mg (51%) of 2-allyl-8-(8-azidooctyloxy)-2,3,4,5-tetrahydro-1H-2-benzazepin-1-one as a colorless oil;

$^1$H NMR(CDCl$_3$) d7.47(s, 1H), 6.95(d, J=6 Hz, 1H), 6.84(dd, J=3, 6 Hz, 1H), 5.89(m, 1H), 5.22(m, complex, 2H), 4.20(d, J=6 Hz, 2H), 3.95(t, J=6 Hz, 2H), 3.22(t, J=6 Hz, 2H), 3.18(t, J:6 Hz, 2H), 2.66(t, J=6 Hz, 2H), 1.90(t, J=6 Hz, 2H), 1.79(t, J=6 Hz, 2H), 1.60(m, 4H), 1.35(m, 6H).

c) A solution of 2-allyl-8-(8-azidooctyloxy)-2,3,4,5-tetrahydro-1H-2-benzazepin-1-one (920 mg, 2.48 mmol) in tetrahydrofuran (20 mL) was treated with 9-borabicyclononane (0.5M/THF, 10 mL, 5.00 mmol), and the mixture was stirred under argon at room temperature for 18 hours. The mixture was then cooled in an ice bath, and EtOH (5 mL) followed by 15% aqueous NaOH (10 mL) and 30% H$_2$O$_2$ (15 mL) were added. The mixture was stirred for 1 hour, then saturated aqueous sodium thiosulfate was added (20 mL). The solution was partitioned between ethyl acetate and brine, and the combined ethyl acetate layers were dried (MgSO$_4$), filtered, and concentrated in vacuo. The residue was purified by chromatography over silica gel to yield 400 mg (42%) of 2-(3-hydroxypropyl)-8-(8-azidooctyloxy)-2,3,4,5-tetrahydro-1H-2-benzazepin-1-one as a colorless oil;

$^1$H NMR(CDCl$_3$) d7.20(d, J=3Hz, 1H), 7.04(d, J=6 Hz, 1H), 6.91(dd, J=3, 6 Hz, 1H), 3.96(t, J=6 Hz, 2H), 3.72(t, J=6Hz, 2H), 3.61(t, J=6 Hz, 2H), 3.26(t, J=6 Hz, 2H), 3.18(t, J=6 Hz, 2H), 2.73(t, J=6Hz, 2H), 2.02 (t, J=6 Hz, 2H), 1.77(m, 4H), 1.60(m, 2H), 1.36(m, 8H).

d) 2-(3-hydroxypropyl)-8-(8-azidooctyloxy)-2,3,4,5-tetrahydro-1H-2-benzazepin-1-one was subjected to standard Swern conditions followed by PDC oxidation as described in part (e) of Example 14 to yield 140 mg (45%) of 2-(2-carboxyethyl)-8-(8-azidooctyloxy)-2,3,4,5-tetrahydro-1H-2-benzazepin-1-one methyl ester as a colorless oil;

$^1$H NMR(CDCl$_3$) d7.18(d, J=3 Hz, 1H), 7.00(d, J=9 Hz, 1H), 6.89(dd, J=3, 9 Hz, 1H), 3.96(t, J=6 Hz, 2H), 3.84(t, J=6 Hz, 2H), 3.70 (s, 3H), 3.26(m, 4H), 2.74(m, 4H), 1.97(t, J=6 Hz, 2H), 1.77(t, J=6 Hz, 2H), 1.60(t, J=6 Hz, 2H), 1.35(m, 6H);

$^{13}$C NMR(CDCl$_3$) d172.38(CO), 171.21(CO), 158.04, 136.72, 129.40, 129.34, 117.78, 113.57, 68.05, 51.76, 51.41, 47.37, 44.13, 33.64, 29.86, 29.13, 19.02, 28.77, 26.59, 25.87; MS(FAB) 417.2(MH+).

e) A solution of 2-(2-carboxyethyl)-8-(8-azidooctyloxy)-2,3,4,5-tetrahydro-1H-2-benzazepin-1-one methyl ester (70 mg, 0.168 mmol) in MeOH (1 mL) was treated with 10% Pd/C (20 mg) and the resulting suspension was reduced under an atmosphere of hydrogen (30 psi) for 2 hours. The solution was then filtered through Celite ®, and the filtrate was concentrated in vacuo. The residue was dissolved in tetrahydrofuran (1 mL) and treated with 50% NaOH (0.5 mL), and the resulting mixture was stirred at room temperature. After 1 hour, the solution was treated with trifluoroacetic acid (1 mL), and concentrated in vacuo. The white paste remaining was purified by HPLC (½' C-18 reverse-phase column) eluting with a gradient of 3:7 methanol (0.1% trifluoroaceate)/water (0.1% trifluoroaceate), time 0 to 10 min, to 7:3 methanol (0.1% trifluoroaceate)/water(0.1% trifluoroaceate), time 10 to 40 min, to yield 30 mg (36%) of 2-(2-carboxyethyl)-8-(8-aminooctyloxy)-2,3,4,5-tetrahydro-1H-2-benzazepin-1-one as a colorless oil;

$^1$H NMR(CD$_3$OD) d7.095(m, 2H), 6.96(dd, J=3, 9Hz, 1H), 3.98(t, J=6 Hz, 2H), 3.83(t, J=6 Hz, 2H), 3.27(m, 4H), 2.90(t, J=6 Hz, 2H), 2.69(m, 4H), 2.03(t, J=6 Hz, 2H), 1.78(t, J=6 Hz, 2H), 1.64(t, J=6Hz, 2H), 1.40(m, 6H); MS(FAB) m/z=377.1(MH+-TFA).

EXAMPLE 21

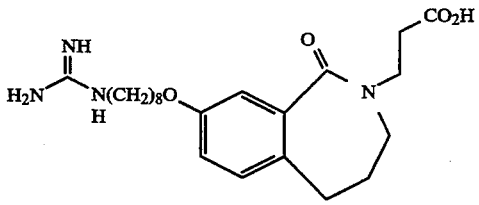

2-(2-carboxyethyl)-8-(8-guanadinooctyloxy)-2,3,4,5-tetrahydro-1H-2-benzazepin-1-one trifluoroacetate a) A solution of 2-(2-carboxyethyl)-8-(8-aminooctyloxy)-2,3,4,5-tetrahydro-1H-2-benzazepin-1-one trifluoroacetate (30 mg, 0.061 mmol) in saturated aqueous $KHCO_3$ (2 mL) was treated with formamidine sulfonic acid (85 mg, 1.08 mmol) and the resulting mixture was stirred at room temperature for 20 minutes. The mixture was neutralized with acetic acid, and the residue was purified by HPLC ($\frac{1}{2}'$ C-18 reverse-phase column) eluting with a gradient of 3:7 methanol (0.1% trifluoroaceate)/water (0.1% trifluoroaceate), time 0 to 10 min, to 7:3 methanol(0.1% trifluoroaceate)/water(0.1% trifluoroaceate), time 10 to 40 min, to yield 7.3 mg (25%) of 2-(2-carboxyethyl)-8-(8-guanadinooctyloxy)-2,3,4,5-tetrahydro-1H-2-benzazepin-1-one trifluoroacetate as a light brown solid;

$^1$H NMR(CD$_3$OD) d7.09(m, 2H), 6.96(dd, J=3, 9 Hz, 1H), 3.98(t, J=6 Hz, 2H), 3.83(t, J=6 Hz, 2H), 3.33(m, 4H), 2.91 (t, J=6Hz, 2H), 2.69(t, J=6 Hz, 4H), 2.30(m, 2H), 1.75(m, 2H), 1.65(m, 2H), 1.40(m, 6H);

$^{13}$C NMR(CD$_3$OD) d175.9(CO), 173.8(CO), 160.0, 137.0, 131.16, 130.79, 118.66, 114.81, 69.17, 45.33, 40.78, 34.32, 31.15, 30.27, 30.18, 30.15, 30.04, 28.59, 27.39, 27.06;

M(FAB) m/z=419.2(MH+).

EXAMPLE 22

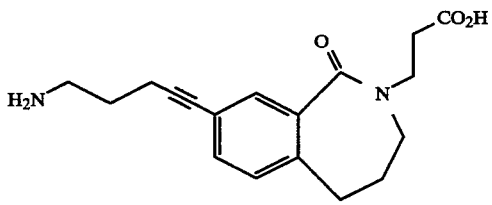

2-(2-carboxyethyl)-8-(5-aminopentynyl)-2,3,4,5-tetrahydro-1H-2-benzazepin-1-one trifluoroacetate a) A solution of 2-(2-carboxyethyl)-8-hydroxy-2,3,4,5-tetrahydro-1H-2-benzazepin-1-one methyl ester (2.20 g, 0.00836 mol) and $NEt_3$ (1.40 mL, 0.0100 mol) in $CH_2Cl_2$ (20 mL) was cooled to 0° C. (ice bath) and treated with trifluoromethanesulfonic anhydride (1.70 mL, 0.0100 mol), and the resulting mixture stirred to 30 minutes. The mixture was then partitioned between ethyl acetate and saturated aqueous $NaHCO_3$. The combined organic layers were dried ($MgSO_4$), filtered, and concentrated in vacuo to an oil, used immediately without purification. A solution of the triflate (400 mg, 1.00 mmol) and 5-((tert-butyloxy)carbonyl)amino-2-pentyne (366 mg, 2.00 mmol) in $NEt_3$ (10 mL) was treated with bis-triphenylphosphine palladium dichloride (20 mg) and CuI (10 mg), and the resulting mixture was de-gassed thoroughly with argon, and heated at reflux for 12 hours. The solution was then cooled, and volatiles removed in vacuo, and the residue was purified by chromatography over silica gel eluting with 1:1 ethyl acetate/hexanes to yield 400 mg (93%) of 2-(2-carboxyethyl)-8-(5-N-Boc-aminopentynyl)-2,3,4,5-tetrahydro-1H-2-benzazepin-1-one methyl ester as a colorless oil;

$^1$H NMR(CDCl$_3$) d7.68(s, 1H), 7.37(d, J=6 Hz, 1H), 7.50(d, J=6 Hz, 1H), 4.7(brs, 1H), 3.84(t, J=6 Hz, 2H), 3.71(s, 3H), 3.25(q, J=6 Hz, 4H), 2.73(t, J=6 Hz, 4H), 2.46(t, J=6 Hz, 2H), 2.00(m, 2H), 1.78(m, 2H);

$^{13}$C NMR(CDCl$_3$) d171.38(CO), 170.49(CO), 155.92, 136.83, 136.06, 133.61,131.68, 128.25, 122.55, 89.55, 80.43, 51.78, 47.18, 44.11, 39.75, 33.58, 29.92, 29.57, 28.72, 28.37, 16.88; MS(FAB) m/z=429.1(MH+).

b) A solution of 2-(2-carboxyethyl)-8-(5-N-Boc-aminopentynyl)-2,3,4,5-tetrahydro-1H-2-benzazepin-1-one methyl ester (66 mg, 0.154 mmol) in EtOH (1 mL) was treated with trifluoroacetic acid (0.5 mL), and the resulting mixture stirred for 18 hours. The volatiles were then removed, and the residue was dissolved in tetrahydrofuran (1 mL), and treated with 50% NaOH (0.5 mL), and the mixture was stirred for 20 minutes at room temperature. Trifluoroacetic acid was then added (3 mL), and the solution was concentrated in vacuo. The residue was purified by HPLC ($\frac{1}{2}'$ C-18 reverse-phase column) eluting with a gradient of 3:7 methanol (0.1% trifluoroaceate)/water (0.1% trifluoroaceate), time 0 to 10 min, to 7:3 methanol (0.1% trifluoroaceate)/water(0.1% trifluoroaceate), time 10 to 40 min, to yield 46 mg (95%) of 2-(2-carboxyethyl)-8-(5-aminopentynyl)-2,3,4,5-tetrahydro-1H-2-benzazepin-1-one trifluoroacetate as a light brown solid; $^1$H NMR(D$_2$O) d7.32(s, 1H), 7.25(d, J=6 Hz, 1H), 7.00(d, J=6 Hz, 1H), 3.63(t, J=6 Hz, 2H, 2.95(m, 4H), 2.58(t, J=6 Hz, 2H), 2.50(t, J=6 Hz, 2H), 2.38(t, J=6 Hz, 2H), 1.80 (m, 4H); MS(FAB) m/z=315(MH+).

EXAMPLE 23

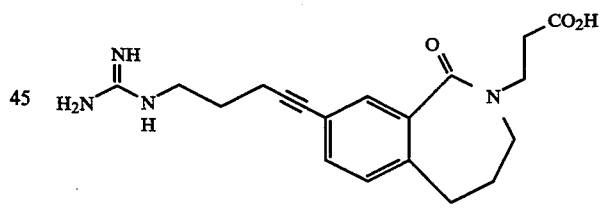

2-(2-Carboxyethyl)-8-(5-guanidinopentynyl)-2,3,4,5-tetrahydro-1H-2-benzazepin-1-one Trifluoroacetate a) A solution of 2-(2-carboxyethyl)-8-(5-aminopentynyl)-2,3,4,5-tetrahydro-1H-2-benzazepin-1-one trifluoroacetate (20 mg, 0.063 mmol) in saturated aqueous $KHCO_3$ (1 mL) was treated with formamidine sulfonic acid (80 mg, 1.0 mmol), and the resulting mixture stirred for 2 hours. The mixture was then treated with acetic acid, and the volatiles were removed. The residue was purified by HPLC ($\frac{1}{2}'$ C-18 reverse-phase column) eluting with a gradient of 3:7 methanol (0.1% trifluoroaceate)/water (0.1% trifluoroaceate), time 0 to 10 min, to 7:3 methanol(0.1% trifluoroaceate)/water(0.1% trifluoroaceate), time 10 to 40 min, to yield 4.5 mg (15%) of 2-(2-carboxyethyl)-8-(5-guanidinopentynyl)-2,3,4,5-tetrahydro-1H-2-benzazepin-1 -one trifluoroacetate as a light brown solid; $^1$H NMR(D$_2$O) d7.40(s, 1H), 7.25(dd, J=3, 6 Hz, 1H), 7.15(d, J=6 Hz, 1H), 3.80(t, J=6 Hz, 2H), 3.30(m, 4H), 3.15(t, J=6 Hz, 2H, 2.00(t, J=6 Hz, 2H), 1.80(m, 2H); MS(FAB) m/z=357.1(MH+).

EXAMPLE 24

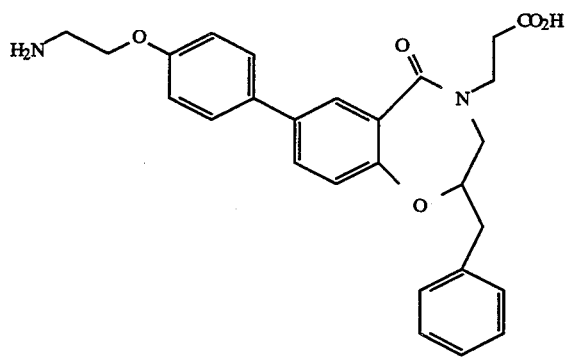

2-(2-Carboxyethyl)-8-(4-(2-aminoethoxy)phenyl)-2,3,4,5-tetrahydro-1H-5-oxa-2-benzazepin-1-one Trifluoroacetate a) A solution of 1-aminopropylene (10.6 grams, 0.186mol) in methanol was added to a methanolic solution of 3-phenylpropyleneoxide (5.07 grams, 0.037mol) and the mixture heated to reflux for 30 minutes. The mixture was allowed to warm to room temperature and concentrated in vacuo to yield 7.2 grams (99%) of N-allyl-3-phenyl-2-hydroxypropylamine. $^1$H NMR (CDCl$_3$, dTMS) 7.34–7.18 (5H, m, Ar—H), 5.84 (1H, ddt, $^3J_{HH}$=17.1 Hz, $^3J_{HH}$=10.2 Hz, $^3J_{HH}$=6 Hz, CH$_2$CH), 5.2–5.0 (2H, m, CH=CH$_2$ ), 3.86 (1H, m, CHOH), 3.19 (2H, m, NCH$_2$CH=CH$_2$), 2.76–2.66 (3H, m, NCH$_2$CH(OH)CHHPh), 2.50 (1H, dd $^2J_{HH}$=12 Hz, $^3J_{HH}$=9 Hz). $^{13}$C NMR (CDCl$_3$) 138.4, 136.5, 129.3, 128.4, 126.3, 116.0, 70.6, 54.0, 51.9, 41.7.

Using the above procedure, but substituting the appropriate alkenyloxide or allyl amine for 3-phenylpropyleneoxide or 1-aminopropylene, respectively, there may be prepared, for example, the following compounds:
N-allyl-2-hydroxypropylamine,
N-(3-but-1-ene)-3-phenyl-2-hydroxypropylamine,
N-(3-but-1-ene)-2-hydroxypropylamine.

b) To a magnetically stirred suspension of 5-iodosalisylic acid (Aldrich, 8.5 grams, 0.032mol), was added oxalyl chloride (8.6 grams, 0.064 mol) and one drop of dimethylformamide. The mixture was stirred until effervescence had ceased and concentrated in vacuo. The resulting residue was diluted with diethyl ether and added to a solution of N-allyl-3-phenyl-2-hydroxypropylamine (6.4 grams, 0.034 mol) in diethyl ether over a period of 30 minutes. The reaction was stirred for 1 hour, filtered, and concentrated in vacuo. The resulting residue was dissolved in methylene chloride and washed with 1N HCl, sat. sodium bicarbonate, dried over sodium sulfate, filtered and concentrated in vacuo to yield 12.26 grams (87%) of N-allyl-N-(2-hydroxy-5-iodobenzoyl)-2-hydroxy-3-phenylpropylamine. The material was used without further purification.

Using the above procedure, but substituting the appropriate hydroxypropylamine for N-allyl-3-phenyl-2-hydroxypropylamine there may be prepared, for example, the following compounds:
N-allyl-N-(2-hydroxy-5-iodobenzoyl)-2-hydroxypropylamine,
N-(3-but-1-ene)-N-(2-hydroxy-5-iodobenzoyl)-2-hydroxy-3-phenylpropylamine,
N-(3-but-1-ene)-N-(2-hydroxy-5-iodobenzoyl)-2-hydroxypropylamine.

c) To a magnetically stirred solution of N-allyl-N-(2-hydroxy-5-iodobenzoyl)-2-hydroxy-3-phenylpropylamine (12.05 grams, 0.027 mol) in 100 mL THF was added triphenylphosphine (7.24 grams, 0.027 mol), and diethyl azodicarboxylate (4.7 grams, 0.027 mol). The mixture was heated to reflux overnight, allowed to cool to room temperature, and concentrated in vacuo. The resulting residue was dissolved in ethyl acetate (10 mL) and diluted with diethyl ether. The solids that form were filtered and the mother liquor was concentrated in vacuo. The yellow oil was purified by column chromatography (SiO$_2$, using 15% diethyl ether/85% hexane to 1:1 diethyl ether/hexane as the eluting solvent gradient, Rf(product, 1:1 Et2O/heaxane)=0.64) to yield 4.31 grams (38%) of 2-allyl-4-benzyl-8-iodo-2,3,4,5-tetrahydro-1H-5-oxa-2-benzazepin-1-one. $^1$H NMR (CDCl$_3$, dTMS) 8.10 (1H, d, $^4J_{HH}$=2 Hz, C9-H), 7.69 (1H, dd, $^4J_{HH}$=2 Hz, $^3J_{HH}$=9 Hz, C7-H), 7.4–7.2 (5H, m, C$_6$H$_5$), 6.76 (1H, d, $^3J_{HH}$=9 Hz, C6-H), 5.79 (1H, ddt, $^3J_{HH}$=17Hz, $^3J_{HH}$=11 Hz, $^3J_{HH}$=6 Hz, CH$_2$CH=CH$_2$), 5.2–5.0 (2H, m, CH=CH$_2$), 5.71 (1H, m, CHOH), 4.31 (1H, ddt, $^2J_{HH}$=15 Hz, $^3J_{HH}$=6 Hz, $^4J_{HH}$=1 Hz, NCHHCH=CH$_2$), 4.00 (1H, ddt, $^2J_{HH}$=15 Hz, $^3J_{HH}$=6 Hz, $^4J_{HH}$=1 Hz, NCHHCH=CH$_2$), 3.34 (1H, dd, $^2J_{HH}$=16 Hz, $^3J_{HH}$=5.1 Hz, C3-H), 3.25 (1H, dd, $^2J_{HH}$=16 Hz, $^3J_{HH}$=4.2 Hz, C3-H), 3.09 (1H, dd, $^2J_{HH}$=14 Hz, $^3J_{HH}$=7 Hz, CHHPh), 2.73 (1H, dd, $^2J_{HH}$=14 Hz, $^3J_{HH}$=7 Hz, CHHPh). $^{13}$C NMR (CDCl$_3$) 166.9, 152.7, 141.4, 139.6, 136.5, 132.6, 129.8, 129.1, 128.8, 127.0, 124.6, 118.4, 86.7, 84.7, 50.4, 48.9, 38.9. IR (NaCl, cm$^{-1}$) 1641, 1589, 1463, 1430, 1264, 1217, 699.

Using the above procedure, but substituting the appropriate hydroxypropylamine for N-allyl-N-(2-hydroxy-5-iodobenzoyl)-2-hydroxy-3phenylpropylamine there may be prepared, for example, the following compounds:
2-allyl-4-methyl-8-iodo-2,3,4,5-tetrahydro-1H-5-oxa-2-benzazepin-1-one,
2-(3-but-1-ene)-4-benzyl-8-iodo-2,3,4,5-tetrahydro-1H-5-oxa-2-benzazepin-1-one,
2-(3-but-1-ene)-4-methyl-8-iodo-2,3,4,5-tetrahydro-1H-5-oxa-2-benzazepin-1-one.

d) To a magnetically stirred solution of 2-allyl-4-benzyl-8-iodo-2,3,4,5-tetrahydro-1H-5-oxa-2-benzazepin-1-one (0.9234 grams, 2.2mmol) in 4 mL THF at room temperature under an atmosphere of nitrogen was added 6.0 mL of a 0.5M solution of 9-borabicylo[3.3.1 ]nonane in THF (3 mmol) and the mixture stirred for 1 hour. The reaction was quenched with 6 mL of a solution of 2 grams of sodium hydroxide and 22 mL of a 1:1 mixture of ethanol and water. To the resulting solution was added 7 mL of a 30% solution hydrogen peroxide in water. After 30 minutes the mixture was partitioned between diethyl ether and water. The organic layer was washed with 10% citric acid and brine, dried over sodium sulfate, concentrated in vacuo, and purified by column chromatography (SIO2, using 1:5 ethyl acetate/methylene chloride as the eluting solvent, R$_f$(product)=0.22) to yield 0.74 grams (77%) of 2-(3-hydroxypropyl)-4-benzyl-8-iodo-2,3,4,5-tetrahydro-1H-5-oxa-2-benzazepin-1-one. 1H NMR (CDCl$_3$, dTMS)

8.08 (1H, d, $^4J_{HH}=2$ Hz, C9-H), 7.71 (1H, dd, $^4J_{HH}=2$ Hz, $^3J_{HH}=8$ Hz, C7-H), 7.4–7.2 (5H, m, C$_6$H$_5$), 6.78 (1H, d, $^3J_{HH}=8$ Hz, C6-H), 4.64 (1H, m, ArOCH), 3.70 (2H, m, CH$_2$OH), 3.58 (2H, bt, $^3J_{HH}=5$ Hz, NCH$_2$CH$_2$), 3.39 (1H, dd, $^2J_{HH}=15$ Hz, $^3J_{HH}=8$ Hz, C3-H), 3.24 (1H, dd, $^2J_{HH}=15$ Hz, $^3J_{HH}=3$ Hz, C3-H), 3.1 (1H. dd, $^2J_{HH}=14$ Hz, $^3J_{HH}=7$ Hz, CHHPh), 2.76 (1H, dd, $^2J_{HH}=14$ Hz, $^3J_{HH}=7$ Hz, CHHPh), 1.68 (2H, m, CH$_2$CH$_2$OH). $^{13}$C NMR (CDCl$_3$) 168.3, 152.6, 141.6, 139.4, 136.2, 132.1, 131.9, 129.2, 129.0, 128.8, 128.4, 127.0, 124.7, 86.8, 85.7, 58.0, 49.9, 44.5, 38.8, 30.3. IR (NaCl, cm$^{-1}$) 3422 (b), 1636, 1463, 1436, 1217, 1064.

Using the above procedure, but substituting the appropriate 5-oxa-2-benzazepin-1-one for 2-allyl-4-benzyl-8-iodo-2,3,4,5-tetrahydro-1H-5-oxa-2-benzazepin-1-one there may be prepared, for example, the following compounds:

2-(3-hydroxypropyl)-4-methyl-8-iodo-2,3,4,5-tetrahydro-1H-5-oxa-2-benzazepin-1-one, 2-(4-hydroxybut-2-yl)-4-benzyl-8-iodo-2,3,4,5-tetrahydro-1H-5-oxa-2-benzazepin-1-one, 2-(4-hydroxybut-2-yl)-4-methyl-8-iodo-2,3,4,5-tetrahydro-1H-5-oxa-2-benzazepin-1-one.

e) To a magnetically stirred solution of 2-(3-hydroxypropyl)-4-benzyl-8-iodo2,3,4,5-tetrahydro-1H-5-oxa-2-benzazepin-1-one (0.75 grams, 1.7mmol) in 5 mL dimethylformamide at room temperature was added a solution of pyridinium dichromate (2.58 grams, 6.86mmol) in 5 mL dimethylformamde. The reaction mixture was stirred overnight, diluted with 75 mL water, washed 3×75 mL diethyl ether, made acidic to a pH of 2 with conc. HCl and extracted 3×75 mL diethyl ether. The combined organics were extracted 3×40 mL 1N sodium hydroxide. The combined aqueous layers were acidified to a pH of 2 with canc HCl and extracted 3×50 mL diethyl ether. These ether layers were combined and dried over magnesium sulfate, filtered, and concentrated in vacuo to yield 0.557 grams (73%) of 2-(2-carboxyethyl)-4-benzyl-8-iodo-2,3,4,5-tetrahydro-1H-5-oxa-2-benzazepin-1-one. $^1$H NMR (CDCl$_3$, dTMS) 8.07 (1H, d, $^4J_{HH}=2$ Hz, C9-H), 7.69 (1H, dd, $^4J_{HH}=2$ Hz, $^3J_{HH}=8$ Hz, C7-H), 7.4–7.2 (5H, m, C$_6$H$_5$), 6.75 (1H, d, $^3J_{HH}=8$ Hz, C6-H), 4.75 (1H, m, ArOCH), 3.89 (1H, dt, $^2J_{HH}=14$ Hz, $^3J_{HH}=6$ Hz, NCHHCH$_2$CO$_2$), 3.69 (1H, dt, $^2J_{HH}=14$ Hz, $^3J_{HH}=6$ Hz, NCHHCH$_2$CO$_2$), 3.44 (2H, d, $^3J_{HH}=3$ Hz, CH$_2$Ph), 3.07 (1H, dd, $^2J_{HH}=14$ Hz, $^3J_{HH}=7$ Hz, C3-H), 2.8–2.7 (3H, m, C3-H, CH$_2$CO$_2$), $^{13}$C NMR (CDCl3) 176.1 167.6, 164.4, 152.8, 141.7, 139.5, 136.4, 129.4, 129.1, 128.9, 128.8, 127.0, 124.7, 86.7, 84.7, 51.4, 45.0, 38.8, 33.0.

Using the above procedure, but substituting the appropriate 5-oxa-2-benzazepin-1-one for 2-(3-hydroxypropyl)-4-benzyl-8-iodo-2,3,4,5-tetrahydro1H-5-oxa-2-benzazepin-1-one there may be prepared, for example, the following compounds:

2-(2-carboxyethyl)-4-methyl-8-iodo-2,3,4,5-tetrahydro-1H-5-oxa-2-benzazepin-1-one, 2-(3-carboxy-2-propyl)-4-benzyl-8-iodo-2,3,4,5-tetrahydro-1H-5-oxa-2-benzazepin-1-one, 2-(3-carboxy-2-propyl)-4-methyl-8-iodo-2,3,4,5-tetrahydro-1H-5-oxa-2-benzazepin-1-one.

f) A solution of diazomethane in ether, prepared by allowing a slurry of 2.98 grams of N-nitroso-N-methylurea and 10 mL ether to react with a solution of 20 grams of KOH in 20 mL water, was carefully added via a pipet to solution of 2-(2-carboxyethyl)-8-iodo-2,3,4,5-tetrahydro-1H-5-oxa-2-benzazepin-1-one (0.42 grams, 0.93mmol) in 20 mL diethyl ether until yellow color persists. The mixture was allowed to stand overnight and concentrated in vacuo. The resulting residue was purified by column chromatography (SiO2, 1:9 ethyl acetate/hexane, R$_f$(product)=0.2) to yield 0.275 grams (64%) of 2-(2-carboxyethyl)-8-iodo-2,3,4,5-tetrahydro-1H-5-oxa-2-benzazepin-1-one methyl ester. $^1$H NMR (CDCl$_3$, dTMS) 8.06 (1H, d, $^4J_{HH}=2$ Hz, C9-H), 7.68 (1H, dd, $^4J_{HH}=2$ Hz, $^3J_{HH}=8$ Hz, C7-H), 7.4–7.2 (5H, m, C$_6$H$_5$), 6.75 (1H, d, $^3J_{HH}$8 Hz, C6-H), 4.76 (1H, m, ArOCH), 3.88 (1H, dt, $^2J_{HH}=14$ Hz, $^3J_{HH}=6$ Hz, NCHHCH$_2$CO$_2$), 3.69 (4H, m, NCHHCH$_2$CO$_2$CH$_3$), 3.44 (2H, m, C3-H), 3.06 (1H, dd, $^2J_{HH}=14$ Hz, $^3J_{HH}=7$ Hz, C3-H), 2.76 (1H, dd, $^2J_{HH}=14$ Hz, $^3J_{HH}=7$ Hz, CHHPh), 2.69 (2H, m, CHHPh, CH$_2$CO$_2$). $^{13}$C NMR (CDCl3) 172.4, 167.2, 164.4, 152.6, 141.4, 139.4, 136.5, 129.6, 129.1, 121.0, 128.8, 127.0, 124.6, 86.6, 84.7, 51.8, 51.3, 45.1, 38.7, 33.0.

Using the above procedure, but substituting the appropriate 5-oxa-2-benzazepin-1-one for 2-(2-carboxyethyl)-8-iodo-2,3,4,5-tetrahydro-1H-5-oxa-2-benzazepin-1-one there may be prepared, for example, the following compounds:

2-(2-carboxyethyl)-4-methyl-8-iodo-2,3,4,5-tetrahydro-1H-5-oxa-2-benzazepin-1-one methyl ester, 2-(3-carboxy-2-propyl)-4-benzyl-8-iodo-2,3,4,5-tetrahydro-1H-5-oxa-2-benzazepin-1-one methyl ester, 2-(3-carboxy-2-propyl)-4-methyl-8-iodo-2,3,4,5-tetrahydro-1H-5-oxa-2-benzazepin-1-one methyl ester.

g) To a magnetically stirred solution of 4-iodophenol (15 grams, 0.068 mol) in 100 mL THF was sequentially added triphenylphosphine (19.67 grams, 0.075 mol), diethyl azodicarboxylate (13.06 grams, 0.073 mol), and 2azidoethanol (5.93 grams, 0.068 mol). The mixture was stirred overnight, concentrated in vacuo, diluted with 90 mL ethyl acetate and diluted with hexane (400 mL), and the resulting solids filtered away. The filtrate was concentrated in vacuo, diluted with diethyl ether, and extracted with 1N NaOH and water. Pentane was added to induce precipatation of a white solid that was again filtered away. The fitrate was concentrated in vacuo, and dissolved in methanol (60 mL). Triethylamine (27 grams, 0.267 mol) and propanedithiol (23 grams, 0.215 mol) were added and the mixture stirred at room temperature overnight. The solution was diluted with 100 mL water and partitioned between methylene chloride and 1N NaOH. The organic layer was extracted with 2×200 mL 1N HCl and the aqueous layer washed with 100 mL methylene chloride, made basic with 2N NaOH and extracted 3×75 mL methylene chloride. The combined organics were dried over sodium carbonate, filtered and concentrated in vacuo to yield 12.97 grams of 2-(4-iodophenoxy)ethyl amine (72%). $^1$H NMR (CDCl$_3$, dTMS) 7.56 (2H, d, $^3J_{HH}=9$ Hz, Ar—H), 6.63 (2H, d, $^3J_{HH}=9$ Hz, Ar—H), 4.03 (2H, t, $^3J_{HH}=5$ Hz, CH$_2$N$_3$), 3.57 (2H, t, $^3J_{HH}=5$ Hz, OCH$_2$). $^{13}$C NMR (CDCl$_3$) 158.0, 138.2, 116.9, 83.4, 66.9, 49.9. IR (NaCl, cm$^{-1}$) 2930, 2107 (s), 1589, 1483, 1284, 1237, 1058, 819.

h) 2-(4-iodophenoxy)ethylamine (10 grams, 0.038 mol) dissolved in THF (50 mL) was allowed to react with di-t-butyl dicarbonate (9.13 grams, 0.041 mol) at room temperature for 1 hour. The reaction mixture was concentrated in vacuo to yield 17.7 grams (99%) of N-Boc-2-(4-iodophenoxy)ethylamine.

i) A slurry of 2-(2-carboxyethyl)-4-benzyl-8-iodo-2,3,4,5-tetrahydro-1H-5-oxa-2-benzazepin-1-one methyl ester (0.155 grams, 0.334mmol), N-Boc-2-(4-iodophenoxy)ethylamine (0.246 grams, 0.664mmol), degassed triethylamine (2 mL), bis(triphenylphosphine)-palladium dichloride (11 mgs, 10 mol %), and coprous iodide (6 mgs, 20 mol %) was heated to reflux overnight. The reaction was concentrated in vacuo, triturating the resulting residue with diethyl ether (30 mL). The ethereal solution was concentrated in vacuo and the residue purified by column chromatography (SiO$_2$, using 1:1 ethyl acetate/heaxane to ethyl aceate as the eluting solvent gradient, R$_f$(product)=0.08) to yield 19.1 mgs (10% ) of 2-(2-carboxyethyl)-4-benzyl-8-(4-(2-N-Boc-amino)ethoxyphenyl)-2,3,4,5-tetrahydro-1H-5-oxa-2-benzazepin-1-one methyl ester. 1H NMR (CDCl$_3$, dTMS) 7.94 (1H, d, $^4J_{HH}$=2 Hz, C9-H), 7.59 (1H, dd, $^4J_{HH}$=2 Hz, $^3J_{HH}$=8 Hz, C7-H), 7.52 (2H, d, $^3J_{HH}$=9 Hz, C8-o-Ar—H), 7.40-7.25 (5H, m, C$_6$H$_5$), 7.05 (1H, d, $^3J_{HH}$=8 Hz, C6-H), 6.96 (2H, d, $^3J_{HH}$=9 Hz, C8-m-Ar—H), 5.03 (1H, bs, NH), 4.76 (1H, m, OCH), 4.06 (2H, t, $^3J_{HH}$=5 Hz, OCH$_2$CH$_2$N), 3.92 (1H, dt, $^2J_{HH}$=14 Hz, $^3J_{HH}$=7 Hz, NCHHCH$_2$CO$_2$), 3.73 (1H, dt, $^2J_{HH}$=14 Hz, $^3J_{HH}$=7 Hz, NCHHCH$_2$CO$_2$), 3.67 (3H, s, CH$_3$), 3.56 (2H, bq, $^3J_{HH}$=6 Hz, CH$_2$NH), 3.51 (1H, dd, 2J$_{HH}$=16 Hz, $^3J_{HH}$=8 Hz, C3-H), 3.43 (1H, dd, $^2J_{HH}$=16 Hz, $^3J_{HH}$=5 Hz, C3-H), 3.12 (1H, dd, $^2J_{HH}$=14 Hz, $^3J_{HH}$=7 Hz, CHHPh), 2.78 (1H, dd, $^2J_{HH}$=14 Hz, $^3J_{HH}$=7 Hz, CHHPh), 2.72 (2H, m, CH$_2$CO$_2$), 1.48 (9H, s, Bu$^t$), $^{13}$C NMR (CDCl3) 172.6, 168.9, 136.8, 136.5, 130.8, 129.1,128.8, 128.7, 128.3. 126.9, 123.0, 114.8, 84.6, 60.4, 51.8, 51.5, 45.0, 38.8, 33.2, 28.3.

Using the above procedure, but substituting the appropriate 5-oxa-2-benzazepin-1 -one for 2-(2-carboxyethyl)-8-iodo-2,3,4,5-tetrahydro-1H-5-oxa-2-benzazepin-1-one there may be prepared, for example, the following compounds:

2-(2-carboxyethyl)-4-methyl-8-(4-(2-N-Boc-amino)ethoxyphenl)-2,3,4,5-tetrahydro-1H-5-oxa-2-benzazepin-1-one methyl ester, 2-(3-carboxy-2-propyl)-4-benzyl-8-(4-(2-N-Boc-amino)ethoxyphenyl)-2,3,4,5-tetrahydro-1H-5-oxa-2-benzazepin-1-one methyl ester, 2-(3-carboxy-2-propyl)-4-methyl-8-(4-(2-N-Boc-amino)ethoxyphenyl)-2,3,4,5-tetrahydro-1H-5-oxa-2-benzazepin-1-one methyl ester, 2-(2-carboxyethyl)-4-benzyl-8-[4-(4-N-Boc-piperazine)-phenyl]-2,3,4,5-tetrahydro-1H-5-oxa-2-benzazepin-1-one methyl ester, 2-(2-carboxyethyl)-4-methyl-8-[4-(4-N-Boc-piperazine)-phenyl]-2,3,4,5-tetrahydro-1H-5-oxa-2-benzazepin-1-one methyl ester, 2-(3-carboxy-2-propyl )-4-benzyl-8-[4-( 4-N-Boc-piperazine)phenyl]-2,3,4,5-tetrahydro-1H-5-oxa-2-benzazepin-1-one methyl ester, 2-(3-carboxy-2-propyl)-4-methyl-8-[4-(4-N-Boc-piperazine)phenyl]-2,3,4,5-tetrahydro-1H-5-oxa-2-benzazepin-1 -one methyl ester, 2-(2-carboxyethyl)-4-benzyl-8-[4-(4-N-Boc-aminomethyl)phenyl]-2,3,4,5-tetrahydro-1H-5-oxa-2-benzazepin-1-one methyl ester, 2-(2-carboxyethyl)-4-methyl-8-[4-(4-N-Boc-aminomethyl)phenyl]-2,3,4,5-tetrahydro-1H-5-oxa-2-benzazepin-1-one methyl ester, 2-( 3-carboxy-2-propyl)-4-benzyl-8-[4-(4-N-Boc-aminomethyl)phenyl]-2,3,4,5-tetrahydro-1H-5-oxa-2-benzazepin-1-one methyl ester, 2-(3-carboxy-2-propyl)-4-methyl-8-[4-(4-N-Boc-aminomethyl)phenyl]-2,3,4,5-tetrahydro-1H-5-oxa-2-benzazepin-1-one methyl ester.

j) To a solution of 2-(2-carboxyethyl)-4-benzyl-8-(4-(2-N-Boc-amino)ethoxyphenyl)-2,3,4,5-tetrahydro-1H-5-oxa-2-benzazepin-1-one methyl ester (19.1 mgs, 0.03 mmol) in 0.5 mL acetonitrile and 0.5 mL water was added a concentrated solution of HCl in ethyl acetate (1 mL) and the reaction allowed to stand for 15 minutes, concentrated in vacuo, dissolved in methanol (1 mL0 and allowed to react with 2N NaOH (1 mL). The reaction was quenched with acetic acid (0.5 mL) and concentrated in vacuo, dissolved in a minimum of water and purified by high-pressure column chromatography (HPLC, ½ reverse-phase C-18 column, 1:4 acetonitrile(0.1%TFA)/water (0.1%TFA) to 3:2 acetonitrile(0.1%TFA)/water (0.1%TFA) as the eluting solvent gradient) to yield 4.2 mgs (30%) of 2-(2-carboxyethyl)-8-(4-(2-aminoethoxy)phenyl)-2,3,4,5-tetrahydro-1H-5-oxa-2-benzazepin-1-one. $^1$H NMR (CD$_3$OD) 7.80 (1H, d, $^4J_{HH}$=2 Hz, C9-H), 7.67 (1H, dd, $^4J_{HH}$=2 Hz, $^3J$=8 Hz, C7-H), 7.58 (2H, d, $^3J_{HH}$=9 Hz, C8-o-Ar—H), 7.40-7.35 (5H, m, C$_6$H$_5$), 7.10 (2H, d, $^3J_{HH}$=9 Hz, C8-m-Ar—H), 7.03 (1H, d, $^3J_{HH}$=8 Hz, C6-H), 4.28 (2H, t, $^3J_{HH}$=4 Hz, OCH$_2$CH$_2$), 3.81 (2H, m, NCH$_2$CH$_2$CO$_2$), 3.61 (1H, dd, 2J$_{HH}$=14 Hz, $^3J_{HH}$=1 Hz, C3-H), 3.44 (1H, dd, $^2J_{HH}$=14 Hz, $^3J_{HH}$=4 Hz, C3-H), 3.41 (2H, t, $^3J_{HH}$=5 Hz, CH$_2$Ph), 2.87 (2H, t, $^3J_{HH}$=7 Hz, CH$_2$NH$_2$), 2.50 (2H, t, $^3J_{HH}$=7 Hz, CH$_2$CO$_2$). HRMS (FAB, MH+) m/z=461.2109 (cald for C$_{27}$H$_{29}$N$_2$O$_5$: 461.2076).

Using the above procedure, but substituting the appropriate 5-oxa-2-benzazepin-1 -one for 2-(2-carboxyethyl)-4-benzyl-8-(4-(2-N-Boc-amino)ethoxyphenyl)-2,3,4,5-tetrahydro-1H-5-oxa-2-benzazepin-1  -one methyl ester there may be prepared, for example, the following compounds:

2-(2-carboxy ethyl )-4-methyl-8-(4-(2-amino)ethoxyphenyl)-2,3,4,5-tetrahydro-1H-5-oxa-2-benzazepin-1-one, 2-(3-carboxy-2-propyl)-4-benzyl-8-(4-(2-amino)ethoxyphenyl)-2,3,4,5-tetrahydro-1H-5-oxa-2-benzazepin-1-one, 2-(3-carboxy-2-propyl)-4-methyl-8-(4-(2-amino)ethoxyphenyl )-2,3,4,5-tetrahydro-1H-5-oxa-2-benzazepin-1-one, 2-(2-carboxyethyl)-4-benzyl-8-[4-(1-piperazine)phenyl]-2,3,4,5-tetrahydro-1H-5-oxa-2-benzazepin-1 -one, 2-(2-carboxyethyl)-4-methyl-8-[4-(1-piperazine)-phenyl]-2,3,4,5-tetrahydro-1-oxa-2-benzazepin-1-one, 2-(3-carboxy-2-propyl)-4-benzyl-8-[4-(1-piperazine )phenyl]-2,3,4,5-tetrahydro-1H-5-oxa-2-benzazepin-1-one, 2-(3-carboxy-2-propyl)-4-methyl-8-[4-(1-piperazine)-phenyl]-2,3,4,5-tetrahydro-1H-5-oxa-2-benzazepin-1-one, 2-(2-carboxyethyl)-4-benzyl-8-[4-(4-aminomethyl)-phenyl]-2,3,4,5-tetrahydro-1H-5-oxa-2-benzazepin-1-one, 2-(2-carboxyethyl )-4-methyl-8-[4-(4-aminomethyl )phenyl]-2,3,4,5-tetrahydro-1H-5-oxa-2-benzazepin-1-one, 2-(3-carboxy-2-propyl)-4-benzyl-8-[4-(4-aminomethyl)-phenyl]-2 ,3,4,5-tetrahydro-1H-5-oxa-2-benzazepin-1-one, 2-(3-carboxy-2-propyl)-4-methyl-8-[4-(4-aminomethyl)-phenyl]-2,3,4,5-tetrahydro-1H-5-oxa-2-benzazepin-1-one.

EXAMPLE 25

Fibrinogen-GP $II_bIII_a$ Receptor ELISA Binding Assay

The method used is essentially that described in Nachman and Leung (J. Clin. Invest., 69:263-269 [1982]). The GP $II_bIII_a$ is essentially purified as described in Fitzgerald et al., (Anal. Biochem. 151:169-177 [1985]).

A. GP $II_bIII_a$ Purification

Outdated human platelets are washed 3 times with 10 mM tris-HCl, 150 mM NaCl (TBS), 1 mM EDTA, pH 7.5, and centrifuged at 2000×g to pellet cells. Cells are lysed in 5 pellet volumes of TBS, 1% Triton X-100, 1 mM $Ca_2Cl_2$, and followed by centrifugation at 30,000×g. The supernatant fraction is collected and the supernatant is loaded onto a concanavalin-A column, previously equilibrated in TBS, 1 mM $Ca_2Cl_2$, 0.1% Triton, 0.05% $NaN_3$ and eluted with 0.2M d-methyl-mannoside. Fractions are pooled and loaded onto a heparin-agarose column. The flowthrough is collected and concentrated on an Amicon YM 30 filter to a volume of approximately 5-10 ml. The concentrate is then applied to an S-300 column (500 ml) and 6 ml fractions are collected. The GP $II_bIII_a$ containing fractions are collected, pooled, and stored at −80° C.

B. Purification of Low Solubility Fraction of Fibrinogen

The purification of fibrinogen is conducted essentially as described by Lipinska et al., (J. Lab. Clin. Med. 507, [1974]). Briefly, a 0.3 % w/v solution of human fibrinogen (Kabi #5302) is dissolved in 150 mM NaCl. Saturated $(NH_4)_2SO_4$ is added dropwise with stirring to the fibrinogen solution to obtain about 16% saturation. The precipitate is spun down in appropriate size bottles at 2000×g. The supernatant is decanted and the precipitate resuspended in 150 mM NaCl (approximately 50% of the original volume). $NH_4SO_4$ is again added dropwise to obtain 16% saturation. The suspension is spun down and the precipitate is resuspended in Tris-saline in a minimal volume (approximately 5% of the original volume). Any remaining insoluble material is spun down at 2000 rpm in a Sorval type centrifuge and the fibrinogen supernatant is decanted and dialyzed overnight at 4° C. against Tris-saline. Characterization of the fibrinogen is by the Bradford protein assay, SDS-PAGE, and/or Western blotting using well known standard procedures.

C. ELISA Assay

Briefly, 96 well plates are coated (Type Nunc 1 Maxisorp ™) with 10 mg/ml purified fibrinogen (100 ml/well), and allowed to stand overnight at 4° C. The plates are washed three times with PBS Tween (0.137 M NaCl, 0.003 M KCl, 0.008M $Na_2HPO_4$, 0.001M $HK_2PO_4$, pH 7.4 at room temperature, 0.05% Tween-20) and blocked for 1 to 2 hours at room temperature with 200 ml/well TNCNT (which is 0.5% BSA, 20 mM Tris, pH 7.5 at room temperature, 120 mM NaCl, 0.2% $NAN_3$, 2 mM $CaCl_2$, 0.05% Tween 20, 0.5% BSA [Calbiochem RIA grade or better]) on a plate shaker. The plates are again washed three times with PBS/Tween and then 50 ml of sample in TNCNT is added. The mixture is incubated for 15 minutes at room temperature on a plate shaker. The stock solution of purified GP $II_bIII_a$ receptor from human platelets, (0.4-1.0 mg/ml GP $II_bIII_a$ in 0.1% Triton X-100, 1 mM $CaCl_2$, 20 mM Tris, 150 mM NaCl, 0.05% $NaN_3$ in 0.3M N-acetyl glucosamine pH 7.5, stored at −70° C.), is reconstituted to about 40 mg/ml in TNCNT. Fifty ml of this diluted GP $II_bIII_a$ is then added to each well and incubated on a plate shaker at room temperature. After one hour, the plates are washed four times with PBS/Tween and 100 ml of a polyclonal or monoclonal antibody specific for GP IIIa such as AP3 (1 mg/ml) (See e.g. Newman et al., Blood, 65:227-232 [1985]) in ELISA buffer (PBS, 0.5% BSA, 0.05% Tween 20, 0.01% Thimerasol) is added. After a one hour incubation at room temperature on a plate shaker, the samples are washed 4 times with PBS/Tween. One hundred ml of GAM-HRP (horse radish peroxidase conjugate of goat anti-mouse IgG [Pel-Freeze Cat. 715305-1]dissolved in ELISA buffer) previously diluted to 1:10,000 is then added and the samples are incubated 1 hour at room temperature on a plate shaker. The samples are then washed 4 times with PBS/Tween and 100 ml $OPD/H_2O_2$ substrate is added ($OPD/H_2O_2$ substrate: 10 mg o-phenylenediamine in 15 ml phosphate/citrate buffer, at room temperature and covered with foil; just before use, 6.25 ml of 30% $H_2O_2$ is added to give a final solution of 0.67 mg OPD/ml in 0.0125% $H_2O_2$). (The phosphate/citrate buffer consists of 16 mM Citric Acid, 50 mM $Na_2HPO_4$, pH 5.0). The color develops within about 3 to 20 minutes and the reaction is stopped with 100 ml 1M $H_2SO_4$. The optical density at 492 nm vs 405 nm is recorded and $IC_{50}$ values are determined.

EXAMPLE 26

Human Vitronectin-Vitronectin Receptor ($a_vb_3$) ELISA Assay

A. Human Vitronectin Purification

Human vitronectin (Vn) is isolated from human plasma and purified by affinity chromatography by the method of Yatohgo et. al., (Cell Structure and Function 13:281-292 [1988]).

B. Human Vitronectin Receptor ($a_vb_3$) Purification

Human vitronection receptor (VnR) is purified from human placenta by the method of Pytela et al., (Methods Enzymol., 144: 475 [1987]). Alternatively the $a_vb_3$ receptor can be purified from some cell lines (e.g., human embryonic kidney 293 cells) transfected with DNA sequences for both the $a_v$ and $b_3$ subunits. The subunits are purified by employing octylglucoside extraction followed by Con-A, Heparin-Sepharose, and S-300 Chromatography.

C. Monoclonal Antibodies

Anti-GP $II_bIII_a$ monoclonal antibodies specific for human GP $III_a$ are prepared by the method of Newman et al. (Blood, 65:227-232 [1985]), or a similar procedure. This mouse Mab is specific for the $b_3$ subunit of the vitronectin receptor.

Rabbit Fab 2 anti-mouse Fc fragment horse radish peroxidase conjugate (anti-MuFc HRP) is obtained from PelFreeze (cat. no. 715305-1).

D. ELISA Assay

Maxisorp microtiter plates are coated with 2 mg/ml human vitronectin dissolved in PBS (50 ml/well) and stored overnight at 4° C. The plates are washed two times with PBS-0.05% Tween-20 (wash buffer) and blocked by incubating with about 150 ml/well of assay buffer (1%, BSA [RIA grade or better] in 50 mM Tris-HCl, 100 mM NaCl, 1 mM $MgCl_2$, $CaCl_2$, $MnCl_2$ pH 7.4) for 60 minutes. Dilutions of standards are prepared and putative inhibitors (Table 3) are dissolved in assay buffer. The blocked plates are emptied and 25 ml/well of inhibitor or standard solution is added to each well. Twenty-five ml of a 30 mg/ml solution of purified $a_vb_3$ in assay buffer is pipetted into the coated plate. The final concentration of receptor in the assay well is about 15 mg/ml. The plate is incubated on a shaker for 60 minutes. Meanwhile, for each microtite plate, 6 ml buffer solution containing 1.5 mg/ml of mouse monoclonal antibody specific for $b_3$ is prepared. To this solution is added ml of the secondary antibody, which is anti-mouse-Fc-HRP antibody conjugate. For example, for one plate, prepare 6 ml of a 1.5 mg/ml mouse Mab solution to which is added 1 ml of anti-mouse-Fc-HRP antibody stock, (this represents a 1:6000 dilution of the antibody—HRP conjugate). This mixture is allowed to incubate during the receptor-inhibitor incubation. The assay plates are washed 4 times with PBS-Tween and 50 ml/well of the antibody mixture is then pipetted into the plate for a 60 minute incubation. The plate is washed 4 times and the color reaction is developed with 50 ml/well of 0.67 mg/ml o-phenyldiamine in PBS containing 0.012% $H_2O_2$. Alternatively, 16 mM citric acid, 50 mM $Na_2PO_4$ at pH 5.0 can be used as a substrate buffer. The reaction is stopped with 50 ml/well 1M $H_2SO_4$. The plates are read at 492–405 nm and the data analyzed by four-parameter fit.

EXAMPLE 27

GP $II_bIII_a$-von Willebrand factor (vWF) ELISA Assay

A. ELISA Assay

Microtiter plates are coated with 1.0 mg/ml GP $II_bIII_a$, prepared by the method of Fitzgerald et al., (*Anal. Biochem.* 151:169-177 [1985]) and allowed to incubate overnight in coat buffer. The plates are then washed three times in wash buffer (0.05% Tween 20 in PBS) and 150 ml of assay buffer is added and allowed to incubate for 1-2 hours at room temperature on plate shaker. The plates are washed three times and 50 ml of 2X inhibitor in assay buffer (Assay buffer: 0.5% BSA/50 mM Tris, 100 mM NaCl, 1.0 mM $CaCl_2$, 1.0 mM $MgCl_2$, 1.0 mM $MnCl_2$; coat buffer is the same but without BSA) is added. Fifty ml of 4.0 mg/ml vWF (prepared as described by Ledford et al., *Thrombosis and Haemostasis*, 64(4): 569-575 [1990]) in assay buffer is then added and allowed to incubate for one hour at room temperature on plate-shaker. The plates are washed three times and the antibody mixture is added (1:5000 of mouse anti-vWF and 1:5000 of rabbit-anti-mouse-Fc-HRP, both commercially available) in assay buffer and incubated for 1 hour at room temperature on plate-shaker. Plates are again washed three times and 100 ml of substrate solution (10 mg OPD, 6.5 ml $H_2O_2$, 15 ml phosphate citrate buffer) is added and incubated at room temperature. The color change of OPD/$H_2O_2$ reagent is read at 492 nm with a 405 nm reference wavelength on the filter photometer.

EXAMPLE 28

In Vitro Human Platelet Aggregation Assay

Platelet aggregation assays are performed in human platelet rich plasma (PRP). Fifty milliliters of whole human blood (9 parts) is drawn on 3.6% sodium citrate (1 part) from a donor who has not taken aspirin or related medications for at least two weeks. The blood is centrifuged at 160×g for 10 minutes at 22° C. and allowed to stand for 5 minutes after which the PRP is decanted. Platelet poor plasma (PPP) is isolated from the remaining blood after centrifugation at 2000×g for 25 minutes. The platelet count of the PRP is diluted to about 300,000 platelets per microliter with PPP.

A 225 ml aliquot of PRP plus 25 ml of either a dilution of the test inhibitor sample or a control (PBS) is incubated for 5 minutes in a Chrono-log Whole Blood Aggregometer at 25° C. An aggregating agent (collagen, 1 mg/ml; U46619, 100 ng/ml; or ADP, 17 mM) is added and the transmission is recorded.

EXAMPLE 29

Results of ELISA Assays for 1, 3, 4, and 7 Substituted Benzodiazepinediones

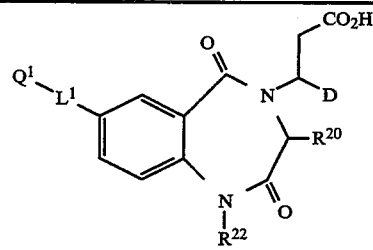

| Cmpd # | $Q^1$ | $L^1$ | $R^{22}$ | $R^{20}$ | D | $IC_{50}(\mu M)$ Fg/IIbIIIa |
|---|---|---|---|---|---|---|
| 1 | amine | $(CH_2)_3$ | H | H | H | 8.3 |
| 2 | guanidine | $(CH_2)_3$ | H | H | H | 0.714 |
| 3 | amine | $(CH_2)_3$ | $CH_3$ | H | H | 28.0 |
| 4 | guanidine | $(CH_2)_3$ | $CH_3$ | H | H | 0.466 |
| 5 | amine | $CH_2CC$ | $CH_3$ | H | H | 7.0 |
| 6 | guanidine | $CH_2CC$ | $CH_3$ | H | H | 0.170 |
| 7 | amine | $(CH_2)_3$ | $CH_3$ | $CH_3$ | H | 30.0 |
| 8 | guanidine | $(CH_2)_3$ | $CH_3$ | $CH_3$ | H | >100.0 |
| 9 | amine | $CH_2CC$ | $CH_3$ | $CH_3$ | H | 70.0 |
| 10 | guanidine | $CH_2CC$ | $CH_3$ | $CH_3$ | H | 30.0 |
| 11 | amine | $(CH_2)_3$ | $CH_3$ | Ph | H | 600.0 |
| 12 | guanidine | $(CH_2)_3$ | $CH_3$ | Ph | H | 2.30 |
| 13 | amine | $CCCH_2$ | $CH_3$ | Ph | H | >1000.0 |
| 14 | guanidine | $CCCH_2$ | $CH_3$ | Ph | H | 25.0 |
| 15 | amine | $(CH_2)_3$ | $CH_3$ | $-(CH_2)_2-$ | | >100.0 |
| 16 | guanidine | $(CH_2)_3$ | $CH_3$ | $-(CH_2)_2-$ | | >100.0 |
| 17 | amine | $(CH_2)_3$ | $CH_3$ | $-(CH_2)_2-$ | | >100.0 |
| 18 | guanidine | $(CH_2)_3$ | $CH_3$ | $-(CH_2)_2-$ | | >100.0 |
| 19 | amine | $(CH_2)_4$ | $CH_3$ | H | H | 5.0 |

-continued

| | | | | | | |
|---|---|---|---|---|---|---|
| 20 | guanidine | (CH$_2$)$_4$ | CH$_3$ | H | H | 0.250 |
| 21 | amine | (CH$_2$)$_2$CC | CH$_3$ | H | H | 6.0 |
| 22 | guanidine | (CH$_2$)$_2$CC | CH$_3$ | H | H | 0.140 |
| 23 | amine | (CH$_2$)$_4$ | CH$_3$ | CH$_3$ | H | >100.0 |
| 24 | guanidine | (CH$_2$)$_4$ | CH$_3$ | CH$_3$ | H | 100.0 |
| 25 | amine | (CH$_2$)$_2$CC | CH$_3$ | CH$_3$ | H | >100.0 |
| 26 | guanidine | (CH$_2$)$_2$CC | CH$_3$ | CH$_3$ | H | 80.0 |
| 27 | amine | (CH$_2$)$_5$ | CH$_3$ | H | H | 1.9 |
| 28 | guanidine | (CH$_2$)$_5$ | CH$_3$ | H | H | 0.055 |
| 29 | amine | (CH$_2$)$_5$ | H | H | H | 2.92 |
| 30 | guanidine | (CH$_2$)$_5$ | H | H | H | 0.204 |
| 31 | amine | (CH$_2$)$_3$CC | H | H | H | 1.43 |
| 32 | guanidine | (CH$_2$)$_3$CC | H | H | H | 0.254 |
| 33 | amine | (CH$_2$)$_3$CC | CH$_3$ | H | H | 0.096 |
| 34 | guanidine | (CH$_2$)$_3$CC | CH$_3$ | H | H | 0.0036 |
| 35 | amine | (CH$_2$)$_3$CC | CH$_2$(mNO$_2$C$_6$H$_4$) | H | H | 0.013 |
| 36 | guanidine | (CH$_2$)$_3$CC | CH$_2$(mNO$_2$C$_6$H$_4$) | H | H | 0.0032 |
| 37 | amine | (CH$_2$)$_3$CC | CH$_3$ | H | CH$_3$ | 0.061 |
| 38 | guanidine | (CH$_2$)$_3$CC | CH$_3$ | H | CH$_3$ | 0.018 |
| 39 | amine | (CH$_2$)$_6$ | CH$_3$ | H | H | 0.070 |
| 40 | guanidine | (CH$_2$)$_6$ | CH$_3$ | H | H | 0.120 |
| 41 | amine | (CH$_2$)$_4$CC | CH$_3$ | H | H | 0.100 |
| 42 | guanidine | (CH$_2$)$_4$CC | CH$_3$ | H | H | 0.060 |
| 43 | amine | p(CH$_2$)C$_6$H$_4$CC | CH$_3$ | H | H | 0.012 |
| 44 | guanidine | p(CH$_2$)C$_6$H$_4$CC | CH$_3$ | H | H | 0.012 |
| 45 | amine | p(CH$_2$)C$_6$H$_4$(CH$_2$)$_2$ | CH$_3$ | H | H | 0.085 |
| 46 | guanidine | p(CH$_2$)C$_6$H$_4$(CH$_2$)$_2$ | CH$_3$ | H | H | 0.265 |
| 47 | amine | mC$_6$H$_4$(CH$_2$)$_2$ | CH$_3$ | H | H | 10.0 |
| 48 | bis-guanidine | mC$_6$H$_4$(CH$_2$)$_2$ | CH$_3$ | H | H | 3.0 |
| 49 | amine | mC$_6$H$_4$CC | CH$_3$ | H | H | 6.0 |
| 50 | bis-guanidine | mC$_6$H$_4$CC | CH$_3$ | H | H | 25.0 |
| 51 | amine | (CH$_2$)$_6$ | CH$_3$ | H | Ph | 0.200 |
| 52 | guanidine | (CH$_2$)$_6$ | CH$_3$ | H | Ph | 0.390 |
| 53 | amine | (CH$_2$)$_4$CC | CH$_3$ | H | Ph | 0.240 |
| 54 | guanidine | (CH$_2$)$_4$CC | CH$_3$ | H | Ph | 0.100 |
| 55 | amine | (CH$_2$)$_4$CC | CH$_2$(mNO$_2$C$_6$H$_4$) | H | H | 0.008 |
| 56 | guanidine | (CH$_2$)$_4$CC | CH$_2$(mNO$_2$C$_6$H$_4$) | H | H | 0.006 |
| 57 | nitrile | pC$_6$H$_4$CC | CH$_3$ | H | H | 30.0 |
| 58 | amine | (CH$_2$)$_3$CC | CH$_2$(pClC$_6$H$_4$) | H | H | 0.062 |
| 59 | guanidine | (CH$_2$)$_3$CC | CH$_2$(pClC$_6$H$_4$) | H | H | 0.009 |
| 60 | amine | (CH$_2$)$_4$CC | CH$_2$(pClC$_6$H$_4$) | H | H | 0.014 |
| 61 | guanidine | (CH$_2$)$_4$CC | CH$_2$(pClC$_6$H$_4$) | H | H | 0.043 |
| 62 | amine | (CH$_2$)$_5$ | CH$_2$(pClC$_6$H$_4$) | H | H | 0.176 |
| 63 | guanidine | (CH$_2$)$_5$ | CH$_2$(pClC$_6$H$_4$) | H | H | 0.011 |
| 64 | amine | (CH$_2$)$_6$ | CH$_2$(pClC$_6$H$_4$) | H | H | 0.014 |
| 65 | guanidine | (CH$_2$)$_6$ | CH$_2$(pClC$_6$H$_4$) | H | H | 0.050 |
| 66 | amine | (CH$_2$)$_7$ | CH$_2$(pClC$_6$H$_4$) | H | H | 0.026 |
| 67 | guanidine | (CH$_2$)$_7$ | CH$_2$(pClC$_6$H$_4$) | H | H | 0.200 |
| 68 | amine | (CH$_2$)$_5$ | CH(C$_6$H$_5$)$_2$ | H | H | 0.020(2) |
| 69 | guanidine | (CH$_2$)$_5$ | CH(C$_6$H$_5$)$_2$ | H | H | 0.082 |
| 71 | guanidine | (CH$_2$)$_3$CC | CH(C$_6$H$_5$)$_2$ | H | H | 0.008 |
| 72 | amine | (CH$_2$)$_6$ | CH(C$_6$H$_5$)$_2$ | H | H | 0.022 |
| 73 | amine | (CH$_2$CH$_2$)$_2$p-C$_6$H$_4$ | CH$_2$(pClC$_6$H$_4$) | H | H | 0.007 |
| 74 | guanidine | (CH$_2$CH$_2$)$_2$p-C$_6$H$_4$ | CH$_2$(pClC$_6$H$_4$) | H | H | 0.019 |
| 75 | guanidine | (CH$_2$)$_5$ | CH$_2$($\beta$-napth) | H | H | 0.011(2) |
| 76 | amine | (CH$_2$)$_5$ | CH$_2$($\beta$-napth) | H | H | 0.077 |
| 77 | guanidine | (CH$_2$)$_5$ | CH$_2$($\alpha$-napth) | H | H | 0.008 |
| 78 | amine | (CH$_2$)$_5$ | CH$_2$($\alpha$-napth) | H | H | 0.066 |
| 79 | guanidine | (CH$_2$)$_5$ | CH$_2$(pOMeC$_6$H$_4$) | H | H | 0.011 |
| 80 | amine | (CH$_2$)$_5$ | CH$_2$(pOMeC$_6$H$_4$) | H | H | 0.160 |
| 81 | amine | (CH$_2$)$_6$ | CH$_2$(pOMeC$_6$H$_4$) | H | H | 0.023 |
| 82 | amine | (CH$_2$)$_6$ | CH$_2$($\alpha$-napth) | H | H | 0.015 |
| 83 | amine | (CH$_2$)$_6$ | CH$_2$($\beta$-napth) | H | H | 0.017 |
| 84 | guanidine | (CH$_2$)$_6$ | CH$_2$(pOMeC$_6$H$_4$) | H | H | 0.024 |
| 85 | guanidine | (CH$_2$)$_6$ | CH$_2$($\alpha$-napth) | H | H | 0.014 |
| 86 | guanidine | (CH$_2$)$_6$ | CH$_2$($\beta$-napth) | H | H | 0.055 |
| 87 | amine | (CH$_2$)$_4$CC | CH$_2$(pNO$_2$C$_6$H$_4$) | H | H | 0.031 |
| 88 | guanidine | (CH$_2$)$_4$CC | CH$_2$(pNO$_2$C$_6$H$_4$) | H | H | 0.031 |
| 89 | guanidine | (CH$_2$)$_6$ | CH$_2$(pCF$_3$C$_6$H$_4$) | H | H | 0.047 |
| 90 | amine | (CH$_2$)$_6$ | CH$_2$(pCF$_3$C$_6$H$_4$) | H | H | 0.005 |
| 91 | guanidine | (CH$_2$)$_6$ | CH$_2$(mOPhC$_6$H$_4$) | H | H | 0.009 |
| 92 | guanidine | (CH$_2$)$_5$ | CH$_2$(mOPhC$_6$H$_4$) | H | H | 0.011 |
| 93 | guanidine | (CH$_2$)$_5$ | CH$_2$(pCF$_3$C$_6$H$_4$) | H | H | 0.014 |
| 94 | amine | (CH$_2$)$_6$ | CH$_2$(mOPhC$_6$H$_4$) | H | H | 0.009 |
| 95 | amine | (CH$_2$)$_5$ | CH$_2$(mOPhC$_6$H$_4$) | H | H | 0.108 |
| 96 | amine | (CH$_2$)$_5$ | CH$_2$(pCF$_3$C$_6$H$_4$) | H | H | 0.186 |
| 97 | amine | (CH$_2$)$_3$CC | CH$_2$(o,pF$_2$C$_6$H$_4$) | H | H | 0.130 |
| 98 | guanidine | (CH$_2$)$_3$CC | CH$_2$(o,pF$_2$C$_6$H$_4$) | H | H | 0.024 |
| 99 | amine | (CH$_2$)$_4$CC | CH$_2$(o,pF$_2$C$_6$H$_4$) | H | H | 0.027 |
| 100 | guanidine | (CH$_2$)$_4$CC | CH$_2$(o,pF$_2$C$_6$H$_4$) | H | H | 0.025 |
| 101 | amine | (CH$_2$)$_5$ | CH$_2$(o,pF$_2$C$_6$H$_4$) | H | H | 0.200 |
| 102 | guanidine | (CH$_2$)$_5$ | CH$_2$(o,pF$_2$C$_6$H$_4$) | H | H | 0.016 |

-continued

| | | | | | | |
|---|---|---|---|---|---|---|
| 103 | amine | $(CH_2)_6$ | $CH_2(o,pF_2C_6H_4)$ | H | H | 0.021 |
| 104 | guanidine | $(CH_2)_6$ | $CH_2(o,pF_2C_6H_4)$ | H | H | 0.038 |
| 105 | AcNH | $(CH_2)_6$ | $CH_2(pCl_6H_4)$ | H | H | 8.5 |

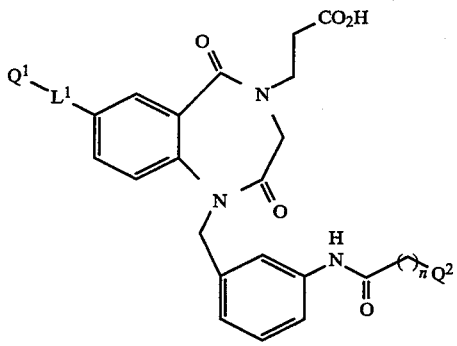

| Cmpd # | $Q^1=Q^2$ | $L^1$ | n | $IC_{50}(\mu M)$ Fg/IIbIIIa |
|---|---|---|---|---|
| 106 | amine | $(CH_2)_3CC$ | 1 | 0.068 |
| 107 | guanidine | $(CH_2)_3CC$ | 1 | 0.018 |
| 108 | amine | $(CH_2)_6$ | 1 | 0.012 |
| 109 | guanidine | $(CH_2)_6$ | 1 | 0.017 |
| 110 | amine | $(CH_2)_6$ | 2 | 0.008 |
| 111 | guanidine | $(CH_2)_6$ | 2 | 0.010 |
| 112 | amine | $(CH_2)_6$ | 3 | 0.008 |
| 113 | guanidine | $(CH_2)_6$ | 3 | 0.010 |
| 114 | amine | $(CH_2)_6$ | 4 | 0.008 |
| 115 | guanidine | $(CH_2)_6$ | 4 | 0.013 |
| 116 | amine | $(CH_2)_6$ | 5 | 0.011 |
| 117 | guanidine | $(CH_2)_6$ | 5 | 0.013 |

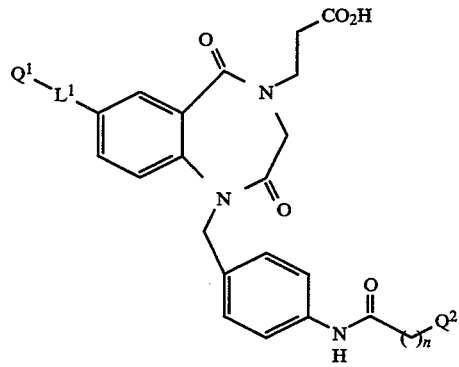

| Cmpd # | $Q^1$ | $L^1$ | n | $IC_{50}(\mu M)$ Fg/IIbIIIa |
|---|---|---|---|---|
| 118 | amine | $(CH_2)_6$ | 2 | 0.019 |
| 119 | guanidine | $(CH_2)_6$ | 2 | 0.013 |

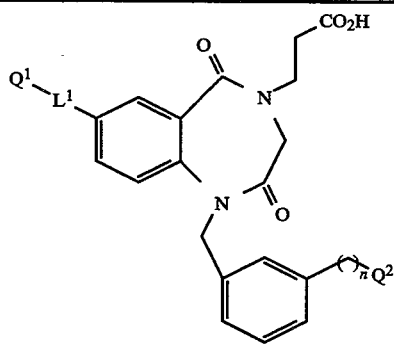

| Cmpd # | $Q^1=Q^2$ | $L^1$ | n | $IC_{50}(\mu M)$ Fg/IIbIIIa |
|---|---|---|---|---|
| 120 | amine | $(CH_2)_6$ | 4 | 0.024 |
| 121 | guanidine | $(CH_2)_6$ | 4 | 0.020 |

-continued

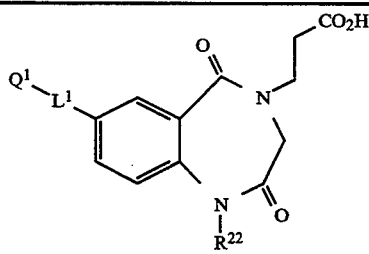

| Cmpd # | Q¹ | L¹ | R²² | IC$_{50}$(μM) Fg/IIbIIIa |
|---|---|---|---|---|
| 122 | amine | (CH$_2$)$_6$ | CH$_2$(mNH$_2$C$_6$H$_4$) | 0.012(2) |
| 123 | amine | (CH$_2$)$_6$ | CH$_2$(mNHCOBu$^n$C$_6$H$_4$) | 0.015(2) |
| 124 | guanidine | (CH$_2$)$_6$ | CH$_2$(mNHCOBu$^n$C$_6$H$_4$) | 0.012(2) |
| 125 | amine | (CH$_2$)$_6$ | (CH$_2$)$_5$NH$_2$ | 0.064 |
| 126 | guanidine | (CH$_2$)$_6$ | (CH$_2$)$_5$NHC(NH)NH$_2$ | 0.040 |
| 127 | amine | (CH$_2$)$_6$ | CH$_2$(mNHCO(pgC$_6$H$_4$)C$_6$H$_4$) | 0.008 |
| 128 | amine | (CH$_2$)$_6$ | CH$_2$(pNH$_2$C$_6$H$_4$) | 0.024 |
| 129 | guanidine | (CH$_2$)$_6$ | (CH$_2$)$_4$CO$_2$H | |
| 130 | amine | (CH$_2$)$_6$ | (CH$_2$)$_4$CO$_2$H | |
| 131 | guanidine | (CH$_2$)$_5$ | (CH$_2$)$_4$CO$_2$H | 0.014 |
| 132 | amine | (CH$_2$)$_5$ | (CH$_2$)$_4$CO$_2$H | 0.931 |
| 133 | guanidine | (CH$_2$)$_5$ | CH$_2$(pCO$_2$HC6H4) | 0.016 |
| 134 | guanidine | (CH$_2$)$_6$ | CH$_2$(pCO$_2$HC6H4) | 0.019 |
| 135 | amine | (CH$_2$)$_6$ | CH$_2$(pCO$_2$HC6H4) | 0.008 |
| 136 | amine | (CH$_2$)$_5$ | CH$_2$(pCO$_2$HC6H4) | 0.176 | g = NH(CNH)NH$_2$

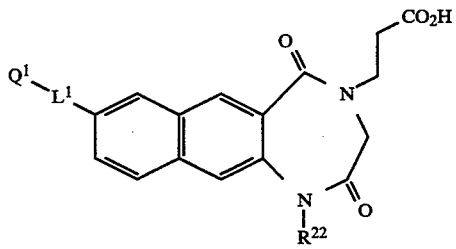

| Cmpd # | Q¹ | L¹ | R²² | IC$_{50}$(μM) Fg/IIbIIIa |
|---|---|---|---|---|
| 137 | amine | CH$_2$CC | CH$_3$ | 0.351 |
| 138 | guanidine | CH$_2$CC | CH$_3$ | 0.009 |
| 139 | amine | (CH$_2$)$_4$ | CH$_3$ | 0.153 |
| 140 | guanidine | (CH$_2$)$_4$ | CH$_3$ | 0.069 |

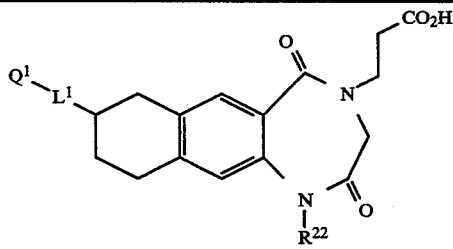

| Cmpd # | Q¹ | L¹ | R²² | IC$_{50}$(μM) Fg/IIbIIIa |
|---|---|---|---|---|
| 141 | amine | (CH$_2$)$_3$ | CH$_3$ | 1.8 |
| 142 | guanidine | (CH$_2$)$_3$ | CH$_3$ | 0.068 |
| 143 | amine | (CH$_2$)$_4$ | CH$_3$ | 0.048 |

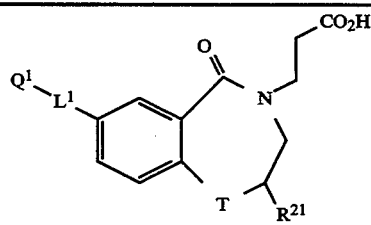

| Cmpd # | Q¹ | L¹ | T | R²¹ | IC$_{50}$(μM) Fg/IIbIIIa |
|---|---|---|---|---|---|
| 144 | amine | (CH$_2$)$_3$CC | O | H | 12.0 |
| 145 | guanidine | (CH$_2$)$_3$CC | O | H | 4.0 |
| 146 | amine | (CH$_2$)$_5$ | O | H | 80.0 |

-continued

| | | | | | | |
|---|---|---|---|---|---|---|
| 147 | guanidine | (CH$_2$)$_5$ | O | H | | 3.0 |
| 148 | amine | (CH$_2$)$_3$CC | O | CH$_2$Ph | | 5.9 |
| 149 | guanidine | (CH$_2$)$_3$CC | O | CH$_2$Ph | | 0.823 |
| 150 | amine | p-[(CH$_2$)$_2$O]C$_6$H$_4$ | O | CH$_2$Ph | | 0.119 |
| 151 | amine | (CH$_2$)$_8$O | CH$_2$ | H | | >100 |
| 152 | guanidine | (CH$_2$)$_8$O | CH$_2$ | H | | 50.0 |
| 153 | amine | (CH$_2$)$_3$CC | CH$_2$ | H | | >100 |
| 154 | guanidine | (CH$_2$)$_3$CC | CH$_2$ | H | | 20.0 |
| 155 | amine | (CH$_2$)$_5$ | CH$_2$ | H | | >100 |
| 156 | guanidine | (CH$_2$)$_5$ | CH$_2$ | H | | ca. 100 |
| 157 | amidine | p-C$_6$H$_4$CH$_2$O | CH$_2$ | H | | 0.137 |

EXAMPLE 30

Results of ELISA for Benzoylamide

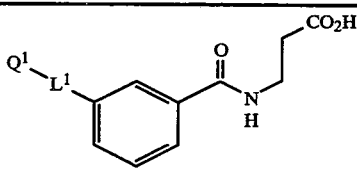

| Cmpd # | Q$^1$ | L$^1$ | IC$_{50}$($\mu$M) Fg/IIbIIIa |
|---|---|---|---|
| 158 | guanidine | (CH$_2$)$_3$ | 2.3 |
| 159 | guanidine | CH$_2$CC | 0.552 |
| 160 | guanidine | (CH$_2$)$_2$CC | 1.01 |
| 161 | amine | (CH$_2$)$_3$CC | 9.0 |
| 162 | guanidine | (CH$_2$)$_3$CC | 1.0 |
| 163 | amine | (CH$_2$)$_4$CC | 2.7 |
| 164 | guanidine | (CH$_2$)$_4$CC | 3.4 |

EXAMPLE 31

Results of ELISA and Platelet Aggregation (PA) Assays for 1,3,4, and 7 Substituted Benzodiazepinediones

| G# | IC$_{50}$($\mu$M) Fg/IIbIIIa | IC$_{50}$ ($\mu$M) Vn/VnR | IC$_{50}$($\mu$M) vWF/IIbIIIa | PA IC$_{50}$ ($\mu$M) (citrate) | PA IC$_{50}$ ($\mu$M) (heparin) |
|---|---|---|---|---|---|
| 2 | 0.714 | >10.0 | | >5.0 | |
| 22 | 0.140 | >10.0 | | 8.96 | |
| 33 | 0.096 | >10.0 | 0.390 | 85.5 | |
| 34 | 0.0036 | >10.0 | | 3.1(2) | 7.5 |
| 35 | 0.013 | >10.0 | | 2.4(3) | 8.0,9.53 |
| 36 | 0.0032 | (3.0) | 0.0004 | 0.94 | |
| 27 | 1.9 | >10.0 | 0.780 | | |
| 28 | 0.055 | >10.0 | 0.024 | | |
| 20 | 0.245 | >10.0 | 0.096 | | |
| 43 | 0.012 | >10.0 | | 1.7 | 3.34* |
| 44 | 0.012 | >10.0 | | 8.8 | 14.3 |
| 55 | 0.008 | >10.0 | | | 2.2 |
| 56 | 0.006 | >10.0 | | | 15.0 |
| 38 | 0.018 | | | 1.19 | |
| 42 | 0.009 | >10.0 | | 2.66 | |
| 60 | 0.014 | >10.0 | | 2.12 | |
| 63 | 0.011 | >10.0 | | 2.55 | |
| 64 | 0.014 | >10.0 | | 1.20 | 4.76 |
| 66 | 0.026 | >10.0 | | 3.88 | |
| 107 | 0.018 | >10.0 | | 0.61 | 0.89 |
| 68 | 0.028 | >10.0 | | 1.66 | 3.4 |
| 69 | 0.082 | >10.0 | | 2.09 | 3.9 |
| 71 | 0.008 | >10.0 | | 0.34 | 0.95 |
| 70 | 0.0024 | >10.0 | | 0.44 | 1.3 |
| 72 | 0.022 | >10.0 | | 0.46 | 1.1 |
| 108 | 0.012 | >10.0 | | 0.55 | 1.09 |
| 109 | 0.017 | >10.0 | | 1.19 | |
| 110 | 0.008 | >10.0 | | 0.28 | 0.83 |
| 111 | 0.010 | >10.0 | | 1.14 | 1.49 |
| 73 | 0.007 | | | 0.67 | 2.3 |
| 74 | 0.019 | | | 1.80 | 4.79 |

-continued

| G# | IC$_{50}$($\mu$M) Fg/IIbIIIa | IC$_{50}$ ($\mu$M) Vn/VnR | IC$_{50}$($\mu$M) vWF/IIbIIIa | PA IC$_{50}$ ($\mu$M) (citrate) | PA IC$_{50}$ ($\mu$M) (heparin) |
|---|---|---|---|---|---|
| 122 | 0.010 | | | 0.49 | |
| 112 | 0.008 | | | 0.40 | |
| 113 | 0.010 | | | 0.87 | |
| 124 | 0.012(2) | | | 2.76 | |
| 123 | 0.015(2) | | | 0.64 | |
| 75 | 0.011(2) | | | 6.88 | |
| 76 | 0.077 | | | 28.9 | |
| 77 | 0.008 | | | 2.65 | |
| 78 | 0.066 | | | 6.53 | |
| 81 | 0.023 | | | 0.98 | |
| 82 | 0.015 | | | 0.76 | |
| 83 | 0.017 | | | 3.19 | |
| 84 | 0.024 | | | 10.4 | |
| 85 | 0.014 | | | 6.20 | |
| 127 | 0.008 | | | 0.35 | |
| 114 | 0.008 | | | 0.31 | |
| 115 | 0.018 | | | 0.92 | |
| 116 | 0.011 | | | 0.27 | |
| 117 | 0.013 | | | 0.64 | |

While the invention has necessarily been described in conjunction with preferred embodiments, one of ordinary skill, after reading the foregoing specification, will be to effect various changes, substitutions of equivalents, and alterations to the subject matter set forth herein, without departing from the spirit and the scope thereof. Hence, the invention can be practiced in ways other than those specfically described herein. It is therefore intended that the protection granted by Letters Patent hereon be limited only by the appended claims and the equivalents thereof.

What is claimed is:

1. A compound represented by structural formula (I):

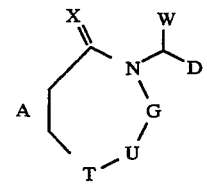

(I)

where the partial structure

represents

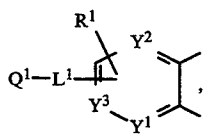

where
R$^1$ and R$^2$ are one to three optional groups independently selected from hydrogen, halo(F, Cl, Br, I), cyano, carboxamido, carbamoyloxy, formyloxy, formyl, azido, nitro, ureido, thioureido, hydroxy, mercapto, sulfonamido, and an optionally substituted radical selected from C$_1$-C$_{12}$ alkyl, C$_2$-C$_{12}$ alkenyl, C$_3$-C$_{12}$ alkynyl, C$_3$-C$_{12}$ cycloalkyl, C$_6$-C$_{14}$aryl, C$_6$-C$_{10}$ aryl-C$_1$-C$_8$ alkyl, C$_1$-C$_{12}$ alkyloxy, C$_6$-C$_{14}$ aryloxy, and C$_1$-C$_{12}$ acylamino, where the substituents are selected from halo(F, Cl, Br, I), cyano, azido, nitro, hydroxy, mercapto, sulfonamido, ureido, thioureido, carboxamido, carbamoyloxy, formyloxy, formyl, C$_1$-C$_4$ alkyl, C$_1$-C$_4$ alkoxy, phenyl, and phenoxy;
Y$^1$, Y$^2$ and Y$^3$ are independently selected from CH, CR$^1$ and CR$^2$;
X is O;
Q$^1$ is selected from the group consisting of
(A) an amino group selected from
—NH$_2$,
—NR$^3$H,
—NR$^3$R$^4$, and
—NR$^3$R$^4$R$^5$,
where R$^3$, R$^4$, and R$^5$ are independently selected from
(i) an optionally substituted radical selected from
(a) —NR$^6$R$^7$,
(b) —C(=NR$^8$)—NR$^6$R$^7$,
(c) —N=CR$^9$—NR$^6$R$^7$,
(d) —NR$^{10}$—CR$^9$=NR$^8$, and
(e) —NR$^{10}$—C(=NR$^8$)—NR$^6$R$^7$,
where each R$^6$, R$^7$, R$^8$, R$^9$, and R$^{10}$ is independently selected from
hydrogen,
C$_1$-C$_4$ alkoxy,
C$_1$-C$_4$ alkyl, and
halo(F, Cl, Br, I)-C$_1$-C$_4$-alkyl,
(ii) optionally substituted C$_1$-C$_{12}$ alkyl,
(iii) optionally substituted C$_3$-C$_{12}$ cycloalkyl,
(iv) optionally substituted C$_6$-C$_{14}$ aryl,
(v) optionally substituted C$_1$-C$_6$ alkyl-C$_6$-C$_{14}$ aryl.
(vi) optionally substituted C$_1$-C$_8$ alkoxy,
(vii) optionally substituted C$_6$-C$_{14}$ aryloxy,
where the substituents are one to three R$^{11}$, each R$^{11}$ independently selected from
(a) optionally substituted C$_6$-C$_{12}$ aryloxy,
(b) optionally substituted C$_6$-C$_{12}$ arylamino,
(c) optionally substituted C$_6$-C$_{12}$ aroyl,
where the substituents are one to three R$^{12}$, each R$^{12}$ independently selected from
nitro,
amino,
C$_1$-C$_8$ alkylamino,
di-(C$_1$-C$_8$) alkylamino,
amidino,
aminomethyleneimino,
imino,
imino-C$_1$-C$_4$ alkyl,
iminomethyleneamino,
guanidino,
C$_6$-C$_{10}$ arylamino,
C$_1$-C$_8$ acylamino,
C$_1$-C$_4$ alkylsulfonamino,
azido,
cyano,
hydroxy,
hydroxy-C$_1$-C$_8$-alkyl,
C$_1$-C$_8$-alkoxy,
phenyloxy,
C$_1$-C$_8$ alkanoyloxy,
C$_1$-C$_8$ alkanoyl,
C$_6$-C$_{12}$ aroyl,
benzamido,
phenyl,
halo(F, Cl, Br, I),
halo-C$_1$-C$_8$-alkyl, and
C$_1$-C$_8$-alkyl,
(d) halo(F, Cl, Br,
(e) hydroxy,
(f) mercapto,
(g) formyl,
(h) formyloxy,
(i) carboxy,
(j) amino,
(k) ureido.
(l) amidino,
(m) guanidino,
(n) aminomethyleneimino,
(o) imino,
(p) glycyl,
(q) phthalimido,
(r) succinimido,
(s) morpholino, and
(t) C$_3$-C$_7$ cycloalkyl,
optionally R$^3$ and R$^4$ taken together may form optionally substituted
tetramethylene,
pentamethylene,
3-oxopentamethylene, and
3-azapentamethylene,
where the substituents are selected from one to three R$^{12}$,
(B) an amidino group selected from
—C(=NH)—NH$_2$,
—C(=NH)—NHR$^3$,
—C(=NR$^4$)—NHR$^3$,
—C(=NH)—NR$^3$R$^4$, and
—C(=NR$^5$)—NR$^3$R$^4$,
where R$^3$, R$^4$, and R$^5$ are defined above,
(C) an aminoalkyleneimino group selected from
—N=CH—NH$_2$,
—N=CH—NHR$^3$,
—N=CH—NR$^3$R$^4$, and
—N=CR$^5$—NR$^3$R$^4$
where R$^3$, R$^4$, and R$^5$ are defined above,
(D) an iminoalkyleneamino group selected from
—NH—CH=NH,
—NH—CH=NR$^3$,
—NH—CR$^4$=NR$^3$, and
—NR$^5$—CR$^4$=NR$^3$,
where R$^3$, R$^4$, and R$^5$ are defined above,
(E) a guanidino group selected from
—NH—C(=NH)—NH$_2$,
—NH—C(=NH)—NR$^3$H,
—NH—C(=NH)—NR$^3$R$^4$,
—NH—C(=NR$^5$)—NR$^3$R$^4$,
—NR$^3$—C(=NR$^3$)—NR$^3$R$^4$, —$NR^3$—$C(=NH)$—$NR^3R^4$,
—$NR^3$—$C(=NR^3)$—$NH_2$,
—$NR^3$—$C(=NH)$—$NH_2$,
—$NR^3$—$C(=NR^3)$—$NHR^4$, and
—$NR^3$—$C(=NH)$—$NHR^4$, where $R^3$, $R^4$, and $R^5$ are defined above;

$L^1$ is an optionally substituted bivalent radical selected from the group consisting of
$C_3$-$C_7$-alkylene,
$C_3$-$C_7$-cycloalkylene,
$C_3$-$C_7$-alkenylene,
$C_4$-$C_7$-cycloalkenylene,
$C_5$-$C_8$-cycloalkadienylene,
$C_3$-$C_7$-alkadienylene,
$C_3$-$C_7$-alkynylene,
$C_4$-$C_7$-alkenynylene,
$C_6$-$C_{14}$-arylene,
$C_6$-$C_{14}$-aryl-$C_2$-$C_4$-alkynylene,
$C_1$-$C_3$-alkyl-$C_6$-$C_{14}$-aryl-$C_2$-$C_4$-alkynylene,
$C_6$-$C_{14}$-aryl-$C_2$-$C_4$-alkenylene,
$C_1$-$C_3$-alkyl-$C_6$-$C_{14}$-arylene,
$C_1$-$C_3$-alkyl-$C_6$-$C_{14}$-aryl-$C_2$-$C_4$-alkenylene,
$C_6$-$C_{14}$-aryl-$C_1$-$C_3$-alkylene,
$C_6$-$C_{14}$-aryl-$C_1$-$C_3$-alkyloxyene,
$C_1$-$C_3$-alkyl-$C_6$-$C_{14}$-aryl-$C_1$-$C_2$-alkylene,
$C_1$-$C_3$-alkyloxy-$C_6$-$C_{14}$-arylene,
$C_2$-$C_8$-alkyloxyene,
$C_1$-$C_5$-alkyloxy-$C_1$-$C_5$-alkylene,
$C_6$-$C_{10}$-aryloxyene,
$C_6$-$C_{10}$-aryloxy-$C_1$-$C_5$-alkylene,
$C_6$-$C_{10}$-arylthio-$C_1$-$C_5$-alkylene,

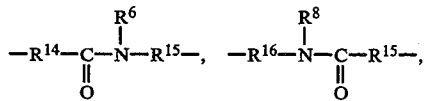

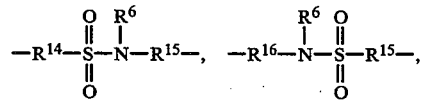

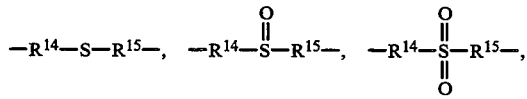

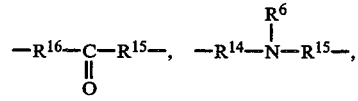

and

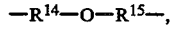

where
$R^{14}$ is selected from
a chemical bond,
$C_1$-$C_8$-alkylene,
$C_3$-$C_7$-cycloalkylene,
$C_2$-$C_5$-alkenylene,
$C_3$-$C_5$-alkynylene.
$C_6$-$C_{10}$-arylene,
$C_1$-$C_3$-alkyl-$C_6$-$C_{12}$-arylene,
$C_1$-$C_2$-alkyl-$C_6$-$C_{10}$-aryl-$C_1$-$C_2$-alkylene,
$C_6$-$C_{10}$-aryl-$C_1$-$C_2$-alkylene, and
$C_6$-$C_{10}$-aryloxy-$C_1$-$C_2$-alkylene, $R^{15}$ is selected from
a chemical bond,
$C_1$-$C_4$-alkylene,
$C_2$-$C_4$-alkenylene,
$C_2$-$C_4$-alkynylene,
$C_6$-$C_{10}$-arylene, and
$C_1$-$C_3$-alkyl-$C_6$-$C_{12}$-arylene, $R^{16}$ is selected from
a chemical bond,
$C_1$-$C_5$-alkylene,
$C_3$-$C_7$-cycloalkylene,
$C_3$-$C_5$-alkenylene,
$C_3$-$C_5$-alkynylene,
$C_6$-$C_{10}$-arylene,
$C_1$-$C_3$-alkyl-$C_6$-$C_{12}$-arylene, and
$C_6$-$C_{10}$-aryl-$C_1$-$C_2$-alkylene, where the substituents are selected from one to three $R^{12}$;

$L^2$ is an optionally substituted bivalent radical selected from the group consisting of

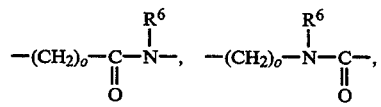

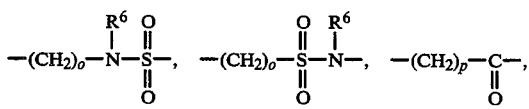

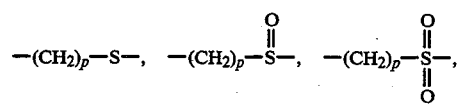

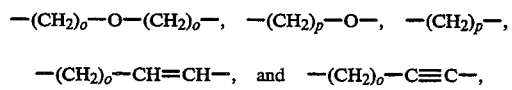

where
o is 1 or 2,
p is 1, 2, 3or 4,
$R^6$ is defined above, and
where the substituents are selected from one to three $R^{12}$;

T-U-G is

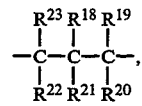

where
$R^{18}$ and $R^{23}$ are independently selected from the group consisting of
(i) hydrogen,
(ii) optionally substituted $C_1$-$C_{12}$ alkyl,
(iii) optionally substituted $C_3$-$C_{12}$ alkenyl,
(iv) optionally substituted $C_3$-$C_{14}$ cycloalkyl,
(v) optionally substituted $C_1$-$C_{12}$ alkyl-$C_6$-$C_{14}$-aryl,
(vi) optionally substituted $C_6$-$C_{14}$ aryl,
(vii) optionally substituted $C_1$-$C_4$ alkylphenyl, and
(viii) optionally substituted $C_1$-$C_{12}$ alkoxy, $R^{19}$ and $R^{20}$ are independently selected from hydrogen, halo(F, Cl, Br, I), $C_1$-$C_4$ alkoxy, $C_1$-$C_4$ alkyl, phenyl, benzyl, and halo(F, Cl, Br, I)-$C_1$-$C_4$-alkyl, $R^{21}$ and $R^{22}$ are independently selected from the group consisting of
(i) hydrogen,
(ii) optionally substituted $C_1$–$C_{12}$-alkyl,
(iii) optionally substituted $C_6$–$C_{14}$-aryl,
(iv) optionally substituted $C_3$–$C_{14}$-cycloalkyl,
(v) optionally substituted $C_1$–$C_{12}$-alkyl-$C_6$–$C_{14}$-aryl, and
(vi) optionally substituted $C_1$–$C_{12}$-alkyl-$C_3$–$C_{14}$-cycloalkyl,
where the substituents are selected from
(a) halo (F, Cl, Br, I),
(b) nitro,
(c) hydroxy,
(d) carboxy,
(e) tetrazole,
(f) hydroxamate,
(g) sulfonamide,
(h) trifluoroimide,
(i) phosphonate,
(j) $C_1$–$C_6$-alkyl,
(k) $C_6$–$C_{14}$-aryl,
(l) benzyl,
(m) $C_3$–$C_{14}$-cycloalkyl,
(n) $COR^{24}$
where $R^{24}$ is selected from the group
$C_1$–$C_8$ alkoxy,
$C_3$–$C_{12}$ alkenoxy,
$C_6$–$C_{12}$ aryloxy,
$C_1$–$C_6$-alkyl-$C_6$–$C_{12}$-aryloxy,
di-$C_1$–$C_8$-alkylamino-$C_1$–$C_8$-alkoxy,
acylamino-$C_1$–$C_8$-alkoxy selected from the group
acetylaminoethoxy,
nicotinoylaminoethoxy, and
succinamidoethoxy,
$C_1$–$C_8$-alkoyloxy-$C_1$–$C_8$-alkoxy, and
$C_6$–$C_{12}$ aryl-$C_1$–$C_8$-alkoxy where the aryl group is unsubstituted or substituted with one to three of the groups
nitro,
halo (F, Cl, Br, I),
$C_1$–$C_4$-alkoxy,
amino,
hydroxy,
hydroxy-$C_2$–$C_8$-alkoxy, and
dihydroxy-$C_3$–$C_8$-alkoxy, and
(o) $CONR^{25}R^{26}$
where $R^{25}$ and $R^{26}$ are independently selected from
hydrogen,
$C_1$–$C_{10}$-alkyl,
$C_3$–$C_{10}$-alkenyl,
$C_6C_{14}$-aryl,
$C_1$–$C_6$-alkyl-$C_6$–$C_{10}$-aryl,
optionally $R^{25}$ and $R^{26}$ taken together may form
trimethylene,
tetramethylene,
pentamethylene, and
3-oxopentamethylene, and
(vii) $Q^2$-$L^3$
where
$Q^2$ is selected from
hydrogen, and
$Q^1$, and
$L^3$ is selected from
a chemical bond,
$L^1$, and
$L^2$;
D is selected from the group consisting of $R^{22}$, and
—(C═O)-Xaa, where Xaa is one to three D or L α-amino acid residues;
W is

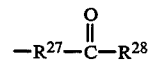

where
$R^{27}$ is selected from the group consisting of
methylene, and
ethylene; and
$R^{28}$ is selected from the group consisting of
(i) hydroxy,
(ii) $C_1$–$C_8$-alkoxy,
(iii) $C_3$–$C_{12}$-alkenoxy,
(iv) $C_6$–$C_{12}$-aryloxy,
(v) $C_1$–$C_6$-alkyl-$C_6$–$C_{12}$-aryloxy,
(vi) di-$C_1$–$C_8$-alkylamino-$C_1$–$C_8$-alkoxy,
(vii) acylamino-$C_1$–$C_8$-alkoxy selected from the group
(a) acetylaminoethoxy,
(b) nicotinoylaminoethoxy, and
(c) succinamidoethoxy,
(viii) $C_1$–$C_8$-alkoyloxy-$C_1$–$C_8$-alkoxy,
(ix) $C_6$–$C_{12}$-aryl-$C_1$–$C_8$-alkoxy
where the aryl group is unsubstituted or substituted with one to three of the groups
(a) nitro,
(b) halo (F, Cl, Br, I),
(c) $C_1$–$C_4$-alkoxy, and
(d) amino,
(x) hydroxy-$C_2$–$C_8$-alkoxy,
(xi) dihydroxy-$C_3$–$C_8$-alkoxy, and
(xii) $NR^{29}R^{30}$
where $R^{29}$ and $R^{30}$ are independently selected from the group
(a) hydrogen,
(b) $C_1$–$C_8$-alkyl,
(c) $C_3$–$C_8$-alkenyl,
(d) $C_6$–$C_{12}$-aryl
where the aryl group is unsubstituted or substituted with one to three of the groups
nitro,
halo (F, Cl, Br, I),
$C_1$–$C_4$-alkoxy, and
amino, and
(e) $C_6$–$C_{12}$-aryl-$C_1$–$C_8$-alkyl
where the aryl group is unsubstituted or substituted with one to three of the groups
nitro,
halo (F, Cl, Br, I), and
$C_1$–$C_4$-alkoxy; and
pharmaceutically acceptable salts thereof.

2. The compound of claim 1 represented by formula VI:

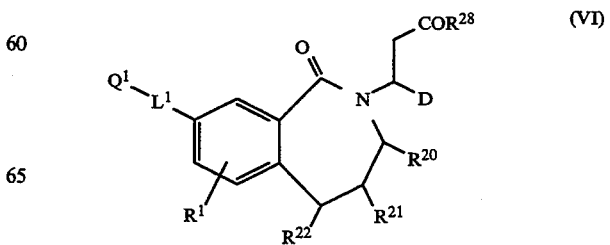

where
$R^1$ is one to three groups independently selected from hydrogen and halogen(F, Cl, Br, I);
$Q^1$ is selected from the group consisting of
(A) an amino group,
(B) an amidino group,
(C) an aminoalkyleneimino group,
(D) an iminoalkyleneamino group, and
(E) a guanidino group;
$L^1$ is an optionally substituted bivalent radical selected from the group consisting of
$C_3$–$C_7$-alkylene,
$C_3$–$C_7$-cycloalkylene,
$C_3$–$C_7$-alkenylene,
$C_4$–$C_7$-cycloalkenylene,
$C_5$–$C_8$-cycloalkadienylene,
$C_3$–$C_7$-alkadienylene,
$C_3$–$C_7$-alkynylene,
$C_4$–$C_7$-alkenynylene,
$C_6$–$C_{14}$-arylene,
$C_6$–$C_{14}$-aryl-$C_2$–$C_4$-alkynylene,
$C_1$–$C_3$-alkyl-$C_6$–$C_{14}$-aryl-$C_2$–$C_4$-alkynylene,
$C_6$–$C_{14}$-aryl-$C_2$–$C_4$-alkenylene,
$C_1$–$C_3$-alkyl-$C_6$–$C_{14}$-arylene,
$C_1$–$C_3$-alkyl-$C_6$–$C_{14}$-aryl-$C_2$–$C_4$-alkenylene,
$C_6$–$C_{14}$-aryl-$C_1$–$C_3$-alkylene,
$C_6$–$C_{14}$-aryl-$C_1$–$C_3$-alkyloxyene,
$C_1$–$C_3$-alkyl-$C_6$–$C_{14}$-aryl-$C_1$–$C_2$-alkylene,
$C_1$–$C_3$-alkyloxy-$C_6$–$C_{14}$-arylene,
$C_2$–$C_8$-alkyloxyene,
$C_1$–$C_5$-alkyloxy-$C_1$–$C_5$-alkylene,
$C_6$–$C_{10}$-aryloxyene,
$C_6$–$C_{10}$-aryloxy-$C_1$–$C_5$-alkylene,
$C_6$–$C_{10}$-arylthio-$C_1$–$C_5$-alkylene,

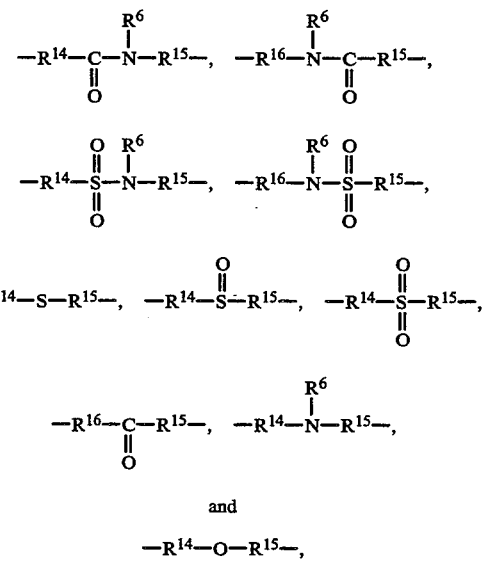

where
$R^6$ is selected from
hydrogen,
$C_1$–$C_4$-alkoxy,
$C_1$–$C_4$-alkyl, and
halo (F, Cl, Br, I)$C_1$–$C_4$-alkyl,
$R^{14}$ is selected from
a chemical bond,
$C_1$–$C_8$-alkylene,
$C_3$–$C_7$-cycloalkylene,
$C_2$–$C_5$-alkenylene,
$C_3$–$C_5$-alkynylene,
$C_6$–$C_{10}$-arylene,
$C_1$–$C_3$-alkyl-$C_6$–$C_{12}$-arylene,
$C_1$–$C_2$-alkyl-$C_6$–$C_{10}$-aryl-$C_1$–$C_2$-alkylene,
$C_6$–$C_{10}$-aryl-$C_1$–$C_2$-alkylene, and
$C_6$–$C_{10}$-aryloxy-$C_1$–$C_2$-alkylene,
$R^{15}$ is selected from
a chemical bond,
$C_1$–$C_4$-alkylene,
$C_2$–$C_4$-alkenylene,
$C_2$–$C_4$-alkynylene,
$C_6$–$C_{10}$-arylene, and
$C_1$–$C_3$-alkyl-$C_6$–$C_{12}$-arylene,
$R^{16}$ is selected from
a chemical bond,
$C_1$–$C_5$-alkylene,
$C_3$–$C_7$-cycloalkylene,
$C_3$–$C_5$-alkenylene,
$C_3$–$C_8$-alkynylene,
$C_6$–$C_{10}$-arylene,
$C_1$–$C_3$-alkyl-$C_6$–$C_{12}$-arylene, and
$C_6$–$C_{10}$-aryl-$C_1$–$C_2$-alkylene,
where the substituents are selected from one to three $R^{12}$;
$R^{20}$ is hydrogen;
$R^{21}$ and $R^{22}$ are selected from the group consisting of (i) hydrogen, (ii) optionally substituted $C_1$–$C_{12}$-alkyl, (iii) optionally substituted $C_6$–$C_{14}$-aryl, (iv) optionally substituted $C_3$–$C_{14}$-cycloalkyl, (v) optionally substituted $C_1$–$C_{12}$-alkyl-$C_6$–$C_{14}$-aryl, (vi) optionally substituted $C_1$–$C_{12}$-alkyl-$C_3$–$C_{14}$-cycloalkyl, where the substituents are selected from (a) halo (F, Cl, Br, I), (b) nitro, (c) hydroxy, (d) carboxy, (e) tetrazole, (f) hydroxamate, (g) sulfonamide, (h) trifluoroimide, (i) phosphonate, (j) $C_1$–$C_6$-alkyl, (k) $C_6$–$C_{14}$-aryl, (l) benzyl, (m) $C_3$–$C_{14}$-cycloalkyl, (n) $COR^{24}$ where $R^{24}$ is selected from the group $C_1$–$C_8$-alkoxy, $C_3$–$C_{12}$-alkenoxy, $C_6$–$C_{12}$-aryloxy, di-$C_1$–$C_8$-alkylamino-$C_1$–$C_8$-alkoxy, acylamino-$C_1$–$C_8$-alkoxy selected from the group acetylaminoethoxy, nicotinoylaminoethoxy, succinamidoethoxy, and pivaloyloxyethoxy, and $C_6$–$C_{12}$-aryl-$C_1$–$C_8$-alkoxy where the aryl group is unsubstituted or substituted with one to three of the groups nitro, halo (F, Cl, Br, I), $C_1$–$C_4$-alkoxy, amino, hydroxy, hydroxy-$C_2$–$C_8$-alkoxy, and dihydroxy-$C_3$–$C_8$alkoxy, (o) $CONR^{25}R^{26}$ where $R^{25}$ and $R^{26}$ are independently selected from hydrogen, $C_1$–$C_{10}$-alkyl, $C_3$–$C_{10}$-alkenyl, $C_6$–$C_{14}$-aryl, $C_1$–$C_6$-alkyl-$C_6$–$C_{10}$-aryl, optionally $R^{25}$ and $R^{26}$ taken together may form trimethylene, tetramethylene, pentamethylene, and 3-oxopentamethylene, and (vii) $Q^2$-$L^3$- where $Q^2$ is selected from hydrogen and $Q^1$, and $L^3$ is selected from a chemical bond and $L^1$ where $R^{15}$ bonds $L^1$ to position 4 or 5 of the benzazepine-one;
D is $R^{21}$;
$R^{28}$ is selected from the group consisting of (i) hydroxy, (ii) $C_1$–$C_8$-alkoxy, (iii) $C_3$–$C_{12}$-alkenoxy, (iv) $C_6$–$C_{12}$-aryloxy, (v) $C_1$–$C_6$-alkyl-$C_6$–$C_{12}$-aryloxy, (vi) di-$C_1$–$C_8$-alkylamino-$C_1$–$C_8$-alkoxy, (vii) acylamino-$C_1$–$C_8$-alkoxy selected from the group (a) acetylaminoethoxy, (b) nicotinoylaminoethoxy, and (c) succinamidoethoxy, (viii) $C_1$–$C_8$-alkoyloxy-$C_1$–$C_8$-alkoxy, (ix) $C_6$–$C_{12}$-aryl-$C_1$–$C_8$-alkoxy where the aryl group is unsubstituted or substituted with one to three of the groups (a) nitro, (b) halo (F, Cl, Br, I), (c) $C_1$–$C_4$-alkoxy, and (d) amino, (x) hydroxy-$C_2$–$C_8$-alkoxy, (xi) dihydroxy-$C_3$–$C_8$-alkoxy, and (xii) $NR^{29}R^{30}$ where $R^{29}$ and $R^{30}$ are independently selected from the group (a) hydrogen, (b) $C_1$–$C_8$-alkyl, (c) $C_3$–$C_8$-alkenyl, (d) $C_6$–$C_{12}$-aryl where the aryl group is unsubstituted or substituted with one to three of the groups nitro, halo (F, Cl, Br, I), $C_1$–$C_4$-alkoxy, and amino, and (e) $C_6$–$C_{12}$-aryl-$C_1$–$C_8$-alkyl where the aryl group is unsubstituted or substituted with one to three of the groups nitro, halo (F, Cl, Br, I), and $C_1$–$C_4$-alkoxy; and pharmaceutically acceptable salts thereof.

3. The compound of claim 2 where $Q^1$ is an amidino group and $L^1$ is selected from the group consisting of $C_6$–$C_{14}$-aryl-$C_2$–$C_4$-alkynylene,
$C_6$–$C_{14}$-aryl-$C_1$–$C_3$-alkylene,
$C_6$–$C_{14}$-aryl-$C_1$–$C_3$-alkyloxyene, and

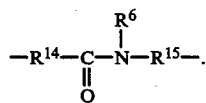

4. The compound of claim 3 where $R^{28}$ is selected from hydroxy and $C_1$–$C_8$ alkoxy.

5. The compound of claim 4 where $R^{21}$ and $R^{22}$ are selected from the group consisting of
hydrogen,
$C_1$–$C_{12}$-alkyl, and
$C_3$–$C_{14}$-cycloalkyl.

6. The compound of claim 5 where D is selected from hydrogen or methyl.

7. A pharmaceutical composition comprising a pharmaceutically acceptable excipient and the compound of claim 1.

8. A method of inhibiting platelet aggregation in a mammal comprising administering a platelet aggregation inhibiting amount of the composition of claim 7 to the mammal.

9. A method for reducing platelet aggregation in a mammal comprising administering a pharmaceutically effective amount of the composition of claim 7 to the mammal.

10. A method for treating a mammal having an increased propensity for thrombus formation comprising administering a pharmaceutically effective amount of the composition of claim 7 to the mammal.

* * * * *